US010865251B2

(12) United States Patent
Chen et al.

(10) Patent No.: US 10,865,251 B2
(45) Date of Patent: Dec. 15, 2020

(54) ANTI-CD3 ANTIBODIES AND METHODS OF USE

(71) Applicant: Genentech, Inc., South San Francisco, CA (US)

(72) Inventors: Xiaocheng Chen, South San Francisco, CA (US); Mark S. Dennis, South San Francisco, CA (US); Allen J. Ebens, Jr., San Carlos, CA (US); Robert F. Kelley, South San Francisco, CA (US); Mary A. Mathieu, South San Francisco, CA (US); Liping L. Sun, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 16/144,452

(22) Filed: Sep. 27, 2018

(65) Prior Publication Data
US 2019/0112389 A1    Apr. 18, 2019

Related U.S. Application Data

(62) Division of application No. 14/574,132, filed on Dec. 17, 2014, now Pat. No. 10,174,124.

(60) Provisional application No. 62/091,441, filed on Dec. 12, 2014, provisional application No. 62/053,582, filed on Sep. 22, 2014, provisional application No. 62/026,594, filed on Jul. 18, 2014, provisional application No. 61/949,950, filed on Mar. 7, 2014, provisional application No. 61/917,346, filed on Dec. 17, 2013.

(51) Int. Cl.
C07K 16/28      (2006.01)
C07K 16/32      (2006.01)
A61K 39/395    (2006.01)
C07K 16/30      (2006.01)
A61K 45/06      (2006.01)
A61K 31/573    (2006.01)
A61K 47/68      (2017.01)
A61K 39/00      (2006.01)

(52) U.S. Cl.
CPC ............ C07K 16/32 (2013.01); A61K 31/573 (2013.01); A61K 39/39558 (2013.01); A61K 45/06 (2013.01); A61K 47/6881 (2017.08); C07K 16/283 (2013.01); C07K 16/2809 (2013.01); C07K 16/2827 (2013.01); C07K 16/2863 (2013.01); C07K 16/2887 (2013.01); C07K 16/2896 (2013.01); C07K 16/30 (2013.01); A61K 2039/505 (2013.01); C07K 2317/21 (2013.01); C07K 2317/24 (2013.01); C07K 2317/31 (2013.01); C07K 2317/33 (2013.01); C07K 2317/34 (2013.01); C07K 2317/522 (2013.01); C07K 2317/524 (2013.01); C07K 2317/526 (2013.01); C07K 2317/54 (2013.01); C07K 2317/55 (2013.01); C07K 2317/56 (2013.01); C07K 2317/622 (2013.01); C07K 2317/71 (2013.01); C07K 2317/73 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 5,500,362 | A | 3/1996 | Robinson et al. |
| 5,624,821 | A | 4/1997 | Winter et al. |
| 5,648,260 | A | 7/1997 | Winter et al. |
| 5,731,168 | A | 3/1998 | Carter et al. |
| 5,821,337 | A | 10/1998 | Carter et al. |
| 5,869,046 | A | 2/1999 | Presta et al. |
| 6,194,551 | B1 | 2/2001 | Idusogie et al. |
| 6,248,516 | B1 | 6/2001 | Winter et al. |
| 6,455,043 | B1 | 9/2002 | Grillo-Lopez |
| 6,602,684 | B1 | 8/2003 | Umana et al. |
| 6,737,056 | B1 | 5/2004 | Presta |
| 7,332,581 | B2 | 2/2008 | Presta |
| 7,371,826 | B2 | 5/2008 | Presta |
| 7,612,181 | B2 | 11/2009 | Wu et al. |
| 7,682,612 | B1 | 3/2010 | White et al. |
| 7,695,936 | B2 | 4/2010 | Carter et al. |
| 7,799,900 | B2 | 9/2010 | Adams et al. |
| 8,219,149 | B2 | 7/2012 | Lafata et al. |
| 8,258,268 | B2 | 9/2012 | Wu et al. |
| 8,562,992 | B2 | 10/2013 | Adams et al. |
| 8,709,421 | B2 | 4/2014 | Heiss et al. |
| 8,722,859 | B2 | 5/2014 | Miller et al. |
| 8,969,526 | B2 | 3/2015 | Baehner et al. |

(Continued)

FOREIGN PATENT DOCUMENTS

| | | |
|---|---|---|
| CN | 101675077 B | 9/2013 |
| EP | 1870459 A1 | 12/2007 |

(Continued)

OTHER PUBLICATIONS

Anderson et al., "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11):2826-34 (1992).

(Continued)

Primary Examiner — Zachary S Skelding
(74) Attorney, Agent, or Firm — Clark & Elbing LLP; Karen L. Elbing

(57) ABSTRACT

The invention provides anti-cluster of differentiation 3 (CD3) antibodies and methods of using the same.

20 Claims, 169 Drawing Sheets
(53 of 169 Drawing Sheet(s) Filed in Color)
Specification includes a Sequence Listing.

(56) References Cited

U.S. PATENT DOCUMENTS

| | | | |
|---|---|---|---|
| 9,011,864 B2 | 4/2015 | Schulz et al. |
| 9,017,676 B2 | 4/2015 | Lindhofer |
| 9,308,257 B2 | 4/2016 | Sharma, Sr. et al. |
| 9,315,567 B2 | 4/2016 | Chang et al. |
| 9,493,563 B2 | 11/2016 | Blein et al. |
| 9,587,021 B2 | 3/2017 | Huang et al. |
| 9,657,102 B2 | 5/2017 | Smith et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0095243 A1 | 5/2005 | Chan et al. |
| 2005/0123546 A1 | 6/2005 | Umana et al. |
| 2009/0252683 A1 | 10/2009 | Kischel et al. |
| 2010/0015133 A1 | 1/2010 | Lgawa et al. |
| 2010/0150918 A1 | 6/2010 | Kufer et al. |
| 2010/0331527 A1 | 12/2010 | Davis et al. |
| 2011/0123532 A1 | 5/2011 | Gurney et al. |
| 2012/0244577 A1 | 9/2012 | Dixit et al. |
| 2012/0251531 A1 | 10/2012 | Baehner et al. |
| 2013/0129723 A1 | 5/2013 | Blankenship et al. |
| 2013/0165638 A1 | 6/2013 | Hsu et al. |
| 2013/0171095 A1 | 7/2013 | Bernett et al. |
| 2013/0287774 A1 | 10/2013 | Zugmaier et al. |
| 2014/0079689 A1 | 3/2014 | Elliott et al. |
| 2014/0088295 A1 | 3/2014 | Smith et al. |
| 2014/0112914 A1 | 4/2014 | Nezu et al. |
| 2014/0170149 A1 | 6/2014 | Neijssen et al. |
| 2014/0187753 A1 | 7/2014 | Blein et al. |
| 2014/0302064 A1 | 10/2014 | Moore |
| 2014/0377270 A1 | 12/2014 | Moore et al. |
| 2015/0098900 A1 | 4/2015 | Ebens et al. |
| 2015/0133640 A1 | 5/2015 | Blein et al. |
| 2015/0166661 A1 | 6/2015 | Chen et al. |
| 2015/0284475 A1 | 10/2015 | Zhou et al. |
| 2016/0000916 A1 | 1/2016 | Crotts et al. |
| 2016/0017058 A1 | 1/2016 | Kim et al. |
| 2016/0075785 A1 | 3/2016 | Ast et al. |
| 2016/0090416 A1 | 3/2016 | Gunde et al. |
| 2016/0145339 A1 | 5/2016 | Zhou et al. |
| 2016/0159906 A1 | 6/2016 | Sun et al. |
| 2016/0368985 A1 | 12/2016 | Hotzel et al. |
| 2016/0368994 A1 | 12/2016 | Kelley et al. |
| 2017/0008971 A1 | 1/2017 | Dennis et al. |
| 2017/0022274 A1 | 1/2017 | Chang et al. |
| 2017/0158773 A1 | 6/2017 | Adams et al. |
| 2017/0204194 A1 | 7/2017 | Chen et al. |
| 2017/0209573 A1 | 7/2017 | Bacac et al. |
| 2017/0224818 A1 | 8/2017 | Lindhofer et al. |
| 2017/0267783 A1 | 9/2017 | Nezu et al. |
| 2018/0057593 A1 | 3/2018 | Dennis |

FOREIGN PATENT DOCUMENTS

| | | |
|---|---|---|
| EP | 1870459 A4 | 9/2010 |
| EP | 2482212 A1 | 8/2012 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2008-291036 A | 12/2008 |
| JP | 2009-539413 A | 11/2009 |
| JP | 2013-515509 A | 5/2013 |
| JP | 2013-528569 A | 7/2013 |
| JP | 2013/529084 A | 7/2013 |
| JP | 2015-509952 A | 4/2015 |
| WO | WO-94/04679 A1 | 3/1994 |
| WO | WO-94/29351 A2 | 12/1994 |
| WO | WO-96/01126 A1 | 1/1996 |
| WO | WO-96/27011 A1 | 9/1996 |
| WO | WO-97/30087 A1 | 8/1997 |
| WO | WO-98/50431 A2 | 11/1998 |
| WO | WO-98/58964 A1 | 12/1998 |
| WO | WO-98/50431 A3 | 1/1999 |
| WO | WO-99/22764 A1 | 5/1999 |
| WO | WO-99/51642 A1 | 10/1999 |
| WO | WO-00/61739 A1 | 10/2000 |
| WO | WO-01/29246 A1 | 4/2001 |
| WO | WO-02/31140 A1 | 4/2002 |
| WO | WO-03/011878 A2 | 2/2003 |
| WO | WO-03/084570 A1 | 10/2003 |
| WO | WO-03/085107 A1 | 10/2003 |
| WO | WO-03/085119 A1 | 10/2003 |
| WO | WO-03/087131 A2 | 10/2003 |
| WO | WO-2004/056312 A2 | 7/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/100402 A1 | 10/2005 |
| WO | WO-2006/029879 A2 | 3/2006 |
| WO | WO-2007/042261 A2 | 4/2007 |
| WO | WO-2007/110205 A2 | 10/2007 |
| WO | WO-2007/146968 A2 | 12/2007 |
| WO | WO-2008/077546 A1 | 7/2008 |
| WO | WO-2008/119566 A2 | 10/2008 |
| WO | WO-2008/119567 A2 | 10/2008 |
| WO | WO-2009/070642 A1 | 6/2009 |
| WO | WO-2010/077643 A1 | 7/2010 |
| WO | WO-2010/114940 A1 | 10/2010 |
| WO | WO-2011/028952 A1 | 3/2011 |
| WO | WO-2011/090754 A1 | 7/2011 |
| WO | WO-2011/090762 A1 | 7/2011 |
| WO | WO-2011/121110 A1 | 10/2011 |
| WO | WO-2011/131746 A2 | 10/2011 |
| WO | WO-2011/143545 A1 | 11/2011 |
| WO | WO-2012/058768 A1 | 5/2012 |
| WO | WO-2012/058768 A8 | 6/2012 |
| WO | WO-2012/073985 A1 | 6/2012 |
| WO | WO-2012075581 A1 | 6/2012 |
| WO | WO-2012123949 A1 | 9/2012 |
| WO | WO-2012/143524 A2 | 10/2012 |
| WO | WO-2012/158818 A2 | 11/2012 |
| WO | WO-2012/162067 A2 | 11/2012 |
| WO | WO-2013/128027 A1 | 9/2013 |
| WO | WO-2013128194 A1 | 9/2013 |
| WO | WO-2014/022540 A1 | 2/2014 |
| WO | WO-2014/028560 A2 | 2/2014 |
| WO | WO-2014/047231 A1 | 3/2014 |
| WO | WO-2014/028560 A3 | 5/2014 |
| WO | WO-2014/083178 A1 | 6/2014 |
| WO | WO-2014108483 A1 | 7/2014 |
| WO | WO-2014/122251 A2 | 8/2014 |
| WO | WO-2014/141152 A2 | 9/2014 |
| WO | WO-2014/144722 A2 | 9/2014 |
| WO | WO-2014/153002 A1 | 9/2014 |
| WO | WO-2014/122251 A3 | 10/2014 |
| WO | WO-2014170063 A1 | 10/2014 |
| WO | WO-2014/141152 A3 | 12/2014 |
| WO | WO-2014/191113 A1 | 12/2014 |
| WO | WO-2014/191113 A8 | 12/2014 |
| WO | WO-2014/193973 A2 | 12/2014 |
| WO | WO-2015/006749 A2 | 1/2015 |
| WO | WO-2015/013671 A1 | 1/2015 |
| WO | WO-2015/095392 A1 | 6/2015 |
| WO | WO-2015143079 A1 | 9/2015 |
| WO | WO-2015184203 A1 | 12/2015 |
| WO | WO-2015184207 A1 | 12/2015 |
| WO | WO-2016014942 A1 | 1/2016 |
| WO | WO-2016/019969 A1 | 2/2016 |
| WO | WO-2016/020065 A1 | 2/2016 |
| WO | WO-2016/036678 A1 | 3/2016 |
| WO | WO-2016/179003 A1 | 11/2016 |
| WO | WO-2016/191750 A1 | 12/2016 |
| WO | WO-2016/201300 A1 | 12/2016 |
| WO | WO-2016/204966 A1 | 12/2016 |
| WO | WO-2016/205520 A1 | 12/2016 |
| WO | WO-2016/205531 A2 | 12/2016 |

(56) References Cited

FOREIGN PATENT DOCUMENTS

| WO | WO-2017/132279 A1 | 8/2017 |
|----|-------------------|--------|
| WO | WO-2018/093821 A1 | 5/2018 |

OTHER PUBLICATIONS

Atwell et al., "Stable heterodimers from remodeling the domain interface of a homodimer using a phage display library," J Mol Biol. 270(1):26-35 (1997).
Baeuerle et al., "Bispecific T-cell engaging antibodies for cancer therapy," Cancer Res. 69(12):4941-4 (2009).
Bortoletto et al., "Optimizing anti-CD3 affinity for effective T cell targeting against tumor cells," Eur J Immunol. 32(11):3102-7 (2002).
Brüggemann et al., "Comparison of the effector functions of human immunoglobulins using a matched set of chimeric antibodies," J Exp Med. 166(5):1351-61 (1987).
Carter, "Bispecific human IgG by design," J Immunol Methods. 248(1-2):7-15 (2001).
Clynes et al., "Fc receptors are required in passive and active immunity to melanoma," Proc Natl Acad Sci U S A. 95(2):652-6 (1998).
Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
Donaldson et al., "Design and development of masked therapeutic antibodies to limit off-target effects: application to anti-EGFR antibodies," Cancer Biol Ther. 8(22); 2145-50 (2009) (7 pages).
Duncan et al., "The binding site for C1q on IgG," Nature. 332(6166):738-40 (1988).
Edelman et al., "The covalent structure of an entire gammaG immunoglobulin molecule," Proc Natl Acad Sci U S A. 63(1):78-85 (1969).
Gazzano-Santoro et al., "A non-radioactive complement-dependent cytotoxicity assay for anti-CD20 monoclonal antibody," J Immunol Methods. 202(2):163-71 (1997).
Guyer et al., "Immunoglobulin binding by mouse intestinal epithelial cell receptors," J Immunol. 117(2):587-93 (1976).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-502 (1985).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Systems pharmacology modeling of anti-CD20/CD3 T-cell dependent bispecific antibody and its application to clinical trial design," American Conference on Pharmacometrics 7; Oct. 25; Bellevue, WA. (2016) (1 page).
Hudson et al., "Engineered antibodies," Nat Med. 9(1):129-34 (2003).
Idusogie et al., "Mapping of the C1q binding site on rituxan, a chimeric antibody with a human IgG1 Fc," J Immunol. 164(8):4178-84 (2000).
Jager et al., "The trifunctional antibody ertumaxomab destroys tumor cells that express low levels of human epidermal growth factor receptor 2," Cancer Res. 69(10):4270-6 (2009).
Junttila et al., "Antitumor efficacy of a bispecific antibody that targets HER2 and activates T cells," Cancer Res. 74(19):5561-71 (2014).

Kanda et al., "Comparison of cell lines for stable production of fucose-negative antibodies with enhanced ADCC," Biotechnol Bioeng. 94(4):680-8 (2006).
Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005).
Kiewe et al., "Phase I trial of the trifunctional anti-HER2 x anti-CD3 antibody ertumaxomab in metastatic breast cancer," Clin Cancer Res. 12(10):3085-91 (2006).
Kim et al., "Localization of the site of the murine IgG1 molecule that is involved in binding to the murine intestinal Fc receptor," Eur J Immunol. 24(10):2429-34 (1994).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Law et al., "Expression and characterization of recombinant soluble human CD3 molecules: presentation of antigenic epitopes defined on the native TCR-CD3 complex," Int Immunol. 14(4): 389-400 (2002).
Leabman et al., "Effects of altered FcgammaR binding on antibody pharmacokinetics in cynomolgus monkeys," MAbs. 5(6):896-903 (2013).
Li, "Successful QSP modeling in drug development starts with the right questions," American Conference on Pharmacometrics 8, Oct. 16, Fort Lauderdale, FL. (2017) (20 pages).
Lippow et al., "Computational design of antibody affinity improvement beyond in vivo maturation," available in PMC Jan. 7, 2010, published in final edited form as: Nat Biotechnol. 25(10):1171-6 (2007) (14 pages).
Lum et al., "Targeting T cells with bispecific antibodies for cancer therapy," available in PMC Oct. 8, 2013, published in final edited form as: BioDrugs. 25(6):365-79 (2011) (24 pages).
Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sel. 25(10):571-80 (2012).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Okazaki et al., "Fucose depletion from human IgG1 oligosaccharide enhances binding enthalpy and association rate between IgG1 and FcgammaIIIa," J Mol Biol. 336(5):1239-49 (2004).
Pessano et al., "The T3/T cell receptor complex: antigenic distinction between the two 20-kd T3 (T3-delta and T3-epsilon) subunits," EMBO J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Ravetch et al., "Fc receptors," Annu Rev Immunol. 9:457-92 (1991).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Seimetz et al., "Development and approval of the trifunctional antibody catumaxomab (anti-EpCAM x anti-CD3) as a targeted cancer immunotherapy," Cancer Treat Rev. 36(6):458-67 (2010).

(56) References Cited

OTHER PUBLICATIONS

Shalaby et al., "Bispecific HER2 x CD3 antibodies enhance T-cell cytotoxicity in vitro and localize to HER2-overexpressing xenografts in nude mice," Clin Immunol Immunopathol. 74(2):185-92 (1995).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).
Sondermann et al., "The 3.2-A crystal structure of the human IgG1 Fc fragment-Fc gammaRIII complex," Nature. 406(6793):267-73 (2000).
Spiess et al., "Bispecific antibodies with natural architecture produced by co-culture of bacteria expressing two distinct half-antibodies," Nat Biotechnol. 31(8):753-8 (2013) (7 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).
Wright et al., "Effect of glycosylation on antibody function: implications for genetic engineering," Trends Biotechnol. 15(1):26-32 (1997).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).
Zhu et al. "Identification of heavy chain residues in a humanized anti-CD3 antibody important for efficient antigen binding and T cell activation," J Immunol. 155(4):1903-10 (1995).
Communication pursuant to Article 94(3) dated Apr. 10, 2017, for Chen et al., "Anti-CD3 Antibodies and Methods of Use," European Patent Application No. 14828608.1, filed Dec. 17, 2014 (7 pages).
Communication pursuant to Article 94(3) dated Aug. 2, 2018, for Chen et al., "Anti-CD3 Antibodies and Methods of Use," European Patent Application No. 14828608.1, filed Dec. 17, 2014 (10 pages).
Communication pursuant to Article 94(3) dated Nov. 5, 2018, for Dennis, "Masked Anti-CD3 Antibodies and Methods of Use," European Patent Application No. 16724772.5, filed Apr. 29, 2016 (10 pages).
Communication pursuant to Article 94(3) dated Nov. 8, 2017, for Chen et al., "Anti-CD3 Antibodies and Methods of Use," European Patent Application No. 14828608.1, filed Dec. 17, 2014 (11 pages).
Examination Report dated Aug. 24, 2018, for Chen et al., "Anti-CD3 Antibodies and Methods of Use," Singaporean Patent Application No. 10201800250X, filed Dec. 17, 2014 (4 pages).
Examination Report dated Nov. 12, 2018, for Chen et al., "Anti-CD3 Antibodies and Methods of Use," New Zealand Patent Application No. 721309, filed Dec. 17, 2014 (5 pages).
Extended European Search Report dated May 29, 2017, for Chen et al., "Anti-CD3 Antibodies and Methods of Use," European Patent Application No. 17156352.1, filed Dec. 17, 2014 (10 pages).
International Preliminary Report on Patentability dated Dec. 19, 2017, for Hotzel et al., "Humanized and Affinity Matured Antibodies to FCRH5 and Methods of Use," International Patent Application No. PCT/US2016/037879, filed Jun. 16, 2016 (12 pages).
International Preliminary Report on Patentability dated Jun. 21, 2016, for Chen et al., "Anti-CD3 Antibodies and Methods of Use," International Patent Application No. PCT/US2014/070951, filed Dec. 17, 2014 (19 pages).
International Preliminary Report on Patentability dated Nov. 7, 2017, for Dennis, "Masked Anti-CD3 Antibodies and Methods of Use," International Patent Application No. PCT/US2016/030127, filed Apr. 29, 2016 (9 pages).
International Search Report and Written Opinion dated Aug. 3, 2016 for Dennis, "Masked Anti-CD3 Antibodies and Methods of Use," International Patent Application No. PCT/US2016/030127, filed Apr. 29, 2016 (15 pages).
International Search Report and Written Opinion dated May 28, 2015, for Chen et al., "Anti-CD3 Antibodies and Methods of Use," International Patent Application No. PCT/US2014/070951, filed Dec. 17, 2014 (33 pages).
International Search Report and Written Opinion dated Nov. 4, 2016, for Hotzel et al., "Humanized and Affinity Matured Antibodies to FCRH5 and Methods of Use," International Patent Application No. PCT/US2016/037879, filed Jun. 16, 2016 (20 pages).
Invitation to Pay Additional Fees dated Apr. 9, 2015, for Chen et al., "Anti-CD3 Antibodies and Methods of Use," International Patent Application No. PCT/US2014/070951, filed Dec. 17, 2014 (12 pages).
Invitation to Pay Additional Fees dated Sep. 12, 2016, for Hotzel et al., "Humanized and Affinity Matured Antibodies to FCRH5 and Methods of Use," International Patent Application No. PCT/US2016/037879, filed Jun. 16, 2016 (8 pages).
Notice of Reasons for Rejection dated Dec. 19, 2017, for Chen et al., "Anti-CD3 Antibodies and Methods of Use," Japanese Patent Application No. 2016-539276, filed Dec. 17, 2014 (6 pages).
Notice of Reasons for Rejection dated Jul. 31, 2018, for Chen et al., "Anti-CD3 Antibodies and Methods of Use," Japanese Patent Application No. 2016-539276, filed Dec. 17, 2014 (6 pages).
Search Report dated Aug. 8, 2017, for Chen et al., "Anti-CD3 Antibodies and Methods of Use," Singaporean Patent Application No. 11201604990P, filed Dec. 17, 2014 (6 pages).
Search Report dated Aug. 24, 2018, for Chen et al., "Anti-CD3 Antibodies and Methods of Use," Singaporean Patent Application No. 10201800250X, filed Dec. 17, 2014 (3 pages).
Search Report dated Aug. 25, 2018, for Chen et al., "Anti-CD3 Antibodies and Methods of Use," Taiwanese Patent Application No. 103144203, filed Dec. 17, 2014 (2 pages).
Written Opinion dated Aug. 8, 2017, for Chen et al., "Anti-CD3 Antibodies and Methods of Use," Singaporean Patent Application No. 11201604990P, filed Dec. 17, 2014 (7 pages).
Brown et al., "Tolerance to single, but not multiple, amino acid replacements in antibody VH CDR2: a means of minimizing B cell wastage from somatic hypermutation?" J Immunol. 156(9):3285-91 (1996).
Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).
Kegg Drug Database, "Drug: Trastuzumab," <https://www.genome.jp/dbget-bin/www_bget?dr:D03257>, retrieved on Jan. 8, 2019 (2 pages).
Liu et al., "Improvement in soluble expression levels of a diabody by exchanging expression vectors," Protein Expr Purif. 62(1):15-20 (2008) (6 pages).
Shen et al., "Preparation and characterization for bispecific antibodies of anti-CD3 x anti-idiotype to B cell lymphocytic leukemia," J Tongji Med Univ. 19(3):166-9 (1999) (4 pages).
Notice of Reasons for Rejection of Japanese Patent Application No. 2017-221759, dated Dec. 11, 2018 (6 pages).
Office Action for Chinese Patent Application No. 201480075726.X, dated Dec. 29, 2018 (11 pages).
Office Action for Eurasian Patent Application No. 201691266, dated Dec. 5, 2018 (5 pages).
Brekke et al., "Human IgG isotype-specific amino acid residues affecting complement-mediated cell lysis and phagocytosis," Eur J Immunol. 24(10):2542-7 (1994).
Clark et al., "Affinity enhancement of an in vivo matured therapeutic antibody using structure-based computational design," Protein Sci. 15(5):949-60 (2006).
Stanglmaier et al., "Bi20 (FBTA05), a novel trifunctional bispecific antibody (anti-CD20 x anti-CD3), mediates efficient killing of

(56) References Cited

OTHER PUBLICATIONS

B-cell lymphoma cells even with very low CD20 expression levels," Int J Cancer. 123(5):1181-9 (2008).
Examination Report for Australian Patent Application No. 2014364805, dated Feb. 11, 2019 (3 pages).
Notification of Defects in Israeli Patent Application No. 245945, dated Mar. 14, 2019 (6 pages).
Brack et al., "A Bispecific HER2—Targeting FynomAb with Superior Antitumor Activity and Novel Mode of Action," Mol Cancer Ther. 13(8): 2030-39 (2014) (11 pages).
Brinkmann et al., "The making of bispecific anitbodies," MABS. 9(2): 182-212 (2017).
Choi et al., "Bispecific antibodies engage T cells for antitumor immunotherapy," Expert Opin. Biol. Ther. 11(7): 843-53 (2011).
Desnoyers et al., "Tumor-Specific Activation of an EGFR—Targeting Probody Enhances Therapeutic Index," Sci. Transl. Med. 5(207):207ra144 (2013) (10 pages).
Drent et al., "A Rational Strategy for Reducing On-Target Off-Tumor Effects of CD38-Chimeric Antigen Receptors by Affinity Optimization," Molecular Therapy. 25(8): 1946-58 (2017).
Huang et al., "In Vivo Deamidation Characterization of Monoclonal Antibody by LC/MS/MS," Anal. Chem. 77(5): 1432-9 (2005).
Kelley et al., " Thermodynamic Analysis of an Antibody Functional Epitope," Biochemistry. 32(27): 6828-35 (1993).
Kortt et al., "Dimeric and trimeric antibodies: high avidity scFvs for cancer targeting," Biomolecular Engineering. 18:95-108 (2001) (15 pages).
Liu et al., "Affinity-Tuned ErbB2 or EGFR Chimeric Antigen Receptor T Cells Exhibit an Increased Therapeutic Index against Tumors in Mice," Cancer Res. 75(17): 3596-607 (2015) (13 pages).
Liu et al., "Heteroantibody duplexes target cells for lysis by cytotoxic T lymphocytes," Proc Natl Acad Sci U S A. 82(24):8648-52 (1985).
Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).
Saphire et al., "Crystal structure of a neutralizing human IgG against HIV-1: a template for vaccine design," Science. 293(5532):1155-9 (2001).
Spiess et al., "Alternative molecular formats and therapeutic applications for bispecific antibodies," Molecular Immunology. 67:95-106 (2015).
Weidle et al., "The Intriguing Options of Multispecific Antibody Formats for Treatment of Cancer," Cancer Genomics & Proteomics. 10:1-18 (2013) (18 pages).
Wuellner et al., "Bispecific CD3/HER2 Targeting FynomAb Induces Redirected T Cell-Mediated Cytolysis with High Potency and Enhanced Tumor Selectivity," Antibodies. 4(4): 426-440 (2015) (15 pages).
Yan et al., "Succinimide Formation at Asn 55 in the Complementarity Determining Region of a Recombinant Monoclonal Antibody IgG1 Heavy Chain," Biotechnology. 98(10): 3509-21 (2009).
Communication pursuant to Article 94(3) EPC for European Patent Application No. 14828608.1, dated Jul. 31, 2019 (4 pages).
Communication pursuant to Article 94(3) EPC for European Patent Application No. 17156352.1, dated Jul. 31, 2019 (4 pages).
Decision Concerning a Rejection of an Invention for Moroccan Patent Application No. 39078, dated Feb. 21, 2019 (9 pages).
Decision to Grant Patent for Japanese Patent Application No. 2017-221759, dated Apr. 9, 2019 (6 pages).
Examination Report for Gulf Cooperation Council Patent Application No. 2014-34716, dated Mar. 19, 2019 (5 pages).
Examination Report for Malaysian Patent Application No. PI 2016001124, dated Sep. 20, 2019 (2 pages).
Notice of Reasons for Rejection for Japanese Patent Application No. 2019-044073, dated Jan. 21, 2020 (4 pages).
Office Action for Colombian Patent Application No. NC2019/0009685, dated Sep. 13, 2019 (15 pages).
Office Action for Eurasian Patent Application No. 201691266, dated Oct. 31, 2019 (5 pages).
Office Action for U.S. Appl. No. 15/473,242, dated Jul. 25, 2019 (9 pages).
Search Report and Office Action for Taiwanese Patent Application No. 107134362, dated Oct. 17, 2019 (7 pages).
Second Office Action for Chinese Patent Application No. 201480075726.X, dated Oct. 21, 2019 (9 pages).
Buhmann et al. "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).
Chu et al. "Immunotherapy with long-lived anti-CD20 x anti-CD3 bispecific antibodies stimulates potent t cell-mediated killing of human b cell lines and of circuating and lymphoid b cells in monkeys: a potential therapy for b cell lymphomas and lukemias," Blood. 124(21):311(2014) (1 page).
Diefenbach et al. "An individualized risk mitigation approach for safety: experience from the mosunetuzumab (CD20/CD3 bispecific antibody) development program in relation to neurotoxicity risk," 61st Ash Annual Meeting & Exposition 10 (2019).
Lee et al. "Current concepts in the diagnosis and management of cytokine release syndrome," retrieved from <www.ncbi.nlm.nih.gov/pmc/articles/PMC4093680/?report-printable> on Feb. 19, 2020, Blood 124(2):188-95 (2014) (18 pages).
Li et al. "Exposure-response analyses indicate a promising benefit/risk profile of mosunetuzumab in relapsed and refractory non-Hodgkin lymphoma," 61st Ash Annual Meeting & Exposition (2019).
Nishimoto et al. "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Reusch et al. "Anti-CD3 x anti-epidermal growth facto receptor (EGFR) bispecific antibody redirects T-cell cytolytic activity to EGFR-positive cancers in vitro and in an animal model," Clin Cancer Res. 12(1):183-90 (2006) (9 pages).
Communication Pursuant to Article 94(3) EPC for European Patent Application No. 17808689.8, dated Apr. 30, 2020 (8 pages).
Decision to Grant Patent for Japanese Patent Application No. 2019-044073, dated Aug. 18, 2020 (8 pages).
Notice of Reasons for Rejection for Japanese Patent Application No. 2017-557140, dated Jun. 23, 2020 (10 pages).
Office Action for Costa Rican Patent Application No. 2016-0314, dated Jul. 30, 2020 (10 pages).
Office Action for U.S. Appl. No. 15/813,657, dated Feb. 18, 2020 (18 pages).
Technical Report Notification for Costa Rican Patent Application No. 2016-0000314, dated Feb. 12, 2020 (10 pages).

Figure 1

QDGNEEMGGITQTPYKVSISGTTVILTCPQYPGSEILWQHNDKNIGGDEDDKNIGSDEDHLSLKEFSELEQSGYYVCYPRG
SKPEDANFYLYLRARVDDGSADDAKKDDAKKDDAAKKDDAKKDGSQSIKGNHLVKVYDYQEDGSVLLTCDAEAKNITWFKD
GKMIGFLTEDKKKWNLGSNAKDPRGMYCKGSQNKSKPLQVYYRM (SEQ ID NO: 282)

Figure 2A

| Clone | ELISA Hu-CD3ε/γ muFc | ELISA Cyno-CD3ε/γ muFc | FACS Jurkat | FACS Human-PBMCs | FACS Cyno-PBMCs | T cell activation | Isotype |
|---|---|---|---|---|---|---|---|
| 13A3 | + | + | + | + | + | weak | IgG2b/k |
| 19B1 | + | + | + | + | + | weak | IgG2b/k |
| 72H6 | + | + | + | + | + | weak | IgG2a/k |
| 30A1 | + | + | + | + | + | weak | IgG1/k |
| 41D9 | + | + | + | + | + | weak | IgG1/λ |
| 71H7 | + | + | + | + | + | weak | IgG1/λ |

| | Commercial hCD3eg KD |
|---|---|
| mu IgG | |
| 30A1 | 0.4 nM |
| 41D9 | 1.4 nM |
| 13A3 | 0.6 nM |
| 19B1 | 0.7 nM |
| 72H6 | 2.5 nM |

| Clone | ELISA | | FACS | | | T cell activation | Isotype |
|---|---|---|---|---|---|---|---|
| | Hu-CD3e 1-27 peptide | Cyno CD3e 1-27 peptide | Jurkat | Human PBMCs | Cyno PBMCs | T cell activation | |
| 39B7 | + | + | + | + | + | + | IgG2b/k |
| 27H5 | + | + | + | + | + | + | IgG2b/k |
| 38E4 | + | + | + | + | + | + | IgG3/k |
| 127B3 | + | + | + | + | + | + | IgG3/k |
| 79B7 | + | + | + | + | + | + | IgG3/k |
| 95A2 | + | + | + | + | + | + | IgG3/k |
| 40D2 | + | + | + | + | + | + | IgG2b/k |
| 118G9 | + | + | + | + | + | + | IgG3/k |
| 18F2 | + | + | + | + | + | + | IgG2a/k |
| 43H8 | + | + | + | + | + | + | IgG3/k |
| 32B8 | + | + | + | + | + | + | IgG3/k |
| 40G5 | + | + | + | + | + | + | IgG2a/k |
| 21B2 | + | + | + | + | + | weak | IgG3/k |
| 24H11 | + | + | + | + | + | + | IgG2b/k |
| 125A1 | + | + | + | + | + | weak | IgG3/k |
| 21A9 | + | + | + | + | + | + | |
| Rab17 | + | + | + | + | + | + | Rabbit IgG1 |

Figure 3B

| IgG | ka (1/Ms) | kd (1/s) | KD (M) |
|---|---|---|---|
| 127B3 | 1.30E+05 | 9.67E-05 | 7.44E-10 |
| 14C7 | 1.66E+05 | 3.79E-05 | 2.28E-10 |
| 40D2 | 1.97E+05 | 1.11E-04 | 5.63E-10 |
| 79B7 | 1.52E+05 | 3.41E-05 | 2.24E-10 |
| 40G5 | 1.56E+05 | 2.48E-05 | 1.59E-10 |
| 18F12 | 1.34E+05 | 1.59E-05 | 1.19E-10 |
| 38E4 | 4.41E+05 | 3.45E-05 | 7.83E-11 |
| 95A2 | 2.90E+05 | 1.87E-05 | 6.44E-11 |
| 43H8 | 2.66E+05 | 1.23E-04 | 4.61E-10 |
| 118G9 | 1.79E+05 | 3.74E-05 | 2.09E-10 |
| 27H5-1 | 2.34E+05 | 1.15E-04 | 4.92E-10 |
| 39B7 | 2.20E+05 | 7.31E-05 | 3.31E-10 |
| muSP34 | 1.61E+05 | 4.00E-05 | 2.49E-10 |

Figure 3C

| IgG | ka (1/Ms) | kd (1/s) | KD (nM) |
|---|---|---|---|
| mu38E4 | 5.60E+04 | 5.32E-05 | 0.95 |
| mu40G5 | 3.11E+04 | 2.69E-05 | 0.86 |
| Rab17 | 2.86E+04 | 2.42E-04 | 8.46 |

Figure 4A
Light chain, Kappa: Mouse antibody aligned to 72H6 (xCD3)

Heavy chain: Mouse antibody aligned to 72H6 (xCD3)

Figure 4B

13A3
DIVLTQSPSSLAVSAGEKVTMSCKSSSQSLLNSRTRKNYLAWYQQKPGQSPKLLIYWAS
TRESGVPDRFTGSGSGTDFTLTISSVQAEDLAVYYCKQSYILRTFGGGTKLEIK
(SEQ ID NO: 227)

19B1
GIVMTQSPSSLAVSAGEKVTMSCKSSSQSLLNSRTRKNYLAWYQQKPGQSPKLLIYWA
STRESGVPDRFTGSGSGTDFTLTISSVQAEDLAVYYCKQSYILRTFGGGTKLEIK
(SEQ ID NO: 243)

72H6
EIVLSQSPSSLAVSAGEKVTMSCKSSSQSLLNSRTRKNYLAWYQQKPGQSPKLLIYWAS
TRESGVPDRFTGSGSGTDFTLTISSVQAEDLAVYYCKQSYTLRTFGGGTKLEIK
(SEQ ID NO: 241)

30A1
NIVMTQSPSSLAVSAGEKVTMSCKSSSQSLLSGRTRKNYLAWYQQKPGQSPKLLIYWA
STRESGVPDRFTGSGSGTDFTLTISSVQAEDLAVYYCKQSYYLLITFGAGTKLELK
(SEQ ID NO: 231)

41D9a
QAVVTQESALTTSPGGTVILTCRSSTGAVTTSNYANWVQEKPDHLFTGLIGGTSNRAPG
VPVRFSGSLIGDKAALTITGAQTEDDAMYFCALWYSTHFVFGGGTKVTV
(SEQ ID NO: 221)

71H7
QAVVTQESALTTSPGGTVILTCRSSTGAVTTSNYANWVQEKPDHLFTGLIGGTSNRAPG
VPVRFSGSLIGDKAALTITGAQTEDDAMYFCALWYSTHFVFGGGTKVTV
(SEQ ID NO: 245)

Figure 4C

13A3
EVQLQQSGPELVKPGASVRISCKASGYTFTSYYIHWMKQRPGQGLEWIGWIYPGNVNT
KYNEKFKGKATLTADNSSSTANMQLSSLTSEDSAVYFCARNHDYYFDYWGQGTTLTVSS
(SEQ ID NO: 226)

19B1
EVQLQQSGPELVKPGASVRISCKASGYTFTSYYIHWMKQRPGQGLEWIGWIYPGNVNT
KYNEKFKGKATLTADNSSSTANMQLSSLTSEDSAVYFCARNHDYYFDYWGQGTTLTVSS
(SEQ ID NO: 242)

72H6
EVQLQQSGPELVKPGASVKISCKASGYSFTSYYIHWVKQRPGQGLEWIGWIFPGSDNT
KYNEKFKGKATLTADTSSSTAYMQLSSLTSEDSAVYFCARNGNYAMDYWGQGTSVTVS
S    (SEQ ID NO: 240)

30A1
QVQLKESGPGLVAPSQSLSITCTVSGFSLTNYAIHWVRQPPGKGLDWLGVIWAGGNTK
YNSALMSRLSFSKDNSKSQVFLEINSLQTDDTAMYYCAREDSSGYVALDYWGQGTSVT
VSS    (SEQ ID NO: 230)

41D9a
QIQLVQSGPELKKPGETVKISCKASGYTFTNYGMNWVKQAPGKGLKWMGWINTNTGK
PTYAEEFKGRFVFSLETSASTTYLQINNLKNEDTATYFCARRGDYRYAWFLYWGQGTLVT
VSA (SEQ ID NO: 220)

71H7
QIQLVQSGPELKKPGETVKISCKASGYTFTNYGMNWVKQAPGKGLKWMGWINTNTGK
PTYAEDFKGRFAFSLETSASTAYLQINNLKNEDTATYFCARRGDYRYAWFTYWGQGTLVT
VSA (SEQ ID NO: 244)

Figure 5A

14C7
DVVMTQTPSSLAVSTGEKVTMTCKSSQSLLNIRTRKNCLAWYQQKPGQSPKLLIFWASTRYSGVPDRFTGSGSGTDFTLTIRSVQPEDLAV
YYCTQSYTLRTFGGGTKLEIK (SEQ ID NO: 247)

127B3
DIVMTQSPSSLAVSAGEKVTMSCKSSQSLLNSRTRKNYLAWYQQKPGQSPKLLIYWASTRESGVPDRFTGSGSGTDFTLTISSVQTEDLAV
YYCCQSFILRTFGGGTKLEIK (SEQ ID NO: 249)

18F12
DIVMTQSPSSLAVSAGEKVTMTCKSSQSLLNSRTRKNYLAWYQQKPGQSPKLLIYWASTRESGVPDRFTGSGSGTDFTLTISSVQAEDLAV
YYCKQSFILRTFGGGTKLELK (SEQ ID NO: 251)

27H5-1
DIVMTQSPSSLAVSVGEKVTMSCKSSQSLLNSRTRKNYLAWYQQKPGQSPKLLIYWASTRESGVPVRFTGSGSGTDFTLTISSVQAEDLAV
YYCTQSFILRTFGGGTKLEIK (SEQ ID NO: 253)

38E4
DIVMTQSPSFLAVSAGEKVTMSCKSSQSLLNSRTRKNYLAWYQQKPGQRPGQSPKLLIYWASTRESGVPDRFTGSGSGTDFTLTISSVQAEDLAI
YYCKQSFILRTFGGGTKLEIK (SEQ ID NO: 286)

39B7
DIVMTQSPSSLAVSAGEKVTMTCKSSQSLLNSRTRKNYLAWYQQKPGQSPKLLIYWTSTRKSGVPDRFTGSGSGTDFTLTISSVQAEDLAV
YYCKQSFILRTFGGGTKLEIK (SEQ ID NO: 255)

40D2
DIVMTQSPSSLAVSAGEKVTMSCKSSQSLLNSRTRKNYLTWYQQKPGQSPKLLIFWASTRESGVPDRFTGSGSGTDFTLTISSVQAEDLAV
YYCTQSFILRTFGGGTKLEIK (SEQ ID NO: 257)

40G5
DIVLTQSPSSLAVSAGEKVTMSCKSSQSLLNSRTRKNYLAWYQQKPGQSPKLLIYWASTRDSGVPDRFTGSGSGTDFTLTISSVQAEDLAV
YYCTQSYTLRTFGGGTKLEIK (SEQ ID NO: 259)

79B7
DIVMTQSPSSLAVSAGEKVTMSCKSSQSLLNSRTRKNYLAWYQQKPGQSPKLLIYWASTRESGVPDRFTGSGSGTDFTLTISSVQAEDLAV
YYCCQSFILRTFGGGTKLEIK (SEQ ID NO: 261)

95A2
DIVMTQSPSSLAVSAGEMVTLHCKSSQSLLNIRTRKNYLAWYLQKPGQSPRLLIYWASTRASGVPDRFTGSGSGTDFTLTISSVQPEDLAV
YYCTQSFILRTFGGGTKLELK (SEQ ID NO: 261)

118G9
DIVMTQSPSSLAVSAGEKVTMSCKSSQSLLNSRTRKNYLAWYQQKPGLSPKLLIYWASTRESGVPERFTGSGSGTDFTLTISSVQTEDLAV
YYCTQSFILRTFGGGTRLEIK (SEQ ID NO: 263)

Figure 5B

14C7
EVQLQQSGPELVKPGTSVKISCKASGFSFTNYYIHWMKQRPGQGLEWIGWIYPGSDNTKFNDKFKGKATLTADTSSTTAYMQLSSL
TSEDSAVYYCARDSITNYFDYWGQGTTLTVSS (SEQ ID NO: 246)

127B3
QVQLQQSGSELVRPGASLKLSCKASGYTFTSYWMHWVRQRPGQGLEWIGNFYPGDLTVNYDEKFKNKVTLAVDTSSTAFLQLSSL
TSEDSAVYYCTRDAYSRYFFDYWGQGTTLTVSS (SEQ ID NO: 248)

18F12
QVQLQQSGPELVKPGASVKISCKASGYSFTNYYMHWVKQRPGQGLEWIGWISPGSGSIKYNEKFKGKATLTADTSSSTAYMQLSSL
TSEDSAVYYCARDGYSLYFFDFWGQGTTLTVSS (SEQ ID NO: 250)

27H5-1
QVQLQQSGPELVKPGTSVKISCKTSGYSFINYYTHWVKQRPGQGLEWIGWIYPGNGNIKYNEKFMGKATLTADTSSTTAHMHLSSL
VSEDSAVYYCARDSYGSYYFDYWGQGTTLTVSS (SEQ ID NO: 252)

38E4
QVQLQQSGPELVKPGASVTISCTASGFTFTSYYIHWVRQRPGQGLEWIGWIYPENDNTKYNEKFKDKATLTADTSSTAYMQLSSL
TSEDSAVYYCARDGYSRYYFDYWGQGTTLTVSS (SEQ ID NO: 285)

39B7
QVQLQQSGPELVKPGTSVKISCKTSGYNFINYYTHWVKQRPGQGLEWIGWIYPGNGNIKYNEKFMGKATLTADTSSTTAHMHLSSL
VSEDSAVYYCARDSYGSYYFDYWGQGTTLTVSS (SEQ ID NO: 254)

40D2
QVQLQQSGPELVKPGASLKISCKASGYSFANYYTHWVRQRPGQGLEWIGWLYPGNGDTRYNEKFKDKATLTADTSSNTASMQLNSL
TSEDSAVYYCTRDSYGNYFFDYWGQGTTLIVSS (SEQ ID NO: 256)

40G5
QVQLQQSGPELVKPGTSVKISCKASGYTFTNYYIHWVRQRPGQGLEWIGWIYPGDVSTKYNEKFKGKTTLTADKSSSTAYMLLSGL
TSEDSAIYFCARDGYSFYYFDYWGQGTTLTVSS (SEQ ID NO: 291)

79B7
QVQLQQSGSELVRPGASLKLSCKASGYTFTSYWMHWVRQRPGQGLEWIGNSYPGDLNVNYDEKFKNKVTLAVDTSSTAFLQLSSL
TSEDSAVYYCTRDAYSRYFFDYWGQGTTLTVSS (SEQ ID NO: 258)

95A2
QVQLQQSGPEMVKPGASVYFCARDSSASYYFFDYWGQGTTLTVSS (SEQ ID NO: 260)
TSEDSAVYFCARDSSASYYFFDYWGQGTTLTVSS

118G9
QVQLQQPGSELVRPGASVTLSCTASGYSFTSYWMHWVKQRPGQGLEWVGNIYPGGEIINYAEKFKTKGTLTVDISSSTAYMHLSSL
TSDDSAVYYCTRDTTGNYFFDYWGQGTTLTVSS (SEQ ID NO: 262)

Figure 6A

21A9
DIQMTQSPSSLAVSLGERATINCKSSQSVLYSSNNKNYLVWYQQKLGQPPKLLIYRASTR
ESGVPDRFSGSGSGTDFTLTISSLQAEDVAVYYCQQYSVPWTFGQGTKVEIK
(SEQ ID NO: 235)

Rab17
DMTQTPSSKSVPVGDTVTINCQASETVYSNNYLAWFQQKPGQPPKRLIYGVSTLDSGVP
PRFSGSGSGTQFTLTISDVVCDDAATYYCAGYKTSSSYAIAFGGGTELEIL
(SEQ ID NO: 265)

Figure 6B

21A9
EVQLVESGGGVVQPGGSLKLSCAASGFTFSGSAMHWVRQASEKGLEWVGRIRSRANSYA
TAYAASVKDRFTISRDNSKNTAYLQMNSLKTEDTAVYYCIRDTMVRGIDYWGQGTLVTVSS
(SEQ ID NO: 234)

Rab 17
QSVKESEGGLFKPTDTLTLTCTVSGCSLSSCAISWVRQAPGKGLEWIGFMSVTGSAYYAN
WAKSRSTITRNTNENTVTLKMTRLTAADTAIYFCARVGIGSGLNIWGQGTLVTVSS
(SEQ ID NO: 264)

Light chain, Kappa: Mouse antibody aligned to K4H1

Heavy chain: Mouse antibody aligned to K4H1

Light chain, Lambda: Mouse antibody aligned to human germlines

Heavy chain: Mouse antibody aligned to human germlines

Light chain, Kappa: Humanized antibody aligned to K4H1

Heavy chain: Humanized antibody aligned to K4H1

Figure 8F

Light chain, Kappa: Mouse antibody aligned to K4H1

Figure 9A murine 13A3 = 0.7 nM

Humanized 13A3 variants:

| Heavy chain | K4 graft | K4 graft + S43A |
|---|---|---|
| VH1 graft | 1.5 nM | 1.8 nM |
| VH1 graft + R71A | 1.0 nM | 1.4 nM |
| VH1 graft + V37M + V67A + R71A + T73N | 0.8 nM | ND |
| VH1 graft + V37M + V67A + R71A + T73N + Y91F | 1.2 nM | 1.4 nM |

Figure 9B murine 30A1 = 0.4 nM

Humanized 30A1 variants:

| Heavy chain | K4 graft | K4 graft + S43A |
|---|---|---|
| VH3 graft | 2.9 nM | 1.4 nM |
| VH3 graft + A24V | 1.7 nM | 1.7 nM |
| VH3 graft + R71K + L78V | 1.8 nM | 2.2 nM |
| VH3 graft + A24V + R71K + L78V | 2.3 nM | 1.5 nM |
| VH3 graft + A24V + V48L + F67L + I69F + R71K + L78V | 2.4 nM | 1.4 nM |
| VH4 graft + V71K + F78V | 15.4 nM | 5.7 nM |
| VH4 graft + I37V + I48L + V67L + I69F + V71K + F78V | 2.4 nM | 1.7 nM |

Figure 9C murine 41D9 = 1.1 nM

Humanized 41D9 variants:

Heavy chain

VH7 graft + V2I + A78T + Y91F

λ7 graft + F36V + Q38E + A43L + P44F + T46G + Y49G + G69D + Y87F

ND

Figure 9D murine SP34 = 7 nM

Humanized SP34 variants:

| Light chain | VH3 graft +T93V | VH3 graft +G49A +T93V | VH3 graft +N73D +T93V | VH3 graft G49A + N73D + T93V |
|---|---|---|---|---|
| λ7 graft + Y49G | 15.9 nM | | weak binding | 14.5 nM |
| λ7 graft + T46G + Y49G | | | 3.5 nM | 8 nM |
| λ7 graft + F36V + Q38E + A43L + P44F + T46G + Y49G + T58V + Y87F | | 21 nM | 3.1 nM | |
| λ2 graft + Y49G | | no binding | | |
| λ2 graft + A43L + P44F + L46G + M47L + Y49G | | weak binding | 13 nM | 47 nM |

Figure 9E murine 38E4 = 0.75 nM

Humanized 38E4 variants:

Heavy chain

VH1 graft + R71A

K4 graft + P43S 0.5 nM

Figure 9F murine 40G5c CDRs were derived from consensus sequence

Humanized 40G5c variants:

| Heavy chain | K4 graft |
|---|---|
| VH1 graft + V67A + R71A | 37 nM |
| VH1 graft + I69L + R71A | 36 nM |
| VH1 graft + V67A + I69L + R71A | 24 nM |

Figure 10

| Variants | hCD3ε1-27-Fc (nM) | huCD3εγ (nM) | cyCD3εγ (nM) | Commercial hCD3εγ |
|---|---|---|---|---|
| hu13A3.v2 | | | | 1 |
| hu30A1.v2 | | | | 2 |
| hu41D9a | | | | ND |
| huSP34.v52 | 11 | 19 | 12 | 4 |
| hu38E4.v1 | 1.0 | 0.5 | 0.7 | |
| hu40G5c | 13 | 12 | 14 | |

Figure 11

| | Version | ka (1/Ms) | kd (1/s) | KD (nM) |
|---|---|---|---|---|
| 38E4 | v1 | 6.06E+06 | 0.0051 | 0.8 |
| 38E4 | v2 | 2.29E+06 | 0.0036 | 1.6 |
| 38E4 | v3 | 4.11E+06 | 0.0140 | 3.4 |
| 38E4 | v4 | 3.25E+05 | 0.0034 | 10 |
| 40G5 | c | 1.20E+06 | 0.01764 | 15 |
| 38E4 | v5 | 2.05E+06 | 0.0225 | 11 |
| 38E4 | v6 | 5.11E+04 | 0.0017 | 34 |
| 38E4 | v7 | 2.83E+05 | 0.0246 | 87 |
| 38E4 | v8 | 1.12E+06 | 0.2018 | 180 |
| 38E4 | v9 | 7.26E+04 | 0.0166 | 229 |

Figure 12A

| | Single Cycle Kinetics | | | | Full Cycle Kinetics | | | |
|---|---|---|---|---|---|---|---|---|
| L3 mutants | ka (1/Ms) | kd (1/s) | KD (nM) | ratio (fold) | ka (1/Ms) | kd (1/s) | KD (nM) | ratio (fold) |
| K89A | 4.28E+05 | 1.02E-03 | 2.4 | 0.7 | | | | |
| Q90A | | | | | 1.78E+05 | 4.22E-03 | 23.8 | 29.9 |
| S91A | 3.44E+05 | 1.35E-03 | 3.9 | 1.2 | | | | |
| F92A | | | | | 1.46E+06 | 2.32E-02 | 15.9 | 20.0 |
| I93A | | | | | 3.08E+06 | 1.24E-02 | 4.0 | 5.1 |
| L94A | 2.83E+05 | 2.95E-04 | 1.0 | 0.3 | | | | |
| R96A | | | NB | NB | | | | |
| T97A | 2.96E+05 | 8.60E-04 | 2.9 | 0.9 | | | | |
| H3 mutants | ka (1/Ms) | kd (1/s) | KD (nM) | ratio (fold) | ka (1/Ms) | kd (1/s) | KD (nM) | ratio (fold) |
| R94A | 5.55E+04 | 4.35E-03 | 78.4 | 23.3 | | | | |
| D95A | 1.27E+05 | 3.09E-03 | 24.3 | 7.2 | | | | |
| D95T | | | | | 51140 | 0.001749 | 34.2 | 43.0 |
| D95S | | | | | 1.12E+06 | 0.2018 | 179.5 | 225.8 |
| G96A | | | | | 1.86E+06 | 3.57E-03 | 1.9 | 2.4 |
| Y97A | | | NB | | | | | |
| S98A | 3.85E+05 | 1.47E-03 | 3.8 | 1.1 | | | | |
| R99A | | | NB | | | | | |
| Y100A | | | | | 4.60E+04 | 1.91E-02 | 414.5 | 521.4 |
| Y100aA | | | | | 2.83E+05 | 2.46E-02 | 87.0 | 109.5 |
| F100bA | | | NB | | | | | |
| D101A | 1.42E+05 | 3.42E-03 | 24.1 | 7.2 | | | | |
| Y102A | 3.22E+05 | 1.32E-03 | 4.1 | 1.2 | | | | |
| hu38E4.v1 | 3.20E+05 | 1.08E-03 | 3.4 | 1.0 | | | | |
| hu38E4.v1 | | | | | 5.44E+06 | 4.33E-03 | 0.8 | 1.0 |

Figure 13D

| SP34v52 Affinity KD (nM) | |
|---|---|
| WT | 12 |
| Q1A | NB |
| D2A | NB |
| G3A | 172 |
| N4A | 20 |
| E5A | 19000 |
| E6A | 17 |
| M7A | 17 |
| G8A | 27 |
| G9A | 25 |

| 38E4v1 Affinity KD (nM) | |
|---|---|
| WT | 3 |
| Q1A | 1000 |
| D2A | 1500 |
| G3A | 7 |
| N4A | 3 |
| E5A | 7 |
| E6A | 65 |
| M7A | 13 |
| G8A | 8 |
| G9A | 6 |

A 16mer peptide sequence: pyroGlu-D-G-N-E-E-M-G-G-I-T-Q-T-P-Y-K

Figure 17

Monovalent Binding Affinity

| Antibody | anti-CD20/2H7 | | | | anti-CD3/UCHT1 | | |
|---|---|---|---|---|---|---|---|
| clone | v16 | v114 | v511 | v9 | vM1 | v1 |
| Kd (nM)* | 54 | 44 | 53 | 4.2 | 318 | NA |

*monovalent binding Kd measured by scatchard

Bivalent Binding Affinity

| Antibody | anti-CD20/2H7 w/UCHT1v9 | | | anti-CD3/UCHT1 w/2H7v16 | | |
|---|---|---|---|---|---|---|
| clone | v16 | v114 | v511 | v1 | vM1 | v9 |
| Kd (nM)* | 46 | 4.5 | 2.3 | 300 | 40 | 3 |

*monovalent binding Kd measured by scatchard

| Sample name | TDBs ka (1/Ms) | kd (1/s) | KD (M) | KD (nM) | Fabs ka (1/Ms) | kd (1/s) | KD (nM) |
|---|---|---|---|---|---|---|---|
| 40G5c (E. coli) | 3.58E+05 | 0.0256 | 7.15E-08 | 71.5 | 4.01E+05 | 0.02533 | 63.2 |
| 40G5c (CHO) | 5.97E+05 | 0.03069 | 5.15E-08 | 51.5 | | | |
| sp34.v52 | 6.09E+05 | 0.00535 | 8.78E-09 | 8.8 | | | |
| 38E4v1 | 4.03E+06 | 0.00515 | 1.28E-09 | 1.3 | 6.06E+06 | 0.005074 | 0.8 |
| 38E4v2 | 2.11E+06 | 0.00513 | 2.43E-09 | 2.4 | 2.29E+06 | 0.003586 | 1.6 |
| 38E4v3 | 4.98E+06 | 0.01599 | 3.21E-09 | 3.2 | 4.11E+06 | 0.014 | 3.4 |
| 38E4v4 | 7.21E+05 | 0.0984 | 1.37E-07 | 136.5 | 3.25E+05 | 0.003361 | 10.3 |
| 38E4v5 | 3.22E+06 | 0.05154 | 1.60E-08 | 16.0 | 2.05E+06 | 0.02246 | 11.0 |
| 38E4v6 | 2.34E+04 | 0.8784 | 3.76E-05 | 37600.0 | 51140 | 0.001749 | 34.2 |
| 38E4v7 | 1.14E+06 | 0.2897 | 2.54E-07 | 254.2 | 2.83E+05 | 0.02464 | 87.0 |
| 38E4v8 | 1.13E+04 | 0.04426 | 3.93E-06 | 3933.0 | 1.12E+06 | 0.2018 | 179.5 |
| 38E4v9 | 1.59E+04 | 1.018 | 6.42E-05 | 64210.0 | 72610 | 0.0166 | 228.6 |

Figure 24

Donor#4

Figures 38A-38C
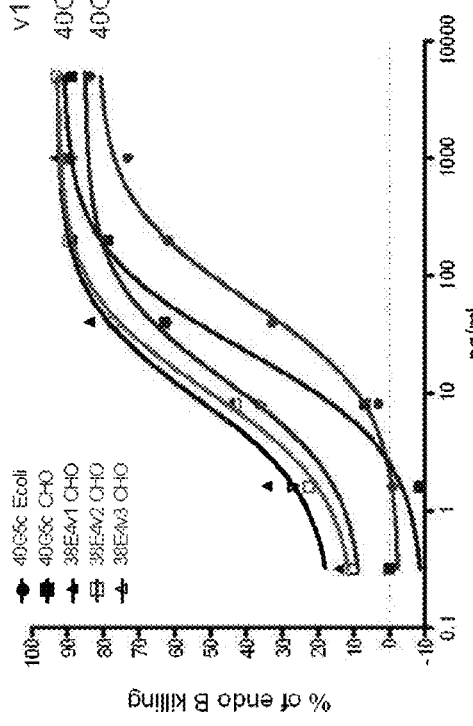
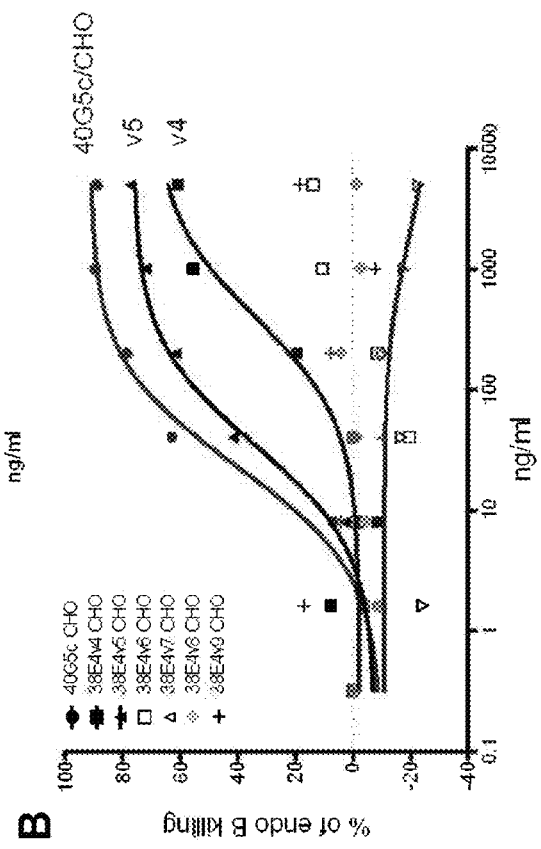

Donor#1

Donor#1

Donor#2

Donor#2

Figure 49

| CD20 arm | CD3 arm | Format | Potency in vitro |
|---|---|---|---|
| 2H7v16 | UCHT1v9 | K&H | high |
| 2H7v16 | 72H6 | K&H | no |
| 2H7v16 | 13A3 | K&H | low |
| 2H7v16 | 30A1 | K&H | low |
| 2H7v16 | 41D9a | K&H | low |
| 2H7v16 | SP34v52 | K&H | high |
| 2H7v16 | 40G5c | K&H | high |
| 2H7v16 | 38E4c, 38E4V1-V9 | K&H | high |
| 2H7v16 | 21B2 | K&H | very low |
| 2H7v16 | 125A1 | K&H | very low |
| 2H7v16 | 21A9 | K&H | high |

Figure 50

Light chain, Kappa: Humanized antibody aligned to K1H3

Heavy chain: Humanized antibody aligned to K1H3

Figure 51

Light chain, Kappa: Humanized antibody aligned to K4H1

| Kabat number | 1 2 3 4 5 6 7 8 9 10 11 12 13 14 15 16 17 18 19 20 21 22 23 24 25 26 27 a b c d e f 28 29 30 31 32 33 34 35 36 |
|---|---|
| K4H1 | D I V M T Q S P D S L A V S L G E R A T I N C K S S Q S V L Y S S N N K N Y L A W Y |
| hu40G5c | D I V M T Q S P D S L A V S L G E R A T I N C K S S Q S L N S . . . . R K N Y L A W Y |

| Kabat number | 37 38 39 40 41 42 43 44 45 46 47 48 49 50 51 52 53 54 55 56 57 58 59 60 61 62 63 64 65 66 67 68 69 70 71 72 |
|---|---|
| K4H1 | Q Q K P G Q P P K L L I Y W A S T R E S G V P D R F S G S G S G T D F |
| hu40G5c | Q Q K P G Q P P K L L I Y W A S T R E S G V P D R F S G S G S G T D F |

| Kabat number | 72 73 74 75 76 77 78 79 80 81 82 83 84 85 86 87 88 89 90 91 92 93 94 95 96 97 98 99 100 101 102 103 104 105 106 107 |
|---|---|
| K4H1 | T L T I S S L Q A E D V A V Y Y C Q Q Y Y S T P . . . F T F G Q G T K V E I K |
| hu40G5c | T L T I S S L Q A E D V A V Y Y C T Q S F I L . . . R T F G Q G T K V E I K SEQ ID NO: 185 |

Heavy chain: Humanized antibody aligned to K4H1

| Kabat number | 1 2 3 4 5 6 7 8 9 10 11 12 13 14 15 16 17 18 19 20 21 22 23 24 25 26 27 28 29 30 31 32 33 34 35 36 |
|---|---|
| K4H1 | E V Q L V Q S G A E V K K P G A S V K V S C K A S G Y T F T S Y Y I H W V R Q A P G Q G |
| hu40G5c | E V Q L V Q S G A E V K K P G A S V K V S C K A S G Y T F T N Y Y I H W V R Q A P G Q G |

| Kabat number | 45 46 47 48 49 50 51 52 53 54 55 56 57 58 59 60 61 62 63 64 65 66 67 68 69 70 71 72 73 74 75 76 77 78 79 80 81 82 a b c 83 84 |
|---|---|
| K4H1 | L E W I G W I N P . . G S G N T N Y A Q K F Q G R V T I T R D T S T S T A Y L E L S S L R S |
| hu40G5c | L E W I G W I Y P . . G D G N T K Y N E K F K G R A T . . . T A D T S T S T A Y L E L S S L R S |

| Kabat number | 85 86 87 88 89 90 91 92 93 94 95 96 97 98 99 100 a b 101 102 103 104 105 106 107 108 109 110 111 112 113 |
|---|---|
| K4H1 | E D T A V Y Y C A R . . . . D S Y S N Y . . F D Y W G Q G T L V T V S S |
| hu40G5c | E D T A V Y Y C A R . . . . D S Y S N Y . . F D Y W G Q G T L V T V S S SEQ ID NO: 184 |

Figures 60E-60F
E
43: 76% huCD20+B, 4.0% huCD8+T, and 7.5% huCD4+T of huCD45+ cells.
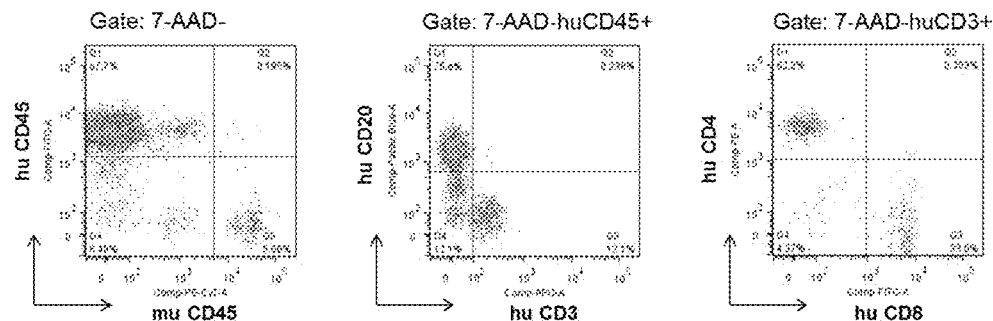
46: 75% huCD20+B, 3.7% huCD8+T, and 10% huCD4+T of huCD45+ cells.
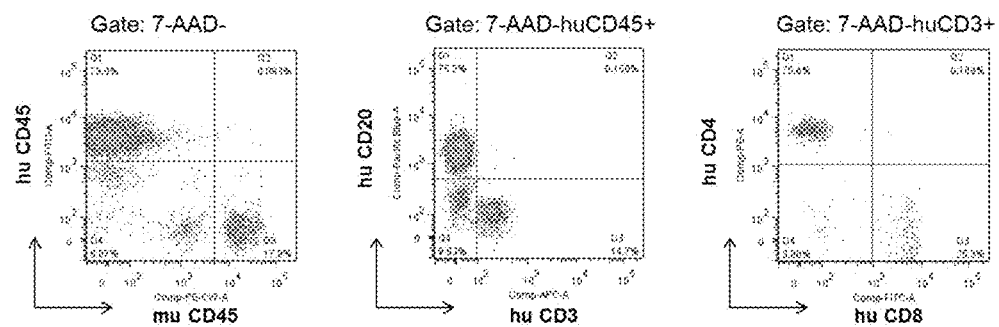
F
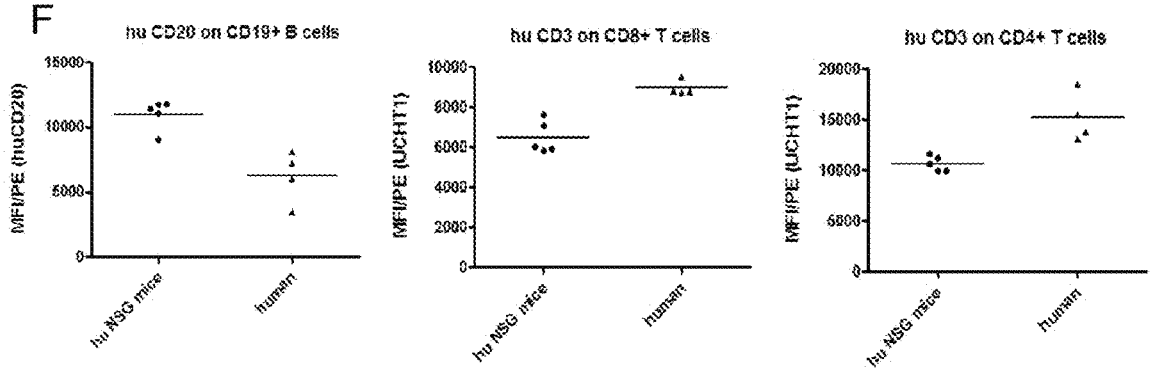

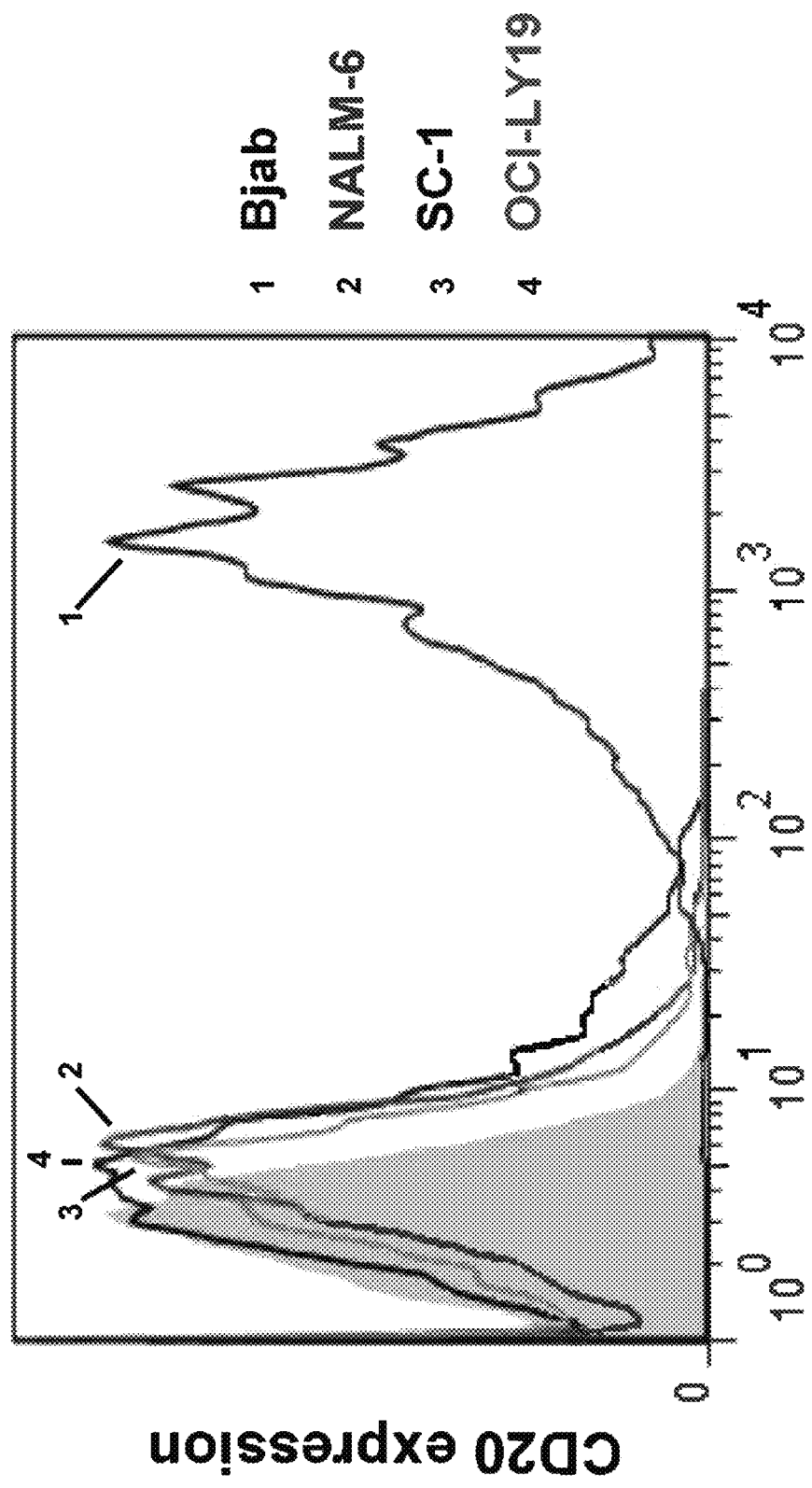

Figures 69A-69B
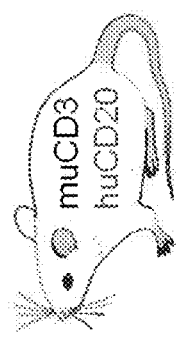
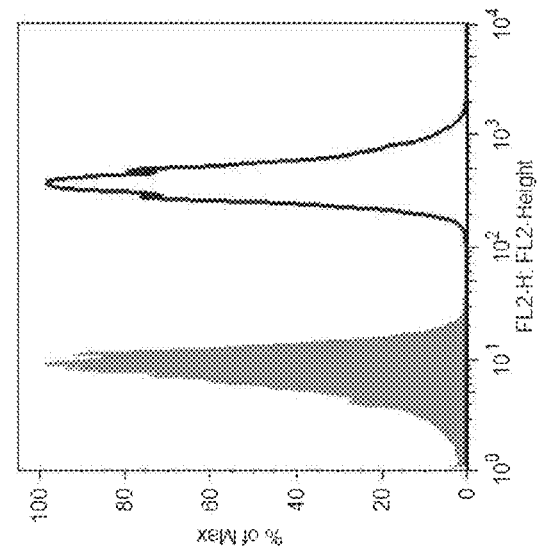
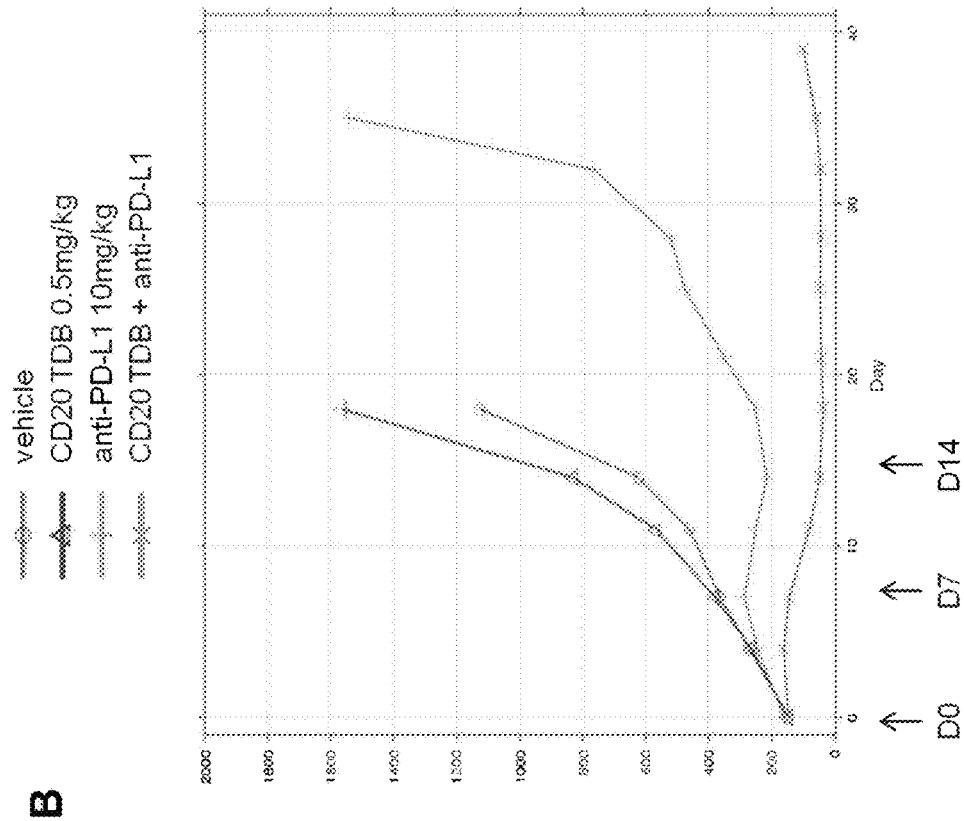

| CLONE | ELISA* | IP* | FACS* | DOMAIN | Epitope** | Tested as bispecific | Blocked by 4D5 | Note |
|---|---|---|---|---|---|---|---|---|
| 2C4 | +++ | ++ | +++ | 2 | 22-584 | Y | N | Medium activity |
| 2H11 | + | ++ | ++ | 4 | 529-645 | Y | Y | Low activity |
| 3E8 | + | +++ | +++ | 4 | 512-625 | N | Y | |
| 3H4 | + | ++ | + | 4 | 541-599 | Y | Y | High activity |
| 4D5 | ++ | ++ | +++ | 4 | 561-625 | Y | Y | High activity |
| 5B8 | + | + | + | ? | | Y | Y | Low activity |
| 6E9 | ++ | ++ | NEG | ? | | N | N | FACS neg. |
| 7C2 | ++ | ++ | +++ | 1 | 22-53 | Y | N | Low activity |
| 7F3 | +++ | +++ | +++ | 1 | 22-53 | N | N | Domain1 |

| CD3 arm | Monov. $K_D$ (nM, biacore) | Reactivity |
|---|---|---|
| humanized 38E4v1 | 1.3 | hu, cyno |
| murine 38E4 | 0.75 | hu, cyno |
| murine SP34 | 1.9 | hu, cyno |
| humanized 40G5c | 51 | hu, cyno |
| 2C11 | 22 | mouse |

Figure 85

Figure 107 anti-RET41205.v6 Light Chain Variable Region

DIQMTQSPSSLSASVGDRVTITCRASKSISKYLAWYQQKPGKANKLLIISSGSTLQSGVPSRFSGSGSGTDFTLTISSLQPEDFAT YYCQQHNEYPWTFGQGTKVEIK (SEQ ID NO:620)

anti-RET41205.v6 Heavy Chain Variable Region

EVQLVESGPGLVKPSETLSLTCTVSGYSITSDYVWNWIRQPPGKGLEWIGYIHYSGGTSYNPSLKSRVTISRDTSKNQFSLKLS SVTAADTAVYYCARGNYDWAFAYWGQGTLVTVSS (SEQ ID NO:619)

SEQUENCE LISTING

```
<160> NUMBER OF SEQ ID NOS: 650

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Tyr Pro Gly Asp Gly Asn Thr Lys Tyr Asn Glu Lys Phe Lys
1               5                   10                  15

Gly

<210> SEQ ID NO 3
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 3

Asp Ser Tyr Ser Asn Tyr Tyr Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Leu Asn Ser Arg Thr Arg Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Thr Gln Ser Phe Ile Leu Arg Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Tyr Tyr Ile His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Trp Ile Tyr Pro Glu Asn Asp Asn Thr Lys Tyr Asn Glu Lys Phe Lys
1               5                   10                  15

Asp
```

```
<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Asp Gly Tyr Ser Arg Tyr Tyr Phe Asp Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Lys Ser Ser Gln Ser Leu Leu Asn Ser Arg Thr Arg Lys Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Trp Thr Ser Thr Arg Lys Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Lys Gln Ser Phe Ile Leu Arg Thr
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Asp Ala Tyr Ser Arg Tyr Tyr Phe Asp Tyr
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Lys Gln Ser Phe Ala Leu Arg Thr
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Lys Ala Ser Phe Ile Leu Arg Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Lys Gln Ser Ala Ile Leu Arg Thr
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Thr Gly Tyr Ser Arg Tyr Tyr Phe Asp Tyr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Asp Gly Tyr Ser Arg Tyr Ala Phe Asp Tyr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Ser Gly Tyr Ser Arg Tyr Tyr Phe Asp Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Asp Gly Tyr Ser Arg Ala Tyr Phe Asp Tyr
1               5                   10
```

```
<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Asp Ser Tyr Ser Asn Tyr Tyr Phe Asp Tyr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Thr Gln Ser Phe Ile Leu Arg Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Gly Tyr Thr Met Asn
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Leu Ile Asn Pro Tyr Lys Gly Val Ser Thr Tyr Asn Gln Lys Phe Lys
1               5                   10                  15

Asp

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Ser Gly Tyr Tyr Gly Asp Ser Asp Trp Tyr Phe Asp Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Arg Ala Ser Gln Asp Ile Arg Asn Tyr Leu Asn
1               5                   10
```

```
<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Tyr Thr Ser Arg Leu Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Gln Gly Asn Thr Leu Pro Trp Thr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Leu Ile Asn Pro Tyr Lys Gly Val Thr Thr Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Leu Ile Asn Pro Tyr Lys Gly Val Ser Thr Tyr Ala Asp Ser Val Lys
1               5                   10                  15

Gly

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Thr Tyr Ala Met Asn
1               5

<210> SEQ ID NO 32
<211> LENGTH: 19
<212> TYPE: PRT
<213> ORGANISM: Artificial Sequence
<220> FEATURE:
<223> OTHER INFORMATION: Synthetic Construct

<400> SEQUENCE: 32
```

```
Arg Ile Arg Ser Lys Tyr Asn Asn Tyr Ala Thr Tyr Tyr Ala Asp Ser
1               5                   10                  15

Val Lys Asp

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

His Gly Asn Phe Gly Asn Ser Tyr Val Ser Trp Phe Ala Tyr
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

Arg Ser Ser Thr Gly Ala Val Thr Thr Ser Asn Tyr Ala Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Gly Thr Asn Lys Arg Ala Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Ala Leu Trp Tyr Ser Asn Leu Trp Val
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct

<400> SEQUENCE: 37

Asn Tyr Gly Met Asn
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct

<400> SEQUENCE: 38
```

```
Trp Ile Asn Thr Asn Thr Gly Lys Pro Thr Tyr Ala Glu Glu Phe Lys
1               5                   10                  15
Gly

<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Arg Gly Asp Tyr Arg Tyr Ala Trp Phe Leu Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Arg Ser Ser Thr Gly Ala Val Thr Thr Ser Asn Tyr Ala Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Gly Thr Ser Asn Arg Ala Pro
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Ala Leu Trp Tyr Ser Thr His Phe Val
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Ser Tyr Tyr Ile His
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 44

Trp Ile Tyr Pro Gly Asn Val Asn Thr Lys Tyr Asn Glu Lys Phe Lys
1               5                   10                  15
Gly

<210> SEQ ID NO 45
<211> LENGTH: 8
<212> TYPE: PRT
<213> ORGANISM: Artificial Sequence
<220> FEATURE:
<223> OTHER INFORMATION: Synthetic Construct

<400> SEQUENCE: 45

Asn His Asp Tyr Tyr Phe Asp Tyr
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Lys Ser Ser Gln Ser Leu Leu Asn Ser Arg Thr Arg Lys Asn Tyr Leu
1               5                   10                  15
Ala

<210> SEQ ID NO 47
<211> LENGTH: 7
<212> TYPE: PRT
<213> ORGANISM: Artificial Sequence
<220> FEATURE:
<223> OTHER INFORMATION: Synthetic Construct

<400> SEQUENCE: 47

Trp Ala Ser Thr Arg Glu Ser
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Lys Gln Ser Tyr Ile Leu Arg Thr
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Construct

<400> SEQUENCE: 49

Asn Tyr Ala Ile His
1               5

<210> SEQ ID NO 50
<211> LENGTH: 16
<212> TYPE: PRT
<213> ORGANISM: Artificial Sequence
```

```
<220> FEATURE:
<223> OTHER INFORMATION: Synthetic Construct

<400> SEQUENCE: 50

Val Ile Trp Ala Gly Gly Asn Thr Lys Tyr Asn Ser Ala Leu Met Ser
1               5                   10                  15

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Glu Asp Ser Ser Gly Tyr Val Ala Leu Asp Tyr
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Synthetic Construct

<400> SEQUENCE: 52

Lys Ser Ser Gln Ser Leu Leu Ser Gly Arg Thr Arg Lys Asn Tyr Leu
1               5                   10                  15

Ala

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Trp Ala Ser Thr Arg Glu Ser
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Lys Gln Ser Tyr Tyr Leu Leu Thr
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Phe Ser Leu Thr Asn Tyr Ala Ile His
1               5                   10

<210> SEQ ID NO 56
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 56

Gly Val Ile Trp Ala Gly Gly Asn Thr Lys Tyr Asn Ser Ala Leu Met
1               5                   10                  15

Ser

<210> SEQ ID NO 57
<211> LENGTH: 28
<212> TYPE: PRT
<213> ORGANISM: Artificial Sequence
<220> FEATURE:
<223> OTHER INFORMATION: Synthetic Construct

<400> SEQUENCE: 57

Gln Met Asn Ser Leu Arg Ala Glu Asp Thr Ala Val Tyr Tyr Cys Ala
1               5                   10                  15

Arg Glu Asp Ser Ser Gly Tyr Val Ala Leu Asp Tyr
            20                  25

<210> SEQ ID NO 58
<211> LENGTH: 17
<212> TYPE: PRT
<213> ORGANISM: Artificial Sequence
<220> FEATURE:
<223> OTHER INFORMATION: Synthetic Construct

<400> SEQUENCE: 58

Lys Ser Ser Gln Ser Leu Leu Ser Gly Arg Thr Arg Lys Asn Tyr Leu
1               5                   10                  15

Ala

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Trp Ala Ser Thr Arg Glu Ser
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Lys Gln Ser Tyr Tyr Leu Leu Thr
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct

<400> SEQUENCE: 61

Gly Ser Ala Met His
```

```
<210> SEQ ID NO 62
<211> LENGTH: 19
<212> TYPE: PRT
<213> ORGANISM: Artificial Sequence
<220> FEATURE:
<223> OTHER INFORMATION: Synthetic Construct

<400> SEQUENCE: 62

Arg Ile Arg Ser Arg Ala Asn Ser Tyr Ala Thr Ala Tyr Ala Ala Ser
1               5                   10                  15

Val Lys Asp

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Asp Thr Met Val Arg Gly Ile Asp Tyr
1               5

<210> SEQ ID NO 64
<211> LENGTH: 17
<212> TYPE: PRT
<213> ORGANISM: Artificial Sequence
<220> FEATURE:
<223> OTHER INFORMATION: Synthetic Construct

<400> SEQUENCE: 64

Lys Ser Ser Gln Ser Val Leu Tyr Ser Ser Asn Asn Lys Asn Tyr Leu
1               5                   10                  15

Val

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Arg Ala Ser Thr Arg Glu Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln Gln Tyr Tyr Ser Val Pro Trp Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 67

Ser Asp Tyr Ile His
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Trp Ile Tyr Phe Gly Asn Val Asn Thr Lys Tyr Asn Glu Lys Phe Lys
1               5                   10                  15

Gly

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct

<400> SEQUENCE: 69

Asp Gly Gly Tyr Tyr Phe Asp Tyr
1               5

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Lys Ser Ser Gln Ser Leu Leu Asn Ser Arg Thr Arg Lys Asn Tyr Leu
1               5                   10                  15

Ala

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct

<400> SEQUENCE: 71

Trp Ala Ser Thr Arg Glu Ser
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Construct

<400> SEQUENCE: 72

Lys Gln Ser Phe Thr Leu Arg Thr
1               5

<210> SEQ ID NO 73
<211> LENGTH: 5
<212> TYPE: PRT
<213> ORGANISM: Artificial Sequence
```

<220> FEATURE:
<223> OTHER INFORMATION: Synthetic Construct

<400> SEQUENCE: 73

Ser His Tyr Leu His
1               5

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Trp Ile Asn Pro Gly Asp Gly Asn Val Lys Tyr Asn Glu Lys Phe Lys
1               5                   10                  15
Asp

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Asp Gly Ala Tyr Tyr Phe Asp Tyr
1               5

<210> SEQ ID NO 76
<211> LENGTH: 17
<212> TYPE: PRT
<213> ORGANISM: Artificial Sequence
<220> FEATURE:
<223> OTHER INFORMATION: Synthetic Construct

<400> SEQUENCE: 76

Lys Ser Ser Gln Ser Leu Leu Asn Ser Arg Thr Arg Lys Asn Tyr Leu
1               5                   10                  15
Ala

<210> SEQ ID NO 77
<211> LENGTH: 7
<212> TYPE: PRT
<213> ORGANISM: Artificial Sequence
<220> FEATURE:
<223> OTHER INFORMATION: Synthetic Construct

<400> SEQUENCE: 77

Trp Ala Ser Thr Arg Glu Ser
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Construct

<400> SEQUENCE: 78

Lys Gln Ser Tyr Thr Leu Arg Thr
1               5

<210> SEQ ID NO 79

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 79

Ser Tyr Tyr Ile His
1               5

<210> SEQ ID NO 80
<211> LENGTH: 17
<212> TYPE: PRT
<213> ORGANISM: Artificial Sequence
<220> FEATURE:
<223> OTHER INFORMATION: Synthetic Construct

<400> SEQUENCE: 80

Trp Ile Phe Pro Gly Ser Asp Asn Thr Lys Tyr Asn Glu Lys Phe Lys
1               5                   10                  15

Gly

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Asn Gly Asn Tyr Ala Met Asp Tyr
1               5

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct

<400> SEQUENCE: 82

Lys Ser Ser Gln Ser Leu Leu Asn Ser Arg Thr Arg Lys Asn Tyr Leu
1               5                   10                  15

Ala

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Trp Ala Ser Thr Arg Glu Ser
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct

<400> SEQUENCE: 84

Lys Gln Ser Tyr Thr Leu Arg Thr
1               5
```

```
<210> SEQ ID NO 85
<211> LENGTH: 5
<212> TYPE: PRT
<213> ORGANISM: Artificial Sequence
<220> FEATURE:
<223> OTHER INFORMATION: Synthetic Construst

<400> SEQUENCE: 85

Ser Tyr Tyr Ile His
1               5

<210> SEQ ID NO 86
<211> LENGTH: 17
<212> TYPE: PRT
<213> ORGANISM: Artificial Sequence
<220> FEATURE:
<223> OTHER INFORMATION: Synthetic Construct

<400> SEQUENCE: 86

Trp Ile Tyr Pro Gly Asn Val Asn Thr Lys Tyr Asn Glu Lys Phe Lys
1               5                   10                  15

Gly

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

Asn His Asp Tyr Tyr Phe Asp Tyr
1               5

<210> SEQ ID NO 88
<211> LENGTH: 17
<212> TYPE: PRT
<213> ORGANISM: Artificial Sequence
<220> FEATURE:
<223> OTHER INFORMATION: Synthetic Construct

<400> SEQUENCE: 88

Lys Ser Ser Gln Ser Leu Leu Asn Ser Arg Thr Arg Lys Asn Tyr Leu
1               5                   10                  15

Ala

<210> SEQ ID NO 89
<211> LENGTH: 7
<212> TYPE: PRT
<213> ORGANISM: Artificial Sequence
<220> FEATURE:
<223> OTHER INFORMATION: Synthetic Construct

<400> SEQUENCE: 89

Trp Ala Ser Thr Arg Glu Ser
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90
```

```
Lys Gln Ser Tyr Ile Leu Arg Thr
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Construct

<400> SEQUENCE: 91

Asn Tyr Gly Met Asn
1               5

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct

<400> SEQUENCE: 92

Trp Ile Asn Thr Asn Thr Gly Lys Pro Thr Tyr Ala Glu Asp Phe Lys
1               5                   10                  15

Gly

<210> SEQ ID NO 93
<211> LENGTH: 11
<212> TYPE: PRT
<213> ORGANISM: Artificial Sequence
<220> FEATURE:
<223> OTHER INFORMATION: Synthetic Construct

<400> SEQUENCE: 93

Arg Gly Asp Tyr Arg Tyr Ala Trp Phe Thr Tyr
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic Construct

<400> SEQUENCE: 94

Arg Ser Ser Thr Gly Ala Val Thr Thr Ser Asn Tyr Ala Asn
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct

<400> SEQUENCE: 95

Gly Thr Ser Asn Arg Ala Pro
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 96

Ala Leu Trp Tyr Ser Thr His Phe Val
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct

<400> SEQUENCE: 97

Asn Tyr Tyr Ile His
1               5

<210> SEQ ID NO 98
<211> LENGTH: 17
<212> TYPE: PRT
<213> ORGANISM: Artificial Sequence
<220> FEATURE:
<223> OTHER INFORMATION: Synthetic Construct

<400> SEQUENCE: 98

Trp Ile Tyr Pro Gly Ser Asp Asn Thr Lys Phe Asn Asp Lys Phe Lys
1               5                   10                  15

Gly

<210> SEQ ID NO 99
<211> LENGTH: 10
<212> TYPE: PRT
<213> ORGANISM: Artificial Sequence
<220> FEATURE:
<223> OTHER INFORMATION: Synthetic Construct

<400> SEQUENCE: 99

Asp Ser Ile Thr Asn Tyr Tyr Phe Asp Tyr
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Synthetic Construct

<400> SEQUENCE: 100

Lys Ser Ser Gln Ser Leu Leu Asn Ile Arg Thr Arg Lys Asn Cys Leu
1               5                   10                  15

Ala

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101

Trp Ala Ser Thr Arg Tyr Ser
1               5

<210> SEQ ID NO 102
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 102

Thr Gln Ser Tyr Thr Leu Arg Thr
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic Construct

<400> SEQUENCE: 103

Ser Tyr Trp Met His
1               5

<210> SEQ ID NO 104
<211> LENGTH: 17
<212> TYPE: PRT
<213> ORGANISM: Artificial Sequence
<220> FEATURE:
<223> OTHER INFORMATION: Synthetic Construct

<400> SEQUENCE: 104

Asn Phe Tyr Pro Gly Asp Leu Thr Val Asn Tyr Asp Glu Lys Phe Lys
1               5                   10                  15

Asn

<210> SEQ ID NO 105
<211> LENGTH: 10
<212> TYPE: PRT
<213> ORGANISM: Artificial Sequence
<220> FEATURE:
<223> OTHER INFORMATION: Synthetic Construct

<400> SEQUENCE: 105

Asp Ala Tyr Ser Arg Tyr Phe Phe Asp Tyr
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Synthetic Construct

<400> SEQUENCE: 106

Lys Ser Ser Gln Ser Leu Leu Asn Ser Arg Thr Arg Lys Asn Tyr Leu
1               5                   10                  15

Ala

<210> SEQ ID NO 107
<211> LENGTH: 7
<212> TYPE: PRT
<213> ORGANISM: Artificial Sequence
<220> FEATURE:
<223> OTHER INFORMATION: Synthetic Construct

<400> SEQUENCE: 107

Trp Ala Ser Thr Arg Glu Ser
1               5

<210> SEQ ID NO 108
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 108

Cys Gln Ser Phe Ile Leu Arg Thr
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic Construct

<400> SEQUENCE: 109

Asn Tyr Tyr Met His
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic Construct

<400> SEQUENCE: 110

Trp Ile Ser Pro Gly Ser Gly Ser Ile Lys Tyr Asn Glu Lys Phe Lys
1               5                   10                  15

Gly

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Asp Gly Tyr Ser Leu Tyr Phe Phe Asp Phe
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Synthetic Construct

<400> SEQUENCE: 112

Lys Ser Ser Gln Ser Leu Leu Asn Ser Arg Thr Arg Lys Asn Tyr Leu
1               5                   10                  15

Ala

<210> SEQ ID NO 113
<211> LENGTH: 7
<212> TYPE: PRT
<213> ORGANISM: Artificial Sequence
<220> FEATURE:
<223> OTHER INFORMATION: Synthetic Construct

<400> SEQUENCE: 113

Trp Ala Ser Thr Arg Glu Ser
1               5
```

<210> SEQ ID NO 114
<211> LENGTH: 8
<212> TYPE: PRT
<213> ORGANISM: Artificial Sequence
<220> FEATURE:
<223> OTHER INFORMATION: Synthetic Construct

<400> SEQUENCE: 114

Lys Gln Ser Phe Ile Leu Arg Thr
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic Construct

<400> SEQUENCE: 115

Asn Tyr Tyr Thr His
1               5

<210> SEQ ID NO 116
<211> LENGTH: 17
<212> TYPE: PRT
<213> ORGANISM: Artificial Sequence
<220> FEATURE:
<223> OTHER INFORMATION: Synthetic Construct

<400> SEQUENCE: 116

Trp Ile Tyr Pro Gly Asn Gly Asn Ile Lys Tyr Asn Glu Lys Phe Met
1               5                   10                  15

Gly

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Asp Ser Tyr Gly Ser Tyr Tyr Phe Asp Tyr
1               5                   10

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct

<400> SEQUENCE: 118

Lys Ser Ser Gln Ser Leu Leu Asn Ser Arg Thr Arg Lys Asn Tyr Leu
1               5                   10                  15

Ala

<210> SEQ ID NO 119
<211> LENGTH: 7
<212> TYPE: PRT
<213> ORGANISM: Artificial Sequence
<220> FEATURE:
<223> OTHER INFORMATION: Synthetic Construct

<400> SEQUENCE: 119

```
Trp Ala Ser Thr Arg Glu Ser
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic Construct

<400> SEQUENCE: 120

Thr Gln Ser Phe Ile Leu Arg Thr
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic Construct

<400> SEQUENCE: 121

Asn Tyr Tyr Thr His
1               5

<210> SEQ ID NO 122
<211> LENGTH: 17
<212> TYPE: PRT
<213> ORGANISM: Artificial Sequence
<220> FEATURE:
<223> OTHER INFORMATION: Synthetic Construct

<400> SEQUENCE: 122

Trp Ile Tyr Pro Gly Asn Gly Asn Ile Lys Tyr Asn Glu Lys Phe Met
1               5                   10                  15

Gly

<210> SEQ ID NO 123
<211> LENGTH: 10
<212> TYPE: PRT
<213> ORGANISM: Artificial Sequence
<220> FEATURE:
<223> OTHER INFORMATION: Synthetic Construct

<400> SEQUENCE: 123

Asp Ser Tyr Gly Ser Tyr Tyr Phe Asp Tyr
1               5                   10

<210> SEQ ID NO 124
<211> LENGTH: 17
<212> TYPE: PRT
<213> ORGANISM: Artificial Sequence
<220> FEATURE:
<223> OTHER INFORMATION: Synthetic Construct

<400> SEQUENCE: 124

Lys Ser Ser Gln Ser Leu Leu Asn Ser Arg Thr Arg Lys Asn Tyr Leu
1               5                   10                  15

Ala

<210> SEQ ID NO 125
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 125

Trp Ala Ser Thr Arg Glu Ser
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 126

Lys Gln Ser Phe Ile Leu Arg Thr
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic Construct

<400> SEQUENCE: 127

Asn Tyr Tyr Thr His
1               5

<210> SEQ ID NO 128
<211> LENGTH: 17
<212> TYPE: PRT
<213> ORGANISM: Artificial Sequence
<220> FEATURE:
<223> OTHER INFORMATION: Synthetic Construct

<400> SEQUENCE: 128

Trp Leu Tyr Pro Gly Asn Gly Asp Thr Arg Tyr Asn Glu Lys Phe Lys
1               5                   10                  15

Asp

<210> SEQ ID NO 129
<211> LENGTH: 10
<212> TYPE: PRT
<213> ORGANISM: Artificial Sequence
<220> FEATURE:
<223> OTHER INFORMATION: Synthetic Construct

<400> SEQUENCE: 129

Asp Ser Tyr Gly Asn Tyr Phe Phe Asp Tyr
1               5                   10

<210> SEQ ID NO 130
<211> LENGTH: 17
<212> TYPE: PRT
<213> ORGANISM: Artificial Sequence
<220> FEATURE:
<223> OTHER INFORMATION: Synthetic Construct

<400> SEQUENCE: 130

Lys Ser Ser Gln Ser Leu Leu Asn Ser Arg Thr Arg Lys Asn Tyr Leu
1               5                   10                  15

Ala

<210> SEQ ID NO 131
<211> LENGTH: 7

```
<212> TYPE: PRT
<213> ORGANISM: Artificial Sequence
<220> FEATURE:
<223> OTHER INFORMATION: Synthetic Construct

<400> SEQUENCE: 131

Trp Ala Ser Thr Arg Glu Ser
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic Construct

<400> SEQUENCE: 132

Lys Gln Ser Phe Ile Leu Arg Thr
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic Construct

<400> SEQUENCE: 133

Ser Tyr Trp Met His
1               5

<210> SEQ ID NO 134
<211> LENGTH: 17
<212> TYPE: PRT
<213> ORGANISM: Artificial Sequence
<220> FEATURE:
<223> OTHER INFORMATION: Synthetic Construct

<400> SEQUENCE: 134

Asn Ser Tyr Pro Gly Asp Leu Asn Val Asn Tyr Asp Glu Lys Phe Lys
1               5                   10                  15

Asn

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Asp Ala Tyr Ser Arg Tyr Phe Phe Asp Tyr
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Synthetic Construct

<400> SEQUENCE: 136

Lys Ser Ser Gln Ser Leu Leu Asn Ser Arg Thr Arg Lys Asn Tyr Leu
1               5                   10                  15

Ala
```

```
<210> SEQ ID NO 137
<211> LENGTH: 7
<212> TYPE: PRT
<213> ORGANISM: Artificial Sequence
<220> FEATURE:
<223> OTHER INFORMATION: Synthetic Construct

<400> SEQUENCE: 137

Trp Ala Ser Thr Arg Glu Ser
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic Construct

<400> SEQUENCE: 138

Cys Gln Ser Phe Ile Leu Arg Thr
1               5

<210> SEQ ID NO 139
<211> LENGTH: 5
<212> TYPE: PRT
<213> ORGANISM: Artificial Sequence
<220> FEATURE:
<223> OTHER INFORMATION: Synthetic Construct

<400> SEQUENCE: 139

Ser Tyr Tyr Ile His
1               5

<210> SEQ ID NO 140
<211> LENGTH: 17
<212> TYPE: PRT
<213> ORGANISM: Artificial Sequence
<220> FEATURE:
<223> OTHER INFORMATION: Synthetic Construct

<400> SEQUENCE: 140

Trp Leu Tyr Pro Gly Asp Val Ser Thr Arg Tyr Asn Glu Lys Phe Arg
1               5                   10                  15

Asp

<210> SEQ ID NO 141
<211> LENGTH: 10
<212> TYPE: PRT
<213> ORGANISM: Artificial Sequence
<220> FEATURE:
<223> OTHER INFORMATION: Synthetic Construct

<400> SEQUENCE: 141

Asp Ser Ser Ala Ser Tyr Tyr Phe Asp Phe
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Synthetic Construct

<400> SEQUENCE: 142

Lys Ser Ser Gln Ser Leu Leu Asn Ile Arg Thr Arg Lys Asn Tyr Leu
1               5                   10                  15
```

Ala

<210> SEQ ID NO 143
<211> LENGTH: 7
<212> TYPE: PRT
<213> ORGANISM: Artificial Sequence
<220> FEATURE:
<223> OTHER INFORMATION: Synthetic Construct

<400> SEQUENCE: 143

Trp Ala Ser Thr Arg Ala Ser
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic Construct

<400> SEQUENCE: 144

Thr Gln Ser Phe Ile Leu Arg Thr
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic Construct

<400> SEQUENCE: 145

Ser Tyr Trp Met His
1               5

<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Asn Ile Tyr Pro Gly Gly Glu Ile Ile Asn Tyr Ala Glu Lys Phe Lys
1               5                   10                  15

Thr

<210> SEQ ID NO 147
<211> LENGTH: 10
<212> TYPE: PRT
<213> ORGANISM: Artificial Sequence
<220> FEATURE:
<223> OTHER INFORMATION: Synthetic Construct

<400> SEQUENCE: 147

Asp Thr Thr Gly Asn Tyr Phe Phe Asp Tyr
1               5                   10

<210> SEQ ID NO 148
<211> LENGTH: 17
<212> TYPE: PRT
<213> ORGANISM: Artificial Sequence
<220> FEATURE:
<223> OTHER INFORMATION: Synthetic Construct

<400> SEQUENCE: 148

Lys Ser Ser Gln Ser Leu Leu Asn Ser Arg Thr Arg Lys Asn Tyr Leu
1               5                   10                  15

Ala

<210> SEQ ID NO 149
<211> LENGTH: 7
<212> TYPE: PRT
<213> ORGANISM: Artificial Sequence
<220> FEATURE:
<223> OTHER INFORMATION: Synthetic Construct

<400> SEQUENCE: 149

Trp Ala Ser Thr Arg Glu Ser
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 150

Thr Gln Ser Phe Ile Leu Arg Thr
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic Construct

<400> SEQUENCE: 151

Ser Cys Ala Ile Ser
1               5

<210> SEQ ID NO 152
<211> LENGTH: 16
<212> TYPE: PRT
<213> ORGANISM: Artificial Sequence
<220> FEATURE:
<223> OTHER INFORMATION: Synthetic Construct

<400> SEQUENCE: 152

Phe Met Ser Val Thr Gly Ser Ala Tyr Tyr Ala Asn Trp Ala Lys Ser
1               5                   10                  15

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Val Gly Ile Gly Ser Gly Leu Asn Ile
1               5

<210> SEQ ID NO 154
<211> LENGTH: 13
<212> TYPE: PRT
<213> ORGANISM: Artificial Sequence
<220> FEATURE:
<223> OTHER INFORMATION: Synthetic Construct

<400> SEQUENCE: 154

Gln Ala Ser Glu Thr Val Tyr Ser Asn Asn Tyr Leu Ala
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Synthetic Construct

<400> SEQUENCE: 155

Gly Val Ser Thr Leu Asp Ser
1               5

<210> SEQ ID NO 156
<211> LENGTH: 12
<212> TYPE: PRT
<213> ORGANISM: Artificial Sequence
<220> FEATURE:
<223> OTHER INFORMATION: Synthetic Construct

<400> SEQUENCE: 156

Ala Gly Tyr Lys Thr Ser Ser Ser Tyr Ala Ile Ala
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Gly Tyr Thr Phe Thr Ser Tyr Asn Met His
1               5                   10

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

Ala Ile Tyr Pro Gly Asn Gly Asp Thr Ser Tyr Asn Gln Lys Phe Lys
1               5                   10                  15

Gly

<210> SEQ ID NO 159
<211> LENGTH: 13
<212> TYPE: PRT
<213> ORGANISM: Artificial Sequence
<220> FEATURE:
<223> OTHER INFORMATION: Synthetic Construct

<400> SEQUENCE: 159

Val Val Tyr Tyr Ser Asn Ser Tyr Trp Tyr Phe Asp Val
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 160

Arg Ala Ser Ser Ser Val Ser Tyr Met His
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Synthetic Construct

<400> SEQUENCE: 161

Ala Pro Ser Asn Leu Ala Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Construct

<400> SEQUENCE: 162

Gln Gln Trp Ser Phe Asn Pro Pro Thr
1               5

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct

<400> SEQUENCE: 163

Arg Phe Gly Val His
1               5

<210> SEQ ID NO 164
<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Val Ile Trp Arg Gly Gly Ser Thr Asp Tyr Asn Ala Ala Phe Met Ser
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Synthetic Construct

<400> SEQUENCE: 165

Val Ile Trp Arg Gly Gly Ser Thr Asp Tyr Asn Ala Ala Phe Met Ser
1               5                   10                  15

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 166

Lys Ala Ser Gln Asp Val Ser Asn Ile Val Val
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Synthetic Construct

<400> SEQUENCE: 167

Ser Ala Ser Tyr Arg Tyr Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic Construct

<400> SEQUENCE: 168

Gln Gln His Tyr Ser Ser Pro Tyr Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic Construct

<400> SEQUENCE: 169

Asp Thr Tyr Ile His
1               5

<210> SEQ ID NO 170
<211> LENGTH: 17
<212> TYPE: PRT
<213> ORGANISM: Artificial Sequence
<220> FEATURE:
<223> OTHER INFORMATION: Synthetic Construct

<400> SEQUENCE: 170

Arg Ile Tyr Pro Thr Asn Gly Tyr Thr Arg Tyr Ala Asp Ser Val Lys
1               5                   10                  15

Gly

<210> SEQ ID NO 171
<211> LENGTH: 11
<212> TYPE: PRT
<213> ORGANISM: Artificial Sequence
<220> FEATURE:
<223> OTHER INFORMATION: Synthetic Construct

<400> SEQUENCE: 171

Trp Gly Gly Asp Gly Phe Tyr Ala Met Asp Tyr
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 172

Arg Ala Ser Gln Asp Val Asn Thr Ala Val Ala
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Synthetic Construct

<400> SEQUENCE: 173

Ser Ala Ser Phe Leu Tyr Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Construct

<400> SEQUENCE: 174

Gln Gln His Tyr Thr Thr Pro Pro Thr
1               5

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct

<400> SEQUENCE: 175

Gly Phe Thr Ile Thr Asn Tyr Gly Ile His
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Synthetic Construct

<400> SEQUENCE: 176

Gly Arg Ile Tyr Pro Asp Ser Gly Ala Thr Tyr Tyr Ala Asp Ser
1               5                   10                  15

<210> SEQ ID NO 177
<211> LENGTH: 11
<212> TYPE: PRT
<213> ORGANISM: Artificial Sequence
<220> FEATURE:
<223> OTHER INFORMATION: Synthetic Construct

<400> SEQUENCE: 177

Lys Leu Trp Ile Ser Ile Ala Gly Met Asp Tyr
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 178

Arg Ala Ser Gln Asp Val Ser Thr Ala Val Ala
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Synthetic Construct

<400> SEQUENCE: 179

Ser Ala Ser Phe Leu Tyr Ser
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Construct

<400> SEQUENCE: 180

Gln His Ser Tyr Ala Thr Pro Phe Thr
1               5

<210> SEQ ID NO 181
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Asp,Thr, or Ser
<220> FEATURE:
<221> NAME/KEY: MISC_FEATURE
<222> LOCATION: (2)..(2)
<223> OTHER INFORMATION: Xaa is Gly, Ala, or Ser
<220> FEATURE:
<221> NAME/KEY: MISC_FEATURE
<222> LOCATION: (5)..(5)
<223> OTHER INFORMATION: Xaa is Arg or Asn
<220> FEATURE:
<221> NAME/KEY: MISC_FEATURE
<222> LOCATION: (6)..(6)
<223> OTHER INFORMATION: Xaa is Tyr or Ala
<220> FEATURE:
<221> NAME/KEY: MISC_FEATURE
<222> LOCATION: (7)..(7)
<223> OTHER INFORMATION: Xaa is Tyr or Ala

<400> SEQUENCE: 181

Xaa Xaa Tyr Ser Xaa Xaa Xaa Phe Asp Tyr
1               5                   10

<210> SEQ ID NO 182
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Lys or Thr
<220> FEATURE:
<221> NAME/KEY: MISC_FEATURE
<222> LOCATION: (2)..(2)
<223> OTHER INFORMATION: Xaa is Gln or Ala
```

```
<220> FEATURE:
<221> NAME/KEY: MISC_FEATURE
<222> LOCATION: (4)..(4)
<223> OTHER INFORMATION: Xaa is Phe or Ala
<220> FEATURE:
<221> NAME/KEY: MISC_FEATURE
<222> LOCATION: (5)..(5)
<223> OTHER INFORMATION: Xaa is Ile or Ala

<400> SEQUENCE: 182

Xaa Xaa Ser Xaa Xaa Leu Arg Thr
1               5

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Ser or Thr
<220> FEATURE:
<221> NAME/KEY: MISC_FEATURE
<222> LOCATION: (12)..(12)
<223> OTHER INFORMATION: Xaa is Asn or Ala
<220> FEATURE:
<221> NAME/KEY: MISC_FEATURE
<222> LOCATION: (13)..(13)
<223> OTHER INFORMATION: Xaa is Gln or Asp
<220> FEATURE:
<221> NAME/KEY: MISC_FEATURE
<222> LOCATION: (14)..(14)
<223> OTHER INFORMATION: Xaa is Lys or Ser
<220> FEATURE:
<221> NAME/KEY: MISC_FEATURE
<222> LOCATION: (15)..(15)
<223> OTHER INFORMATION: Xaa is Phe or Val
<220> FEATURE:
<221> NAME/KEY: MISC_FEATURE
<222> LOCATION: (17)..(17)
<223> OTHER INFORMATION: Xaa is Asp or Gly

<400> SEQUENCE: 183

Leu Ile Asn Pro Tyr Lys Gly Val Xaa Thr Tyr Xaa Xaa Xaa Xaa Lys
1               5                   10                  15

Xaa

<210> SEQ ID NO 184
<211> LENGTH: 119
<212> TYPE: PRT
<213> ORGANISM: Artificial Sequence
<220> FEATURE:
<223> OTHER INFORMATION: Synthetic Construct

<400> SEQUENCE: 184

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
```

85                  90                  95

Ala Arg Asp Ser Tyr Ser Asn Tyr Tyr Phe Asp Tyr Trp Gly Gln Gly
                100                 105                 110

Thr Leu Val Thr Val Ser Ser
        115

<210> SEQ ID NO 185
<211> LENGTH: 112
<212> TYPE: PRT
<213> ORGANISM: Artificial Sequence
<220> FEATURE:
<223> OTHER INFORMATION: Synthetic Construct

<400> SEQUENCE: 185

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

<210> SEQ ID NO 186
<211> LENGTH: 119
<212> TYPE: PRT
<213> ORGANISM: Artificial Sequence
<220> FEATURE:
<223> OTHER INFORMATION: Synthetic Construct

<400> SEQUENCE: 186

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Asp Gly Asn Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Ser Tyr Ser Asn Tyr Tyr Phe Asp Tyr Trp Gly Gln Gly
                100                 105                 110

Thr Thr Leu Thr Val Ser Ser
        115

<210> SEQ ID NO 187
<211> LENGTH: 112
<212> TYPE: PRT
<213> ORGANISM: Artificial Sequence
<220> FEATURE:

<223> OTHER INFORMATION: Synthetic Construct

<400> SEQUENCE: 187

```
Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
            100                 105                 110
```

<210> SEQ ID NO 188
<211> LENGTH: 119
<212> TYPE: PRT
<213> ORGANISM: Artificial Sequence
<220> FEATURE:
<223> OTHER INFORMATION: Synthetic Construct

<400> SEQUENCE: 188

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115
```

<210> SEQ ID NO 189
<211> LENGTH: 112
<212> TYPE: PRT
<213> ORGANISM: Artificial Sequence
<220> FEATURE:
<223> OTHER INFORMATION: Synthetic Construct

<400> SEQUENCE: 189

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
```

```
                50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Phe Ile Leu Arg Thr Phe Gly Gln Gly Thr Lys Val Glu Ile Lys
                100                 105                 110

<210> SEQ ID NO 190
<211> LENGTH: 119
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
                 20                  25                  30

Tyr Ile His Trp Val Arg Gln Ala Pro Gly Gln Gly Leu Glu Trp Ile
             35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Ala Tyr Ser Arg Tyr Tyr Phe Asp Tyr Trp Gly Gln Gly
                100                 105                 110

Thr Leu Val Thr Val Ser Ser
            115

<210> SEQ ID NO 191
<211> LENGTH: 112
<212> TYPE: PRT
<213> ORGANISM: Artificial Sequence
<220> FEATURE:
<223> OTHER INFORMATION: Synthetic Construct

<400> SEQUENCE: 191

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Thr Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Phe Ile Leu Arg Thr Phe Gly Gln Gly Thr Lys Val Glu Ile Lys
                100                 105                 110

<210> SEQ ID NO 192
<211> LENGTH: 119
```

```
<212> TYPE: PRT
<213> ORGANISM: Artificial Sequence
<220> FEATURE:
<223> OTHER INFORMATION: Synthetic Construct

<400> SEQUENCE: 192

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 193
<211> LENGTH: 112
<212> TYPE: PRT
<213> ORGANISM: Artificial Sequence
<220> FEATURE:
<223> OTHER INFORMATION: Synthetic Construct

<400> SEQUENCE: 193

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ala Leu Arg Thr Phe Gly Gln Gly Thr Lys Val Glu Ile Lys
            100                 105                 110

<210> SEQ ID NO 194
<211> LENGTH: 119
<212> TYPE: PRT
<213> ORGANISM: Artificial Sequence
<220> FEATURE:
<223> OTHER INFORMATION: Synthetic Construct

<400> SEQUENCE: 194

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
```

```
                35                  40                  45
Gly Trp Ile Tyr Pro Glu Asn Asp Asn Thr Lys Tyr Asn Glu Lys Phe
 50                  55                  60
Lys Asp Arg Val Thr Ile Thr Ala Asp Thr Ser Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Asp Gly Tyr Ser Arg Tyr Tyr Phe Asp Tyr Trp Gly Gln Gly
                100                 105                 110
Thr Leu Val Thr Val Ser Ser
                115

<210> SEQ ID NO 195
<211> LENGTH: 112
<212> TYPE: PRT
<213> ORGANISM: Artificial Sequence
<220> FEATURE:
<223> OTHER INFORMATION: Synthetic Construct

<400> SEQUENCE: 195

Asp Ile Val Met Thr Gln Ser Pro Asp Ser Leu Ala Val Ser Leu Gly
  1               5                  10                  15
Glu Arg Ala Thr Ile Asn Cys Lys Ser Ser Gln Ser Leu Leu Asn Ser
                 20                  25                  30
Arg Thr Arg Lys Asn Tyr Leu Ala Trp Tyr Gln Gln Lys Pro Gly Gln
                 35                  40                  45
Ser Pro Lys Leu Leu Ile Tyr Trp Thr Ser Thr Arg Lys Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Lys Ala
                 85                  90                  95
Ser Phe Ile Leu Arg Thr Phe Gly Gln Gly Thr Lys Val Glu Ile Lys
                100                 105                 110

<210> SEQ ID NO 196
<211> LENGTH: 119
<212> TYPE: PRT
<213> ORGANISM: Artificial Sequence
<220> FEATURE:
<223> OTHER INFORMATION: Synthetic Construct

<400> SEQUENCE: 196

Glu Val Gln Leu Val Gln Ser Gly Ala Glu Val Lys Lys Pro Gly Ala
  1               5                  10                  15
Ser Val Lys Val Ser Cys Lys Ala Ser Gly Phe Thr Phe Thr Ser Tyr
                 20                  25                  30
Tyr Ile His Trp Val Arg Gln Ala Pro Gly Gln Gly Leu Glu Trp Ile
                 35                  40                  45
Gly Trp Ile Tyr Pro Glu Asn Asp Asn Thr Lys Tyr Asn Glu Lys Phe
 50                  55                  60
Lys Asp Arg Val Thr Ile Thr Ala Asp Thr Ser Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Asp Gly Tyr Ser Arg Tyr Tyr Phe Asp Tyr Trp Gly Gln Gly
                100                 105                 110
```

```
Thr Leu Val Thr Val Ser Ser
        115

<210> SEQ ID NO 197
<211> LENGTH: 112
<212> TYPE: PRT
<213> ORGANISM: Artificial Sequence
<220> FEATURE:
<223> OTHER INFORMATION: Synthetic Construct

<400> SEQUENCE: 197

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Ala Ile Leu Arg Thr Phe Gly Gln Gly Thr Lys Val Glu Ile Lys
            100                 105                 110

<210> SEQ ID NO 198
<211> LENGTH: 119
<212> TYPE: PRT
<213> ORGANISM: Artificial Sequence
<220> FEATURE:
<223> OTHER INFORMATION: Synthetic Construct

<400> SEQUENCE: 198

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Thr Gly Tyr Ser Arg Tyr Tyr Phe Asp Tyr Trp Gly Gln Gly
            100                 105                 110

Thr Leu Val Thr Val Ser Ser
        115

<210> SEQ ID NO 199
<211> LENGTH: 112
<212> TYPE: PRT
<213> ORGANISM: Artificial Sequence
<220> FEATURE:
<223> OTHER INFORMATION: Synthetic Construct

<400> SEQUENCE: 199

Asp Ile Val Met Thr Gln Ser Pro Asp Ser Leu Ala Val Ser Leu Gly
```

```
                1               5                   10                  15
Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
                35                  40                  45

Ser Pro Lys Leu Leu Ile Tyr Trp Thr Ser Thr Arg Lys Ser Gly Val
            50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
                35                  40                  45

Gly Trp Ile Tyr Pro Glu Asn Asp Asn Thr Lys Tyr Asn Glu Lys Phe
            50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Ala Phe Asp Tyr Trp Gly Gln Gly
                100                 105                 110

Thr Leu Val Thr Val Ser Ser
        115

<210> SEQ ID NO 201
<211> LENGTH: 112
<212> TYPE: PRT
<213> ORGANISM: Artificial Sequence
<220> FEATURE:
<223> OTHER INFORMATION: Synthetic Construct

<400> SEQUENCE: 201

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
                35                  40                  45

Ser Pro Lys Leu Leu Ile Tyr Trp Thr Ser Thr Arg Lys Ser Gly Val
            50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110
```

<210> SEQ ID NO 202
<211> LENGTH: 119
<212> TYPE: PRT
<213> ORGANISM: Artificial Sequence
<220> FEATURE:
<223> OTHER INFORMATION: Synthetic Construct

<400> SEQUENCE: 202

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
            35                  40                  45

Gly Trp Ile Tyr Pro Glu Asn Asp Asn Thr Lys Tyr Asn Glu Lys Phe
        50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Tyr Ser Arg Tyr Tyr Phe Asp Tyr Trp Gly Gln Gly
            100                 105                 110

Thr Leu Val Thr Val Ser Ser
        115
```

<210> SEQ ID NO 203
<211> LENGTH: 112
<212> TYPE: PRT
<213> ORGANISM: Artificial Sequence
<220> FEATURE:
<223> OTHER INFORMATION: Synthetic Construct

<400> SEQUENCE: 203

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Thr Ser Thr Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110
```

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct -continued

<400> SEQUENCE: 204

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Ala Tyr Phe Asp Tyr Trp Gly Gln Gly
            100                 105                 110

Thr Leu Val Thr Val Ser Ser
        115

<210> SEQ ID NO 205
<211> LENGTH: 112
<212> TYPE: PRT
<213> ORGANISM: Artificial Sequence
<220> FEATURE:
<223> OTHER INFORMATION: Synthetic Construct

<400> SEQUENCE: 205

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 206
<211> LENGTH: 119
<212> TYPE: PRT
<213> ORGANISM: Artificial Sequence
<220> FEATURE:
<223> OTHER INFORMATION: Synthetic Construct

<400> SEQUENCE: 206

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

```
Lys Asp Arg Val Thr Ile Thr Ala Asp Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
            115

<210> SEQ ID NO 207
<211> LENGTH: 112
<212> TYPE: PRT
<213> ORGANISM: Artificial Sequence
<220> FEATURE:
<223> OTHER INFORMATION: Synthetic Construct

<400> SEQUENCE: 207

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Thr Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Phe Ile Leu Arg Thr Phe Gly Gln Gly Thr Lys Val Glu Ile Lys
            100                 105                 110

<210> SEQ ID NO 208
<211> LENGTH: 122
<212> TYPE: PRT
<213> ORGANISM: Artificial Sequence
<220> FEATURE:
<223> OTHER INFORMATION: Synthetic Construct

<400> SEQUENCE: 208

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Phe Thr Gly Tyr
             20                  25                  30

Thr Met Asn Trp Val Arg Gln Ala Pro Gly Lys Asp Leu Glu Trp Val
         35                  40                  45

Ala Leu Ile Asn Pro Tyr Lys Gly Val Ser Thr Tyr Asn Gln Lys Phe
 50                  55                  60

Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
            115                 120

<210> SEQ ID NO 209
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Leu Lys
            100                 105

<210> SEQ ID NO 210
<211> LENGTH: 122
<212> TYPE: PRT
<213> ORGANISM: Artificial Sequence
<220> FEATURE:
<223> OTHER INFORMATION: Synthetic Construct

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Thr Thr Tyr Ala Asp Ser Val
50                  55                  60

Lys Gly Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 211
<211> LENGTH: 107
<212> TYPE: PRT
<213> ORGANISM: Artificial Sequence
<220> FEATURE:
<223> OTHER INFORMATION: Synthetic Construct

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30
```

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                    85                  90                  95

Thr Phe Gly Gln Gly Thr Lys Val Glu Ile Lys
                100                 105

<210> SEQ ID NO 212
<211> LENGTH: 122
<212> TYPE: PRT
<213> ORGANISM: Artificial Sequence
<220> FEATURE:
<223> OTHER INFORMATION: Synthetic Construct

<400> SEQUENCE: 212

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly Tyr
                20                  25                  30

Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Ala Asp Ser Val
 50                  55                  60

Lys Gly Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser
                115                 120

<210> SEQ ID NO 213
<211> LENGTH: 107
<212> TYPE: PRT
<213> ORGANISM: Artificial Sequence
<220> FEATURE:
<223> OTHER INFORMATION: Synthetic Construct

<400> SEQUENCE: 213

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                    85                  90                  95

Thr Phe Gly Gln Gly Thr Lys Val Glu Ile Lys
                100                 105

<210> SEQ ID NO 214
<211> LENGTH: 125
<212> TYPE: PRT
<213> ORGANISM: Artificial Sequence
<220> FEATURE:
<223> OTHER INFORMATION: Synthetic Construct

<400> SEQUENCE: 214

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 215
<211> LENGTH: 109
<212> TYPE: PRT
<213> ORGANISM: Artificial Sequence
<220> FEATURE:
<223> OTHER INFORMATION: Synthetic Construct

<400> SEQUENCE: 215

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 216
<211> LENGTH: 125
<212> TYPE: PRT
<213> ORGANISM: Mus musculus

<400> SEQUENCE: 216

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

```
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Gln Ser Ile
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 217
<211> LENGTH: 109
<212> TYPE: PRT
<213> ORGANISM: Mus musculus

<400> SEQUENCE: 217

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu
            100                 105

<210> SEQ ID NO 218
<211> LENGTH: 120
<212> TYPE: PRT
<213> ORGANISM: Artificial Sequence
<220> FEATURE:
<223> OTHER INFORMATION: Synthetic Construct

<400> SEQUENCE: 218

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Asn Thr Gly Lys Pro Thr Tyr Ala Glu Glu Phe
 50                  55                  60

Lys Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg Arg Gly Asp Tyr Arg Tyr Ala Trp Phe Leu Tyr Trp Gly Gln
            100                 105                 110
```

```
Gly Thr Leu Val Thr Val Ser Ser
        115                 120
```

<210> SEQ ID NO 219
<211> LENGTH: 109
<212> TYPE: PRT
<213> ORGANISM: Artificial Sequence
<220> FEATURE:
<223> OTHER INFORMATION: Synthetic Construct

<400> SEQUENCE: 219

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Ser Asn Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Thr
                85                  90                  95

His Phe Val Phe Gly Thr Gly Thr Lys Val Thr Val Leu
            100                 105
```

<210> SEQ ID NO 220
<211> LENGTH: 120
<212> TYPE: PRT
<213> ORGANISM: Artificial Sequence
<220> FEATURE:
<223> OTHER INFORMATION: Synthetic Construct

<400> SEQUENCE: 220

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Lys Pro Thr Tyr Ala Glu Glu Phe
    50                  55                  60

Lys Gly Arg Phe Val Phe Ser Leu Glu Thr Ser Ala Ser Thr Thr Tyr
65                  70                  75                  80

Leu Gln Ile Asn Asn Leu Lys Asn Glu Asp Thr Ala Thr Tyr Phe Cys
                85                  90                  95

Ala Arg Arg Gly Asp Tyr Arg Tyr Ala Trp Phe Leu Tyr Trp Gly Gln
            100                 105                 110

Gly Thr Leu Val Thr Val Ser Ala
        115                 120
```

<210> SEQ ID NO 221
<211> LENGTH: 108
<212> TYPE: PRT
<213> ORGANISM: Artificial Sequence
<220> FEATURE:
<223> OTHER INFORMATION: Synthetic Construct

<400> SEQUENCE: 221

```
Gln Ala Val Val Thr Gln Glu Ser Ala Leu Thr Thr Ser Pro Gly Gly
```

```
                1               5                  10                 15
            Thr Val Ile Leu Thr Cys Arg Ser Ser Thr Gly Ala Val Thr Ser
                            20                  25                  30

Asn Tyr Ala Asn Trp Val Gln Glu Lys Pro Asp His Leu Phe Thr Gly
                        35                  40                  45

Leu Ile Gly Gly Thr Ser Asn Arg Ala Pro Gly Val Pro Val Arg Phe
                    50                  55                  60

Ser Gly Ser Leu Ile Gly Asp Lys Ala Ala Leu Thr Ile Thr Gly Ala
            65                  70                  75                  80

Gln Thr Glu Asp Asp Ala Met Tyr Phe Cys Ala Leu Trp Tyr Ser Thr
                            85                  90                  95

His Phe Val Phe Gly Gly Gly Thr Lys Val Thr Val
                            100                 105
```

<210> SEQ ID NO 222
<211> LENGTH: 117
<212> TYPE: PRT
<213> ORGANISM: Artificial Sequence
<220> FEATURE:
<223> OTHER INFORMATION: Synthetic Construct

<400> SEQUENCE: 222

```
            Glu Val Gln Leu Val Gln Ser Gly Ala Glu Val Lys Lys Pro Gly Ala
            1               5                  10                  15

Ser Val Lys Val Ser Cys Lys Ala Ser Gly Tyr Thr Phe Thr Ser Tyr
                            20                  25                  30

Tyr Ile His Trp Val Arg Gln Ala Pro Gly Gln Gly Leu Glu Trp Ile
                        35                  40                  45

Gly Trp Ile Tyr Pro Gly Asn Val Asn Thr Lys Tyr Asn Glu Lys Phe
                    50                  55                  60

Lys Gly Arg Val Thr Ile Thr Arg Asp Thr Ser Thr Ser Thr Ala Tyr
            65                  70                  75                  80

Leu Glu Leu Ser Ser Leu Arg Ser Glu Asp Thr Ala Val Tyr Tyr Cys
                            85                  90                  95

Ala Arg Asn His Asp Tyr Tyr Phe Asp Tyr Trp Gly Gln Gly Thr Leu
                            100                 105                 110

Val Thr Val Ser Ser
                    115
```

<210> SEQ ID NO 223
<211> LENGTH: 112
<212> TYPE: PRT
<213> ORGANISM: Artificial Sequence
<220> FEATURE:
<223> OTHER INFORMATION: Synthetic Construct

<400> SEQUENCE: 223

```
            Asp Ile Val Met Thr Gln Ser Pro Asp Ser Leu Ala Val Ser Leu Gly
            1               5                  10                  15

Glu Arg Ala Thr Ile Asn Cys Lys Ser Ser Gln Ser Leu Leu Asn Ser
                            20                  25                  30

Arg Thr Arg Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                    50                  55                  60

Pro Asp Arg Phe Ser Gly Ser Gly Ser Gly Thr Asp Phe Thr Leu Thr
            65                  70                  75                  80
```

```
Ile Ser Ser Leu Gln Ala Glu Asp Val Ala Val Tyr Tyr Cys Lys Gln
                85                  90                  95

Ser Tyr Ile Leu Arg Thr Phe Gly Gln Gly Thr Lys Val Glu Ile Lys
            100                 105                 110

<210> SEQ ID NO 224
<211> LENGTH: 117
<212> TYPE: PRT
<213> ORGANISM: Artificial Sequence
<220> FEATURE:
<223> OTHER INFORMATION: Synthetic Construct

<400> SEQUENCE: 224

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Arg Leu Glu Trp Met
        35                  40                  45

Gly Trp Ile Tyr Pro Gly Asn Val Asn Thr Lys Tyr Asn Glu Lys Phe
    50                  55                  60

Lys Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn His Asp Tyr Tyr Phe Asp Tyr Trp Gly Gln Gly Thr Leu
            100                 105                 110

Val Thr Val Ser Ser
            115

<210> SEQ ID NO 225
<211> LENGTH: 112
<212> TYPE: PRT
<213> ORGANISM: Artificial Sequence
<220> FEATURE:
<223> OTHER INFORMATION: Synthetic Construct

<400> SEQUENCE: 225

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ile Leu Arg Thr Phe Gly Gln Gly Thr Lys Val Glu Ile Lys
            100                 105                 110

<210> SEQ ID NO 226
<211> LENGTH: 117
<212> TYPE: PRT
<213> ORGANISM: Mus musculus

<400> SEQUENCE: 226
```

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Ile His Trp Met Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Asn Ser Ser Thr Ala Asn
65                  70                  75                  80

Met Gln Leu Ser Ser Leu Thr Ser Glu Asp Ser Ala Val Tyr Phe Cys
            85                  90                  95

Ala Arg Asn His Asp Tyr Tyr Phe Asp Tyr Trp Gly Gln Gly Thr Thr
            100                 105                 110

Leu Thr Val Ser Ser
            115

<210> SEQ ID NO 227
<211> LENGTH: 112
<212> TYPE: PRT
<213> ORGANISM: Mus musculus

<400> SEQUENCE: 227

Asp Ile Val Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
            85                  90                  95

Ser Tyr Ile Leu Arg Thr Phe Gly Gly Gly Thr Lys Leu Glu Ile Lys
            100                 105                 110

<210> SEQ ID NO 228
<211> LENGTH: 119
<212> TYPE: PRT
<213> ORGANISM: Artificial Sequence
<220> FEATURE:
<223> OTHER INFORMATION: Synthetic Construct

<400> SEQUENCE: 228

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Ala Ile His Trp Ile Arg Gln Pro Pro Gly Lys Gly Leu Glu Trp Ile
        35                  40                  45

Gly Val Ile Trp Ala Gly Gly Asn Thr Lys Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala

```
            85                  90                  95

Arg Glu Asp Ser Ser Gly Tyr Val Ala Leu Asp Tyr Trp Gly Gln Gly
            100                 105                 110

Thr Leu Val Thr Val Ser Ser
        115

<210> SEQ ID NO 229
<211> LENGTH: 112
<212> TYPE: PRT
<213> ORGANISM: Artificial Sequence
<220> FEATURE:
<223> OTHER INFORMATION: Synthetic Construct

<400> SEQUENCE: 229

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Ser Gly
            20                  25                  30

Arg Thr Arg Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Tyr Leu Leu Thr Phe Gly Gln Gly Thr Lys Val Glu Ile Lys
            100                 105                 110

<210> SEQ ID NO 230
<211> LENGTH: 119
<212> TYPE: PRT
<213> ORGANISM: Mus musculus

<400> SEQUENCE: 230

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Ile His Trp Val Arg Gln Pro Pro Gly Lys Gly Leu Asp Trp Leu
        35                  40                  45

Gly Val Ile Trp Ala Gly Gly Asn Thr Lys Tyr Asn Ser Ala Leu Met
    50                  55                  60

Ser Arg Leu Ser Phe Ser Lys Asp Asn Ser Lys Ser Gln Val Phe Leu
65                  70                  75                  80

Glu Ile Asn Ser Leu Gln Thr Asp Asp Thr Ala Met Tyr Tyr Cys Ala
                85                  90                  95

Arg Glu Asp Ser Ser Gly Tyr Val Ala Leu Asp Tyr Trp Gly Gln Gly
            100                 105                 110

Thr Ser Val Thr Val Ser Ser
        115

<210> SEQ ID NO 231
<211> LENGTH: 112
<212> TYPE: PRT
<213> ORGANISM: Mus musculus

<400> SEQUENCE: 231
```

-continued

Asn Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Ser Gly
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Leu Thr Phe Gly Ala Gly Thr Lys Leu Glu Leu Lys
            100                 105                 110

<210> SEQ ID NO 232
<211> LENGTH: 119
<212> TYPE: PRT
<213> ORGANISM: Artificial Sequence
<220> FEATURE:
<223> OTHER INFORMATION: Synthetic Construct

<400> SEQUENCE: 232

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
            20                  25                  30

Ala Ile His Trp Val Arg Gln Ala Pro Gly Lys Gly Leu Glu Trp Val
        35                  40                  45

Gly Val Ile Trp Ala Gly Gly Asn Thr Lys Tyr Asn Ser Ala Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Asp Ser Ser Gly Tyr Val Ala Leu Asp Tyr Trp Gly Gln Gly
            100                 105                 110

Thr Leu Val Thr Val Ser Ser
        115

<210> SEQ ID NO 233
<211> LENGTH: 112
<212> TYPE: PRT
<213> ORGANISM: Artificial Sequence
<220> FEATURE:
<223> OTHER INFORMATION: Synthetic Construct

<400> SEQUENCE: 233

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Tyr Leu Leu Thr Phe Gly Gln Gly Thr Lys Val Glu Ile Lys
            100                 105                 110

<210> SEQ ID NO 234
<211> LENGTH: 120
<212> TYPE: PRT
<213> ORGANISM: Artificial Sequence
<220> FEATURE:
<223> OTHER INFORMATION: Synthetic Construct

<400> SEQUENCE: 234

Glu Val Gln Leu Val Glu Ser Gly Gly Gly Val Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Glu Lys Gly Leu Glu Trp Val
        35                  40                  45

Gly Arg Ile Arg Ser Arg Ala Asn Ser Tyr Ala Thr Ala Tyr Ala Ala
    50                  55                  60

Ser Val Lys Asp Arg Phe Thr Ile Ser Arg Asp Asn Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Ile Arg Asp Thr Met Val Arg Gly Ile Asp Tyr Trp Gly Gln
            100                 105                 110

Gly Thr Leu Val Thr Val Ser Ser
            115                 120

<210> SEQ ID NO 235
<211> LENGTH: 113
<212> TYPE: PRT
<213> ORGANISM: Artificial Sequence
<220> FEATURE:
<223> OTHER INFORMATION: Synthetic Construct

<400> SEQUENCE: 235

Asp Ile Gln Met Thr Gln Ser Pro Ser Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Leu Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Val Pro Trp Thr Phe Gly Gln Gly Thr Lys Val Glu Ile
            100                 105                 110

Lys

<210> SEQ ID NO 236
<211> LENGTH: 117
<212> TYPE: PRT
<213> ORGANISM: Artificial Sequence

```
<220> FEATURE:
<223> OTHER INFORMATION: Synthetic Construct

<400> SEQUENCE: 236

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Asp
            20                  25                  30

Tyr Ile His Trp Met Arg Gln Arg Pro Gly Gln Gly Leu Glu Trp Ile
        35                  40                  45

Gly Trp Ile Tyr Phe Gly Asn Val Asn Thr Lys Tyr Asn Glu Lys Phe
    50                  55                  60

Lys Gly Lys Ala Ile Leu Thr Ala Asp Lys Phe Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Gly Gly Tyr Tyr Phe Asp Tyr Trp Gly Gln Gly Thr Thr
            100                 105                 110

Leu Thr Val Ser Ser
        115

<210> SEQ ID NO 237
<211> LENGTH: 112
<212> TYPE: PRT
<213> ORGANISM: Artificial Sequence
<220> FEATURE:
<223> OTHER INFORMATION: Synthetic Construct

<400> SEQUENCE: 237

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Thr Leu Arg Thr Phe Gly Gln Gly Thr Lys Val Glu Ile Lys
            100                 105                 110

<210> SEQ ID NO 238
<211> LENGTH: 117
<212> TYPE: PRT
<213> ORGANISM: Artificial Sequence
<220> FEATURE:
<223> OTHER INFORMATION: Synthetic Construct

<400> SEQUENCE: 238

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser His
            20                  25                  30

Tyr Leu His Trp Val Lys Gln Ser Pro Gly Gln Gly Leu Glu Trp Ile
        35                  40                  45
```

```
Val Trp Ile Asn Pro Gly Asp Gly Asn Val Lys Tyr Asn Glu Lys Phe
     50                  55                  60

Lys Asp Lys Thr Thr Val Thr Ala Asp Arg Ser Ser Thr Thr Val His
 65                  70                  75                  80

Met Phe Leu Ser Ser Leu Thr Ser Glu Asp Ser Ala Ile Tyr Phe Cys
                 85                  90                  95

Ala Arg Asp Gly Ala Tyr Tyr Phe Asp Tyr Trp Gly Gln Gly Thr Thr
                100                 105                 110

Leu Thr Val Ser Ser
            115

<210> SEQ ID NO 239
<211> LENGTH: 112
<212> TYPE: PRT
<213> ORGANISM: Artificial Sequence
<220> FEATURE:
<223> OTHER INFORMATION: Synthetic Construct

<400> SEQUENCE: 239

Asp Ile Val Met Thr Gln Ser Pro Ser Ser Leu Ala Val Ser Ala Gly
 1               5                  10                  15

Glu Thr Val Thr Met Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Thr Val Gln Ala Glu Asp Leu Ala Val Tyr Tyr Cys Lys Gln
                 85                  90                  95

Ser Tyr Thr Leu Arg Thr Phe Gly Gln Gly Thr Lys Val Glu Ile Lys
                100                 105                 110

<210> SEQ ID NO 240
<211> LENGTH: 117
<212> TYPE: PRT
<213> ORGANISM: Artificial Sequence
<220> FEATURE:
<223> OTHER INFORMATION: Synthetic Construct

<400> SEQUENCE: 240

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Ser Tyr
                 20                  25                  30

Tyr Ile His Trp Val Lys Gln Arg Pro Gly Gln Gly Leu Glu Trp Ile
             35                  40                  45

Gly Trp Ile Phe Pro Gly Ser Asp Asn Thr Lys Tyr Asn Glu Lys Phe
     50                  55                  60

Lys Gly Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Asn Gly Asn Tyr Ala Met Asp Tyr Trp Gly Gln Gly Thr Ser
                100                 105                 110

Val Thr Val Ser Ser
            115
```

<210> SEQ ID NO 241
<211> LENGTH: 112
<212> TYPE: PRT
<213> ORGANISM: Artificial Sequence
<220> FEATURE:
<223> OTHER INFORMATION: Synthetic Construct

<400> SEQUENCE: 241

Glu Ile Val Leu Ser Gln Ser Pro Ser Leu Ala Val Ser Ala Gly
1               5                   10                  15

Glu Lys Val Thr Met Ser Cys Lys Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Thr Leu Arg Thr Phe Gly Gly Gly Thr Lys Leu Glu Ile Lys
            100                 105                 110

<210> SEQ ID NO 242
<211> LENGTH: 117
<212> TYPE: PRT
<213> ORGANISM: Artificial Sequence
<220> FEATURE:
<223> OTHER INFORMATION: Synthetic Construct

<400> SEQUENCE: 242

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Ile His Trp Met Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Asn Ser Ser Thr Ala Asn
65                  70                  75                  80

Met Gln Leu Ser Ser Leu Thr Ser Glu Asp Ser Ala Val Tyr Phe Cys
                85                  90                  95

Ala Arg Asn His Asp Tyr Tyr Phe Asp Tyr Trp Gly Gln Gly Thr Thr
            100                 105                 110

Leu Thr Val Ser Ser
        115

<210> SEQ ID NO 243
<211> LENGTH: 112
<212> TYPE: PRT
<213> ORGANISM: Artificial Sequence
<220> FEATURE:
<223> OTHER INFORMATION: Synthetic Construct

<400> SEQUENCE: 243

Gly Ile Val Met Thr Gln Ser Pro Ser Ser Leu Ala Val Ser Ala Gly
1               5                   10                  15

```
Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                85                  90                  95

Ser Tyr Ile Leu Arg Thr Phe Gly Gly Gly Thr Lys Leu Glu Ile Lys
                100                 105                 110

<210> SEQ ID NO 244
<211> LENGTH: 120
<212> TYPE: PRT
<213> ORGANISM: Artificial Sequence
<220> FEATURE:
<223> OTHER INFORMATION: Synthetic Construct

<400> SEQUENCE: 244

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Asn Thr Gly Lys Pro Thr Tyr Ala Glu Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Arg Gly Asp Tyr Arg Tyr Ala Trp Phe Thr Tyr Trp Gly Gln
                100                 105                 110

Gly Thr Leu Val Thr Val Ser Ala
            115                 120

<210> SEQ ID NO 245
<211> LENGTH: 108
<212> TYPE: PRT
<213> ORGANISM: Artificial Sequence
<220> FEATURE:
<223> OTHER INFORMATION: Synthetic Construct

<400> SEQUENCE: 245

Gln Ala Val Val Thr Gln Glu Ser Ala Leu Thr Thr Ser Pro Gly Gly
 1               5                  10                  15

Thr Val Ile Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Ser Asn Arg Ala Pro Gly Val Pro Val Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Asp Ala Met Tyr Phe Cys Ala Leu Trp Tyr Ser Thr
                85                  90                  95
```

His Phe Val Phe Gly Gly Gly Thr Lys Val Thr Val
            100                 105

<210> SEQ ID NO 246
<211> LENGTH: 119
<212> TYPE: PRT
<213> ORGANISM: Artificial Sequence
<220> FEATURE:
<223> OTHER INFORMATION: Synthetic Construct

<400> SEQUENCE: 246

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Ser Phe Thr Asn Tyr
            20                  25                  30

Tyr Ile His Trp Met Lys Gln Arg Pro Gly Gln Gly Leu Glu Trp Ile
        35                  40                  45

Gly Trp Ile Tyr Pro Gly Ser Asp Asn Thr Lys Phe Asn Asp Lys Phe
    50                  55                  60

Lys Gly Lys Ala Thr Leu Thr Ala Asp Thr Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Ser Ile Thr Asn Tyr Tyr Phe Asp Tyr Trp Gly Gln Gly
            100                 105                 110

Thr Thr Leu Thr Val Ser Ser
        115

<210> SEQ ID NO 247
<211> LENGTH: 112
<212> TYPE: PRT
<213> ORGANISM: Artificial Sequence
<220> FEATURE:
<223> OTHER INFORMATION: Synthetic Construct

<400> SEQUENCE: 247

Asp Val Val Met Thr Gln Thr Pro Ser Ser Leu Ala Val Ser Thr Gly
1               5                   10                  15

Glu Lys Val Thr Met Thr Cys Lys Ser Ser Gln Ser Leu Leu Asn Ile
            20                  25                  30

Arg Thr Arg Lys Asn Cys Leu Ala Trp Tyr Gln Gln Lys Pro Gly Gln
        35                  40                  45

Ser Pro Lys Leu Leu Ile Phe Trp Ala Ser Thr Arg Tyr Ser Gly Val
    50                  55                  60

Pro Asp Arg Phe Thr Gly Ser Gly Ser Gly Thr Asp Phe Thr Leu Thr
65                  70                  75                  80

Ile Arg Ser Val Gln Pro Glu Asp Leu Ala Val Tyr Tyr Cys Thr Gln
                85                  90                  95

Ser Tyr Thr Leu Arg Thr Phe Gly Gly Gly Thr Lys Leu Glu Ile Lys
            100                 105                 110

<210> SEQ ID NO 248
<211> LENGTH: 119
<212> TYPE: PRT
<213> ORGANISM: Artificial Sequence
<220> FEATURE:
<223> OTHER INFORMATION: Synthetic Construct

<400> SEQUENCE: 248

Gln Val Gln Leu Gln Gln Ser Gly Ser Glu Leu Val Arg Pro Gly Ala
1               5                   10                  15

Ser Leu Lys Leu Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Ile
            35                  40                  45

Gly Asn Phe Tyr Pro Gly Asp Leu Thr Val Asn Tyr Asp Glu Lys Phe
        50                  55                  60

Lys Asn Lys Val Thr Leu Ala Val Asp Thr Ser Ser Thr Ala Phe
65                  70                  75                  80

Leu Gln Leu Ser Ser Leu Thr Ser Glu Asp Ser Ala Val Tyr Tyr Cys
                85                  90                  95

Thr Arg Asp Ala Tyr Ser Arg Tyr Phe Phe Asp Tyr Trp Gly Gln Gly
            100                 105                 110

Thr Thr Leu Thr Val Ser Ser
            115

<210> SEQ ID NO 249
<211> LENGTH: 112
<212> TYPE: PRT
<213> ORGANISM: Artificial Sequence
<220> FEATURE:
<223> OTHER INFORMATION: Synthetic Construct

<400> SEQUENCE: 249

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Cys Gln
                85                  90                  95

Ser Phe Ile Leu Arg Thr Phe Gly Gly Gly Thr Lys Leu Glu Ile Lys
            100                 105                 110

<210> SEQ ID NO 250
<211> LENGTH: 119
<212> TYPE: PRT
<213> ORGANISM: Artificial Sequence
<220> FEATURE:
<223> OTHER INFORMATION: Synthetic Construct

<400> SEQUENCE: 250

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asn Tyr
                20                  25                  30

Tyr Met His Trp Val Lys Gln Arg Pro Gly Gln Gly Leu Glu Trp Ile
            35                  40                  45

Gly Trp Ile Ser Pro Gly Ser Gly Ser Ile Tyr Asn Glu Lys Phe
        50                  55                  60

Lys Gly Lys Ala Thr Leu Thr Ala Asp Thr Ser Ser Ser Thr Ala Tyr
65                  70                  75                  80

```
Met Gln Leu Ser Ser Leu Thr Ser Glu Asp Ser Ala Val Tyr Tyr Cys
            85                   90                  95

Ala Arg Asp Gly Tyr Ser Leu Tyr Phe Phe Asp Phe Trp Gly Gln Gly
            100                 105                 110

Thr Thr Leu Thr Val Ser Ser
        115

<210> SEQ ID NO 251
<211> LENGTH: 112
<212> TYPE: PRT
<213> ORGANISM: Artificial Sequence
<220> FEATURE:
<223> OTHER INFORMATION: Synthetic Construct

<400> SEQUENCE: 251

Asp Ile Val Met Thr Gln Ser Pro Ser Ser Leu Ala Val Ser Ala Gly
1               5                   10                  15

Glu Lys Val Thr Met Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
            85                  90                  95

Ser Phe Ile Leu Arg Thr Phe Gly Gly Gly Thr Lys Leu Glu Leu Lys
            100                 105                 110

<210> SEQ ID NO 252
<211> LENGTH: 119
<212> TYPE: PRT
<213> ORGANISM: Artificial Sequence
<220> FEATURE:
<223> OTHER INFORMATION: Synthetic Construct

<400> SEQUENCE: 252

Gln Val Gln Leu Gln Gln Ser Gly Pro Glu Leu Val Lys Pro Gly Thr
1               5                   10                  15

Ser Val Lys Ile Ser Cys Lys Thr Ser Gly Tyr Ser Phe Ile Asn Tyr
            20                  25                  30

Tyr Thr His Trp Val Lys Gln Arg Pro Gly Gln Gly Leu Glu Trp Ile
        35                  40                  45

Gly Trp Ile Tyr Pro Gly Asn Gly Asn Ile Lys Tyr Asn Glu Lys Phe
    50                  55                  60

Met Gly Lys Ala Thr Leu Thr Ala Asp Thr Ser Ser Thr Thr Ala His
65                  70                  75                  80

Met His Leu Ser Ser Leu Val Ser Glu Asp Ser Ala Val Tyr Tyr Cys
            85                  90                  95

Ala Arg Asp Ser Tyr Gly Ser Tyr Tyr Phe Asp Tyr Trp Gly Gln Gly
            100                 105                 110

Thr Thr Leu Thr Val Ser Ser
        115

<210> SEQ ID NO 253
<211> LENGTH: 112
<212> TYPE: PRT
```

<213> ORGANISM: Artificial Sequence
<220> FEATURE:
<223> OTHER INFORMATION: Synthetic Construct

<400> SEQUENCE: 253

Asp Ile Val Met Thr Gln Ser Pro Ser Leu Ala Val Ser Val Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
                100                 105                 110

<210> SEQ ID NO 254
<211> LENGTH: 119
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Gln Gln Ser Gly Pro Glu Leu Val Lys Pro Gly Thr
1               5                   10                  15

Ser Val Lys Ile Ser Cys Lys Thr Ser Gly Tyr Asn Phe Ile Asn Tyr
            20                  25                  30

Tyr Thr His Trp Val Lys Gln Arg Pro Gly Gln Gly Leu Glu Trp Ile
        35                  40                  45

Gly Trp Ile Tyr Pro Gly Asn Gly Asn Ile Lys Tyr Asn Glu Lys Phe
    50                  55                  60

Met Gly Lys Ala Thr Leu Thr Ala Asp Thr Ser Ser Thr Thr Ala His
65                  70                  75                  80

Met His Leu Ser Ser Leu Val Ser Glu Asp Ser Ala Val Tyr Tyr Cys
                85                  90                  95

Ala Arg Asp Ser Tyr Gly Ser Tyr Tyr Phe Asp Tyr Trp Gly Gln Gly
                100                 105                 110

Thr Thr Leu Thr Val Ser Ser
        115

<210> SEQ ID NO 255
<211> LENGTH: 112
<212> TYPE: PRT
<213> ORGANISM: Artificial Sequence
<220> FEATURE:
<223> OTHER INFORMATION: Synthetic Construct

<400> SEQUENCE: 255

Asp Ile Val Met Thr Gln Ser Pro Ser Leu Ala Val Ser Ala Gly
1               5                   10                  15

Glu Lys Val Thr Met Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Ile Leu Arg Thr Phe Gly Gly Gly Thr Lys Leu Glu Ile Lys
                100                 105                 110

<210> SEQ ID NO 256
<211> LENGTH: 119
<212> TYPE: PRT
<213> ORGANISM: Artificial Sequence
<220> FEATURE:
<223> OTHER INFORMATION: Synthetic Construct

<400> SEQUENCE: 256

Gln Val Gln Leu Gln Gln Ser Gly Pro Glu Leu Val Lys Pro Gly Ala
1               5                   10                  15

Ser Leu Lys Ile Ser Cys Lys Ala Ser Gly Tyr Ser Phe Ala Asn Tyr
                20                  25                  30

Tyr Thr His Trp Val Arg Gln Arg Pro Gly Gln Gly Leu Glu Trp Ile
            35                  40                  45

Gly Trp Leu Tyr Pro Gly Asn Gly Asp Thr Arg Tyr Asn Glu Lys Phe
        50                  55                  60

Lys Asp Lys Ala Thr Leu Thr Ala Asp Thr Ser Ser Asn Thr Ala Ser
65                  70                  75                  80

Met Gln Leu Asn Ser Leu Thr Ser Glu Asp Ser Ala Val Tyr Tyr Cys
                85                  90                  95

Thr Arg Asp Ser Tyr Gly Asn Tyr Phe Phe Asp Tyr Trp Gly Gln Gly
                100                 105                 110

Thr Thr Leu Ile Val Ser Ser
            115

<210> SEQ ID NO 257
<211> LENGTH: 112
<212> TYPE: PRT
<213> ORGANISM: Artificial Sequence
<220> FEATURE:
<223> OTHER INFORMATION: Synthetic Construct

<400> SEQUENCE: 257

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Phe Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Ile Leu Arg Thr Phe Gly Gly Gly Thr Lys Leu Glu Leu Lys
                100                 105                 110

```
<210> SEQ ID NO 258
<211> LENGTH: 119
<212> TYPE: PRT
<213> ORGANISM: Artificial Sequence
<220> FEATURE:
<223> OTHER INFORMATION: Synthetic Construct

<400> SEQUENCE: 258

Gln Val Gln Leu Gln Gln Ser Gly Ser Glu Leu Val Arg Pro Gly Ala
1               5                   10                  15

Ser Leu Lys Leu Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Ile
        35                  40                  45

Gly Asn Ser Tyr Pro Gly Asp Leu Asn Val Asn Tyr Asp Glu Lys Phe
    50                  55                  60

Lys Asn Lys Val Thr Leu Ala Val Asp Thr Ser Ser Thr Ala Phe
65                  70                  75                  80

Leu Gln Leu Ser Ser Leu Thr Ser Glu Asp Ser Ala Val Tyr Tyr Cys
            85                  90                  95

Thr Arg Asp Ala Tyr Ser Arg Tyr Phe Phe Asp Tyr Trp Gly Gln Gly
            100                 105                 110

Thr Thr Leu Thr Val Ser Ser
        115

<210> SEQ ID NO 259
<211> LENGTH: 112
<212> TYPE: PRT
<213> ORGANISM: Artificial Sequence
<220> FEATURE:
<223> OTHER INFORMATION: Synthetic Construct

<400> SEQUENCE: 259

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Cys Gln
            85                  90                  95

Ser Phe Ile Leu Arg Thr Phe Gly Gly Gly Thr Lys Leu Glu Ile Lys
            100                 105                 110

<210> SEQ ID NO 260
<211> LENGTH: 119
<212> TYPE: PRT
<213> ORGANISM: Artificial Sequence
<220> FEATURE:
<223> OTHER INFORMATION: Synthetic Construct

<400> SEQUENCE: 260

Gln Val Gln Leu Gln Gln Ser Gly Pro Glu Met Val Lys Pro Gly Ala
1               5                   10                  15

Ser Val Thr Ile Ser Cys Lys Thr Ser Gly Phe Thr Phe Thr Ser Tyr
            20                  25                  30
```

```
Tyr Ile His Trp Met Met Gln Arg Pro Gly Gln Gly Leu Glu Trp Ile
            35                  40                  45

Gly Trp Leu Tyr Pro Gly Asp Val Ser Thr Arg Tyr Asn Glu Lys Phe
        50                  55                  60

Arg Asp Lys Ala Thr Leu Thr Ala Asp Lys Ser Ser Thr Thr Ala Tyr
 65                  70                  75                  80

Leu Tyr Leu Ser Ser Leu Thr Ser Glu Asp Ser Ala Val Tyr Phe Cys
                85                  90                  95

Ala Arg Asp Ser Ser Ala Ser Tyr Tyr Phe Asp Phe Trp Gly Gln Gly
                100                 105                 110

Thr Thr Leu Thr Val Ser Ser
            115

<210> SEQ ID NO 261
<211> LENGTH: 112
<212> TYPE: PRT
<213> ORGANISM: Artificial Sequence
<220> FEATURE:
<223> OTHER INFORMATION: Synthetic Construct

<400> SEQUENCE: 261

Asp Ile Val Met Thr Gln Ser Pro Ser Ser Leu Ala Val Ser Ala Gly
 1               5                  10                  15

Glu Met Val Thr Leu His Cys Lys Ser Ser Gln Ser Leu Leu Asn Ile
            20                  25                  30

Arg Thr Arg Lys Asn Tyr Leu Ala Trp Tyr Leu Gln Lys Pro Gly Gln
            35                  40                  45

Ser Pro Arg Leu Leu Ile Tyr Trp Ala Ser Thr Arg Ala Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Gln Pro Glu Asp Leu Ala Val Tyr Tyr Cys Thr Gln
                85                  90                  95

Ser Phe Ile Leu Arg Thr Phe Gly Gly Gly Thr Lys Leu Glu Leu Lys
                100                 105                 110

<210> SEQ ID NO 262
<211> LENGTH: 119
<212> TYPE: PRT
<213> ORGANISM: Artificial Sequence
<220> FEATURE:
<223> OTHER INFORMATION: Synthetic Construct

<400> SEQUENCE: 262

Gln Val Gln Leu Gln Gln Pro Gly Ser Glu Leu Val Arg Pro Gly Ala
 1               5                  10                  15

Ser Val Thr Leu Ser Cys Thr Ala Ser Gly Tyr Ser Phe Thr Ser Tyr
            20                  25                  30

Trp Met His Trp Val Lys Gln Arg Pro Gly Gln Gly Leu Glu Trp Val
            35                  40                  45

Gly Asn Ile Tyr Pro Gly Gly Glu Ile Ile Asn Tyr Ala Glu Lys Phe
        50                  55                  60

Lys Thr Lys Gly Thr Leu Thr Val Asp Ile Ser Ser Ser Thr Ala Tyr
 65                  70                  75                  80

Met His Leu Ser Ser Leu Thr Ser Asp Asp Ser Ala Val Tyr Tyr Cys
                85                  90                  95

Thr Arg Asp Thr Thr Gly Asn Tyr Phe Phe Asp Tyr Trp Gly Gln Gly
```

```
                    100                 105                 110

Thr Thr Leu Thr Val Ser Ser
            115

<210> SEQ ID NO 263
<211> LENGTH: 112
<212> TYPE: PRT
<213> ORGANISM: Artificial Sequence
<220> FEATURE:
<223> OTHER INFORMATION: Synthetic Construct

<400> SEQUENCE: 263

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Leu
        35                  40                  45

Ser Pro Lys Leu Leu Ile Tyr Trp Ala Ser Thr Arg Glu Ser Gly Val
    50                  55                  60

Pro Glu Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Thr Gln
                85                  90                  95

Ser Phe Ile Leu Arg Thr Phe Gly Gly Gly Thr Arg Leu Glu Ile Lys
            100                 105                 110

<210> SEQ ID NO 264
<211> LENGTH: 116
<212> TYPE: PRT
<213> ORGANISM: Artificial Sequence
<220> FEATURE:
<223> OTHER INFORMATION: Synthetic Construct

<400> SEQUENCE: 264

Gln Ser Val Lys Glu Ser Glu Gly Gly Leu Phe Lys Pro Thr Asp Thr
1               5                   10                  15

Leu Thr Leu Thr Cys Thr Val Ser Gly Cys Ser Leu Ser Ser Cys Ala
            20                  25                  30

Ile Ser Trp Val Arg Gln Ala Pro Gly Lys Gly Leu Glu Trp Ile Gly
        35                  40                  45

Phe Met Ser Val Thr Gly Ser Ala Tyr Tyr Ala Asn Trp Ala Lys Ser
    50                  55                  60

Arg Ser Thr Ile Thr Arg Asn Thr Asn Glu Asn Thr Val Thr Leu Lys
65                  70                  75                  80

Met Thr Arg Leu Thr Ala Ala Asp Thr Ala Ile Tyr Phe Cys Ala Arg
                85                  90                  95

Val Gly Ile Gly Ser Gly Leu Asn Ile Trp Gly Gln Gly Thr Leu Val
            100                 105                 110

Thr Val Ser Ser
            115

<210> SEQ ID NO 265
<211> LENGTH: 110
<212> TYPE: PRT
<213> ORGANISM: Artificial Sequence
<220> FEATURE:
<223> OTHER INFORMATION: Synthetic Construct

<400> SEQUENCE: 265
```

```
Asp Met Thr Gln Thr Pro Ser Ser Lys Ser Val Pro Val Gly Asp Thr
1               5                   10                  15

Val Thr Ile Asn Cys Gln Ala Ser Glu Thr Val Tyr Ser Asn Asn Tyr
            20                  25                  30

Leu Ala Trp Phe Gln Gln Lys Pro Gly Gln Pro Pro Lys Arg Leu Ile
        35                  40                  45

Tyr Gly Val Ser Thr Leu Asp Ser Gly Val Pro Pro Arg Phe Ser Gly
    50                  55                  60

Ser Gly Ser Gly Thr Gln Phe Thr Leu Thr Ile Ser Asp Val Val Cys
65              70                  75                  80

Asp Asp Ala Ala Thr Tyr Tyr Cys Ala Gly Tyr Lys Ser Thr Ser Ser
                85                  90                  95

Tyr Ala Ile Ala Phe Gly Gly Gly Thr Glu Leu Glu Ile Leu
                100                 105                 110
```

<210> SEQ ID NO 266
<211> LENGTH: 122
<212> TYPE: PRT
<213> ORGANISM: Artificial Sequence
<220> FEATURE:
<223> OTHER INFORMATION: Synthetic Construct

<400> SEQUENCE: 266

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
                100                 105                 110

Gly Gln Gly Thr Leu Val Thr Val Ser Ser
                115                 120
```

<210> SEQ ID NO 267
<211> LENGTH: 106
<212> TYPE: PRT
<213> ORGANISM: Artificial Sequence
<220> FEATURE:
<223> OTHER INFORMATION: Synthetic Construct

<400> SEQUENCE: 267

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
```

```
                65                  70                  75                  80
Asp Phe Ala Thr Tyr Tyr Cys Gln Gln Trp Ser Phe Asn Pro Pro Thr
                    85                  90                  95

Phe Gly Gln Gly Thr Lys Val Glu Ile Lys
                100                 105

<210> SEQ ID NO 268
<211> LENGTH: 120
<212> TYPE: PRT
<213> ORGANISM: Artificial Sequence
<220> FEATURE:
<223> OTHER INFORMATION: Synthetic Construct

<400> SEQUENCE: 268

Gln Val Gln Leu Lys Gln Ser Gly Pro Gly Leu Val Gln Pro Ser Gln
1               5                  10                  15

Ser Leu Ser Ile Thr Cys Thr Val Ser Gly Phe Ser Leu Thr Arg Phe
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Asn Ala Ala Phe Met
        50                  55                  60

Ser Arg Leu Thr Ile Thr Lys Asp Asn Ser Lys Ser Gln Val Phe Phe
65                  70                  75                  80

Lys Leu Asn Ser Leu Lys Val Asp Asp Thr Ala Ile Tyr Tyr Cys Ser
                85                  90                  95

Asn His Tyr Tyr Gly Ser Ser Asp Tyr Ala Leu Asp Asn Trp Gly Gln
                100                 105                 110

Gly Ile Ser Val Thr Val Ser Ser
        115                 120

<210> SEQ ID NO 269
<211> LENGTH: 107
<212> TYPE: PRT
<213> ORGANISM: Artificial Sequence
<220> FEATURE:
<223> OTHER INFORMATION: Synthetic Construct

<400> SEQUENCE: 269

Asp Ile Val Met Thr Gln Ser His Lys Ile Met Ser Thr Ser Val Gly
1               5                  10                  15

Asp Arg Val Ser Ile Thr Cys Lys Ala Ser Gln Asp Val Ser Asn Ile
                20                  25                  30

Val Val Trp Phe Gln Gln Lys Pro Gly Gln Ser Pro Asn Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Tyr
                85                  90                  95

Thr Phe Gly Gly Gly Thr Lys Leu Glu Ile Lys
                100                 105

<210> SEQ ID NO 270
<211> LENGTH: 120
<212> TYPE: PRT
<213> ORGANISM: Artificial Sequence
<220> FEATURE:
```

<223> OTHER INFORMATION: Synthetic Construct

<400> SEQUENCE: 270

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 271
<211> LENGTH: 107
<212> TYPE: PRT
<213> ORGANISM: Artificial Sequence
<220> FEATURE:
<223> OTHER INFORMATION: Synthetic Construct

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 272
<211> LENGTH: 120
<212> TYPE: PRT
<213> ORGANISM: Artificial Sequence
<220> FEATURE:
<223> OTHER INFORMATION: Synthetic Construct

<400> SEQUENCE: 272

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Thr Asn Tyr
            20                  25                  30

Gly Ile His Trp Val Arg Gln Ala Pro Gly Lys Gly Leu Glu Trp Val
        35                  40                  45

Gly Arg Ile Tyr Pro Asp Ser Gly Ala Thr Tyr Tyr Ala Asp Ser Val

```
                    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                     85                  90                  95

Ala Arg Lys Leu Trp Ile Ser Ile Ala Gly Met Asp Tyr Trp Gly Gln
                100                 105                 110

Gly Thr Leu Val Thr Val Ser Ser
            115                 120

<210> SEQ ID NO 273
<211> LENGTH: 108
<212> TYPE: PRT
<213> ORGANISM: Artificial Sequence
<220> FEATURE:
<223> OTHER INFORMATION: Synthetic Construct

<400> SEQUENCE: 273

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Ser Tyr Ala Thr Pro Phe
                 85                  90                  95

Thr Phe Gly Gln Gly Thr Lys Val Glu Ile Lys Arg
            100                 105

<210> SEQ ID NO 274
<211> LENGTH: 340
<212> TYPE: PRT
<213> ORGANISM: Artificial Sequence
<220> FEATURE:
<223> OTHER INFORMATION: Synthetic Construct

<400> SEQUENCE: 274

Gln Asp Gly Asn Glu Glu Met Gly Gly Ile Thr Gln Thr Pro Tyr Lys
 1               5                  10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
             35                  40                  45

Glu Asp Asp Lys Asn Ile Gly Ser Asp Glu Asp His Leu Ser Leu Lys
         50                  55                  60

Glu Phe Ser Glu Leu Glu Gln Ser Gly Tyr Tyr Val Cys Tyr Pro Arg
 65                  70                  75                  80

Gly Ser Lys Pro Glu Asp Ala Asn Phe Tyr Leu Tyr Leu Met Ala Arg
                 85                  90                  95

Val Ala Glu Asn Ser Met Glu Met Asp Lys Ile Glu Pro Arg Gly Pro
            100                 105                 110

Thr Ile Lys Pro Cys Pro Pro Cys Lys Cys Pro Ala Pro Asn Leu Leu
            115                 120                 125
```

```
Gly Gly Pro Ser Val Phe Ile Phe Pro Pro Lys Ile Lys Asp Val Leu
130                 135                 140

Met Ile Ser Leu Ser Pro Ile Val Thr Cys Val Val Asp Val Ser
145                 150                 155                 160

Glu Asp Asp Pro Asp Val Gln Ile Ser Trp Phe Val Asn Asn Val Glu
                165                 170                 175

Val His Thr Ala Gln Thr Gln Thr His Arg Glu Asp Tyr Asn Ser Thr
                180                 185                 190

Leu Arg Val Val Ser Ala Leu Pro Ile Gln His Gln Asp Trp Met Ser
            195                 200                 205

Gly Lys Glu Phe Lys Cys Lys Val Asn Asn Lys Asp Leu Pro Ala Pro
210                 215                 220

Ile Glu Arg Thr Ile Ser Lys Pro Lys Gly Ser Val Arg Ala Pro Gln
225                 230                 235                 240

Val Tyr Val Leu Pro Pro Glu Glu Glu Met Thr Lys Lys Gln Val
                245                 250                 255

Thr Leu Thr Cys Met Val Thr Asp Phe Met Pro Glu Asp Ile Tyr Val
                260                 265                 270

Glu Trp Thr Asn Asn Gly Lys Thr Glu Leu Asn Tyr Lys Asn Thr Glu
            275                 280                 285

Pro Val Leu Asp Ser Asp Gly Ser Tyr Phe Met Tyr Ser Lys Leu Arg
            290                 295                 300

Val Glu Lys Lys Asn Trp Val Glu Arg Asn Ser Tyr Ser Cys Ser Val
305                 310                 315                 320

Val His Glu Gly Leu His Asn His His Thr Thr Lys Ser Phe Ser Arg
                325                 330                 335

Thr Pro Gly Lys
            340

<210> SEQ ID NO 275
<211> LENGTH: 333
<212> TYPE: PRT
<213> ORGANISM: Artificial Sequence
<220> FEATURE:
<223> OTHER INFORMATION: Synthetic Construct

<400> SEQUENCE: 275

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
                20                  25                  30

Trp Phe Lys Asp Gly Lys Met Ile Gly Phe Leu Thr Glu Asp Lys Lys
            35                  40                  45

Lys Trp Asn Leu Gly Ser Asn Ala Lys Asp Pro Arg Gly Met Tyr Gln
50                  55                  60

Cys Lys Gly Ser Gln Asn Lys Ser Lys Pro Leu Gln Val Tyr Tyr Arg
65                  70                  75                  80

Met Ala Gln Asn Ala Ile Glu Leu Asn Ala Ala Thr Ile Ser Lys Val
                85                  90                  95

Thr Asp Lys Ile Glu Pro Arg Gly Pro Thr Ile Lys Pro Cys Pro Pro
                100                 105                 110

Cys Lys Cys Pro Ala Pro Asn Leu Leu Gly Gly Pro Ser Val Phe Ile
            115                 120                 125

Phe Pro Pro Lys Ile Lys Asp Val Leu Met Ile Ser Leu Ser Pro Ile
            130                 135                 140
```

```
Val Thr Cys Val Val Asp Val Ser Glu Asp Pro Asp Val Gln
145                 150                 155                 160

Ile Ser Trp Phe Val Asn Asn Val Glu Val His Thr Ala Gln Thr Gln
                    165                 170                 175

Thr His Arg Glu Asp Tyr Asn Ser Thr Leu Arg Val Val Ser Ala Leu
                180                 185                 190

Pro Ile Gln His Gln Asp Trp Met Ser Gly Lys Glu Phe Lys Cys Lys
                195                 200                 205

Val Asn Asn Lys Asp Leu Pro Ala Pro Ile Glu Arg Thr Ile Ser Lys
            210                 215                 220

Pro Lys Gly Ser Val Arg Ala Pro Gln Val Tyr Val Leu Pro Pro Pro
225                 230                 235                 240

Glu Glu Glu Met Thr Lys Lys Gln Val Thr Leu Thr Cys Met Val Thr
                245                 250                 255

Asp Phe Met Pro Glu Asp Ile Tyr Val Glu Trp Thr Asn Asn Gly Lys
                260                 265                 270

Thr Glu Leu Asn Tyr Lys Asn Thr Glu Pro Val Leu Asp Ser Asp Gly
                275                 280                 285

Ser Tyr Phe Met Tyr Ser Lys Leu Arg Val Glu Lys Lys Asn Trp Val
290                 295                 300

Glu Arg Asn Ser Tyr Ser Cys Ser Val Val His Glu Gly Leu His Asn
305                 310                 315                 320

His His Thr Thr Lys Ser Phe Ser Arg Thr Pro Gly Lys
                325                 330

<210> SEQ ID NO 276
<211> LENGTH: 331
<212> TYPE: PRT
<213> ORGANISM: Artificial Sequence
<220> FEATURE:
<223> OTHER INFORMATION: Synthetic Construct

<400> SEQUENCE: 276

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
                20                  25                  30

Gly Ser Glu Ala Gln Trp Gln His Asn Gly Lys Asn Lys Glu Asp Ser
            35                  40                  45

Gly Asp Arg Leu Phe Leu Pro Glu Phe Ser Glu Met Glu Gln Ser Gly
        50                  55                  60

Tyr Tyr Val Cys Tyr Pro Arg Gly Ser Asn Pro Glu Asp Ala Ser His
65                  70                  75                  80

His Leu Tyr Leu Met Ala Arg Val Ala Glu Asn Pro Met Glu Met Asp
                85                  90                  95

Lys Ile Glu Pro Arg Gly Pro Thr Ile Lys Pro Cys Pro Pro Cys Lys
                100                 105                 110

Cys Pro Ala Pro Asn Leu Leu Gly Gly Pro Ser Val Phe Ile Phe Pro
            115                 120                 125

Pro Lys Ile Lys Asp Val Leu Met Ile Ser Leu Ser Pro Ile Val Thr
        130                 135                 140

Cys Val Val Val Asp Val Ser Glu Asp Asp Pro Asp Val Gln Ile Ser
145                 150                 155                 160

Trp Phe Val Asn Asn Val Glu Val His Thr Ala Gln Thr Gln Thr His
                165                 170                 175
```

-continued

Arg Glu Asp Tyr Asn Ser Thr Leu Arg Val Val Ser Ala Leu Pro Ile
            180                 185                 190

Gln His Gln Asp Trp Met Ser Gly Lys Glu Phe Lys Cys Lys Val Asn
        195                 200                 205

Asn Lys Asp Leu Pro Ala Pro Ile Glu Arg Thr Ile Ser Lys Pro Lys
    210                 215                 220

Gly Ser Val Arg Ala Pro Gln Val Tyr Val Leu Pro Pro Glu Glu
225                 230                 235                 240

Glu Met Thr Lys Lys Gln Val Thr Leu Thr Cys Met Val Thr Asp Phe
                245                 250                 255

Met Pro Glu Asp Ile Tyr Val Glu Trp Thr Asn Asn Gly Lys Thr Glu
            260                 265                 270

Leu Asn Tyr Lys Asn Thr Glu Pro Val Leu Asp Ser Asp Gly Ser Tyr
        275                 280                 285

Phe Met Tyr Ser Lys Leu Arg Val Glu Lys Lys Asn Trp Val Glu Arg
    290                 295                 300

Asn Ser Tyr Ser Cys Ser Val Val His Glu Gly Leu His Asn His His
305                 310                 315                 320

Thr Thr Lys Ser Phe Ser Arg Thr Pro Gly Lys
                325                 330

<210> SEQ ID NO 277
<211> LENGTH: 332
<212> TYPE: PRT
<213> ORGANISM: Artificial Sequence
<220> FEATURE:
<223> OTHER INFORMATION: Synthetic Construct

<400> SEQUENCE: 277

Gln Ser Phe Glu Glu Asn Arg Lys Leu Asn Val Tyr Asn Gln Glu Asp
1               5                   10                  15

Gly Ser Val Leu Leu Thr Cys His Val Lys Asn Thr Asn Ile Thr Trp
            20                  25                  30

Phe Lys Glu Gly Lys Met Ile Asp Ile Leu Thr Ala His Lys Asn Lys
        35                  40                  45

Trp Asn Leu Gly Ser Asn Thr Lys Asp Pro Arg Gly Val Tyr Gln Cys
    50                  55                  60

Lys Gly Ser Lys Asp Lys Ser Lys Thr Leu Gln Val Tyr Tyr Arg Met
65                  70                  75                  80

Ala Gln Asn Ala Ile Glu Leu Asn Ala Ala Thr Ile Ser Lys Val Thr
                85                  90                  95

Asp Lys Ile Glu Pro Arg Gly Pro Thr Ile Lys Pro Cys Pro Pro Cys
            100                 105                 110

Lys Cys Pro Ala Pro Asn Leu Leu Gly Gly Pro Ser Val Phe Ile Phe
        115                 120                 125

Pro Pro Lys Ile Lys Asp Val Leu Met Ile Ser Leu Ser Pro Ile Val
130                 135                 140

Thr Cys Val Val Val Asp Val Ser Glu Asp Asp Pro Asp Val Gln Ile
145                 150                 155                 160

Ser Trp Phe Val Asn Asn Val Glu Val His Thr Ala Gln Thr Gln Thr
                165                 170                 175

His Arg Glu Asp Tyr Asn Ser Thr Leu Arg Val Val Ser Ala Leu Pro
            180                 185                 190

Ile Gln His Gln Asp Trp Met Ser Gly Lys Glu Phe Lys Cys Lys Val
        195                 200                 205

```
Asn Asn Lys Asp Leu Pro Ala Pro Ile Glu Arg Thr Ile Ser Lys Pro
    210                 215                 220
Lys Gly Ser Val Arg Ala Pro Gln Val Tyr Val Leu Pro Pro Glu
225                 230                 235                 240
Glu Glu Met Thr Lys Lys Gln Val Thr Leu Thr Cys Met Val Thr Asp
                    245                 250                 255
Phe Met Pro Glu Asp Ile Tyr Val Glu Trp Thr Asn Asn Gly Lys Thr
                260                 265                 270
Glu Leu Asn Tyr Lys Asn Thr Glu Pro Val Leu Asp Ser Asp Gly Ser
            275                 280                 285
Tyr Phe Met Tyr Ser Lys Leu Arg Val Glu Lys Lys Asn Trp Val Glu
290                 295                 300
Arg Asn Ser Tyr Ser Cys Ser Val Val His Glu Gly Leu His Asn His
305                 310                 315                 320
His Thr Thr Lys Ser Phe Ser Arg Thr Pro Gly Lys
                325                 330
```

<210> SEQ ID NO 278
<211> LENGTH: 28
<212> TYPE: PRT
<213> ORGANISM: Artificial Sequence
<220> FEATURE:
<223> OTHER INFORMATION: Synthetic Construct

<400> SEQUENCE: 278

```
Gln Asp Gly Asn Glu Glu Met Gly Gly Ile Thr Gln Thr Pro Tyr Lys
1               5                   10                  15
Val Ser Ile Ser Gly Thr Thr Val Ile Leu Thr Cys
            20                  25
```

<210> SEQ ID NO 279
<211> LENGTH: 28
<212> TYPE: PRT
<213> ORGANISM: Artificial Sequence
<220> FEATURE:
<223> OTHER INFORMATION: Synthetic Construct

<400> SEQUENCE: 279

```
Gln Asp Gly Asn Glu Glu Met Gly Ser Ile Thr Gln Thr Pro Tyr Gln
1               5                   10                  15
Val Ser Ile Ser Gly Thr Thr Val Ile Leu Thr Cys
            20                  25
```

<210> SEQ ID NO 280
<211> LENGTH: 254
<212> TYPE: PRT
<213> ORGANISM: Artificial Sequence
<220> FEATURE:
<223> OTHER INFORMATION: Synthetic Construct

<400> SEQUENCE: 280

```
Gln Asp Gly Asn Glu Glu Met Gly Gly Ile Thr Gln Thr Pro Tyr Lys
1               5                   10                  15
Val Ser Ile Ser Gly Thr Thr Val Ile Leu Thr Asp Lys Thr His Thr
            20                  25                  30
Cys Pro Pro Cys Pro Ala Pro Glu Leu Leu Gly Gly Pro Ser Val Phe
        35                  40                  45
Leu Phe Pro Pro Lys Pro Lys Asp Thr Leu Met Ile Ser Arg Thr Pro
    50                  55                  60
Glu Val Thr Cys Val Val Val Asp Val Ser His Glu Asp Pro Glu Val
```

```
                65                  70                  75                  80
Lys Phe Asn Trp Tyr Val Asp Gly Val Glu Val His Asn Ala Lys Thr
                    85                  90                  95
Lys Pro Arg Glu Glu Gln Tyr Asn Ser Thr Tyr Arg Val Val Ser Val
                100                 105                 110
Leu Thr Val Leu His Gln Asp Trp Leu Asn Gly Lys Glu Tyr Lys Cys
                115                 120                 125
Lys Val Ser Asn Lys Ala Leu Pro Ala Pro Ile Glu Lys Thr Ile Ser
130                 135                 140
Lys Ala Lys Gly Gln Pro Arg Glu Pro Gln Val Tyr Thr Leu Pro Pro
145                 150                 155                 160
Ser Arg Glu Glu Met Thr Lys Asn Gln Val Ser Leu Thr Cys Leu Val
                    165                 170                 175
Lys Gly Phe Tyr Pro Ser Asp Ile Ala Val Glu Trp Glu Ser Asn Gly
                180                 185                 190
Gln Pro Glu Asn Asn Tyr Lys Thr Thr Pro Pro Val Leu Asp Ser Asp
                195                 200                 205
Gly Ser Phe Phe Leu Tyr Ser Lys Leu Thr Val Asp Lys Ser Arg Trp
210                 215                 220
Gln Gln Gly Asn Val Phe Ser Cys Ser Val Met His Glu Ala Leu His
225                 230                 235                 240
Asn His Tyr Thr Gln Lys Ser Leu Ser Leu Ser Pro Gly Lys
                245                 250

<210> SEQ ID NO 281
<211> LENGTH: 254
<212> TYPE: PRT
<213> ORGANISM: Artificial Sequence
<220> FEATURE:
<223> OTHER INFORMATION: Synthetic Construct

<400> SEQUENCE: 281

Gln Asp Gly Asn Glu Glu Met Gly Ser Ile Thr Gln Thr Pro Tyr Gln
1               5                   10                  15
Val Ser Ile Ser Gly Thr Thr Val Ile Leu Thr Asp Lys Thr His Thr
                20                  25                  30
Cys Pro Pro Cys Pro Ala Pro Glu Leu Leu Gly Gly Pro Ser Val Phe
            35                  40                  45
Leu Phe Pro Pro Lys Pro Lys Asp Thr Leu Met Ile Ser Arg Thr Pro
        50                  55                  60
Glu Val Thr Cys Val Val Val Asp Val Ser His Glu Asp Pro Glu Val
65                  70                  75                  80
Lys Phe Asn Trp Tyr Val Asp Gly Val Glu Val His Asn Ala Lys Thr
                    85                  90                  95
Lys Pro Arg Glu Glu Gln Tyr Asn Ser Thr Tyr Arg Val Val Ser Val
                100                 105                 110
Leu Thr Val Leu His Gln Asp Trp Leu Asn Gly Lys Glu Tyr Lys Cys
                115                 120                 125
Lys Val Ser Asn Lys Ala Leu Pro Ala Pro Ile Glu Lys Thr Ile Ser
130                 135                 140
Lys Ala Lys Gly Gln Pro Arg Glu Pro Gln Val Tyr Thr Leu Pro Pro
145                 150                 155                 160
Ser Arg Glu Glu Met Thr Lys Asn Gln Val Ser Leu Thr Cys Leu Val
                    165                 170                 175
Lys Gly Phe Tyr Pro Ser Asp Ile Ala Val Glu Trp Glu Ser Asn Gly
```

```
                180                 185                 190

Gln Pro Glu Asn Asn Tyr Lys Thr Thr Pro Val Leu Asp Ser Asp
            195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 282
<211> LENGTH: 205
<212> TYPE: PRT
<213> ORGANISM: Artificial Sequence
<220> FEATURE:
<223> OTHER INFORMATION: Synthetic Construct

<400> SEQUENCE: 282

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Asp Asp Gly Ser Ala Asp Ala Lys Lys Asp Ala Ala Lys Lys
            100                 105                 110

Asp Asp Ala Lys Lys Asp Asp Ala Lys Lys Asp Gly Ser Gln Ser Ile
        115                 120                 125

Lys Gly Asn His Leu Val Lys Val Tyr Asp Tyr Gln Glu Asp Gly Ser
    130                 135                 140

Val Leu Leu Thr Cys Asp Ala Glu Ala Lys Asn Ile Thr Trp Phe Lys
145                 150                 155                 160

Asp Gly Lys Met Ile Gly Phe Leu Thr Glu Asp Lys Lys Lys Trp Asn
                165                 170                 175

Leu Gly Ser Asn Ala Lys Asp Pro Arg Gly Met Tyr Cys Lys Gly Ser
            180                 185                 190

Gln Asn Lys Ser Lys Pro Leu Gln Val Tyr Tyr Arg Met
        195                 200                 205

<210> SEQ ID NO 283
<211> LENGTH: 27
<212> TYPE: PRT
<213> ORGANISM: Artificial Sequence
<220> FEATURE:
<223> OTHER INFORMATION: Synthetic Construct

<400> SEQUENCE: 283

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25
```

<210> SEQ ID NO 284
<211> LENGTH: 16
<212> TYPE: PRT
<213> ORGANISM: Artificial Sequence
<220> FEATURE:
<223> OTHER INFORMATION: Synthetic Construct

<400> SEQUENCE: 284

Gln Asp Gly Asn Glu Glu Met Gly Gly Ile Thr Gln Thr Pro Tyr Lys
1               5                   10                  15

<210> SEQ ID NO 285
<211> LENGTH: 119
<212> TYPE: PRT
<213> ORGANISM: Artificial Sequence
<220> FEATURE:
<223> OTHER INFORMATION: Synthetic Construct

<400> SEQUENCE: 285

Gln Val Gln Leu Gln Gln Ser Gly Pro Glu Leu Val Lys Pro Gly Ala
1               5                   10                  15

Ser Val Thr Ile Ser Cys Thr Ala Ser Gly Phe Thr Phe Thr Ser Tyr
                20                  25                  30

Tyr Ile His Trp Val Arg Gln Arg Pro Gly Gln Gly Leu Glu Trp Ile
            35                  40                  45

Gly Trp Ile Tyr Pro Glu Asn Asp Asn Thr Lys Tyr Asn Glu Lys Phe
        50                  55                  60

Lys Asp Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Thr Leu Thr Val Ser Ser
        115

<210> SEQ ID NO 286
<211> LENGTH: 112
<212> TYPE: PRT
<213> ORGANISM: Artificial Sequence
<220> FEATURE:
<223> OTHER INFORMATION: Synthetic Construct

<400> SEQUENCE: 286

Asp Ile Val Met Thr Gln Ser Pro Ser Phe Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Arg Pro Gly Gln
            35                  40                  45

Ser Pro Lys Leu Leu Ile Tyr Trp Thr Ser Thr Arg Lys Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Lys Gln
                85                  90                  95

Ser Phe Ile Leu Arg Thr Phe Gly Gly Gly Thr Lys Leu Glu Ile Lys
            100                 105                 110

```
<210> SEQ ID NO 287
<211> LENGTH: 119
<212> TYPE: PRT
<213> ORGANISM: Artificial Sequence
<220> FEATURE:
<223> OTHER INFORMATION: Synthetic Construct

<400> SEQUENCE: 287
```

| Glu | Val | Gln | Leu | Val | Gln | Ser | Gly | Ala | Glu | Val | Lys | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Ile | Val | Ser | Cys | Lys | Ala | Ser | Gly | Phe | Thr | Phe | Thr | Ser | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Ile | His | Trp | Val | Arg | Gln | Ala | Pro | Gly | Gln | Gly | Leu | Glu | Trp | Ile |
|-----|-----|-----|-----|-----|-----|-----|-----|-----|-----|-----|-----|-----|-----|-----|-----|
|     |     |     35|     |     |     |     | 40  |     |     |     |     | 45  |     |     |     |

| Gly | Trp | Ile | Tyr | Pro | Glu | Asn | Asp | Asn | Arg | Lys | Tyr | Asn | Glu | Lys | Phe |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Asp | Arg | Val | Thr | Ile | Ser | Ala | Asp | Thr | Ser | Glu | Ser | Phe | Ala | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Gln | Leu | His | Ser | Leu | Arg | Ser | Glu | Asp | Thr | Ala | Val | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Asp | Gly | Tyr | Ser | Arg | Tyr | Tyr | Phe | Asp | Tyr | Trp | Gly | Gln | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Leu | Val | Thr | Val | Ser | Ser |
|-----|-----|-----|-----|-----|-----|-----|
|     |     |     | 115 |     |     |     |

```
<210> SEQ ID NO 288
<211> LENGTH: 112
<212> TYPE: PRT
<213> ORGANISM: Artificial Sequence
<220> FEATURE:
<223> OTHER INFORMATION: Synthetic Construct

<400> SEQUENCE: 288
```

| Asp | Ile | Val | Met | Thr | Gln | Ser | Pro | Asp | Ser | Leu | Ala | Val | Ser | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Arg | Ala | Thr | Ile | Asn | Cys | Lys | Ser | Ser | Gln | Ser | Leu | Leu | Asn | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Thr | Arg | Lys | Asn | Tyr | Leu | Ala | Trp | Tyr | Gln | Gln | Lys | Pro | Gly | Gln |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ser | Pro | Lys | Leu | Leu | Ile | Tyr | Trp | Thr | Ser | Thr | Arg | Lys | Ser | Gly | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Pro | Asp | Arg | Phe | Ser | Gly | Ser | Gly | Ser | Gly | Thr | Asp | Phe | Thr | Leu | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Ser | Ser | Leu | Gln | Ala | Glu | Asp | Val | Ala | Val | Tyr | Tyr | Cys | Lys | Gln |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Phe | Ile | Leu | Arg | Thr | Phe | Gly | Gln | Gly | Thr | Lys | Val | Glu | Ile | Lys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

```
<210> SEQ ID NO 289
<211> LENGTH: 119
<212> TYPE: PRT
<213> ORGANISM: Artificial Sequence
<220> FEATURE:
<223> OTHER INFORMATION: Synthetic Construct

<400> SEQUENCE: 289
```

| Glu | Val | Gln | Leu | Val | Gln | Ser | Gly | Ala | Glu | Val | Lys | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Val | Ser | Cys | Lys | Ala | Ser | Gly | Phe | Thr | Phe | Thr | Ser | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

```
Tyr Ile His Trp Val Arg Gln Ala Pro Gly Gln Gly Leu Glu Trp Ile
            35                  40                  45

Gly Trp Ile Tyr Pro Glu Asn Asp Asn Arg Lys Tyr Asn Glu Lys Phe
        50                  55                  60

Lys Asp Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
            115
```

<210> SEQ ID NO 290
<211> LENGTH: 112
<212> TYPE: PRT
<213> ORGANISM: Artificial Sequence
<220> FEATURE:
<223> OTHER INFORMATION: Synthetic Construct

<400> SEQUENCE: 290

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110
```

<210> SEQ ID NO 291
<211> LENGTH: 119
<212> TYPE: PRT
<213> ORGANISM: Artificial Sequence
<220> FEATURE:
<223> OTHER INFORMATION: Synthetic Construct

<400> SEQUENCE: 291

```
Gln Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asn Tyr
            20                  25                  30

Tyr Ile His Trp Val Arg Gln Arg Pro Gly Gln Gly Leu Glu Trp Ile
            35                  40                  45

Gly Trp Ile Tyr Pro Gly Asp Val Ser Thr Lys Tyr Asn Glu Lys Phe
        50                  55                  60

Lys Gly Lys Thr Thr Leu Thr Ala Asp Lys Ser Ser Ser Thr Ala Tyr
65                  70                  75                  80

Met Leu Leu Ser Gly Leu Thr Ser Glu Asp Ser Ala Ile Tyr Phe Cys
                85                  90                  95

Ala Arg Asp Gly Tyr Ser Phe Tyr Tyr Phe Asp Tyr Trp Gly Gln Gly
```

-continued

```
                100                 105                 110

Thr Thr Leu Thr Val Ser Ser
            115

<210> SEQ ID NO 292
<211> LENGTH: 112
<212> TYPE: PRT
<213> ORGANISM: Artificial Sequence
<220> FEATURE:
<223> OTHER INFORMATION: Synthetic Construct

<400> SEQUENCE: 292

Asp Ile Val Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Thr Trp Tyr Gln Gln Lys Pro Gly Gln
        35                  40                  45

Ser Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Tyr Thr Leu Arg Thr Phe Gly Gly Gly Thr Lys Leu Glu Ile Lys
            100                 105                 110

<210> SEQ ID NO 293
<211> LENGTH: 30
<212> TYPE: PRT
<213> ORGANISM: Artificial Sequence
<220> FEATURE:
<223> OTHER INFORMATION: Synthetic Construct

<400> SEQUENCE: 293

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr
            20                  25                  30

<210> SEQ ID NO 294
<211> LENGTH: 14
<212> TYPE: PRT
<213> ORGANISM: Artificial Sequence
<220> FEATURE:
<223> OTHER INFORMATION: Synthetic Construct

<400> SEQUENCE: 294

Trp Val Lys Gln Arg Pro Gly Gln Gly Leu Glu Trp Ile Gly
1               5                   10

<210> SEQ ID NO 295
<211> LENGTH: 32
<212> TYPE: PRT
<213> ORGANISM: Artificial Sequence
<220> FEATURE:
<223> OTHER INFORMATION: Synthetic Construct

<400> SEQUENCE: 295

Lys Ala Thr Leu Thr Ala Asp Thr Ser Ser Ser Thr Ala Tyr Met Gln
1               5                   10                  15

Leu Ser Ser Leu Thr Ser Glu Asp Ser Ala Val Tyr Tyr Cys Ala Arg
```

<210> SEQ ID NO 296
<211> LENGTH: 11
<212> TYPE: PRT
<213> ORGANISM: Artificial Sequence
<220> FEATURE:
<223> OTHER INFORMATION: Synthetic Construct

<400> SEQUENCE: 296

Trp Gly Gln Gly Thr Thr Leu Thr Val Ser Ser
1               5                   10

<210> SEQ ID NO 297
<211> LENGTH: 23
<212> TYPE: PRT
<213> ORGANISM: Artificial Sequence
<220> FEATURE:
<223> OTHER INFORMATION: Synthetic Construct

<400> SEQUENCE: 297

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 298
<211> LENGTH: 15
<212> TYPE: PRT
<213> ORGANISM: Artificial Sequence
<220> FEATURE:
<223> OTHER INFORMATION: Synthetic Construct

<400> SEQUENCE: 298

Trp Tyr Gln Gln Lys Pro Gly Gln Ser Pro Lys Leu Leu Ile Tyr
1               5                   10                  15

<210> SEQ ID NO 299
<211> LENGTH: 32
<212> TYPE: PRT
<213> ORGANISM: Artificial Sequence
<220> FEATURE:
<223> OTHER INFORMATION: Synthetic Construct

<400> SEQUENCE: 299

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 300
<211> LENGTH: 10
<212> TYPE: PRT
<213> ORGANISM: Artificial Sequence
<220> FEATURE:
<223> OTHER INFORMATION: Synthetic Construct

<400> SEQUENCE: 300

Phe Gly Gly Gly Thr Lys Leu Glu Ile Lys
1               5                   10

<210> SEQ ID NO 301
<211> LENGTH: 30
<212> TYPE: PRT
<213> ORGANISM: Artificial Sequence
<220> FEATURE:

<223> OTHER INFORMATION: Synthetic Construct

<400> SEQUENCE: 301

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 302
<211> LENGTH: 14
<212> TYPE: PRT
<213> ORGANISM: Artificial Sequence
<220> FEATURE:
<223> OTHER INFORMATION: Synthetic Construct

<400> SEQUENCE: 302

Trp Val Arg Gln Ala Pro Gly Gln Gly Leu Glu Trp Ile Gly
1               5                   10

<210> SEQ ID NO 303
<211> LENGTH: 32
<212> TYPE: PRT
<213> ORGANISM: Artificial Sequence
<220> FEATURE:
<223> OTHER INFORMATION: Synthetic Construct

<400> SEQUENCE: 303

Arg Ala Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 304
<211> LENGTH: 11
<212> TYPE: PRT
<213> ORGANISM: Artificial Sequence
<220> FEATURE:
<223> OTHER INFORMATION: Synthetic Construct

<400> SEQUENCE: 304

Trp Gly Gln Gly Thr Leu Val Thr Val Ser Ser
1               5                   10

<210> SEQ ID NO 305
<211> LENGTH: 23
<212> TYPE: PRT
<213> ORGANISM: Artificial Sequence
<220> FEATURE:
<223> OTHER INFORMATION: Synthetic Construct

<400> SEQUENCE: 305

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 306
<211> LENGTH: 15
<212> TYPE: PRT
<213> ORGANISM: Artificial Sequence
<220> FEATURE:
<223> OTHER INFORMATION: Synthetic Construct

<400> SEQUENCE: 306

Trp Tyr Gln Gln Lys Pro Gly Gln Pro Pro Lys Leu Leu Ile Tyr

-continued

```
                1               5                   10                  15
```

<210> SEQ ID NO 307
<211> LENGTH: 32
<212> TYPE: PRT
<213> ORGANISM: Artificial Sequence
<220> FEATURE:
<223> OTHER INFORMATION: Synthetic Construct

<400> SEQUENCE: 307

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
                20                  25                  30
```

<210> SEQ ID NO 308
<211> LENGTH: 10
<212> TYPE: PRT
<213> ORGANISM: Artificial Sequence
<220> FEATURE:
<223> OTHER INFORMATION: Synthetic Construct

<400> SEQUENCE: 308

```
Phe Gly Gln Gly Thr Lys Val Glu Ile Lys
1               5                   10
```

<210> SEQ ID NO 309
<211> LENGTH: 30
<212> TYPE: PRT
<213> ORGANISM: Artificial Sequence
<220> FEATURE:
<223> OTHER INFORMATION: Synthetic Construct

<400> SEQUENCE: 309

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr
                20                  25                  30
```

<210> SEQ ID NO 310
<211> LENGTH: 14
<212> TYPE: PRT
<213> ORGANISM: Artificial Sequence
<220> FEATURE:
<223> OTHER INFORMATION: Synthetic Construct

<400> SEQUENCE: 310

```
Trp Val Arg Gln Ala Pro Gly Gln Gly Leu Glu Trp Ile Gly
1               5                   10
```

<210> SEQ ID NO 311
<211> LENGTH: 32
<212> TYPE: PRT
<213> ORGANISM: Artificial Sequence
<220> FEATURE:
<223> OTHER INFORMATION: Synthetic Construct

<400> SEQUENCE: 311

```
Arg Val Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
                20                  25                  30
```

<210> SEQ ID NO 312
<211> LENGTH: 11

```
<212> TYPE: PRT
<213> ORGANISM: Artificial Sequence
<220> FEATURE:
<223> OTHER INFORMATION: Synthetic Construct

<400> SEQUENCE: 312

Trp Gly Gln Gly Thr Leu Val Thr Val Ser Ser
1               5                   10

<210> SEQ ID NO 313
<211> LENGTH: 23
<212> TYPE: PRT
<213> ORGANISM: Artificial Sequence
<220> FEATURE:
<223> OTHER INFORMATION: Synthetic Construct

<400> SEQUENCE: 313

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 314
<211> LENGTH: 15
<212> TYPE: PRT
<213> ORGANISM: Artificial Sequence
<220> FEATURE:
<223> OTHER INFORMATION: Synthetic Construct

<400> SEQUENCE: 314

Trp Tyr Gln Gln Lys Pro Gly Gln Ser Pro Lys Leu Leu Ile Tyr
1               5                   10                  15

<210> SEQ ID NO 315
<211> LENGTH: 32
<212> TYPE: PRT
<213> ORGANISM: Artificial Sequence
<220> FEATURE:
<223> OTHER INFORMATION: Synthetic Construct

<400> SEQUENCE: 315

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 316
<211> LENGTH: 10
<212> TYPE: PRT
<213> ORGANISM: Artificial Sequence
<220> FEATURE:
<223> OTHER INFORMATION: Synthetic Construct

<400> SEQUENCE: 316

Phe Gly Gln Gly Thr Lys Val Glu Ile Lys
1               5                   10

<210> SEQ ID NO 317
<211> LENGTH: 30
<212> TYPE: PRT
<213> ORGANISM: Artificial Sequence
<220> FEATURE:
<223> OTHER INFORMATION: Synthetic Construct

<400> SEQUENCE: 317

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Tyr Ser Phe Thr
            20                  25                  30
```

<210> SEQ ID NO 318
<211> LENGTH: 14
<212> TYPE: PRT
<213> ORGANISM: Artificial Sequence
<220> FEATURE:
<223> OTHER INFORMATION: Synthetic Construct

<400> SEQUENCE: 318

```
Trp Val Arg Gln Ala Pro Gly Lys Asp Leu Glu Trp Val Ala
1               5                   10
```

<210> SEQ ID NO 319
<211> LENGTH: 32
<212> TYPE: PRT
<213> ORGANISM: Artificial Sequence
<220> FEATURE:
<223> OTHER INFORMATION: Synthetic Construct

<400> SEQUENCE: 319

```
Arg Phe Thr Ile Ser Val Asp Lys Ser Lys Asn Thr Ala Tyr Leu Gln
1               5                   10                  15
Met Asn Ser Leu Arg Ala Glu Asp Thr Ala Val Tyr Tyr Cys Ala Arg
            20                  25                  30
```

<210> SEQ ID NO 320
<211> LENGTH: 11
<212> TYPE: PRT
<213> ORGANISM: Artificial Sequence
<220> FEATURE:
<223> OTHER INFORMATION: Synthetic Construct

<400> SEQUENCE: 320

```
Trp Gly Gln Gly Thr Leu Val Thr Val Ser Ser
1               5                   10
```

<210> SEQ ID NO 321
<211> LENGTH: 23
<212> TYPE: PRT
<213> ORGANISM: Artificial Sequence
<220> FEATURE:
<223> OTHER INFORMATION: Synthetic Construct

<400> SEQUENCE: 321

```
Asp Ile Gln Met Thr Gln Ser Pro Ser Ser Leu Ser Ala Ser Val Gly
1               5                   10                  15
Asp Arg Val Thr Ile Thr Cys
            20
```

<210> SEQ ID NO 322
<211> LENGTH: 15
<212> TYPE: PRT
<213> ORGANISM: Artificial Sequence
<220> FEATURE:
<223> OTHER INFORMATION: Synthetic Construct

<400> SEQUENCE: 322

```
Trp Tyr Gln Gln Lys Pro Gly Lys Ala Pro Lys Leu Leu Ile Tyr
1               5                   10                  15
```

<210> SEQ ID NO 323
<211> LENGTH: 32

```
<212> TYPE: PRT
<213> ORGANISM: Artificial Sequence
<220> FEATURE:
<223> OTHER INFORMATION: Synthetic Construct

<400> SEQUENCE: 323

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 324
<211> LENGTH: 10
<212> TYPE: PRT
<213> ORGANISM: Artificial Sequence
<220> FEATURE:
<223> OTHER INFORMATION: Synthetic Construct

<400> SEQUENCE: 324

Phe Gly Gln Gly Thr Lys Leu Glu Leu Lys
1               5                   10

<210> SEQ ID NO 325
<211> LENGTH: 30
<212> TYPE: PRT
<213> ORGANISM: Artificial Sequence
<220> FEATURE:
<223> OTHER INFORMATION: Synthetic Construct

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr
            20                  25                  30

<210> SEQ ID NO 326
<211> LENGTH: 14
<212> TYPE: PRT
<213> ORGANISM: Artificial Sequence
<220> FEATURE:
<223> OTHER INFORMATION: Synthetic Construct

<400> SEQUENCE: 326

Trp Val Arg Gln Ala Pro Gly Lys Gly Leu Glu Trp Val Ala
1               5                   10

<210> SEQ ID NO 327
<211> LENGTH: 32
<212> TYPE: PRT
<213> ORGANISM: Artificial Sequence
<220> FEATURE:
<223> OTHER INFORMATION: Synthetic Construct

<400> SEQUENCE: 327

Arg Phe Thr Ile Ser Val Asp Lys Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 328
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 328

Trp Gly Gln Gly Thr Leu Val Thr Val Ser Ser
1               5                   10

<210> SEQ ID NO 329
<211> LENGTH: 23
<212> TYPE: PRT
<213> ORGANISM: Artificial Sequence
<220> FEATURE:
<223> OTHER INFORMATION: Synthetic Construct

<400> SEQUENCE: 329

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 330
<211> LENGTH: 15
<212> TYPE: PRT
<213> ORGANISM: Artificial Sequence
<220> FEATURE:
<223> OTHER INFORMATION: Synthetic Construct

<400> SEQUENCE: 330

Trp Tyr Gln Gln Lys Pro Gly Lys Ala Pro Lys Leu Leu Ile Tyr
1               5                   10                  15

<210> SEQ ID NO 331
<211> LENGTH: 32
<212> TYPE: PRT
<213> ORGANISM: Artificial Sequence
<220> FEATURE:
<223> OTHER INFORMATION: Synthetic Construct

<400> SEQUENCE: 331

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 332
<211> LENGTH: 10
<212> TYPE: PRT
<213> ORGANISM: Artificial Sequence
<220> FEATURE:
<223> OTHER INFORMATION: Synthetic Construct

<400> SEQUENCE: 332

Phe Gly Gln Gly Thr Lys Val Glu Ile Lys
1               5                   10

<210> SEQ ID NO 333
<211> LENGTH: 30
<212> TYPE: PRT
<213> ORGANISM: Artificial Sequence
<220> FEATURE:
<223> OTHER INFORMATION: Synthetic Construct

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr
            20                  25                  30
```

<210> SEQ ID NO 334
<211> LENGTH: 14
<212> TYPE: PRT
<213> ORGANISM: Artificial Sequence
<220> FEATURE:
<223> OTHER INFORMATION: Synthetic Construct

<400> SEQUENCE: 334

Trp Val Arg Gln Ala Pro Gly Lys Gly Leu Glu Trp Val Ala
1               5                   10

<210> SEQ ID NO 335
<211> LENGTH: 32
<212> TYPE: PRT
<213> ORGANISM: Artificial Sequence
<220> FEATURE:
<223> OTHER INFORMATION: Synthetic Construct

<400> SEQUENCE: 335

Arg Phe Thr Ile Ser Val Asp Lys Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 336
<211> LENGTH: 11
<212> TYPE: PRT
<213> ORGANISM: Artificial Sequence
<220> FEATURE:
<223> OTHER INFORMATION: Synthetic Construct

<400> SEQUENCE: 336

Trp Gly Gln Gly Thr Leu Val Thr Val Ser Ser
1               5                   10

<210> SEQ ID NO 337
<211> LENGTH: 23
<212> TYPE: PRT
<213> ORGANISM: Artificial Sequence
<220> FEATURE:
<223> OTHER INFORMATION: Synthetic Construct

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 338
<211> LENGTH: 15
<212> TYPE: PRT
<213> ORGANISM: Artificial Sequence
<220> FEATURE:
<223> OTHER INFORMATION: Synthetic Construct

<400> SEQUENCE: 338

Trp Tyr Gln Gln Lys Pro Gly Lys Ala Pro Lys Leu Leu Ile Tyr
1               5                   10                  15

<210> SEQ ID NO 339
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 339

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 340
<211> LENGTH: 10
<212> TYPE: PRT
<213> ORGANISM: Artificial Sequence
<220> FEATURE:
<223> OTHER INFORMATION: Synthetic Construct

<400> SEQUENCE: 340

Phe Gly Gln Gly Thr Lys Val Glu Ile Lys
1               5                   10

<210> SEQ ID NO 341
<211> LENGTH: 30
<212> TYPE: PRT
<213> ORGANISM: Artificial Sequence
<220> FEATURE:
<223> OTHER INFORMATION: Synthetic Construct

<400> SEQUENCE: 341

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn
            20                  25                  30

<210> SEQ ID NO 342
<211> LENGTH: 14
<212> TYPE: PRT
<213> ORGANISM: Artificial Sequence
<220> FEATURE:
<223> OTHER INFORMATION: Synthetic Construct

<400> SEQUENCE: 342

Trp Val Arg Gln Ala Pro Gly Lys Gly Leu Glu Trp Val Ala
1               5                   10

<210> SEQ ID NO 343
<211> LENGTH: 32
<212> TYPE: PRT
<213> ORGANISM: Artificial Sequence
<220> FEATURE:
<223> OTHER INFORMATION: Synthetic Construct

<400> SEQUENCE: 343

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 344
<211> LENGTH: 11
<212> TYPE: PRT
<213> ORGANISM: Artificial Sequence
<220> FEATURE:
<223> OTHER INFORMATION: Synthetic Construct

<400> SEQUENCE: 344

Trp Gly Gln Gly Thr Leu Val Thr Val Ser Ser
1               5                   10
```

<210> SEQ ID NO 345
<211> LENGTH: 22
<212> TYPE: PRT
<213> ORGANISM: Artificial Sequence
<220> FEATURE:
<223> OTHER INFORMATION: Synthetic Construct

<400> SEQUENCE: 345

Glu Ala Val Val Thr Gln Glu Pro Ser Leu Thr Val Ser Pro Gly Gly
1               5                   10                  15

Thr Val Thr Leu Thr Cys
            20

<210> SEQ ID NO 346
<211> LENGTH: 15
<212> TYPE: PRT
<213> ORGANISM: Artificial Sequence
<220> FEATURE:
<223> OTHER INFORMATION: Synthetic Construct

<400> SEQUENCE: 346

Trp Val Gln Gln Lys Pro Gly Gln Ala Pro Arg Gly Leu Ile Gly
1               5                   10                  15

<210> SEQ ID NO 347
<211> LENGTH: 32
<212> TYPE: PRT
<213> ORGANISM: Artificial Sequence
<220> FEATURE:
<223> OTHER INFORMATION: Synthetic Construct

<400> SEQUENCE: 347

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Tyr Cys
            20                  25                  30

<210> SEQ ID NO 348
<211> LENGTH: 10
<212> TYPE: PRT
<213> ORGANISM: Artificial Sequence
<220> FEATURE:
<223> OTHER INFORMATION: Synthetic Construct

<400> SEQUENCE: 348

Phe Gly Gly Gly Thr Lys Leu Thr Val Leu
1               5                   10

<210> SEQ ID NO 349
<211> LENGTH: 30
<212> TYPE: PRT
<213> ORGANISM: Artificial Sequence
<220> FEATURE:
<223> OTHER INFORMATION: Synthetic Construct

<400> SEQUENCE: 349

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn
            20                  25                  30

<210> SEQ ID NO 350
<211> LENGTH: 14
<212> TYPE: PRT
<213> ORGANISM: Artificial Sequence
<220> FEATURE:
<223> OTHER INFORMATION: Synthetic Construct

<400> SEQUENCE: 350

Trp Val Arg Gln Ala Pro Gly Lys Gly Leu Glu Trp Val Ala
1               5                   10

<210> SEQ ID NO 351
<211> LENGTH: 32
<212> TYPE: PRT
<213> ORGANISM: Artificial Sequence
<220> FEATURE:
<223> OTHER INFORMATION: Synthetic Construct

<400> SEQUENCE: 351

Arg Phe Thr Ile Ser Arg Asp Asp Ser Gln Ser Ile Leu Tyr Leu Gln
1               5                   10                  15

Met Asn Asn Leu Lys Thr Glu Asp Thr Ala Met Tyr Tyr Cys Val Arg
            20                  25                  30

<210> SEQ ID NO 352
<211> LENGTH: 11
<212> TYPE: PRT
<213> ORGANISM: Artificial Sequence
<220> FEATURE:
<223> OTHER INFORMATION: Synthetic Construct

<400> SEQUENCE: 352

Trp Gly Gln Gly Thr Leu Val Thr Val Ser Ser
1               5                   10

<210> SEQ ID NO 353
<211> LENGTH: 22
<212> TYPE: PRT
<213> ORGANISM: Artificial Sequence
<220> FEATURE:
<223> OTHER INFORMATION: Synthetic Construct

<400> SEQUENCE: 353

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 354
<211> LENGTH: 15
<212> TYPE: PRT
<213> ORGANISM: Artificial Sequence
<220> FEATURE:
<223> OTHER INFORMATION: Synthetic Construct

<400> SEQUENCE: 354

Trp Val Gln Glu Lys Pro Asp His Leu Phe Thr Gly Leu Ile Gly
1               5                   10                  15

<210> SEQ ID NO 355
<211> LENGTH: 32
<212> TYPE: PRT
<213> ORGANISM: Artificial Sequence
<220> FEATURE:
<223> OTHER INFORMATION: Synthetic Construct

<400> SEQUENCE: 355

Gly Val Pro Ala Arg Phe Ser Gly Ser Leu Ile Gly Asp Lys Ala Ala
1               5                   10                  15

```
Leu Thr Ile Thr Gly Ala Gln Thr Glu Asp Glu Ala Ile Tyr Phe Cys
            20                  25                  30
```

<210> SEQ ID NO 356
<211> LENGTH: 10
<212> TYPE: PRT
<213> ORGANISM: Artificial Sequence
<220> FEATURE:
<223> OTHER INFORMATION: Synthetic Construct

<400> SEQUENCE: 356

```
Phe Gly Gly Gly Thr Lys Leu Thr Val Leu
1               5                   10
```

<210> SEQ ID NO 357
<211> LENGTH: 30
<212> TYPE: PRT
<213> ORGANISM: Artificial Sequence
<220> FEATURE:
<223> OTHER INFORMATION: Synthetic Construct

<400> SEQUENCE: 357

```
Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr
            20                  25                  30
```

<210> SEQ ID NO 358
<211> LENGTH: 14
<212> TYPE: PRT
<213> ORGANISM: Artificial Sequence
<220> FEATURE:
<223> OTHER INFORMATION: Synthetic Construct

<400> SEQUENCE: 358

```
Trp Val Arg Gln Ala Pro Gly Gln Gly Leu Glu Trp Met Gly
1               5                   10
```

<210> SEQ ID NO 359
<211> LENGTH: 32
<212> TYPE: PRT
<213> ORGANISM: Artificial Sequence
<220> FEATURE:
<223> OTHER INFORMATION: Synthetic Construct

<400> SEQUENCE: 359

```
Arg Phe Val Phe Ser Leu Asp Thr Ser Val Ser Thr Ala Tyr Leu Gln
1               5                   10                  15
Ile Cys Ser Leu Lys Ala Glu Asp Thr Ala Val Tyr Tyr Cys Ala Arg
            20                  25                  30
```

<210> SEQ ID NO 360
<211> LENGTH: 11
<212> TYPE: PRT
<213> ORGANISM: Artificial Sequence
<220> FEATURE:
<223> OTHER INFORMATION: Synthetic Construct

<400> SEQUENCE: 360

```
Trp Gly Gln Gly Thr Leu Val Thr Val Ser Ser
1               5                   10
```

<210> SEQ ID NO 361
<211> LENGTH: 22
<212> TYPE: PRT
<213> ORGANISM: Artificial Sequence
<220> FEATURE:
<223> OTHER INFORMATION: Synthetic Construct

<400> SEQUENCE: 361

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 362
<211> LENGTH: 15
<212> TYPE: PRT
<213> ORGANISM: Artificial Sequence
<220> FEATURE:
<223> OTHER INFORMATION: Synthetic Construct

<400> SEQUENCE: 362

Trp Phe Gln Gln Lys Pro Gly Gln Ala Pro Arg Thr Leu Ile Tyr
1               5                   10                  15

<210> SEQ ID NO 363
<211> LENGTH: 32
<212> TYPE: PRT
<213> ORGANISM: Artificial Sequence
<220> FEATURE:
<223> OTHER INFORMATION: Synthetic Construct

<400> SEQUENCE: 363

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Phe Cys
            20                  25                  30

<210> SEQ ID NO 364
<211> LENGTH: 10
<212> TYPE: PRT
<213> ORGANISM: Artificial Sequence
<220> FEATURE:
<223> OTHER INFORMATION: Synthetic Construct

<400> SEQUENCE: 364

Phe Gly Thr Gly Thr Lys Val Thr Val Leu
1               5                   10

<210> SEQ ID NO 365
<211> LENGTH: 30
<212> TYPE: PRT
<213> ORGANISM: Artificial Sequence
<220> FEATURE:
<223> OTHER INFORMATION: Synthetic Construct

<400> SEQUENCE: 365

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 366
<211> LENGTH: 14
<212> TYPE: PRT
<213> ORGANISM: Artificial Sequence
<220> FEATURE:
<223> OTHER INFORMATION: Synthetic Construct

<400> SEQUENCE: 366

```
Trp Val Lys Gln Ala Pro Gly Lys Gly Leu Lys Trp Met Gly
1               5                   10
```

<210> SEQ ID NO 367
<211> LENGTH: 32
<212> TYPE: PRT
<213> ORGANISM: Artificial Sequence
<220> FEATURE:
<223> OTHER INFORMATION: Synthetic Construct

<400> SEQUENCE: 367

```
Arg Phe Val Phe Ser Leu Glu Thr Ser Ala Ser Thr Thr Tyr Leu Gln
1               5                   10                  15

Ile Asn Asn Leu Lys Asn Glu Asp Thr Ala Thr Tyr Phe Cys Ala Arg
            20                  25                  30
```

<210> SEQ ID NO 368
<211> LENGTH: 11
<212> TYPE: PRT
<213> ORGANISM: Artificial Sequence
<220> FEATURE:
<223> OTHER INFORMATION: Synthetic Construct

<400> SEQUENCE: 368

```
Trp Gly Gln Gly Thr Leu Val Thr Val Ser Ala
1               5                   10
```

<210> SEQ ID NO 369
<211> LENGTH: 22
<212> TYPE: PRT
<213> ORGANISM: Artificial Sequence
<220> FEATURE:
<223> OTHER INFORMATION: Synthetic Construct

<400> SEQUENCE: 369

```
Gln Ala Val Val Thr Gln Glu Ser Ala Leu Thr Thr Ser Pro Gly Gly
1               5                   10                  15

Thr Val Ile Leu Thr Cys
            20
```

<210> SEQ ID NO 370
<211> LENGTH: 15
<212> TYPE: PRT
<213> ORGANISM: Artificial Sequence
<220> FEATURE:
<223> OTHER INFORMATION: Synthetic Construct

<400> SEQUENCE: 370

```
Trp Val Gln Glu Lys Pro Asp His Leu Phe Thr Gly Leu Ile Gly
1               5                   10                  15
```

<210> SEQ ID NO 371
<211> LENGTH: 32
<212> TYPE: PRT
<213> ORGANISM: Artificial Sequence
<220> FEATURE:
<223> OTHER INFORMATION: Synthetic Construct

<400> SEQUENCE: 371

```
Gly Val Pro Val Arg Phe Ser Gly Ser Leu Ile Gly Asp Lys Ala Ala
1               5                   10                  15

Leu Thr Ile Thr Gly Ala Gln Thr Glu Asp Asp Ala Met Tyr Phe Cys
            20                  25                  30
```

<210> SEQ ID NO 372

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 372

Phe Gly Gly Gly Thr Lys Val Thr Val
1               5

<210> SEQ ID NO 373
<211> LENGTH: 30
<212> TYPE: PRT
<213> ORGANISM: Artificial Sequence
<220> FEATURE:
<223> OTHER INFORMATION: Synthetic Construct

<400> SEQUENCE: 373

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 374
<211> LENGTH: 14
<212> TYPE: PRT
<213> ORGANISM: Artificial Sequence
<220> FEATURE:
<223> OTHER INFORMATION: Synthetic Construct

<400> SEQUENCE: 374

Trp Val Arg Gln Ala Pro Gly Gln Gly Leu Glu Trp Ile Gly
1               5                   10

<210> SEQ ID NO 375
<211> LENGTH: 32
<212> TYPE: PRT
<213> ORGANISM: Artificial Sequence
<220> FEATURE:
<223> OTHER INFORMATION: Synthetic Construct

<400> SEQUENCE: 375

Arg Val Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 376
<211> LENGTH: 11
<212> TYPE: PRT
<213> ORGANISM: Artificial Sequence
<220> FEATURE:
<223> OTHER INFORMATION: Synthetic Construct

<400> SEQUENCE: 376

Trp Gly Gln Gly Thr Leu Val Thr Val Ser Ser
1               5                   10

<210> SEQ ID NO 377
<211> LENGTH: 23
<212> TYPE: PRT
<213> ORGANISM: Artificial Sequence
<220> FEATURE:
<223> OTHER INFORMATION: Synthetic Construct

<400> SEQUENCE: 377
```

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 378
<211> LENGTH: 15
<212> TYPE: PRT
<213> ORGANISM: Artificial Sequence
<220> FEATURE:
<223> OTHER INFORMATION: Synthetic Construct

<400> SEQUENCE: 378

```
Trp Tyr Gln Gln Lys Pro Gly Gln Pro Pro Lys Leu Leu Ile Tyr
1               5                   10                  15
```

<210> SEQ ID NO 379
<211> LENGTH: 32
<212> TYPE: PRT
<213> ORGANISM: Artificial Sequence
<220> FEATURE:
<223> OTHER INFORMATION: Synthetic Construct

<400> SEQUENCE: 379

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 380
<211> LENGTH: 10
<212> TYPE: PRT
<213> ORGANISM: Artificial Sequence
<220> FEATURE:
<223> OTHER INFORMATION: Synthetic Construct

<400> SEQUENCE: 380

```
Phe Gly Gln Gly Thr Lys Val Glu Ile Lys
1               5                   10
```

<210> SEQ ID NO 381
<211> LENGTH: 30
<212> TYPE: PRT
<213> ORGANISM: Artificial Sequence
<220> FEATURE:
<223> OTHER INFORMATION: Synthetic Construct

<400> SEQUENCE: 381

```
Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr
            20                  25                  30
```

<210> SEQ ID NO 382
<211> LENGTH: 14
<212> TYPE: PRT
<213> ORGANISM: Artificial Sequence
<220> FEATURE:
<223> OTHER INFORMATION: Synthetic Construct

<400> SEQUENCE: 382

```
Trp Met Lys Gln Arg Pro Gly Gln Gly Leu Glu Trp Ile Gly
1               5                   10
```

<210> SEQ ID NO 383

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 383

Lys Ala Thr Leu Thr Ala Asp Asn Ser Ser Thr Ala Asn Met Gln
1               5                   10                  15

Leu Ser Ser Leu Thr Ser Glu Asp Ser Ala Val Tyr Phe Cys Ala Arg
            20                  25                  30

<210> SEQ ID NO 384
<211> LENGTH: 11
<212> TYPE: PRT
<213> ORGANISM: Artificial Sequence
<220> FEATURE:
<223> OTHER INFORMATION: Synthetic Construct

<400> SEQUENCE: 384

Trp Gly Gln Gly Thr Thr Leu Thr Val Ser Ser
1               5                   10

<210> SEQ ID NO 385
<211> LENGTH: 23
<212> TYPE: PRT
<213> ORGANISM: Artificial Sequence
<220> FEATURE:
<223> OTHER INFORMATION: Synthetic Construct

<400> SEQUENCE: 385

Asp Ile Val Leu Thr Gln Ser Pro Ser Ser Leu Ala Val Ser Ala Gly
1               5                   10                  15

Glu Lys Val Thr Met Ser Cys
            20

<210> SEQ ID NO 386
<211> LENGTH: 15
<212> TYPE: PRT
<213> ORGANISM: Artificial Sequence
<220> FEATURE:
<223> OTHER INFORMATION: Synthetic Construct

<400> SEQUENCE: 386

Trp Tyr Gln Gln Lys Pro Gly Gln Ser Pro Lys Leu Leu Ile Tyr
1               5                   10                  15

<210> SEQ ID NO 387
<211> LENGTH: 32
<212> TYPE: PRT
<213> ORGANISM: Artificial Sequence
<220> FEATURE:
<223> OTHER INFORMATION: Synthetic Construct

<400> SEQUENCE: 387

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 388
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 388

Phe Gly Gly Gly Thr Lys Leu Glu Ile Lys
1               5                   10

<210> SEQ ID NO 389
<211> LENGTH: 30
<212> TYPE: PRT
<213> ORGANISM: Artificial Sequence
<220> FEATURE:
<223> OTHER INFORMATION: Synthetic Construct

<400> SEQUENCE: 389

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 390
<211> LENGTH: 14
<212> TYPE: PRT
<213> ORGANISM: Artificial Sequence
<220> FEATURE:
<223> OTHER INFORMATION: Synthetic Construct

<400> SEQUENCE: 390

Trp Val Arg Gln Ala Pro Gly Gln Arg Leu Glu Trp Met Gly
1               5                   10

<210> SEQ ID NO 391
<211> LENGTH: 32
<212> TYPE: PRT
<213> ORGANISM: Artificial Sequence
<220> FEATURE:
<223> OTHER INFORMATION: Synthetic Construct

<400> SEQUENCE: 391

Arg Val Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 392
<211> LENGTH: 11
<212> TYPE: PRT
<213> ORGANISM: Artificial Sequence
<220> FEATURE:
<223> OTHER INFORMATION: Synthetic Construct

<400> SEQUENCE: 392

Trp Gly Gln Gly Thr Leu Val Thr Val Ser Ser
1               5                   10

<210> SEQ ID NO 393
<211> LENGTH: 23
<212> TYPE: PRT
<213> ORGANISM: Artificial Sequence
<220> FEATURE:
<223> OTHER INFORMATION: Synthetic Construct

<400> SEQUENCE: 393

Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 394
<211> LENGTH: 15
<212> TYPE: PRT
<213> ORGANISM: Artificial Sequence
<220> FEATURE:
<223> OTHER INFORMATION: Synthetic Construct

<400> SEQUENCE: 394

Trp Tyr Gln Gln Lys Pro Gly Gln Pro Pro Lys Leu Leu Ile Tyr
1               5                   10                  15

<210> SEQ ID NO 395
<211> LENGTH: 32
<212> TYPE: PRT
<213> ORGANISM: Artificial Sequence
<220> FEATURE:
<223> OTHER INFORMATION: Synthetic Construct

<400> SEQUENCE: 395

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 396
<211> LENGTH: 10
<212> TYPE: PRT
<213> ORGANISM: Artificial Sequence
<220> FEATURE:
<223> OTHER INFORMATION: Synthetic Construct

<400> SEQUENCE: 396

Phe Gly Gln Gly Thr Lys Val Glu Ile Lys
1               5                   10

<210> SEQ ID NO 397
<211> LENGTH: 30
<212> TYPE: PRT
<213> ORGANISM: Artificial Sequence
<220> FEATURE:
<223> OTHER INFORMATION: Synthetic Construct

<400> SEQUENCE: 397

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 398
<211> LENGTH: 14
<212> TYPE: PRT
<213> ORGANISM: Artificial Sequence
<220> FEATURE:
<223> OTHER INFORMATION: Synthetic Construct

<400> SEQUENCE: 398

Trp Ile Arg Gln Pro Pro Gly Lys Gly Leu Glu Trp Ile Gly
1               5                   10

<210> SEQ ID NO 399
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 399

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 400
<211> LENGTH: 11
<212> TYPE: PRT
<213> ORGANISM: Artificial Sequence
<220> FEATURE:
<223> OTHER INFORMATION: Synthetic Construct

<400> SEQUENCE: 400

Trp Gly Gln Gly Thr Leu Val Thr Val Ser Ser
1               5                   10

<210> SEQ ID NO 401
<211> LENGTH: 23
<212> TYPE: PRT
<213> ORGANISM: Artificial Sequence
<220> FEATURE:
<223> OTHER INFORMATION: Synthetic Construct

<400> SEQUENCE: 401

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 402
<211> LENGTH: 15
<212> TYPE: PRT
<213> ORGANISM: Artificial Sequence
<220> FEATURE:
<223> OTHER INFORMATION: Synthetic Construct

<400> SEQUENCE: 402

Trp Tyr Gln Gln Lys Pro Gly Gln Pro Pro Lys Leu Leu Ile Tyr
1               5                   10                  15

<210> SEQ ID NO 403
<211> LENGTH: 32
<212> TYPE: PRT
<213> ORGANISM: Artificial Sequence
<220> FEATURE:
<223> OTHER INFORMATION: Synthetic Construct

<400> SEQUENCE: 403

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 404
<211> LENGTH: 10
<212> TYPE: PRT
<213> ORGANISM: Artificial Sequence
<220> FEATURE:
<223> OTHER INFORMATION: Synthetic Construct

<400> SEQUENCE: 404

Phe Gly Gln Gly Thr Lys Val Glu Ile Lys
1               5                   10
```

```
<210> SEQ ID NO 405
<211> LENGTH: 30
<212> TYPE: PRT
<213> ORGANISM: Artificial Sequence
<220> FEATURE:
<223> OTHER INFORMATION: Synthetic Construct

<400> SEQUENCE: 405

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30

<210> SEQ ID NO 406
<211> LENGTH: 14
<212> TYPE: PRT
<213> ORGANISM: Artificial Sequence
<220> FEATURE:
<223> OTHER INFORMATION: Synthetic Construct

<400> SEQUENCE: 406

Trp Val Arg Gln Pro Pro Gly Lys Gly Leu Asp Trp Leu Gly
1               5                   10

<210> SEQ ID NO 407
<211> LENGTH: 32
<212> TYPE: PRT
<213> ORGANISM: Artificial Sequence
<220> FEATURE:
<223> OTHER INFORMATION: Synthetic Construct

<400> SEQUENCE: 407

Arg Leu Ser Phe Ser Lys Asp Asn Ser Lys Ser Gln Val Phe Leu Glu
1               5                   10                  15

Ile Asn Ser Leu Gln Thr Asp Asp Thr Ala Met Tyr Tyr Cys Ala Arg
            20                  25                  30

<210> SEQ ID NO 408
<211> LENGTH: 11
<212> TYPE: PRT
<213> ORGANISM: Artificial Sequence
<220> FEATURE:
<223> OTHER INFORMATION: Synthetic Construct

<400> SEQUENCE: 408

Trp Gly Gln Gly Thr Ser Val Thr Val Ser Ser
1               5                   10

<210> SEQ ID NO 409
<211> LENGTH: 23
<212> TYPE: PRT
<213> ORGANISM: Artificial Sequence
<220> FEATURE:
<223> OTHER INFORMATION: Synthetic Constuct

<400> SEQUENCE: 409

Asn Ile Val Met Thr Gln Ser Pro Ser Ser Leu Ala Val Ser Ala Gly
1               5                   10                  15

Glu Lys Val Thr Met Ser Cys
            20

<210> SEQ ID NO 410
<211> LENGTH: 15
<212> TYPE: PRT
```

```
<213> ORGANISM: Artificial Sequence
<220> FEATURE:
<223> OTHER INFORMATION: Synthetic Construct

<400> SEQUENCE: 410

Trp Tyr Gln Gln Lys Pro Gly Gln Ser Pro Lys Leu Leu Ile Tyr
1               5                   10                  15

<210> SEQ ID NO 411
<211> LENGTH: 32
<212> TYPE: PRT
<213> ORGANISM: Artificial Sequence
<220> FEATURE:
<223> OTHER INFORMATION: Synthetic Construct

<400> SEQUENCE: 411

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 412
<211> LENGTH: 10
<212> TYPE: PRT
<213> ORGANISM: Artificial Sequence
<220> FEATURE:
<223> OTHER INFORMATION: Synthetic Construct

<400> SEQUENCE: 412

Phe Gly Ala Gly Thr Lys Leu Glu Leu Lys
1               5                   10

<210> SEQ ID NO 413
<211> LENGTH: 25
<212> TYPE: PRT
<213> ORGANISM: Artificial Sequence
<220> FEATURE:
<223> OTHER INFORMATION: Synthetic Construct

<400> SEQUENCE: 413

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 414
<211> LENGTH: 13
<212> TYPE: PRT
<213> ORGANISM: Artificial Sequence
<220> FEATURE:
<223> OTHER INFORMATION: Synthetic Construct

<400> SEQUENCE: 414

Trp Val Arg Gln Ala Pro Gly Lys Gly Leu Glu Trp Val
1               5                   10

<210> SEQ ID NO 415
<211> LENGTH: 15
<212> TYPE: PRT
<213> ORGANISM: Artificial Sequence
<220> FEATURE:
<223> OTHER INFORMATION: Synthetic Construct

<400> SEQUENCE: 415

Arg Phe Thr Ile Ser Arg Asp Asn Ser Lys Asn Thr Leu Tyr Leu
1               5                   10                  15
```

<210> SEQ ID NO 416
<211> LENGTH: 11
<212> TYPE: PRT
<213> ORGANISM: Artificial Sequence
<220> FEATURE:
<223> OTHER INFORMATION: Synthetic Construct

<400> SEQUENCE: 416

```
Trp Gly Gln Gly Thr Leu Val Thr Val Ser Ser
1               5                   10
```

<210> SEQ ID NO 417
<211> LENGTH: 23
<212> TYPE: PRT
<213> ORGANISM: Artificial Sequence
<220> FEATURE:
<223> OTHER INFORMATION: Synthetic Construct

<400> SEQUENCE: 417

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 418
<211> LENGTH: 15
<212> TYPE: PRT
<213> ORGANISM: Artificial Sequence
<220> FEATURE:
<223> OTHER INFORMATION: Synthetic Construct

<400> SEQUENCE: 418

```
Trp Tyr Gln Gln Lys Pro Gly Gln Pro Pro Lys Leu Leu Ile Tyr
1               5                   10                  15
```

<210> SEQ ID NO 419
<211> LENGTH: 32
<212> TYPE: PRT
<213> ORGANISM: Artificial Sequence
<220> FEATURE:
<223> OTHER INFORMATION: Synthetic Construct

<400> SEQUENCE: 419

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 420
<211> LENGTH: 10
<212> TYPE: PRT
<213> ORGANISM: Artificial Sequence
<220> FEATURE:
<223> OTHER INFORMATION: Synthetic Construct

<400> SEQUENCE: 420

```
Phe Gly Gln Gly Thr Lys Val Glu Ile Lys
1               5                   10
```

<210> SEQ ID NO 421
<211> LENGTH: 30
<212> TYPE: PRT
<213> ORGANISM: Artificial Sequence
<220> FEATURE:
<223> OTHER INFORMATION: Synthetic Construct

<400> SEQUENCE: 421

Glu Val Gln Leu Val Glu Ser Gly Gly Gly Val Val Gln Pro Gly Gly
1               5                   10                  15

Ser Leu Lys Leu Ser Cys Ala Ala Ser Gly Phe Thr Phe Ser
            20                  25                  30

<210> SEQ ID NO 422
<211> LENGTH: 14
<212> TYPE: PRT
<213> ORGANISM: Artificial Sequence
<220> FEATURE:
<223> OTHER INFORMATION: Synthetic Construct

<400> SEQUENCE: 422

Trp Val Arg Gln Ala Ser Glu Lys Gly Leu Glu Trp Val Gly
1               5                   10

<210> SEQ ID NO 423
<211> LENGTH: 32
<212> TYPE: PRT
<213> ORGANISM: Artificial Sequence
<220> FEATURE:
<223> OTHER INFORMATION: Synthetic Construct

<400> SEQUENCE: 423

Arg Phe Thr Ile Ser Arg Asp Asn Ser Lys Asn Thr Ala Tyr Leu Gln
1               5                   10                  15

Met Asn Ser Leu Lys Thr Glu Asp Thr Ala Val Tyr Tyr Cys Ile Arg
            20                  25                  30

<210> SEQ ID NO 424
<211> LENGTH: 11
<212> TYPE: PRT
<213> ORGANISM: Artificial Sequence
<220> FEATURE:
<223> OTHER INFORMATION: Synthetic Construct

<400> SEQUENCE: 424

Trp Gly Gln Gly Thr Leu Val Thr Val Ser Ser
1               5                   10

<210> SEQ ID NO 425
<211> LENGTH: 23
<212> TYPE: PRT
<213> ORGANISM: Artificial Sequence
<220> FEATURE:
<223> OTHER INFORMATION: Synthetic Construct

<400> SEQUENCE: 425

Asp Ile Gln Met Thr Gln Ser Pro Ser Ser Leu Ala Val Ser Leu Gly
1               5                   10                  15

Glu Arg Ala Thr Ile Asn Cys
            20

<210> SEQ ID NO 426
<211> LENGTH: 15
<212> TYPE: PRT
<213> ORGANISM: Artificial Sequence
<220> FEATURE:
<223> OTHER INFORMATION: Synthetic Construct

<400> SEQUENCE: 426

Trp Tyr Gln Gln Lys Leu Gly Gln Pro Pro Lys Leu Leu Ile Tyr
1               5                   10                  15

```
<210> SEQ ID NO 427
<211> LENGTH: 32
<212> TYPE: PRT
<213> ORGANISM: Artificial Sequence
<220> FEATURE:
<223> OTHER INFORMATION: Synthetic Construct

<400> SEQUENCE: 427

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 428
<211> LENGTH: 10
<212> TYPE: PRT
<213> ORGANISM: Artificial Sequence
<220> FEATURE:
<223> OTHER INFORMATION: Synthetic Construct

<400> SEQUENCE: 428

Phe Gly Gln Gly Thr Lys Val Glu Ile Lys
1               5                   10

<210> SEQ ID NO 429
<211> LENGTH: 30
<212> TYPE: PRT
<213> ORGANISM: Artificial Sequence
<220> FEATURE:
<223> OTHER INFORMATION: Synthetic Construct

<400> SEQUENCE: 429

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr
            20                  25                  30

<210> SEQ ID NO 430
<211> LENGTH: 14
<212> TYPE: PRT
<213> ORGANISM: Artificial Sequence
<220> FEATURE:
<223> OTHER INFORMATION: Synthetic Construct

<400> SEQUENCE: 430

Trp Met Arg Gln Arg Pro Gly Gln Gly Leu Glu Trp Ile Gly
1               5                   10

<210> SEQ ID NO 431
<211> LENGTH: 32
<212> TYPE: PRT
<213> ORGANISM: Artificial Sequence
<220> FEATURE:
<223> OTHER INFORMATION: Synthetic Construct

<400> SEQUENCE: 431

Lys Ala Ile Leu Thr Ala Asp Lys Phe Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 432
<211> LENGTH: 11
<212> TYPE: PRT
```

```
<213> ORGANISM: Artificial Sequence
<220> FEATURE:
<223> OTHER INFORMATION: Synthetic Construct

<400> SEQUENCE: 432

Trp Gly Gln Gly Thr Thr Leu Thr Val Ser Ser
1               5                   10

<210> SEQ ID NO 433
<211> LENGTH: 23
<212> TYPE: PRT
<213> ORGANISM: Artificial Sequence
<220> FEATURE:
<223> OTHER INFORMATION: Synthetic Construct

<400> SEQUENCE: 433

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 434
<211> LENGTH: 15
<212> TYPE: PRT
<213> ORGANISM: Artificial Sequence
<220> FEATURE:
<223> OTHER INFORMATION: Synthetic Construct

<400> SEQUENCE: 434

Trp Tyr Gln Gln Lys Pro Gly Gln Ser Pro Lys Leu Leu Ile Tyr
1               5                   10                  15

<210> SEQ ID NO 435
<211> LENGTH: 32
<212> TYPE: PRT
<213> ORGANISM: Artificial Sequence
<220> FEATURE:
<223> OTHER INFORMATION: Synthetic Construct

<400> SEQUENCE: 435

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 436
<211> LENGTH: 10
<212> TYPE: PRT
<213> ORGANISM: Artificial Sequence
<220> FEATURE:
<223> OTHER INFORMATION: Synthetic Construct

<400> SEQUENCE: 436

Phe Gly Gln Gly Thr Lys Val Glu Ile Lys
1               5                   10

<210> SEQ ID NO 437
<211> LENGTH: 30
<212> TYPE: PRT
<213> ORGANISM: Artificial Sequence
<220> FEATURE:
<223> OTHER INFORMATION: Synthetic Construct

<400> SEQUENCE: 437

Gln Val Gln Leu Gln Gln Ser Gly Pro Glu Leu Val Lys Pro Gly Ala
1               5                   10                  15
```

Ser Val Lys Met Ser Cys Lys Ala Ser Gly Tyr Thr Phe Thr
            20                  25                  30

<210> SEQ ID NO 438
<211> LENGTH: 14
<212> TYPE: PRT
<213> ORGANISM: Artificial Sequence
<220> FEATURE:
<223> OTHER INFORMATION: Synthetic Construct

<400> SEQUENCE: 438

Trp Val Lys Gln Ser Pro Gly Gln Gly Leu Glu Trp Ile Val
1               5                   10

<210> SEQ ID NO 439
<211> LENGTH: 32
<212> TYPE: PRT
<213> ORGANISM: Artificial Sequence
<220> FEATURE:
<223> OTHER INFORMATION: Synthetic Construct

<400> SEQUENCE: 439

Lys Thr Thr Val Thr Ala Asp Arg Ser Ser Thr Thr Val His Met Phe
1               5                   10                  15

Leu Ser Ser Leu Thr Ser Glu Asp Ser Ala Ile Tyr Phe Cys Ala Arg
            20                  25                  30

<210> SEQ ID NO 440
<211> LENGTH: 11
<212> TYPE: PRT
<213> ORGANISM: Artificial Sequence
<220> FEATURE:
<223> OTHER INFORMATION: Synthetic Construct

<400> SEQUENCE: 440

Trp Gly Gln Gly Thr Thr Leu Thr Val Ser Ser
1               5                   10

<210> SEQ ID NO 441
<211> LENGTH: 23
<212> TYPE: PRT
<213> ORGANISM: Artificial Sequence
<220> FEATURE:
<223> OTHER INFORMATION: Synthetic Construct

<400> SEQUENCE: 441

Asp Ile Val Met Thr Gln Ser Pro Ser Ser Leu Ala Val Ser Ala Gly
1               5                   10                  15

Glu Thr Val Thr Met Asn Cys
            20

<210> SEQ ID NO 442
<211> LENGTH: 15
<212> TYPE: PRT
<213> ORGANISM: Artificial Sequence
<220> FEATURE:
<223> OTHER INFORMATION: Synthetic Construct

<400> SEQUENCE: 442

Trp Tyr Gln Gln Lys Pro Gly Gln Ser Pro Lys Leu Leu Ile Tyr
1               5                   10                  15

<210> SEQ ID NO 443
<211> LENGTH: 32
<212> TYPE: PRT

```
<213> ORGANISM: Artificial Sequence
<220> FEATURE:
<223> OTHER INFORMATION: Synthetic Construct

<400> SEQUENCE: 443

Gly Val Pro Asp Arg Phe Thr Gly Ser Gly Ser Gly Thr Asp Phe Thr
1               5                   10                  15

Leu Thr Ile Ser Thr Val Gln Ala Glu Asp Leu Ala Val Tyr Tyr Cys
            20                  25                  30

<210> SEQ ID NO 444
<211> LENGTH: 10
<212> TYPE: PRT
<213> ORGANISM: Artificial Sequence
<220> FEATURE:
<223> OTHER INFORMATION: Synthetic Construct

<400> SEQUENCE: 444

Phe Gly Gln Gly Thr Lys Val Glu Ile Lys
1               5                   10

<210> SEQ ID NO 445
<211> LENGTH: 30
<212> TYPE: PRT
<213> ORGANISM: Artificial Sequence
<220> FEATURE:
<223> OTHER INFORMATION: Synthetic Construct

<400> SEQUENCE: 445

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr
            20                  25                  30

<210> SEQ ID NO 446
<211> LENGTH: 14
<212> TYPE: PRT
<213> ORGANISM: Artificial Sequence
<220> FEATURE:
<223> OTHER INFORMATION: Synthetic Construct

<400> SEQUENCE: 446

Trp Val Lys Gln Arg Pro Gly Gln Gly Leu Glu Trp Ile Gly
1               5                   10

<210> SEQ ID NO 447
<211> LENGTH: 32
<212> TYPE: PRT
<213> ORGANISM: Artificial Sequence
<220> FEATURE:
<223> OTHER INFORMATION: Synthetic Construct

<400> SEQUENCE: 447

Lys Ala Thr Leu Thr Ala Asp Thr Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 448
<211> LENGTH: 11
<212> TYPE: PRT
<213> ORGANISM: Artificial Sequence
<220> FEATURE:
<223> OTHER INFORMATION: Synthetic Construct

<400> SEQUENCE: 448
```

-continued

Trp Gly Gln Gly Thr Ser Val Thr Val Ser Ser
1               5                   10

<210> SEQ ID NO 449
<211> LENGTH: 23
<212> TYPE: PRT
<213> ORGANISM: Artificial Sequence
<220> FEATURE:
<223> OTHER INFORMATION: Synthetic Construct

<400> SEQUENCE: 449

Glu Ile Val Leu Ser Gln Ser Pro Ser Leu Ala Val Ser Ala Gly
1               5                   10                  15

Glu Lys Val Thr Met Ser Cys
            20

<210> SEQ ID NO 450
<211> LENGTH: 15
<212> TYPE: PRT
<213> ORGANISM: Artificial Sequence
<220> FEATURE:
<223> OTHER INFORMATION: Synthetic Construct

<400> SEQUENCE: 450

Trp Tyr Gln Gln Lys Pro Gly Gln Ser Pro Lys Leu Leu Ile Tyr
1               5                   10                  15

<210> SEQ ID NO 451
<211> LENGTH: 32
<212> TYPE: PRT
<213> ORGANISM: Artificial Sequence
<220> FEATURE:
<223> OTHER INFORMATION: Synthetic Construct

<400> SEQUENCE: 451

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 452
<211> LENGTH: 10
<212> TYPE: PRT
<213> ORGANISM: Artificial Sequence
<220> FEATURE:
<223> OTHER INFORMATION: Synthetic Construct

<400> SEQUENCE: 452

Phe Gly Gly Gly Thr Lys Leu Glu Ile Lys
1               5                   10

<210> SEQ ID NO 453
<211> LENGTH: 30
<212> TYPE: PRT
<213> ORGANISM: Artificial Sequence
<220> FEATURE:
<223> OTHER INFORMATION: Synthetic Construct

<400> SEQUENCE: 453

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr
            20                  25                  30

-continued

```
<210> SEQ ID NO 454
<211> LENGTH: 14
<212> TYPE: PRT
<213> ORGANISM: Artificial Sequence
<220> FEATURE:
<223> OTHER INFORMATION: Synthetic Construct

<400> SEQUENCE: 454

Trp Met Lys Gln Arg Pro Gly Gln Gly Leu Glu Trp Ile Gly
1               5                   10

<210> SEQ ID NO 455
<211> LENGTH: 32
<212> TYPE: PRT
<213> ORGANISM: Artificial Sequence
<220> FEATURE:
<223> OTHER INFORMATION: Synthetic Construct

<400> SEQUENCE: 455

Lys Ala Thr Leu Thr Ala Asp Asn Ser Ser Thr Ala Asn Met Gln
1               5                   10                  15

Leu Ser Ser Leu Thr Ser Glu Asp Ser Ala Val Tyr Phe Cys Ala Arg
            20                  25                  30

<210> SEQ ID NO 456
<211> LENGTH: 11
<212> TYPE: PRT
<213> ORGANISM: Artificial Sequence
<220> FEATURE:
<223> OTHER INFORMATION: Synthetic Construct

<400> SEQUENCE: 456

Trp Gly Gln Gly Thr Thr Leu Thr Val Ser Ser
1               5                   10

<210> SEQ ID NO 457
<211> LENGTH: 23
<212> TYPE: PRT
<213> ORGANISM: Artificial Sequence
<220> FEATURE:
<223> OTHER INFORMATION: Synthetic Construct

<400> SEQUENCE: 457

Gly Ile Val Met Thr Gln Ser Pro Ser Ser Leu Ala Val Ser Ala Gly
1               5                   10                  15

Glu Lys Val Thr Met Ser Cys
            20

<210> SEQ ID NO 458
<211> LENGTH: 15
<212> TYPE: PRT
<213> ORGANISM: Artificial Sequence
<220> FEATURE:
<223> OTHER INFORMATION: Synthetic Construct

<400> SEQUENCE: 458

Trp Tyr Gln Gln Lys Pro Gly Gln Ser Pro Lys Leu Leu Ile Tyr
1               5                   10                  15

<210> SEQ ID NO 459
<211> LENGTH: 32
<212> TYPE: PRT
<213> ORGANISM: Artificial Sequence
<220> FEATURE:
<223> OTHER INFORMATION: Synthetic Construct

<400> SEQUENCE: 459
```

```
Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
                20                  25                  30

<210> SEQ ID NO 460
<211> LENGTH: 10
<212> TYPE: PRT
<213> ORGANISM: Artificial Sequence
<220> FEATURE:
<223> OTHER INFORMATION: Synthetic Construct

<400> SEQUENCE: 460

Phe Gly Gly Gly Thr Lys Leu Glu Ile Lys
1               5                   10

<210> SEQ ID NO 461
<211> LENGTH: 30
<212> TYPE: PRT
<213> ORGANISM: Artificial Sequence
<220> FEATURE:
<223> OTHER INFORMATION: Synthetic Construct

<400> SEQUENCE: 461

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
                20                  25                  30

<210> SEQ ID NO 462
<211> LENGTH: 14
<212> TYPE: PRT
<213> ORGANISM: Artificial Sequence
<220> FEATURE:
<223> OTHER INFORMATION: Synthetic Construct

<400> SEQUENCE: 462

Trp Val Lys Gln Ala Pro Gly Lys Gly Leu Lys Trp Met Gly
1               5                   10

<210> SEQ ID NO 463
<211> LENGTH: 32
<212> TYPE: PRT
<213> ORGANISM: Artificial Sequence
<220> FEATURE:
<223> OTHER INFORMATION: Synthetic Construct

<400> SEQUENCE: 463

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Arg
                20                  25                  30

<210> SEQ ID NO 464
<211> LENGTH: 11
<212> TYPE: PRT
<213> ORGANISM: Artificial Sequence
<220> FEATURE:
<223> OTHER INFORMATION: Synthetic Construct

<400> SEQUENCE: 464

Trp Gly Gln Gly Thr Leu Val Thr Val Ser Ala
1               5                   10
```

```
<210> SEQ ID NO 465
<211> LENGTH: 22
<212> TYPE: PRT
<213> ORGANISM: Artificial Sequence
<220> FEATURE:
<223> OTHER INFORMATION: Synthetic Construct

<400> SEQUENCE: 465

Gln Ala Val Val Thr Gln Glu Ser Ala Leu Thr Thr Ser Pro Gly Gly
1               5                   10                  15

Thr Val Ile Leu Thr Cys
            20

<210> SEQ ID NO 466
<211> LENGTH: 15
<212> TYPE: PRT
<213> ORGANISM: Artificial Sequence
<220> FEATURE:
<223> OTHER INFORMATION: Synthetic Construct

<400> SEQUENCE: 466

Trp Val Gln Glu Lys Pro Asp His Leu Phe Thr Gly Leu Ile Gly
1               5                   10                  15

<210> SEQ ID NO 467
<211> LENGTH: 32
<212> TYPE: PRT
<213> ORGANISM: Artificial Sequence
<220> FEATURE:
<223> OTHER INFORMATION: Synthetic Construct

<400> SEQUENCE: 467

Gly Val Pro Val Arg Phe Ser Gly Ser Leu Ile Gly Asp Lys Ala Ala
1               5                   10                  15

Leu Thr Ile Thr Gly Ala Gln Thr Glu Asp Asp Ala Met Tyr Phe Cys
            20                  25                  30

<210> SEQ ID NO 468
<211> LENGTH: 9
<212> TYPE: PRT
<213> ORGANISM: Artificial Sequence
<220> FEATURE:
<223> OTHER INFORMATION: Synthetic Construct

<400> SEQUENCE: 468

Phe Gly Gly Gly Thr Lys Val Thr Val
1               5

<210> SEQ ID NO 469
<211> LENGTH: 30
<212> TYPE: PRT
<213> ORGANISM: Artificial Sequence
<220> FEATURE:
<223> OTHER INFORMATION: Synthetic Construct

<400> SEQUENCE: 469

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Ser Phe Thr
            20                  25                  30

<210> SEQ ID NO 470
<211> LENGTH: 14
<212> TYPE: PRT
<213> ORGANISM: Artificial Sequence
<220> FEATURE:
```

-continued

<223> OTHER INFORMATION: Synthetic Construct

<400> SEQUENCE: 470

Trp Met Lys Gln Arg Pro Gly Gln Gly Leu Glu Trp Ile Gly
1               5                   10

<210> SEQ ID NO 471
<211> LENGTH: 32
<212> TYPE: PRT
<213> ORGANISM: Artificial Sequence
<220> FEATURE:
<223> OTHER INFORMATION: Synthetic Construct

<400> SEQUENCE: 471

Lys Ala Thr Leu Thr Ala Asp Thr Ser Ser Thr Thr Ala Tyr Met Gln
1               5                   10                  15
Leu Ser Ser Leu Thr Ser Glu Asp Ser Ala Val Tyr Tyr Cys Ala Arg
            20                  25                  30

<210> SEQ ID NO 472
<211> LENGTH: 11
<212> TYPE: PRT
<213> ORGANISM: Artificial Sequence
<220> FEATURE:
<223> OTHER INFORMATION: Synthetic Construct

<400> SEQUENCE: 472

Trp Gly Gln Gly Thr Thr Leu Thr Val Ser Ser
1               5                   10

<210> SEQ ID NO 473
<211> LENGTH: 23
<212> TYPE: PRT
<213> ORGANISM: Artificial Sequence
<220> FEATURE:
<223> OTHER INFORMATION: Synthetic Construct

<400> SEQUENCE: 473

Asp Val Val Met Thr Gln Thr Pro Ser Ser Leu Ala Val Ser Thr Gly
1               5                   10                  15
Glu Lys Val Thr Met Thr Cys
            20

<210> SEQ ID NO 474
<211> LENGTH: 15
<212> TYPE: PRT
<213> ORGANISM: Artificial Sequence
<220> FEATURE:
<223> OTHER INFORMATION: Synthetic Construct

<400> SEQUENCE: 474

Trp Tyr Gln Gln Lys Pro Gly Gln Ser Pro Lys Leu Leu Ile Phe
1               5                   10                  15

<210> SEQ ID NO 475
<211> LENGTH: 32
<212> TYPE: PRT
<213> ORGANISM: Artificial Sequence
<220> FEATURE:
<223> OTHER INFORMATION: Synthetic Construct

<400> SEQUENCE: 475

Gly Val Pro Asp Arg Phe Thr Gly Ser Gly Ser Gly Thr Asp Phe Thr
1               5                   10                  15
Leu Thr Ile Arg Ser Val Gln Pro Glu Asp Leu Ala Val Tyr Tyr Cys

```
                        20                  25                  30

<210> SEQ ID NO 476
<211> LENGTH: 10
<212> TYPE: PRT
<213> ORGANISM: Artificial Sequence
<220> FEATURE:
<223> OTHER INFORMATION: Synthetic Construct

<400> SEQUENCE: 476

Phe Gly Gly Gly Thr Lys Leu Glu Ile Lys
1               5                   10

<210> SEQ ID NO 477
<211> LENGTH: 30
<212> TYPE: PRT
<213> ORGANISM: Artificial Sequence
<220> FEATURE:
<223> OTHER INFORMATION: Synthetic Construct

<400> SEQUENCE: 477

Gln Val Gln Leu Gln Gln Ser Gly Ser Glu Leu Val Arg Pro Gly Ala
1               5                   10                  15

Ser Leu Lys Leu Ser Cys Lys Ala Ser Gly Tyr Thr Phe Thr
            20                  25                  30

<210> SEQ ID NO 478
<211> LENGTH: 14
<212> TYPE: PRT
<213> ORGANISM: Artificial Sequence
<220> FEATURE:
<223> OTHER INFORMATION: Synthetic Construct

<400> SEQUENCE: 478

Trp Val Arg Gln Arg Pro Gly Gln Gly Leu Glu Trp Ile Gly
1               5                   10

<210> SEQ ID NO 479
<211> LENGTH: 32
<212> TYPE: PRT
<213> ORGANISM: Artificial Sequence
<220> FEATURE:
<223> OTHER INFORMATION: Synthetic Construct

<400> SEQUENCE: 479

Lys Val Thr Leu Ala Val Asp Thr Ser Ser Thr Ala Phe Leu Gln
1               5                   10                  15

Leu Ser Ser Leu Thr Ser Glu Asp Ser Ala Val Tyr Tyr Cys Thr Arg
            20                  25                  30

<210> SEQ ID NO 480
<211> LENGTH: 11
<212> TYPE: PRT
<213> ORGANISM: Artificial Sequence
<220> FEATURE:
<223> OTHER INFORMATION: Synthetic Construct

<400> SEQUENCE: 480

Trp Gly Gln Gly Thr Thr Leu Thr Val Ser Ser
1               5                   10

<210> SEQ ID NO 481
<211> LENGTH: 23
<212> TYPE: PRT
<213> ORGANISM: Artificial Sequence
<220> FEATURE:
```

```
<223> OTHER INFORMATION: Synthetic Construct

<400> SEQUENCE: 481

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 482
<211> LENGTH: 15
<212> TYPE: PRT
<213> ORGANISM: Artificial Sequence
<220> FEATURE:
<223> OTHER INFORMATION: Synthetic Construct

<400> SEQUENCE: 482

Trp Tyr Gln Gln Lys Pro Gly Gln Ser Pro Lys Leu Leu Ile Tyr
1               5                   10                  15

<210> SEQ ID NO 483
<211> LENGTH: 32
<212> TYPE: PRT
<213> ORGANISM: Artificial Sequence
<220> FEATURE:
<223> OTHER INFORMATION: Synthetic Construct

<400> SEQUENCE: 483

Gly Val Pro Asp Arg Phe Thr Gly Ser Gly Ser Gly Thr Asp Phe Thr
1               5                   10                  15

Leu Thr Ile Ser Ser Val Gln Thr Glu Asp Leu Ala Val Tyr Tyr Cys
            20                  25                  30

<210> SEQ ID NO 484
<211> LENGTH: 10
<212> TYPE: PRT
<213> ORGANISM: Artificial Sequence
<220> FEATURE:
<223> OTHER INFORMATION: Synthetic Construct

<400> SEQUENCE: 484

Phe Gly Gly Gly Thr Lys Leu Glu Ile Lys
1               5                   10

<210> SEQ ID NO 485
<211> LENGTH: 30
<212> TYPE: PRT
<213> ORGANISM: Artificial Sequence
<220> FEATURE:
<223> OTHER INFORMATION: Synthetic Construct

<400> SEQUENCE: 485

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr
            20                  25                  30

<210> SEQ ID NO 486
<211> LENGTH: 14
<212> TYPE: PRT
<213> ORGANISM: Artificial Sequence
<220> FEATURE:
<223> OTHER INFORMATION: Synthetic Construct

<400> SEQUENCE: 486

Trp Val Lys Gln Arg Pro Gly Gln Gly Leu Glu Trp Ile Gly
```

<210> SEQ ID NO 487
<211> LENGTH: 32
<212> TYPE: PRT
<213> ORGANISM: Artificial Sequence
<220> FEATURE:
<223> OTHER INFORMATION: Synthetic Construct

<400> SEQUENCE: 487

Lys Ala Thr Leu Thr Ala Asp Thr Ser Ser Thr Ala Tyr Met Gln
1               5                   10                  15

Leu Ser Ser Leu Thr Ser Glu Asp Ser Ala Val Tyr Tyr Cys Ala Arg
            20                  25                  30

<210> SEQ ID NO 488
<211> LENGTH: 11
<212> TYPE: PRT
<213> ORGANISM: Artificial Sequence
<220> FEATURE:
<223> OTHER INFORMATION: Synthetic Construct

<400> SEQUENCE: 488

Trp Gly Gln Gly Thr Thr Leu Thr Val Ser Ser
1               5                   10

<210> SEQ ID NO 489
<211> LENGTH: 23
<212> TYPE: PRT
<213> ORGANISM: Artificial Sequence
<220> FEATURE:
<223> OTHER INFORMATION: Synthetic Construct

<400> SEQUENCE: 489

Asp Ile Val Met Thr Gln Ser Pro Ser Ser Leu Ala Val Ser Ala Gly
1               5                   10                  15

Glu Lys Val Thr Met Thr Cys
            20

<210> SEQ ID NO 490
<211> LENGTH: 15
<212> TYPE: PRT
<213> ORGANISM: Artificial Sequence
<220> FEATURE:
<223> OTHER INFORMATION: Synthetic Construct

<400> SEQUENCE: 490

Trp Tyr Gln Gln Lys Pro Gly Gln Ser Pro Lys Leu Leu Ile Tyr
1               5                   10                  15

<210> SEQ ID NO 491
<211> LENGTH: 32
<212> TYPE: PRT
<213> ORGANISM: Artificial Sequence
<220> FEATURE:
<223> OTHER INFORMATION: Synthetic Construct

<400> SEQUENCE: 491

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 492
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 492

Phe Gly Gly Gly Thr Lys Leu Glu Leu Lys
1               5                   10

<210> SEQ ID NO 493
<211> LENGTH: 30
<212> TYPE: PRT
<213> ORGANISM: Artificial Sequence
<220> FEATURE:
<223> OTHER INFORMATION: Synthetic Construct

<400> SEQUENCE: 493

Gln Val Gln Leu Gln Gln Ser Gly Pro Glu Leu Val Lys Pro Gly Thr
1               5                   10                  15

Ser Val Lys Ile Ser Cys Lys Thr Ser Gly Tyr Ser Phe Ile
            20                  25                  30

<210> SEQ ID NO 494
<211> LENGTH: 14
<212> TYPE: PRT
<213> ORGANISM: Artificial Sequence
<220> FEATURE:
<223> OTHER INFORMATION: Synthetic Construct

<400> SEQUENCE: 494

Trp Val Lys Gln Arg Pro Gly Gln Gly Leu Glu Trp Ile Gly
1               5                   10

<210> SEQ ID NO 495
<211> LENGTH: 32
<212> TYPE: PRT
<213> ORGANISM: Artificial Sequence
<220> FEATURE:
<223> OTHER INFORMATION: Synthetic Construct

<400> SEQUENCE: 495

Lys Ala Thr Leu Thr Ala Asp Thr Ser Ser Thr Thr Ala His Met His
1               5                   10                  15

Leu Ser Ser Leu Val Ser Glu Asp Ser Ala Val Tyr Tyr Cys Ala Arg
            20                  25                  30

<210> SEQ ID NO 496
<211> LENGTH: 11
<212> TYPE: PRT
<213> ORGANISM: Artificial Sequence
<220> FEATURE:
<223> OTHER INFORMATION: Synthetic Construct

<400> SEQUENCE: 496

Trp Gly Gln Gly Thr Thr Leu Thr Val Ser Ser
1               5                   10

<210> SEQ ID NO 497
<211> LENGTH: 23
<212> TYPE: PRT
<213> ORGANISM: Artificial Sequence
<220> FEATURE:
<223> OTHER INFORMATION: Synthetic Construct

<400> SEQUENCE: 497

Asp Ile Val Met Thr Gln Ser Pro Ser Ser Leu Ala Val Ser Val Gly
```

```
                1               5                  10                  15
Glu Lys Val Thr Met Ser Cys
                20

<210> SEQ ID NO 498
<211> LENGTH: 15
<212> TYPE: PRT
<213> ORGANISM: Artificial Sequence
<220> FEATURE:
<223> OTHER INFORMATION: Synthetic Construct

<400> SEQUENCE: 498

Trp Tyr Gln Gln Lys Pro Gly Gln Ser Pro Lys Leu Leu Ile Tyr
1               5                   10                  15

<210> SEQ ID NO 499
<211> LENGTH: 32
<212> TYPE: PRT
<213> ORGANISM: Artificial Sequence
<220> FEATURE:
<223> OTHER INFORMATION: Synthetic Construct

<400> SEQUENCE: 499

Gly Val Pro Val Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
                20                  25                  30

<210> SEQ ID NO 500
<211> LENGTH: 10
<212> TYPE: PRT
<213> ORGANISM: Artificial Sequence
<220> FEATURE:
<223> OTHER INFORMATION: Synthetic Construct

<400> SEQUENCE: 500

Phe Gly Gly Gly Thr Lys Leu Glu Ile Lys
1               5                   10

<210> SEQ ID NO 501
<211> LENGTH: 30
<212> TYPE: PRT
<213> ORGANISM: Artificial Sequence
<220> FEATURE:
<223> OTHER INFORMATION: Synthetic Construct

<400> SEQUENCE: 501

Gln Val Gln Leu Gln Gln Ser Gly Pro Glu Leu Val Lys Pro Gly Thr
1               5                   10                  15

Ser Val Lys Ile Ser Cys Lys Thr Ser Gly Tyr Asn Phe Ile
                20                  25                  30

<210> SEQ ID NO 502
<211> LENGTH: 14
<212> TYPE: PRT
<213> ORGANISM: Artificial Sequence
<220> FEATURE:
<223> OTHER INFORMATION: Synthetic Construct

<400> SEQUENCE: 502

Trp Val Lys Gln Arg Pro Gly Gln Gly Leu Glu Trp Ile Gly
1               5                   10

<210> SEQ ID NO 503
<211> LENGTH: 32
```

<212> TYPE: PRT
<213> ORGANISM: Artificial Sequence
<220> FEATURE:
<223> OTHER INFORMATION: Synthetic Construct

<400> SEQUENCE: 503

Lys Ala Thr Leu Thr Ala Asp Thr Ser Ser Thr Ala His Met His
1               5                   10                  15

Leu Ser Ser Leu Val Ser Glu Asp Ser Ala Val Tyr Tyr Cys Ala Arg
            20                  25                  30

<210> SEQ ID NO 504
<211> LENGTH: 11
<212> TYPE: PRT
<213> ORGANISM: Artificial Sequence
<220> FEATURE:
<223> OTHER INFORMATION: Synthetic Construct

<400> SEQUENCE: 504

Trp Gly Gln Gly Thr Thr Leu Thr Val Ser Ser
1               5                   10

<210> SEQ ID NO 505
<211> LENGTH: 23
<212> TYPE: PRT
<213> ORGANISM: Artificial Sequence
<220> FEATURE:
<223> OTHER INFORMATION: Synthetic Construct

<400> SEQUENCE: 505

Asp Ile Val Met Thr Gln Ser Pro Ser Ser Leu Ala Val Ser Ala Gly
1               5                   10                  15

Glu Lys Val Thr Met Thr Cys
            20

<210> SEQ ID NO 506
<211> LENGTH: 15
<212> TYPE: PRT
<213> ORGANISM: Artificial Sequence
<220> FEATURE:
<223> OTHER INFORMATION: Synthetic Construct

<400> SEQUENCE: 506

Trp Tyr Gln Gln Lys Pro Gly Gln Ser Pro Lys Leu Leu Ile Tyr
1               5                   10                  15

<210> SEQ ID NO 507
<211> LENGTH: 32
<212> TYPE: PRT
<213> ORGANISM: Artificial Sequence
<220> FEATURE:
<223> OTHER INFORMATION: Synthetic Construct

<400> SEQUENCE: 507

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 508
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 508

Phe Gly Gly Gly Thr Lys Leu Glu Ile Lys
1               5                   10

<210> SEQ ID NO 509
<211> LENGTH: 30
<212> TYPE: PRT
<213> ORGANISM: Artificial Sequence
<220> FEATURE:
<223> OTHER INFORMATION: Synthetic Construct

<400> SEQUENCE: 509

Gln Val Gln Leu Gln Gln Ser Gly Pro Glu Leu Val Lys Pro Gly Ala
1               5                   10                  15

Ser Leu Lys Ile Ser Cys Lys Ala Ser Gly Tyr Ser Phe Ala
            20                  25                  30

<210> SEQ ID NO 510
<211> LENGTH: 14
<212> TYPE: PRT
<213> ORGANISM: Artificial Sequence
<220> FEATURE:
<223> OTHER INFORMATION: Synthetic Construct

<400> SEQUENCE: 510

Trp Val Arg Gln Arg Pro Gly Gln Gly Leu Glu Trp Ile Gly
1               5                   10

<210> SEQ ID NO 511
<211> LENGTH: 32
<212> TYPE: PRT
<213> ORGANISM: Artificial Sequence
<220> FEATURE:
<223> OTHER INFORMATION: Synthetic Construct

<400> SEQUENCE: 511

Lys Ala Thr Leu Thr Ala Asp Thr Ser Ser Asn Thr Ala Ser Met Gln
1               5                   10                  15

Leu Asn Ser Leu Thr Ser Glu Asp Ser Ala Val Tyr Tyr Cys Thr Arg
            20                  25                  30

<210> SEQ ID NO 512
<211> LENGTH: 11
<212> TYPE: PRT
<213> ORGANISM: Artificial Sequence
<220> FEATURE:
<223> OTHER INFORMATION: Synthetic Construct

<400> SEQUENCE: 512

Trp Gly Gln Gly Thr Thr Leu Ile Val Ser Ser
1               5                   10

<210> SEQ ID NO 513
<211> LENGTH: 23
<212> TYPE: PRT
<213> ORGANISM: Artificial Sequence
<220> FEATURE:
<223> OTHER INFORMATION: Synthetic Construct

<400> SEQUENCE: 513

Asp Ile Val Met Thr Gln Ser Pro Ser Ser Leu Ala Val Ser Ala Gly
1               5                   10                  15

Glu Lys Val Thr Met Ser Cys
            20
```

<210> SEQ ID NO 514
<211> LENGTH: 15
<212> TYPE: PRT
<213> ORGANISM: Artificial Sequence
<220> FEATURE:
<223> OTHER INFORMATION: Synthetic Construct

<400> SEQUENCE: 514

Trp Tyr Gln Gln Lys Pro Gly Gln Ser Pro Lys Leu Leu Ile Phe
1               5                   10                  15

<210> SEQ ID NO 515
<211> LENGTH: 32
<212> TYPE: PRT
<213> ORGANISM: Artificial Sequence
<220> FEATURE:
<223> OTHER INFORMATION: Synthetic Construct

<400> SEQUENCE: 515

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 516
<211> LENGTH: 10
<212> TYPE: PRT
<213> ORGANISM: Artificial Sequence
<220> FEATURE:
<223> OTHER INFORMATION: Synthetic Construct

<400> SEQUENCE: 516

Phe Gly Gly Gly Thr Lys Leu Glu Leu Lys
1               5                   10

<210> SEQ ID NO 517
<211> LENGTH: 30
<212> TYPE: PRT
<213> ORGANISM: Artificial Sequence
<220> FEATURE:
<223> OTHER INFORMATION: Synthetic Construct

<400> SEQUENCE: 517

Gln Val Gln Leu Gln Gln Ser Gly Ser Glu Leu Val Arg Pro Gly Ala
1               5                   10                  15

Ser Leu Lys Leu Ser Cys Lys Ala Ser Gly Tyr Thr Phe Thr
            20                  25                  30

<210> SEQ ID NO 518
<211> LENGTH: 14
<212> TYPE: PRT
<213> ORGANISM: Artificial Sequence
<220> FEATURE:
<223> OTHER INFORMATION: Synthetic Construct

<400> SEQUENCE: 518

Trp Val Arg Gln Arg Pro Gly Gln Gly Leu Glu Trp Ile Gly
1               5                   10

<210> SEQ ID NO 519
<211> LENGTH: 32
<212> TYPE: PRT
<213> ORGANISM: Artificial Sequence
<220> FEATURE:
<223> OTHER INFORMATION: Synthetic Construct

<400> SEQUENCE: 519

Lys Val Thr Leu Ala Val Asp Thr Ser Ser Thr Ala Phe Leu Gln
1               5                   10                  15

Leu Ser Ser Leu Thr Ser Glu Asp Ser Ala Val Tyr Tyr Cys Thr Arg
            20                  25                  30

<210> SEQ ID NO 520
<211> LENGTH: 11
<212> TYPE: PRT
<213> ORGANISM: Artificial Sequence
<220> FEATURE:
<223> OTHER INFORMATION: Synthetic Construct

<400> SEQUENCE: 520

Trp Gly Gln Gly Thr Thr Leu Thr Val Ser Ser
1               5                   10

<210> SEQ ID NO 521
<211> LENGTH: 23
<212> TYPE: PRT
<213> ORGANISM: Artificial Sequence
<220> FEATURE:
<223> OTHER INFORMATION: Synthetic Construct

<400> SEQUENCE: 521

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 522
<211> LENGTH: 15
<212> TYPE: PRT
<213> ORGANISM: Artificial Sequence
<220> FEATURE:
<223> OTHER INFORMATION: Synthetic Construct

<400> SEQUENCE: 522

Trp Tyr Gln Gln Lys Pro Gly Gln Ser Pro Lys Leu Leu Ile Tyr
1               5                   10                  15

<210> SEQ ID NO 523
<211> LENGTH: 32
<212> TYPE: PRT
<213> ORGANISM: Artificial Sequence
<220> FEATURE:
<223> OTHER INFORMATION: Synthetic Construct

<400> SEQUENCE: 523

Gly Val Pro Asp Arg Phe Thr Gly Ser Gly Ser Gly Thr Asp Phe Thr
1               5                   10                  15

Leu Thr Ile Ser Ser Val Gln Thr Glu Asp Leu Ala Val Tyr Tyr Cys
            20                  25                  30

<210> SEQ ID NO 524
<211> LENGTH: 10
<212> TYPE: PRT
<213> ORGANISM: Artificial Sequence
<220> FEATURE:
<223> OTHER INFORMATION: Synthetic Construct

<400> SEQUENCE: 524

Phe Gly Gly Gly Thr Lys Leu Glu Ile Lys
1               5                   10

<210> SEQ ID NO 525
<211> LENGTH: 30
<212> TYPE: PRT
<213> ORGANISM: Artificial Sequence
<220> FEATURE:
<223> OTHER INFORMATION: Synthetic Construct

<400> SEQUENCE: 525

Gln Val Gln Leu Gln Gln Ser Gly Pro Glu Met Val Lys Pro Gly Ala
1               5                   10                  15

Ser Val Thr Ile Ser Cys Lys Thr Ser Gly Phe Thr Phe Thr
            20                  25                  30

<210> SEQ ID NO 526
<211> LENGTH: 14
<212> TYPE: PRT
<213> ORGANISM: Artificial Sequence
<220> FEATURE:
<223> OTHER INFORMATION: Synthetic Construct

<400> SEQUENCE: 526

Trp Met Met Gln Arg Pro Gly Gln Gly Leu Glu Trp Ile Gly
1               5                   10

<210> SEQ ID NO 527
<211> LENGTH: 32
<212> TYPE: PRT
<213> ORGANISM: Artificial Sequence
<220> FEATURE:
<223> OTHER INFORMATION: Synthetic Construct

<400> SEQUENCE: 527

Lys Ala Thr Leu Thr Ala Asp Lys Ser Ser Thr Thr Ala Tyr Leu Tyr
1               5                   10                  15

Leu Ser Ser Leu Thr Ser Glu Asp Ser Ala Val Tyr Phe Cys Ala Arg
            20                  25                  30

<210> SEQ ID NO 528
<211> LENGTH: 11
<212> TYPE: PRT
<213> ORGANISM: Artificial Sequence
<220> FEATURE:
<223> OTHER INFORMATION: Synthetic Construct

<400> SEQUENCE: 528

Trp Gly Gln Gly Thr Thr Leu Thr Val Ser Ser
1               5                   10

<210> SEQ ID NO 529
<211> LENGTH: 23
<212> TYPE: PRT
<213> ORGANISM: Artificial Sequence
<220> FEATURE:
<223> OTHER INFORMATION: Synthetic Construct

<400> SEQUENCE: 529

Asp Ile Val Met Thr Gln Ser Pro Ser Ser Leu Ala Val Ser Ala Gly
1               5                   10                  15

Glu Met Val Thr Leu His Cys
            20

<210> SEQ ID NO 530
<211> LENGTH: 15
<212> TYPE: PRT
<213> ORGANISM: Artificial Sequence

```
<220> FEATURE:
<223> OTHER INFORMATION: Synthetic Construct

<400> SEQUENCE: 530

Trp Tyr Leu Gln Lys Pro Gly Gln Ser Pro Arg Leu Leu Ile Tyr
1               5                   10                  15

<210> SEQ ID NO 531
<211> LENGTH: 32
<212> TYPE: PRT
<213> ORGANISM: Artificial Sequence
<220> FEATURE:
<223> OTHER INFORMATION: Synthetic Construct

<400> SEQUENCE: 531

Gly Val Pro Asp Arg Phe Thr Gly Ser Gly Ser Gly Thr Asp Phe Thr
1               5                   10                  15

Leu Thr Ile Ser Ser Val Gln Pro Glu Asp Leu Ala Val Tyr Tyr Cys
            20                  25                  30

<210> SEQ ID NO 532
<211> LENGTH: 10
<212> TYPE: PRT
<213> ORGANISM: Artificial Sequence
<220> FEATURE:
<223> OTHER INFORMATION: Synthetic Construct

<400> SEQUENCE: 532

Phe Gly Gly Gly Thr Lys Leu Glu Leu Lys
1               5                   10

<210> SEQ ID NO 533
<211> LENGTH: 30
<212> TYPE: PRT
<213> ORGANISM: Artificial Sequence
<220> FEATURE:
<223> OTHER INFORMATION: Synthetic Construct

<400> SEQUENCE: 533

Gln Val Gln Leu Gln Gln Pro Gly Ser Glu Leu Val Arg Pro Gly Ala
1               5                   10                  15

Ser Val Thr Leu Ser Cys Thr Ala Ser Gly Tyr Ser Phe Thr
            20                  25                  30

<210> SEQ ID NO 534
<211> LENGTH: 14
<212> TYPE: PRT
<213> ORGANISM: Artificial Sequence
<220> FEATURE:
<223> OTHER INFORMATION: Synthetic Construct

<400> SEQUENCE: 534

Trp Val Lys Gln Arg Pro Gly Gln Gly Leu Glu Trp Val Gly
1               5                   10

<210> SEQ ID NO 535
<211> LENGTH: 32
<212> TYPE: PRT
<213> ORGANISM: Artificial Sequence
<220> FEATURE:
<223> OTHER INFORMATION: Synthetic Construct

<400> SEQUENCE: 535

Lys Gly Thr Leu Thr Val Asp Ile Ser Ser Ser Thr Ala Tyr Met His
1               5                   10                  15
```

Leu Ser Ser Leu Thr Ser Asp Asp Ser Ala Val Tyr Tyr Cys Thr Arg
            20                  25                  30

<210> SEQ ID NO 536
<211> LENGTH: 11
<212> TYPE: PRT
<213> ORGANISM: Artificial Sequence
<220> FEATURE:
<223> OTHER INFORMATION: Synthetic Construct

<400> SEQUENCE: 536

Trp Gly Gln Gly Thr Thr Leu Thr Val Ser Ser
1               5                   10

<210> SEQ ID NO 537
<211> LENGTH: 23
<212> TYPE: PRT
<213> ORGANISM: Artificial Sequence
<220> FEATURE:
<223> OTHER INFORMATION: Synthetic Construct

<400> SEQUENCE: 537

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 538
<211> LENGTH: 15
<212> TYPE: PRT
<213> ORGANISM: Artificial Sequence
<220> FEATURE:
<223> OTHER INFORMATION: Synthetic Construct

<400> SEQUENCE: 538

Trp Tyr Gln Gln Lys Pro Gly Leu Ser Pro Lys Leu Leu Ile Tyr
1               5                   10                  15

<210> SEQ ID NO 539
<211> LENGTH: 32
<212> TYPE: PRT
<213> ORGANISM: Artificial Sequence
<220> FEATURE:
<223> OTHER INFORMATION: Synthetic Construct

<400> SEQUENCE: 539

Gly Val Pro Glu Arg Phe Thr Gly Ser Gly Ser Gly Thr Asp Phe Thr
1               5                   10                  15

Leu Thr Ile Ser Ser Val Gln Thr Glu Asp Leu Ala Val Tyr Tyr Cys
            20                  25                  30

<210> SEQ ID NO 540
<211> LENGTH: 10
<212> TYPE: PRT
<213> ORGANISM: Artificial Sequence
<220> FEATURE:
<223> OTHER INFORMATION: Synthetic Construct

<400> SEQUENCE: 540

Phe Gly Gly Gly Thr Arg Leu Glu Ile Lys
1               5                   10

<210> SEQ ID NO 541
<211> LENGTH: 29
<212> TYPE: PRT
<213> ORGANISM: Artificial Sequence

```
<220> FEATURE:
<223> OTHER INFORMATION: Synthetic Construct

<400> SEQUENCE: 541

Gln Ser Val Lys Glu Ser Glu Gly Gly Leu Phe Lys Pro Thr Asp Thr
1               5                   10                  15

Leu Thr Leu Thr Cys Thr Val Ser Gly Cys Ser Leu Ser
            20                  25

<210> SEQ ID NO 542
<211> LENGTH: 14
<212> TYPE: PRT
<213> ORGANISM: Artificial Sequence
<220> FEATURE:
<223> OTHER INFORMATION: Synthetic Construct

<400> SEQUENCE: 542

Trp Val Arg Gln Ala Pro Gly Lys Gly Leu Glu Trp Ile Gly
1               5                   10

<210> SEQ ID NO 543
<211> LENGTH: 32
<212> TYPE: PRT
<213> ORGANISM: Artificial Sequence
<220> FEATURE:
<223> OTHER INFORMATION: Synthetic Construct

<400> SEQUENCE: 543

Arg Ser Thr Ile Thr Arg Asn Thr Asn Glu Asn Thr Val Thr Leu Lys
1               5                   10                  15

Met Thr Arg Leu Thr Ala Ala Asp Thr Ala Ile Tyr Phe Cys Ala Arg
            20                  25                  30

<210> SEQ ID NO 544
<211> LENGTH: 11
<212> TYPE: PRT
<213> ORGANISM: Artificial Sequence
<220> FEATURE:
<223> OTHER INFORMATION: Synthetic Construct

<400> SEQUENCE: 544

Trp Gly Gln Gly Thr Leu Val Thr Val Ser Ser
1               5                   10

<210> SEQ ID NO 545
<211> LENGTH: 21
<212> TYPE: PRT
<213> ORGANISM: Artificial Sequence
<220> FEATURE:
<223> OTHER INFORMATION: Synthetic Construct

<400> SEQUENCE: 545

Asp Met Thr Gln Thr Pro Ser Ser Lys Ser Val Pro Val Gly Asp Thr
1               5                   10                  15

Val Thr Ile Asn Cys
            20

<210> SEQ ID NO 546
<211> LENGTH: 15
<212> TYPE: PRT
<213> ORGANISM: Artificial Sequence
<220> FEATURE:
<223> OTHER INFORMATION: Synthetic Construct

<400> SEQUENCE: 546
```

```
Trp Phe Gln Gln Lys Pro Gly Gln Pro Pro Lys Arg Leu Ile Tyr
1               5                   10                  15
```

<210> SEQ ID NO 547
<211> LENGTH: 32
<212> TYPE: PRT
<213> ORGANISM: Artificial Sequence
<220> FEATURE:
<223> OTHER INFORMATION: Synthetic Construct

<400> SEQUENCE: 547

```
Gly Val Pro Pro Arg Phe Ser Gly Ser Gly Ser Gly Thr Gln Phe Thr
1               5                   10                  15

Leu Thr Ile Ser Asp Val Val Cys Asp Asp Ala Ala Thr Tyr Tyr Cys
            20                  25                  30
```

<210> SEQ ID NO 548
<211> LENGTH: 10
<212> TYPE: PRT
<213> ORGANISM: Artificial Sequence
<220> FEATURE:
<223> OTHER INFORMATION: Synthetic Construct

<400> SEQUENCE: 548

```
Phe Gly Gly Gly Thr Glu Leu Glu Ile Leu
1               5                   10
```

<210> SEQ ID NO 549
<211> LENGTH: 30
<212> TYPE: PRT
<213> ORGANISM: Artificial Sequence
<220> FEATURE:
<223> OTHER INFORMATION: Synthetic Construct

<400> SEQUENCE: 549

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30
```

<210> SEQ ID NO 550
<211> LENGTH: 49
<212> TYPE: PRT
<213> ORGANISM: Artificial Sequence
<220> FEATURE:
<223> OTHER INFORMATION: Synthetic Construct

<400> SEQUENCE: 550

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala
```

<210> SEQ ID NO 551
<211> LENGTH: 58
<212> TYPE: PRT
<213> ORGANISM: Artificial Sequence
<220> FEATURE:
<223> OTHER INFORMATION: Synthetic Construct

<400> SEQUENCE: 551

```
Pro Gly Lys Gly Leu Glu Trp Val Ala Arg Ile Tyr Pro Thr Asn Gly
1               5                   10                  15

Tyr Thr Arg Tyr Ala Asp Ser Val Lys Gly Arg Phe Thr Ile Ser Ala
            20                  25                  30

Asp Thr Ser Lys Asn Thr Ala Tyr Leu Gln Met Asn Ser Leu Arg Ala
        35                  40                  45

Glu Asp Thr Ala Val Tyr Tyr Cys Ser Arg
    50                  55
```

<210> SEQ ID NO 552
<211> LENGTH: 11
<212> TYPE: PRT
<213> ORGANISM: Artificial Sequence
<220> FEATURE:
<223> OTHER INFORMATION: Synthetic Construct

<400> SEQUENCE: 552

```
Trp Gly Gln Gly Thr Leu Val Thr Val Ser Ser
1               5                   10
```

<210> SEQ ID NO 553
<211> LENGTH: 23
<212> TYPE: PRT
<213> ORGANISM: Artificial Sequence
<220> FEATURE:
<223> OTHER INFORMATION: Synthetic Construct

<400> SEQUENCE: 553

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 554
<211> LENGTH: 49
<212> TYPE: PRT
<213> ORGANISM: Artificial Sequence
<220> FEATURE:
<223> OTHER INFORMATION: Synthetic Construct

<400> SEQUENCE: 554

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr
```

<210> SEQ ID NO 555
<211> LENGTH: 32
<212> TYPE: PRT
<213> ORGANISM: Artificial Sequence
<220> FEATURE:
<223> OTHER INFORMATION: Synthetic Construct

<400> SEQUENCE: 555

```
Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 556
<211> LENGTH: 10
<212> TYPE: PRT
<213> ORGANISM: Artificial Sequence
<220> FEATURE:
<223> OTHER INFORMATION: Synthetic Construct

<400> SEQUENCE: 556

Phe Gly Gln Gly Thr Lys Val Glu Ile Lys
1               5                   10

<210> SEQ ID NO 557
<211> LENGTH: 25
<212> TYPE: PRT
<213> ORGANISM: Artificial Sequence
<220> FEATURE:
<223> OTHER INFORMATION: Synthetic Construct

<400> SEQUENCE: 557

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 558
<211> LENGTH: 14
<212> TYPE: PRT
<213> ORGANISM: Artificial Sequence
<220> FEATURE:
<223> OTHER INFORMATION: Synthetic Construct

<400> SEQUENCE: 558

Trp Val Arg Gln Ala Pro Gly Lys Gly Leu Glu Trp Val Gly
1               5                   10

<210> SEQ ID NO 559
<211> LENGTH: 32
<212> TYPE: PRT
<213> ORGANISM: Artificial Sequence
<220> FEATURE:
<223> OTHER INFORMATION: Synthetic Construct

<400> SEQUENCE: 559

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 560
<211> LENGTH: 11
<212> TYPE: PRT
<213> ORGANISM: Artificial Sequence
<220> FEATURE:
<223> OTHER INFORMATION: Synthetic Construct

<400> SEQUENCE: 560

Trp Gly Gln Gly Thr Leu Val Thr Val Ser Ser
1               5                   10

<210> SEQ ID NO 561
<211> LENGTH: 23
<212> TYPE: PRT
<213> ORGANISM: Artificial Sequence
<220> FEATURE:
<223> OTHER INFORMATION: Synthetic Construct

<400> SEQUENCE: 561

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 562
<211> LENGTH: 15
<212> TYPE: PRT
<213> ORGANISM: Artificial Sequence
<220> FEATURE:
<223> OTHER INFORMATION: Synthetic Construct

<400> SEQUENCE: 562

Trp Tyr Gln Gln Lys Pro Gly Lys Ala Pro Lys Pro Leu Ile Tyr
1               5                   10                  15

<210> SEQ ID NO 563
<211> LENGTH: 32
<212> TYPE: PRT
<213> ORGANISM: Artificial Sequence
<220> FEATURE:
<223> OTHER INFORMATION: Synthetic Construct

<400> SEQUENCE: 563

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 564
<211> LENGTH: 10
<212> TYPE: PRT
<213> ORGANISM: Artificial Sequence
<220> FEATURE:
<223> OTHER INFORMATION: Synthetic Construct

<400> SEQUENCE: 564

Phe Gly Gln Gly Thr Lys Val Glu Ile Lys
1               5                   10

<210> SEQ ID NO 565
<211> LENGTH: 30
<212> TYPE: PRT
<213> ORGANISM: Artificial Sequence
<220> FEATURE:
<223> OTHER INFORMATION: Synthetic Construct

<400> SEQUENCE: 565

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr
            20                  25                  30

<210> SEQ ID NO 566
<211> LENGTH: 14
<212> TYPE: PRT
<213> ORGANISM: Artificial Sequence
<220> FEATURE:
<223> OTHER INFORMATION: Synthetic Construct

<400> SEQUENCE: 566

Trp Val Arg Gln Ser Pro Gly Lys Gly Leu Glu Trp Leu Gly
1               5                   10

```
<210> SEQ ID NO 567
<211> LENGTH: 32
<212> TYPE: PRT
<213> ORGANISM: Artificial Sequence
<220> FEATURE:
<223> OTHER INFORMATION: Synthetic Construct

<400> SEQUENCE: 567

Arg Leu Thr Ile Thr Lys Asp Asn Ser Lys Ser Gln Val Phe Phe Lys
 1               5                  10                  15

Leu Asn Ser Leu Lys Val Asp Asp Thr Ala Ile Tyr Tyr Cys Ser Asn
                20                  25                  30

<210> SEQ ID NO 568
<211> LENGTH: 11
<212> TYPE: PRT
<213> ORGANISM: Artificial Sequence
<220> FEATURE:
<223> OTHER INFORMATION: Synthetic Construct

<400> SEQUENCE: 568

Trp Gly Gln Gly Ile Ser Val Thr Val Ser Ser
 1               5                  10

<210> SEQ ID NO 569
<211> LENGTH: 23
<212> TYPE: PRT
<213> ORGANISM: Artificial Sequence
<220> FEATURE:
<223> OTHER INFORMATION: Synthetic Construct

<400> SEQUENCE: 569

Asp Ile Val Met Thr Gln Ser His Lys Ile Met Ser Thr Ser Val Gly
 1               5                  10                  15

Asp Arg Val Ser Ile Thr Cys
                20

<210> SEQ ID NO 570
<211> LENGTH: 15
<212> TYPE: PRT
<213> ORGANISM: Artificial Sequence
<220> FEATURE:
<223> OTHER INFORMATION: Synthetic Construct

<400> SEQUENCE: 570

Trp Phe Gln Gln Lys Pro Gly Gln Ser Pro Asn Leu Leu Ile Tyr
 1               5                  10                  15

<210> SEQ ID NO 571
<211> LENGTH: 32
<212> TYPE: PRT
<213> ORGANISM: Artificial Sequence
<220> FEATURE:
<223> OTHER INFORMATION: Synthetic Construct

<400> SEQUENCE: 571

Gly Val Pro Asp Arg Phe Thr Gly Ser Gly Ser Gly Thr Asp Phe Thr
 1               5                  10                  15

Phe Thr Ile Ser Ser Val Gln Ala Glu Asp Leu Ala Val Tyr Tyr Cys
                20                  25                  30

<210> SEQ ID NO 572
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 572

Phe Gly Gly Gly Thr Lys Leu Glu Ile Lys
1               5                   10

<210> SEQ ID NO 573
<211> LENGTH: 25
<212> TYPE: PRT
<213> ORGANISM: Artificial Sequence
<220> FEATURE:
<223> OTHER INFORMATION: Synthetic Construct

<400> SEQUENCE: 573

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 574
<211> LENGTH: 13
<212> TYPE: PRT
<213> ORGANISM: Artificial Sequence
<220> FEATURE:
<223> OTHER INFORMATION: Synthetic Construct

<400> SEQUENCE: 574

Trp Val Arg Gln Ala Pro Gly Lys Gly Leu Glu Trp Val
1               5                   10

<210> SEQ ID NO 575
<211> LENGTH: 35
<212> TYPE: PRT
<213> ORGANISM: Artificial Sequence
<220> FEATURE:
<223> OTHER INFORMATION: Synthetic Construct

<400> SEQUENCE: 575

Val Lys Gly Arg Phe Thr Ile Ser Ala Asp Thr Ser Lys Asn Thr Ala
1               5                   10                  15

Tyr Leu Gln Met Asn Ser Leu Arg Ala Glu Asp Thr Ala Val Tyr Tyr
            20                  25                  30

Cys Ala Arg
        35

<210> SEQ ID NO 576
<211> LENGTH: 11
<212> TYPE: PRT
<213> ORGANISM: Artificial Sequence
<220> FEATURE:
<223> OTHER INFORMATION: Synthetic Construct

<400> SEQUENCE: 576

Trp Gly Gln Gly Thr Leu Val Thr Val Ser Ser
1               5                   10

<210> SEQ ID NO 577
<211> LENGTH: 23
<212> TYPE: PRT
<213> ORGANISM: Artificial Sequence
<220> FEATURE:
<223> OTHER INFORMATION: Synthetic Construct

<400> SEQUENCE: 577

Asp Ile Gln Met Thr Gln Ser Pro Ser Ser Leu Ser Ala Ser Val Gly
```

```
1               5                   10                  15
Asp Arg Val Thr Ile Thr Cys
            20
```

<210> SEQ ID NO 578
<211> LENGTH: 15
<212> TYPE: PRT
<213> ORGANISM: Artificial Sequence
<220> FEATURE:
<223> OTHER INFORMATION: Synthetic Construct

<400> SEQUENCE: 578

```
Trp Tyr Gln Gln Lys Pro Gly Lys Ala Pro Lys Leu Leu Ile Tyr
1               5                   10                  15
```

<210> SEQ ID NO 579
<211> LENGTH: 32
<212> TYPE: PRT
<213> ORGANISM: Artificial Sequence
<220> FEATURE:
<223> OTHER INFORMATION: Synthetic Construct

<400> SEQUENCE: 579

```
Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30
```

<210> SEQ ID NO 580
<211> LENGTH: 11
<212> TYPE: PRT
<213> ORGANISM: Artificial Sequence
<220> FEATURE:
<223> OTHER INFORMATION: Synthetic Construct

<400> SEQUENCE: 580

```
Phe Gly Gln Gly Thr Lys Val Glu Ile Lys Arg
1               5                   10
```

<210> SEQ ID NO 581
<211> LENGTH: 10
<212> TYPE: PRT
<213> ORGANISM: Artificial Sequence
<220> FEATURE:
<223> OTHER INFORMATION: Synthetic Construct

<400> SEQUENCE: 581

```
Gly Phe Thr Phe Thr Asp Tyr Thr Met Asp
1               5                   10
```

<210> SEQ ID NO 582
<211> LENGTH: 17
<212> TYPE: PRT
<213> ORGANISM: Artificial Sequence
<220> FEATURE:
<223> OTHER INFORMATION: Synthetic Construct

<400> SEQUENCE: 582

```
Asp Val Asn Pro Asn Ser Gly Gly Ser Ile Tyr Asn Gln Arg Phe Lys
1               5                   10                  15
Gly
```

<210> SEQ ID NO 583
<211> LENGTH: 10
<212> TYPE: PRT

<213> ORGANISM: Artificial Sequence
<220> FEATURE:
<223> OTHER INFORMATION: Synthetic Construct

<400> SEQUENCE: 583

Asn Leu Gly Pro Ser Phe Tyr Phe Asp Tyr
1               5                   10

<210> SEQ ID NO 584
<211> LENGTH: 11
<212> TYPE: PRT
<213> ORGANISM: Artificial Sequence
<220> FEATURE:
<223> OTHER INFORMATION: Synthetic Construct

<400> SEQUENCE: 584

Lys Ala Ser Gln Asp Val Ser Ile Gly Val Ala
1               5                   10

<210> SEQ ID NO 585
<211> LENGTH: 7
<212> TYPE: PRT
<213> ORGANISM: Artificial Sequence
<220> FEATURE:
<223> OTHER INFORMATION: Synthetic Construct

<400> SEQUENCE: 585

Ser Ala Ser Tyr Arg Tyr Thr
1               5

<210> SEQ ID NO 586
<211> LENGTH: 9
<212> TYPE: PRT
<213> ORGANISM: Artificial Sequence
<220> FEATURE:
<223> OTHER INFORMATION: Synthetic Construct

<400> SEQUENCE: 586

Gln Gln Tyr Tyr Ile Tyr Pro Tyr Thr
1               5

<210> SEQ ID NO 587
<211> LENGTH: 5
<212> TYPE: PRT
<213> ORGANISM: Artificial Sequence
<220> FEATURE:
<223> OTHER INFORMATION: Synthetic Construct

<400> SEQUENCE: 587

Gly Tyr Trp Met Asn
1               5

<210> SEQ ID NO 588
<211> LENGTH: 17
<212> TYPE: PRT
<213> ORGANISM: Artificial Sequence
<220> FEATURE:
<223> OTHER INFORMATION: Synthetic Construct

<400> SEQUENCE: 588

Met Ile His Pro Ser Asp Ser Glu Ile Arg Ala Asn Gln Lys Phe Arg
1               5                   10                  15

Asp

<210> SEQ ID NO 589
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 589

Gly Thr Tyr Asp Gly Gly Phe Glu Tyr
1               5

<210> SEQ ID NO 590
<211> LENGTH: 15
<212> TYPE: PRT
<213> ORGANISM: Artificial Sequence
<220> FEATURE:
<223> OTHER INFORMATION: Synthetic Construct

<400> SEQUENCE: 590

Arg Ala Ser Gln Ser Val Ser Gly Ser Arg Phe Thr Tyr Met His
1               5                   10                  15

<210> SEQ ID NO 591
<211> LENGTH: 7
<212> TYPE: PRT
<213> ORGANISM: Artificial Sequence
<220> FEATURE:
<223> OTHER INFORMATION: Synthetic Construct

<400> SEQUENCE: 591

Tyr Ala Ser Ile Leu Glu Ser
1               5

<210> SEQ ID NO 592
<211> LENGTH: 10
<212> TYPE: PRT
<213> ORGANISM: Artificial Sequence
<220> FEATURE:
<223> OTHER INFORMATION: Synthetic Construct

<400> SEQUENCE: 592

Gln His Ser Trp Glu Ile Pro Pro Trp Thr
1               5                   10

<210> SEQ ID NO 593
<211> LENGTH: 119
<212> TYPE: PRT
<213> ORGANISM: Artificial Sequence
<220> FEATURE:
<223> OTHER INFORMATION: Synthetic Construct

<400> SEQUENCE: 593

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110
```

```
-continued

Thr Leu Val Thr Val Ser Ser
        115

<210> SEQ ID NO 594
<211> LENGTH: 107
<212> TYPE: PRT
<213> ORGANISM: Artificial Sequence
<220> FEATURE:
<223> OTHER INFORMATION: Synthetic Construct

<400> SEQUENCE: 594

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 595
<211> LENGTH: 118
<212> TYPE: PRT
<213> ORGANISM: Artificial Sequence
<220> FEATURE:
<223> OTHER INFORMATION: Synthetic Construct

<400> SEQUENCE: 595

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Gly Tyr
            20                  25                  30

Trp Met Asn Trp Leu Lys Gln Arg Pro Gly Gln Gly Leu Glu Trp Ile
        35                  40                  45

Gly Met Ile His Pro Ser Asp Ser Glu Ile Arg Ala Asn Gln Lys Phe
    50                  55                  60

Arg Asp Lys Ala Thr Leu Thr Val Asp Lys Ser Ser Thr Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Thr Tyr Asp Gly Gly Phe Glu Tyr Trp Gly Gln Gly Thr
            100                 105                 110

Thr Leu Thr Val Ser Ser
        115

<210> SEQ ID NO 596
<211> LENGTH: 112
<212> TYPE: PRT
<213> ORGANISM: Artificial Sequence
<220> FEATURE:
<223> OTHER INFORMATION: Synthetic Construct

<400> SEQUENCE: 596
```

```
Asp Ile Val Leu Thr Gln Ser Pro Ala Ser Leu Val Val Ser Leu Gly
1               5                   10                  15

Gln Arg Ala Thr Ile Ser Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Ala
    50                  55                  60

Arg Phe Ser Gly Gly Gly Ser Gly Thr Asp Phe Thr Leu Asn Ile His
65                  70                  75                  80

Pro Val Glu Glu Asp Asp Thr Ala Thr Tyr Tyr Cys Gln His Ser Trp
                85                  90                  95

Glu Ile Pro Pro Trp Thr Phe Gly Gly Gly Thr Lys Leu Glu Ile Lys
            100                 105                 110

<210> SEQ ID NO 597
<211> LENGTH: 25
<212> TYPE: PRT
<213> ORGANISM: Artificial Sequence
<220> FEATURE:
<223> OTHER INFORMATION: Synthetic Construct

<400> SEQUENCE: 597

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 598
<211> LENGTH: 14
<212> TYPE: PRT
<213> ORGANISM: Artificial Sequence
<220> FEATURE:
<223> OTHER INFORMATION: Synthetic Construct

<400> SEQUENCE: 598

Trp Val Arg Gln Ala Pro Gly Lys Gly Leu Glu Trp Val Ala
1               5                   10

<210> SEQ ID NO 599
<211> LENGTH: 32
<212> TYPE: PRT
<213> ORGANISM: Artificial Sequence
<220> FEATURE:
<223> OTHER INFORMATION: Synthetic Construct

<400> SEQUENCE: 599

Arg Phe Thr Leu Ser Val Asp Arg Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 600
<211> LENGTH: 11
<212> TYPE: PRT
<213> ORGANISM: Artificial Sequence
<220> FEATURE:
<223> OTHER INFORMATION: Synthetic Construct

<400> SEQUENCE: 600

Trp Gly Gln Gly Thr Leu Val Thr Val Ser Ser
1               5                   10
```

```
<210> SEQ ID NO 601
<211> LENGTH: 23
<212> TYPE: PRT
<213> ORGANISM: Artificial Sequence
<220> FEATURE:
<223> OTHER INFORMATION: Synthetic Construct

<400> SEQUENCE: 601

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 602
<211> LENGTH: 15
<212> TYPE: PRT
<213> ORGANISM: Artificial Sequence
<220> FEATURE:
<223> OTHER INFORMATION: Synthetic Construct

<400> SEQUENCE: 602

Trp Tyr Gln Gln Lys Pro Gly Lys Ala Pro Lys Leu Leu Ile Tyr
1               5                   10                  15

<210> SEQ ID NO 603
<211> LENGTH: 32
<212> TYPE: PRT
<213> ORGANISM: Artificial Sequence
<220> FEATURE:
<223> OTHER INFORMATION: Synthetic Construct

<400> SEQUENCE: 603

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 604
<211> LENGTH: 10
<212> TYPE: PRT
<213> ORGANISM: Artificial Sequence
<220> FEATURE:
<223> OTHER INFORMATION: Synthetic Construct

<400> SEQUENCE: 604

Phe Gly Gln Gly Thr Lys Val Glu Ile Lys
1               5                   10

<210> SEQ ID NO 605
<211> LENGTH: 30
<212> TYPE: PRT
<213> ORGANISM: Artificial Sequence
<220> FEATURE:
<223> OTHER INFORMATION: Synthetic Construct

<400> SEQUENCE: 605

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr
            20                  25                  30

<210> SEQ ID NO 606
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 606

Trp Leu Lys Gln Arg Pro Gly Gln Gly Leu Glu Trp Ile Gly
1               5                   10

<210> SEQ ID NO 607
<211> LENGTH: 32
<212> TYPE: PRT
<213> ORGANISM: Artificial Sequence
<220> FEATURE:
<223> OTHER INFORMATION: Synthetic Construct

<400> SEQUENCE: 607

Lys Ala Thr Leu Thr Val Asp Lys Ser Ser Thr Thr Ala Tyr Met Gln
1               5                   10                  15

Leu Ser Ser Pro Thr Ser Glu Asp Ser Ala Val Tyr Tyr Cys Ala Arg
            20                  25                  30

<210> SEQ ID NO 608
<211> LENGTH: 11
<212> TYPE: PRT
<213> ORGANISM: Artificial Sequence
<220> FEATURE:
<223> OTHER INFORMATION: Synthetic Construct

<400> SEQUENCE: 608

Trp Gly Gln Gly Thr Thr Leu Thr Val Ser Ser
1               5                   10

<210> SEQ ID NO 609
<211> LENGTH: 23
<212> TYPE: PRT
<213> ORGANISM: Artificial Sequence
<220> FEATURE:
<223> OTHER INFORMATION: Synthetic Construct

<400> SEQUENCE: 609

Asp Ile Val Leu Thr Gln Ser Pro Ala Ser Leu Val Val Ser Leu Gly
1               5                   10                  15

Gln Arg Ala Thr Ile Ser Cys
            20

<210> SEQ ID NO 610
<211> LENGTH: 15
<212> TYPE: PRT
<213> ORGANISM: Artificial Sequence
<220> FEATURE:
<223> OTHER INFORMATION: Synthetic Construct

<400> SEQUENCE: 610

Trp Tyr Gln Gln Lys Pro Gly Gln Pro Pro Lys Leu Leu Ile Lys
1               5                   10                  15

<210> SEQ ID NO 611
<211> LENGTH: 32
<212> TYPE: PRT
<213> ORGANISM: Artificial Sequence
<220> FEATURE:
<223> OTHER INFORMATION: Synthetic Construct

<400> SEQUENCE: 611

Gly Val Pro Ala Arg Phe Ser Gly Gly Gly Ser Gly Thr Asp Phe Thr
1               5                   10                  15
```

Leu Asn Ile His Pro Val Glu Glu Asp Asp Thr Ala Thr Tyr Tyr Cys
            20                  25                  30

<210> SEQ ID NO 612
<211> LENGTH: 10
<212> TYPE: PRT
<213> ORGANISM: Artificial Sequence
<220> FEATURE:
<223> OTHER INFORMATION: Synthetic Construct

<400> SEQUENCE: 612

Phe Gly Gly Gly Thr Lys Leu Glu Ile Lys
1               5                   10

<210> SEQ ID NO 613
<211> LENGTH: 6
<212> TYPE: PRT
<213> ORGANISM: Artificial Sequence
<220> FEATURE:
<223> OTHER INFORMATION: Synthetic Construct

<400> SEQUENCE: 613

Ser Asp Tyr Val Trp Asn
1               5

<210> SEQ ID NO 614
<211> LENGTH: 16
<212> TYPE: PRT
<213> ORGANISM: Artificial Sequence
<220> FEATURE:
<223> OTHER INFORMATION: Synthetic Construct

<400> SEQUENCE: 614

Tyr Ile His Tyr Ser Gly Gly Thr Ser Tyr Asn Pro Ser Leu Lys Ser
1               5                   10                  15

<210> SEQ ID NO 615
<211> LENGTH: 9
<212> TYPE: PRT
<213> ORGANISM: Artificial Sequence
<220> FEATURE:
<223> OTHER INFORMATION: Synthetic Construct

<400> SEQUENCE: 615

Gly Asn Tyr Asp Trp Ala Phe Ala Tyr
1               5

<210> SEQ ID NO 616
<211> LENGTH: 11
<212> TYPE: PRT
<213> ORGANISM: Artificial Sequence
<220> FEATURE:
<223> OTHER INFORMATION: Synthetic Construct

<400> SEQUENCE: 616

Arg Ala Ser Lys Ser Ile Ser Lys Tyr Leu Ala
1               5                   10

<210> SEQ ID NO 617
<211> LENGTH: 7
<212> TYPE: PRT
<213> ORGANISM: Artificial Sequence
<220> FEATURE:
<223> OTHER INFORMATION: Synthetic Construct

<400> SEQUENCE: 617

Ser Gly Ser Thr Leu Gln Ser

-continued

<210> SEQ ID NO 618
<211> LENGTH: 9
<212> TYPE: PRT
<213> ORGANISM: Artificial Sequence
<220> FEATURE:
<223> OTHER INFORMATION: Synthetic Construct

<400> SEQUENCE: 618

Gln Gln His Asn Glu Tyr Pro Trp Thr
1               5

<210> SEQ ID NO 619
<211> LENGTH: 118
<212> TYPE: PRT
<213> ORGANISM: Artificial Sequence
<220> FEATURE:
<223> OTHER INFORMATION: Synthetic Construct

<400> SEQUENCE: 619

Glu Val Gln Leu Val Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Val Trp Asn Trp Ile Arg Gln Pro Pro Gly Lys Gly Leu Glu Trp
        35                  40                  45

Ile Gly Tyr Ile His Tyr Ser Gly Gly Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Tyr Asp Trp Ala Phe Ala Tyr Trp Gly Gln Gly Thr
            100                 105                 110

Leu Val Thr Val Ser Ser
        115

<210> SEQ ID NO 620
<211> LENGTH: 107
<212> TYPE: PRT
<213> ORGANISM: Artificial Sequence
<220> FEATURE:
<223> OTHER INFORMATION: Synthetic Construct

<400> SEQUENCE: 620

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Asn Lys Leu Leu Ile
        35                  40                  45

Ser Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gln Gly Thr Lys Val Glu Ile Lys
            100                 105

<210> SEQ ID NO 621
<211> LENGTH: 30
<212> TYPE: PRT
<213> ORGANISM: Artificial Sequence
<220> FEATURE:
<223> OTHER INFORMATION: Synthetic Construct

<400> SEQUENCE: 621

Glu Val Gln Leu Val Glu Ser Gly Pro Gly Leu Val Lys Pro Ser Glu
1               5                   10                  15
Thr Leu Ser Leu Thr Cys Thr Val Ser Gly Tyr Ser Ile Thr
            20                  25                  30

<210> SEQ ID NO 622
<211> LENGTH: 14
<212> TYPE: PRT
<213> ORGANISM: Artificial Sequence
<220> FEATURE:
<223> OTHER INFORMATION: Synthetic Construct

<400> SEQUENCE: 622

Trp Ile Arg Gln Pro Pro Gly Lys Gly Leu Glu Trp Ile Gly
1               5                   10

<210> SEQ ID NO 623
<211> LENGTH: 32
<212> TYPE: PRT
<213> ORGANISM: Artificial Sequence
<220> FEATURE:
<223> OTHER INFORMATION: Synthetic Construct

<400> SEQUENCE: 623

Arg Val Thr Ile Ser Arg Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 624
<211> LENGTH: 11
<212> TYPE: PRT
<213> ORGANISM: Artificial Sequence
<220> FEATURE:
<223> OTHER INFORMATION: Synthetic Construct

<400> SEQUENCE: 624

Trp Gly Gln Gly Thr Leu Val Thr Val Ser Ser
1               5                   10

<210> SEQ ID NO 625
<211> LENGTH: 23
<212> TYPE: PRT
<213> ORGANISM: Artificial Sequence
<220> FEATURE:
<223> OTHER INFORMATION: Synthetic Construct

<400> SEQUENCE: 625

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 626
<211> LENGTH: 15
<212> TYPE: PRT

```
<213> ORGANISM: Artificial Sequence
<220> FEATURE:
<223> OTHER INFORMATION: Synthetic Construct

<400> SEQUENCE: 626

Trp Tyr Gln Gln Lys Pro Gly Lys Ala Asn Lys Leu Leu Ile Ser
1               5                   10                  15

<210> SEQ ID NO 627
<211> LENGTH: 32
<212> TYPE: PRT
<213> ORGANISM: Artificial Sequence
<220> FEATURE:
<223> OTHER INFORMATION: Synthetic Construct

<400> SEQUENCE: 627

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 628
<211> LENGTH: 10
<212> TYPE: PRT
<213> ORGANISM: Artificial Sequence
<220> FEATURE:
<223> OTHER INFORMATION: Synthetic Construct

<400> SEQUENCE: 628

Phe Gly Gln Gly Thr Lys Val Glu Ile Lys
1               5                   10

<210> SEQ ID NO 629
<211> LENGTH: 471
<212> TYPE: PRT
<213> ORGANISM: Artificial Sequence
<220> FEATURE:
<223> OTHER INFORMATION: Synthetic Construct

<400> SEQUENCE: 629

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Pro
                20                  25                  30

Gly Leu Val Lys Pro Ser Glu Thr Leu Ser Leu Thr Cys Thr Val Ser
                35                  40                  45

Gly Tyr Ser Ile Thr Ser Asp Tyr Val Trp Asn Trp Ile Arg Gln Pro
    50                  55                  60

Pro Gly Lys Gly Leu Glu Trp Ile Gly Tyr Ile His Tyr Ser Gly Gly
65              70                  75                  80

Thr Ser Tyr Asn Pro Ser Leu Lys Ser Arg Val Thr Ile Ser Arg Asp
                85                  90                  95

Thr Ser Lys Asn Gln Phe Ser Leu Lys Leu Ser Ser Val Thr Ala Ala
                100                 105                 110

Asp Thr Ala Val Tyr Tyr Cys Ala Arg Gly Asn Tyr Asp Trp Ala Phe
            115                 120                 125

Ala Tyr Trp Gly Gln Gly Thr Leu Val Thr Val Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
```

```
            165                 170                 175
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                    245                 250                 255

Glu Leu Leu Gly Gly Pro Ser Val Phe Leu Phe Pro Pro Lys Pro Lys
                    260                 265                 270

Asp Thr Leu Met Ile Ser Arg Thr Pro Glu Val Thr Cys Val Val Val
                    275                 280                 285

Asp Val Ser His Glu Asp Pro Glu Val Lys Phe Asn Trp Tyr Val Asp
                    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                    325                 330                 335

Trp Leu Asn Gly Lys Glu Tyr Lys Cys Lys Val Ser Asn Lys Ala Leu
                    340                 345                 350

Pro Ala Pro Ile Glu Lys Thr Ile Ser Lys Ala Lys Gly Gln Pro Arg
                    355                 360                 365

Glu Pro Gln Val Tyr Thr Leu Pro Pro Ser Arg Glu Glu Met Thr Lys
                    370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                    405                 410                 415

Thr Thr Pro Pro Val Leu Asp Ser Asp Gly Ser Phe Phe Leu Tyr Ser
                    420                 425                 430

Lys Leu Thr Val Asp Lys Ser Arg Trp Gln Gln Gly Asn Val Phe Ser
                    435                 440                 445

Cys Ser Val Met His Glu Ala Leu His Asn His Tyr Thr Gln Lys Ser
                    450                 455                 460

Leu Ser Leu Ser Pro Gly Lys
465                 470

<210> SEQ ID NO 630
<211> LENGTH: 237
<212> TYPE: PRT
<213> ORGANISM: Artificial Sequence
<220> FEATURE:
<223> OTHER INFORMATION: Synthetic Construct

<400> SEQUENCE: 630

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
            35                  40                  45

Ser Lys Ser Ile Ser Lys Tyr Leu Ala Trp Tyr Gln Gln Lys Pro Gly
```

```
            50                  55                  60
Lys Ala Asn Lys Leu Leu Ile Ser Ser Gly Ser Thr Leu Gln Ser Gly
 65                  70                  75                  80

Val Pro Ser Arg Phe Ser Gly Ser Gly Ser Gly Thr Asp Phe Thr Leu
                 85                  90                  95

Thr Ile Ser Ser Leu Gln Pro Glu Asp Phe Ala Thr Tyr Tyr Cys Gln
                100                 105                 110

Gln His Asn Glu Tyr Pro Trp Thr Phe Gly Gln Gly Thr Lys Val Glu
            115                 120                 125

Ile Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 631
<211> LENGTH: 5
<212> TYPE: PRT
<213> ORGANISM: Artificial Sequence
<220> FEATURE:
<223> OTHER INFORMATION: Synthetic Construct

<400> SEQUENCE: 631

Asp Tyr Tyr Ile His
1               5

<210> SEQ ID NO 632
<211> LENGTH: 17
<212> TYPE: PRT
<213> ORGANISM: Artificial Sequence
<220> FEATURE:
<223> OTHER INFORMATION: Synthetic Construct

<400> SEQUENCE: 632

Trp Ile Tyr Pro Gly Asp Val Ser Thr Arg Phe Asn Glu Lys Phe Lys
1               5                   10                  15

Gly

<210> SEQ ID NO 633
<211> LENGTH: 10
<212> TYPE: PRT
<213> ORGANISM: Artificial Sequence
<220> FEATURE:
<223> OTHER INFORMATION: Synthetic Construct

<400> SEQUENCE: 633

Asp Ser Tyr Gly Asn Tyr Phe Phe Asp Tyr
1               5                   10

<210> SEQ ID NO 634
<211> LENGTH: 17
```

```
<212> TYPE: PRT
<213> ORGANISM: Artificial Sequence
<220> FEATURE:
<223> OTHER INFORMATION: Synthetic Construct

<400> SEQUENCE: 634

Lys Ser Ser Gln Ser Leu Leu Asn Ser Arg Thr Arg Lys Asn Tyr Leu
1               5                   10                  15

Ala

<210> SEQ ID NO 635
<211> LENGTH: 7
<212> TYPE: PRT
<213> ORGANISM: Artificial Sequence
<220> FEATURE:
<223> OTHER INFORMATION: Synthetic Construct

<400> SEQUENCE: 635

Trp Ala Ser Thr Arg Glu Ser
1               5

<210> SEQ ID NO 636
<211> LENGTH: 9
<212> TYPE: PRT
<213> ORGANISM: Artificial Sequence
<220> FEATURE:
<223> OTHER INFORMATION: Synthetic Construct

<400> SEQUENCE: 636

Cys Thr Gln Ser Phe Ile Leu Arg Thr
1               5

<210> SEQ ID NO 637
<211> LENGTH: 119
<212> TYPE: PRT
<213> ORGANISM: Artificial Sequence
<220> FEATURE:
<223> OTHER INFORMATION: Synthetic Construct

<400> SEQUENCE: 637

Gln Val Gln Leu Gln Gln Ser Gly Pro Glu Leu Val Lys Ser Gly Ala
1               5                   10                  15

Ser Val Arg Ile Ser Cys Lys Ala Ser Gly Tyr Thr Phe Thr Asp Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Asp Val Ser Thr Arg Phe Asn Glu Lys Phe
    50                  55                  60

Lys Gly Lys Ala Thr Leu Ser Ala Asp Lys Ser Ser Asn Thr Ala Ser
65                  70                  75                  80

Met His Leu Ser Ser Leu Thr Ser Glu Asp Ser Ala Val Tyr Phe Cys
                85                  90                  95

Ala Arg Asp Ser Tyr Gly Asn Tyr Phe Phe Asp Tyr Trp Gly Gln Gly
                100                 105                 110

Thr Thr Leu Thr Val Ser Ser
        115

<210> SEQ ID NO 638
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 638

```
Ser Ile Val Met Thr Gln Thr Pro Ser Ser Leu Ala Val Ser Ala Gly
1               5                   10                  15

Glu Gln Val Thr Met Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Val Gln Ala Glu Asp Leu Ala Phe Tyr Tyr Cys Thr Gln
                85                  90                  95

Ser Phe Ile Leu Arg Thr Phe Gly Gly Gly Thr Lys Leu Glu Leu Lys
            100                 105                 110
```

<210> SEQ ID NO 639
<211> LENGTH: 119
<212> TYPE: PRT
<213> ORGANISM: Artificial Sequence
<220> FEATURE:
<223> OTHER INFORMATION: Synthetic Construct

<400> SEQUENCE: 639

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Val Ser Thr Lys Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Phe Tyr Tyr Phe Asp Tyr Trp Gly Gln Gly
            100                 105                 110

Thr Leu Val Thr Val Ser Ser
        115
```

<210> SEQ ID NO 640
<211> LENGTH: 112
<212> TYPE: PRT
<213> ORGANISM: Artificial Sequence
<220> FEATURE:
<223> OTHER INFORMATION: Sythetic Construct

<400> SEQUENCE: 640

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Tyr Thr Leu Arg Thr Phe Gly Gln Gly Thr Lys Val Glu Ile Lys
            100                 105                 110
```

<210> SEQ ID NO 641
<211> LENGTH: 125
<212> TYPE: PRT
<213> ORGANISM: Artificial Sequence
<220> FEATURE:
<223> OTHER INFORMATION: Synthetic Construct

<400> SEQUENCE: 641

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
             35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

<210> SEQ ID NO 642
<211> LENGTH: 109
<212> TYPE: PRT
<213> ORGANISM: Artificial Sequence
<220> FEATURE:
<223> OTHER INFORMATION: Synthetic Construct

<400> SEQUENCE: 642

```
Glu Ala Val Val Thr Gln Glu Pro Ser Leu Thr Val Ser Pro Gly Gly
 1               5                   10                  15

Thr Val Thr Leu Thr Cys Arg Ser Ser Thr Gly Ala Val Thr Thr Ser
                 20                  25                  30

Asn Tyr Ala Asn Trp Phe Gln Gln Lys Pro Gly Gln Ala Pro Arg Thr
             35                  40                  45

Leu Ile Tyr Gly Thr Asn Lys Arg Ala Pro Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
            100                 105
```

<210> SEQ ID NO 643
<211> LENGTH: 30
<212> TYPE: PRT

<213> ORGANISM: Artificial Sequence
<220> FEATURE:
<223> OTHER INFORMATION: Synthetic Construct

<400> SEQUENCE: 643

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn
            20                  25                  30

<210> SEQ ID NO 644
<211> LENGTH: 14
<212> TYPE: PRT
<213> ORGANISM: Artificial Sequence
<220> FEATURE:
<223> OTHER INFORMATION: Synthetic Construct

<400> SEQUENCE: 644

Trp Val Arg Gln Ala Pro Gly Lys Gly Leu Glu Trp Val Gly
1               5                   10

<210> SEQ ID NO 645
<211> LENGTH: 32
<212> TYPE: PRT
<213> ORGANISM: Artificial Sequence
<220> FEATURE:
<223> OTHER INFORMATION: Synthetic Construct

<400> SEQUENCE: 645

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 646
<211> LENGTH: 11
<212> TYPE: PRT
<213> ORGANISM: Artificial Sequence
<220> FEATURE:
<223> OTHER INFORMATION: Synthetic Construct

<400> SEQUENCE: 646

Trp Gly Gln Gly Thr Leu Val Thr Val Ser Ser
1               5                   10

<210> SEQ ID NO 647
<211> LENGTH: 22
<212> TYPE: PRT
<213> ORGANISM: Artificial Sequence
<220> FEATURE:
<223> OTHER INFORMATION: Synthetic Construct

<400> SEQUENCE: 647

Glu Ala Val Val Thr Gln Glu Pro Ser Leu Thr Val Ser Pro Gly Gly
1               5                   10                  15

Thr Val Thr Leu Thr Cys
            20

<210> SEQ ID NO 648
<211> LENGTH: 15
<212> TYPE: PRT
<213> ORGANISM: Artificial Sequence
<220> FEATURE:
<223> OTHER INFORMATION: Synthetic Construct

<400> SEQUENCE: 648

```
Trp Phe Gln Gln Lys Pro Gly Gln Ala Pro Arg Thr Leu Ile Tyr
1               5                   10                  15

<210> SEQ ID NO 649
<211> LENGTH: 32
<212> TYPE: PRT
<213> ORGANISM: Artificial Sequence
<220> FEATURE:
<223> OTHER INFORMATION: Synthetic Construct

<400> SEQUENCE: 649

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Tyr Cys
                20                  25                  30

<210> SEQ ID NO 650
<211> LENGTH: 10
<212> TYPE: PRT
<213> ORGANISM: Artificial Sequence
<220> FEATURE:
<223> OTHER INFORMATION: Synthetic Construct

<400> SEQUENCE: 650

Phe Gly Gly Gly Thr Lys Leu Thr Val Leu
1               5                   10
```

ANTI-CD3 ANTIBODIES AND METHODS OF USE

This application is a divisional application of U.S. application Ser. No. 14/574,132, filed on Dec. 17, 2014, which claims benefit of the filing date of U.S. Provisional Application No. 62/091,441, filed on Dec. 12, 2014; U.S. Provisional Application No. 62/053,582, filed on Sep. 22, 2014; U.S. Provisional Application No. 62/026,594, filed on Jul. 18, 2014; U.S. Provisional Application No. 61/949,950, filed on Mar. 7, 2014; and U.S. Provisional Application No. 61/917,346, filed on Dec. 17, 2013.

FIELD OF THE INVENTION

The present invention relates to anti-cluster of differentiation 3 (CD3) antibodies and methods of using the same.

BACKGROUND

Cell proliferative disorders, such as cancer, are characterized by the uncontrolled growth of cell subpopulations. They are the leading cause of death in the developed world and the second leading cause of death in developing countries, with over 12 million new cancer cases diagnosed and 7 million cancer deaths occurring each year. The National Cancer Institute estimates that greater than half a million Americans will die of cancer in 2013, accounting for nearly one out of every four deaths in the country. As the elderly population has grown, the incidence of cancer has concurrently risen, as the probability of developing cancer is more than two-fold higher after the age of seventy. Cancer care thus represents a significant and ever-increasing societal burden.

Longstanding approaches to cancer treatment include chemotherapy, radiation therapy, and surgery to remove solid tumors. Recently, bispecific antibody-based immunotherapies have been developed. Such bispecific antibodies are capable of simultaneously binding cell surface antigens on cytotoxic cells and tumor cells, with the intent that the bound cytotoxic cell will destroy the bound tumor cell. Existing bispecific antibodies currently undergoing clinical trials for treating cancer are limited by their short half-lives and/or variable efficacy. Thus, there is an unmet need in the field for the development of effective bispecific antibodies for use in cancer treatment.

SUMMARY

The present invention relates to anti-cluster of differentiation 3 (CD3) antibodies and methods of using the same.

In one aspect, the invention features an anti-CD3 antibody, wherein the anti-CD3 antibody comprises a binding domain comprising the following six hypervariable regions (HVRs): (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6. In some embodiments, the binding domain comprises (a) a heavy chain variable (VH) domain comprising an amino acid sequence having at least 95% sequence identity to the amino acid sequence of SEQ ID NO: 184; (b) a light chain variable (VL) domain comprising an amino acid sequence having at least 95% sequence identity to the amino acid sequence of SEQ ID NO: 185; or (c) a VH domain as in (a) and a VL domain as in (b). In some embodiments, the VH domain comprises the amino acid sequence of SEQ ID NO: 184. In some embodiments, the VL domain comprises the amino acid sequence of SEQ ID NO: 185. In some embodiments, the binding domain comprises (a) a heavy chain variable (VH) domain comprising an amino acid sequence having at least 95% sequence identity to the amino acid sequence of SEQ ID NO: 186; (b) a light chain variable (VL) domain comprising an amino acid sequence having at least 95% sequence identity to the amino acid sequence of SEQ ID NO: 187; or (c) a VH domain as in (a) and a VL domain as in (b). In some embodiments, the VH domain comprises the amino acid sequence of SEQ ID NO: 186. In some embodiments, the VL domain comprises the amino acid sequence of SEQ ID NO: 187.

In one aspect, the invention features an anti-CD3 antibody, wherein the anti-CD3 antibody comprises a binding domain comprising the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of $X_1X_2YSX_3X_4X_5FDY$, wherein $X_1$ is selected from the group consisting of D, T, and S; $X_2$ is selected from the group consisting of G, A, and S; $X_3$ is R or N; $X_4$ is Y or A; and $X_5$ is Y or A (SEQ ID NO: 181); (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of $X_1X_2SX_3X_4LRT$, wherein $X_1$ is K or T; $X_2$ is Q or A; $X_3$ is F or A; and $X_4$ is I or A (SEQ ID NO: 182). In some embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the binding domain comprises (a) a VH domain comprising an amino acid sequence having at least 95% sequence identity to the amino acid sequence of SEQ ID NO: 188; (b) a VL domain comprising an amino acid sequence having at least 95% sequence identity to the amino acid sequence of SEQ ID NO: 189; or (c) a VH domain as in (a) and a VL domain as in (b). In some embodiments, the VH domain comprises the amino acid sequence of SEQ ID NO: 188. In some embodiments, the VL domain comprises the amino acid sequence of SEQ ID NO: 189.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 13; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the binding domain comprises (a) a VH domain comprising an amino acid sequence having at least 95% sequence identity to the amino acid sequence of SEQ ID NO: 190; (b) a VL domain comprising an amino acid sequence having at least 95% sequence identity to the amino acid sequence of SEQ ID NO: 191; or (c) a VH domain as in (a) and a VL domain as in (b). In some embodiments, the VH domain comprises the amino acid sequence of SEQ ID NO: 190. In some embodiments, the VL domain comprises the amino acid sequence of SEQ ID NO: 191.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 14. In some embodiments, the binding domain comprises (a) a VH domain comprising an amino acid sequence having at least 95% sequence identity to the amino acid sequence of SEQ ID NO: 192; (b) a VL domain comprising an amino acid sequence having at least 95% sequence identity to the amino acid sequence of SEQ ID NO: 193; or (c) a VH domain as in (a) and a VL domain as in (b). In some embodiments, the VH domain comprises the amino acid sequence of SEQ ID NO: 192. In some embodiments, the VL domain comprises the amino acid sequence of SEQ ID NO: 193.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 15. In some embodiments, the binding domain comprises (a) a VH domain comprising an amino acid sequence having at least 95% sequence identity to the amino acid sequence of SEQ ID NO: 194; (b) a VL domain comprising an amino acid sequence having at least 95% sequence identity to the amino acid sequence of SEQ ID NO: 195; or (c) a VH domain as in (a) and a VL domain as in (b). In some embodiments, the VH domain comprises the amino acid sequence of SEQ ID NO: 194. In some embodiments, the VL domain comprises the amino acid sequence of SEQ ID NO: 195.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 16. In some embodiments, the binding domain comprises (a) a VH domain comprising an amino acid sequence having at least 95% sequence identity to the amino acid sequence of SEQ ID NO: 196; (b) a VL domain comprising an amino acid sequence having at least 95% sequence identity to the amino acid sequence of SEQ ID NO: 197; or (c) a VH domain as in (a) and a VL domain as in (b). In some embodiments, the VH domain comprises the amino acid sequence of SEQ ID NO: 196. In some embodiments, the VL domain comprises the amino acid sequence of SEQ ID NO: 197.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 17; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the binding domain comprises (a) a VH domain comprising an amino acid sequence having at least 95% sequence identity to the amino acid sequence of SEQ ID NO: 198; (b) a VL domain comprising an amino acid sequence having at least 95% sequence identity to the amino acid sequence of SEQ ID NO: 199; or (c) a VH domain as in (a) and a VL domain as in (b). In some embodiments, the VH domain comprises the amino acid sequence of SEQ ID NO: 198. In some embodiments, the VL domain comprises the amino acid sequence of SEQ ID NO: 199.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 18; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the binding domain comprises (a) a VH domain comprising an amino acid sequence having at least 95% sequence identity to the amino acid sequence of SEQ ID NO: 200; (b) a VL domain comprising an amino acid sequence having at least 95% sequence identity to the amino acid sequence of SEQ ID NO: 201; or (c) a VH domain as in (a) and a VL domain as in (b). In some embodiments, the VH domain comprises the amino acid sequence of SEQ ID NO: 200. In some embodiments, the VL domain comprises the amino acid sequence of SEQ ID NO: 201.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 19; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the binding domain comprises (a) a VH domain comprising an amino acid sequence having at least 95% sequence identity to the amino acid sequence of SEQ ID NO: 202; (b) a VL domain comprising an amino acid sequence having at least 95% sequence identity to the amino acid sequence of SEQ ID NO: 203; or (c) a VH domain as in (a) and a VL domain as in (b). In some embodiments, the VH domain comprises the amino acid sequence of SEQ ID NO: 202. In some embodiments, the VL domain comprises the amino acid sequence of SEQ ID NO: 203.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 20; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the binding domain comprises (a) a VH domain comprising an amino acid sequence having at least 95% sequence identity to the amino acid sequence of SEQ ID NO: 204; (b) a VL domain comprising an amino acid sequence having at least 95% sequence identity to the amino acid sequence of SEQ ID NO: 205; or (c) a VH domain as in (a) and a VL domain as in (b). In some embodiments, the VH domain comprises the amino acid sequence of SEQ ID NO: 204. In some embodiments, the VL domain comprises the amino acid sequence of SEQ ID NO: 205.

In other embodiments, the binding domain comprises the following six HVRs: (a) an HVR-H1 comprising the amino acid sequence of SEQ ID NO: 7; (b) an HVR-H2 comprising the amino acid sequence of SEQ ID NO: 8; (c) an HVR-H3 comprising the amino acid sequence of SEQ ID NO: 21; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 22. In some embodiments, the binding domain comprises (a) a VH domain comprising an amino acid sequence having at least 95% sequence identity to the amino acid sequence of SEQ ID NO: 206; (b) a VL domain comprising an amino acid sequence having at least 95% sequence identity to the amino acid sequence of SEQ ID NO: 207; or (c) a VH domain as in (a) and a VL domain as in (b). In some embodiments, the VH domain comprises the amino acid sequence of SEQ ID NO: 206. In some embodiments, the VL domain comprises the amino acid sequence of SEQ ID NO: 207.

In some aspects, the invention features an anti-CD3 antibody comprising a binding domain comprising: (a) a VH domain comprising an amino acid sequence of SEQ ID NO: 188 and (b) a VL domain comprising an amino acid sequence of SEQ ID NO: 189; (a) a VH domain comprising an amino acid sequence of SEQ ID NO: 190 and (b) a VL domain comprising an amino acid sequence of SEQ ID NO: 191; (a) a VH domain comprising an amino acid sequence of SEQ ID NO: 192 and (b) a VL domain comprising an amino acid sequence of SEQ ID NO: 193; (a) a VH domain comprising an amino acid sequence of SEQ ID NO: 194 and (b) a VL domain comprising an amino acid sequence of SEQ ID NO: 195; (a) a VH domain comprising an amino acid sequence of SEQ ID NO: 196 and (b) a VL domain comprising an amino acid sequence of SEQ ID NO: 197; (a) a VH domain comprising an amino acid sequence of SEQ ID NO: 198 and (b) a VL domain comprising an amino acid sequence of SEQ ID NO: 199; (a) a VH domain comprising an amino acid sequence of SEQ ID NO: 200 and (b) a VL domain comprising an amino acid sequence of SEQ ID NO: 201; (a) a VH domain comprising an amino acid sequence of SEQ ID NO: 202 and (b) a VL domain comprising an amino acid sequence of SEQ ID NO: 203; (a) a VH domain comprising an amino acid sequence of SEQ ID NO: 204 and (b) a VL domain comprising an amino acid sequence of SEQ ID NO: 205; or (a) a VH domain comprising an amino acid sequence of SEQ ID NO: 206 and (b) a VL domain comprising an amino acid sequence of SEQ ID NO: 207.

In some aspects, the invention features an anti-CD3 antibody, wherein the anti-CD3 antibody comprises a binding domain comprising the following six HVRs: (a) an HVR-H1 comprising the amino acid sequence of SEQ ID NO: 23; (b) an HVR-H2 comprising the amino acid sequence of LINPYKGVX$_1$TYX$_2$X$_3$X$_4$X$_5$KX$_6$, wherein X$_1$ is S or T; X$_2$ is N or A; X$_3$ is Q or D; X$_4$ is K or S; X$_5$ is F or V; and X$_6$ is D or G (SEQ ID NO: 183); (c) an HVR-H3 comprising the amino acid sequence of SEQ ID NO: 25; (d) an HVR-L1 comprising the amino acid sequence of SEQ ID NO: 26; (e) an HVR-L2 comprising the amino acid sequence of SEQ ID NO: 27; and (f) an HVR-L3 comprising the amino acid sequence of SEQ ID NO: 28. In some embodiments, the binding domain comprises the following six HVRs: (a) an HVR-H1 comprising the amino acid sequence of SEQ ID NO: 23; (b) an HVR-H2 comprising the amino acid sequence of SEQ ID NO: 24; (c) an HVR-H3 comprising the amino acid sequence of SEQ ID NO: 25; (d) an HVR-L1 comprising the amino acid sequence of SEQ ID NO: 26; (e) an HVR-L2 comprising the amino acid sequence of SEQ ID NO: 27; and (f) an HVR-L3 comprising the amino acid sequence of SEQ ID NO: 28. In some embodiments, the binding domain comprises (a) a VH domain comprising an amino acid sequence having at least 95% sequence identity to the amino acid sequence of SEQ ID NO: 208; (b) a VL domain comprising an amino acid sequence having at least 95% sequence identity to the amino acid sequence of SEQ ID NO: 209; or (c) a VH domain as in (a) and a VL domain as in (b). In some embodiments, the VH domain comprises the amino acid sequence of SEQ ID NO: 208. In some embodiments, the VL domain comprises the amino acid sequence of SEQ ID NO: 209.

In other embodiments, the binding domain comprises the following six HVRs: (a) an HVR-H1 comprising the amino acid sequence of SEQ ID NO: 23; (b) an HVR-H2 comprising the amino acid sequence of SEQ ID NO: 29; (c) an HVR-H3 comprising the amino acid sequence of SEQ ID NO: 25; (d) an HVR-L1 comprising the amino acid sequence of SEQ ID NO: 26; (e) an HVR-L2 comprising the amino acid sequence of SEQ ID NO: 27; and (f) an HVR-L3 comprising the amino acid sequence of SEQ ID NO: 28. In some embodiments, the binding domain comprises (a) a VH domain comprising an amino acid sequence having at least 95% sequence identity to the amino acid sequence of SEQ ID NO: 210; (b) a VL domain comprising an amino acid sequence having at least 95% sequence identity to the amino acid sequence of SEQ ID NO: 211; or (c) a VH domain as in (a) and a VL domain as in (b). In some embodiments, the VH domain comprises the amino acid sequence of SEQ ID NO: 210. In some embodiments, the VL domain comprises the amino acid sequence of SEQ ID NO: 211.

In other embodiments, the binding domain comprises the following six HVRs: (a) an HVR-H1 comprising the amino acid sequence of SEQ ID NO: 23; (b) an HVR-H2 comprising the amino acid sequence of SEQ ID NO: 30; (c) an HVR-H3 comprising the amino acid sequence of SEQ ID NO: 25; (d) an HVR-L1 comprising the amino acid sequence of SEQ ID NO: 26; (e) an HVR-L2 comprising the amino acid sequence of SEQ ID NO: 27; and (f) an HVR-L3 comprising the amino acid sequence of SEQ ID NO: 28. In some embodiments, the binding domain comprises (a) a VH domain comprising an amino acid sequence having at least 95% sequence identity to the amino acid sequence of SEQ ID NO: 212; (b) a VL domain comprising an amino acid sequence having at least 95% sequence identity to the amino acid sequence of SEQ ID NO: 213; or (c) a VH domain as in (a) and a VL domain as in (b). In some embodiments, the VH domain comprises the amino acid sequence of SEQ ID NO: 212. In some embodiments, the VL domain comprises the amino acid sequence of SEQ ID NO: 213.

In some aspects, the invention features an anti-CD3 antibody comprising a binding domain comprising: (a) a VH domain comprising an amino acid sequence of SEQ ID NO: 208 and (b) a VL domain comprising an amino acid sequence of SEQ ID NO: 209; (a) a VH domain comprising an amino acid sequence of SEQ ID NO: 210 and (b) a VL domain comprising an amino acid sequence of SEQ ID NO: 211; or (a) a VH domain comprising an amino acid sequence of SEQ ID NO: 212 and (b) a VL domain comprising an amino acid sequence of SEQ ID NO: 213.

In some aspects, the invention features an anti-CD3 antibody, wherein the anti-CD3 antibody comprises a binding domain comprising the following six HVRs: (a) an HVR-H1 comprising the amino acid sequence of SEQ ID NO: 31; (b) an HVR-H2 comprising the amino acid sequence of SEQ ID NO: 32; (c) an HVR-H3 comprising the amino acid sequence of SEQ ID NO: 33; (d) an HVR-L1 comprising the amino acid sequence of SEQ ID NO: 34; (e) an HVR-L2 comprising the amino acid sequence of SEQ ID NO: 35; and (f) an HVR-L3 comprising the amino acid sequence of SEQ ID NO: 36. In some embodiments, the binding domain comprises (a) a VH domain comprising an amino acid sequence having at least 95% sequence identity to the amino acid sequence of SEQ ID NO: 214; (b) a VL domain comprising an amino acid sequence having at least 95% sequence identity to the amino acid sequence of SEQ ID NO: 215; or (c) a VH domain as in (a) and a VL domain as in (b). In some embodiments, the VH domain comprises the amino acid sequence of SEQ ID NO: 214. In some embodiments, the VL domain comprises the amino acid sequence of SEQ ID NO: 215. In some embodiments, the binding domain comprises (a) a VH domain comprising an amino acid sequence having at least 95% sequence identity to the amino acid sequence of SEQ ID NO: 216; (b) a VL domain comprising an amino acid sequence having at least 95% sequence identity to the amino acid sequence of SEQ ID NO: 217; or (c) a VH domain as in (a) and a VL domain as in (b). In some embodiments, the VH domain comprises the amino acid sequence of SEQ ID NO: 216. In some embodiments, the VL domain comprises the amino acid sequence of SEQ ID NO: 217.

In some aspects, the invention features an anti-CD3 antibody, wherein the anti-CD3 antibody comprises a binding domain comprising: (a) a VH domain comprising an amino acid sequence of SEQ ID NO: 214 and (b) a VL domain comprising an amino acid sequence of SEQ ID NO: 215, or (a) a VH domain comprising an amino acid sequence of SEQ ID NO: 216 and (b) a VL domain comprising an amino acid sequence of SEQ ID NO: 217.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 37; (b) an HVR-H2 comprising the amino acid sequence of SEQ ID NO: 38; (c) an HVR-H3 comprising the amino acid sequence of SEQ ID NO: 39; (d) an HVR-L1 comprising the amino acid sequence of SEQ ID NO: 40; (e) an HVR-L2 comprising the amino acid sequence of SEQ ID NO: 41; and (f) an HVR-L3 comprising the amino acid sequence of SEQ ID NO: 42. In some embodiments, the binding domain comprises (a) a VH domain comprising an amino acid sequence having at least 95% sequence identity to the amino acid sequence of SEQ ID NO: 218; (b) a VL domain comprising an amino acid sequence having at least 95% sequence identity to the amino acid sequence of SEQ ID NO: 219; or (c) a VH domain as in (a) and a VL domain as in (b). In some embodiments, the VH domain comprises the amino acid sequence of SEQ ID NO: 218. In some embodiments, the VL domain comprises the amino acid sequence of SEQ ID NO: 219. In some embodiments, the binding domain comprises (a) a VH domain comprising an amino acid sequence having at least 95% sequence identity to the amino acid sequence of SEQ ID NO: 220; (b) a VL domain comprising an amino acid sequence having at least 95% sequence identity to the amino acid sequence of SEQ ID NO: 221; or (c) a VH domain as in (a) and a VL domain as in (b). In some embodiments, the VH domain comprises the amino acid sequence of SEQ ID NO: 220. In some embodiments, the VL domain comprises the amino acid sequence of SEQ ID NO: 221.

In some aspects, the invention features an anti-CD3 antibody, wherein the anti-CD3 antibody comprises a binding domain comprising: (a) a VH domain comprising an amino acid sequence of SEQ ID NO: 218 and (b) a VL domain comprising an amino acid sequence of SEQ ID NO: 219, or (a) a VH domain comprising an amino acid sequence of SEQ ID NO: 220 and (b) a VL domain comprising an amino acid sequence of SEQ ID NO: 221.

In some aspects, the invention features an anti-CD3 antibody, wherein the anti-CD3 antibody comprises a binding domain comprising the following six HVRs: (a) an HVR-H1 comprising the amino acid sequence of SEQ ID NO: 43; (b) an HVR-H2 comprising the amino acid sequence of SEQ ID NO: 44; (c) an HVR-H3 comprising the amino acid sequence of SEQ ID NO: 45; (d) an HVR-L1 comprising the amino acid sequence of SEQ ID NO: 46; (e) an HVR-L2 comprising the amino acid sequence of SEQ ID NO: 47; and (f) an HVR-L3 comprising the amino acid sequence of SEQ ID NO: 48. In some embodiments, the binding domain comprises (a) a VH domain comprising an amino acid sequence having at least 95% sequence identity to the amino acid sequence of SEQ ID NO: 222; (b) a VL domain comprising an amino acid sequence having at least 95% sequence identity to the amino acid sequence of SEQ ID NO: 223; or (c) a VH domain as in (a) and a VL domain as in (b). In some embodiments, the VH domain comprises the amino acid sequence of SEQ ID NO: 222. In some embodiments, the VL domain comprises the amino acid sequence of SEQ ID NO: 223. In some embodiments, the binding domain comprises (a) a VH domain comprising an amino acid sequence having at least 95% sequence identity to the amino acid sequence of SEQ ID NO: 224; (b) a VL domain comprising an amino acid sequence having at least 95% sequence identity to the amino acid sequence of SEQ ID NO: 225; or (c) a VH domain as in (a) and a VL domain as in (b). In some embodiments, the VH domain comprises the amino acid sequence of SEQ ID NO: 224. In some embodiments, the VL domain comprises the amino acid sequence of SEQ ID NO: 225. In some embodiments, the binding domain comprises (a) a VH domain comprising an amino acid sequence having at least 95% sequence identity to the amino acid sequence of SEQ ID NO: 226; (b) a VL domain comprising an amino acid sequence having at least 95% sequence identity to the amino acid sequence of SEQ ID NO: 227; or (c) a VH domain as in (a) and a VL domain as in (b). In some embodiments, the VH domain comprises the amino acid sequence of SEQ ID NO: 226. In some embodiments, the VL domain comprises the amino acid sequence of SEQ ID NO: 227.

In some aspects, the invention features an anti-CD3 antibody, wherein the anti-CD3 antibody comprises a binding domain comprising: (a) a VH domain comprising an amino acid sequence of SEQ ID NO: 222 and (b) a VL domain comprising an amino acid sequence of SEQ ID NO: 223; (a) a VH domain comprising an amino acid sequence of SEQ ID NO: 224 and (b) a VL domain comprising an amino acid sequence of SEQ ID NO: 225; (a) a VH domain comprising an amino acid sequence of SEQ ID NO: 226 and (b) a VL domain comprising an amino acid sequence of SEQ ID NO: 227.

In some aspects, the invention features an anti-CD3 antibody, wherein the anti-CD3 antibody comprises a binding domain comprising the following six HVRs: (a) an HVR-H1 comprising the amino acid sequence of SEQ ID NO: 49; (b) an HVR-H2 comprising the amino acid sequence of SEQ ID NO: 50; (c) an HVR-H3 comprising the amino acid sequence of SEQ ID NO: 51; (d) an HVR-L1 comprising the amino acid sequence of SEQ ID NO: 52; (e) an HVR-L2 comprising the amino acid sequence of SEQ ID NO: 53; and (f) an HVR-L3 comprising the amino acid sequence of SEQ ID NO: 54. In some embodiments, the binding domain comprises (a) a VH domain comprising an amino acid sequence having at least 95% sequence identity to the amino acid sequence of SEQ ID NO: 228; (b) a VL domain comprising an amino acid sequence having at least 95% sequence identity to the amino acid sequence of SEQ ID NO: 229; or (c) a VH domain as in (a) and a VL domain as in (b). In some embodiments, the VH domain comprises the amino acid sequence of SEQ ID NO: 228. In some embodiments, the VL domain comprises the amino acid sequence of SEQ ID NO: 229. In some embodiments, the binding domain comprises (a) a VH domain comprising an amino acid sequence having at least 95% sequence identity to the amino acid sequence of SEQ ID NO: 230; (b) a VL domain comprising an amino acid sequence having at least 95% sequence identity to the amino acid sequence of SEQ ID NO: 231; or (c) a VH domain as in (a) and a VL domain as in (b). In some embodiments, the VH domain comprises the amino acid sequence of SEQ ID NO: 230. In some embodiments, the VL domain comprises the amino acid sequence of SEQ ID NO: 231.

In some aspects, the invention features an anti-CD3 antibody, wherein the anti-CD3 antibody comprises a binding domain comprising: (a) a VH domain comprising an amino acid sequence of SEQ ID NO: 228 and (b) a VL domain comprising an amino acid sequence of SEQ ID NO: 229, or (a) a VH domain comprising an amino acid sequence of SEQ ID NO: 230 and (b) a VL domain comprising an amino acid sequence of SEQ ID NO: 231.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 55; (b) an HVR-H2 comprising the amino acid sequence of SEQ ID NO: 56; (c) an HVR-H3 comprising the amino acid sequence of SEQ ID NO: 57; (d) an HVR-L1 comprising the amino acid sequence of SEQ ID NO: 58; (e) an HVR-L2 comprising the amino acid sequence of SEQ ID NO: 59; and (f) an HVR-L3 comprising the amino acid sequence of SEQ ID NO: 60. In some embodiments, the binding domain comprises (a) a VH domain comprising an amino acid sequence having at least 95% sequence identity to the amino acid sequence of SEQ ID NO: 232; (b) a VL domain comprising an amino acid sequence having at least 95% sequence identity to the amino acid sequence of SEQ ID NO: 233; or (c) a VH domain as in (a) and a VL domain as in (b). In some embodiments, the VH domain comprises the amino acid sequence of SEQ ID NO: 232. In some embodiments, the VL domain comprises the amino acid sequence of SEQ ID NO: 233.

In another aspect, the invention features an anti-CD3 antibody, wherein the anti-CD3 antibody comprises a binding domain comprising: (a) a VH domain comprising an amino acid sequence of SEQ ID NO: 232 and (b) a VL domain comprising an amino acid sequence of SEQ ID NO: 233.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 61; (b) an HVR-H2 comprising the amino acid sequence of SEQ ID NO: 62; (c) an HVR-H3 comprising the amino acid sequence of SEQ ID NO: 63; (d) an HVR-L1 comprising the amino acid sequence of SEQ ID NO: 64; (e) an HVR-L2 comprising the amino acid sequence of SEQ ID NO: 65; and (f) an HVR-L3 comprising the amino acid sequence of SEQ ID NO: 66. In some embodiments, the binding domain comprises (a) a VH domain comprising an amino acid sequence having at least 95% sequence identity to the amino acid sequence of SEQ ID NO: 234; (b) a VL domain comprising an amino acid sequence having at least 95% sequence identity to the amino acid sequence of SEQ ID NO: 235; or (c) a VH domain as in (a) and a VL domain as in (b). In some embodiments, the VH domain comprises the amino acid sequence of SEQ ID NO: 234. In some embodiments, the VL domain comprises the amino acid sequence of SEQ ID NO: 235.

In another aspect, the invention features an anti-CD3 antibody, wherein the anti-CD3 antibody comprises a binding domain comprising: (a) a VH domain comprising an amino acid sequence of SEQ ID NO: 234 and (b) a VL domain comprising an amino acid sequence of SEQ ID NO: 235.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 67; (b) an HVR-H2 comprising the amino acid sequence of SEQ ID NO: 68; (c) an HVR-H3 comprising the amino acid sequence of SEQ ID NO: 69; (d) an HVR-L1 comprising the amino acid sequence of SEQ ID NO: 70; (e) an HVR-L2 comprising the amino acid sequence of SEQ ID NO: 71; and (f) an HVR-L3 comprising the amino acid sequence of SEQ ID NO: 72. In some embodiments, the binding domain comprises (a) a VH domain comprising an amino acid sequence having at least 95% sequence identity to the amino acid sequence of SEQ ID NO: 236; (b) a VL domain comprising an amino acid sequence having at least 95% sequence identity to the amino acid sequence of SEQ ID NO: 237; or (c) a VH domain as in (a) and a VL domain as in (b). In some embodiments, the VH domain comprises the amino acid sequence of SEQ ID NO: 236. In some embodiments, the VL domain comprises the amino acid sequence of SEQ ID NO: 237.

In another aspect, the invention features an anti-CD3 antibody, wherein the anti-CD3 antibody comprises a binding domain comprising: (a) a VH domain comprising an amino acid sequence of SEQ ID NO: 236 and (b) a VL domain comprising an amino acid sequence of SEQ ID NO: 237.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 73; (b) an HVR-H2 comprising the amino acid sequence of SEQ ID NO: 74; (c) an HVR-H3 comprising the amino acid sequence of SEQ ID NO: 75; (d) an HVR-L1 comprising the amino acid sequence of SEQ ID NO: 76; (e) an HVR-L2 comprising the amino acid sequence of SEQ ID NO: 77; and (f) an HVR-L3 comprising the amino acid sequence of SEQ ID NO: 78. In some embodiments, the binding domain comprises (a) a VH domain comprising an amino acid sequence having at least 95% sequence identity to the amino acid sequence of SEQ ID NO: 238; (b) a VL domain comprising an amino acid sequence having at least 95% sequence identity to the amino acid sequence of SEQ ID NO: 239; or (c) a VH domain as in (a) and a VL domain as in (b). In some embodiments, the VH domain comprises the amino acid sequence of SEQ ID NO: 238. In some embodiments, the VL domain comprises the amino acid sequence of SEQ ID NO: 239.

In another aspect, the invention features an anti-CD3 antibody, wherein the anti-CD3 antibody comprises a binding domain comprising: (a) a VH domain comprising an amino acid sequence of SEQ ID NO: 238 and (b) a VL domain comprising an amino acid sequence of SEQ ID NO: 239.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 79; (b) an HVR-H2 comprising the amino acid sequence of SEQ ID NO: 80; (c) an HVR-H3 comprising the amino acid sequence of SEQ ID NO: 81; (d) an HVR-L1 comprising the amino acid sequence of SEQ ID NO: 82; (e) an HVR-L2 comprising the amino acid sequence of SEQ ID NO: 83; and (f) an HVR-L3 comprising the amino acid sequence of SEQ ID NO: 84. In some embodiments, the binding domain comprises (a) a VH domain comprising an amino acid sequence having at least 95% sequence identity to the amino acid sequence of SEQ ID NO: 240; (b) a VL domain comprising an amino acid sequence having at least 95% sequence identity to the amino acid sequence of SEQ ID NO: 241; or (c) a VH domain as in (a) and a VL domain as in (b). In some embodiments, the VH domain comprises the amino acid sequence of SEQ ID NO: 240. In some embodiments, the VL domain comprises the amino acid sequence of SEQ ID NO: 241.

In another aspect, the invention features an anti-CD3 antibody, wherein the anti-CD3 antibody comprises a binding domain comprising: (a) a VH domain comprising an amino acid sequence of SEQ ID NO: 240 and (b) a VL domain comprising an amino acid sequence of SEQ ID NO: 241.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 85; (b) an HVR-H2 comprising the amino acid sequence of SEQ ID NO: 86; (c) an HVR-H3 comprising the amino acid sequence of SEQ ID NO: 87; (d) an HVR-L1 comprising the amino acid sequence of SEQ ID NO: 88; (e) an HVR-L2 comprising the amino acid sequence of SEQ ID NO: 89; and (f) an HVR-L3 comprising the amino acid sequence of SEQ ID NO: 90. In some embodiments, the binding domain comprises (a) a VH domain comprising an amino acid sequence having at least 95% sequence identity to the amino acid sequence of SEQ ID NO: 242; (b) a VL domain comprising an amino acid sequence having at least 95% sequence identity to the amino acid sequence of SEQ ID NO: 243; or (c) a VH domain as in (a) and a VL domain as in (b). In some embodiments, the VH domain comprises the amino acid sequence of SEQ ID NO: 242. In some embodiments, the VL domain comprises the amino acid sequence of SEQ ID NO: 243.

In another aspect, the invention features an anti-CD3 antibody, wherein the anti-CD3 antibody comprises a binding domain comprising: (a) a VH domain comprising an amino acid sequence of SEQ ID NO: 242 and (b) a VL domain comprising an amino acid sequence of SEQ ID NO: 243.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 91; (b) an HVR-H2 comprising the amino acid sequence of SEQ ID NO: 92; (c) an HVR-H3 comprising the amino acid sequence of SEQ ID NO: 93; (d) an HVR-L1 comprising the amino acid sequence of SEQ ID NO: 94; (e) an HVR-L2 comprising the amino acid sequence of SEQ ID NO: 95; and (f) an HVR-L3 comprising the amino acid sequence of SEQ ID NO: 96. In some embodiments, the binding domain comprises (a) a VH domain comprising an amino acid sequence having at least 95% sequence identity to the amino acid sequence of SEQ ID NO: 244; (b) a VL domain comprising an amino acid sequence having at least 95% sequence identity to the amino acid sequence of SEQ ID NO: 245; or (c) a VH domain as in (a) and a VL domain as in (b). In some embodiments, the VH domain comprises the amino acid sequence of SEQ ID NO: 244. In some embodiments, the VL domain comprises the amino acid sequence of SEQ ID NO: 245.

In another aspect, the invention features an anti-CD3 antibody, wherein the anti-CD3 antibody comprises a binding domain comprising: (a) a VH domain comprising an amino acid sequence of SEQ ID NO: 244 and (b) a VL domain comprising an amino acid sequence of SEQ ID NO: 245.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 97; (b) an HVR-H2 comprising the amino acid sequence of SEQ ID NO: 98; (c) an HVR-H3 comprising the amino acid sequence of SEQ ID NO: 99; (d) an HVR-L1 comprising the amino acid sequence of SEQ ID NO: 100; (e) an HVR-L2 comprising the amino acid sequence of SEQ ID NO: 101; and (f) an HVR-L3 comprising the amino acid sequence of SEQ ID NO: 102. In some embodiments, the binding domain comprises (a) a VH domain comprising an amino acid sequence having at least 95% sequence identity to the amino acid sequence of SEQ ID NO: 246; (b) a VL domain comprising an amino acid sequence having at least 95% sequence identity to the amino acid sequence of SEQ ID NO: 247; or (c) a VH domain as in (a) and a VL domain as in (b). In some embodiments, the VH domain comprises the amino acid sequence of SEQ ID NO: 246. In some embodiments, the VL domain comprises the amino acid sequence of SEQ ID NO: 247.

In another aspect, the invention features an anti-CD3 antibody, wherein the anti-CD3 antibody comprises a binding domain comprising: (a) a VH domain comprising an amino acid sequence of SEQ ID NO: 246 and (b) a VL domain comprising an amino acid sequence of SEQ ID NO: 247.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 103; (b) an HVR-H2 comprising the amino acid sequence of SEQ ID NO: 104; (c) an HVR-H3 comprising the amino acid sequence of SEQ ID NO: 105; (d) an HVR-L1 comprising the amino acid sequence of SEQ ID NO: 106; (e) an HVR-L2 comprising the amino acid sequence of SEQ ID NO: 107; and (f) an HVR-L3 comprising the amino acid sequence of SEQ ID NO: 108. In some embodiments, the binding domain comprises (a) a VH domain comprising an amino acid sequence having at least 95% sequence identity to the amino acid sequence of SEQ ID NO: 248; (b) a VL domain comprising an amino acid sequence having at least 95% sequence identity to the amino acid sequence of SEQ ID NO: 249; or (c) a VH domain as in (a) and a VL domain as in (b). In some embodiments, the VH domain comprises the amino acid sequence of SEQ ID NO: 248. In some embodiments, the VL domain comprises the amino acid sequence of SEQ ID NO: 249.

In another aspect, the invention features an anti-CD3 antibody, wherein the anti-CD3 antibody comprises a binding domain comprising: (a) a VH domain comprising an amino acid sequence of SEQ ID NO: 248 and (b) a VL domain comprising an amino acid sequence of SEQ ID NO: 249.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 109; (b) an HVR-H2 comprising the amino acid sequence of SEQ ID NO: 110; (c) an HVR-H3 comprising the amino acid sequence of SEQ ID NO: 111; (d) an HVR-L1 comprising the amino acid sequence of SEQ ID NO: 112; (e) an HVR-L2 comprising the amino acid sequence of SEQ ID NO: 113; and (f) an HVR-L3 comprising the amino acid sequence of SEQ ID NO: 114. In some embodiments, the binding domain comprises (a) a VH domain comprising an amino acid sequence having at least 95% sequence identity to the amino acid sequence of SEQ ID NO: 250; (b) a VL domain comprising an amino acid sequence having at least 95% sequence identity to the amino acid sequence of SEQ ID NO: 251; or (c) a VH domain as in (a) and a VL domain as in (b). In some embodiments, the VH domain comprises the amino acid sequence of SEQ ID NO: 250. In some embodiments, the VL domain comprises the amino acid sequence of SEQ ID NO: 251.

In another aspect, the invention features an anti-CD3 antibody, wherein the anti-CD3 antibody comprises a binding domain comprising: (a) a VH domain comprising an amino acid sequence of SEQ ID NO: 250 and (b) a VL domain comprising an amino acid sequence of SEQ ID NO: 251.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 115; (b) an HVR-H2 comprising the amino acid sequence of SEQ ID NO: 116; (c) an HVR-H3 comprising the amino acid sequence of SEQ ID NO: 117; (d) an HVR-L1 comprising the amino acid sequence of SEQ ID NO: 118; (e) an HVR-L2 comprising the amino acid sequence of SEQ ID NO: 119; and (f) an HVR-L3 comprising the amino acid sequence of SEQ ID NO: 120. In some embodiments, the binding domain comprises (a) a VH domain comprising an amino acid sequence having at least 95% sequence identity to the amino acid sequence of SEQ ID NO: 252; (b) a VL domain comprising an amino acid sequence having at least 95% sequence identity to the amino acid sequence of SEQ ID NO: 253; or (c) a VH domain as in (a) and a VL domain as in (b). In some embodiments, the VH domain comprises the amino acid sequence of SEQ ID NO: 252. In some embodiments, the VL domain comprises the amino acid sequence of SEQ ID NO: 253.

In another aspect, the invention features an anti-CD3 antibody, wherein the anti-CD3 antibody comprises a binding domain comprising: (a) a VH domain comprising an amino acid sequence of SEQ ID NO: 252 and (b) a VL domain comprising an amino acid sequence of SEQ ID NO: 253.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 121; (b) an HVR-H2 comprising the amino acid sequence of SEQ ID NO: 122; (c) an HVR-H3 comprising the amino acid sequence of SEQ ID NO: 123; (d) an HVR-L1 comprising the amino acid sequence of SEQ ID NO: 124; (e) an HVR-L2 comprising the amino acid sequence of SEQ ID NO: 125; and (f) an HVR-L3 comprising the amino acid sequence of SEQ ID NO: 126. In some embodiments, the binding domain comprises (a) a VH domain comprising an amino acid sequence having at least 95% sequence identity to the amino acid sequence of SEQ ID NO: 254; (b) a VL domain comprising an amino acid sequence having at least 95% sequence identity to the amino acid sequence of SEQ ID NO: 255; or (c) a VH domain as in (a) and a VL domain as in (b). In some embodiments, the VH domain comprises the amino acid sequence of SEQ ID NO: 254. In some embodiments, the VL domain comprises the amino acid sequence of SEQ ID NO: 255.

In another aspect, the invention features an anti-CD3 antibody, wherein the anti-CD3 antibody comprises a binding domain comprising: (a) a VH domain comprising an amino acid sequence of SEQ ID NO: 254 and (b) a VL domain comprising an amino acid sequence of SEQ ID NO: 255.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 127; (b) an HVR-H2 comprising the amino acid sequence of SEQ ID NO: 128; (c) an HVR-H3 comprising the amino acid sequence of SEQ ID NO: 129; (d) an HVR-L1 comprising the amino acid sequence of SEQ ID NO: 130; (e) an HVR-L2 comprising the amino acid sequence of SEQ ID NO: 131; and (f) an HVR-L3 comprising the amino acid sequence of SEQ ID NO: 132. In some embodiments, the binding domain comprises (a) a VH domain comprising an amino acid sequence having at least 95% sequence identity to the amino acid sequence of SEQ ID NO: 256; (b) a VL domain comprising an amino acid sequence having at least 95% sequence identity to the amino acid sequence of SEQ ID NO: 257; or (c) a VH domain as in (a) and a VL domain as in (b). In some embodiments, the VH domain comprises the amino acid sequence of SEQ ID NO: 256. In some embodiments, the VL domain comprises the amino acid sequence of SEQ ID NO: 257.

In another aspect, the invention features an anti-CD3 antibody, wherein the anti-CD3 antibody comprises a binding domain comprising: (a) a VH domain comprising an amino acid sequence of SEQ ID NO: 256 and (b) a VL domain comprising an amino acid sequence of SEQ ID NO: 257.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 133; (b) an HVR-H2 comprising the amino acid sequence of SEQ ID NO: 134; (c) an HVR-H3 comprising the amino acid sequence of SEQ ID NO: 135; (d) an HVR-L1 comprising the amino acid sequence of SEQ ID NO: 136; (e) an HVR-L2 comprising the amino acid sequence of SEQ ID NO: 137; and (f) an HVR-L3 comprising the amino acid sequence of SEQ ID NO: 138. In some embodiments, the binding domain comprises (a) a VH domain comprising an amino acid sequence having at least 95% sequence identity to the amino acid sequence of SEQ ID NO: 258; (b) a VL domain comprising an amino acid sequence having at least 95% sequence identity to the amino acid sequence of SEQ ID NO: 259; or (c) a VH domain as in (a) and a VL domain as in (b). In some embodiments, the VH domain comprises the amino acid sequence of SEQ ID NO: 258. In some embodiments, the VL domain comprises the amino acid sequence of SEQ ID NO: 259.

In another aspect, the invention features an anti-CD3 antibody, wherein the anti-CD3 antibody comprises a binding domain comprising: (a) a VH domain comprising an amino acid sequence of SEQ ID NO: 258 and (b) a VL domain comprising an amino acid sequence of SEQ ID NO: 259.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 139; (b) an HVR-H2 comprising the amino acid sequence of SEQ ID NO: 140; (c) an HVR-H3 comprising the amino acid sequence of SEQ ID NO: 141; (d) an HVR-L1 comprising the amino acid sequence of SEQ ID NO: 142; (e) an HVR-L2 comprising the amino acid sequence of SEQ ID NO: 143; and (f) an HVR-L3 comprising the amino acid sequence of SEQ ID NO: 144. In some embodiments, the binding domain comprises (a) a VH domain comprising an amino acid sequence having at least 95% sequence identity to the amino acid sequence of SEQ ID NO: 260; (b) a VL domain comprising an amino acid sequence having at least 95% sequence identity to the amino acid sequence of SEQ ID NO: 261; or (c) a VH domain as in (a) and a VL domain as in (b). In some embodiments, the VH domain comprises the amino acid sequence of SEQ ID NO: 260. In some embodiments, the VL domain comprises the amino acid sequence of SEQ ID NO: 261.

In another aspect, the invention features an anti-CD3 antibody, wherein the anti-CD3 antibody comprises a binding domain comprising: (a) a VH domain comprising an amino acid sequence of SEQ ID NO: 260 and (b) a VL domain comprising an amino acid sequence of SEQ ID NO: 261.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 145; (b) an HVR-H2 comprising the amino acid sequence of SEQ ID NO: 146; (c) an HVR-H3 comprising the amino acid sequence of SEQ ID NO: 147; (d) an HVR-L1 comprising the amino acid sequence of SEQ ID NO: 148; (e) an HVR-L2 comprising the amino acid sequence of SEQ ID NO: 149; and (f) an HVR-L3 comprising the amino acid sequence of SEQ ID NO: 150. In some embodiments, the binding domain comprises (a) a VH domain comprising an amino acid sequence having at least 95% sequence identity to the amino acid sequence of SEQ ID NO: 262; (b) a VL domain comprising an amino acid sequence having at least 95% sequence identity to the amino acid sequence of SEQ ID NO: 263; or (c) a VH domain as in (a) and a VL domain as in (b). In some embodiments, the VH domain comprises the amino acid sequence of SEQ ID NO: 262. In some embodiments, the VL domain comprises the amino acid sequence of SEQ ID NO: 263.

In another aspect, the invention features an anti-CD3 antibody, wherein the anti-CD3 antibody comprises a binding domain comprising: (a) a VH domain comprising an amino acid sequence of SEQ ID NO: 262 and (b) a VL domain comprising an amino acid sequence of SEQ ID NO: 263.

In another aspect, the invention features an anti-CD3 antibody, wherein the anti-CD3 antibody comprises a binding domain comprising the following six HVRs: (a) an HVR-H1 comprising the amino acid sequence of SEQ ID NO: 151; (b) an HVR-H2 comprising the amino acid sequence of SEQ ID NO: 152; (c) an HVR-H3 comprising the amino acid sequence of SEQ ID NO: 153; (d) an HVR-L1 comprising the amino acid sequence of SEQ ID NO: 154; (e) an HVR-L2 comprising the amino acid sequence of SEQ ID NO: 155; and (f) an HVR-L3 comprising the amino acid sequence of SEQ ID NO: 156. In some embodiments, the binding domain comprises (a) a VH domain comprising an amino acid sequence having at least 95% sequence identity to the amino acid sequence of SEQ ID NO: 264; (b) a VL domain comprising an amino acid sequence having at least 95% sequence identity to the amino acid sequence of SEQ ID NO: 265; or (c) a VH domain as in (a) and a VL domain as in (b). In some embodiments, the VH domain comprises the amino acid sequence of SEQ ID NO: 264. In some embodiments, the VL domain comprises the amino acid sequence of SEQ ID NO: 265.

In another aspect, the invention features an anti-CD3 antibody, wherein the anti-CD3 antibody comprises a binding domain comprising: (a) a VH domain comprising an amino acid sequence of SEQ ID NO: 264 and (b) a VL domain comprising an amino acid sequence of SEQ ID NO: 265.

In another aspect, the invention features an anti-CD3 antibody, wherein the anti-CD3 antibody binds to an epitope on CD3 comprising amino acid residue Glu6 of CD3. In certain aspects, the invention features an anti-CD3 antibody, wherein the epitope further comprises one or more additional amino acid residues selected from the group consisting of Gln1, Asp2, and Met7 of CD3. In a further aspect, the invention features an anti-CD3 antibody, wherein the epitope comprises amino acid residues Gln1, Asp2, and Glu6 of CD3. In certain aspects, the invention features an anti-CD3 antibody, wherein the epitope comprises amino acid residues Gln1, Asp2, Glu6, and Met7 of CD3. In another aspect, the invention features an anti-CD3 antibody, wherein the epitope does not comprise amino acid residue Glu5 of CD3. In a further aspect, the invention features an anti-CD3 antibody, wherein the epitope does not comprise amino acid residues Gly3 and Glu5 of CD3. In certain aspects, the invention features an anti-CD3 antibody, wherein the epitope consists of amino acid residues Gln1, Asp2, Glu6, and Met7 of CD3.

In related aspects, the invention features an anti-CD3 antibody that binds such an epitope and that is a multispecific antibody. In some embodiments, the multispecific antibody is a bispecific antibody. In some embodiments, the bispecific antibody comprises a second binding domain that binds to a second biological molecule, wherein the second biological molecule is a cell surface antigen. In some embodiments, the cell surface antigen is a tumor antigen. In some embodiments, the tumor antigen is selected from the group consisting of CD20; FcRH5 (Fc Receptor-like 5); HER2; LYPD1; Ly6G6D (lymphocyte antigen 6 complex, locus G61); Ly6-D, MEGT1); PMEL17 (silver homolog; SILV; D12S53E; PMEL17; (SI); (SIL); ME20; gp100); Ly6E (lymphocyte antigen 6 complex, locus E; Ly67, RIG-E, SCA-2, TSA-1); CD19; CD33; CD22 (B-cell receptor CD22-B isoform); CD79a (CD79A, CD79a, immunoglobulin-associated alpha; BMPR1B (bone morphogenetic protein receptor-type IB); CD79b (CD79B, CD79β, 1 Gb (immunoglobulin-associated beta), B29); EDAR (Ectodysplasin A Receptor); GFRA1 (GDNF-Ra1); MRP4 (Multidrug Resistance Protein 4); RET; STEAP1 (six transmembrane epithelial antigen of prostate); TENB2 (putative transmembrane proteoglycan); E16 (LAT1, SLC7A5); 0772P (CA125, MUC16); MPF (MPF, MSLN, SMR, megakaryocyte potentiating factor, mesothelin); Napi2b (NAPI-2B, NPTIIb, SLC34A2, solute carrier family 34 (sodium phosphate), member 2, type II sodium-dependent phosphate transporter 3b); Sema 5b; PSCA hlg (2700050C12Rik, C530008O16Rik, RIKEN cDNA 2700050012, RIKEN cDNA 2700050012 gene); ETBR (Endothelin type B receptor); MSG783 (RNF124, hypothetical protein FLJ20315); STEAP2; TrpM4 (BR22450, FLJ20041, TRPM4, TRPM4B, transient receptor potential cation channel, subfamily M, member 4); CRIPTO (CR, CR1, CRGF, CRIPTO, TDGF1, teratocarcinoma-derived growth factor); CD21 (CR2 (Complement receptor 2) or C3DR (C3d/Epstein Barr virus receptor) or Hs.73792); FcRH2 (IFGP4, IRTA4, SPAP1A (SH2 domain containing phosphatase anchor protein 1a), SPAP1B, SPAP1C); NCA; MDP; IL20Rα; Brevican; EphB2R; ASLG659; PSCA; GEDA; BAFF-R (B cell-activating factor receptor, BLyS receptor 3, BR3); CXCR5 (Burkitt's lymphoma receptor 1; HLA-DOB (Beta subunit of MHC class II molecule); P2X5 (Purinergic receptor P2X ligand-gated ion channel 5; CD72 (B-cell differentiation antigen CD72, Lyb-2); LY64 (Lymphocyte antigen 64 (RP105), type I membrane protein of the leucine rich repeat (LRR) family); FcRH1 (Fc receptor-like protein 1); IRTA2 (Immunoglobulin superfamily receptor translocation associated 2); TMEFF1; TMEM46 (shisa homolog 2 (*Xenopus laevis*); SHISA2); LGR5 (leucine-rich repeat-containing G protein-coupled receptor 5; GPR49, GPR67); LY6K (lymphocyte antigen 6 complex, locus K; LY6K; HSJ001348; FLJ35226); GPR19 (G protein-coupled receptor 19; Mm 4787); GPR54 (KISS1 receptor; KISS1R; GPR54; HOT7T175; AXOR12); ASPHD1 (aspartate beta-hydroxylase domain containing 1; LOC253982); Tyrosinase (TYR; OCAIA; OCA1A; tyrosinase; SHEP3); TMEM118 (ring finger protein, transmembrane 2; RNFT2; FLJ14627); GPR172A (G protein-coupled receptor 172A; GPCR41; FLJ11856; D15Ertd747e); GPC3 (Glypican 3); CLL1 (C-Type Lectin-like molecule 1); B7-H4 (B7x; B7S1); RNF43 (Ring finger protein 43); CD70; CXORF61 (Chromosome X open reading frame 61); HAVCR1; Epiregulin; Amphiregulin; EGFR; EGFR-L858R; EGFR-L861 Q; EGFR-G719A; EGFR-G719S; EGFR-G719C; EGFR-T790M; EGFR-S7681; adipophilin; AIM-2; ALDH1A1; alpha-actinin-4; alpha-foetoprotein; ARTC1; B-RAF; BAGE-1; BCLX (L); BCR-ABL fusion protein (b3a2); beta-catenin; BING-4; CALCA; CASP-5; CASP-8; CD45; Cdc27; CDK4; CDKN2A; CEA; CLPP; COA-1; CPSF; Cw6; cyclin D1; Cyclin-A1; dek-can fusion protein; DKK1; DR1; DR13; EFTUD2; Elongation factor 2; ENAH (hMena); EpCAM; EphA3; ETV6-AML1 fusion protein; EZH2; FLT3-ITD; FN1; G250; MN; CAIX; GAGE-1;2;8; GAGE-3;4;5;6;7; glypican-3; GnTVf; gp100/Pmel17; GPNMB; HERV-K-MEL; hsp70-2; IDO1; IGF2B3; IL13Ralpha2; Intestinal carboxyl esterase; K-ras; Kallikrein 4; KIF20A; KK-LC-1; KM-HN-1; LAGE-1; LDLR-fucosyltransferaseASfusion protein; Lengsin; M-CSF; MAGE-A1; MAGE-A10; MAGE-A12; MAGE-A2; MAGE-A3; MAGE-A4; MAGE-A6; MAGE-A9; MAGE-C1; MAGE-C2; mammaglobin-A; MART2; MCSP; mdm-2; ME1; Melan-A/MART-1; Meloe; MMP-2; MMP-7; MUC1; MUCSAC; mucin; MUM-1f; MUM-2; MUM-3; Myosin class I; N-ras; NA88-A; neo-PAP; NFYC; NY-BR-1; NY-ESO-1/LAGE-2; OA1; OGT; OS-9; p53; PAP; PAX5; PBF; pml-RARalpha fusion protein; PRAME; PRDX5; PSMA; PTPRK; RAB38/NY-MEL-1; RAGE-1; RBAF600; RGSS; RhoC; RNF43; RU2AS; SAGE; secernin 1; SIRT2; SNRPD1; SOX10; Sp17; SSX-2; SSX-4; STEAP1; survivin; SYT-SSX1 or -SSX2 fusion protein; TAG-1; TAG-2; Telomerase; TGF-betaRII; TRAG-3; Triosephosphate isomerase; TRP-1/gp75; TRP-2; TRP2-INT2; tyrosinase; VEGF; WT1; XAGE-1b/GAGED2a; and SLC53SLC35D3. In some embodiments, the tumor antigen is selected from the group consisting of CD20, FcRH5, HER2, LYPD1, LY6G6D, PMEL17, LY6E, CD19, CD33, CD22, CD79A, CD79B, EDAR, GFRA1, MRP4, RET, Steap1, and TenB2. In preferred embodiments, the tumor antigen is selected from the group consisting of CD20, HER2, FcRH5, and LYPD1.

In some embodiments, the binding domain of any one of the preceding anti-CD3 antibodies binds to a human CD3 polypeptide or a cynomolgus monkey (cyno) CD3 polypeptide. In some embodiments, the human CD3 polypeptide or the cyno CD3 polypeptide is a human CD3ε polypeptide or a cyno CD3ε polypeptide, respectively. In some embodiments, the human CD3 polypeptide or the cyno CD3 polypeptide is a human CD3γ polypeptide or a cyno CD3γ polypeptide, respectively.

In some embodiments, any one of the preceding anti-CD3 antibodies binds the human CD3ε polypeptide with a Kd of 250 nM or lower. In some embodiments, the anti-CD3 antibody binds the human CD3ε polypeptide with a Kd of 100 nM or lower. In some embodiments, the anti-CD3 antibody binds the human CD3ε polypeptide with a Kd of 15 nM or lower. In some embodiments, the anti-CD3 antibody binds the human CD3ε polypeptide with a Kd of 10 nM or lower. In some embodiments, the anti-CD3 antibody binds the human CD3ε polypeptide with a Kd of 5 nM or lower.

In some embodiments, any one of the preceding anti-CD3 antibodies may comprise an aglycosylation site mutation. In some embodiments, the aglycosylation site mutation is a substitution mutation. In some embodiments, the substitution mutation is at amino acid residue N297, L234, L235, and/or D265 (EU numbering). In some embodiments, the substitution mutation is selected from the group consisting of N297G, N297A, L234A, L235A, and D265A. In some embodiments, the substitution mutation is an N297G mutation. In some embodiments, the aglycosylation site mutation reduces effector function of the anti-CD3 antibody. In some embodiments, the aglycosylation site mutation reduces effector function of the anti-CD3 antibody. In some embodiments, an anti-CD3 antibody comprises a substitution mutation in the Fc region that reduces effector function.

In some embodiments, any one of the preceding anti-CD3 antibodies can be monoclonal, human, humanized, or chimeric. In some embodiments, any one of the preceding anti-CD3 antibodies can be an antibody fragment that binds CD3. In some embodiments, the antibody fragment is selected from the group consisting of Fab, Fab'-SH, Fv, scFv, and (Fab')₂ fragments. In other embodiments, the anti-CD3 antibody is a full-length antibody. In some embodiments, the anti-CD3 antibody is an IgG antibody (e.g., an IgG1, IgG2, or IgG3 antibody). In some embodiments, the anti-CD3 antibody is a monospecific antibody. In some embodiments, the anti-CD3 antibody is a Bispecific T-Cell Engager (BITE®) antibody).

In some embodiments, the anti-CD3 antibody is a multispecific antibody. In some embodiments, the multispecific antibody is a bispecific antibody. In some embodiments, the bispecific antibody comprises a second binding domain that binds to a second biological molecule, wherein the second biological molecule is a cell surface antigen. In some embodiments, the cell surface antigen is a tumor antigen. In some embodiments, the tumor antigen is selected from the group consisting of CD20; FcRH5 (Fc Receptor-like 5); HER2; LYPD1; Ly6G6D (lymphocyte antigen 6 complex, locus G61); Ly6-D, MEGT1); PMEL17 (silver homolog;

SILV; D12S53E; PMEL17; (SI); (SIL); ME20; gp100); Ly6E (lymphocyte antigen 6 complex, locus E; Ly67, RIG-E, SCA-2, TSA-1); CD19; CD33; CD22 (B-cell receptor CD22-B isoform); CD79a (CD79A, CD79a, immunoglobulin-associated alpha; BMPR1B (bone morphogenetic protein receptor-type IB); CD79b (CD79B, CD79β, 1 Gb (immunoglobulin-associated beta), B29); EDAR (Ectodysplasin A Receptor); GFRA1 (GDNF-Ra1); MRP4 (Multidrug Resistance Protein 4); RET; STEAP1 (six transmembrane epithelial antigen of prostate); TENB2 (putative transmembrane proteoglycan); E16 (LAT1, SLC7A5); 0772P (CA125, MUC16); MPF (MPF, MSLN, SMR, megakaryocyte potentiating factor, mesothelin); Napi2b (NAPI-2B, NPTIIb, SLC34A2, solute carrier family 34 (sodium phosphate), member 2, type II sodium-dependent phosphate transporter 3b); Sema 5b; PSCA hlg (2700050C12Rik, C530008O16Rik, RIKEN cDNA 2700050012, RIKEN cDNA 2700050012 gene); ETBR (Endothelin type B receptor); MSG783 (RNF124, hypothetical protein FLJ20315); STEAP2; TrpM4 (BR22450, FLJ20041, TRPM4, TRPM4B, transient receptor potential cation channel, subfamily M, member 4); CRIPTO (CR, CR1, CRGF, CRIPTO, TDGF1, teratocarcinoma-derived growth factor); CD21 (CR2 (Complement receptor 2) or C3DR (C3d/Epstein Barr virus receptor) or Hs.73792); FcRH2 (IFGP4, IRTA4, SPAP1A (SH2 domain containing phosphatase anchor protein 1a), SPAP1B, SPAP1C); NCA; MDP; IL20Rα; Brevican; EphB2R; ASLG659; PSCA; GEDA; BAFF-R (B cell-activating factor receptor, BLyS receptor 3, BR3); CXCR5 (Burkitt's lymphoma receptor 1; HLA-DOB (Beta subunit of MHC class II molecule); P2X$_5$ (Purinergic receptor P2X ligand-gated ion channel 5; CD72 (B-cell differentiation antigen CD72, Lyb-2); LY64 (Lymphocyte antigen 64 (RP105), type I membrane protein of the leucine rich repeat (LRR) family); FcRH1 (Fc receptor-like protein 1); IRTA2 (Immunoglobulin superfamily receptor translocation associated 2); TMEFF1; TMEM46 (shisa homolog 2 (*Xenopus laevis*); SHISA2); LGR5 (leucine-rich repeat-containing G protein-coupled receptor 5; GPR49, GPR67); LY6K (lymphocyte antigen 6 complex, locus K; LY6K; HSJ001348; FLJ35226); GPR19 (G protein-coupled receptor 19; Mm 4787); GPR54 (KISS1 receptor; KISS1R; GPR54; HOT7T175; AXOR12); ASPHD1 (aspartate beta-hydroxylase domain containing 1; LOC253982); Tyrosinase (TYR; OCAIA; OCA1A; tyrosinase; SHEP3); TMEM118 (ring finger protein, transmembrane 2; RNFT2; FLJ14627); GPR172A (G protein-coupled receptor 172A; GPCR41; FLJ11856; D15Ertd747e); GPC3 (Glypican 3); CLL1 (C-Type Lectin-like molecule 1); B7-H4 (B7x; B7S1); RNF43 (Ring finger protein 43); CD70; CXORF61 (Chromosome X open reading frame 61); HAVCR1; Epiregulin; Amphiregulin; EGFR; EGFR-L858R; EGFR-L861Q; EGFR-G719A; EGFR-G719S; EGFR-G719C; EGFR-T790M; EGFR-S768I; adipophilin; AIM-2; ALDH1A1; alpha-actinin-4; alpha-foetoprotein; ARTC1; B-RAF; BAGE-1; BCLX (L); BCR-ABL fusion protein (b3a2); beta-catenin; BING-4; CALCA; CASP-5; CASP-8; CD45; Cdc27; CDK4; CDKN2A; CEA; CLPP; COA-1; CPSF; Cw6; cyclin D1; Cyclin-A1; dek-can fusion protein; DKK1; DR1; DR13; EFTUD2; Elongation factor 2; ENAH (hMena); EpCAM; EphA3; ETV6-AML1 fusion protein; EZH2; FLT3-ITD; FN1; G250; MN; CAIX; GAGE-1;2;8; GAGE-3;4;5;6;7; glypican-3; GnTVf; gp100/Pmel17; GPNMB; HERV-K-MEL; hsp70-2; IDO1; IGF2B3; IL13Ralpha2; Intestinal carboxyl esterase; K-ras; Kallikrein 4; KIF20A; KK-LC-1; KM-HN-1; LAGE-1; LDLR-fucosyltransferaseASfusion protein; Lengsin; M-CSF; MAGE-A1; MAGE-A10; MAGE-A12; MAGE-A2; MAGE-A3; MAGE-A4; MAGE-A6; MAGE-A9; MAGE-C1; MAGE-C2; mammaglobin-A; MART2; MCSP; mdm-2; ME1; Melan-A/MART-1; Meloe; MMP-2; MMP-7; MUC1; MUCSAC; mucin; MUM-1f; MUM-2; MUM-3; Myosin class I; N-ras; NA88-A; neo-PAP; NFYC; NY-BR-1; NY-ESO-1/LAGE-2; OA1; OGT; OS-9; p53; PAP; PAX5; PBF; pml-RARalpha fusion protein; PRAME; PRDX5; PSMA; PTPRK; RAB38/NY-MEL-1; RAGE-1; RBAF600; RGSS; RhoC; RNF43; RU2AS; SAGE; secernin 1; SIRT2; SNRPD1; SOX10; Sp17; SSX-2; SSX-4; STEAP1; survivin; SYT-SSX1 or -SSX2 fusion protein; TAG-1; TAG-2; Telomerase; TGF-betaRII; TRAG-3; Triosephosphate isomerase; TRP-1/gp75; TRP-2; TRP2-INT2; tyrosinase; VEGF; WT1; XAGE-1b/GAGED2a; and SLC35D3. In some embodiments, the tumor antigen is selected from the group consisting of CD20, FcRH5, HER2, LYPD1, LY6G6D, PMEL17, LY6E, CD19, CD33, CD22, CD79A, CD79B, EDAR, GFRA1, MRP4, RET, Steap1, and TenB2.

In some embodiments, the tumor antigen is CD20 and the second binding domain comprises the following six HVRs: (a) an HVR-H1 comprising the amino acid sequence of SEQ ID NO: 157; (b) an HVR-H2 comprising the amino acid sequence of SEQ ID NO: 158; (c) an HVR-H3 comprising the amino acid sequence of SEQ ID NO: 159; (d) an HVR-L1 comprising the amino acid sequence of SEQ ID NO: 160; (e) an HVR-L2 comprising the amino acid sequence of SEQ ID NO: 161; and (f) an HVR-L3 comprising the amino acid sequence of SEQ ID NO: 162.

In some embodiments, the bispecific antibody that binds to CD20 and CD3 comprises an anti-CD20 arm comprising a first binding domain comprising the following six hypervariable regions (HVRs): an HVR-H1 comprising the amino acid sequence of SEQ ID NO: 157; an HVR-H2 comprising the amino acid sequence of SEQ ID NO: 158; an HVR-H3 comprising the amino acid sequence of SEQ ID NO:159; an HVR-L1 comprising the amino acid sequence of SEQ ID NO: 160; an HVR-L2 comprising the amino acid sequence of SEQ ID NO: 161; and an HVR-L3 comprising the amino acid sequence of SEQ ID NO: 162; and an anti-CD3 arm comprising a second binding domain comprising the amino acid sequences of any one of the following six HVR-H1, HVR-H2, HVR-H3, HVR-L1, HVR-L2, and HVR-L3, respectively: SEQ ID NOs: 1-6; SEQ ID NOs: 7, 8, 181, 10, 11, and 182; SEQ ID NOs: 23, 183, 25, 26, 27, and 28; SEQ ID NOs: 31-36; SEQ ID NOs: 37-42; SEQ ID NOs: 43-48; SEQ ID NOs: 49-54; SEQ ID NOs: 55-60; SEQ ID NOs: 61-66; SEQ ID NOs: 67-72; SEQ ID NOs: 73-78; SEQ ID NOs: 79-84; SEQ ID NOs: 85-90; SEQ ID NOs: 91-96; SEQ ID NOs: 97-102; SEQ ID NOs: 103-108; SEQ ID NOs: 109-114; SEQ ID NOs: 115-120; SEQ ID NOs: 121-126; SEQ ID NOs: 127-132; SEQ ID NOs: 133-138; SEQ ID NOs: 139-144; SEQ ID NOs: 145-150; SEQ ID NOs: 151-156; or SEQ ID NOs 631-636. For clarity, in these embodiments, by the six HVR-H1, HVR-H2, HVR-H3, HVR-L1, HVR-L2, and HVR-L3, respectively: SEQ ID NOs: 1-6, is meant HVR-H1 is SEQ ID NO: 1, HVR-H2 is SEQ ID NO: 2, HVR-H3 is SEQ ID NO: 3, HVR-L1 is SEQ ID NO: 4, HVR-L2 is SEQ ID NO: 5, and HVR-L3 is SEQ ID NO:6. This same notation hold true for the other similar embodiments herein, including the bispecific antibodies that bind to HER2 and CD3, FcRH5 and CD3, and LYPD1 and CD3.

In some embodiments, the second binding domain comprises (a) a VH domain comprising an amino acid sequence having at least 95% sequence identity to the amino acid sequence of SEQ ID NO: 266; (b) a VL domain comprising an amino acid sequence having at least 95% sequence identity to the amino acid sequence of SEQ ID NO: 267; or (c) a VH domain as in (a) and a VL domain as in (b). In some embodiments, the VH domain comprises the amino acid sequence of SEQ ID NO: 266. In some embodiments, the VL domain comprises the amino acid sequence of SEQ ID NO: 267.

In some embodiments, the tumor antigen is FcRH5 and the second binding domain comprises the following six HVRs: (a) an HVR-H1 comprising the amino acid sequence of SEQ ID NO: 163; (b) an HVR-H2 comprising the amino acid sequence of SEQ ID NO: 164; (c) an HVR-H3 comprising the amino acid sequence of SEQ ID NO: 165; (d) an HVR-L1 comprising the amino acid sequence of SEQ ID NO: 166; (e) an HVR-L2 comprising the amino acid sequence of SEQ ID NO: 167; and (f) an HVR-L3 comprising the amino acid sequence of SEQ ID NO: 168. In some embodiments, the second binding domain comprises (a) a VH domain comprising an amino acid sequence having at least 95% sequence identity to the amino acid sequence of SEQ ID NO: 268; (b) a VL domain comprising an amino acid sequence having at least 95% sequence identity to the amino acid sequence of SEQ ID NO: 269; or (c) a VH domain as in (a) and a VL domain as in (b). In some embodiments, the VH domain comprises the amino acid sequence of SEQ ID NO: 268. In some embodiments, the VL domain comprises the amino acid sequence of SEQ ID NO: 269.

In some embodiments, the tumor antigen is HER2 and the second binding domain comprises the following six HVRs: (a) an HVR-H1 comprising the amino acid sequence of SEQ ID NO: 169; (b) an HVR-H2 comprising the amino acid sequence of SEQ ID NO: 170; (c) an HVR-H3 comprising the amino acid sequence of SEQ ID NO: 171; (d) an HVR-L1 comprising the amino acid sequence of SEQ ID NO: 172; (e) an HVR-L2 comprising the amino acid sequence of SEQ ID NO: 173; and (f) an HVR-L3 comprising the amino acid sequence of SEQ ID NO: 174. In some embodiments, the second binding domain comprises (a) a VH domain comprising an amino acid sequence having at least 95% sequence identity to the amino acid sequence of SEQ ID NO: 270; (b) a VL domain comprising an amino acid sequence having at least 95% sequence identity to the amino acid sequence of SEQ ID NO: 271; or (c) a VH domain as in (a) and a VL domain as in (b). In some embodiments, the VH domain comprises the amino acid sequence of SEQ ID NO: 270. In some embodiments, the VL domain comprises the amino acid sequence of SEQ ID NO: 271.

In some embodiments, the tumor antigen is HER2 and the second binding domain comprises the following six HVRs: (a) an HVR-H1 comprising the amino acid sequence of SEQ ID NO: 581; (b) an HVR-H2 comprising the amino acid sequence of SEQ ID NO: 582; (c) an HVR-H3 comprising the amino acid sequence of SEQ ID NO: 583; (d) an HVR-L1 comprising the amino acid sequence of SEQ ID NO: 584; (e) an HVR-L2 comprising the amino acid sequence of SEQ ID NO: 585; and (f) an HVR-L3 comprising the amino acid sequence of SEQ ID NO: 586. In some embodiments, the second binding domain comprises (a) a VH domain comprising an amino acid sequence having at least 95% sequence identity to the amino acid sequence of SEQ ID NO: 593; (b) a VL domain comprising an amino acid sequence having at least 95% sequence identity to the amino acid sequence of SEQ ID NO: 594; or (c) a VH domain as in (a) and a VL domain as in (b). In some embodiments, the VH domain comprises the amino acid sequence of SEQ ID NO: 593. In some embodiments the VL domain comprises the amino acid sequence of SEQ ID NO: 594.

In some embodiments, the tumor antigen is HER2 and the second binding domain comprises the following six HVRs: (a) an HVR-H1 comprising the amino acid sequence of SEQ ID NO: 587; (b) an HVR-H2 comprising the amino acid sequence of SEQ ID NO: 588; (c) an HVR-H3 comprising the amino acid sequence of SEQ ID NO: 589; (d) an HVR-L1 comprising the amino acid sequence of SEQ ID NO: 590; (e) an HVR-L2 comprising the amino acid sequence of SEQ ID NO: 591; and (f) an HVR-L3 comprising the amino acid sequence of SEQ ID NO: 592. In some embodiments, the second binding domain comprises (a) a VH domain comprising an amino acid sequence having at least 95% sequence identity to the amino acid sequence of SEQ ID NO: 595; (b) a VL domain comprising an amino acid sequence having at least 95% sequence identity to the amino acid sequence of SEQ ID NO: 596; or (c) a VH domain as in (a) and a VL domain as in (b). In some embodiments, the VH domain comprises the amino acid sequence of SEQ ID NO: 595. In some embodiments, the VL domain comprises the amino acid sequence of SEQ ID NO: 596.

In some embodiments, the tumor antigen is RET and the second binding domain comprises the following six HVRs: (a) an HVR-H1 comprising the amino acid sequence of SEQ ID NO: 613; (b) an HVR-H2 comprising the amino acid sequence of SEQ ID NO: 614; (c) an HVR-H3 comprising the amino acid sequence of SEQ ID NO: 615; (d) an HVR-L1 comprising the amino acid sequence of SEQ ID NO: 616; (e) an HVR-L2 comprising the amino acid sequence of SEQ ID NO: 617; and (f) an HVR-L3 comprising the amino acid sequence of SEQ ID NO: 618. In some embodiments, the second binding domain comprises (a) a VH domain comprising an amino acid sequence having at least 95% sequence identity to the amino acid sequence of SEQ ID NO: 619; (b) a VL domain comprising an amino acid sequence having at least 95% sequence identity to the amino acid sequence of SEQ ID NO: 620; or (c) a VH domain as in (a) and a VL domain as in (b). In some embodiments, the VH domain comprises the amino acid sequence of SEQ ID NO: 619. In some embodiments, the VL domain comprises the amino acid sequence of SEQ ID NO: 620.

In some embodiments, the tumor antigen is LYPD1 and the second binding domain comprises the following six HVRs: (a) an HVR-H1 comprising the amino acid sequence of SEQ ID NO: 175; (b) an HVR-H2 comprising the amino acid sequence of SEQ ID NO: 176; (c) an HVR-H3 comprising the amino acid sequence of SEQ ID NO: 177; (d) an HVR-L1 comprising the amino acid sequence of SEQ ID NO: 178; (e) an HVR-L2 comprising the amino acid sequence of SEQ ID NO: 179; and (f) an HVR-L3 comprising the amino acid sequence of SEQ ID NO: 180. In some embodiments, the second binding domain comprises (a) a VH domain comprising an amino acid sequence having at least 95% sequence identity to the amino acid sequence of SEQ ID NO: 272; (b) a VL domain comprising an amino acid sequence having at least 95% sequence identity to the amino acid sequence of SEQ ID NO: 273; or (c) a VH domain as in (a) and a VL domain as in (b). In some embodiments, the VH domain comprises the amino acid sequence of SEQ ID NO: 272. In some embodiments, the VL domain comprises the amino acid sequence of SEQ ID NO: 273.

In some aspects, the invention features an anti-CD3 antibody, wherein the anti-CD3 antibody comprises a second binding domain comprising: (a) a VH domain comprising an amino acid sequence of SEQ ID NO: 266 and (b) a VL domain comprising an amino acid sequence of SEQ ID NO: 267; (a) a VH domain comprising an amino acid sequence of SEQ ID NO: 268 and (b) a VL domain comprising an amino acid sequence of SEQ ID NO: 269; (a) a VH domain comprising an amino acid sequence of SEQ ID NO: 270 and (b) a VL domain comprising an amino acid sequence of SEQ ID NO: 271; (a) a VH domain comprising an amino acid sequence of SEQ ID NO: 272 and (b) a VL domain comprising an amino acid sequence of SEQ ID NO: 273; (a) a VH domain comprising an amino acid sequence of SEQ ID NO: 593 and (b) a VL domain comprising an amino acid sequence of SEQ ID NO: 594; (a) a VH domain comprising an amino acid sequence of SEQ ID NO: 595 and (b) a VL domain comprising an amino acid sequence of SEQ ID NO: 596; or (a) a VH domain comprising an amino acid sequence of SEQ ID NO: 619 and (b) a VL domain comprising an amino acid sequence of SEQ ID NO: 620.

In another aspect, the invention features an anti-CD3 antibody, wherein the anti-CD3 antibody comprises an anti-CD3 arm comprising a first binding domain comprising the following six HVRs: (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6; and an anti-CD20 arm comprising a second binding domain comprising the following six HVRs: (a) an HVR-H1 comprising the amino acid sequence of SEQ ID NO: 157; (b) an HVR-H2 comprising the amino acid sequence of SEQ ID NO: 158; (c) an HVR-H3 comprising the amino acid sequence of SEQ ID NO: 159; (d) an HVR-L1 comprising the amino acid sequence of SEQ ID NO: 160; (e) an HVR-L2 comprising the amino acid sequence of SEQ ID NO: 161; and (f) an HVR-L3 comprising the amino acid sequence of SEQ ID NO: 162.

In another aspect, the invention features an anti-CD3 antibody, wherein the anti-CD3 antibody comprises an anti-CD3 arm comprising a first binding domain comprising (a) a VH domain comprising an amino acid sequence of SEQ ID NO: 184 and (b) a VL domain comprising an amino acid sequence of SEQ ID NO: 185, and an anti-CD20 arm comprising a second binding domain comprising (a) a VH domain comprising an amino acid sequence of SEQ ID NO: 266 and (b) a VL domain comprising an amino acid sequence of SEQ ID NO: 267.

In another aspect, the invention features an anti-CD3 antibody, wherein the anti-CD3 antibody comprises an anti-CD3 arm comprising a first binding domain comprising (a) a VH domain comprising an amino acid sequence of SEQ ID NO: 184 and (b) a VL domain comprising an amino acid sequence of SEQ ID NO: 185, and an anti-CD20 arm comprising a second binding domain comprising (a) a VH domain comprising an amino acid sequence of SEQ ID NO: 266 and (b) a VL domain comprising an amino acid sequence of SEQ ID NO: 267, wherein the anti-CD3 antibody comprises an N297G substitution mutation.

In another aspect, the invention features an anti-CD3 antibody, wherein the anti-CD3 antibody comprises an anti-CD3 arm comprising a first binding domain comprising (a) a VH domain comprising an amino acid sequence of SEQ ID NO: 184 and (b) a VL domain comprising an amino acid sequence of SEQ ID NO: 185, and an anti-CD20 arm comprising a second binding domain comprising (a) a VH domain comprising an amino acid sequence of SEQ ID NO: 266 and (b) a VL domain comprising an amino acid sequence of SEQ ID NO: 267, wherein (a) the anti-CD3 arm comprises T366S, L368A, Y407V, and N297G substitution mutations and (b) the anti-CD20 arm comprises T366W and N297G substitution mutations.

In some embodiments, any one of the preceding anti-CD3 antibodies can comprise one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some embodiments, at least one of the one or more heavy chain constant domains is paired with another heavy chain constant domain. In some embodiments, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between said protuberance and cavity. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In some embodiments, the $CH2_1$ and $CH2_2$ domains meet at an interface between said protuberance and cavity.

In some embodiments, the half-life of any one of the preceding anti-CD3 antibodies may be about 7 days.

In some embodiments, the invention features an immunoconjugate comprising any one of the preceding anti-CD3 antibodies conjugated to a cytotoxic agent. Also provided is a composition comprising any one of the preceding anti-CD3 antibodies. In some embodiments, the composition further comprises a pharmaceutically acceptable carrier, excipient, or diluent. In some embodiments, the composition is a pharmaceutical composition. In some embodiments, the composition further comprises a PD-1 axis binding antagonist or an additional therapeutic agent. In another aspect, the invention features an isolated nucleic acid that encodes any of the anti-CD3 antibodies disclosed herein, comprising a vector (e.g., an expression vector) for expressing the antibody.

In another aspect, the invention features host cells comprising the preceding nucleic acids and/or vectors. In some embodiments, the host cell is a mammalian cell (e.g., a Chinese hamster ovary (CHO) cell). In other embodiments, the host cell is a prokaryotic cell (e.g., an *E. coli* cell). A method of producing any one of the preceding anti-CD3 antibodies is also provided, the method comprising culturing the host cell that produces the anti-CD3 antibody and recovering the anti-CD3 antibody from the host cell or the culture medium.

In some aspects, any one of the preceding anti-CD3 antibodies can be for use as a medicament. In some embodiments, any one of the preceding anti-CD3 antibodies can be for use in treating or delaying progression of a cell proliferative disorder or an autoimmune disorder in a subject in need thereof. In some embodiments, any one of the preceding anti-CD3 antibodies can be for use in enhancing immune function in a subject having a cell proliferative disorder or an autoimmune disorder.

In some aspects, the invention features the use of any one of the preceding anti-CD3 antibodies in the manufacture of a medicament for treating or delaying progression of a cell proliferative disorder or an autoimmune disorder. In some aspects, the invention features the use of any one of the preceding anti-CD3 antibodies in the manufacture of a medicament for enhancing immune function in a subject having a cell proliferative disorder or an autoimmune disorder.

A further aspect of the invention is a method of treating or delaying the progression of a cell proliferative disorder or an autoimmune disorder in a subject in need thereof, the method comprising administering to the subject an effective amount any one of the preceding anti-CD3 antibodies. In another aspect, the invention features a method of enhancing immune function in a subject having a cell proliferative disorder or an autoimmune disorder, the method comprising administering to the subject any one of the preceding anti-CD3 antibodies. In some embodiments, the anti-CD3 antibody binds to (a) a CD3 molecule located on an immune effector cell and (b) a second biological molecule located on a target cell other than the immune effector cell. In some embodiments, the anti-CD3 antibody activates the immune effector cell following binding to (a) and (b). In some embodiments, the activated immune effector cell is capable of exerting a cytotoxic effect and/or an apoptotic effect on the target cell. In some embodiments, the anti-CD3 antibody is administered to the subject in a dosage of about 0.01 mg/kg to about 10 mg/kg. In some embodiments, the anti-CD3 antibody is administered to the subject in a dosage of about 0.1 mg/kg to about 10 mg/kg. In some embodiments, the anti-CD3 antibody is administered to the subject in a dosage of about 1 mg/kg. In some embodiments, the anti-CD3 antibody is administered subcutaneously, intravenously, intramuscularly, topically, orally, transdermally, intraperitoneally, intraorbitally, by implantation, by inhalation, intrathecally, intraventricularly, or intranasally. In some embodiments, the anti-CD3 antibody is administered subcutaneously. In some embodiments, the anti-CD3 antibody is administered intravenously.

In some embodiments, the method further comprises administering to the subject a PD-1 axis binding antagonist or an additional therapeutic agent. In some embodiments, the additional therapeutic agent is administered prior to or subsequent to the administration of the anti-CD3 antibody. In some embodiments, the additional therapeutic agent is administered concurrently with the anti-CD3 antibody. In some embodiments, the PD-1 axis binding antagonist is selected from the group consisting of a PD-1 binding antagonist, a PD-L1 binding antagonist, and a PD-L2 binding antagonist. In some embodiments, the PD-1 axis binding antagonist is a PD-1 binding antagonist. In some embodiments, the PD-1 binding antagonist is selected from the group consisting of MDX-1106 (nivolumab), MK-3475 (lambrolizumab), CT-011 (pidilizumab), and AMP-224. In other embodiments, the PD-1 axis binding antagonist is a PD-L1 binding antagonist. In some embodiments, the PD-L1 binding antagonist is selected from the group consisting of: YW243.55.S70, MPDL3280A, MDX-1105, and MEDI4736. In other embodiments, the PD-1 axis binding antagonist is a PD-L2 binding antagonist. In some embodiments, the PD-L2 binding antagonist is an antibody or an immunoadhesin.

In some aspects, the invention features a method of treating or delaying the progression of a cell proliferative disorder or an autoimmune disorder in a subject in need thereof, the method comprising administering to the subject an anti-CD3 antibody and a PD-1 axis binding antagonist, wherein the anti-CD3 antibody comprises an anti-CD3 arm and an anti-CD20 arm. In some aspects, the invention features a method of enhancing immune function in a subject having a cell proliferative disorder or an autoimmune disorder, the method comprising administering to the subject an anti-CD3 antibody and a PD-1 axis binding antagonist, wherein the anti-CD3 antibody comprises an anti-CD3 arm and an anti-CD20 arm (i.e., a CD20 TDB). In some embodiments, (a) the anti-CD3 arm comprises a first binding domain comprising (i) a VH domain comprising an amino acid sequence of SEQ ID NO: 184, and (ii) a VL domain comprising an amino acid sequence of SEQ ID NO: 185; (b) the anti-CD20 arm comprises a second binding domain comprising (i) a VH domain comprising an amino acid sequence of SEQ ID NO: 266, and (ii) a VL domain comprising an amino acid sequence of SEQ ID NO: 267; and/or (c) the PD-1 axis binding antagonist is an anti-PD-L1 antibody.

In some embodiments, the anti-CD3 antibody comprises an anti-CD20 arm comprising a N297G substitution mutation. In some embodiments, the anti-CD3 antibody comprises an anti-CD3 arm comprising T366S, L368A, Y407V, and/or N297G substitution mutation(s) and an anti-CD20 arm comprising T366W and/or N297G substitution mutation(s). In some embodiments, the anti-CD3 antibody comprises an anti-CD3 arm comprising a N297G substitution mutation. In some embodiments, the anti-CD3 antibody comprises an anti-CD20 arm comprising T366S, L368A, Y407V, and/or N297G substitution mutation(s) and an anti-CD3 arm comprising T366W and/or N297G substitution mutation(s).

In some embodiments, the anti-CD3 antibody comprises an anti-HER2 arm comprising a N297G substitution mutation. In some embodiments, the anti-CD3 antibody comprises an anti-CD3 arm comprising T366S, L368A, Y407V, and/or N297G substitution mutation(s) and an anti-HER2 arm comprising N297G, N297A, L234A, L235A, and/or D265A substitution mutation(s). In some embodiments, the anti-CD3 antibody comprises an anti-CD3 arm comprising a N297G substitution mutation. In some embodiments, the anti-CD3 antibody comprises an anti-HER2 arm comprising T366S, L368A, Y407V, and/or N297G substitution mutation(s) and an anti-CD3 arm comprising N297G, N297A, L234A, L235A, and/or D265A substitution mutation(s).

In some embodiments, the method further comprises administering to the subject a glucocorticoid. In some embodiments, the glucocorticoid is selected from the group consisting of dexamethasone, hydrocortisone, cortisone, prednisolone, prednisone, methylprednisone, triamcinolone, paramethasone, betamethasone, fludrocortisone, and pharmaceutically acceptable esters, salts, and complexes thereof. In some embodiments, the glucocorticoid is dexamethasone. In some embodiments, the glucocorticoid is a pharmaceutically acceptable ester, salt, or complex of dexamethasone.

In some embodiments, the method further comprises administering to the subject rituximab.

In some embodiments, the method further comprises administering to the subject obinutuzumab.

In some embodiments, the method further comprises administering to the subject an antibody-drug conjugate (ADC).

In any of the preceding uses or methods, the cell proliferative disorder can be cancer. In some embodiments, the cancer is selected from the group consisting of breast cancer, colorectal cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, glioblastoma, germinal-center B-cell-like (GCB)

DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenström macroglobulinemia, Heavy chain diseases, a Heavy chain disease, γ Heavy chain disease, p Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma. In some embodiments, the preferred cancer is germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), or Burkitt's lymphoma (BL)

In any of the preceding uses or methods, the autoimmune disorder can be selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO) and IgG neuropathy.

In another aspect, the invention features a kit comprising: (a) a composition comprising any one of the preceding anti-CD3 antibodies and (b) a package insert comprising instructions for administering the composition to a subject to treat or delay progression of a cell proliferative disorder.

In any of the preceding uses or methods, the subject can be a human.

BRIEF DESCRIPTION OF THE DRAWINGS

The application file contains at least one drawing executed in color. Copies of this patent or patent application with color drawings will be provided by the Office upon request and payment of the necessary fee.

FIG. 1 shows the amino acid sequence of single-chain human CD3εγ with a 26-mer linker sequence used in CD3 epitope mapping experiments (SEQ ID NO: 282).

FIG. 2A is a table summarizing the characterization of select hybridoma clones. The table summarizes the results of ELISA CD3 binding experiments using human and cyno CD3ε$^{1-27}$-Fc; FACS binding experiments using human Jurkat T cells, human PBMCs, and cyno PBMCs; T cell activation experiments using FACS analysis; and isotype determination experiments.

FIG. 2B is a table summarizing the binding affinities (Kd values) of select hybridoma clones for a commercial human CD3εγ antigen.

FIG. 3A is a table summarizing the characterization of select hybridoma. The table summarizes the results of ELISA CD3 binding experiments using human and cyno CD3ε$^{1-27}$-Fc; FACS binding experiments using human Jurkat T cells, human PBMCs, and cyno PBMCs; T cell activation experiments using FACS analysis; and isotype determination experiments.

FIGS. 3B and 3C are tables summarizing the binding affinities (Kd values) of select hybridoma clones.

FIG. 4A shows the amino acid sequences of the light chain variable domains of the anti-CD3 antibodies. HVR sequences are delimited by the denoted boxes for each of the antibodies.

FIG. 4B shows the amino acid sequences of the light chain variable domains of the anti-CD3 antibodies.

FIG. 4C shows the amino acid sequences of the heavy chain variable domains of the anti-CD3 antibodies.

FIG. 5A shows the amino acid sequences of the light chain variable domains of the anti-CD3 antibodies.

FIG. 5B shows the amino acid sequences of the heavy chain variable domains of the anti-CD3 antibodies.

FIG. 6A shows the amino acid sequences of the light chain variable domains of anti-CD3 antibody 21A9, and Rab17.

FIG. 6B shows the amino acid sequences of the heavy chain variable domain of anti-CD3 antibody 21A9, and Rab17.

FIG. 7 is a sequence alignment of light chain variable domain (top) and heavy chain variable domain (bottom) amino acid sequences of anti-CD3 antibodies showing the consensus sequence, 40G5c, derived from the related clonal antibodies.

Figure 8B:
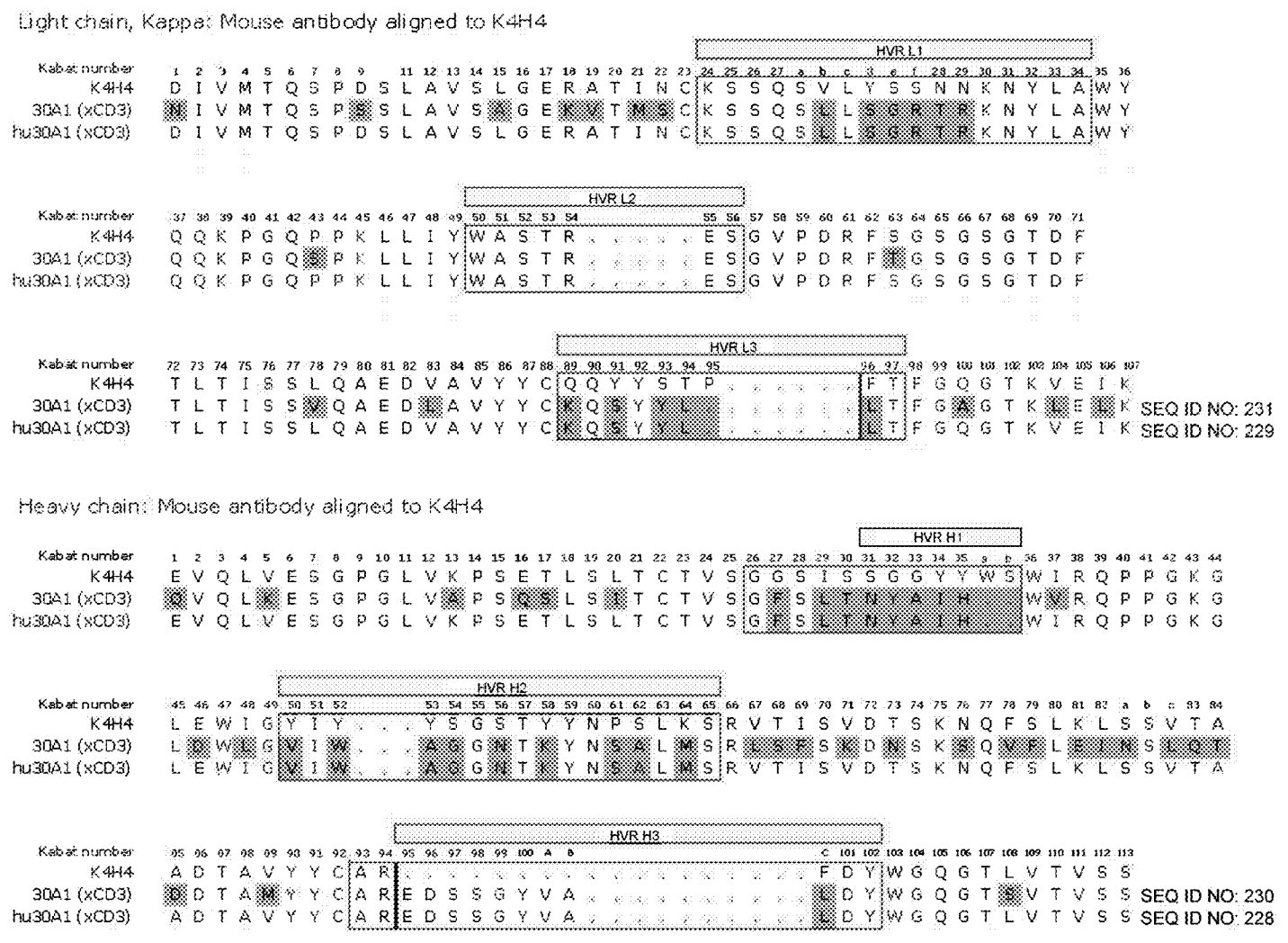
Figure 8D:
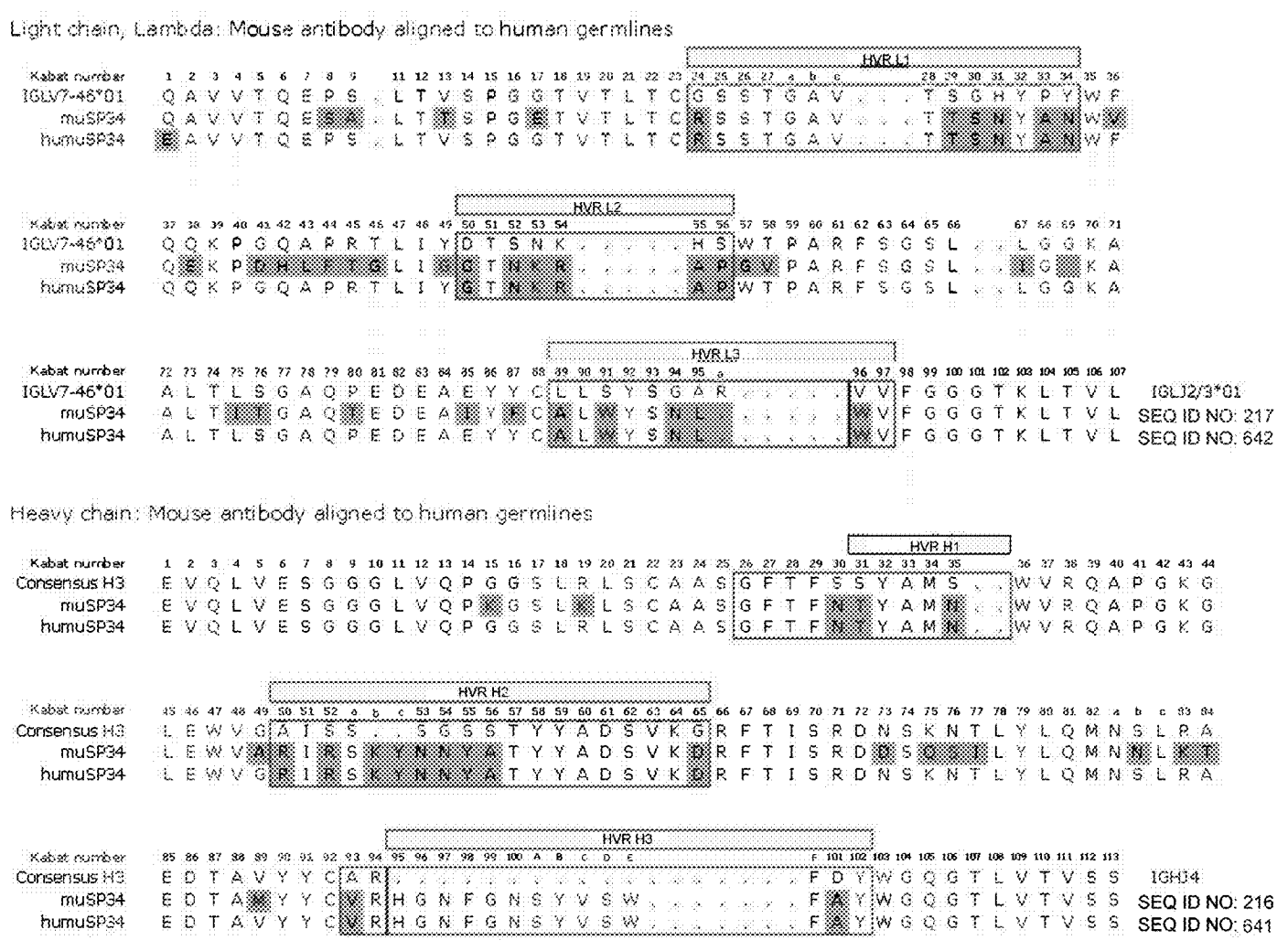
Figure 8F:
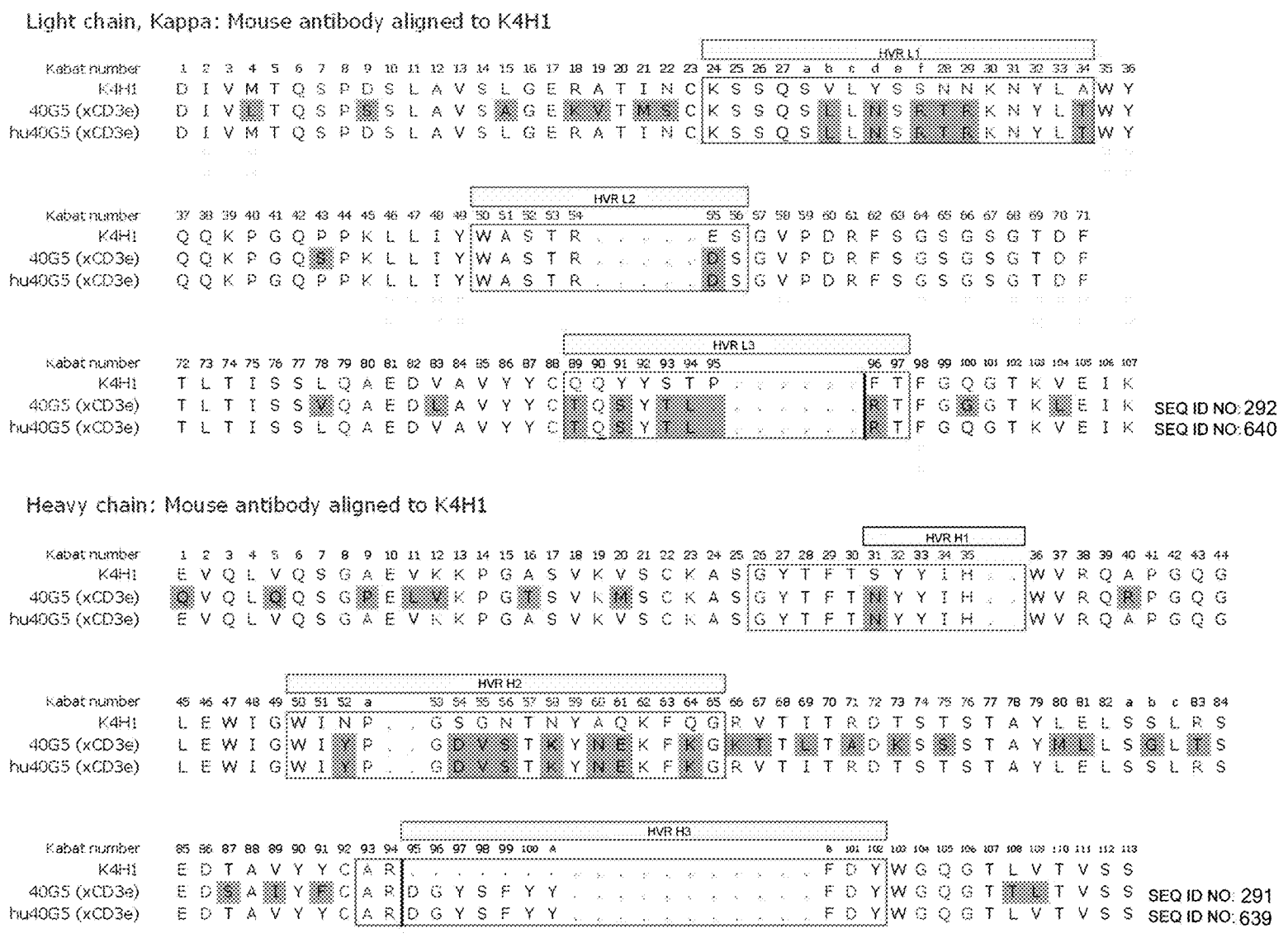

FIG. 8A is a sequence alignment of light chain variable domain (top) and heavy chain variable domain (bottom) amino acid sequences of anti-CD3 antibody 13A3 and a humanized variant thereof (hu13A3).

FIG. 8B is a sequence alignment of light chain variable domain (top) and heavy chain variable domain (bottom) amino acid sequences of anti-CD3 antibody 30A1 and a humanized variant thereof (hu30A1).

FIG. 8C is a sequence alignment of light chain variable domain (top) and heavy chain variable domain (bottom) amino acid sequences of anti-CD3 antibody 41D9a and a humanized variant thereof (hu41D9a).

FIG. 8D is a sequence alignment of light chain variable domain (top) and heavy chain variable domain (bottom) amino acid sequences of anti-CD3 antibody SP34 and a humanized variant thereof (huSP34).

FIG. 8E is a sequence alignment of light chain variable domain (top) and heavy chain variable domain (bottom) amino acid sequences of anti-CD3 antibody 38E4 and a humanized variant thereof (hu38E4).

FIG. 8F is a sequence alignment of light chain variable domain (top) and heavy chain variable domain (bottom)

amino acid sequences of anti-CD3 antibody 40G5 and a humanized variant thereof (hu40G5).

FIG. 9A is a table summarizing selected humanized variants of anti-CD3 antibody 13A3 and their binding affinities, assayed using commercial CD3ε (Creative Biomart, Shirley, N.Y.; Catalog Number CD3E-2194H).

FIG. 9B is a table summarizing selected humanized variants of anti-CD3 antibody 30A1 and their binding affinities, assayed using commercial CD3ε (Creative Biomart, Shirley, N.Y.; Catalog Number CD3E-2194H).

FIG. 9C is a table summarizing selected humanized variants of anti-CD3 antibody 41D9a and their binding affinities, assayed using commercial CD3ε (Creative Biomart, Shirley, N.Y.; Catalog Number CD3E-2194H).

FIG. 9D is a table summarizing selected humanized variants of anti-CD3 antibody SP34 and their binding affinities, assayed using commercial CD3ε (Creative Biomart, Shirley, N.Y.; Catalog Number CD3E-2194H).

FIG. 9E is a table summarizing selected humanized variants of anti-CD3 antibody 38E4 and their binding affinities, assayed using commercial CD3ε (Creative Biomart, Shirley, N.Y.; Catalog Number CD3E-2194H).

FIG. 9F is a table summarizing selected humanized variants of anti-CD3 antibody 40G5c and their binding affinities, assayed using commercial CD3ε (Creative Biomart, Shirley, N.Y.; Catalog Number CD3E-2194H).

FIG. 10 is a table summarizing the binding affinity of humanized anti-CD3 antibodies for various CD3ε antigens.

FIG. 11 is a table summarizing the binding affinity of humanized anti-CD3 antibodies 38E4v1 through 38E4v9 and 40G5c, as measured by Biacore with human CD3εγ on chip and anti-CD3 antibodies in flow through.

FIG. 12A is a table summarizing the relative binding affinities for single alanine, serine, threonine, or glutamate mutants of the humanized anti-CD3 antibody 38E4v1 having a single mutation in either HVR-L3 or HVR-H3, as compared to 38E4v1 using single-cycle or conventional multi-cycle kinetic Biacore analysis.

Figure 12B:
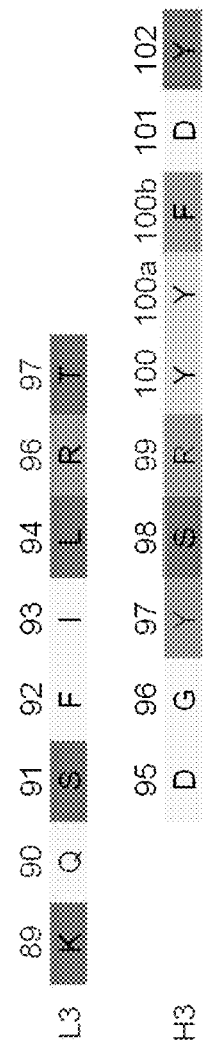

FIG. 12B shows the HVR-L3 (top) and HVR-H3 (bottom) amino acid sequences of the humanized anti-CD3 antibody 38E4v1.

Figure 13A:
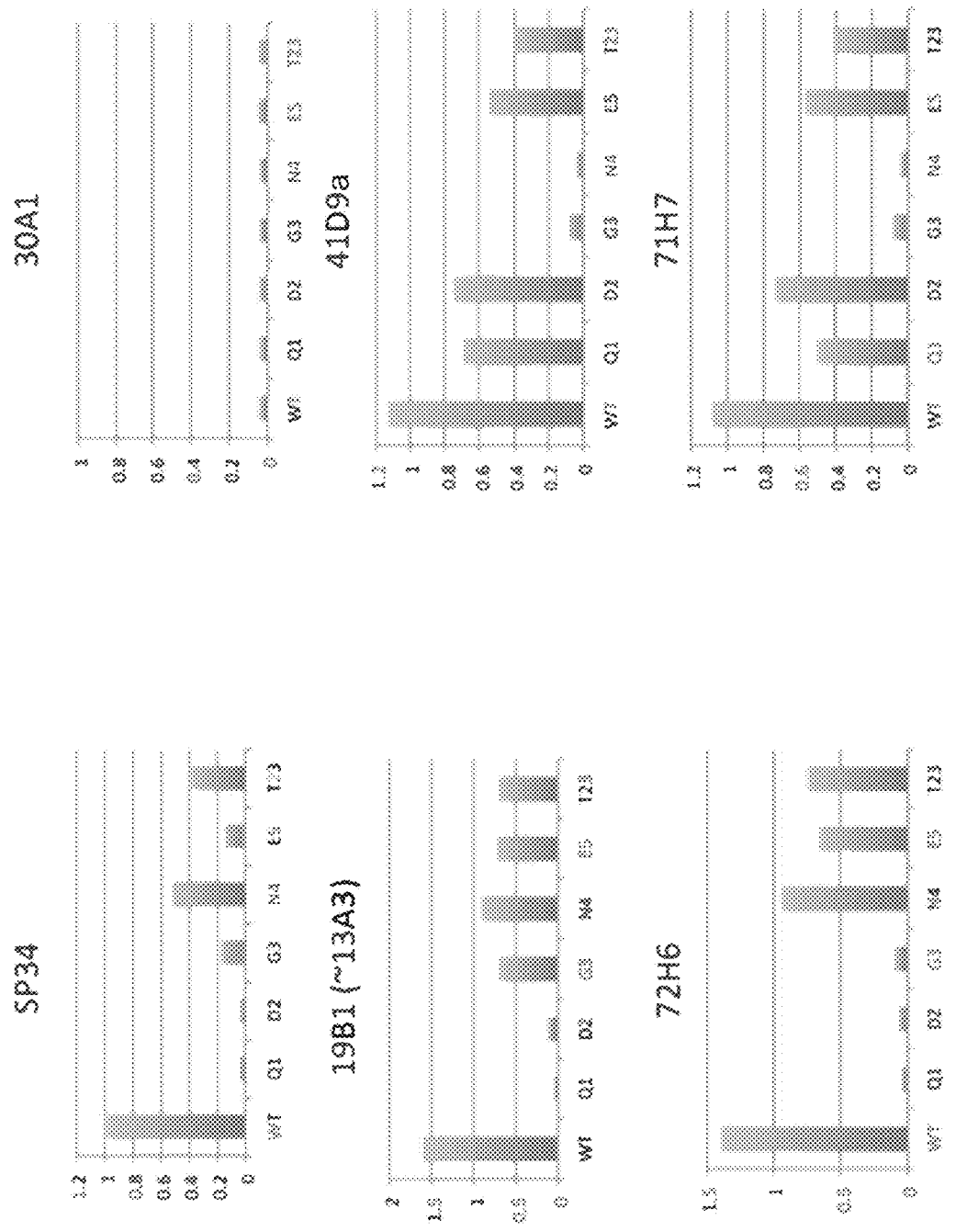

FIG. 13A is a series of graphs showing the relative binding of the denoted anti-CD3 antibody to alanine variants of $CD3\varepsilon^{1-27}$-Fc.

Figure 13B:
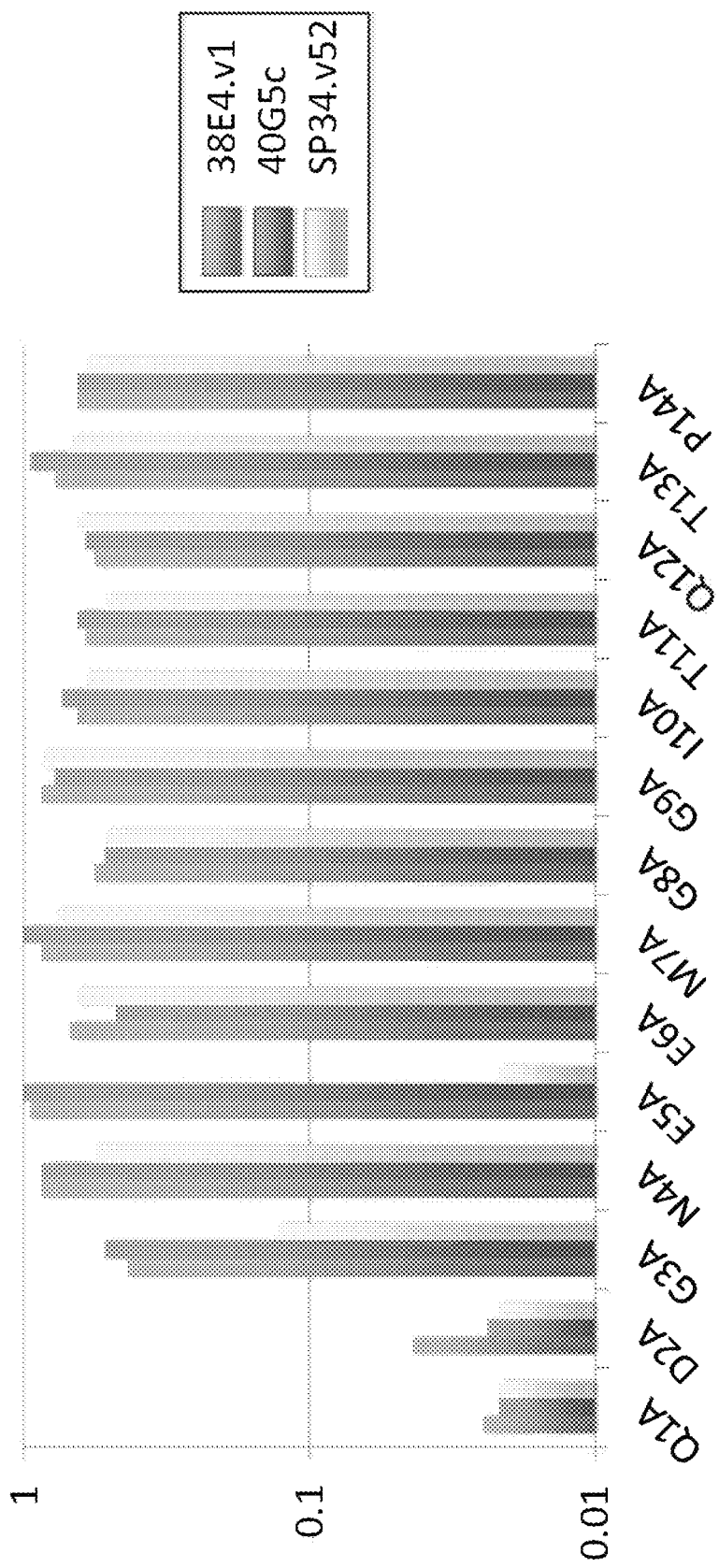

FIG. 13B is a graph showing the relative fraction of CD3εγ alanine scanning phagemid mutants bound to anti-CD3 antibodies 38E4.v1, 40G5c, and SP34.v52, as compared to wild-type CD3εγ phage binding.

Figure 13C:
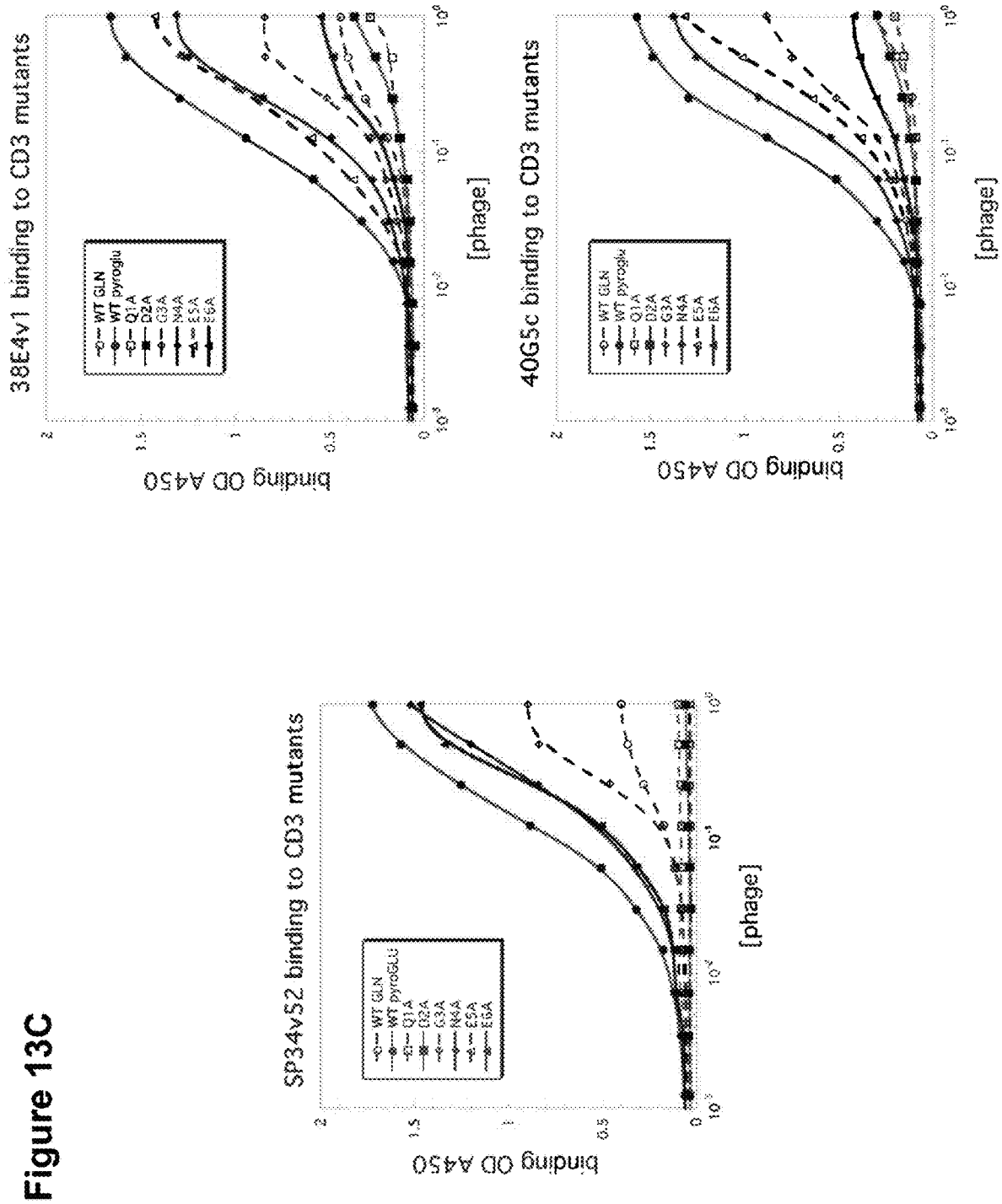

FIG. 13C is a series of graphs showing the relative binding of anti-CD3 antibodies 38E4.v1, 40G5c, and SP34.v52 to selected CD3εγ alanine scanning phagemid mutants as a function of phage concentration.

FIG. 13D is a set of tables showing the relative binding affinities of anti-CD3 antibodies SP34.v52 and 38E4v1 to selected CD3εγ alanine scanning mutants, as assessed by Biacore. NB=no detectable binding.

Figures 14A, 14B, 14C, 14D, 14E, 14F:
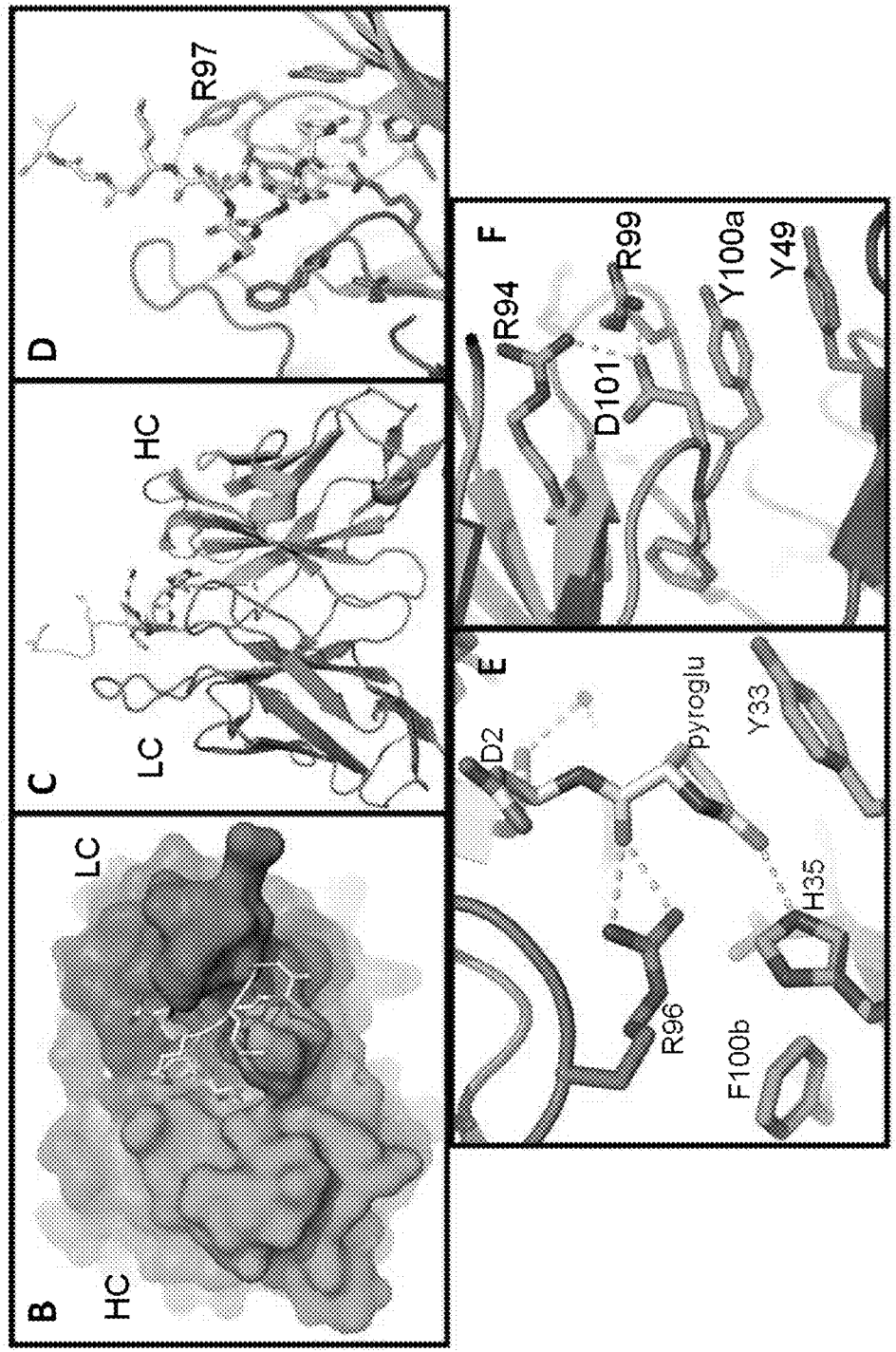

FIG. 14A shows the sequence of the 16-mer CD3ε polypeptide used in co-crystallization trials with 38E4.v1 Fab.

FIGS. 14B-14F is a series of renderings of the crystal structure showing different views of the hu38E4.v1 Fab/CD3ε peptide complex.

Figure 14G:
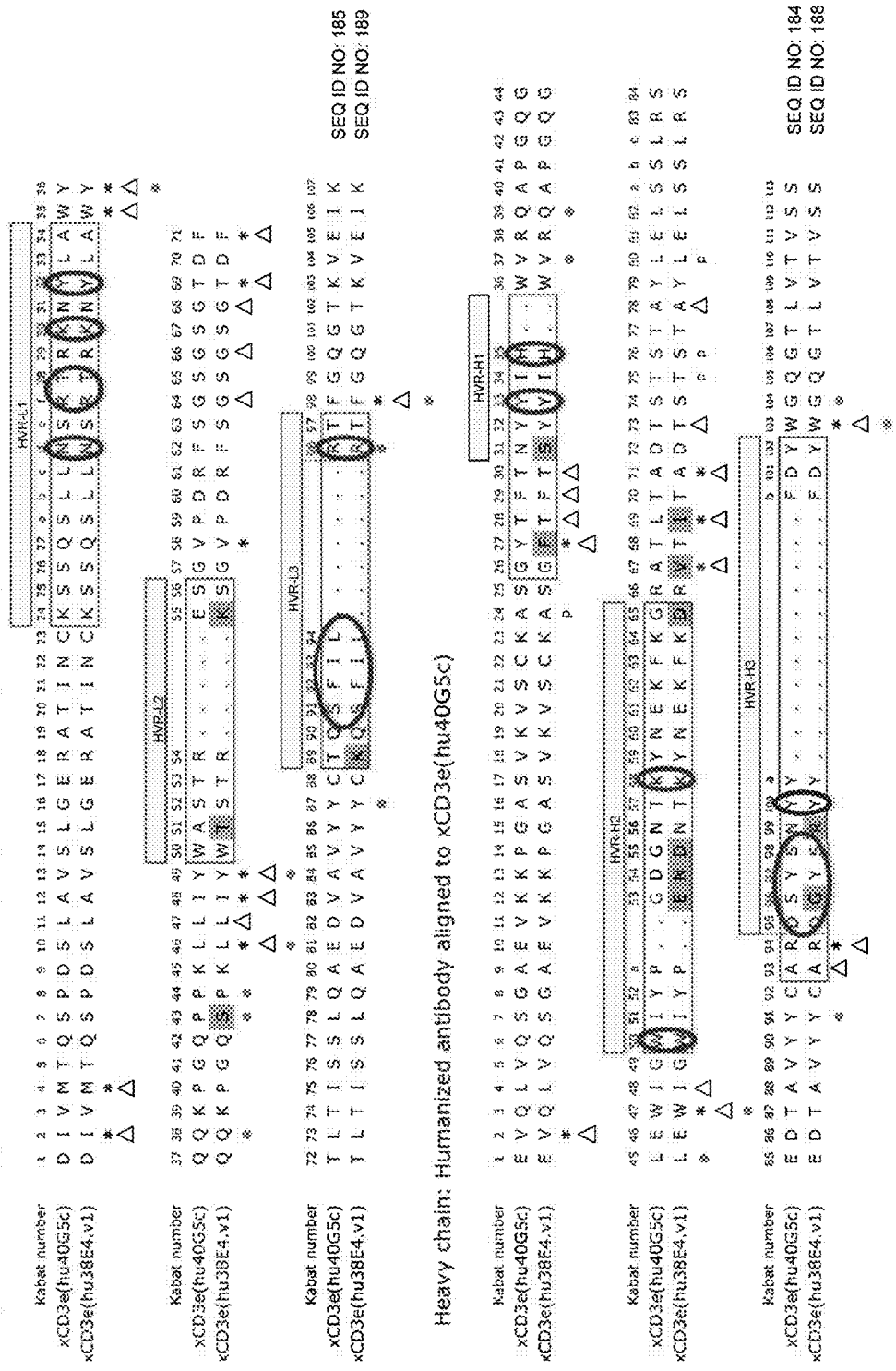

FIG. 14G is a sequence alignment of light chain variable domain (top) and heavy chain variable domain (bottom) amino acid sequences of anti-CD3 antibodies hu40G5c and hu38E4.v1, with residues of each antibody that are important for binding CD3 (contact residues) circled in the alignment. The circled residues were found to be within 5 Å of the CD3 peptide, as determined by crystallographic analysis. Δ denotes vernier positions (for reference, see, e.g., Foote and Winter. *JMB*. 224: 487, 1992); * denotes FW-HVR interactions (for reference, see, e.g., Padlan et al. *Mol. Immunol.* 31: 169, 1994); and • denotes VH-VL interactions (for reference, see, e.g., Padlan et al. *Mol. Immunol.* 31: 169, 1994).

Figure 14H:
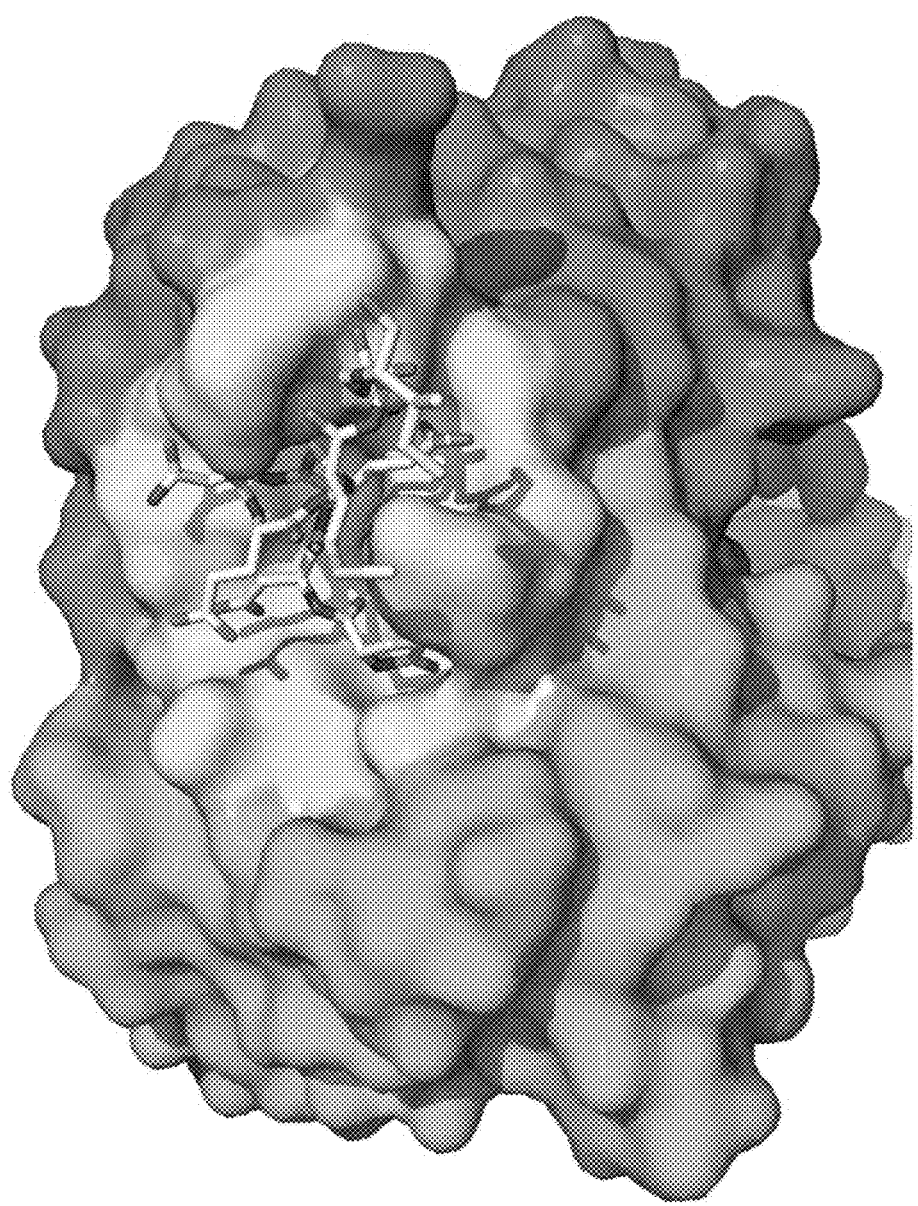

FIG. 14H is a rendering of the crystal structure of CD3ε polypeptide bound by hu38E4.v1 Fab. All antigen contact residues are depicted in yellow. All contact residues are identical between hu38E4.v1 and hu40G5, except G96 (depicted in orange) is S96 in hu40G5.

Figures 14I, 14J, 14K, 14L:
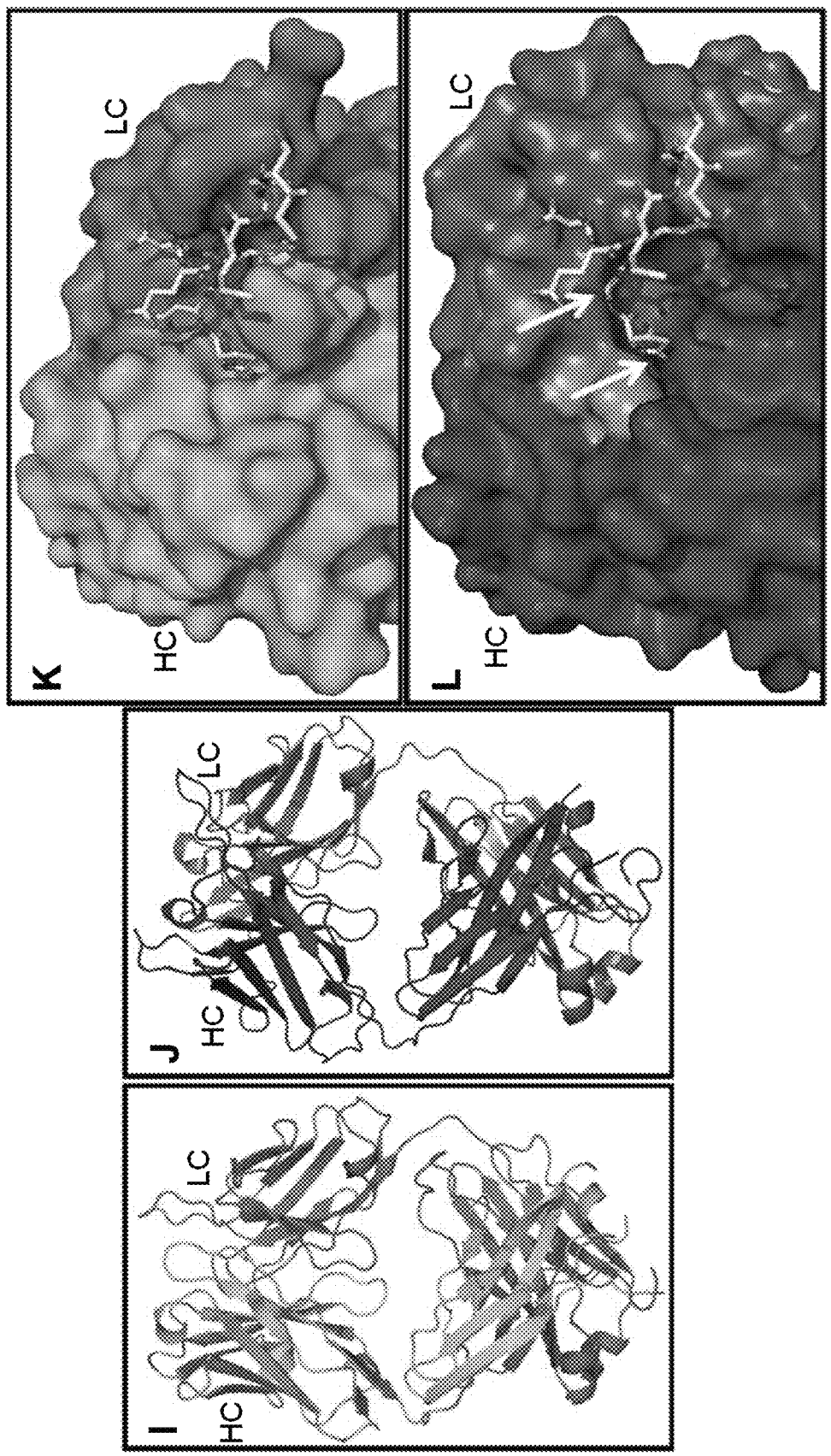

FIGS. 14I and 14J are ribbon diagram renderings of the crystal structures of hu38E4.v1 Fab and SP34v52 Fab, respectively, in the same orientation, overlaid with VL region with a RMS=2.24.

FIG. 14K is a space-filling model rendering of the hu38E4.v1 Fab complexed with the CD3ε N-terminal peptide bound in the cleft between the heavy (cyan) and light (purple) chains.

FIG. 14L is a space-filling model rendering of the SP34v52 Fab with the CD3ε N-terminal peptide superimposed in the same orientation as in the CD3ε/hu38E4.v1 Fab complex depicted in FIG. 14K. Residues R50 and R52 (in orange) of HVR-H2 of the SP34v52 Fab are important for binding CD3. Clear clashes of the CD3 peptide with SP34v52 Fab are indicated by arrows.

Figure 14M:
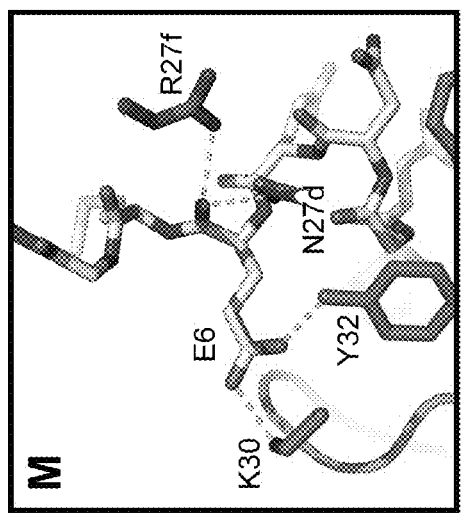

FIG. 14M is a crystal structure rendering of the hu38E4.v1 complexed with the N-terminal peptide of CD3εγ and illustrates the key intermolecular interactions involved in the first pyroglutamine residue and the sixth residue (E6) in CD3εγ. The potential hydrogen bonds are shown as dashed lines.

Figure 14N:
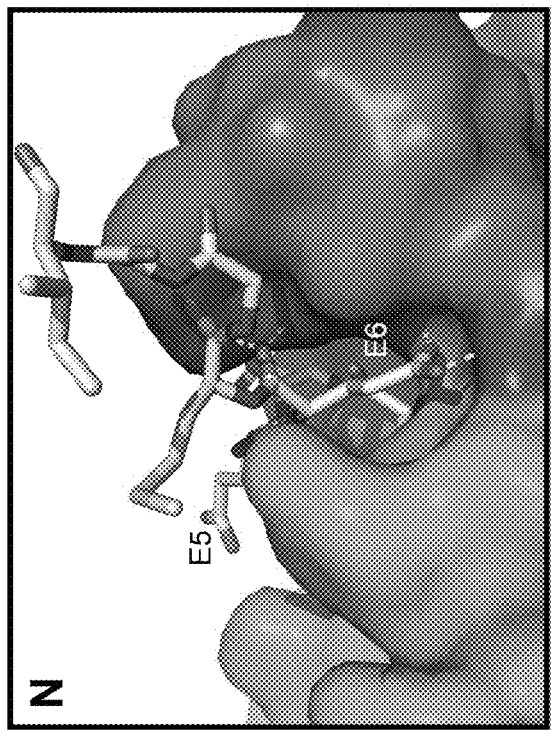

FIG. 14N is a space-filling model rendering of the hu38E4.v1 Fab complexed with the CD3εγ N-terminal peptide bound in the cleft between the heavy (cyan) and light (purple) chains. The fifth residue (E5) as illustrated, points away from the interactive site that contains the sixth residue (E6) of CD3εγ N-terminal peptide and Fab complex.

Figure 15:
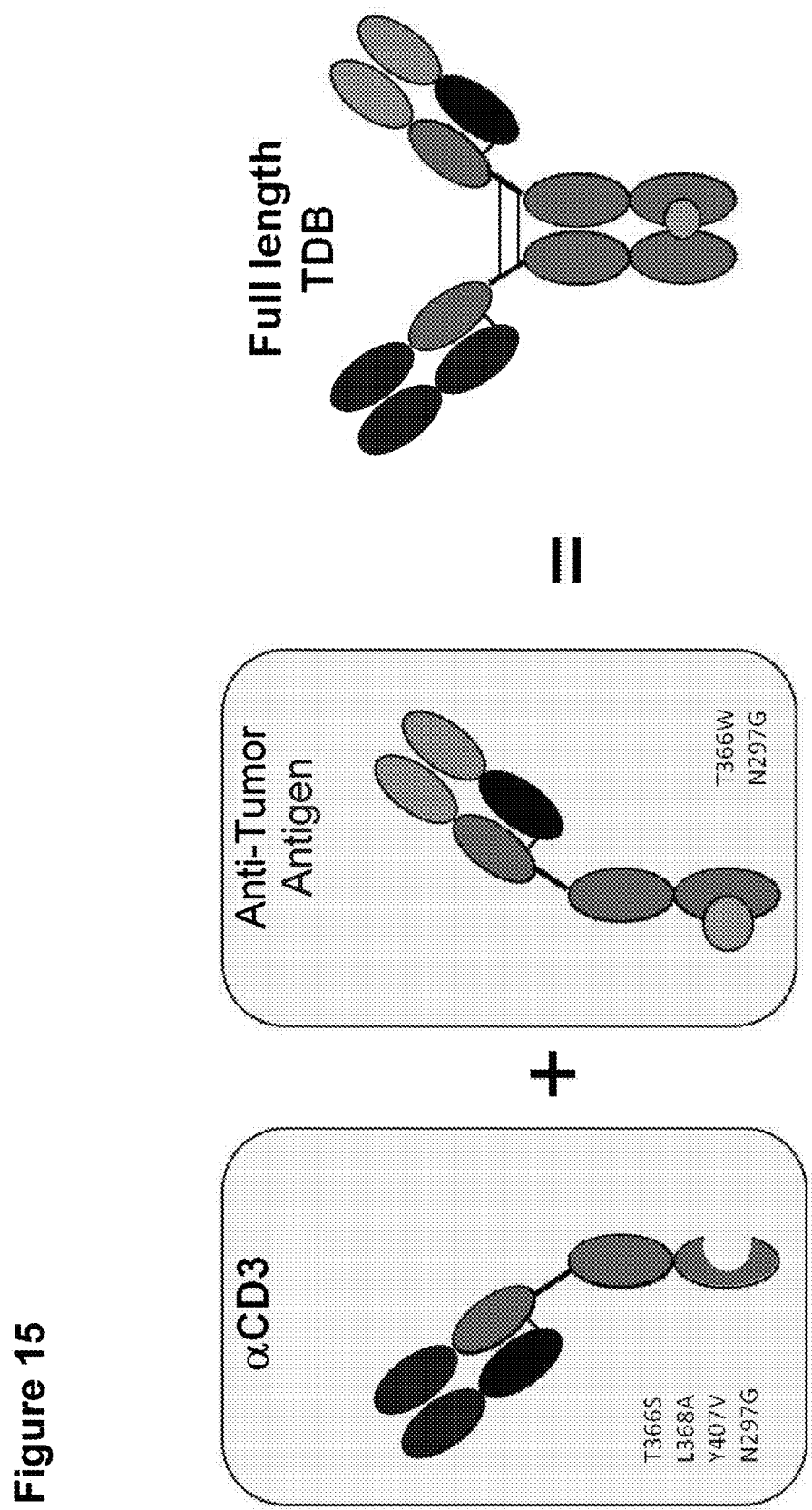

FIG. 15 depicts a schematic generalization of TDB antibody formation. The particular TDB depicted is shown as a full-length TDB in knob-in-hole (KIH) format, which can possess an aglycosylation mutation, if produced by a eukaryotic cell (e.g., a CHO cell). In an alternative format, the knob may be present on the anti-CD3 arm, and the hole may be present on the anti-tumor antigen arm. This format may also possess an aglycosylation mutation, if produced by a eukaryotic cell (e.g., a CHO cell).

Figure 16:
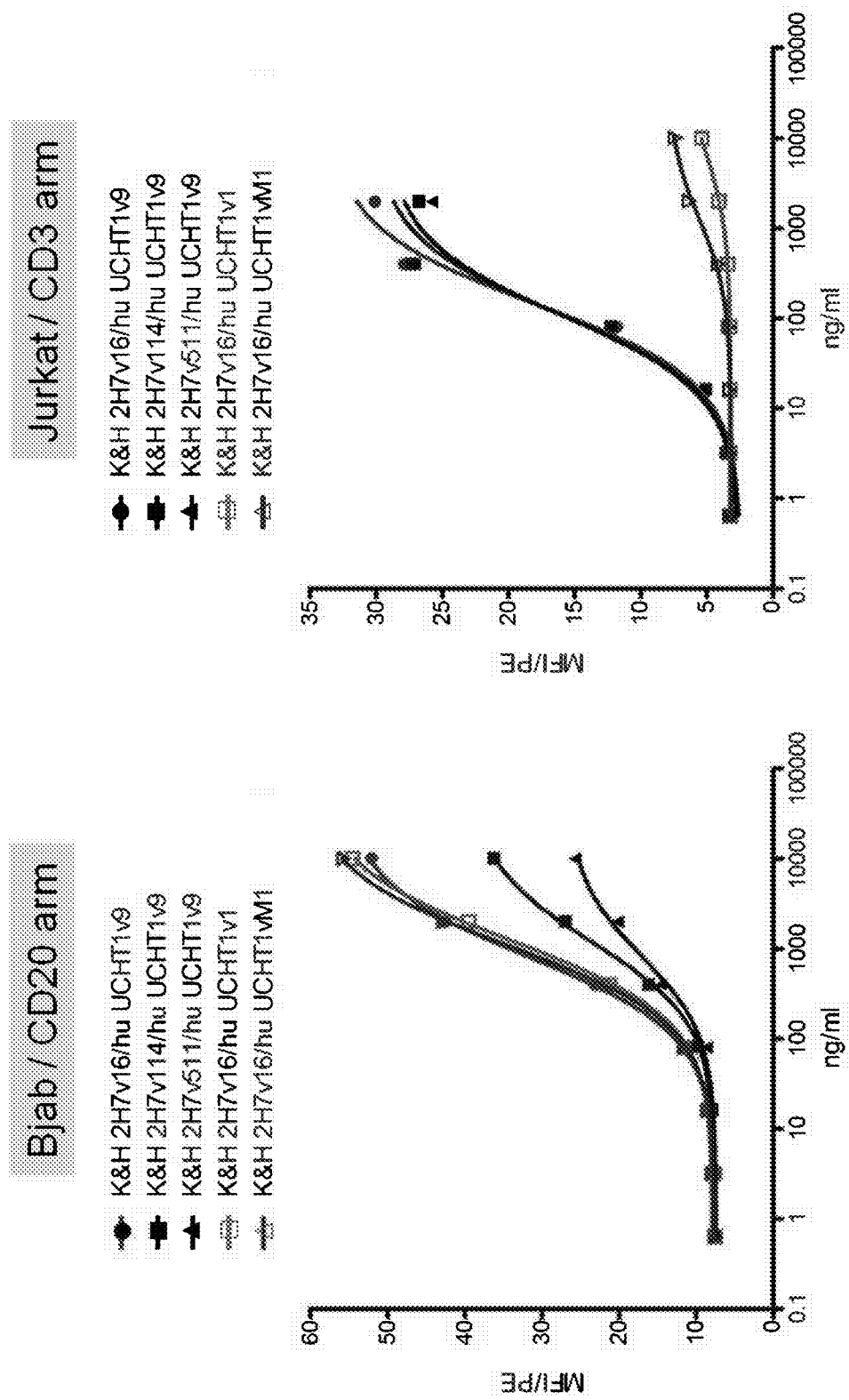

FIG. 16 are graphs showing the results of FACS in vitro binding assays of various CD3/CD20 TDBs having different combinations of UCHT1 series anti-CD3 arms and 2H7 series anti-CD20 arms. Bjab B tumor cell line binding (CD20 binding), left. Jurkat cell binding (CD3 binding), right.

FIG. 17 is a set of tables summarizing the monovalent (top) and (bivalent) binding affinities as Kd values for various CD3/CD20 TDBs having different combinations of UCHT1 series anti-CD3 arms and 2H7 series anti-CD20 arms.

Figure 18:
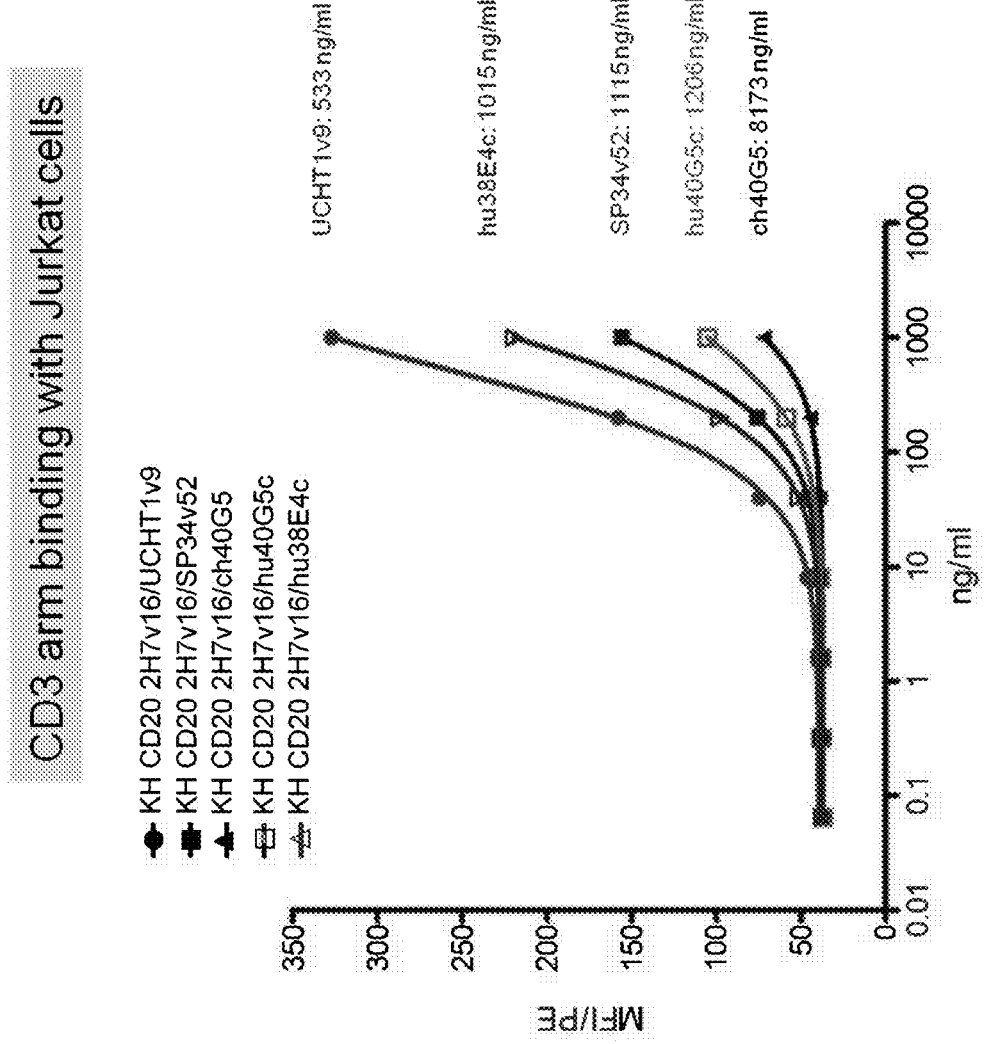

FIG. 18 is a graph showing the results of in vitro Jurkat cell binding (CD3 binding) FACS assays of various CD3/CD20 TDBs having different combinations of anti-CD3 arms with the anti-CD20 arm of 2H7v16.

Figure 19:
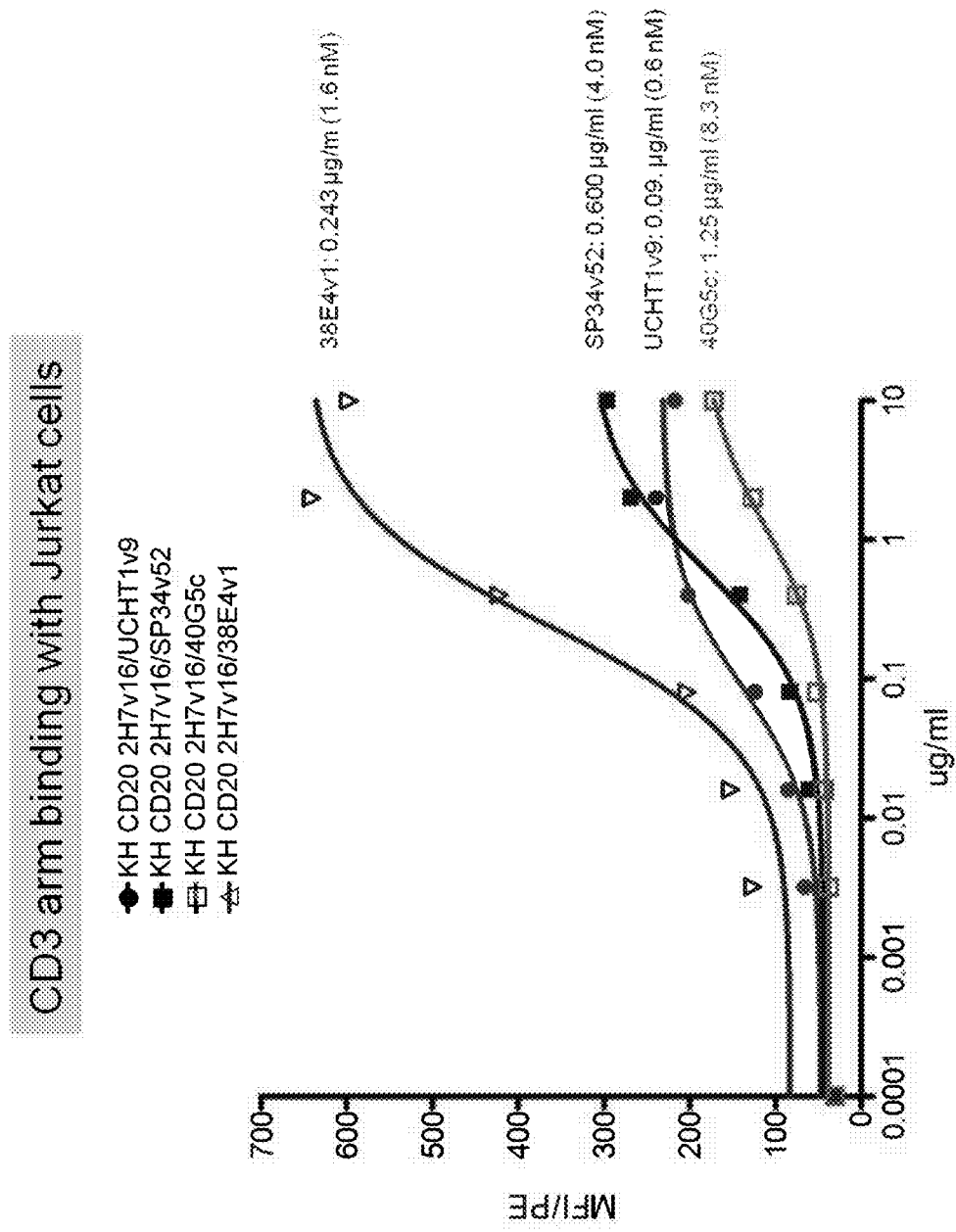

FIG. 19 is a graph showing the results of in vitro Jurkat cell binding (CD3 binding) FACS assays of various CD3/CD20 TDBs having different combinations of anti-CD3 arms with the anti-CD20 arm of 2H7v16.

Figure 20:
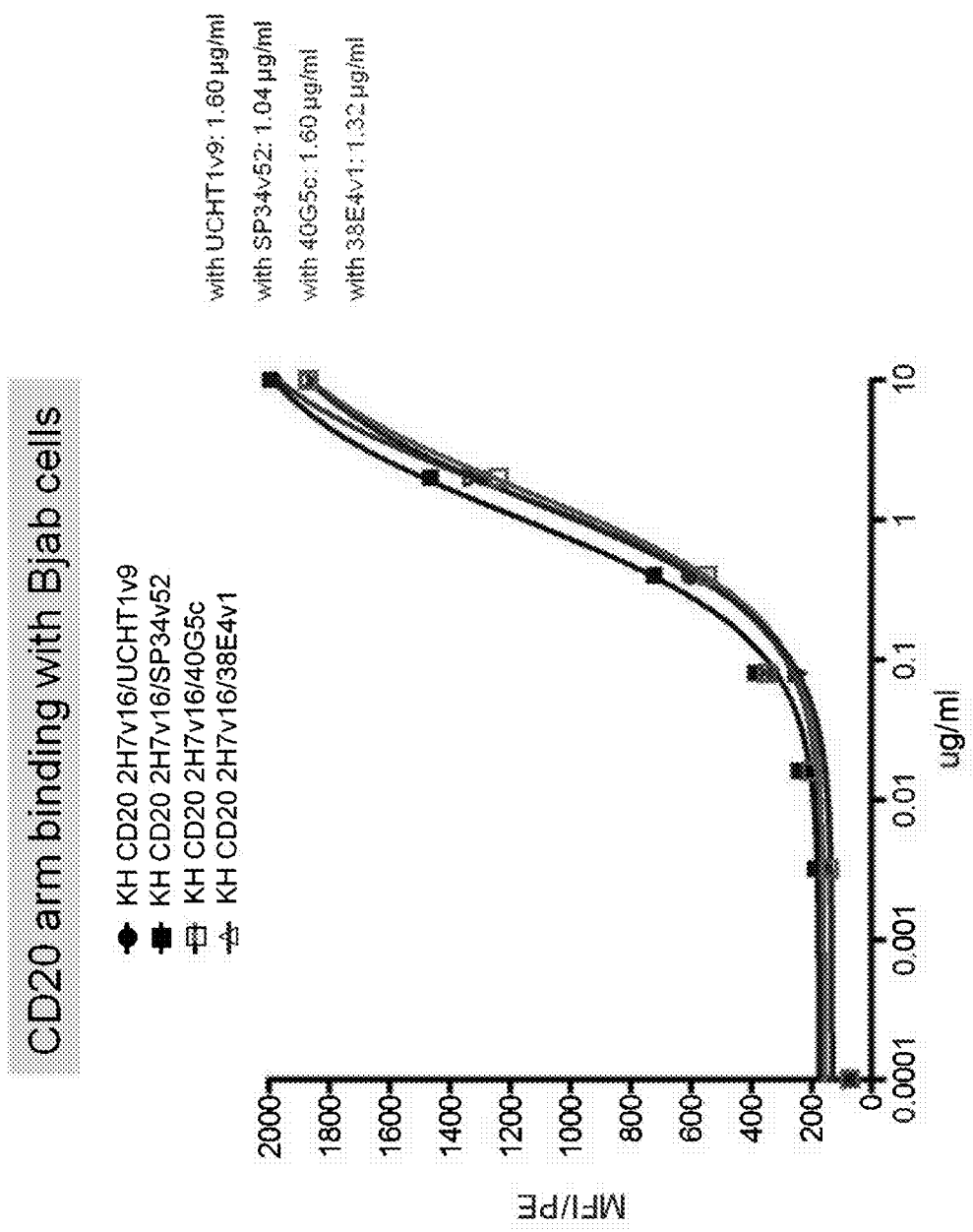

FIG. 20 is a graph showing the results of in vitro Bjab cell binding (CD20 binding) FACS assays of various CD3/CD20 TDBs having different combinations of anti-CD3 arms with the anti-CD20 arm of 2H7v16.

Figures 21A, 21B, 21C:
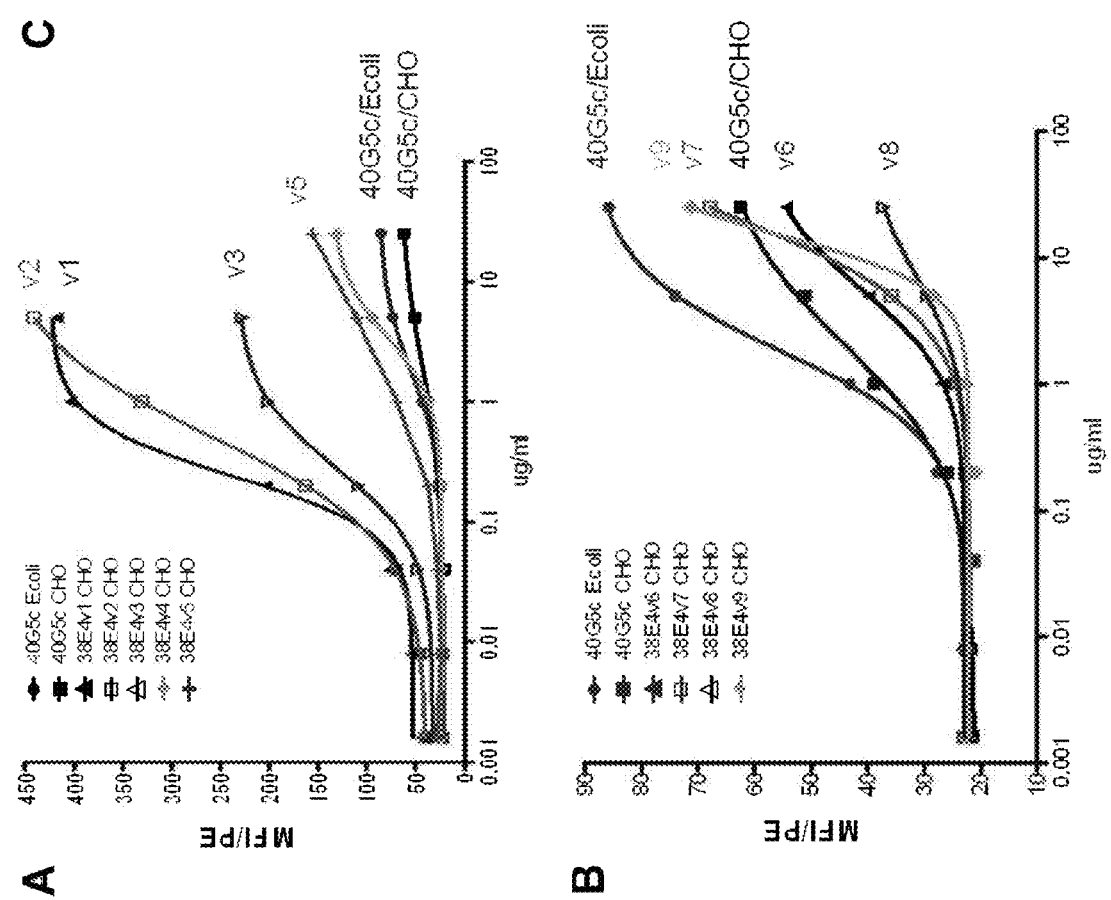

FIGS. 21A and 21B are graphs showing the results of in vitro Jurkat cell binding (CD3 binding) FACS assays of various CD3/CD20 TDBs having different combinations of anti-CD3 arms with the anti-CD20 arm of 2H7v16.

FIG. 21C is a table summarizing the EC50 (µg/ml) for each CD3/CD20 TDB tested in FIGS. 21A and 21B.

Figures 22A, 22B:
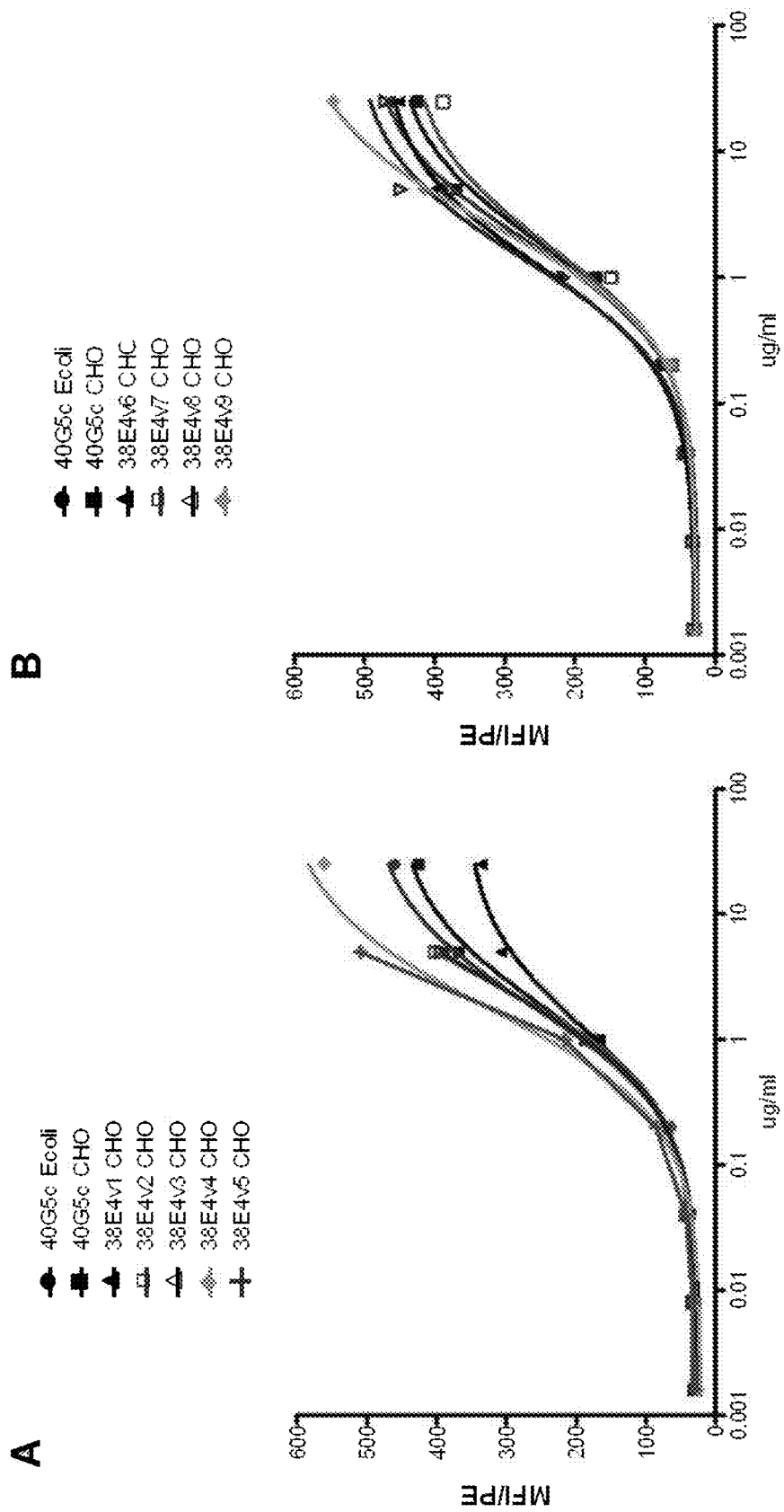

FIGS. 22A and 22B are graphs showing the results of in vitro Bjab cell binding (CD20 binding) FACS assays of various CD3/CD20 TDBs having different combinations of anti-CD3 arms with the anti-CD20 arm of 2H7v16.

Figure 23:
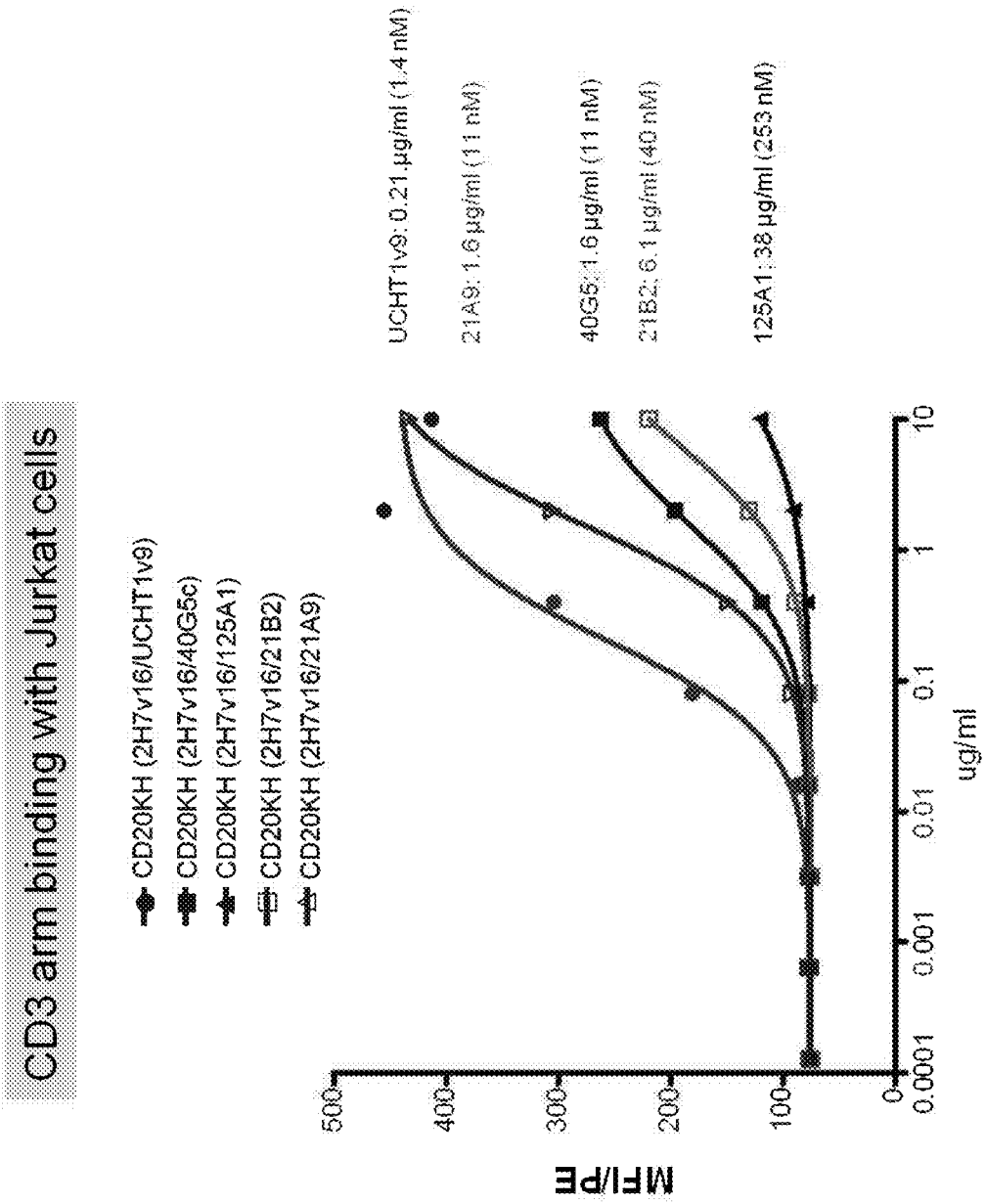

FIG. 23 is a graph showing the results of in vitro Jurkat cell binding (CD3 binding) FACS assays of various CD3/CD20 TDBs having different combinations of anti-CD3 arms with the anti-CD20 arm of 2H7v16.

FIG. 24 is a table summarizing the binding affinities for various CD3/CD20 TDBs and Fabs, as measured by Biacore analysis with human CD3εγ on chip and CD3/CD20 TDB or Fab in flow through.

Figure 25A:
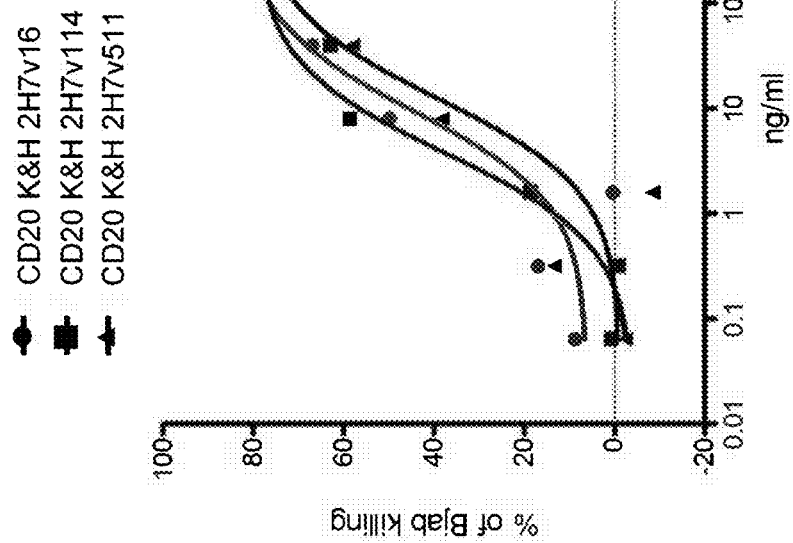

FIG. 25A is a graph showing the percentage of T cell activation, as measured by CD69 and CD25 surface expression, after 24 hours of incubation of specified CD3/CD20 TDB (2H7 series) with 20,000 Bjab cells and 5× purified hu CD8+ T cells.

Figure 25B:
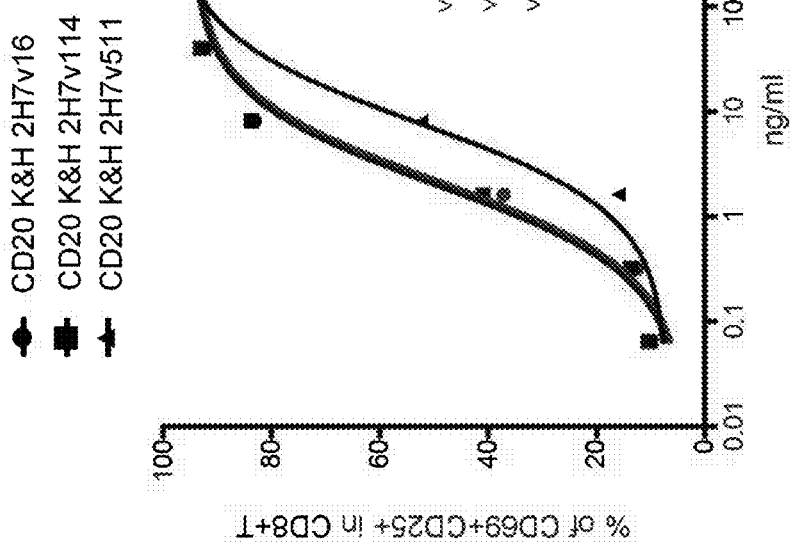

FIG. 25B is a graph showing the percentage of Bjab killing relative to a non-TDB treated control, after 24 hours of incubation of specified CD3/CD20 TDB (2H7 series) with 20,000 Bjab cells and 5× purified huCD8+ T cells, as measured by FACS analysis.

Figure 26A:
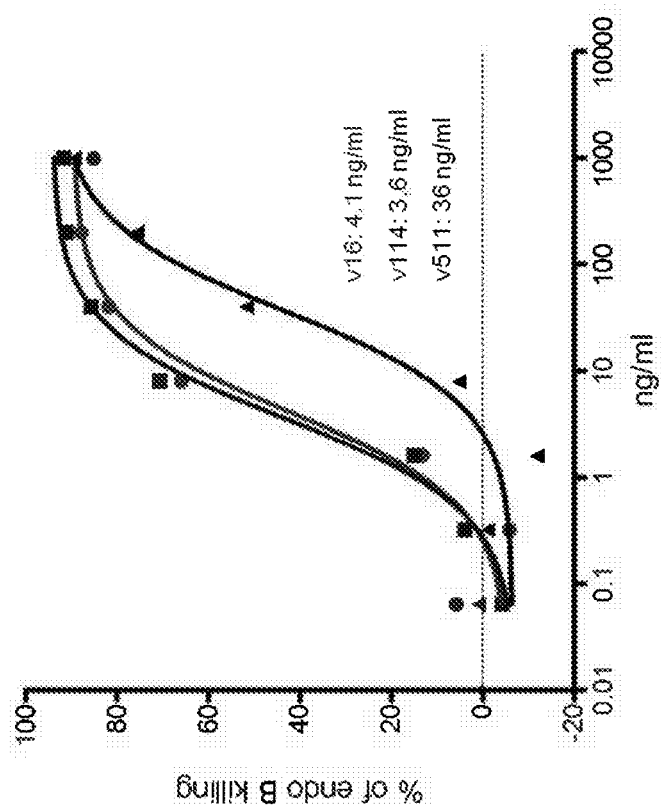

FIG. 26A is a graph showing the percentage of T cell activation, as measured by CD69 and CD25 surface expression, after 24 hours of incubation of specified CD3/CD20 TDB (2H7 series) with 200,000 human PBMCs per well.

Figure 26B:
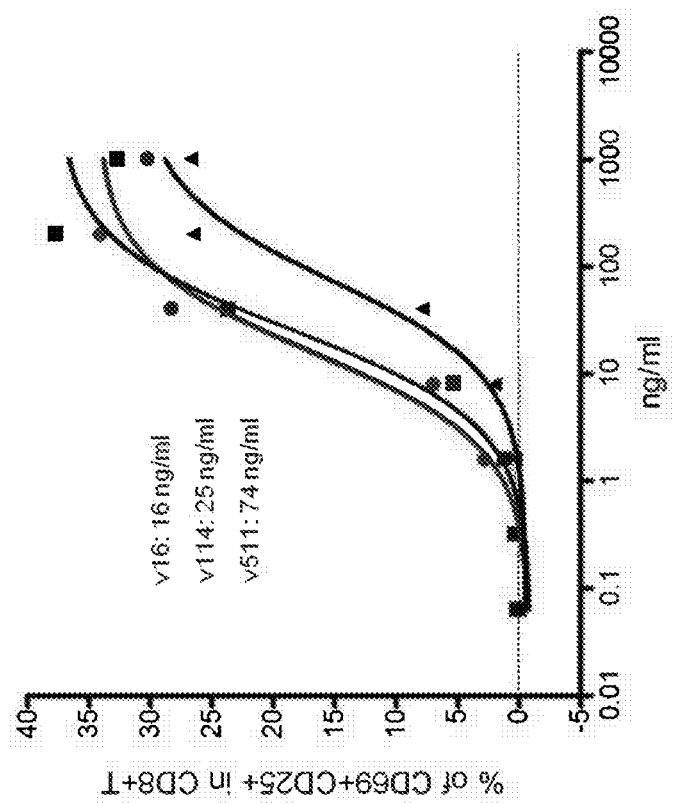

FIG. 26B is a graph showing the percentage of endogenous (endo) B cell killing relative to a non-TDB treated control, after 24 hours of incubation of specified CD3/CD20 TDB (2H7 series) with 200,000 human PBMCs per well, as measured by FACS analysis.

Figure 27A:
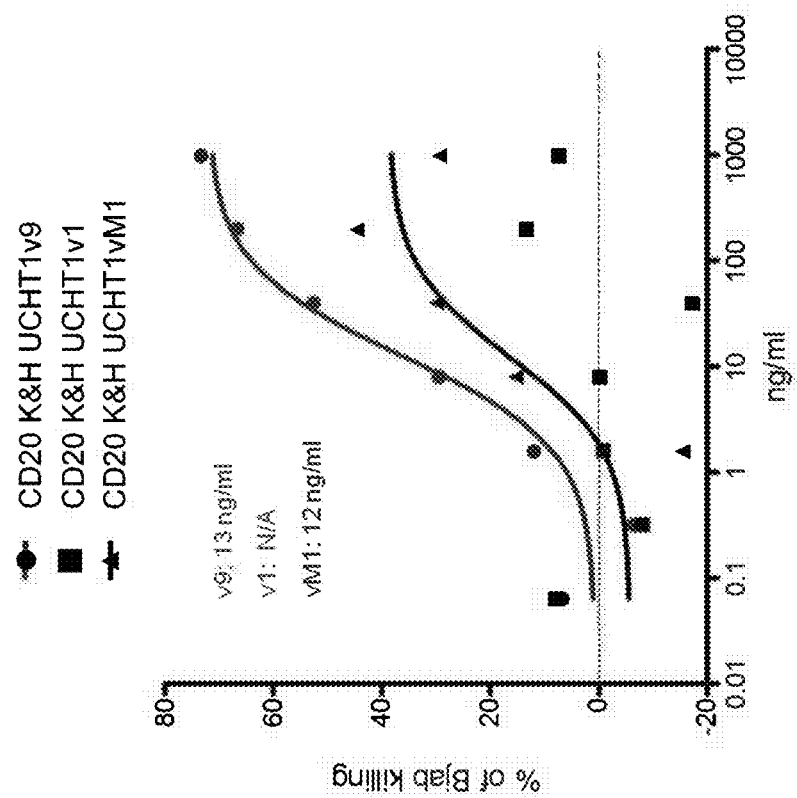

FIG. 27A is a graph showing the percentage of T cell activation, as measured by CD69 and CD25 surface expression, after 24 hours of incubation of specified CD3/CD20 TDB (UCHT1 series) with 20,000 Bjab cells and 5× purified hu CD8+ T cells.

Figure 27B:
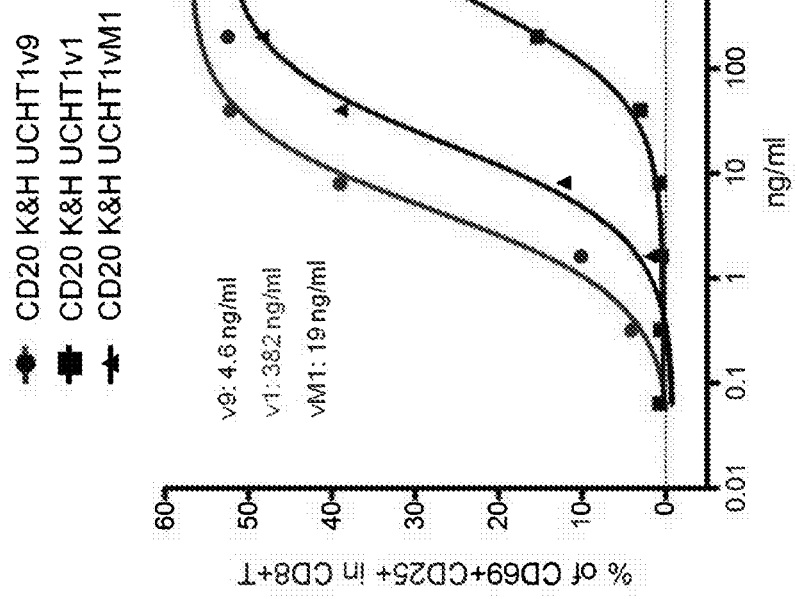

FIG. 27B is a graph showing the percentage of Bjab killing relative to a non-TDB treated control, after 24 hours of incubation of specified CD3/CD20 TDB (UCHT1 series) with 20,000 Bjab cells and 5× purified huCD8+ T cells, as measured by FACS analysis.

Figure 28A:
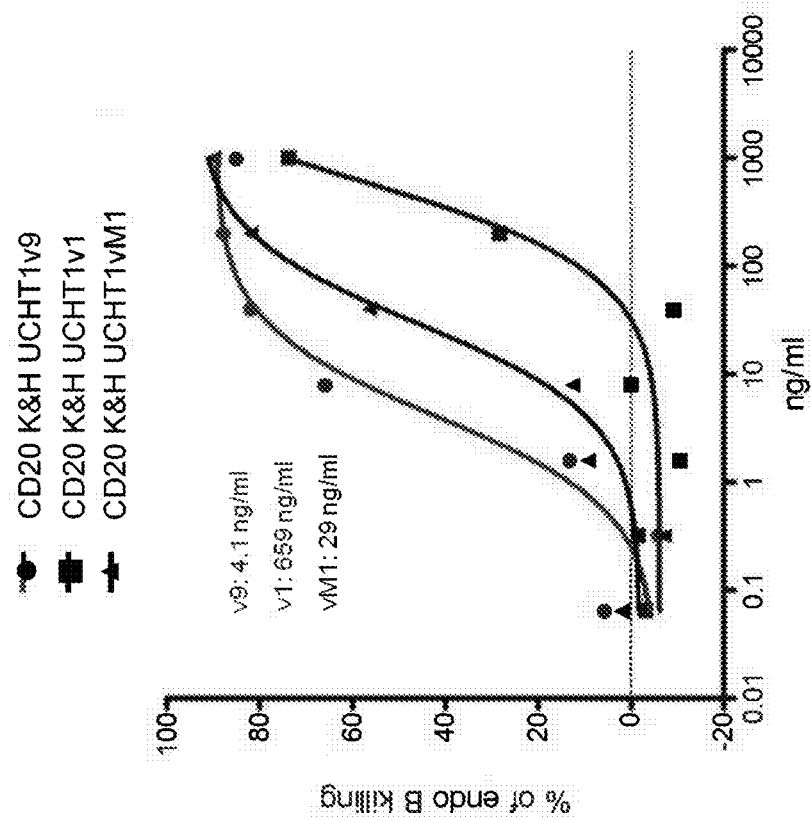

FIG. 28A is a graph showing the percentage of T cell activation, as measured by CD69 and CD25 surface expression, after 24 hours of incubation of specified CD3/CD20 TDB (UCHT1 series) with 200,000 human PBMCs per well.

Figure 28B:
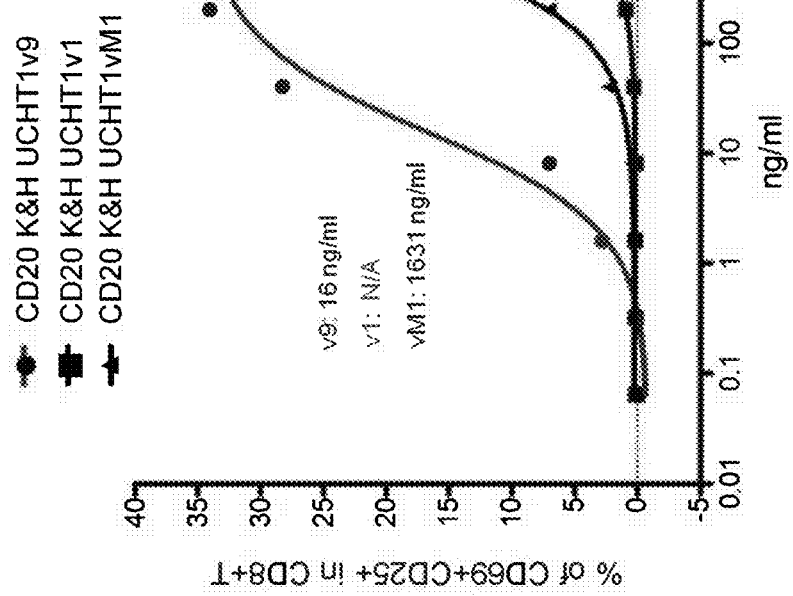

FIG. 28B is a graph showing the percentage of endo B cell killing relative to a non-TDB treated control, after 24 hours of incubation of specified CD3/CD20 TDB (UCHT1 series) with 200,000 human PBMCs per well, as measured by FACS analysis.

Figure 29A:
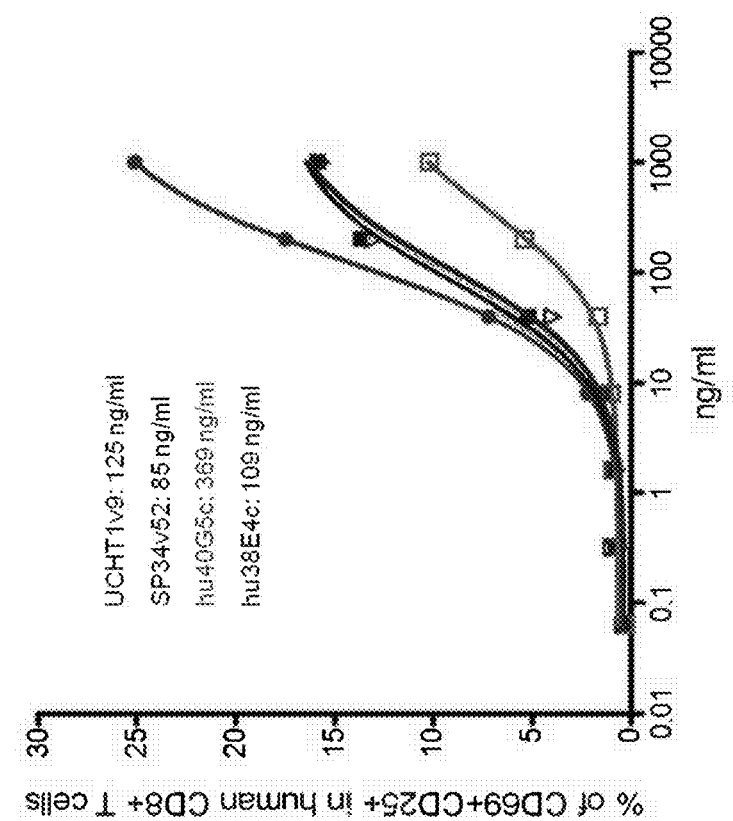

FIG. 29A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #3) per well, as measured by FACS analysis.

Figure 29B:
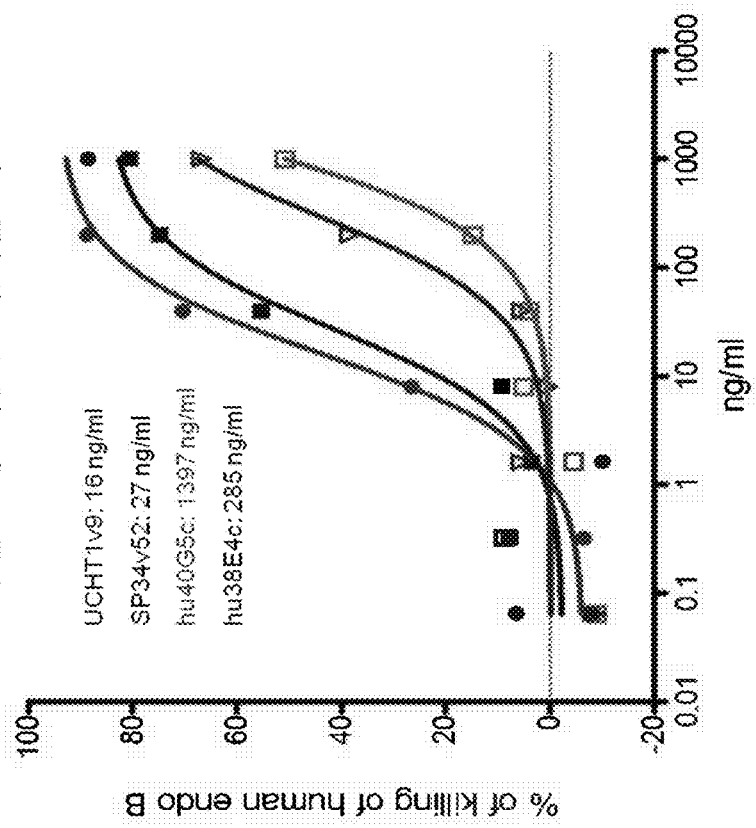

FIG. 29B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 human PBMCs (isolated from Donor #3) per well, as measured by FACS analysis.

Figure 30A:
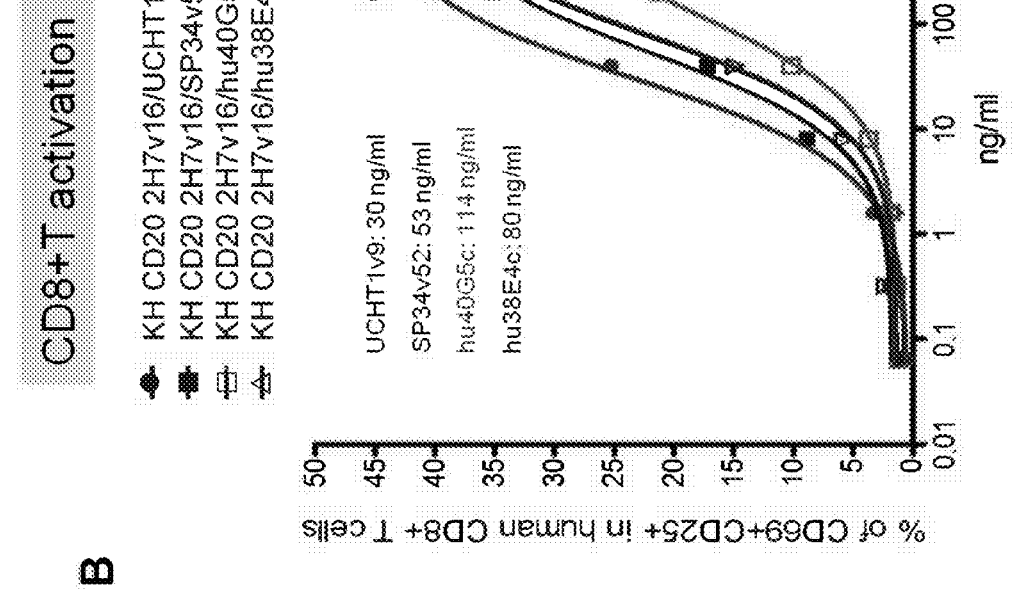

FIG. 30A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #4) per well, as measured by FACS analysis.

Figure 30B:
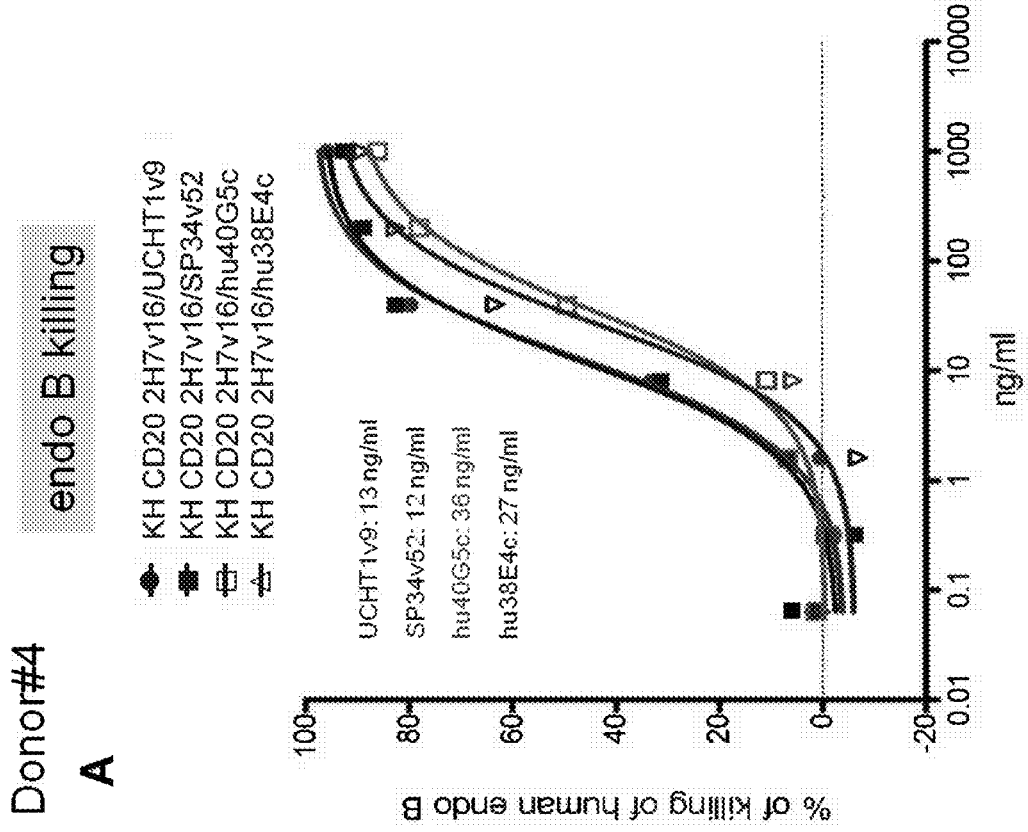

FIG. 30B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 human PBMCs (isolated from Donor #4) per well, as measured by FACS analysis.

Figures 31A, 31B:
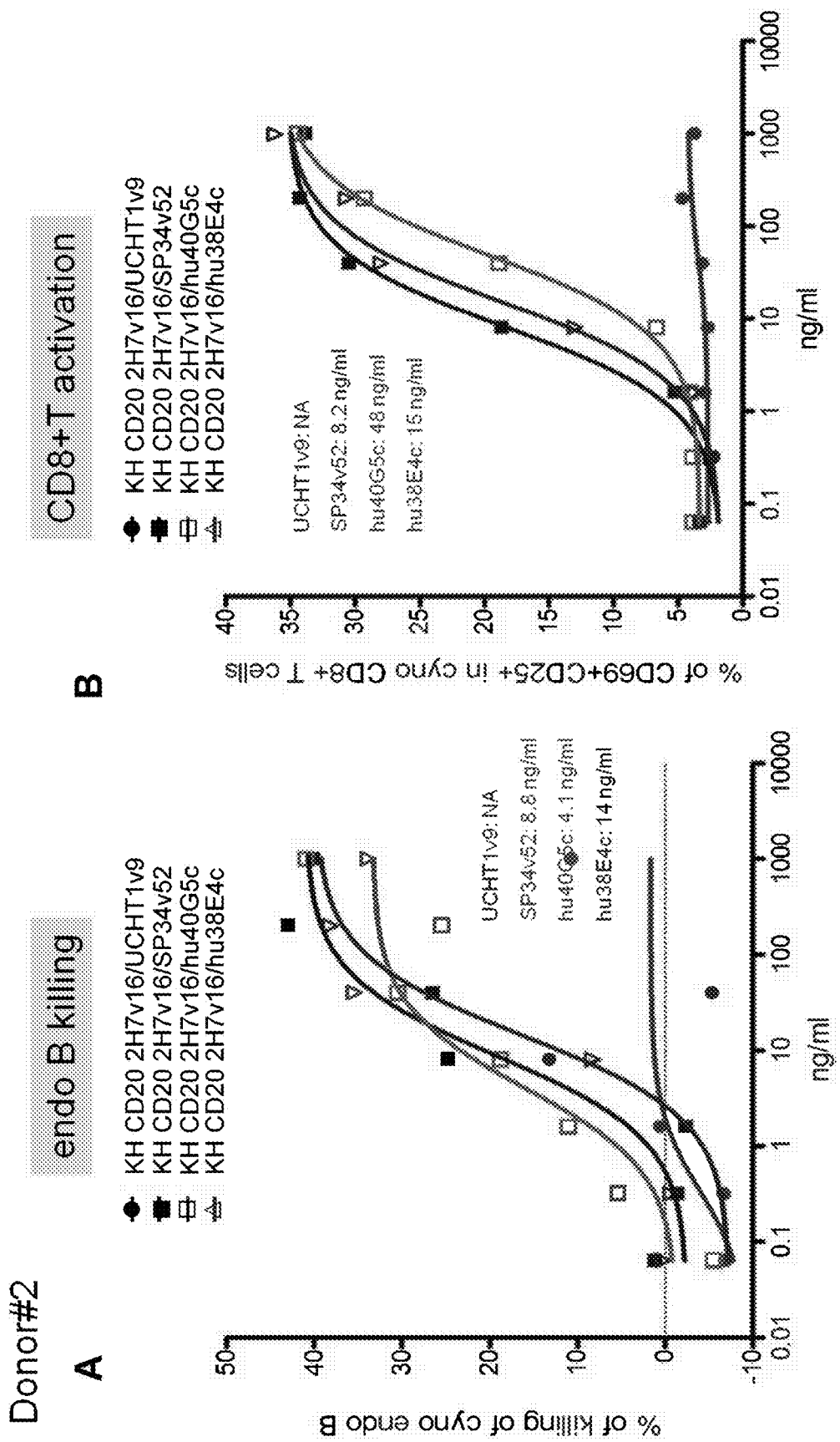

FIG. 31A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 cyno PBMCs (isolated from Donor #2) per well, as measured by FACS analysis.

FIG. 31B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 cyno PBMCs (isolated from Donor #2) per well, as measured by FACS analysis.

Figures 32A, 32B:
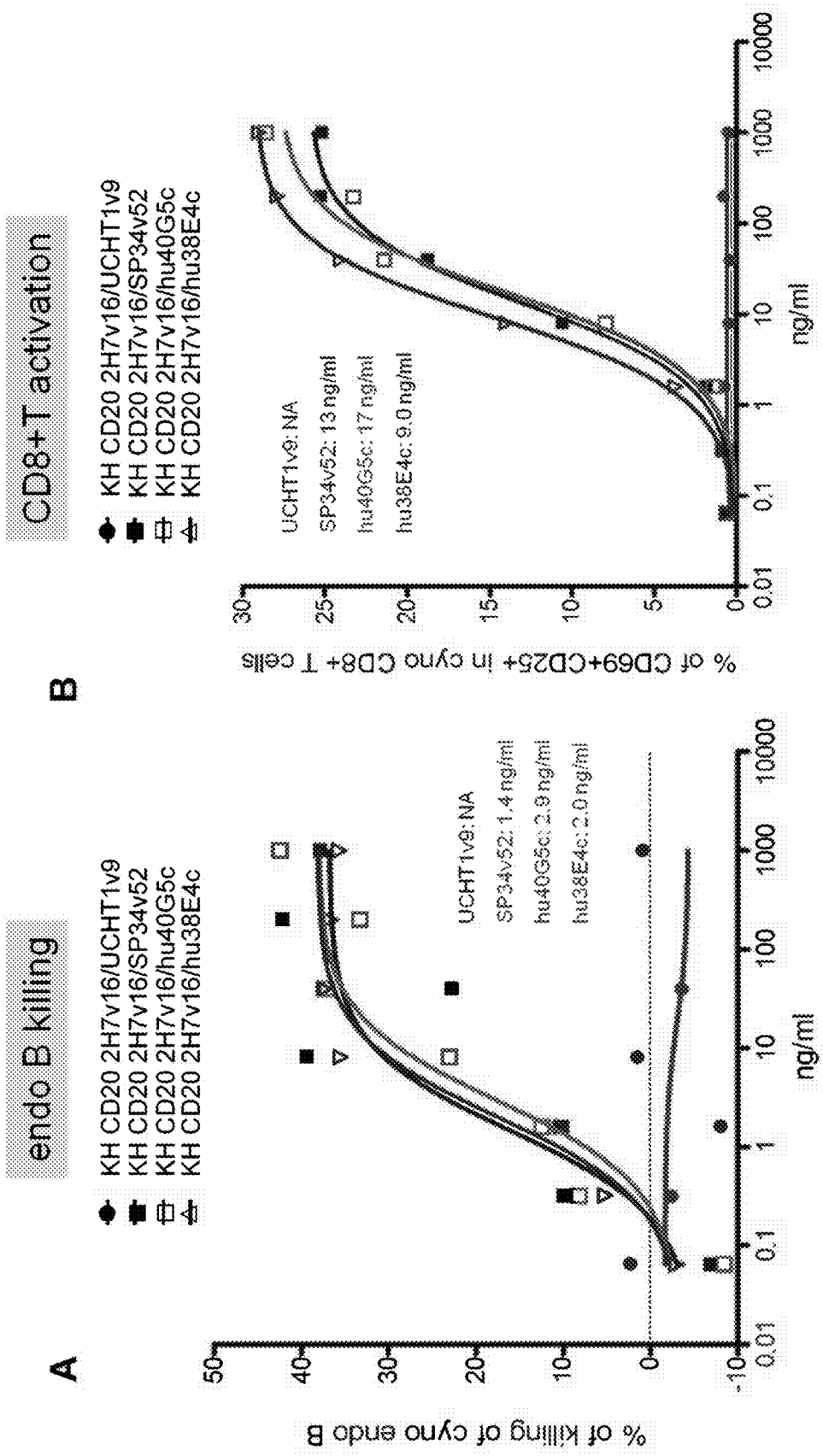

FIG. 32A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 cyno PBMCs (isolated from Donor #3) per well, as measured by FACS analysis.

FIG. 32B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 cyno PBMCs (isolated from Donor #3) per well, as measured by FACS analysis.

Figures 33A, 33B:
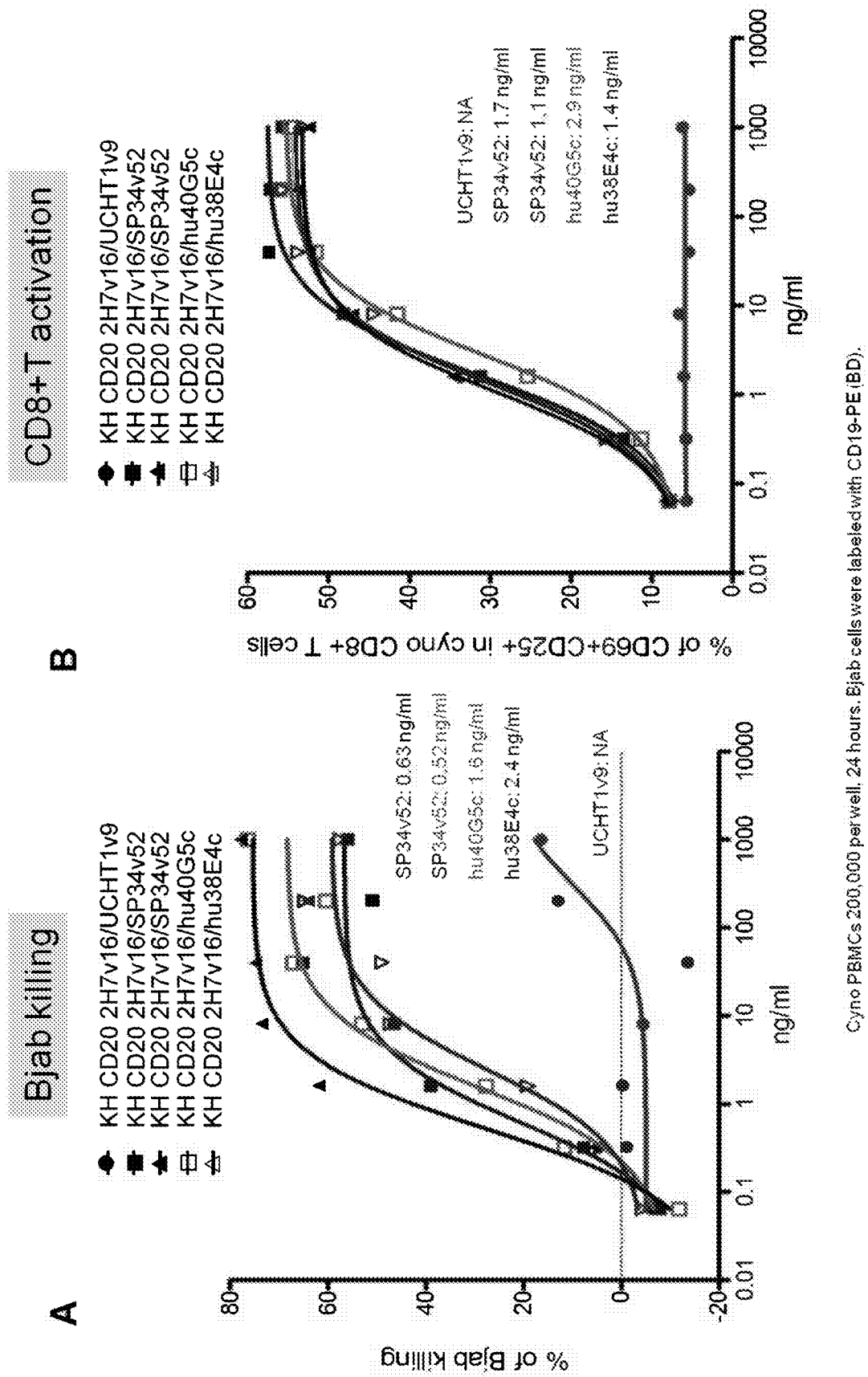

FIG. 33A is a graph showing the percentage of Bjab cell killing relative to a non-TDB treated control, after 24 hours of incubation of various CD3/CD20 TDBs having different combinations of anti-CD3 arms with the anti-CD20 arm of 2H7v16, with 200,000 cyno PBMCs per well, as measured by FACS analysis.

FIG. 33B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 cyno PBMCs per well, as measured by FACS analysis.

Figures 34A, 34B:
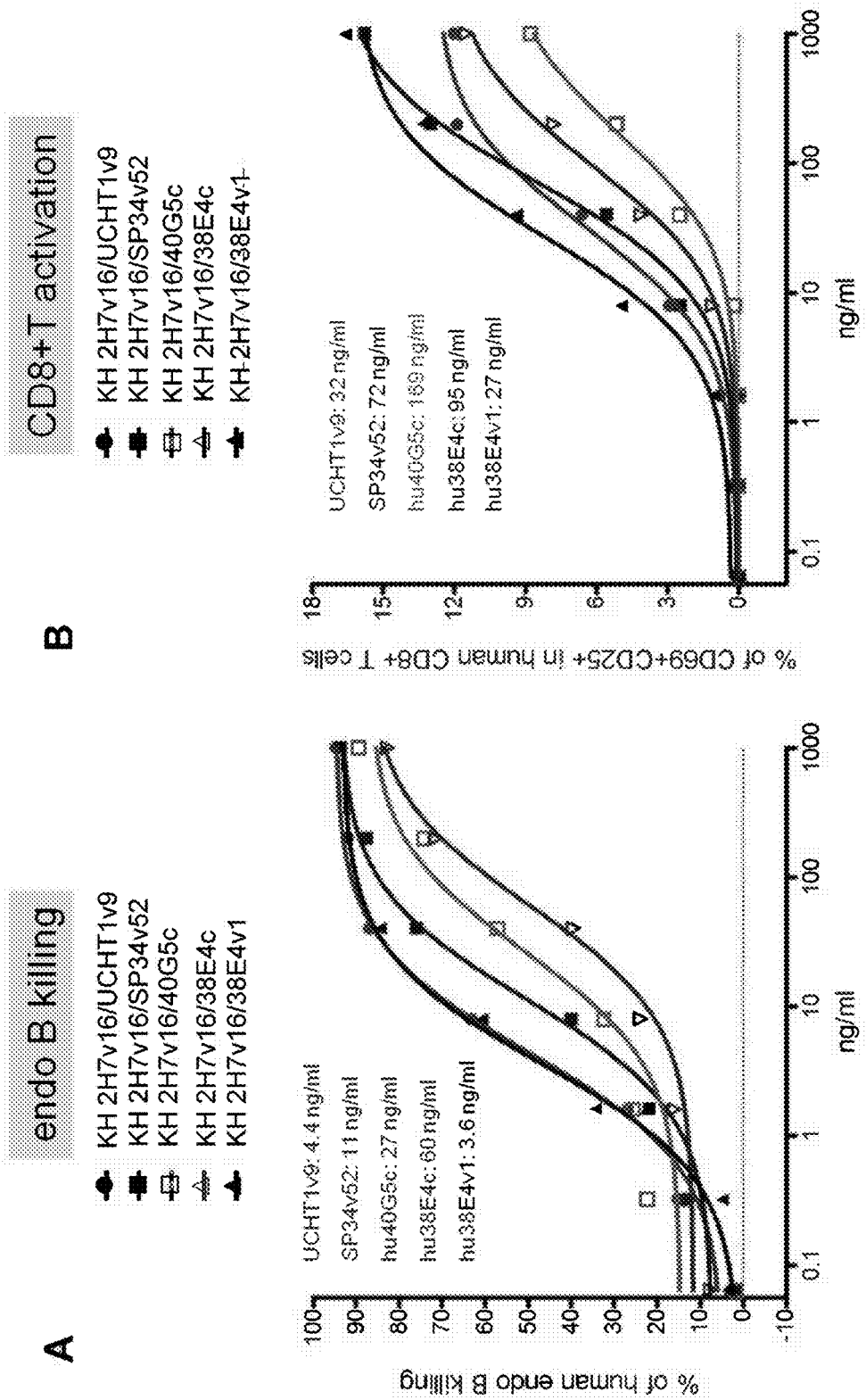

FIG. 34A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #2) per well, as measured by FACS analysis.

FIG. 34B is a graph showing the percentage of T cell activation, as measured by CD69 and CD25 surface expression, after 24 hours of incubation of various CD3/CD20

TDBs having different combinations of anti-CD3 arms with the anti-CD20 arm of 2H7v16, with 200,000 human PBMCs (isolated from Donor #2) per well, as measured by FACS analysis.

Figure 35A:
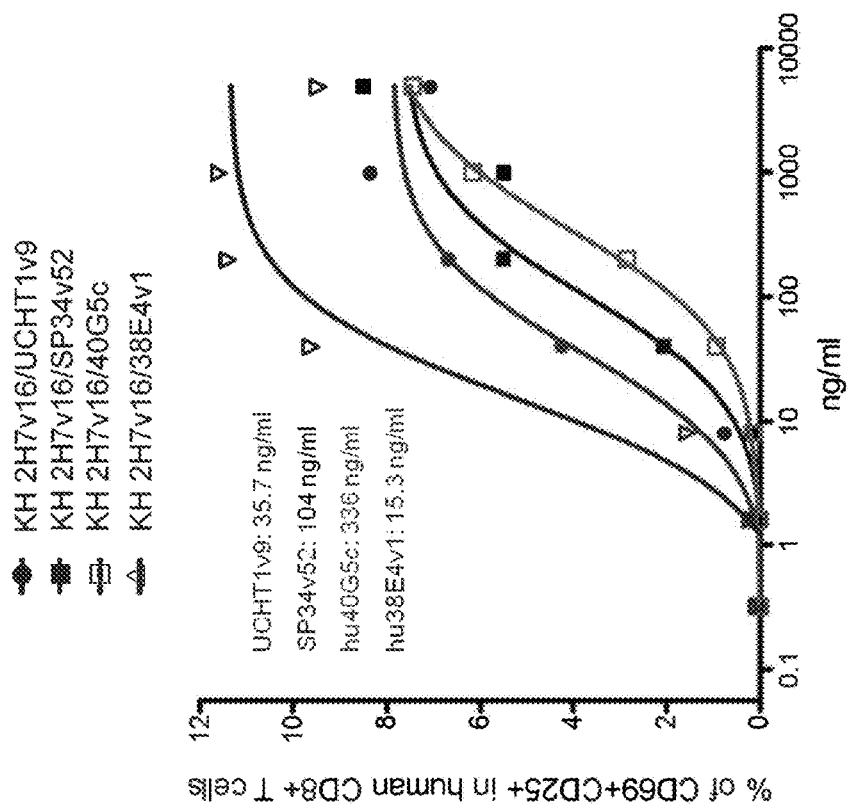

FIG. 35A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #3) per well, as measured by FACS analysis.

Figure 35B:
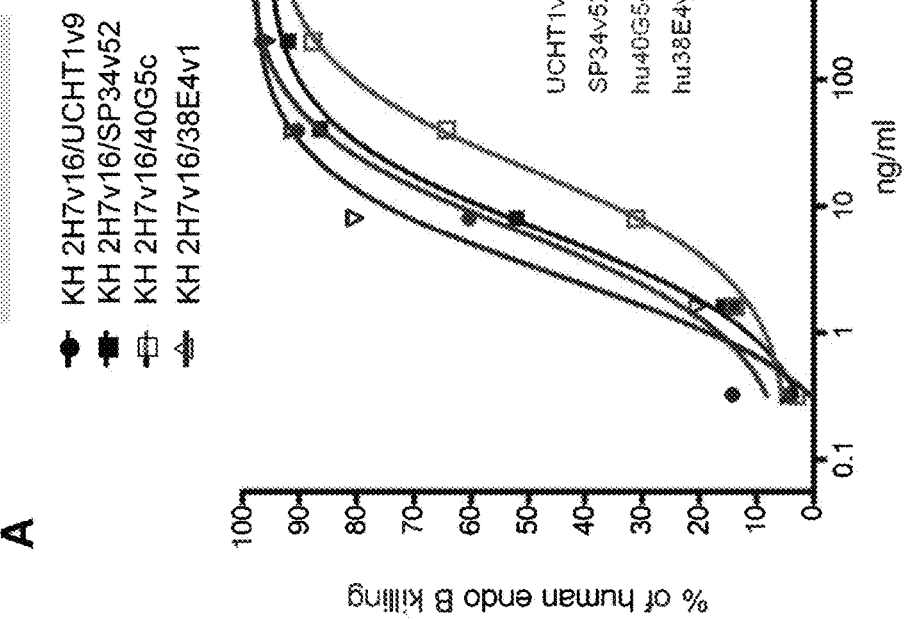

FIG. 35B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 human PBMCs (isolated from Donor #3) per well, as measured by FACS analysis.

Figure 36A:
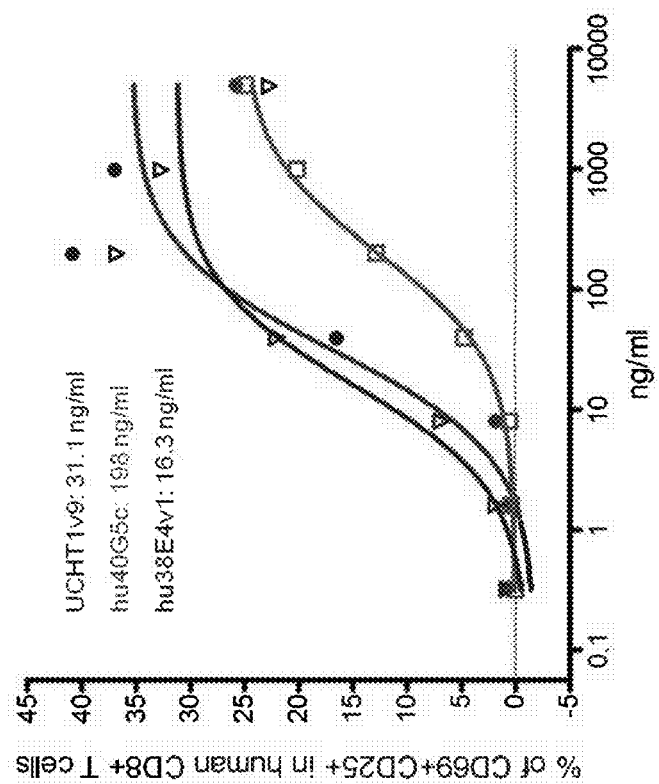

FIG. 36A is a graph showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #4) per well, as measured by FACS analysis.

Figure 36B:
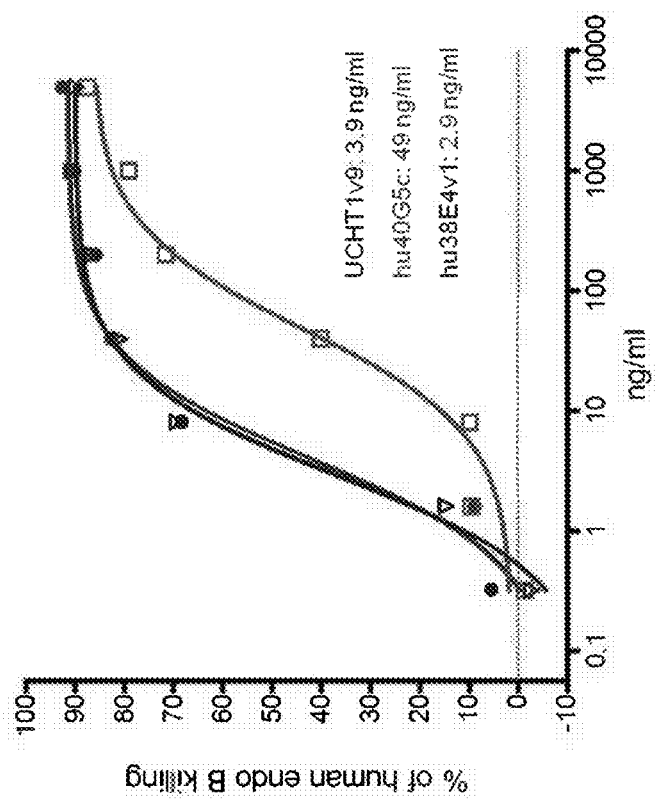

FIG. 36B is a graph showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 human PBMCs (isolated from Donor #4) per well, as measured by FACS analysis.

Figures 37A, 37B, 37C:
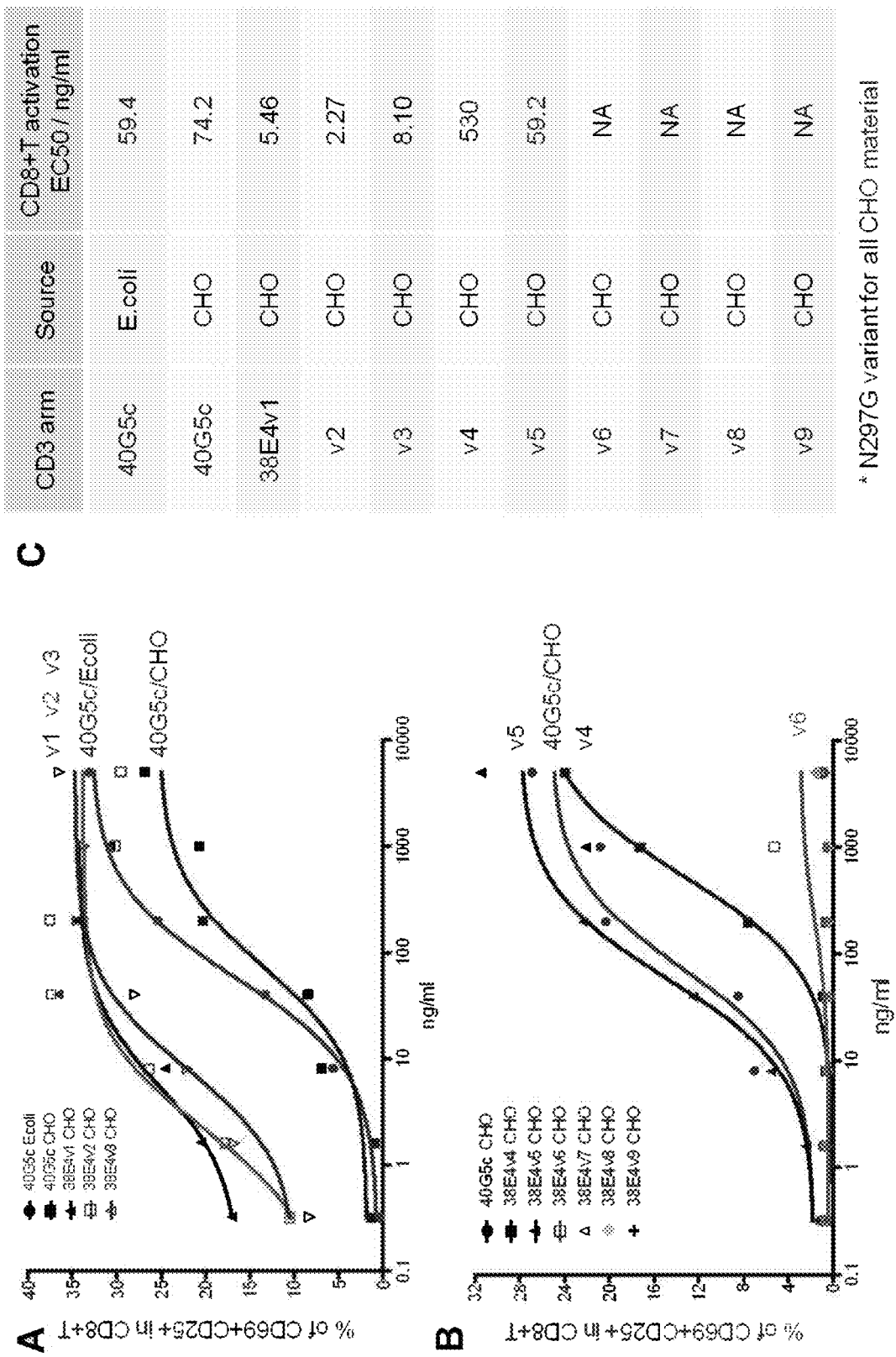

FIGS. 37A and 37B are graphs showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 human PBMCs (isolated from Donor #1) per well, as measured by FACS analysis.

FIG. 37C is a table summarizing the CD8+ T cell activation EC50 (ng/ml) for each CD3/CD20 TDB tested in FIGS. 37A and 37B.

FIGS. 38A and 38B are graphs showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #1) per well, as measured by FACS analysis.

FIG. 38C is a table summarizing the endo B cell killing EC50 (ng/ml) for each CD3/CD20 TDB tested in FIGS. 38A and 38B.

Figures 39A, 39B, 39C:
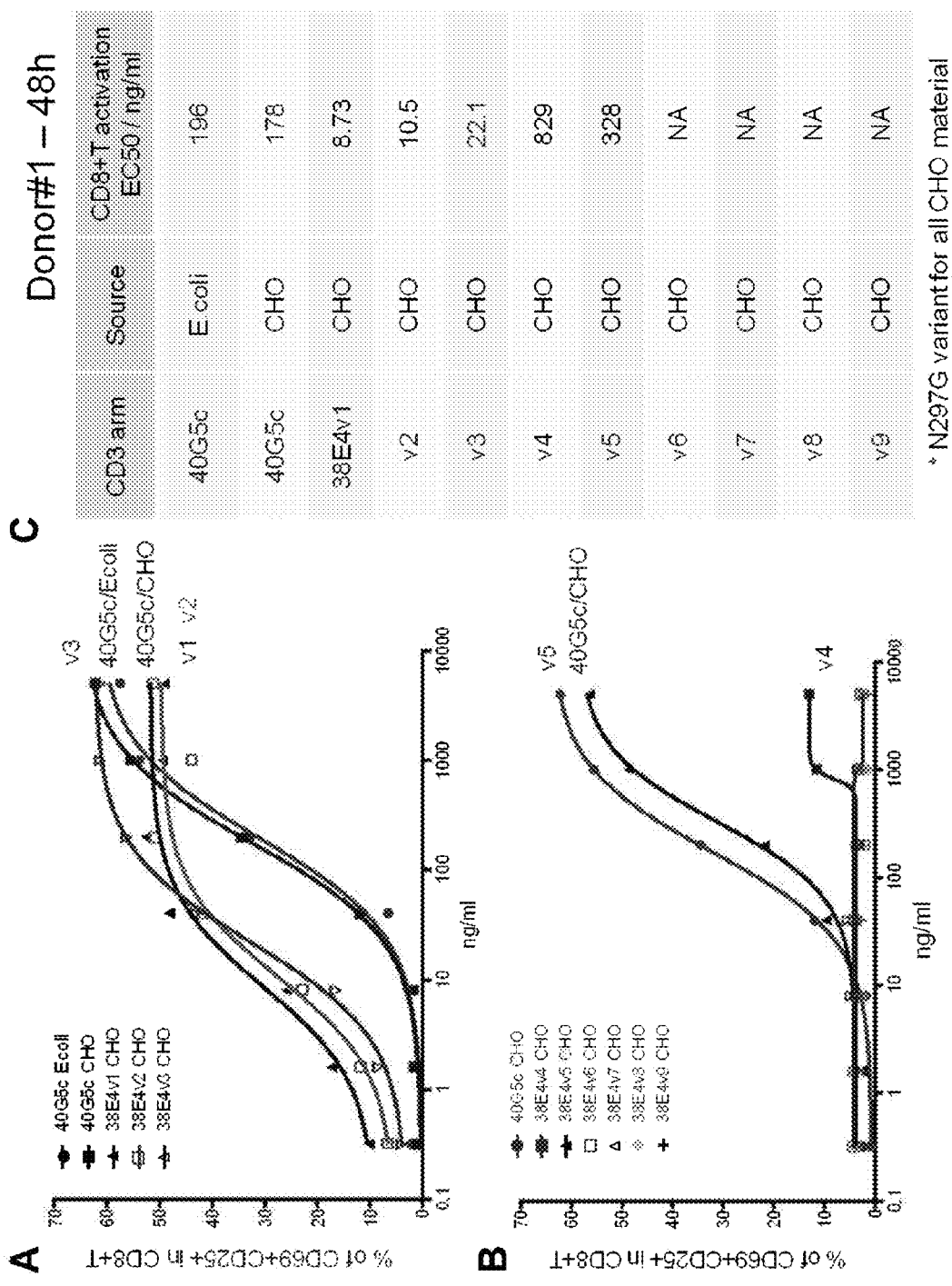

FIGS. 39A and 39B are graphs showing the percentage of T cell activation, as measured by CD69 and CD25 surface expression, after 48 hours of incubation of various CD3/CD20 TDBs having different combinations of anti-CD3 arms with the anti-CD20 arm of 2H7v16, with 200,000 human PBMCs (isolated from Donor #1) per well, as measured by FACS analysis.

FIG. 39C is a table summarizing the CD8+ T cell activation EC50 (ng/ml) for each CD3/CD20 TDB tested in FIGS. 39A and 39B.

Figures 40A, 40B, 40C:
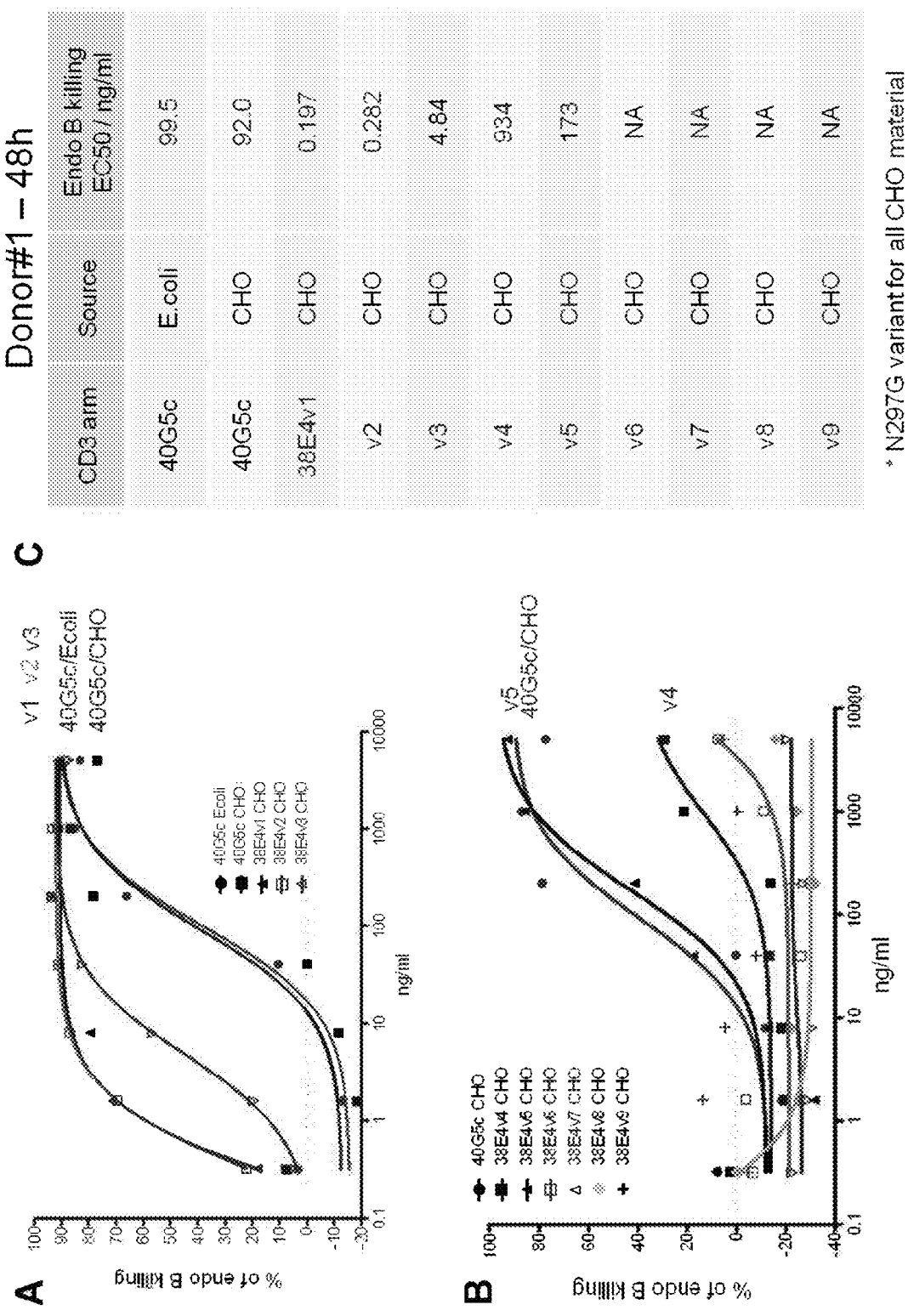

FIGS. 40A and 40B are graphs showing the percentage of endo B cell killing relative to a non-TDB treated control, after 48 hours of incubation of various CD3/CD20 TDBs having different combinations of anti-CD3 arms with the anti-CD20 arm of 2H7v16, with 200,000 human PBMCs (isolated from Donor #1) per well, as measured by FACS analysis.

FIG. 40C is a table summarizing the endo B cell killing EC50 (ng/ml) for each CD3/CD20 TDB tested in FIGS. 40A and 40B.

Figures 41A, 41B, 41C:
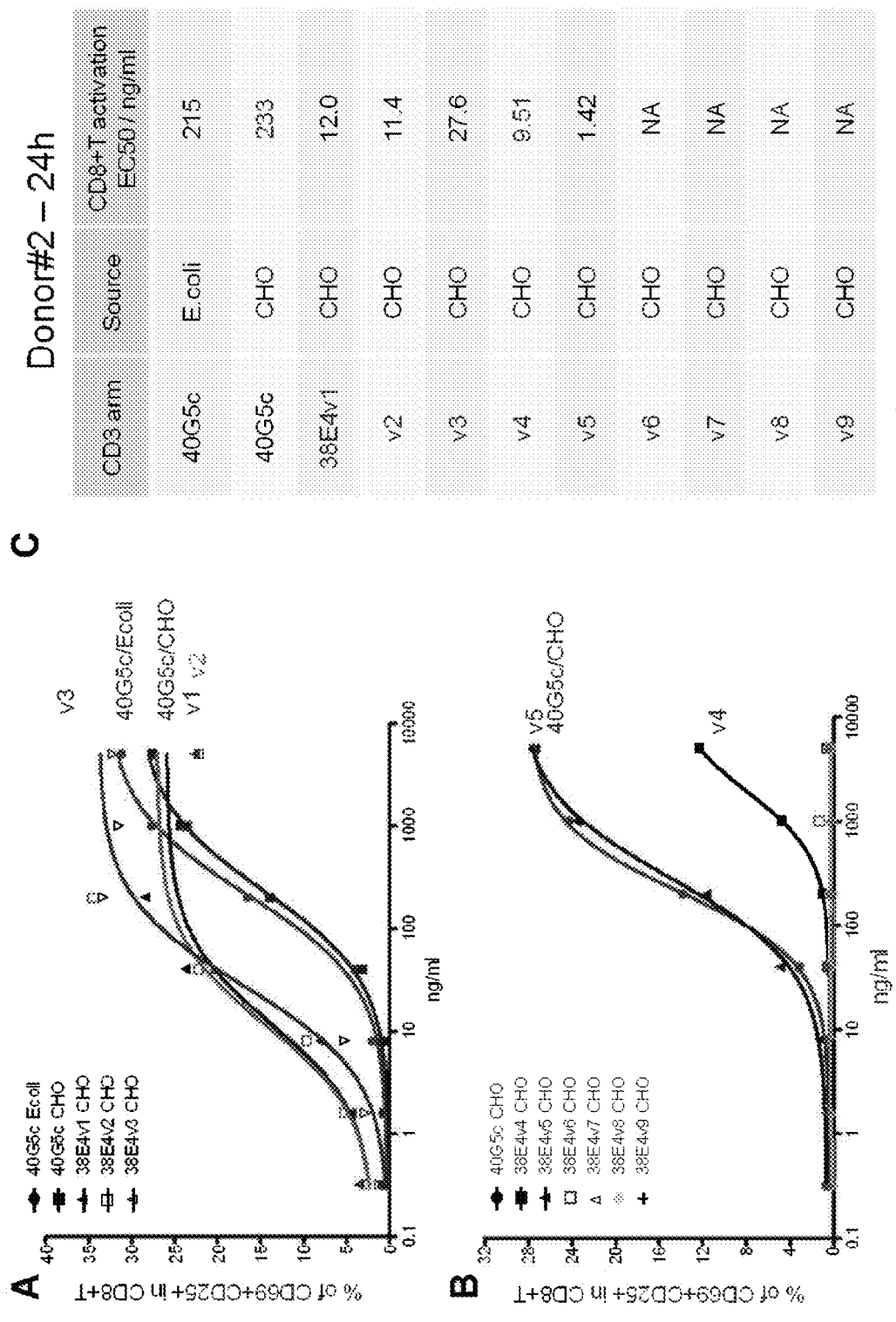

FIGS. 41A and 41B are graphs showing the percentage of T cell activation, as measured by CD69 and CD25 surface expression, after 24 hours of incubation of various CD3/CD20 TDBs having different combinations of anti-CD3 arms with the anti-CD20 arm of 2H7v16, with 200,000 human PBMCs (isolated from Donor #2) per well, as measured by FACS analysis.

FIG. 41C is a table summarizing the CD8+ T cell activation EC50 (ng/ml) for each CD3/CD20 TDB tested in FIGS. 41A and 41B.

Figures 42A, 42B, 42C:
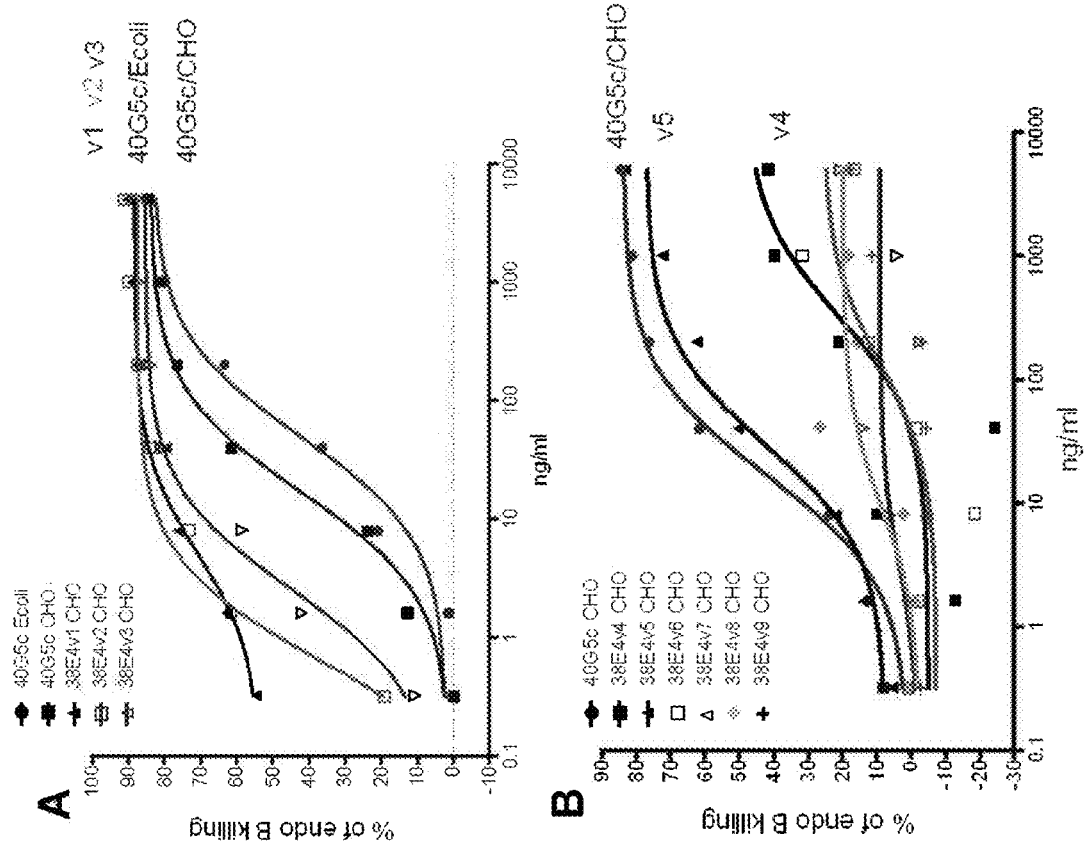

FIGS. 42A and 42B are graphs showing the percentage of endo B cell killing relative to a non-TDB treated control, after 24 hours of incubation of various CD3/CD20 TDBs having different combinations of anti-CD3 arms with the anti-CD20 arm of 2H7v16, with 200,000 human PBMCs (isolated from Donor #2) per well, as measured by FACS analysis.

FIG. 42C is a table summarizing the endo B cell killing EC50 (ng/ml) for each CD3/CD20 TDB tested in FIGS. 42A and 42B.

Figures 43A, 43B, 43C:
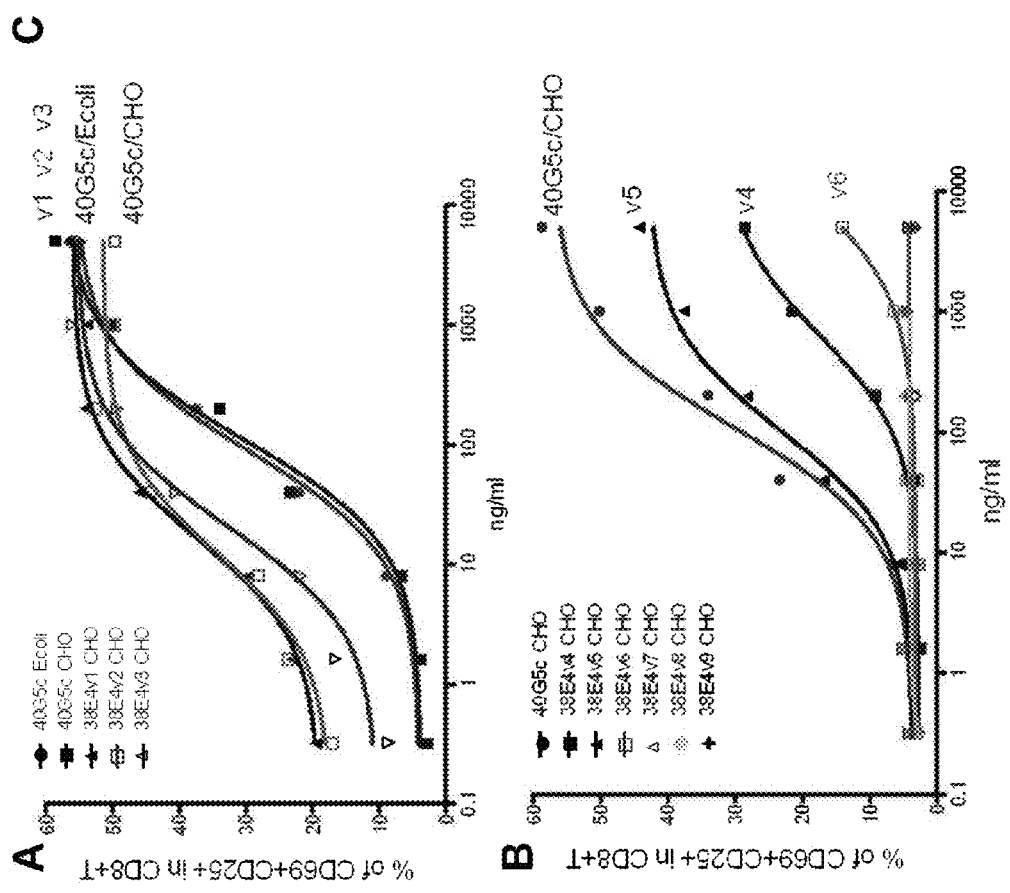

FIGS. 43A and 43B are graphs showing the percentage of T cell activation, as measured by CD69 and CD25 surface expression, after 48 hours of incubation of various CD3/CD20 TDBs having different combinations of anti-CD3 arms with the anti-CD20 arm of 2H7v16, with 200,000 human PBMCs (isolated from Donor #2) per well, as measured by FACS analysis.

FIG. 43C is a table summarizing the CD8+ T cell activation EC50 (ng/ml) for each CD3/CD20 TDB tested in FIGS. 43A and 43B.

Figures 44A, 44B, 44C:
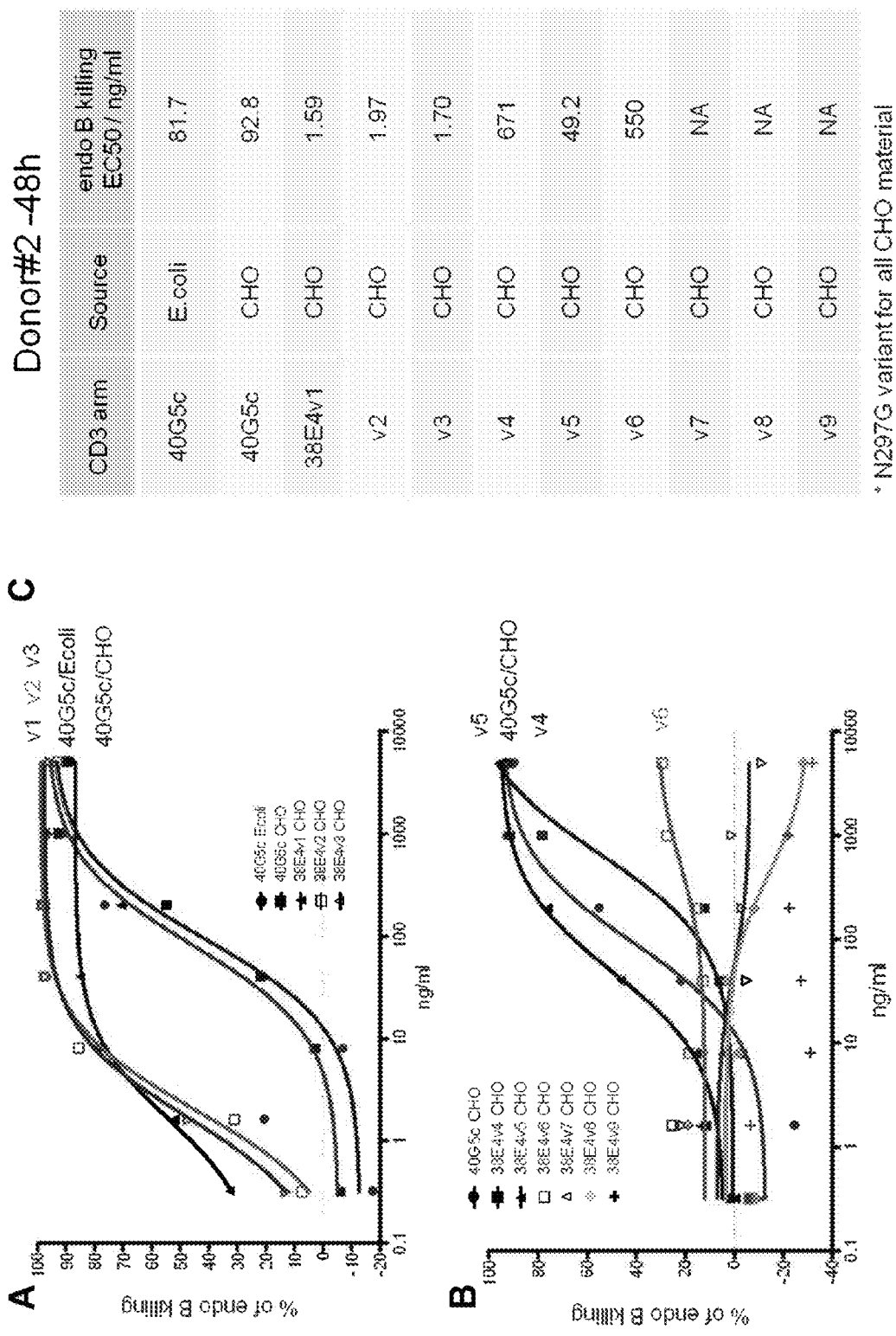

FIGS. 44A and 44B are graphs showing the percentage of endo B cell killing relative to a non-TDB treated control, after 48 hours of incubation of various CD3/CD20 TDBs having different combinations of anti-CD3 arms with the anti-CD20 arm of 2H7v16, with 200,000 human PBMCs (isolated from Donor #2) per well, as measured by FACS analysis.

FIG. 44C is a table summarizing the endo B cell killing EC50 (ng/ml) for each CD3/CD20 TDB tested in FIGS. 44A and 44B.

Figure 45A:
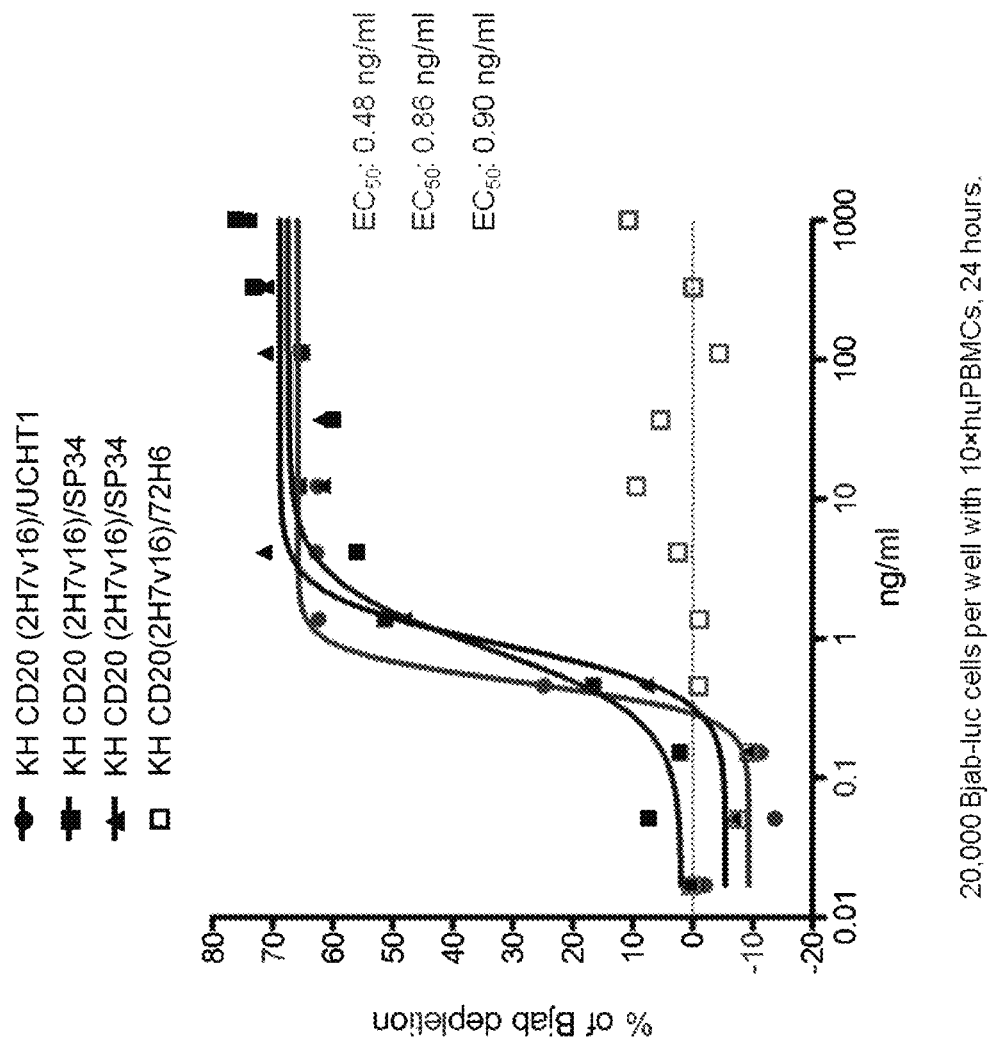

FIG. 45A is a graph showing that certain CD3/CD20 TDBs, such as one having an anti-CD20 arm of 2H7v16 and an anti-CD3 arm of 72H6, do not exhibit in vitro potency, as assessed by Bjab killing assays.

Figure 45B:
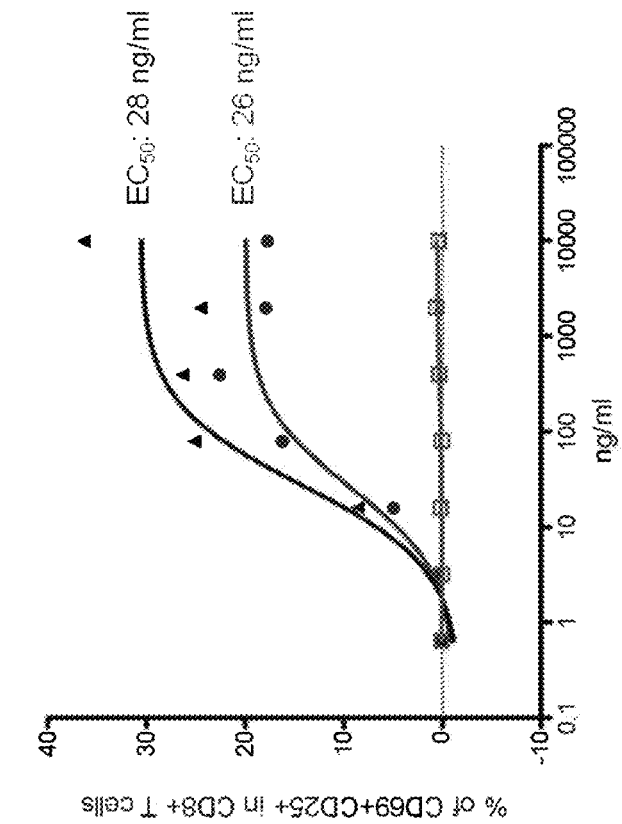
Figure 45C:
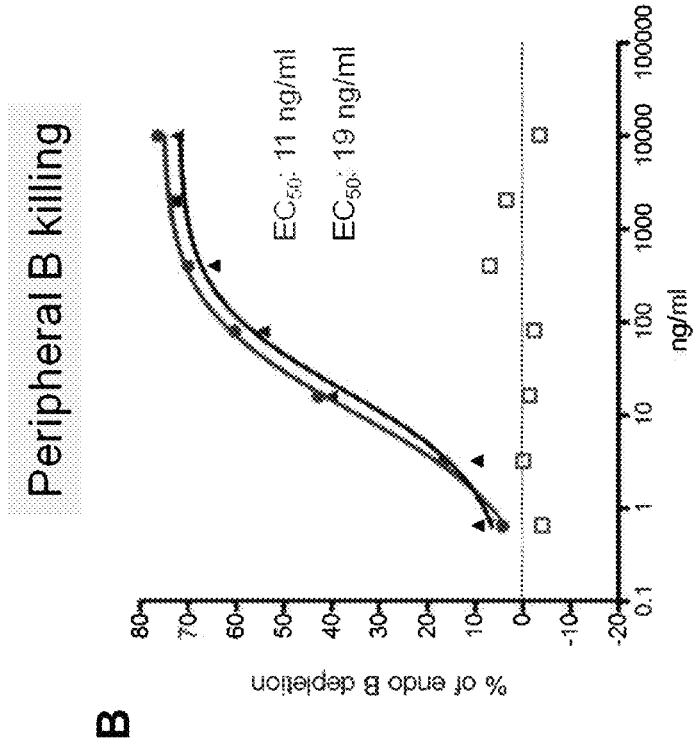

FIGS. 45B and 45C are graphs showing that certain CD3/CD20 TDBs, such as one having an anti-CD20 arm of 2H7v16 and an anti-CD3 arm of 72H6, do not exhibit in vitro potency, as assessed by endo B cell killing (B) and T cell activation (C) assays.

Figure 46A:
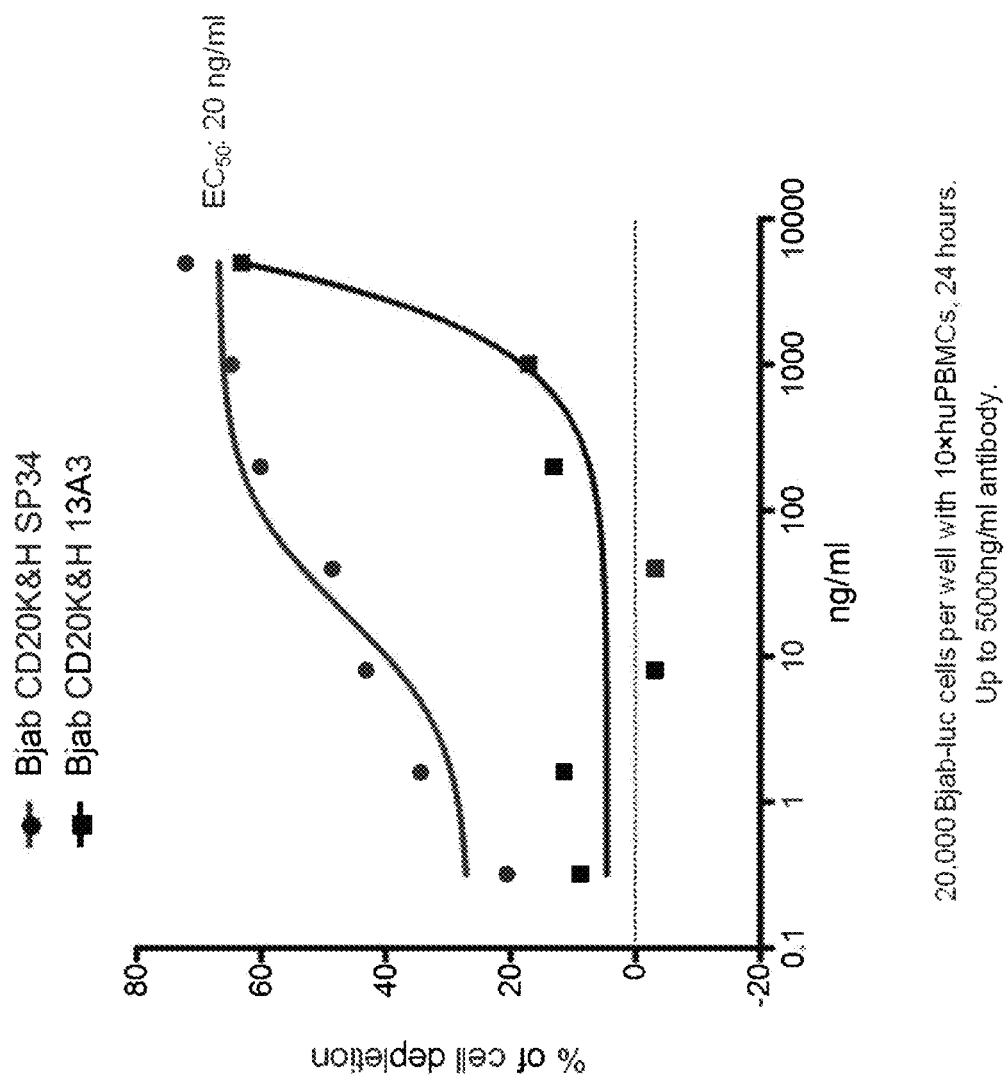

FIG. 46A is a graph showing that certain CD3/CD20 TDBs, such as one having an anti-CD20 arm of 2H7v16 and an anti-CD3 arm of 13A3, exhibit low in vitro potency, as assessed by Bjab killing assays.

Figure 46B:
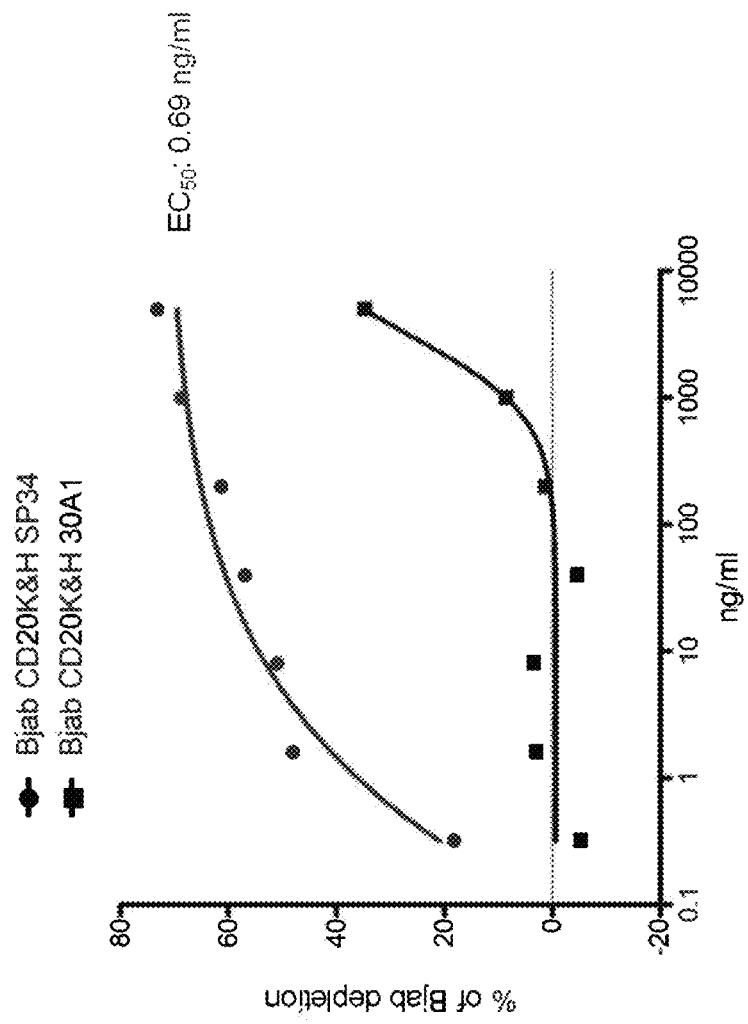

FIG. 46B is a graph showing that certain CD3/CD20 TDBs, such as one having an anti-CD20 arm of 2H7v16 and an anti-CD3 arm of 30A1, exhibit low in vitro potency, as assessed by Bjab killing assays.

Figure 46C:
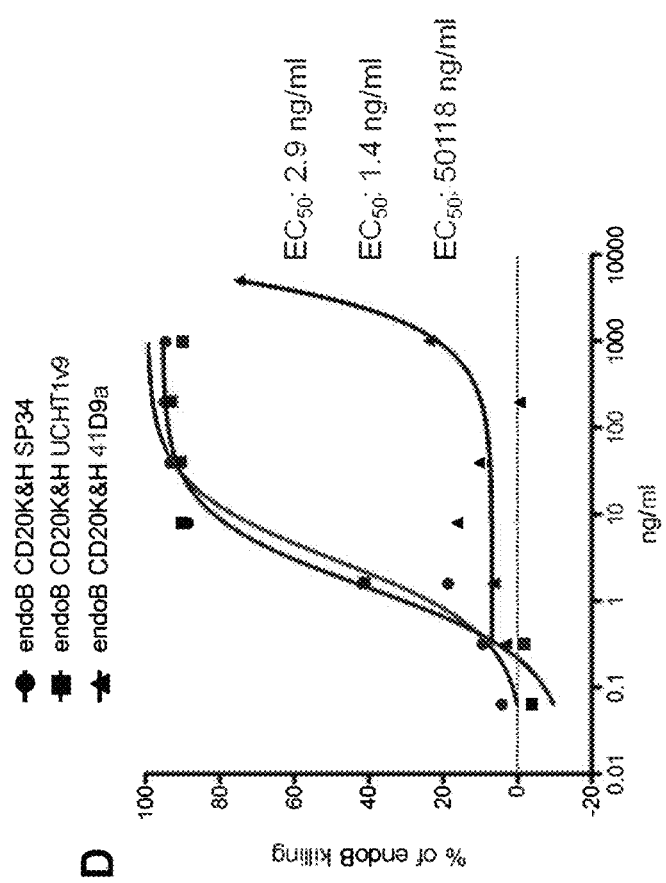

FIG. 46C is a graph showing that certain CD3/CD20 TDBs, such as one having an anti-CD20 arm of 2H7v16 and an anti-CD3 arm of 41D9a, exhibit low in vitro potency, as assessed by Bjab killing assays. Bjab cell killing EC50 (ng/ml) values for each CD3/CD20 TDB tested are shown.

Figure 46D:
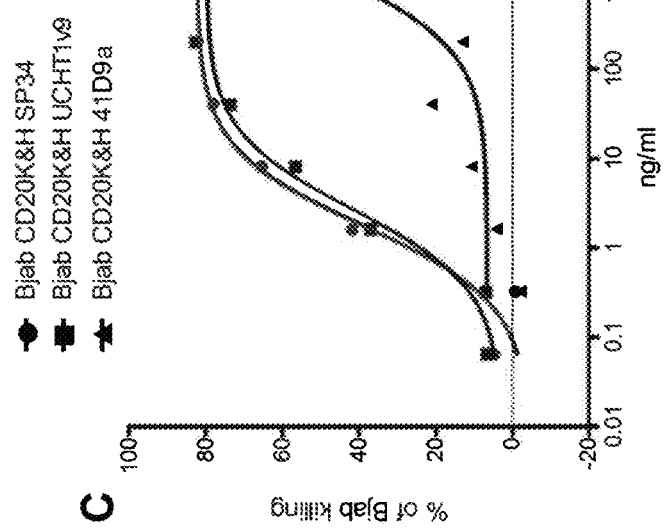

FIG. 46D is a graph showing that certain CD3/CD20 TDBs, such as one having an anti-CD20 arm of 2H7v16 and an anti-CD3 arm of 41D9a, exhibit low in vitro potency, as assessed by endo B cell killing assays. Endo B cell killing EC50 (ng/ml) values for each CD3/CD20 TDB tested are shown.

Figure 46E:
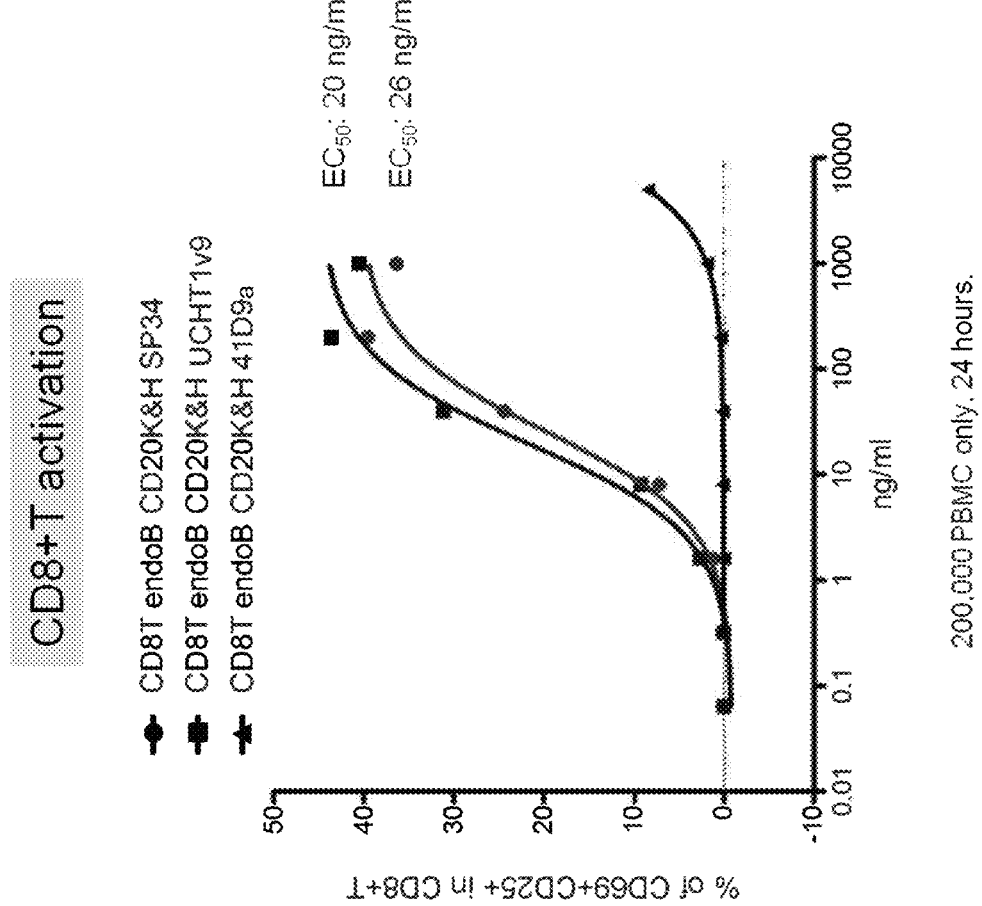

FIG. 46E is a graph showing that certain CD3/CD20 TDBs, such as one having an anti-CD20 arm of 2H7v16 and an anti-CD3 arm of 41D9a, exhibit low in vitro potency, as assessed by T cell activation assays.

Figure 47A:
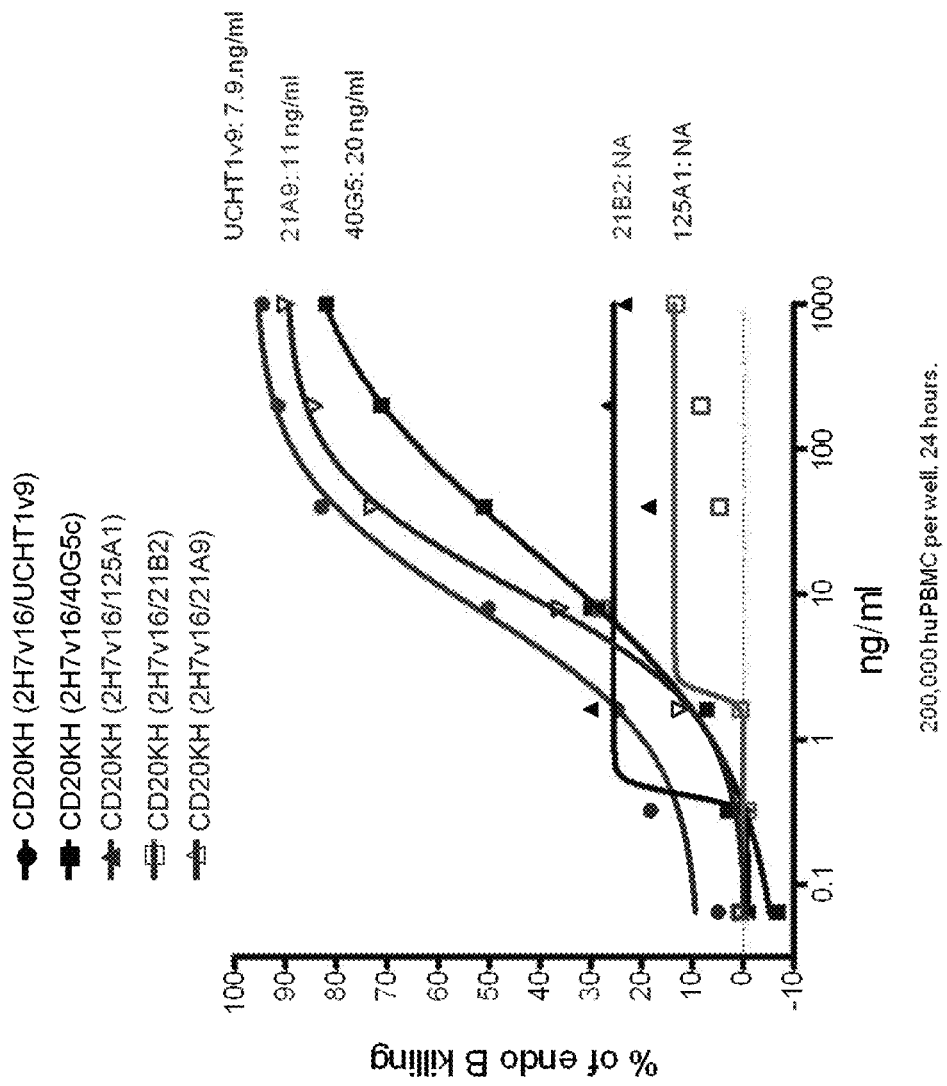

FIG. 47A is a graph showing that certain CD3/CD20 TDBs, such as TDBs having an anti-CD20 arm of 2H7v16 and an anti-CD3 arm of UCHT1v9, 21A9, and 40G5c, exhibit high in vitro potency, as assessed by endo B cell killing assays using 200,000 human PBMCs (isolated from Donor #1) per well, as measured by FACS analysis.

Figure 47B:
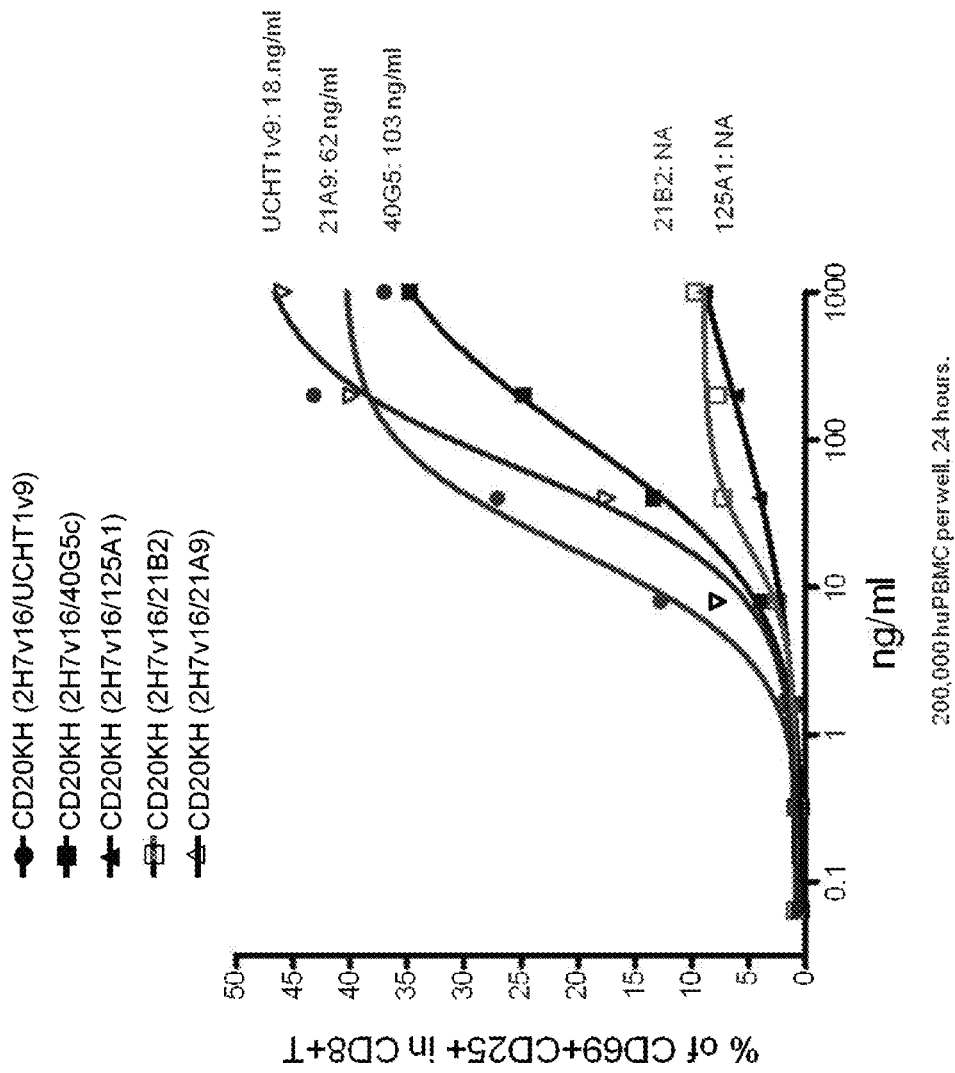

FIG. 47B is a graph showing that certain CD3/CD20 TDBs, such as TDBs having an anti-CD20 arm of 2H7v16 and an anti-CD3 arm of UCHT1v9, 21A9, and 40G5c, exhibit high in vitro potency, as assessed by T cell activation assays using 200,000 human PBMCs (isolated from Donor #1) per well, as measured by FACS analysis.

Figure 48A:
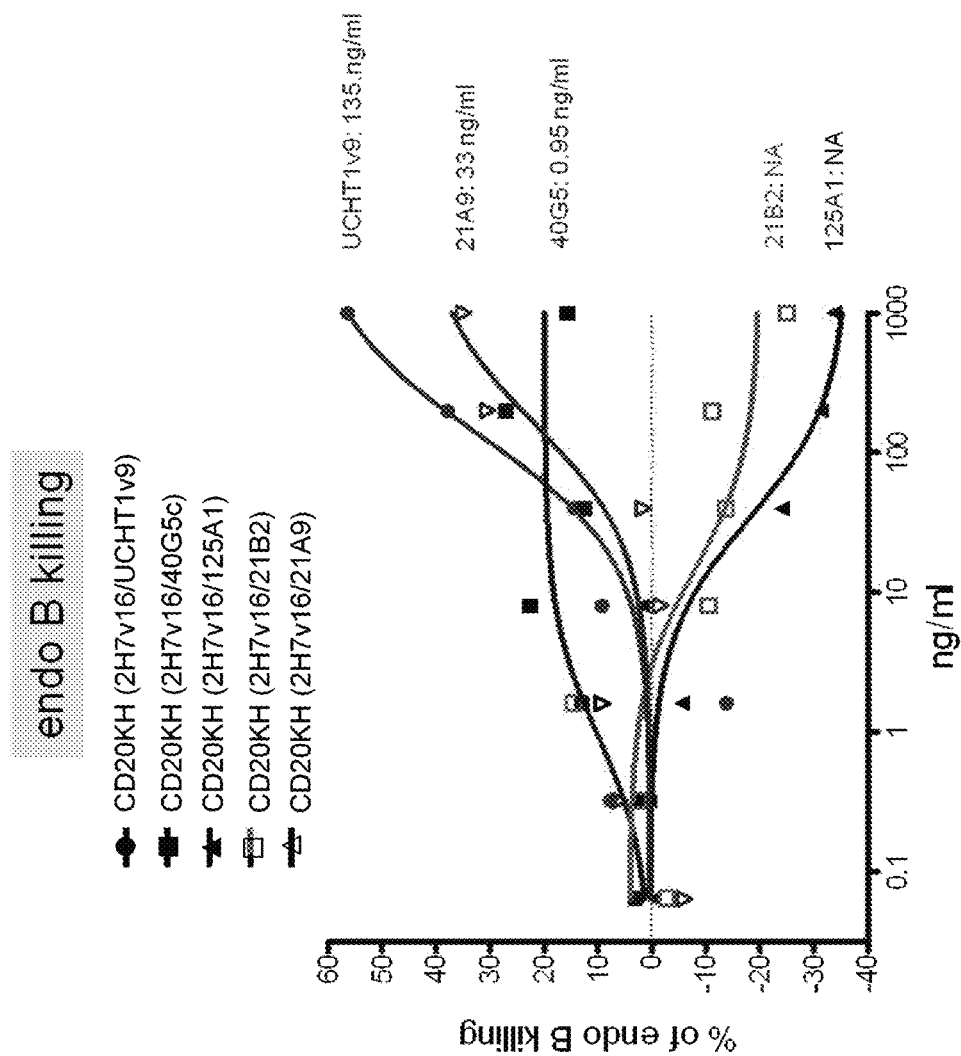

FIG. 48A is a graph showing that certain CD3/CD20 TDBs, such as TDBs having an anti-CD20 arm of 2H7v16 and an anti-CD3 arm of UCHT1v9, 21A9, and 40G5c, exhibit high in vitro potency, as assessed by endo B cell killing assays using 200,000 human PBMCs (isolated from Donor #2) per well, as measured by FACS analysis.

Figure 48B:
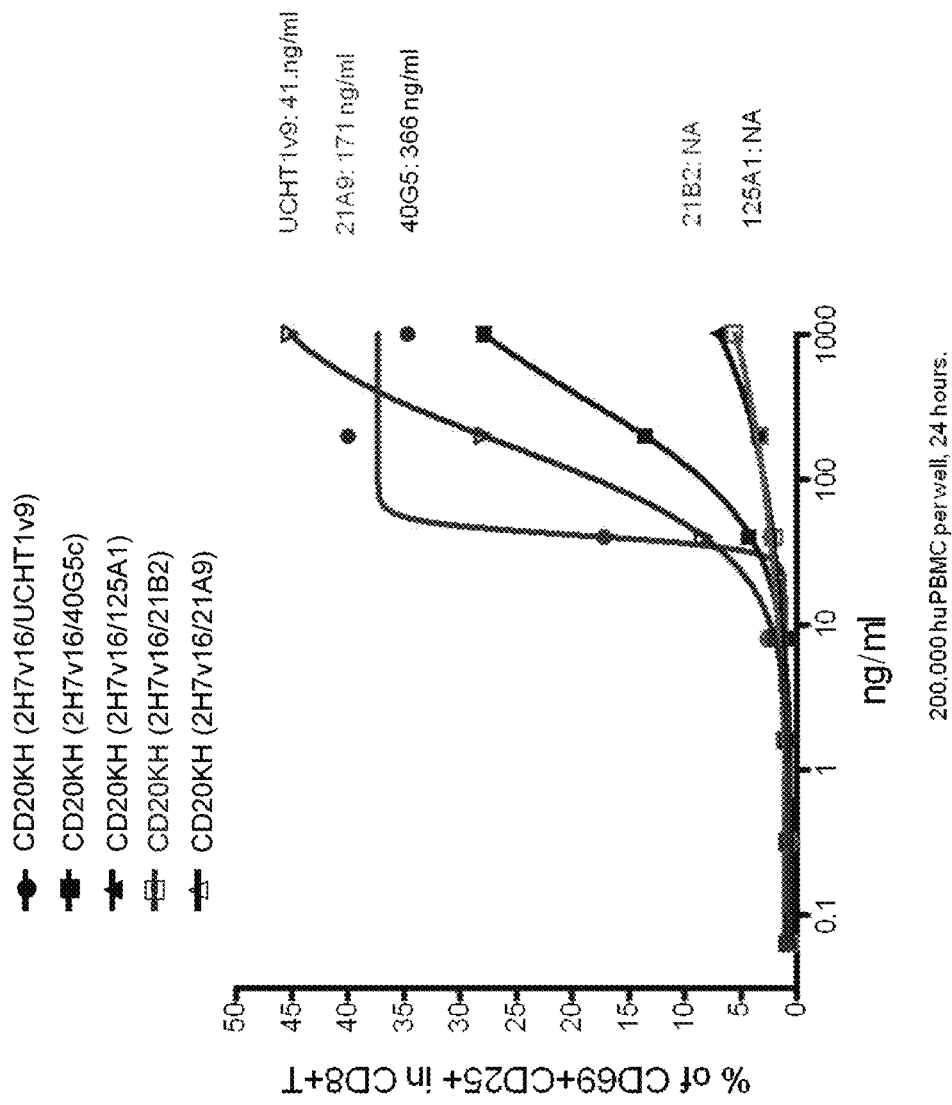

FIG. 48B is a graph showing that certain CD3/CD20 TDBs, such as TDBs having an anti-CD20 arm of 2H7v16 and an anti-CD3 arm of UCHT1v9, 21A9, and 40G5c, exhibit high in vitro potency, as assessed by T cell activation assays using 200,000 human PBMCs (isolated from Donor #2) per well, as measured by FACS analysis.

FIG. 49 is a table summarizing the in vitro potencies of various CD3/CD20 TDBs having different combinations of anti-CD3 arms with the anti-CD20 arm of 2H7v16.

Figure 50:
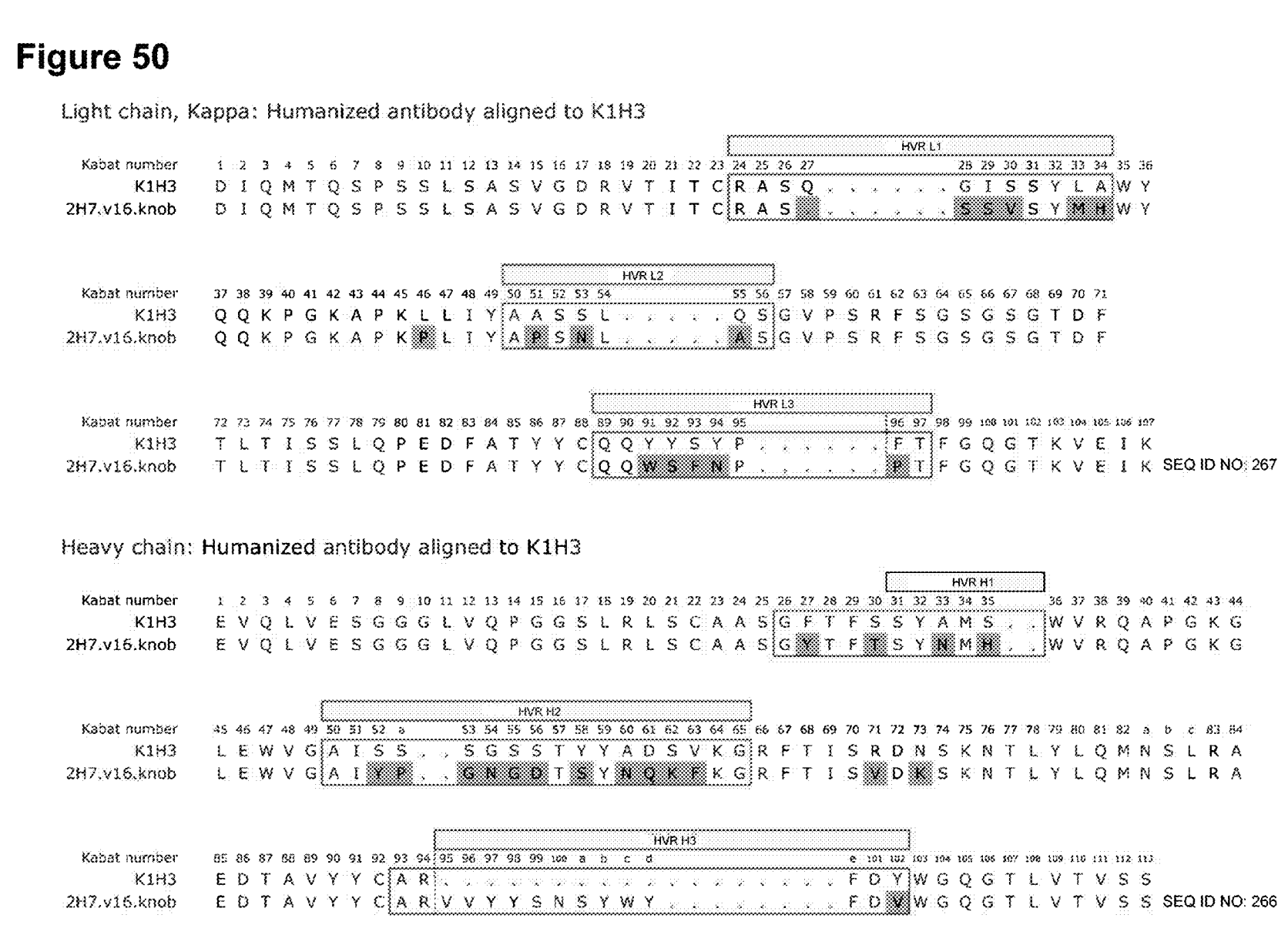

FIG. 50 shows the amino acid sequences of the light chain variable domain (top) and heavy chain variable domain (bottom) of anti-CD20 antibody 2H7.v16.

FIG. 51 shows the amino acid sequences of the light chain variable domain (top) and heavy chain variable domain (bottom) of anti-CD3 antibody hu40G5c.

Figure 52A:
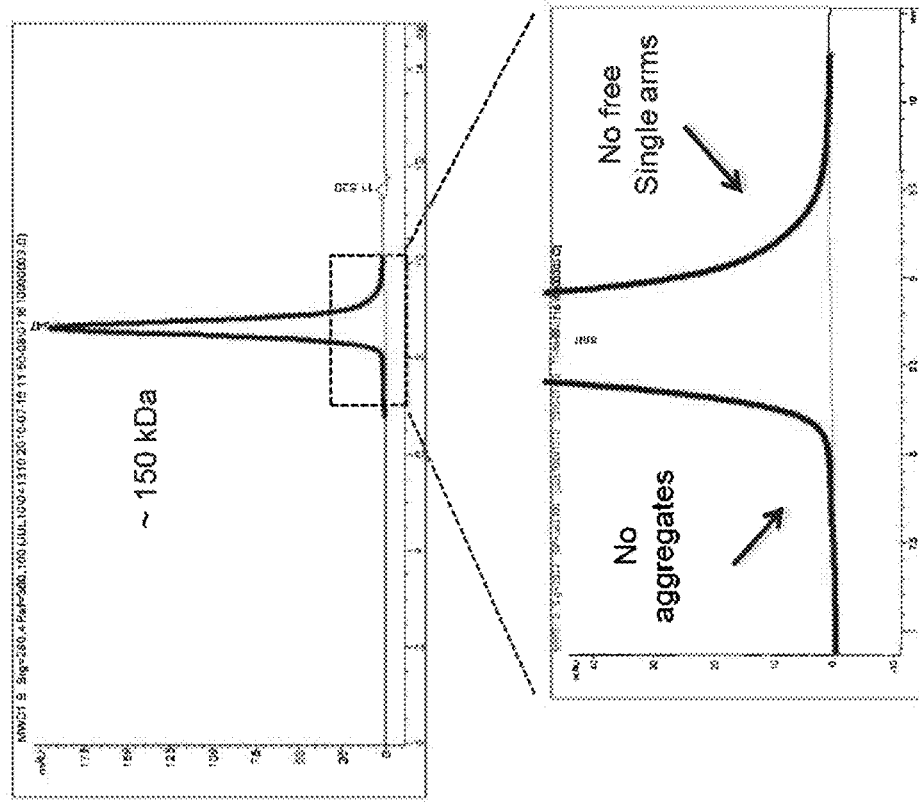
Figure 52B:
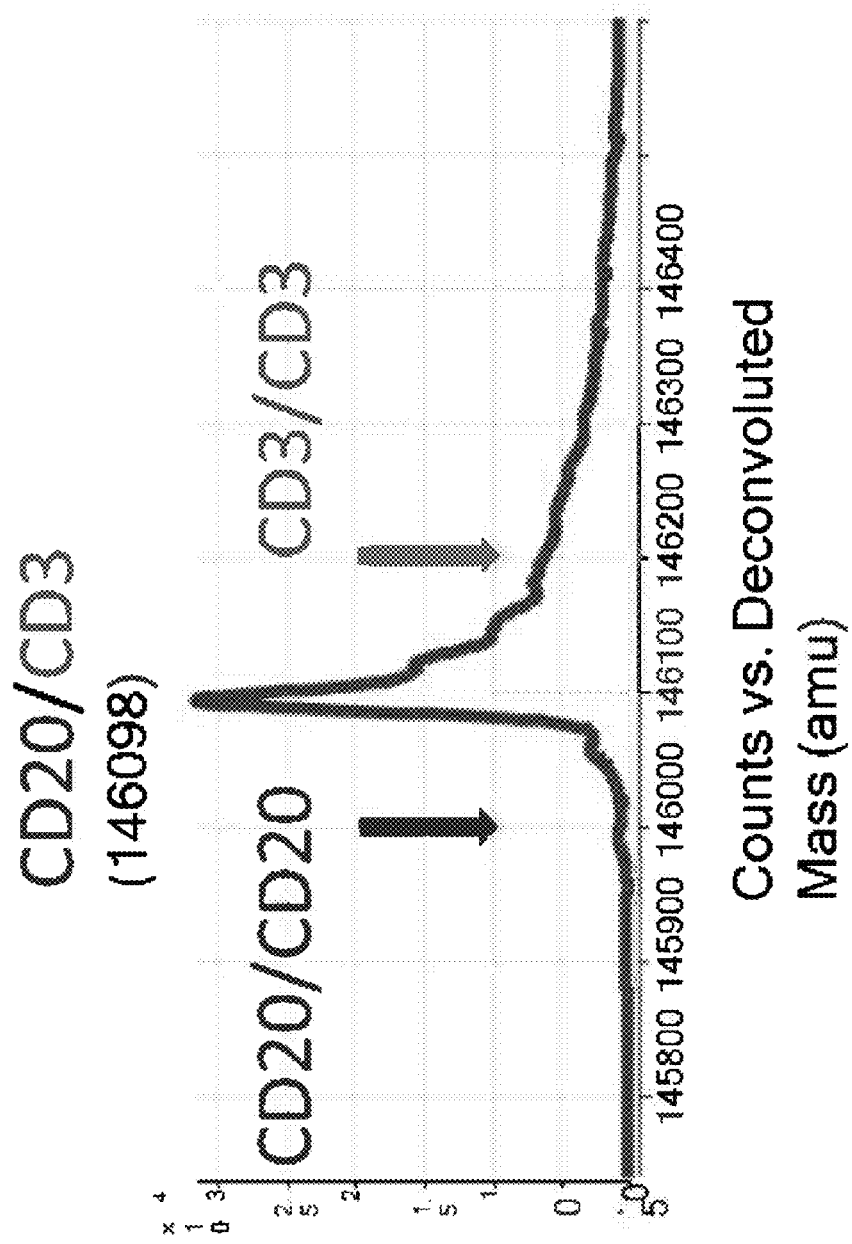

FIGS. 52A and 52B show that purified CD3/CD20 TDB (40G5c/2H7v16) has no detectable aggregate formation as determined by size-exclusion chromatography (SEC) (A) and no detectable homodimer formation (i.e., CD3/CD3 or CD20/CD20 antibody formation) as assessed by mass spectrometry (B).

Figures 53A, 53B:
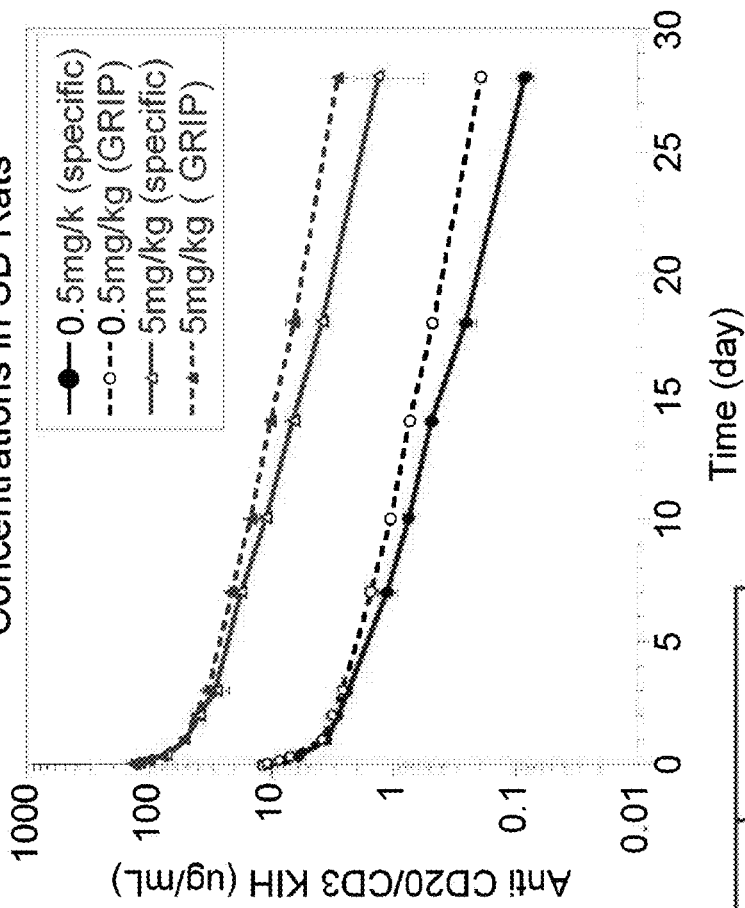

FIG. 53A is a graph showing the pharmacokinetics of serum concentrations of CD3/CD20 TDBs at varying doses in Sprague Dawley (SD) rats over time (in days), as assessed by generic immunoglobulin pharmacokinetic (GRIP) or specific assay.

FIG. 53B is a table summarizing the quantified clearance (ml/day/kg) values of the tested CD3/CD20 TDB antibodies at each dosage tested in FIG. 53A.

Figures 54A, 54B:
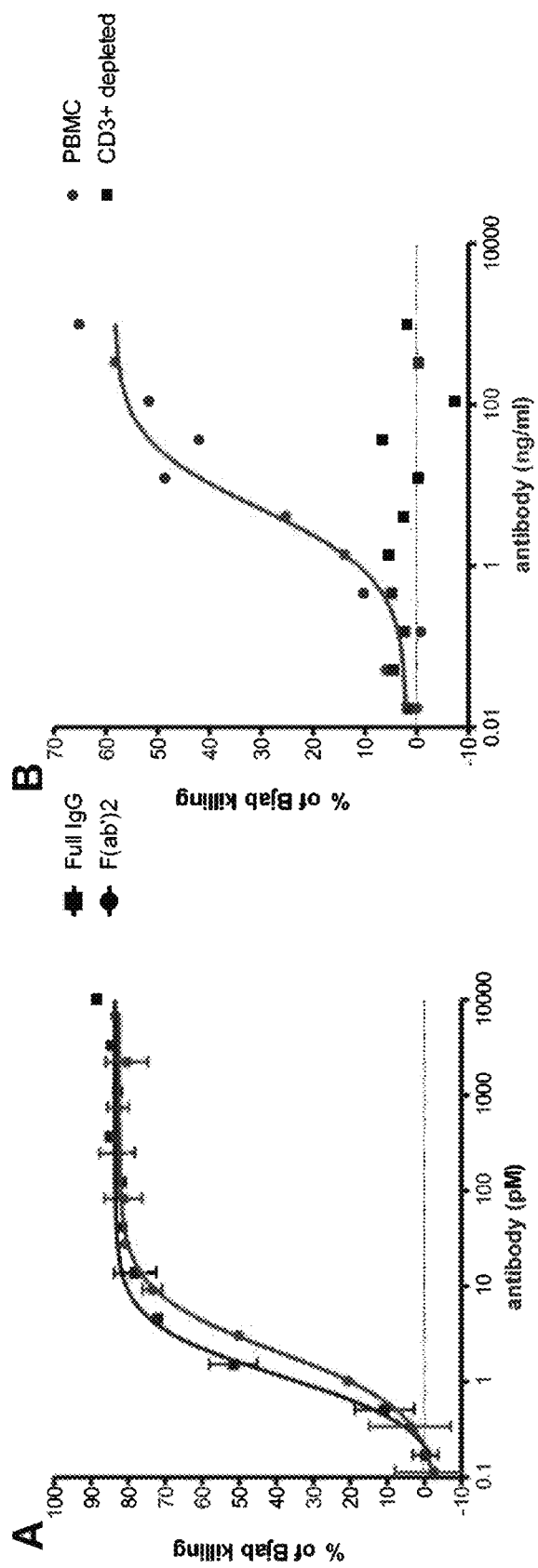

FIG. 54A is a graph showing that F(ab')2 portion of CD20 TDB retained the same potency as the full-length IgG CD20 TDB in B cell killing (Bjab killing) in vitro. 20,000 Bjab cells and 200,000 PBMCs isolated from healthy donor were incubated with various concentration of full length CD20 TDB or F(ab')2 CD20 TDB for 24 hours.

FIG. 54B is a graph showing that B cell killing activity of CD20 TDB is T cell-dependent, as no B cell killing was detected with PBMCs depleted of CD3+ T cells. 20,000 Bjab cells and 200,000 PBMCs isolated from healthy donor, or 200,000 PBMCs depleted of CD3+ T cells, were incubated with various concentration of CD20 TDB for 24 hours.

Figures 54C, 54D:
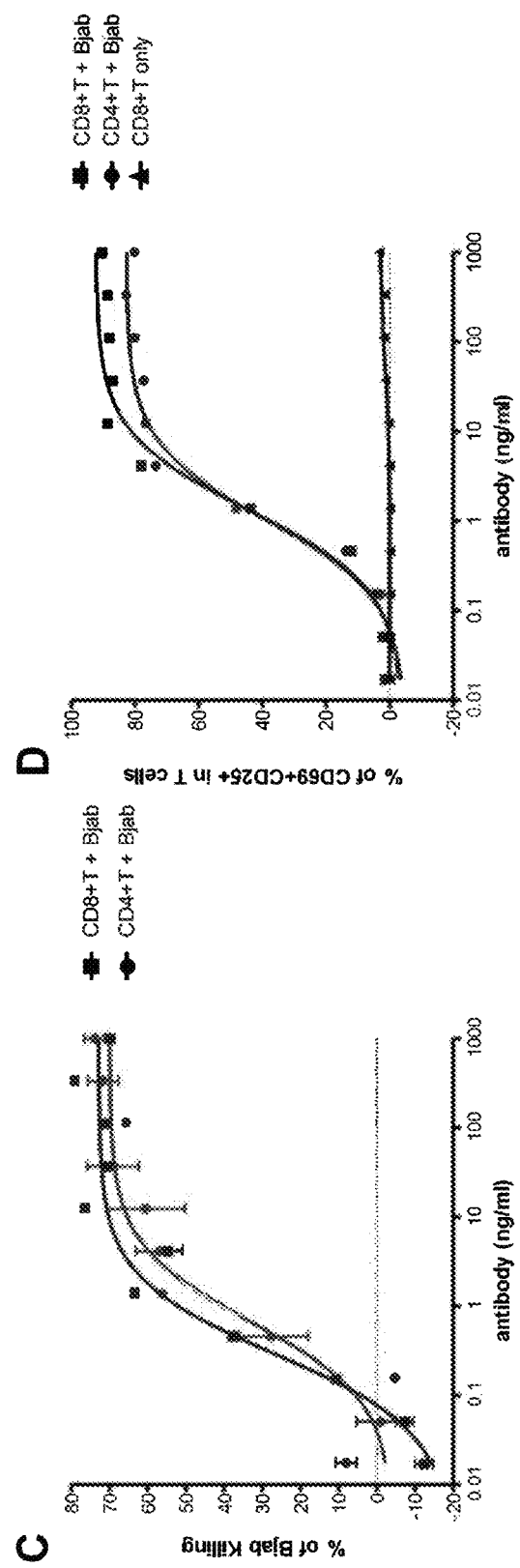

FIG. 54C is a graph showing that comparable B cell killing can be achieved with either CD4+ or CD8+ T cells as effectors. 20,000 Bjab cells and 100,000 purified CD8+ T cells or CD4+ T cells were incubated with various concentration of CD20 TDB for 24 hours. Cell killing and T cell activation marked as CD69+CD25+ were measured and calculated as described below.

FIG. 54D is a graph showing that CD20 TDB is capable of activating both CD4+ and CD8+ T cells. 20,000 Bjab cells and 100,000 purified CD8+ T cells or CD4+ T cells were incubated with various concentration of CD20 TDB for 24 hours. Cell killing and T cell activation marked as CD69+CD25+ were measured and calculated as described below.

Figures 54E, 54F:
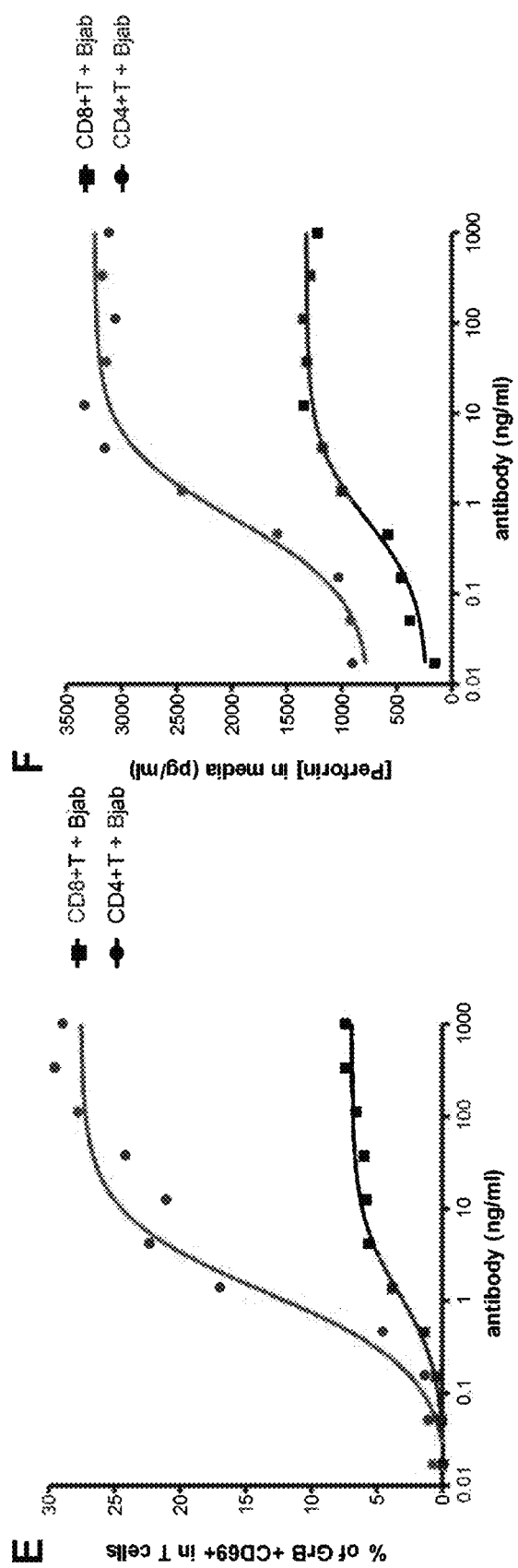

FIG. 54E is a graph showing that Granzyme upregulation is more prevalent within CD8+ T cells upon CD20 TDB addition. 20,000 Bjab cells and 100,000 purified CD8+ T cells or CD4+ T cells were incubated with various concentration of CD20 TDB for 24 hours. Granzyme B induction was also detected by FACS.

Figure 55:
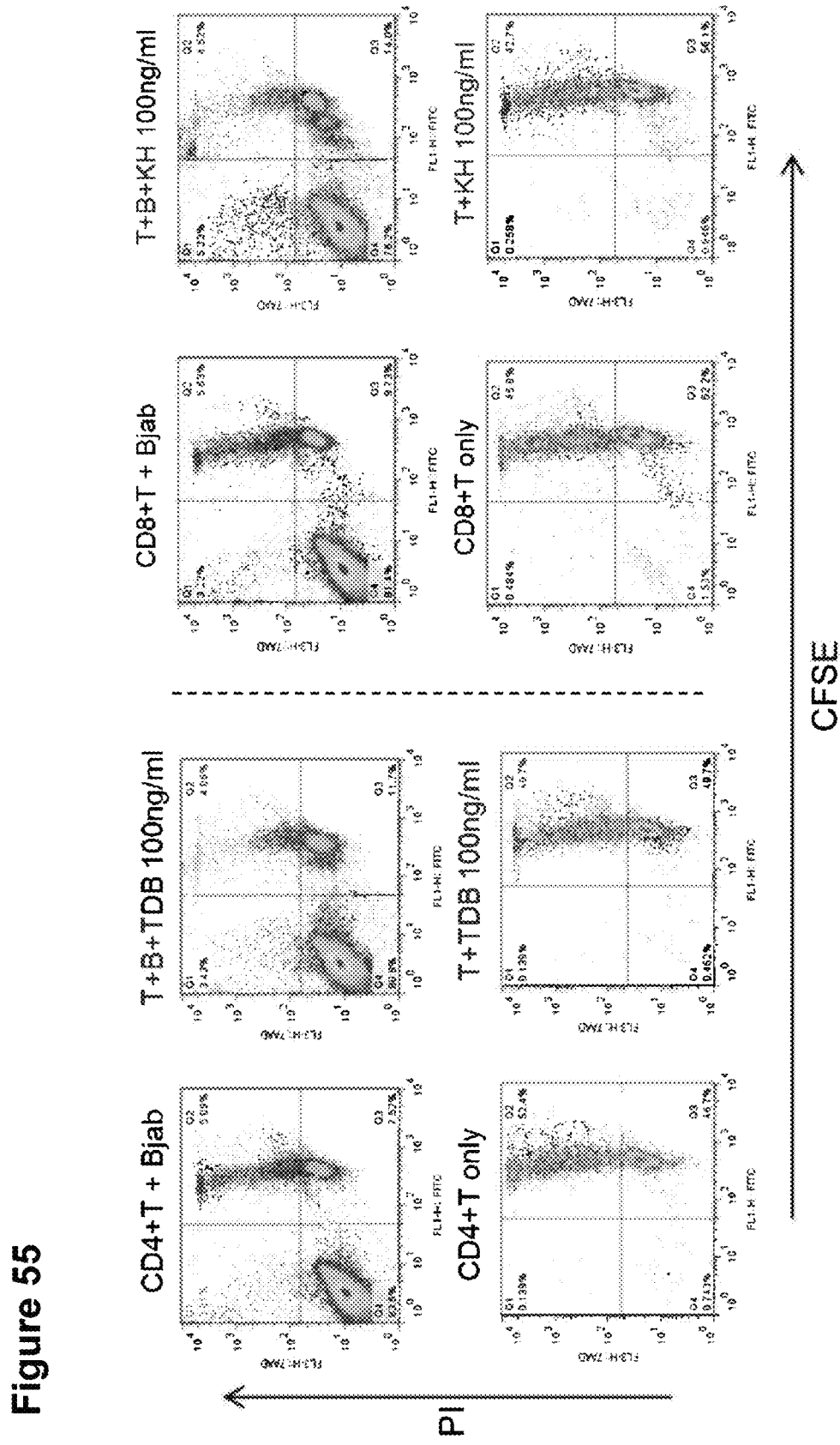

FIG. 54F is a graph showing that a higher level of perforin release is associated with CD8+ T cells upon CD20 TDB addition. 20,000 Bjab cells and 100,000 purified CD8+ T cells or CD4+ T cells were incubated with various concentration of CD20 TDB for 24 hours. Perforin concentration in media was measured by ELISA FIG. 55 is a series of flow cytometry graphs showing that activated T cells are capable of proliferation in the presence of CD20 TDB and Bjab cells.

Figure 56A:
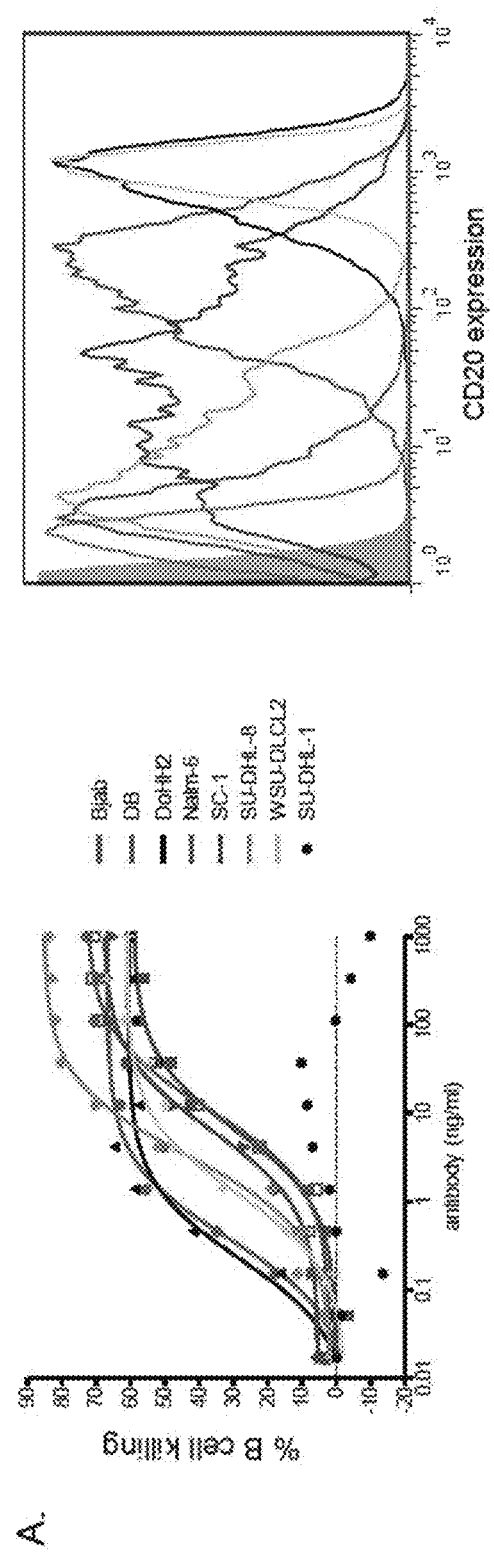

FIG. 56A is a series of graphs showing the dose-response B cell killing curves of 8 B leukemia/lymphoma tumor cell lines (left) and the CD20 expression levels for the given B cell lines with an isotype control in grey, as measured by FACS. B cells were cultured in RPMI 1640 media supplemented with 10% FBS. For the killing assay, 20,000 B cells were incubated with 200,000 PBMCs isolated from healthy donor with various concentration of CD20 TDB for 24 hours.

Figure 56B:
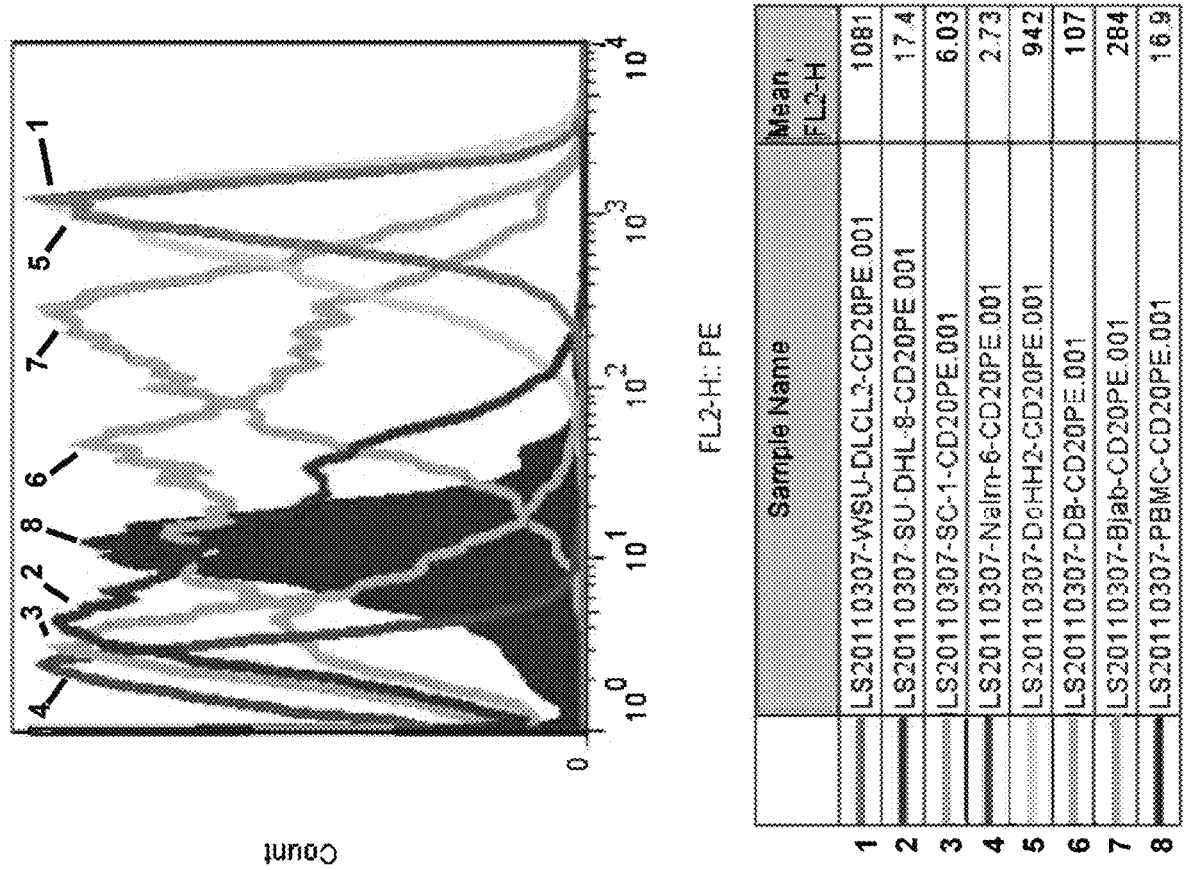

FIG. 56B is a graph showing a wide range in the mean CD20 expression on the 8 B cell lines tested in FIG. 56A. CD4+T or CD8+ T cells, purified from healthy donor whole blood and CFSE-labeled, were incubated alone, with Bjab only, with CD20 TDB only, or with Bjab and CD20 TDB for 24 hours first, then cells were washed and put in fresh media for another 48 hours. CFSE intensity of T cells was detected by FACS, showing proliferation of T cells only in presence of Bjab and CD20 TDB.

Figure 56C:
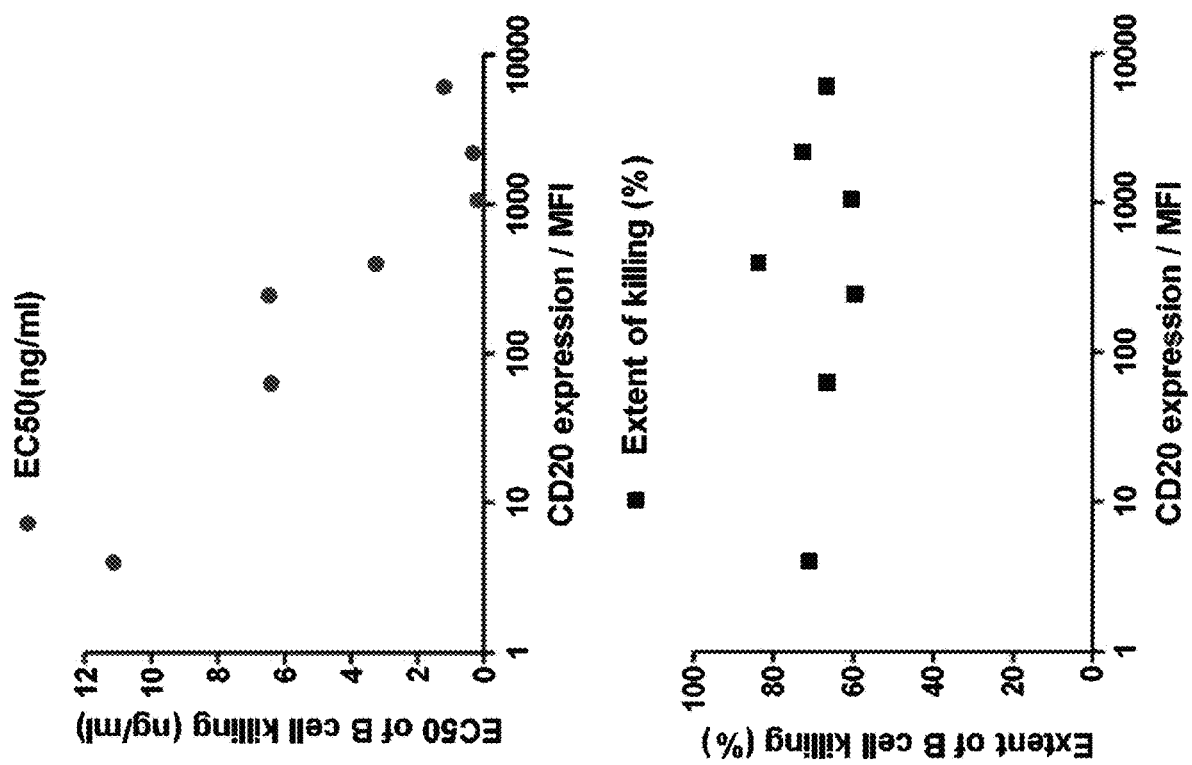

FIG. 56C is a set of graphs showing that CD20 TDB is potent in killing all 8 lines in a dose-dependent manner, with EC50 values of B cell killing (ng/ml) (top) and the percentage of B cell killing (bottom) represented as a function of CD20 expression on the target B cell.

Figure 56D:
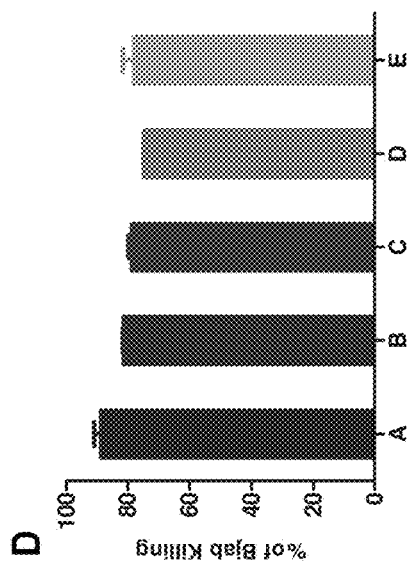

FIG. 56D is a graph showing that TDBs targeting 5 different B cell antigens are comparable in mediating T cell killing of Bjab cells. B cells were cultured in RPMI 1640 media supplemented with 10% FBS. For the killing assay, 20,000 Bjab cells were incubated with 100,000 purified CD8+ T cells from healthy donor with a CD20 TDB (TDB A: 2H7v16/UCHT1v9) or a TDB targeting a different B cell antigen (i.e., TDBs B-E, each targeting a different B cell antigen) at a concentration of 1000 ng/ml for 24 hours.

Figure 56E:
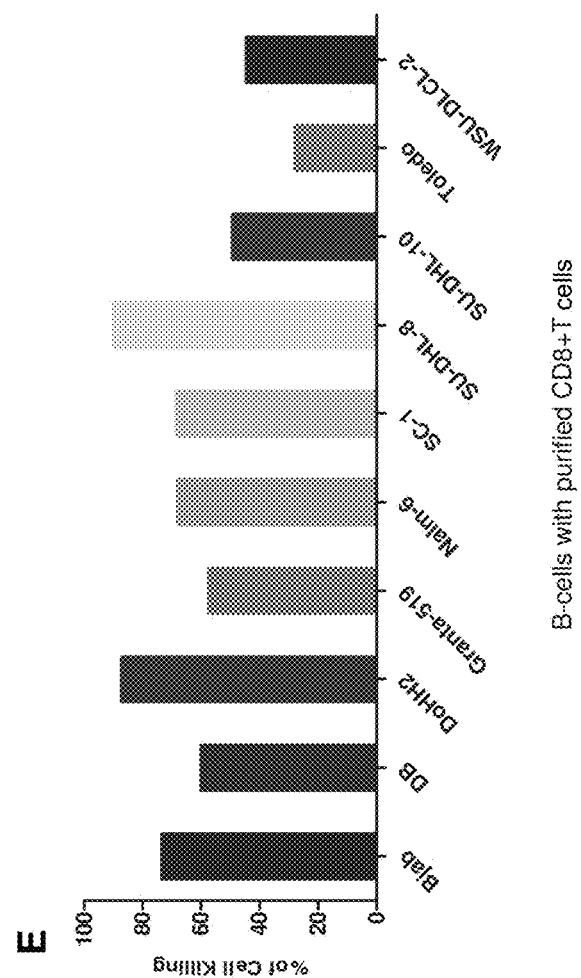

FIG. 56E is a graph showing the extent of B cell killing for 10 B leukemia/lymphoma tumor cell lines. B cells were cultured in RPMI 1640 media supplemented with 10% FBS. For the killing assay, 20,000 B cells were incubated with 100,000 purified CD8+ T cells from healthy donor and 1000 ng/ml CD20 TDB (2H7v16/UCHT1v9) for 24 hours.

Figure 56F:
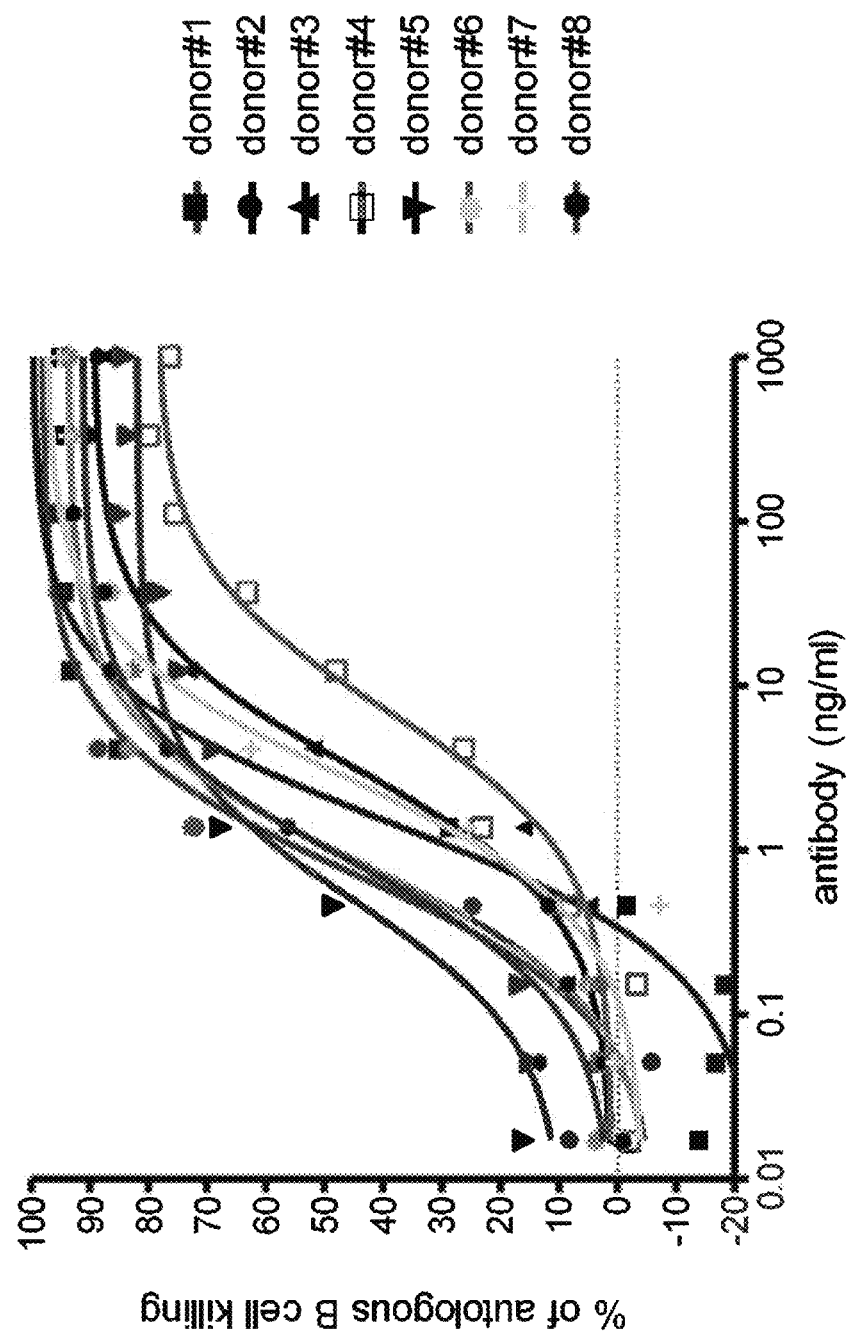

FIG. 56F is a graph showing the dose-responsive killing curves for 8 random donors.

Figure 56G:
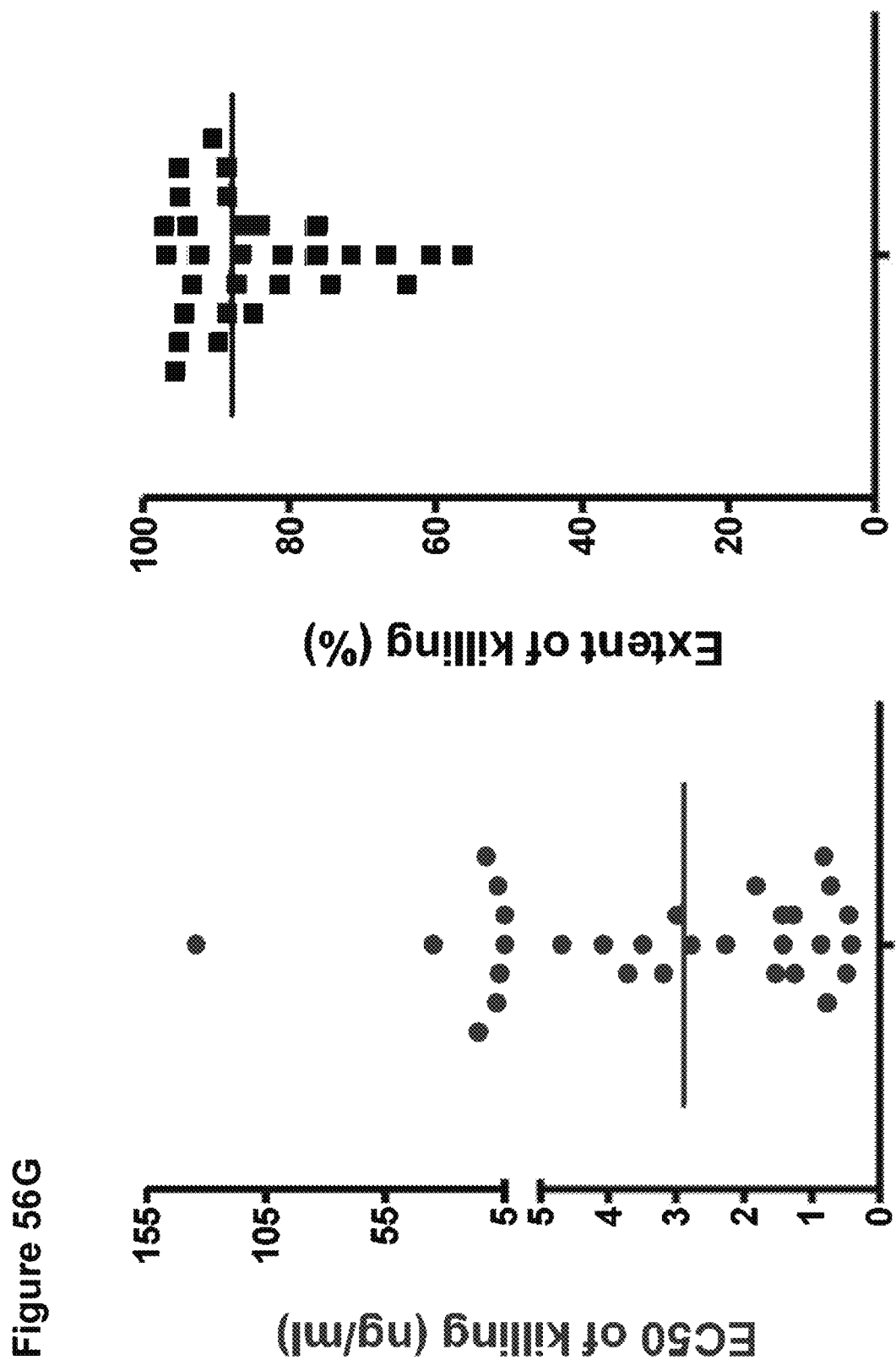

FIG. 56G is a summary plot graph for EC50 (left) and extent of B cell killing (right) with 1000 ng/ml antibody in a 24 hour assay for 30 donors.

Figure 56H:
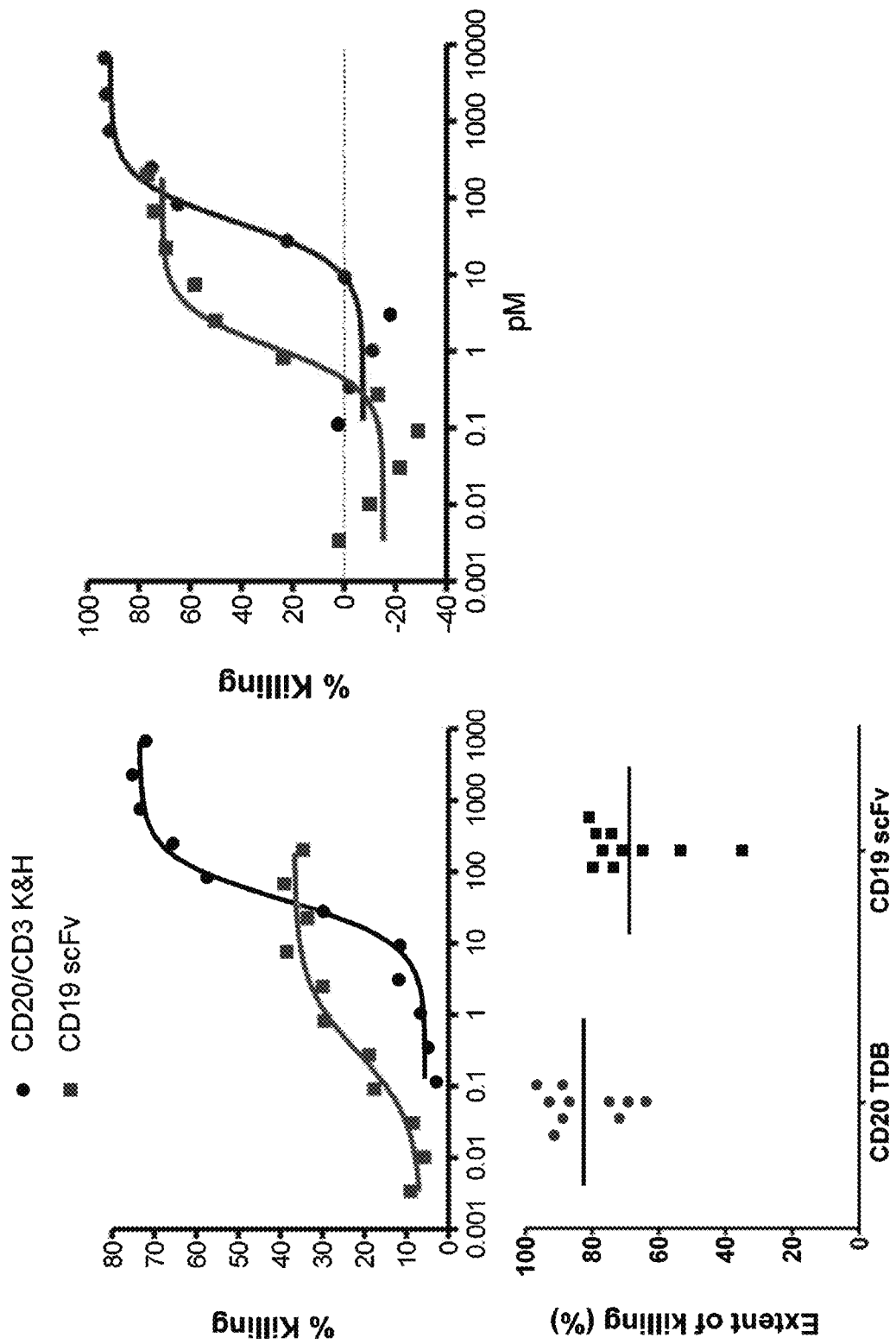

FIG. 56H is a set of graphs showing that the extent of B cell killing within 24 hours by CD20 TDB is very comparable or higher than B cell killing by CD19 scFv. For autologous B cell killing, 200,000 PBMCs isolated from healthy donor were incubated for 24 hours with CD20 TDB at indicated concentration. Reported cell killing was calculated as described below.

Figure 56I:
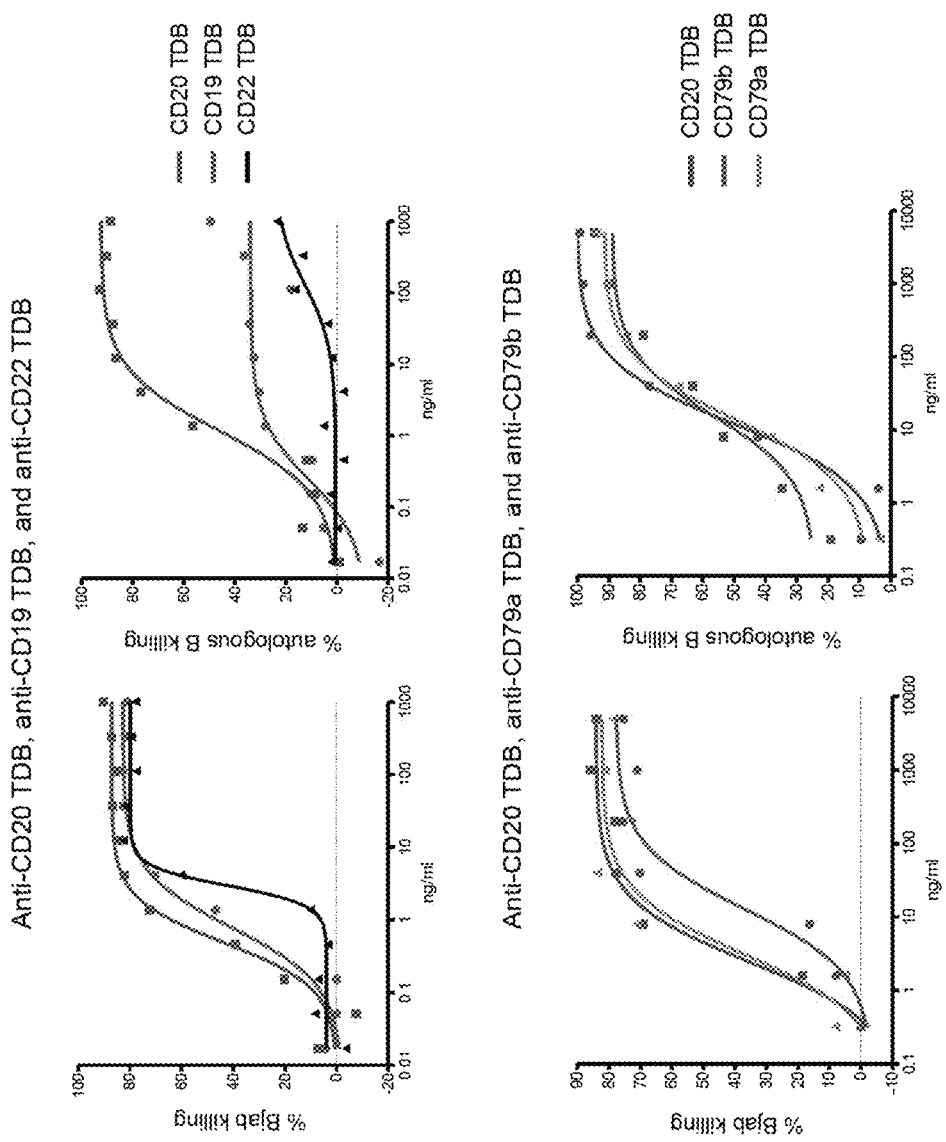

FIG. 56I is a set of graphs showing that the extent of B cell killing within 24 hours by CD20 TDB is comparable or higher than B cell killing by CD19-TDB or CD22-TDB (top panel) or CD79a or CD79b (bottom panel). For autologous B cell killing, 200,000 PBMCs isolated from healthy donor were incubated with 40,000 BJAB cells for 24 hours with CD20, CD19, CD22, CD79a, or CD 79b TDB at the indicated concentration. Reported cell killing was calculated as described below.

Figure 57A:
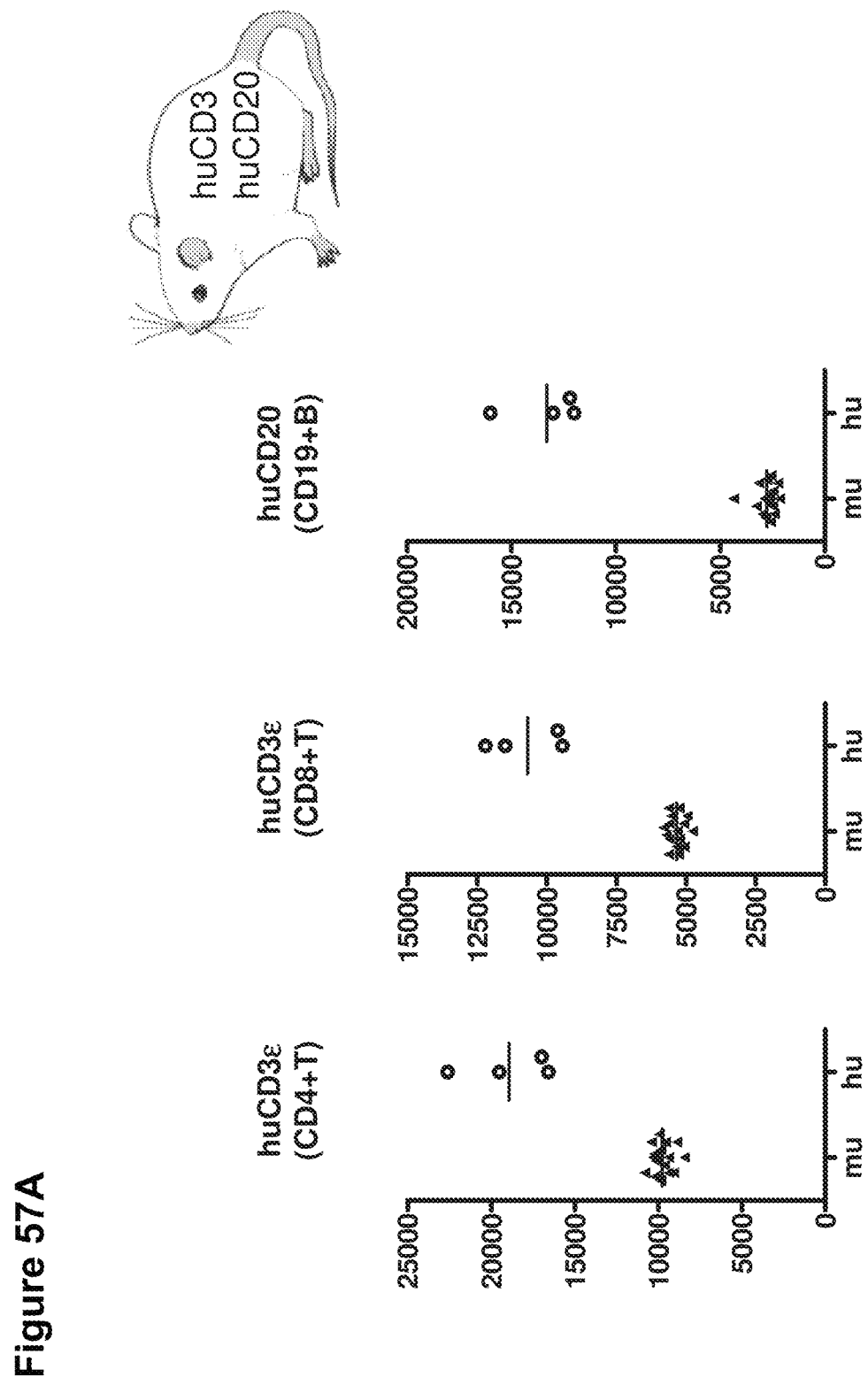

FIG. 57A is a series of graphs showing the relative expression values for human $CD3_\varepsilon$ detected in CD4+ T cells (left panel) and CD8+ T cells (center panel); and human CD20 in CD19+ B cells (right panel) detected in mouse (mu) or human (hu) PBMCs as measured by FACS. Mouse PBMCs were derived from blood of double transgenic huCD3/huCD20 mice; human PBMCs were derived from healthy donor blood.

Figures 57B, 57C:
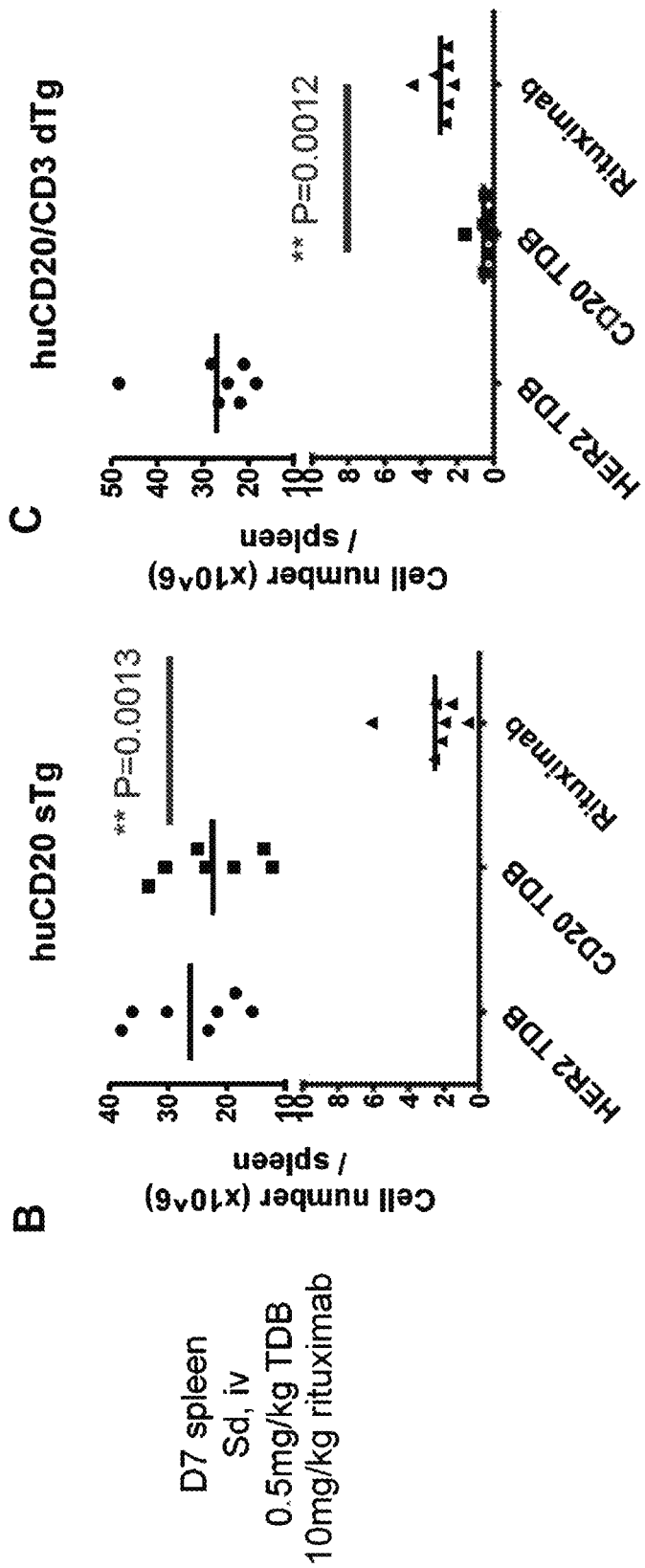

FIG. 57B is a graph showing that CD20 TDB cannot engage murine T cells to deplete B cells without human CD3 expression in human CD20 transgenic mice. huCD20 transgenic mice or huCD20/CD3 double transgenic mice were treated once intravenously with antibodies as indicated (10 mg/kg for rituximab, 0.5 mg/kg for CD20 TDB and HER2 TDB). Mouse spleens were collected at D7 (7 days after antibody treatment). Anti-human CD20 antibody rituximab is used as a positive control. CD3/HER2 TDB used as negative, isotype control.

FIG. 57C is a graph showing that CD20 TDB is able to engage murine T cells expressing huCD3 in human CD3/CD20 double transgenic mice to potently deplete murine B cells expressing huCD20. huCD20 transgenic mice or huCD20/CD3 double transgenic mice were treated once intravenously with antibodies as indicated (10 mg/kg for rituximab, 0.5 mg/kg for CD20 TDB and HER2 TDB). Mouse spleens were collected at D7 (7 days after antibody treatment). CD3/HER2 TDB used as negative, isotype control.

Figure 58A:
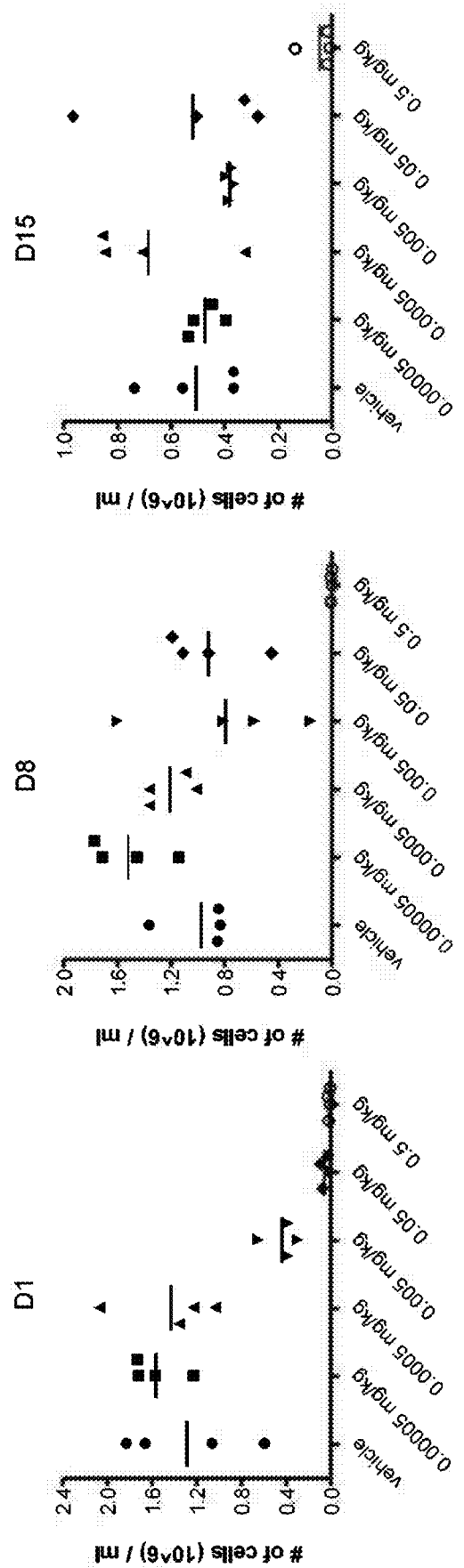

FIG. 58A is a series of graphs of a time-course study showing that treatment with CD20 TDB resulted in sustained B cell depletion up to D15 (15 days after dosing). huCD20/huCD3 double transgenic mice were treated once intravenously with various doses of CD20 TDB. Mouse blood (D1, D8, and D15) was collected.

Figure 58B:
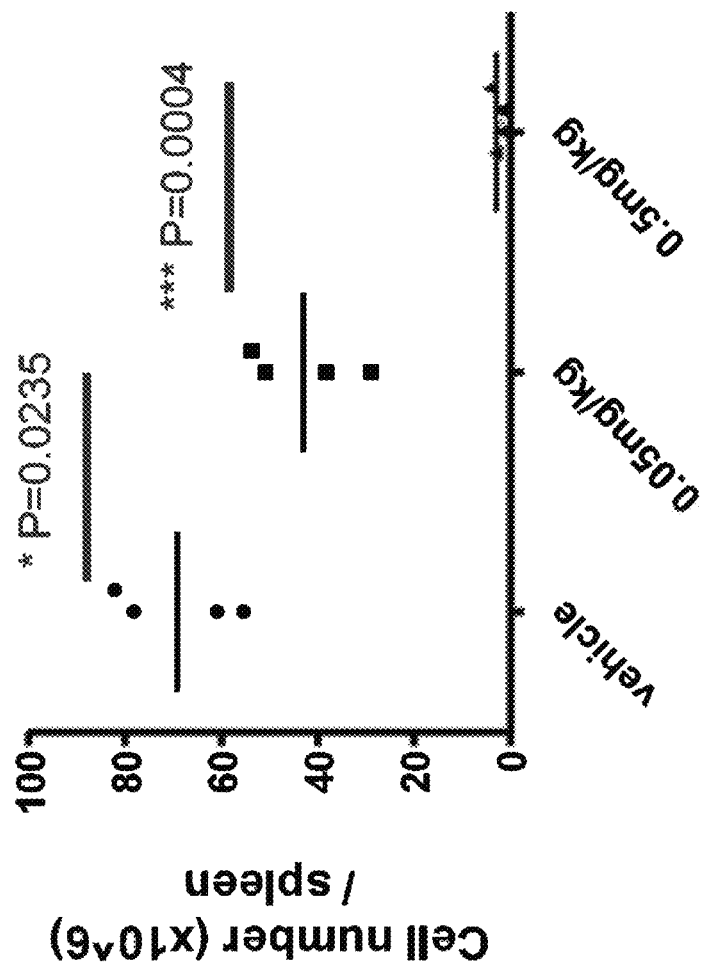

FIG. 58B is a graph showing that near complete B cell depletion in mouse spleens was only achieved at D7 after a single dose of 0.5 mg/kg, while a lower dose of 0.05 mg/kg only resulted in spleen B cell depletion partially. huCD20/CD3 double transgenic mice were treated once intravenously with various dose of CD20 TDB. Spleens (D7) were collected.

Figures 58C, 58D:
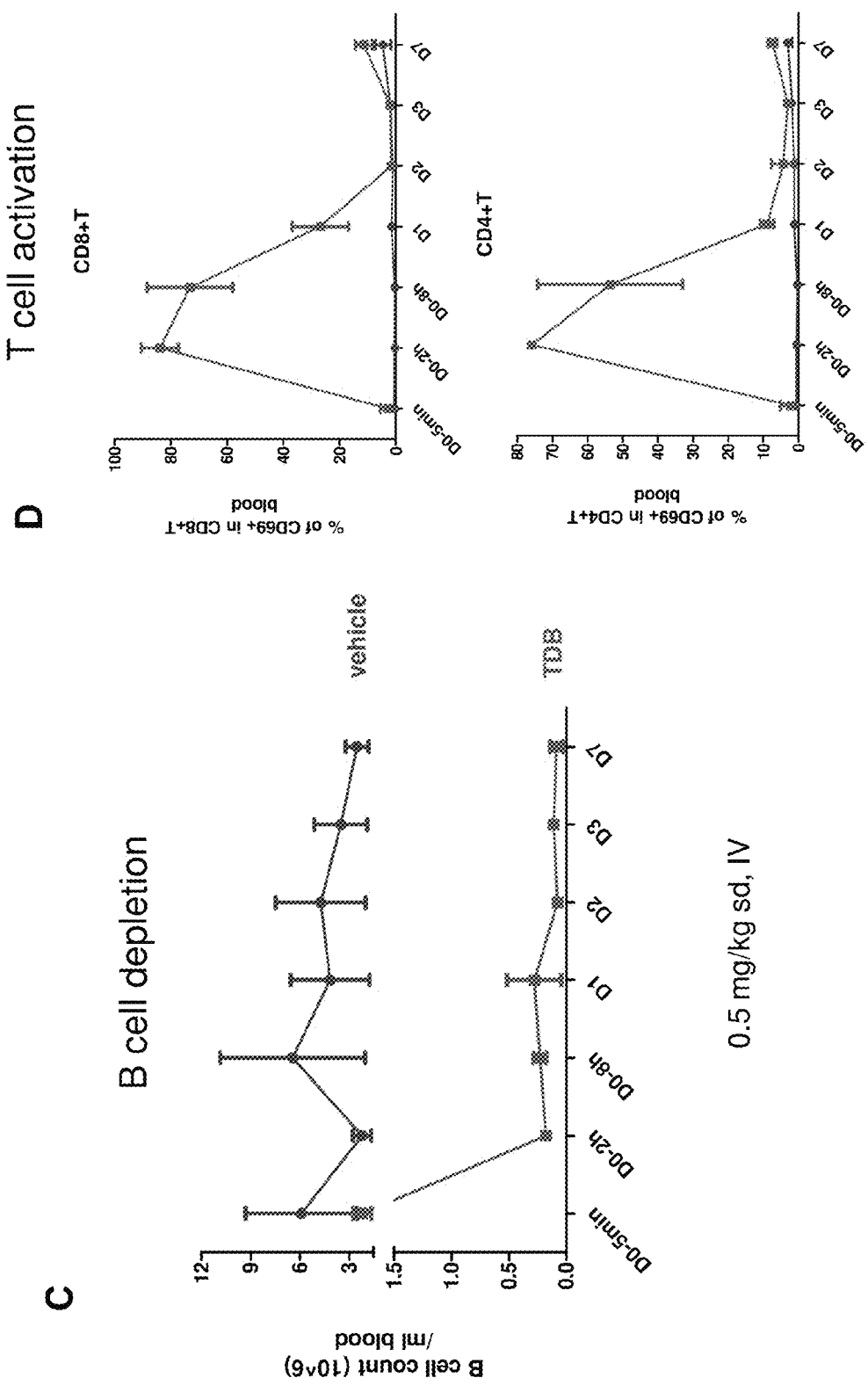

FIG. 58C is a graph showing that robust B cell depletion at D7 is observed in circulation of double transgenic huCD3/huCD20 mice treated with CD20 TDB. huCD20/huCD3 double transgenic mice were treated once intravenously with 0.5 mg/kg of CD20 TDB. Blood was collected at D0-5 min (5 minutes after treatment), D0-2 h, D0-8 h, D1, D2, D3, and D7. B cells expressing huCD20 were measured by FACS.

FIG. 58D is a series of graphs showing T cell activation in double transgenic huCD3/huCD20 mice treated with a CD20 TDB. Treated double transgenic huCD3/huCD20 mice exhibited up to an 80% increase in human $CD3_\varepsilon$ expressing CD8+ T cell count at 2 hours post-CD20 TDB treatment, which returned to baseline level by D2 and D7 (top panel). Similarly, human $CD3_\varepsilon$ expressing CD4+ T cells increased by 80% 2 hours after treatment with CD20 TDB and subsequently returned to baseline level by D2. Double transgenic huCD3/huCD20 mice were treated once intravenously with 0.5 mg/kg of CD20 TDB. Blood was collected at D0-5 min (5 minutes after treatment), D0-2 h, D0-8 h, D1, D2, D3, and D7. CD4+ and CD8+ T cells expressing $CD3_\varepsilon$ were measured by FACS.

Figure 59A:
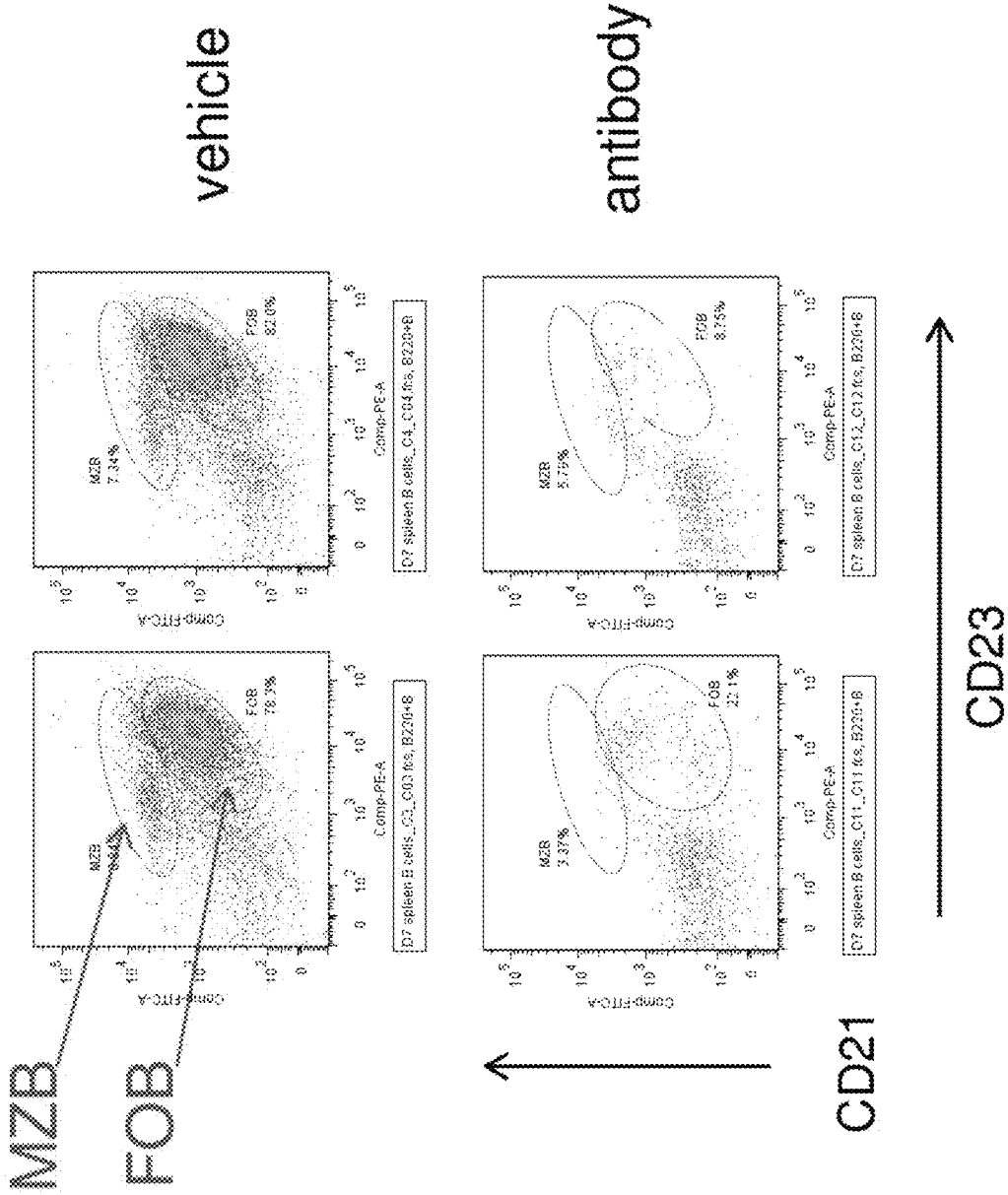

FIG. 59A is a series of flow cytometry graphs showing that CD20 TDB depletes marginal zone B cells (MZB) as efficiently as follicular B cells (FOB) after administration of TDB to double transgenic huCD3/huCD20 mice. Two double transgenic animals (left and right panels, respectively) were treated with vehicle (top panels) or a single intravenous dose of 0.5 mg/kg TDB (bottom panels). Mouse spleens were collected at D7 and analyzed by FACS.

FIG. 59B-59E is a series of graphs showing that CD20 TDB depletes marginal zone B cells (MZB) (B) as efficiently as follicular B cells (FOB) (C) after a single intravenous dose of 0.5 mg/kg TDB, along with activation of CD8+ T cells (D) and proliferation of CD8+ T cells (E) in the spleen at the indicated time points. Mouse spleens were collected at D1, D2, D3, D5, D7, and D14.

Figure 60A:
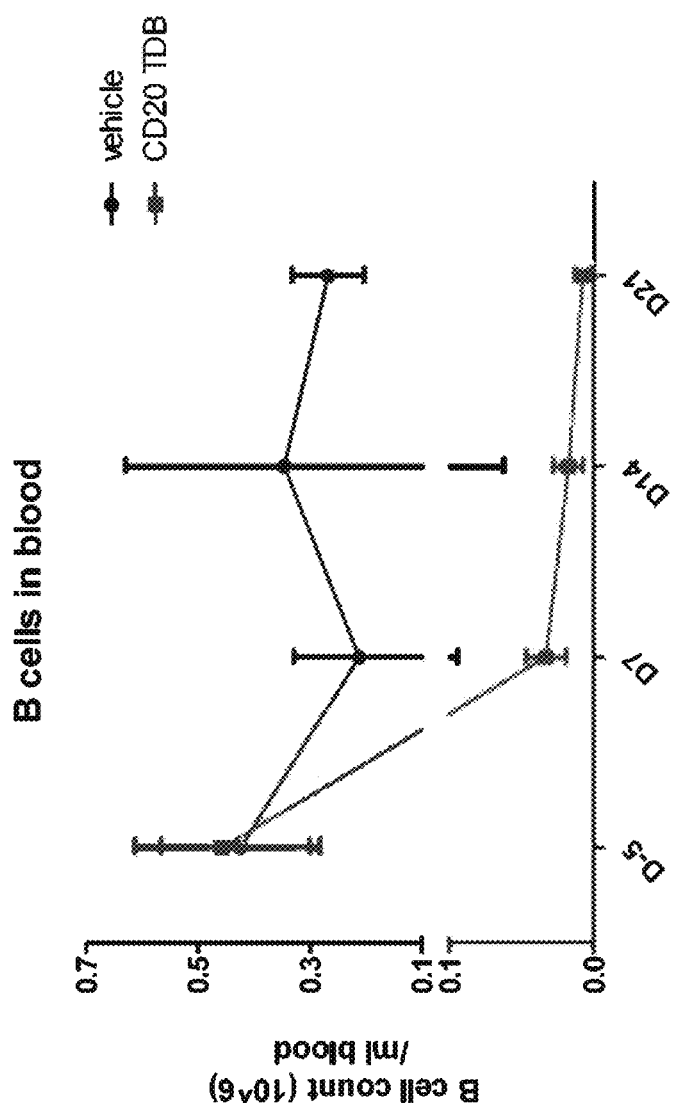

FIG. 60A is a graph showing that humanized NSG mice treated with 3 weekly doses of CD20 TDB at 0.5 mg/kg (repeat dose setting) exhibited depleted B cell levels in blood at D7, with almost no B cells detected at D21. Humanized NSG mice were treated with 3 doses of 0.5 mg/kg CD20 TDB weekly intravenously. Blood was collected at D-5 (5 days before treatment), D7, D14, and D21. Murine B cell counts in blood were measured by FACS.

Figure 60B:
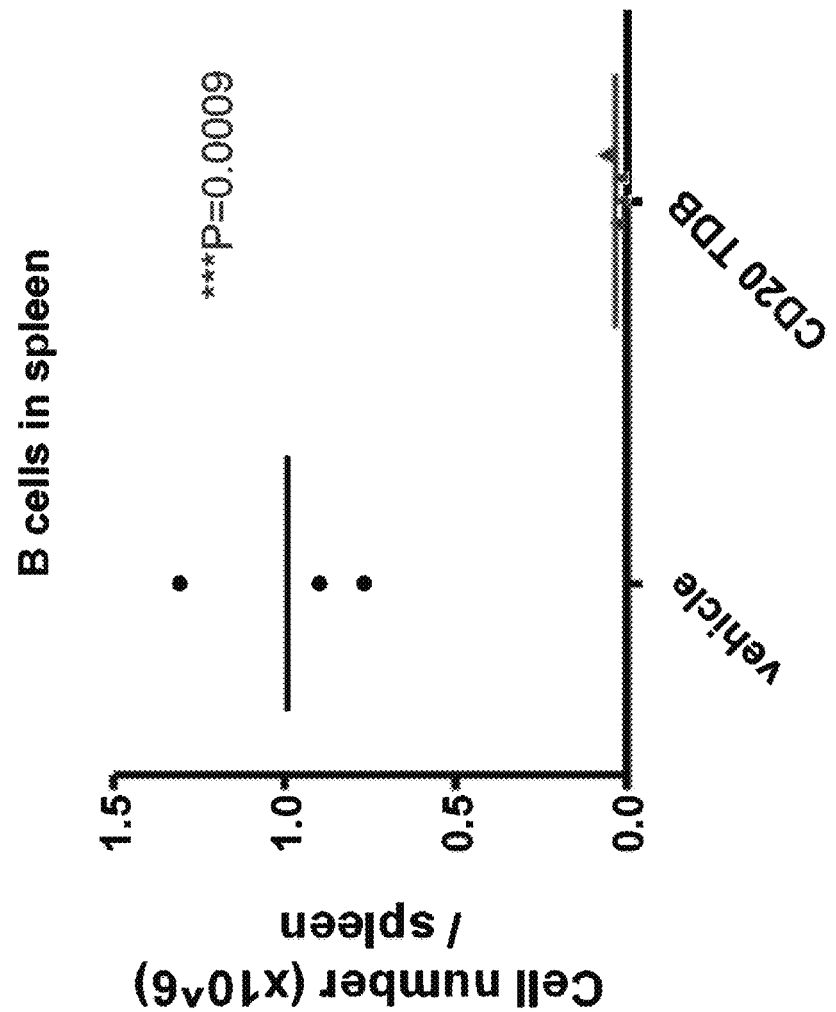

FIG. 60B is a graph showing that robust B cell depletion at D21 is observed in spleens of humanized NSG mice treated with CD20 TDB. Humanized NSG mice were treated with 3 doses of 0.5 mg/kg CD20 TDB weekly via intravenously. Spleens were collected at D21. Murine B cell counts in spleen were measured by FACS.

Figure 60C:
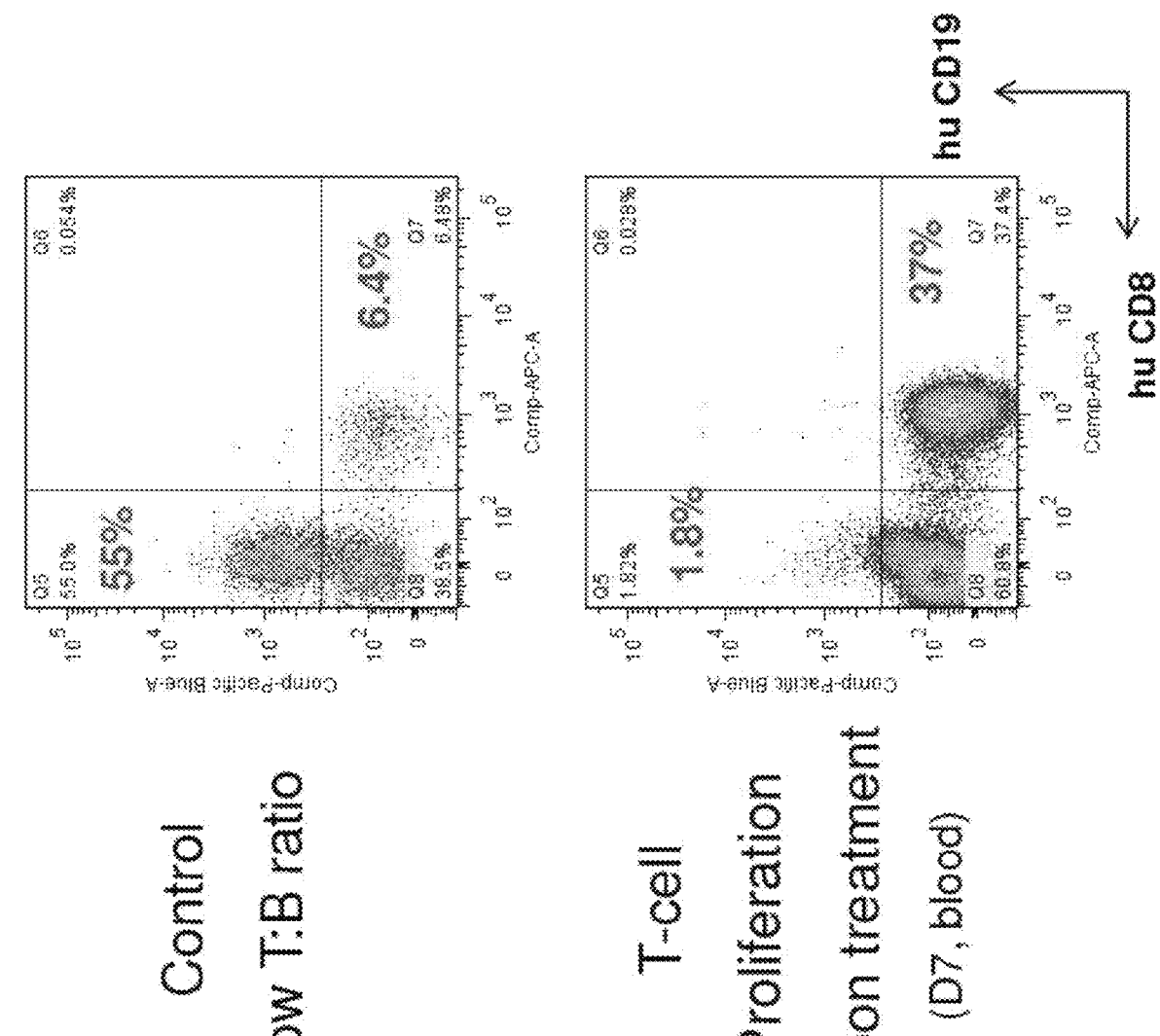

FIG. 60C is a series of flow cytometry graphs showing that huCD8+ T cells proliferate and huCD19+ B cells are depleted 7 days following treatment (D7) of humanized NSG mice with CD20 TDB. Humanized NSG mice were treated with vehicle or 0.5 mg/kg CD20 TDB (2H7v16/UCHT1v9). The spleens of control and CD20 TDB treated humanized NSG mice were collected on D7. B cells expressing huCD19 and T cells expressing huCD8 were measured by FACS.

Figure 60D:
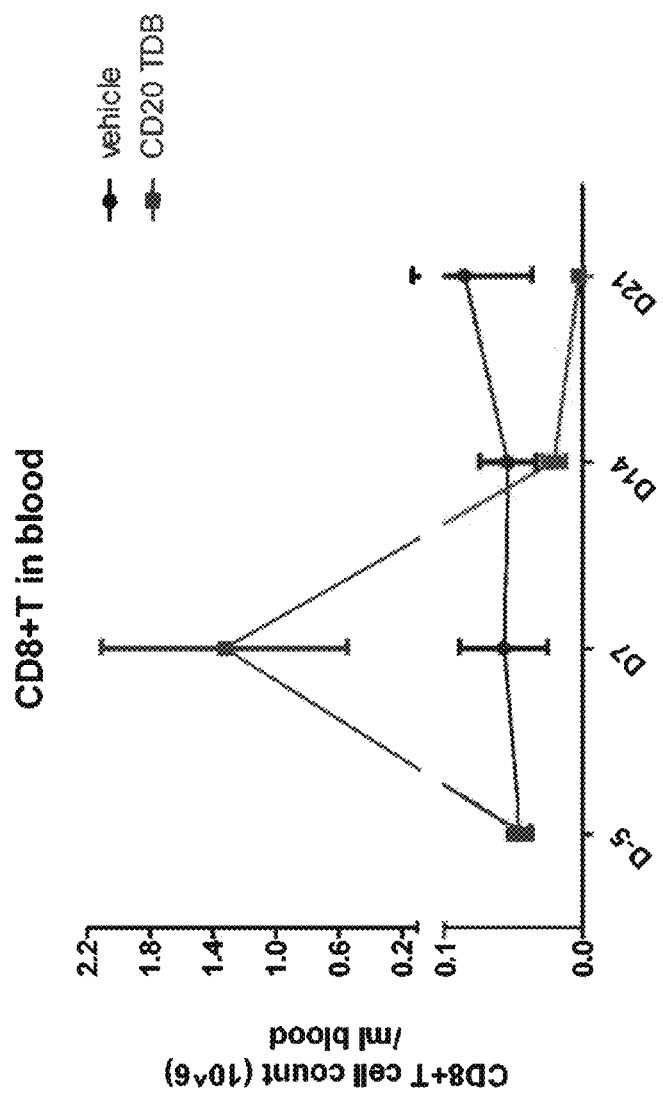

FIG. 60D is a graph showing that humanized NSG mice treated with 3 weekly doses of CD20 TDB at 0.5 mg/kg (repeat dose setting) exhibited an up to 10-fold increase in CD8+ T cell count at D7, which returned to baseline level or lower by D14 and D21. Humanized NSG mice were treated with 3 doses of 0.5 mg/kg CD20 TDB weekly via iv. Blood was collected at D-5 (5 days before treatment), D7, D14, and D21. Murine CD8+ T cell counts in blood, and T cell activation was measured by FACS.

FIG. 60E is a series of flow cytometry graphs showing the baseline levels of huCD20+ B cells (center panels) and huCD8+ and huCD4+ T cells (right panels) from 2 humanized NSG mice as measured by FACS.

FIG. 60F is a series of graphs showing the levels of cell surface expression of huCD3$_\epsilon$ and CD20 expression on CD19+ B cells (left), CD8+ T cells (center), and CD4+ T cells (right) as detected by FACS.

Figure 61A:
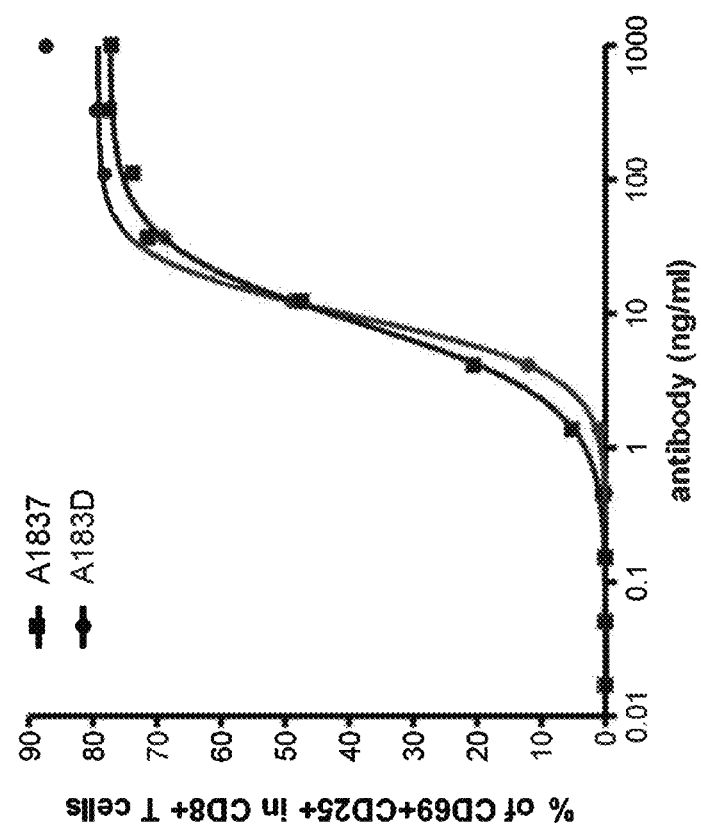
Figure 61B:
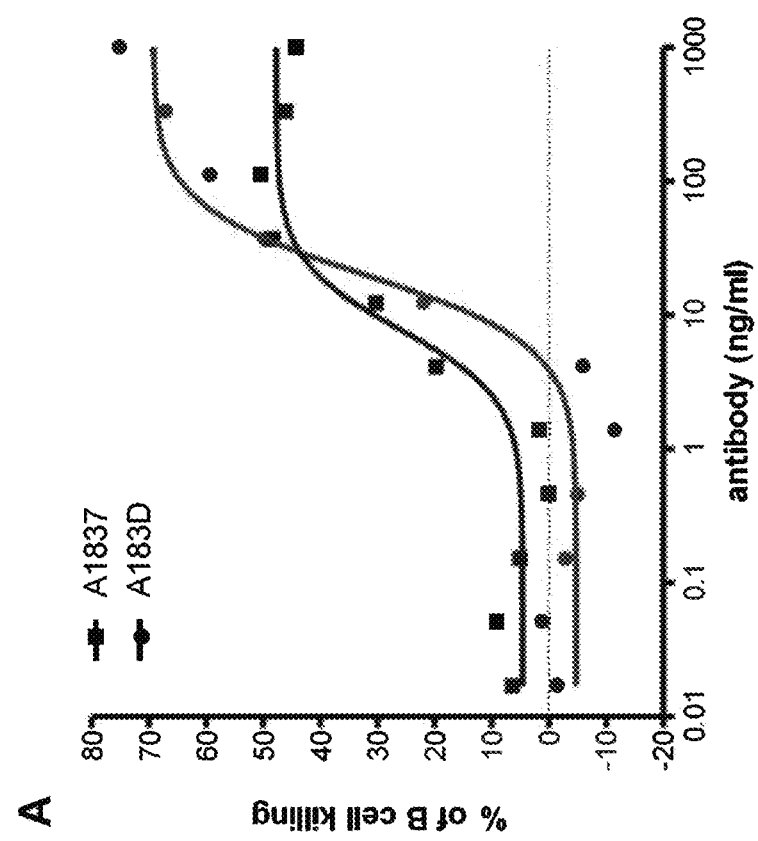

FIG. 61A is a graph showing that CD20 TDB is potent in killing CLL B cells with autologous T cells. 200,000 PBMCs were incubated with various concentration of CD20 TDB for 48 hours in RPMI media supplemented with 10% FBS. FIG. 61B is a graph showing that CD20 TDB is potent in inducing activation of autologous T cells in the presence of CLL B cells. 200,000 PBMCs were incubated with various concentration of CD20 TDB for 48 hours in RPMI media supplemented with 10% FBS.

Figure 61C:
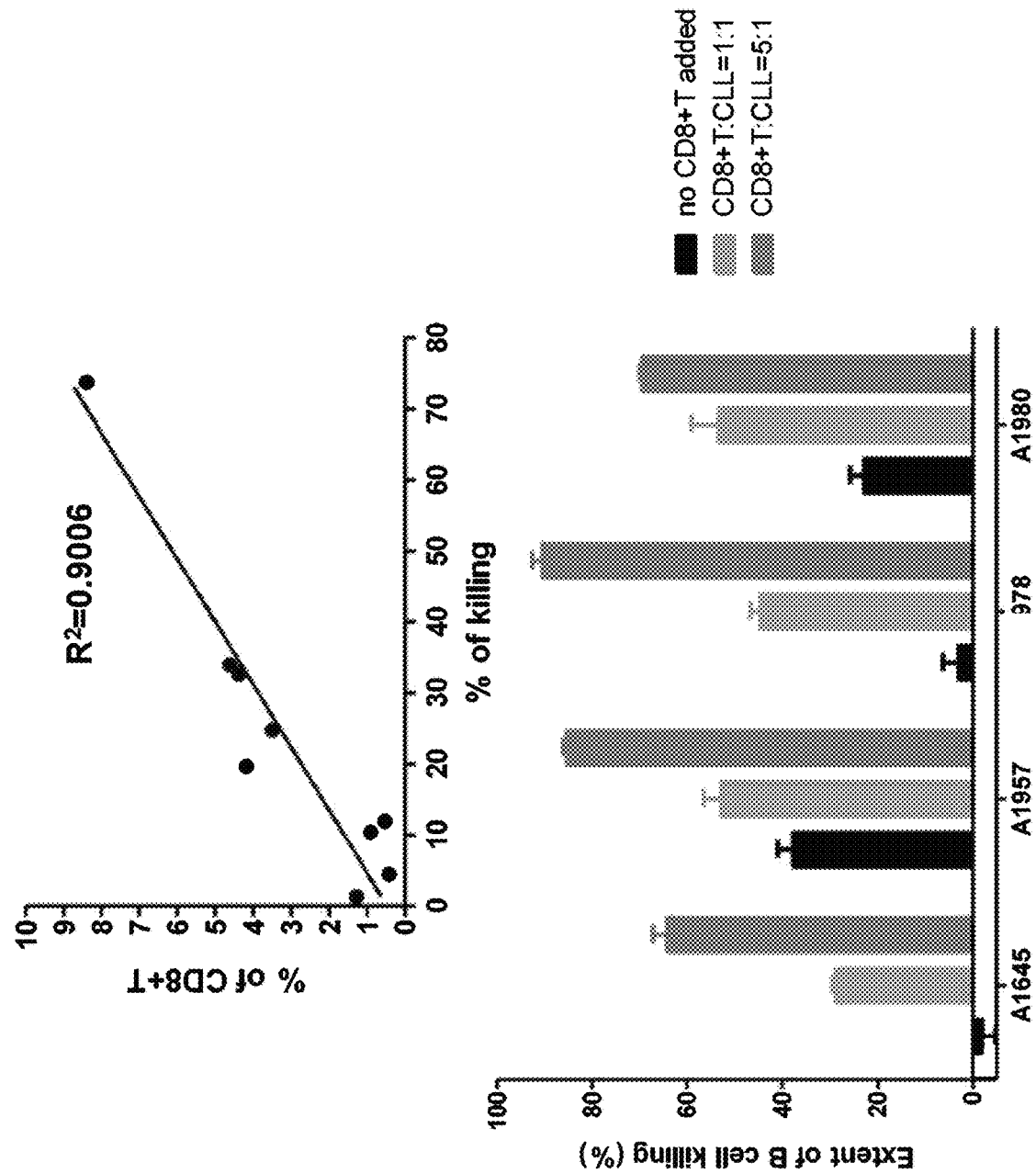

FIG. 61C is a set of graphs showing that T cell count is highly correlative with killing of CLL B cells ex vivo. 200,000 PBMCs were incubated with 1000 ng/ml CD20 TDB for 48 hours, either alone or with added CD8+ T cells purified from healthy donor. The percentage of CD19+CD5+ B cells and CD8+ T cells in CLL PBMCs are 90/0.55 for sample A1645, 76/3.5 for A1957, 87/0.63 for A1978, 69/1.3 for A1980. Cell killing, Granzyme B induction, and T cell activation were measured by FACS as described below.

Figure 62A:
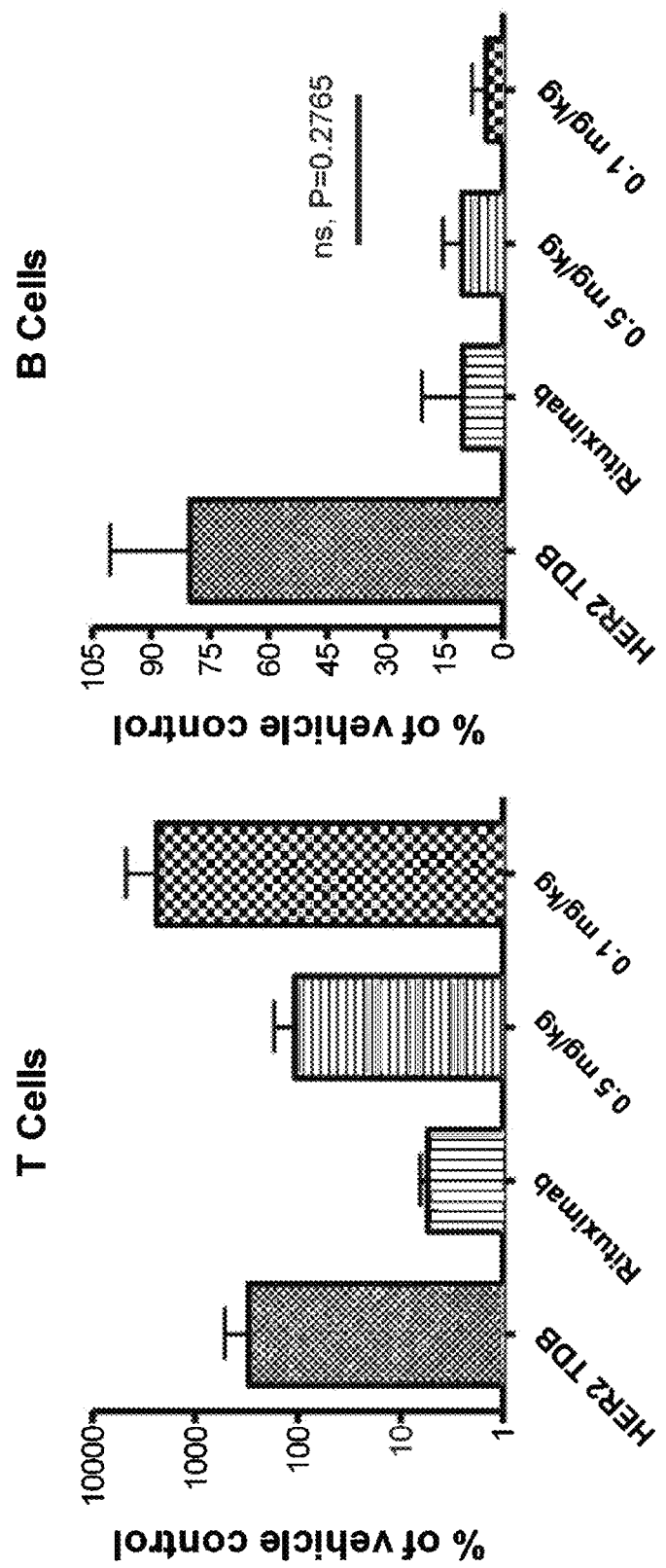

FIG. 62A is a set of graphs showing that T cell activation (left) following 0.1 mg/kg or 0.5 mg/kg dosages of CD20 TDB to NSG mice with engrafted CLL leukemia cells correlated with the potent depletion of engrafted CLL B cells (right).

Figure 62B:
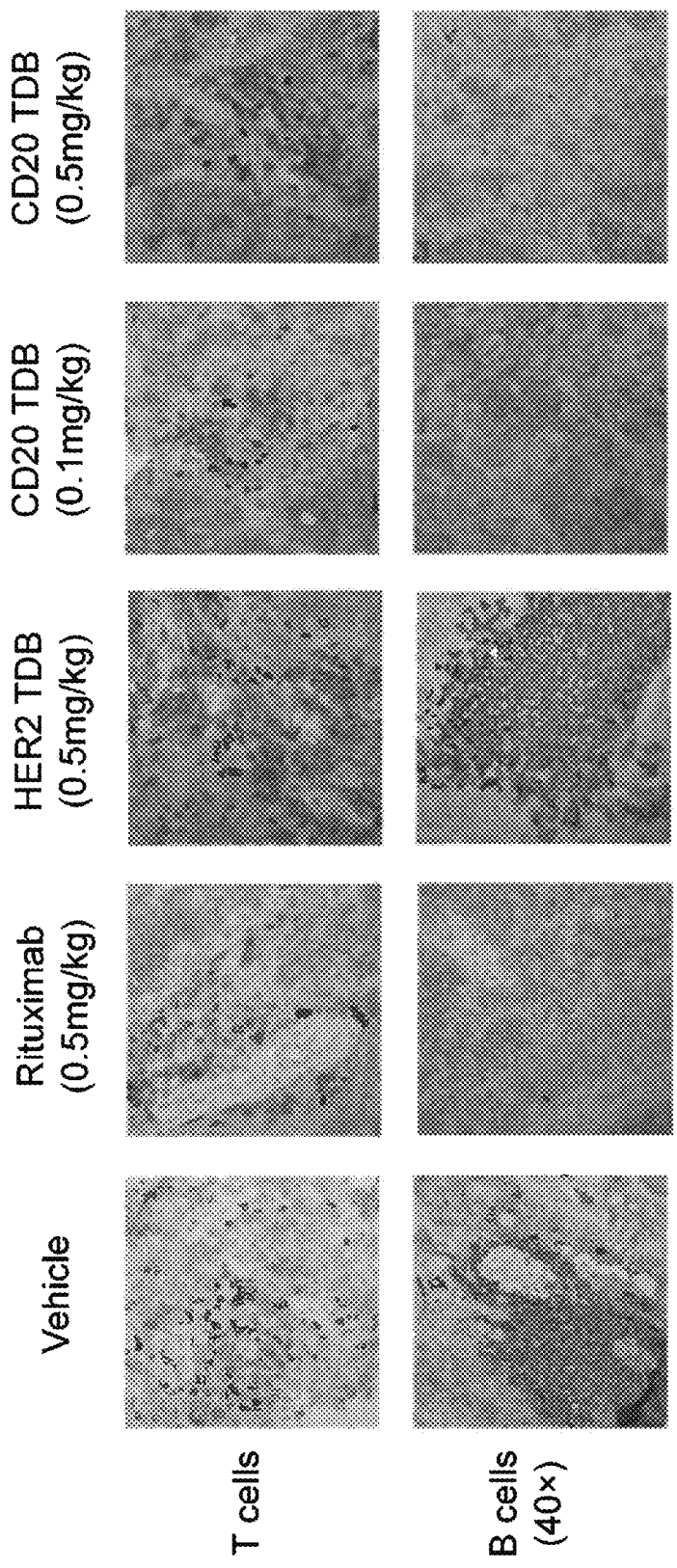

FIG. 62B is a set of immunohistochemistry images of spleen sections from NSG mice with engrafted CLL leukemia cells, showing that few B cells are detectable following CD20 TDB treatment. B cells and T cells were engrafted in NSG mice as described below. Mice were treated once intravenously with HER2 TDB, and rituximab at 0.5 mg/kg, CD20 TDB at 0.1 and 0.5 mg/kg, and spleens were collected for FACS analysis 14 days after treatment.

Figure 63:
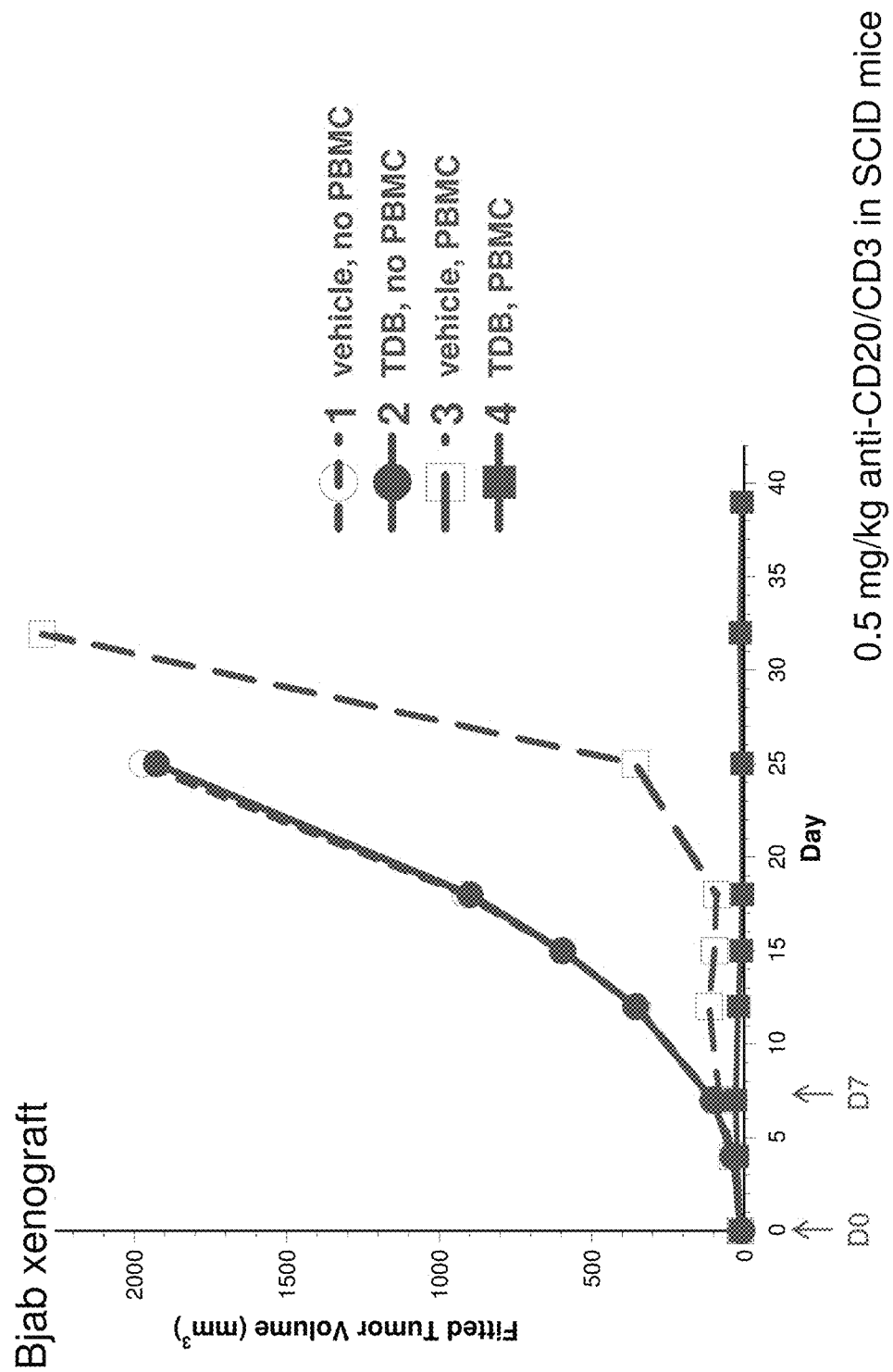

FIG. 63 is a graph showing the fitted tumor volume over time of Bjab engrafted tumors of SCID mice for Group 1 (vehicle: 20 mM Histidine/acetate pH 5.5, 240 mM Sucrose, 0.02% Tween 20); Group 2 (CD20 TDB: 2H7v114/UCHT1.v9; 0.5 mg/kg); Group 3 (vehicle: 20 mM Histidine/acetate pH 5.5, 240 mM Sucrose, 0.02% Tween 20, PBMC); and Group 4 (CD20 TDB: CD20 2H7v114/CD3 UCHT1.v9; 0.5 mg/kg, PBMC). Effector cells were PBMCs derived from healthy human donor. Mice were treated once per week for two weeks.

FIG. 64A is a graph showing the relative level of CD20 expression on Bjab, NALM-6, SC-1, and OCI-LY 19 cells. B cells and T cells were engrafted in NSG mice as described below. Mice were treated once intravenously with HER2 TDB, and rituximab at 0.5 mg/kg, CD20 TDB at 0.1 and 0.5 mg/kg, and spleens were collected for IHC analysis 14 days after treatment.

Figure 64B:
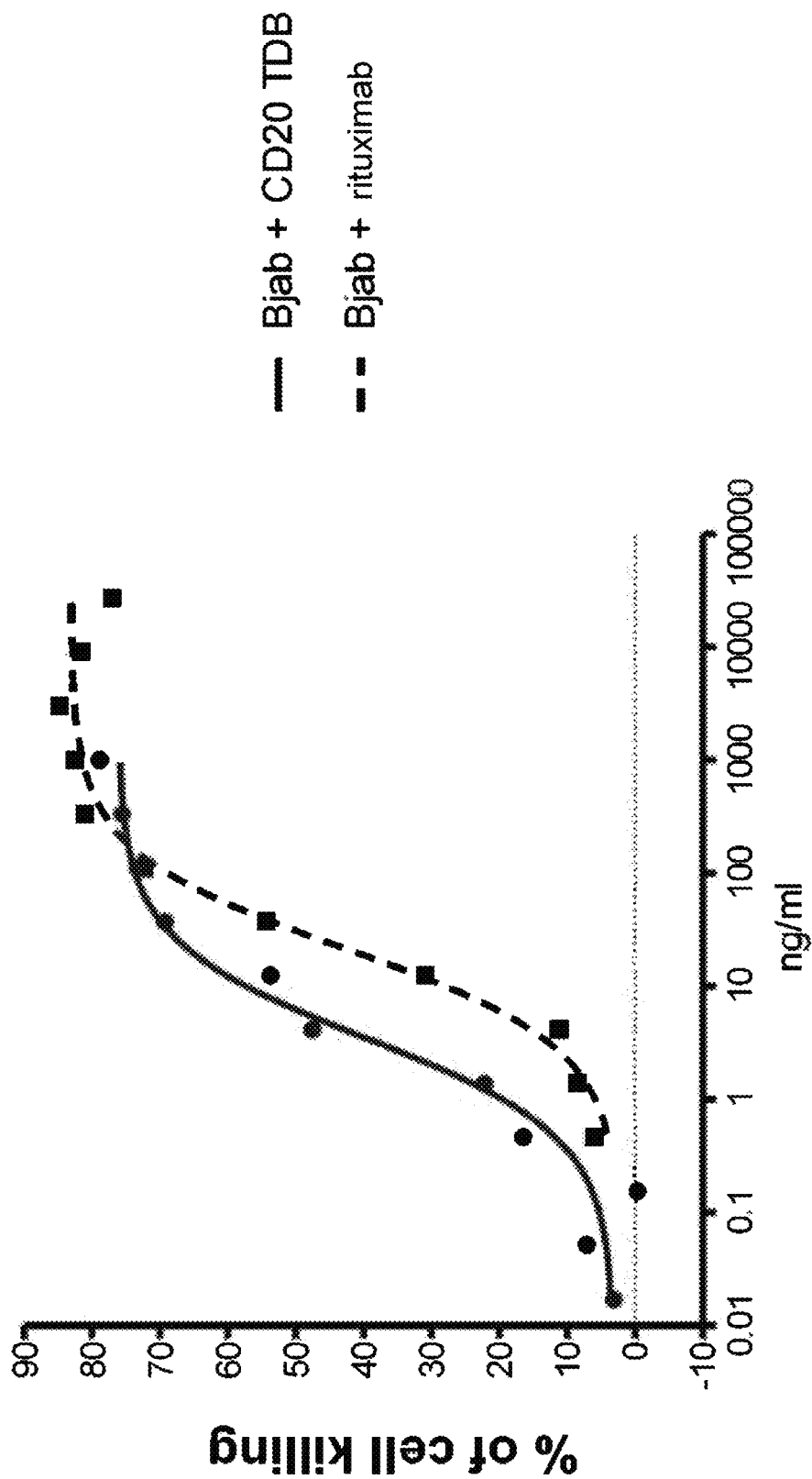

FIG. 64B is a graph showing that rituximab and CD20 TDB are comparable in their efficacy for killing Bjab cells in vitro, which express a high level of CD20 on their cell surface. PBMCs isolated from healthy donor were depleted of B cells, and used as effector cells in the in vitro cell killing assay. 20,000 B cells and 200,000 effector cells were incubated with various concentration of CD20 TDB or rituximab for 24 hours. CD20 TDB expression was detected by FACS.

Figure 64C:
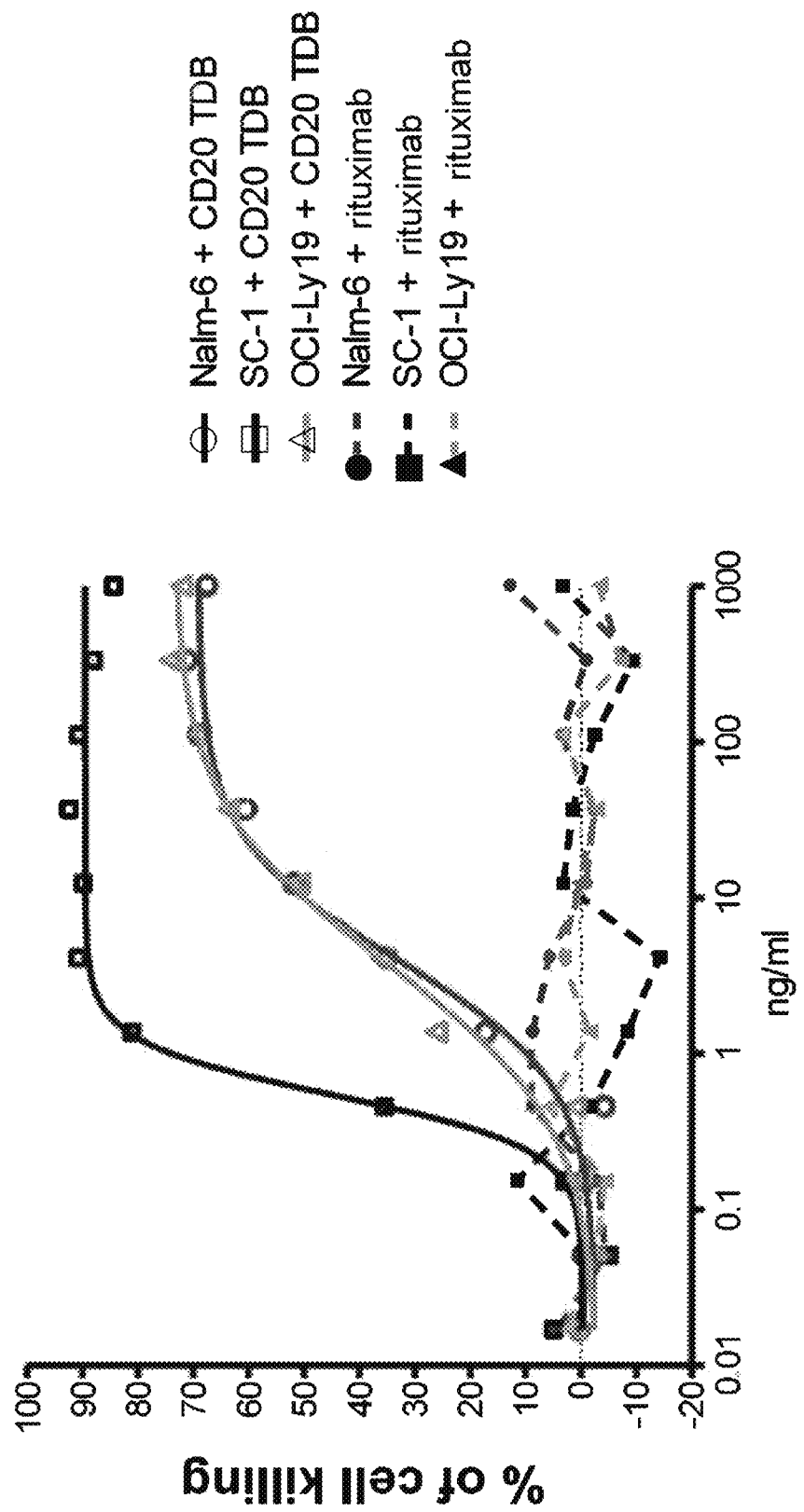

FIG. 64C is a graph showing that CD20 TDB, but not rituximab, is capable of killing NALM-6, SC-1, and OCI-LY 19 cells, which have relatively low levels of CD20 on their cell surface. PBMCs isolated from healthy donor were depleted of B cells, and used as effector cells in the in vitro cell killing assay. 20,000 B cells and 200,000 effector cells were incubated with various concentration of CD20 TDB or rituximab for 24 hours. CD20 TDB expression was detected by FACS.

Figure 64D:
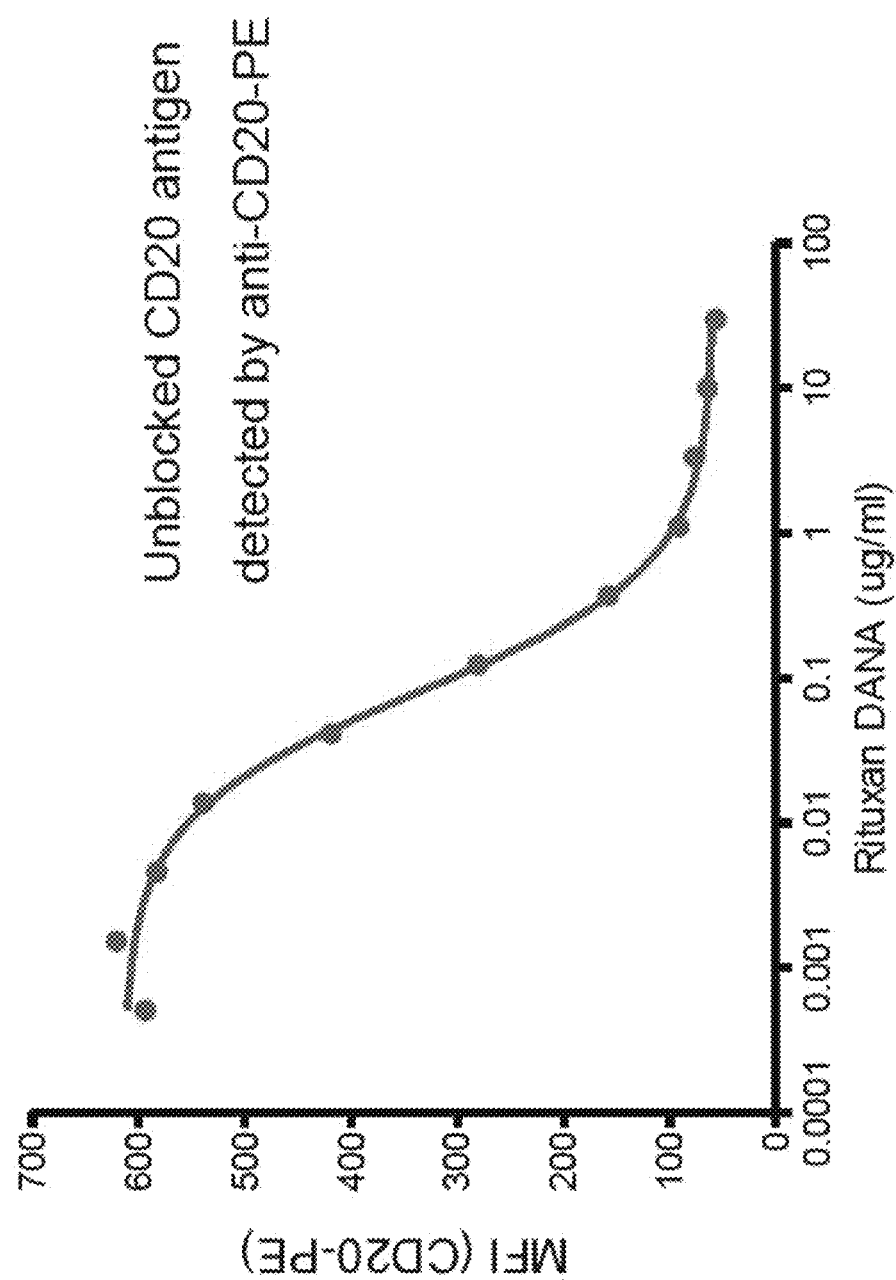

FIG. 64D is a graph showing B cell surface expression levels of unblocked CD20 antigen as a function of the concentration of Rituximab-DANA as measured by FACS. CD20/CD3 double transgenic mice were treated with a single dose of vehicle or Rituximab-DANA (10 mg/kg). Spleens were harvested 5 days post-treatment.

Figure 65A:
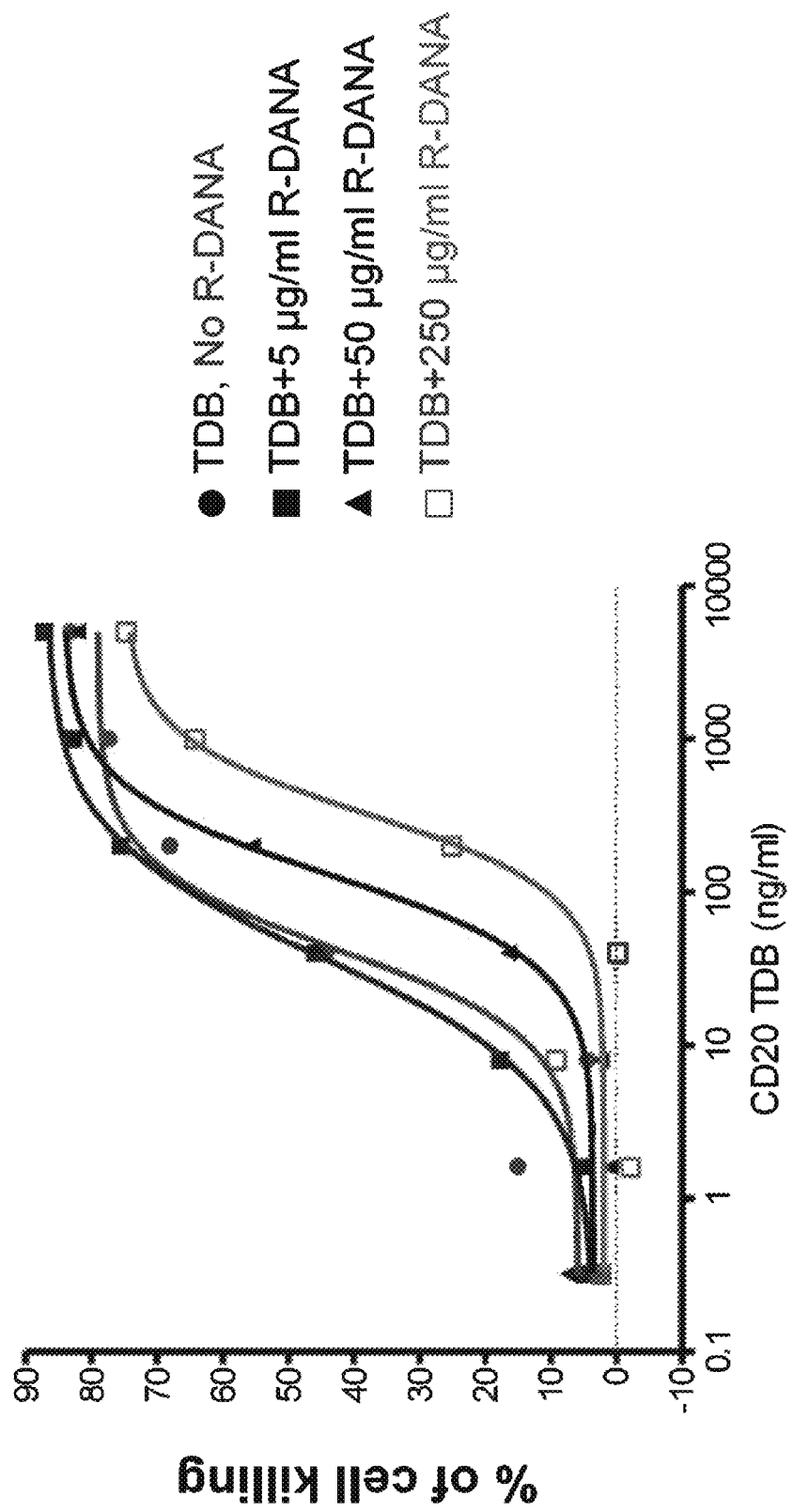
Figure 65B:
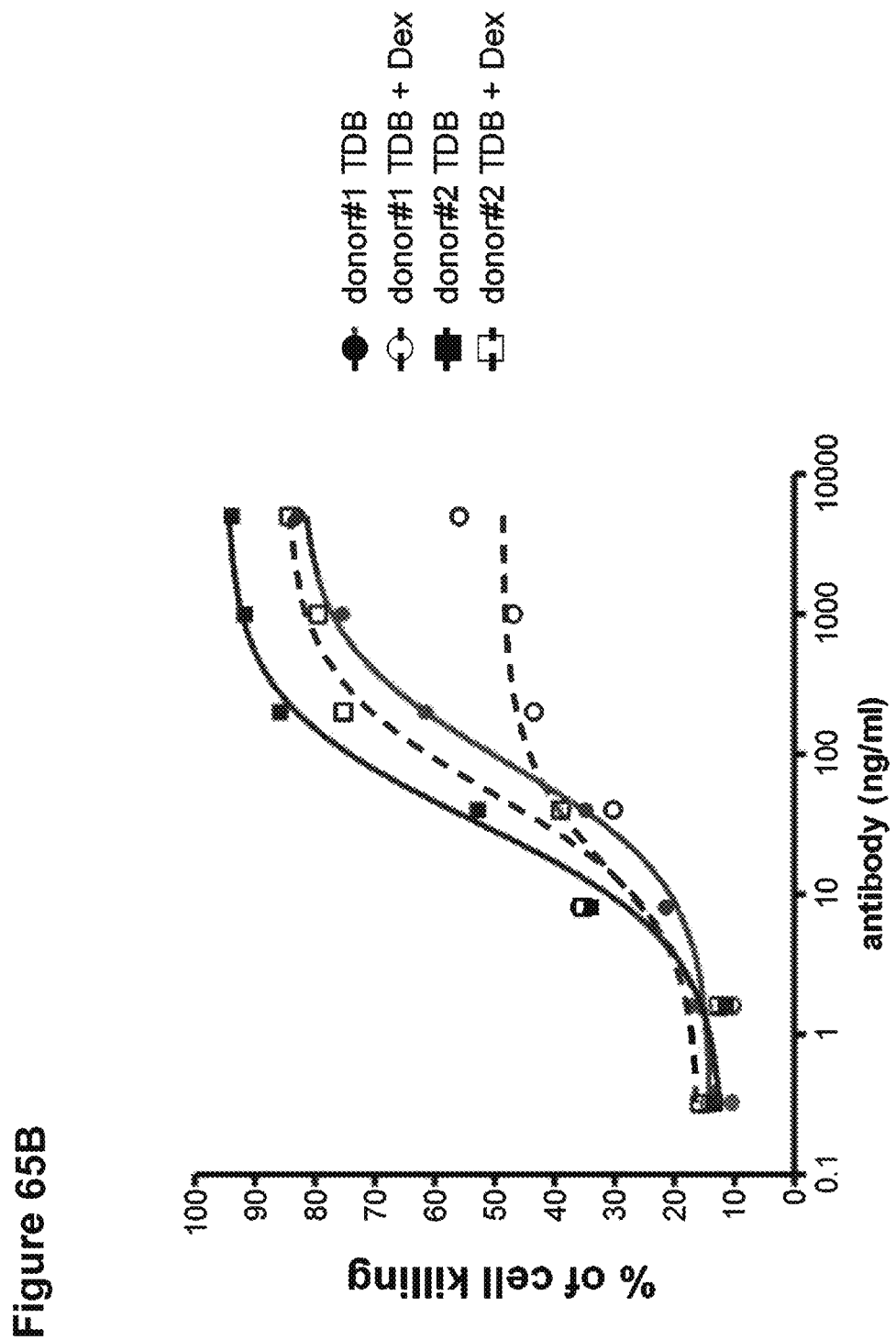

FIGS. 65A and 65B are graphs showing that CD20 TDB is active in killing B cells in vitro in the presence of high levels of rituximab (A) or dexamethasone (B). 200,000 PBMCs isolated from healthy donor were first incubated with rituximab-DANA at indicated concentration for 1 hour, CD20 TDB were then added and incubated for 24 hours. For dexamethasone assay, cells were pre-treated with 1 $\mu$M dexamethasone overnight prior to adding CD20 TDB. Cell killing were calculated as described below.

Figure 66:
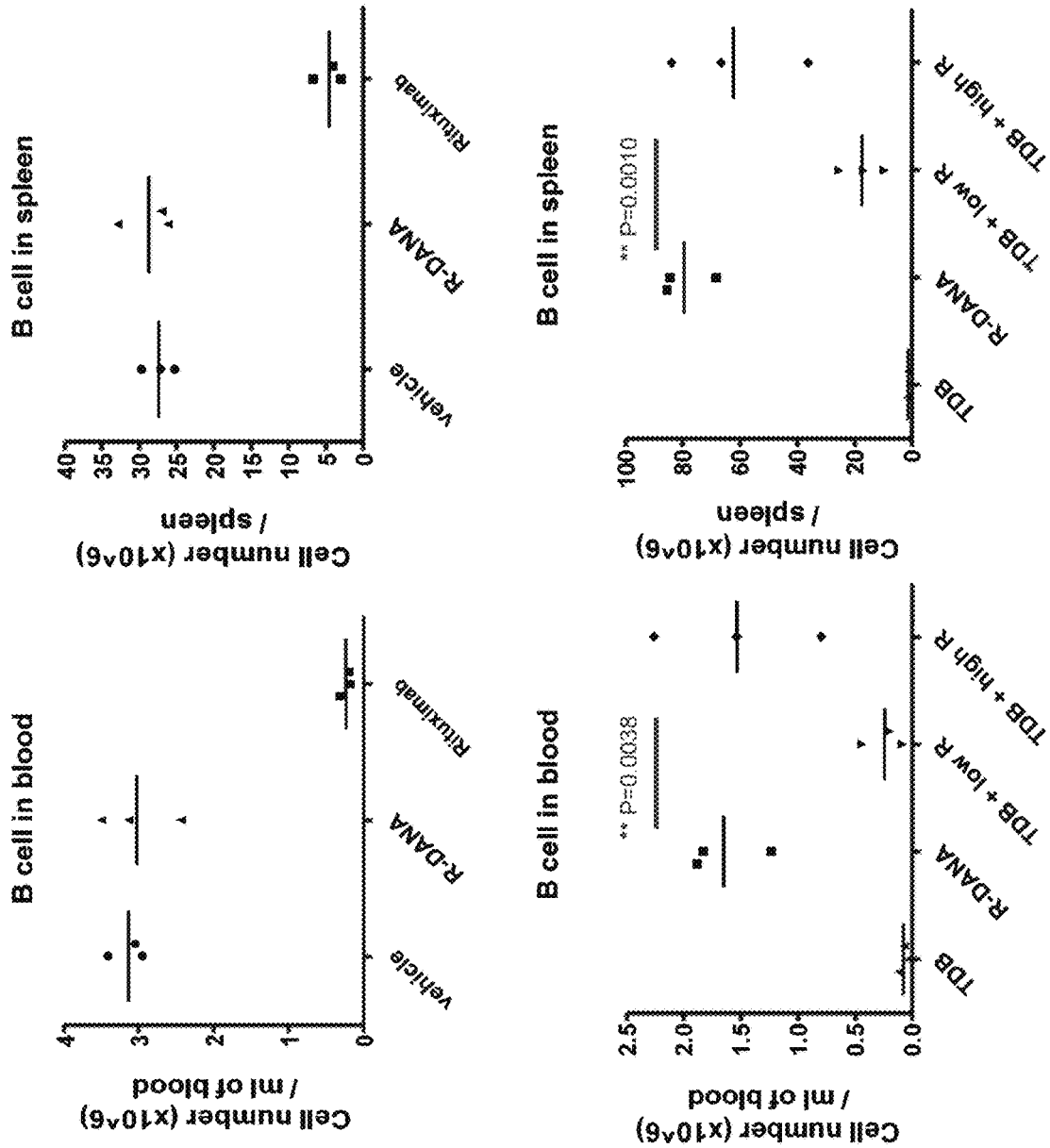

FIG. 66 is a set of graphs showing that CD20 TDB is active in depleting B cells in blood (left) and spleen (right) in mice pre-treated with rituximab-DANA. For single agent treatment, huCD20/CD3 double transgenic mice were treated once intravenously at the dose indicated; for combination treatment, mice were first treated intravenously with rituximab-DANA, and CD20 TDB were injected intravenously 30 minutes later. Blood were collected at D-7, D0-2 h (2 hours after TDB treatment), and D7; spleens were collected at D7. B cell counts were measured by FACS as described below.

Figure 67A:
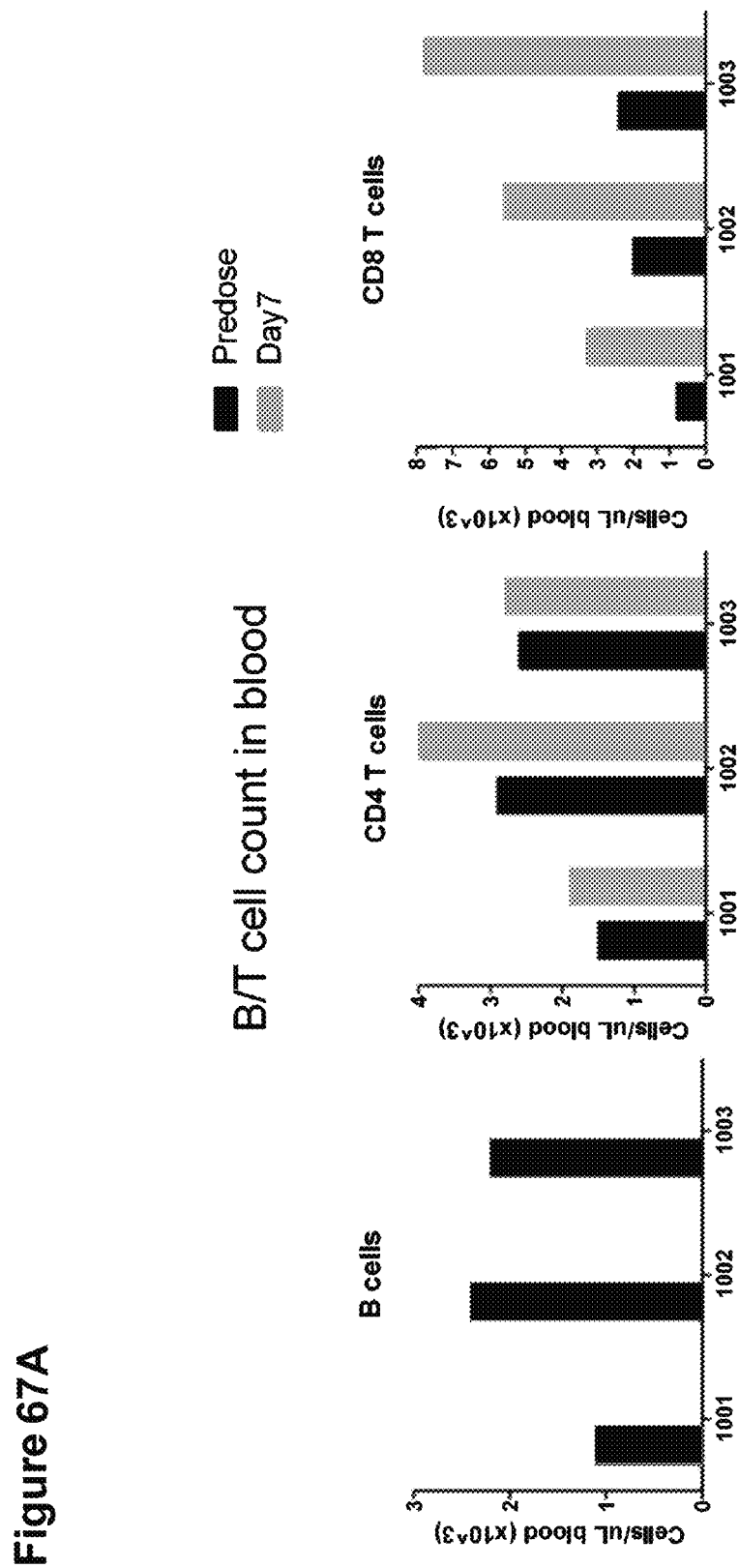

FIG. 67A is a set of graphs showing the B cell (left), CD4+ T cell (middle), and CD8+ T cell (right) count in blood samples from 3 cynomolgus monkeys before and 7 days after treatment with a single intravenous dose of 1 mg/kg CD20 TDB. Three cynomolgus monkeys were treated once intravenously with 1 mg/kg CD20 TDB. Blood were collected at D-7 (7 days prior to dosing), D0-4 hr (4 hours right after dosing), and D7.

Figure 67B:
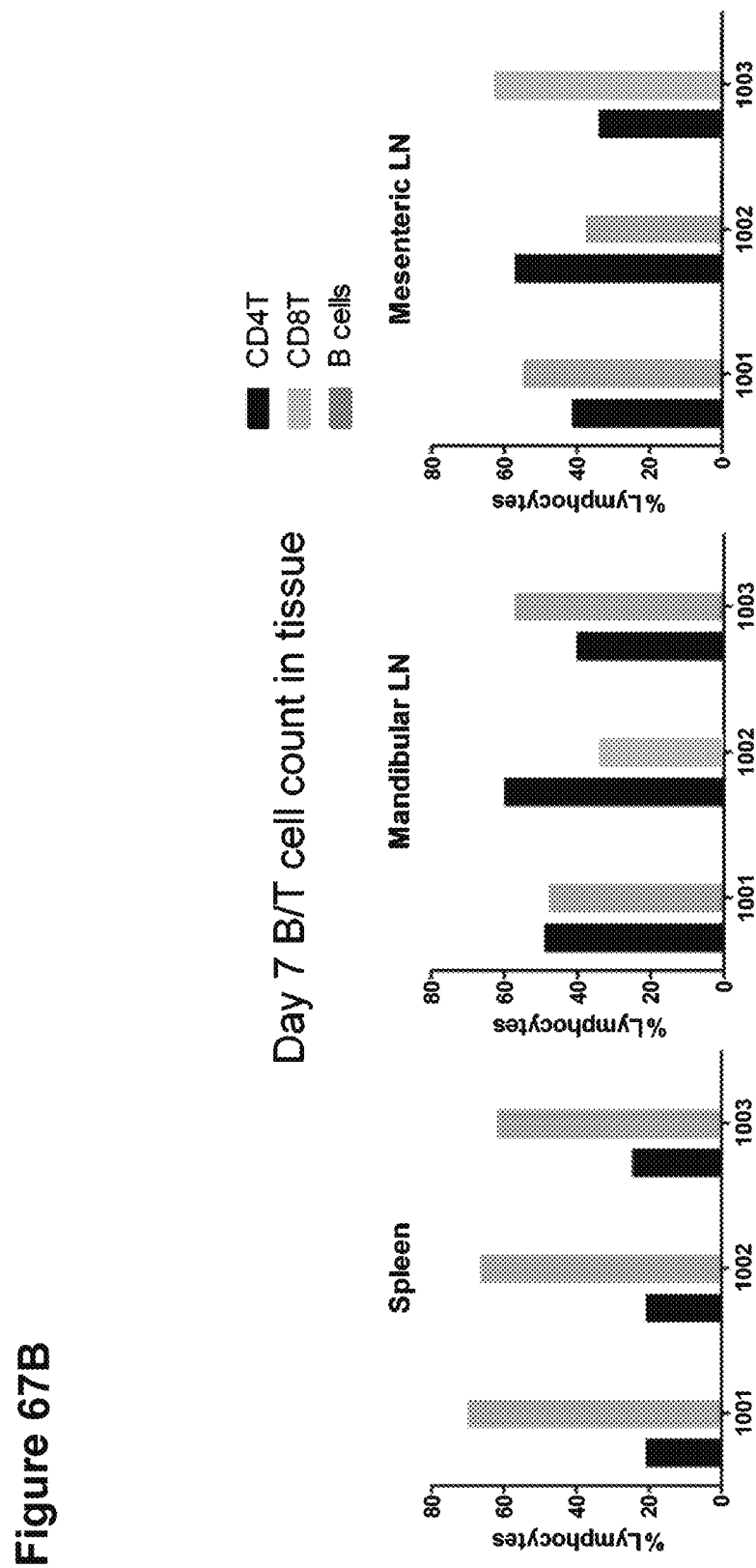

FIG. 67B is a set of graphs showing B cell, CD4+ T cell, and CD8+ T cell levels in the spleen (left), mandibular lymph nodes (middle), and mesenteric lymph nodes (right) of 3 cynomolgus monkeys 7 days after treatment with a single intravenous dose of 1 mg/kg CD20 TDB. Three cynomolgus monkeys were treated once intravenously with 1 mg/kg CD20 TDB. Blood were collected at D-7 (7 days prior to dosing), D0-4 hr (4 hours right after dosing), and D7.

Figure 67C:
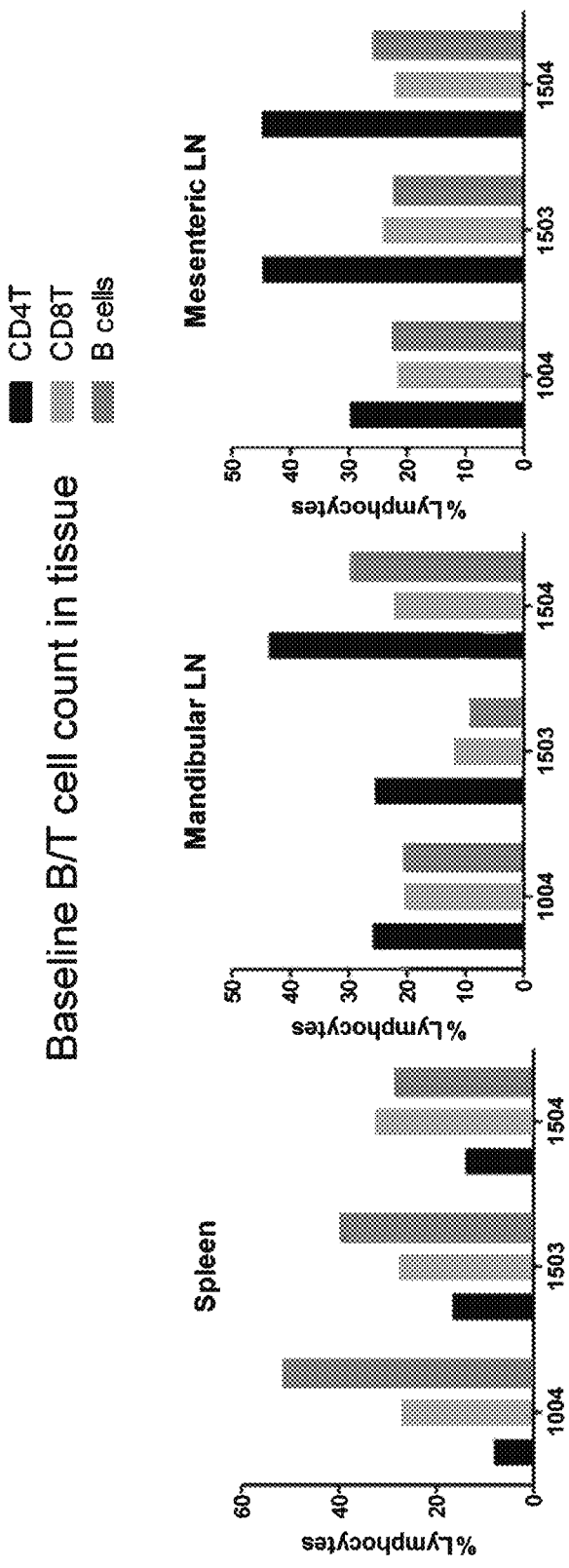

FIG. 67C is a set of graphs showing B cell, CD4+ T cell, and CD8+ T cell levels in the spleen (left), mandibular lymph nodes (middle), and mesenteric lymph nodes (right) of 3 cynomolgus monkeys prior to treatment with a single intravenous dose of 1 mg/kg CD20 TDB. Three cynomolgus monkeys were treated once intravenously with 1 mg/kg CD20 TDB. Blood were collected at D-7 (7 days prior to dosing), D0-4 hr (4 hours right after dosing), and D7.

Figure 67D:
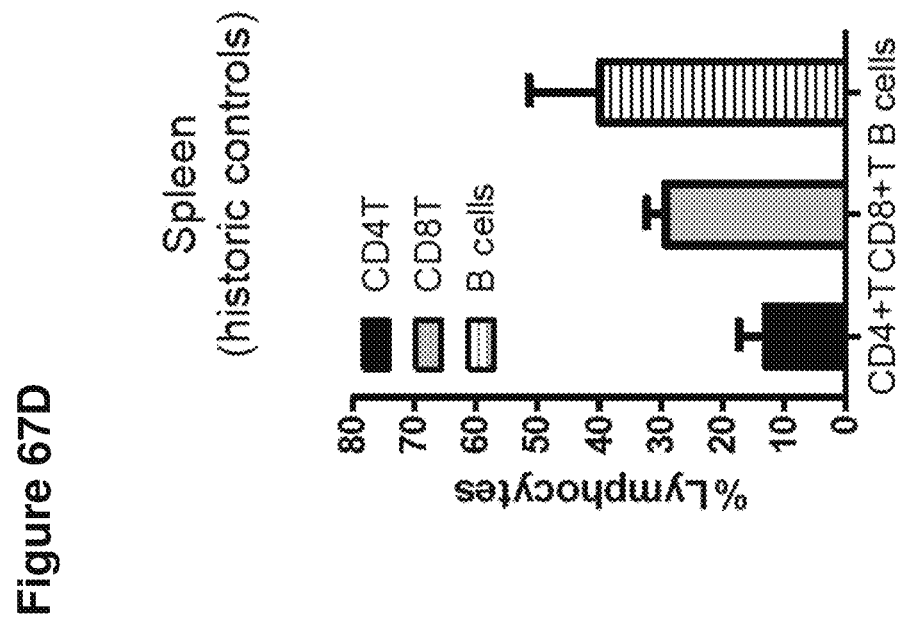

FIG. 67D is a set of graphs showing the baseline levels of B cells and CD4+ and CD8+ T cells as a percentage of total lymphocytes detected in the spleen (left) and the mandibular lymph nodes (right) in vehicle control-treated animals.

Figure 68A:
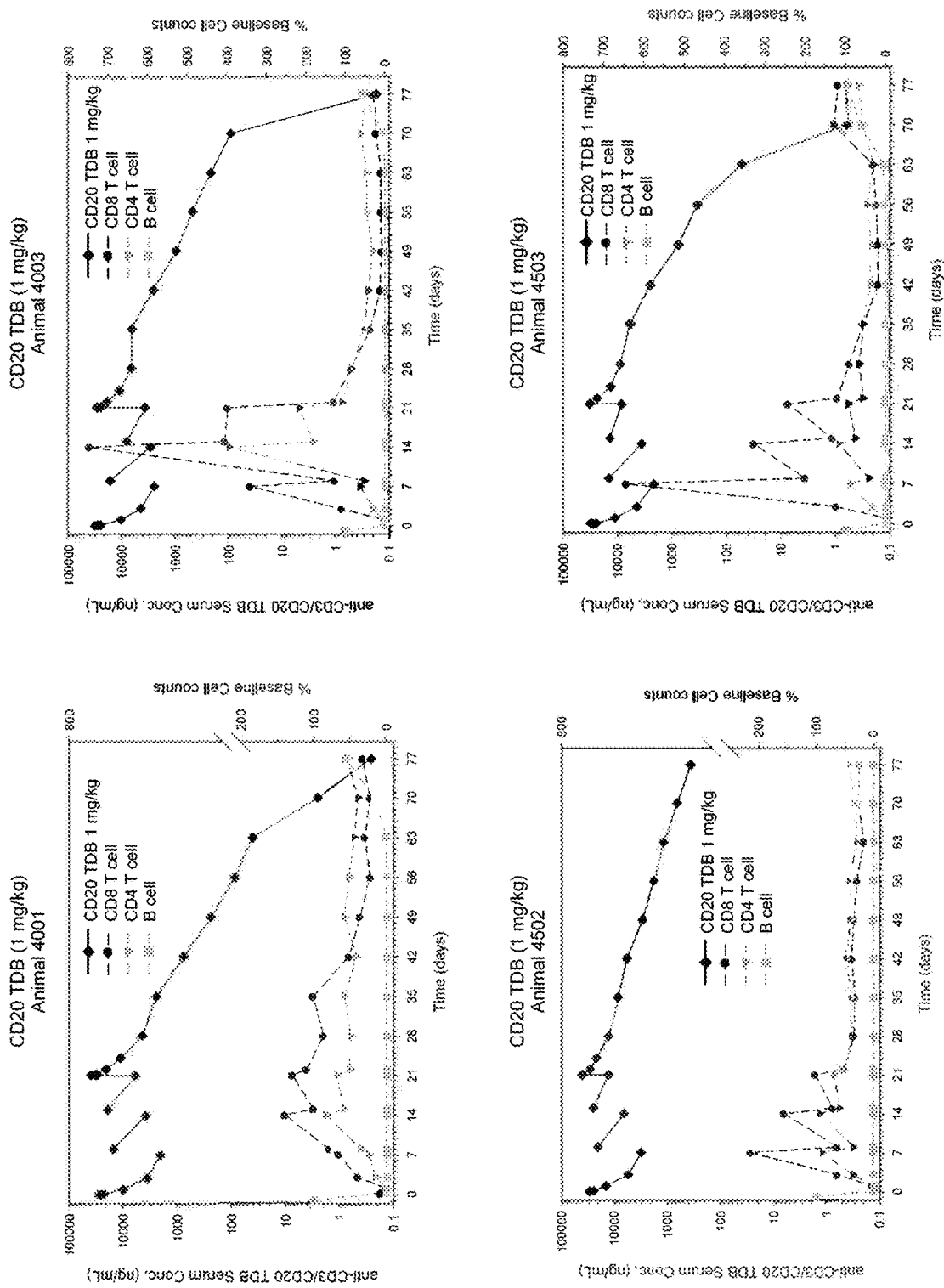

FIG. 68A is a set of graphs showing the CD20 TDB serum concentration from collected blood and serum samples from four cynomolgus monkeys were treated 4-times weekly with 1 mg/kg CD20 TDB via intraveneous administration.

Figure 68B:
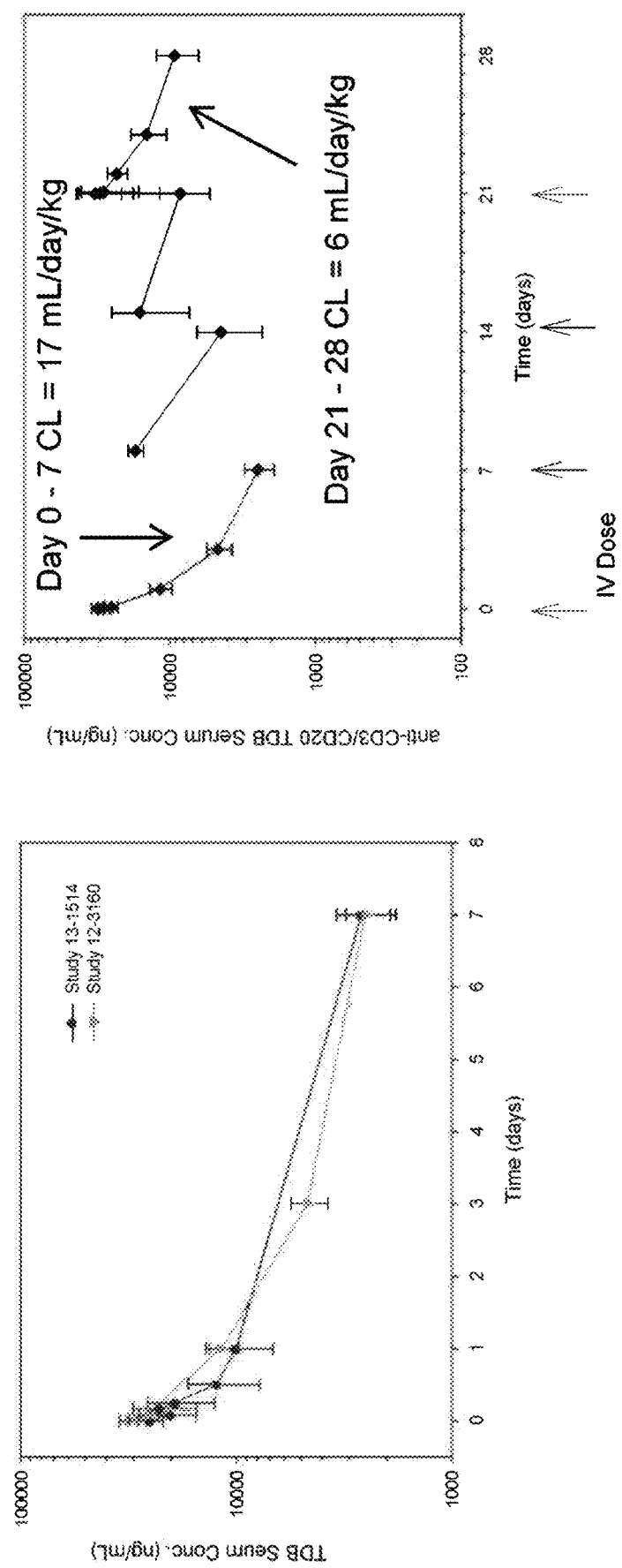

FIG. 68B is a set of graphs showing the CD20 TDB concentration from serum samples collected from animals described in FIGS. 65 and 66A. Mean±s.d. were plotted.

FIG. 69A is histogram showing the expression of PD-L1 expression on A20-huCD20 cells from A20-huCD20 syngeneic Balb/C mice, as assessed by flow cytometry.

FIG. 69B is a graph showing the relative tumor volume over time for Group 1 (vehicle); Group 2 (CD20 TDB at 0.5 mg/kg); Group 3 (anti-PD-L1 antibody at 10 mg/kg); and Group 4 (CD20 TDB at 0.5 mg/kg+anti-PD-L1 antibody).

Figure 70:
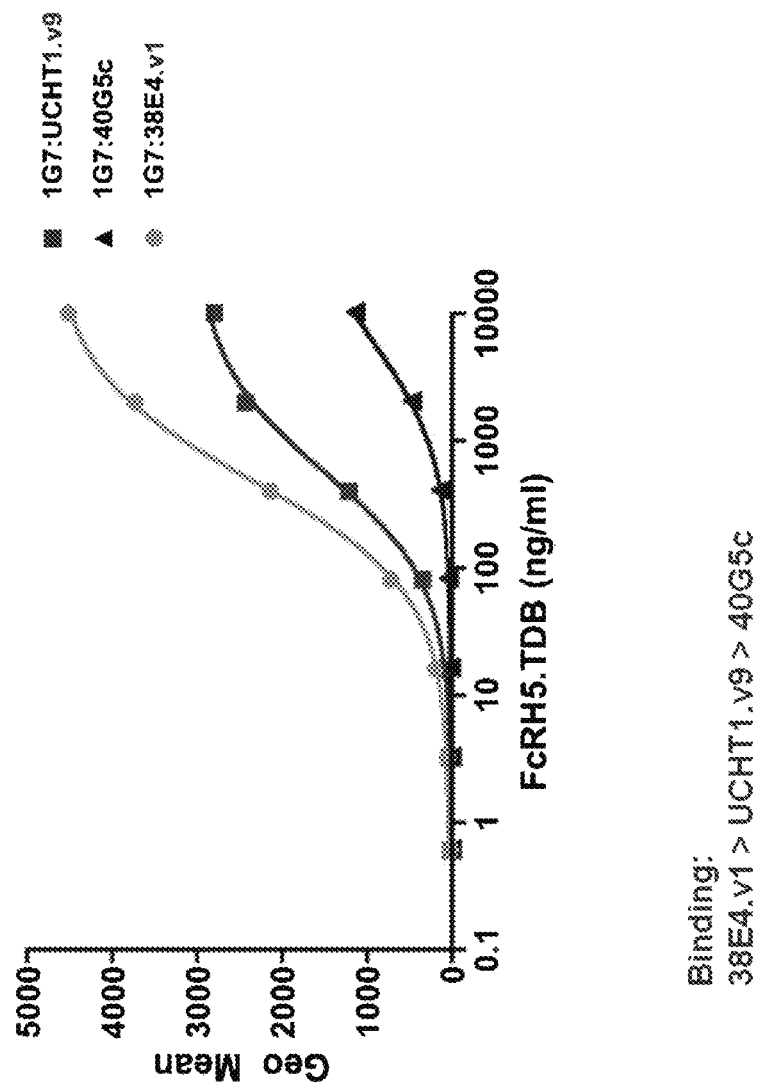

FIG. 70 is a graph showing the binding curves for each of the three tested FcRH5 TDBs tested for in vitro binding to CD8+CD3-expressing T cells.

Figures 71A, 71B:
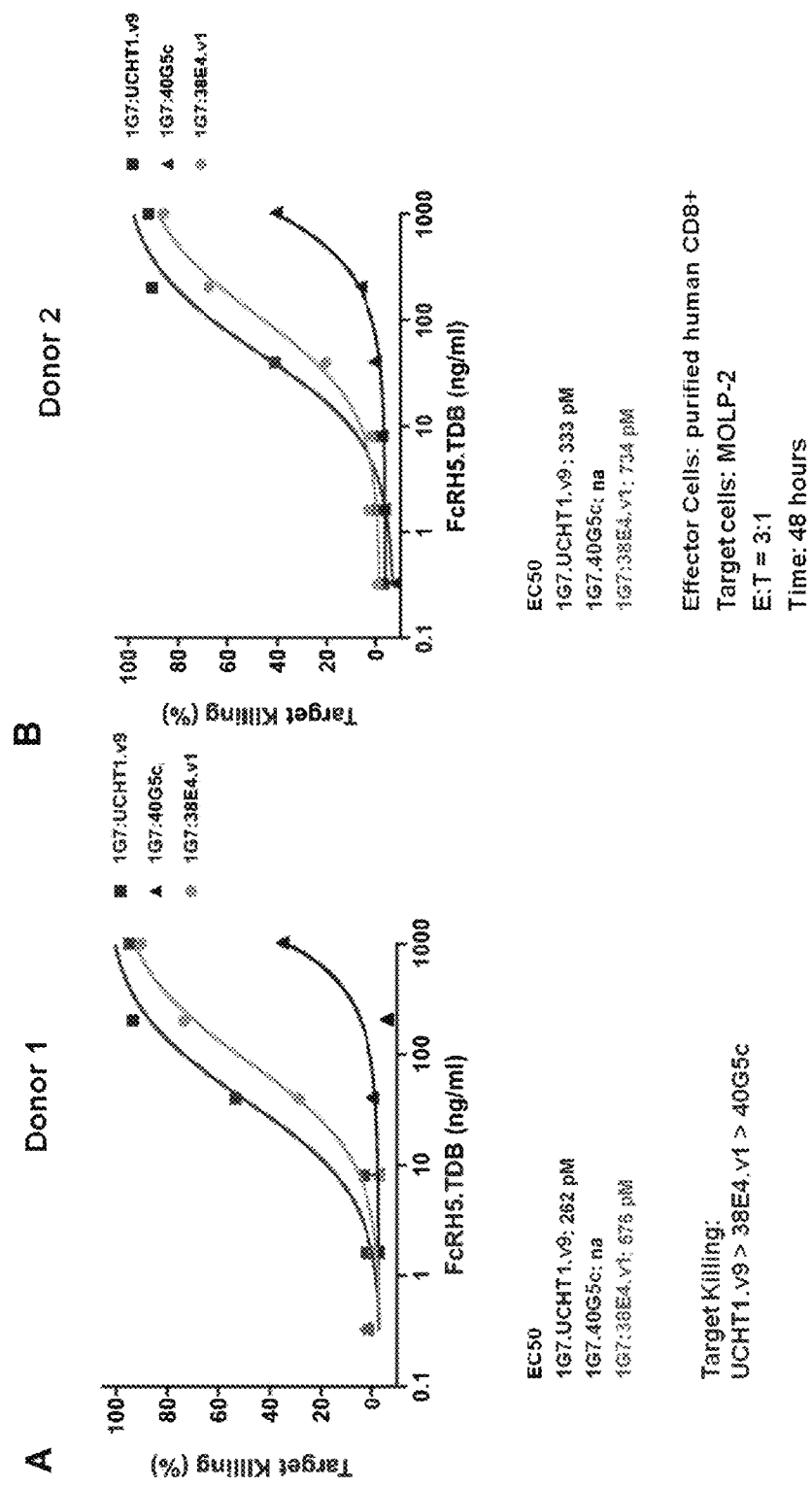

FIG. 71A is a graph showing the percentage of MOLP-2 target cell killing as a function of FcRH5 TDB concentration, with CD8+ T cells purified from human PBMCs from Donor #1.

FIG. 71B is a graph showing the percentage of MOLP-2 target cell killing as a function of FcRH5 TDB concentration, with CD8+ T cells purified from human PBMCs from Donor #2.

Figure 72A:
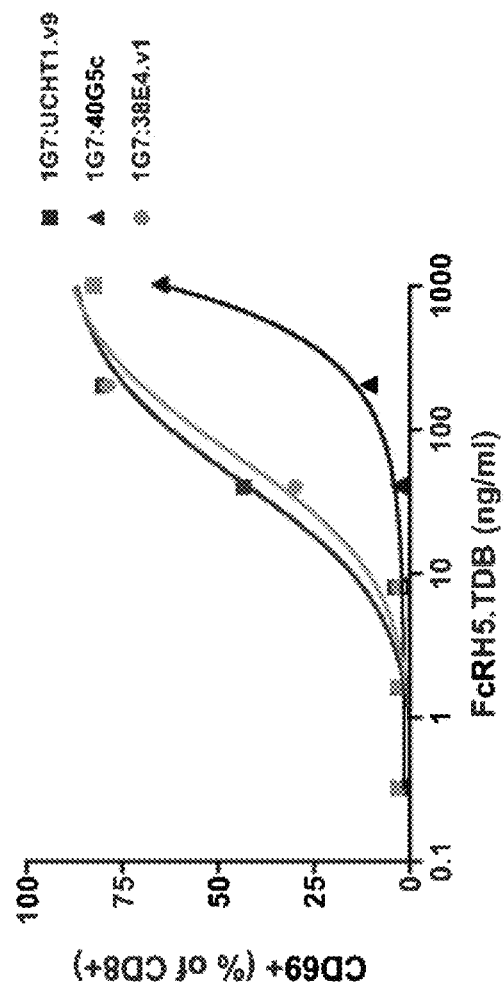

FIG. 72A is a graph showing the percentage of CD8+CD69+ T cells as a function of FcRH5 TDB concentration, as assessed by FACS analysis. Target cells were MOLP-2, and CD8+ T cells were purified from Donor #1.

Figure 72B:
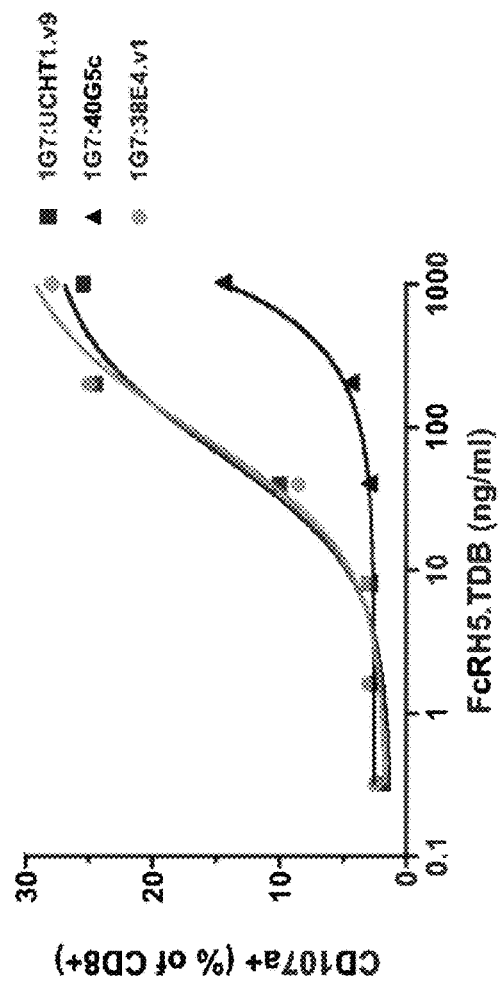

FIG. 72B is a graph showing the percentage of CD8+CD107a+ T cells as a function of FcRH5 TDB concentration, as assessed by FACS analysis. Target cells were MOLP-2, and CD8+ T cells were purified from Donor #1.

Figure 72C:
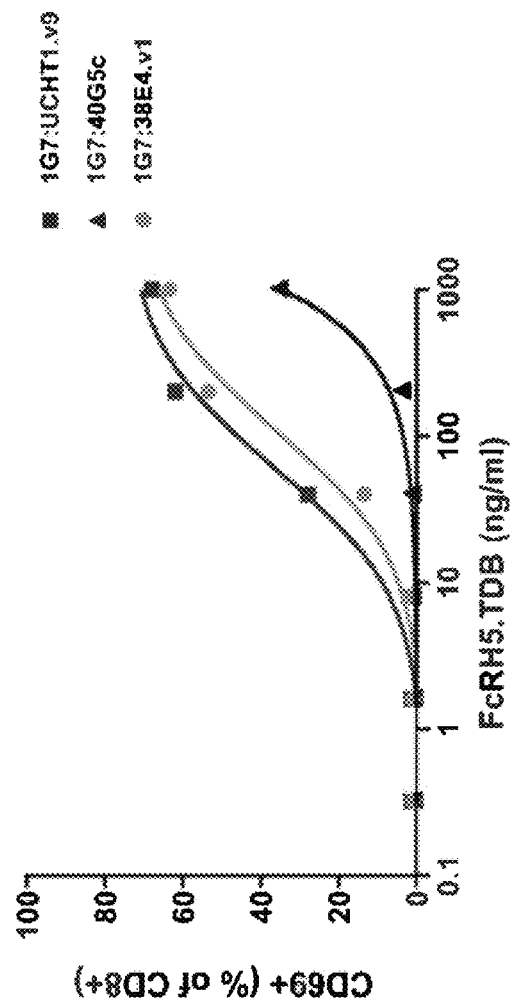

FIG. 72C is a graph showing the percentage of CD8+CD69+ T cells as a function of FcRH5 TDB concentration, as assessed by FACS analysis. Target cells were MOLP-2, and CD8+ T cells were purified from Donor #2.

Figure 72D:
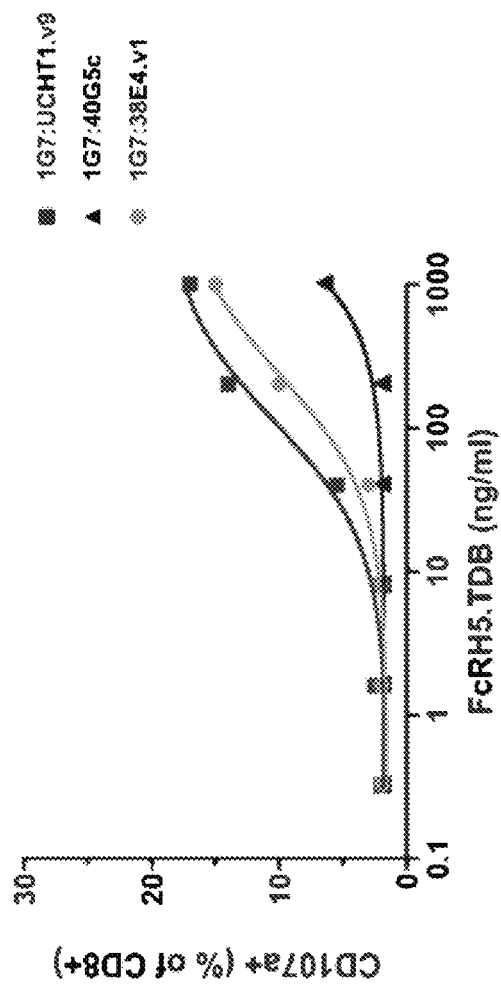

FIG. 72D is a graph showing the percentage of CD8+CD107a+ T cells as a function of FcRH5 TDB concentration, as assessed by FACS analysis. Target cells were MOLP-2, and CD8+ T cells were purified from Donor #2.

Figure 73:
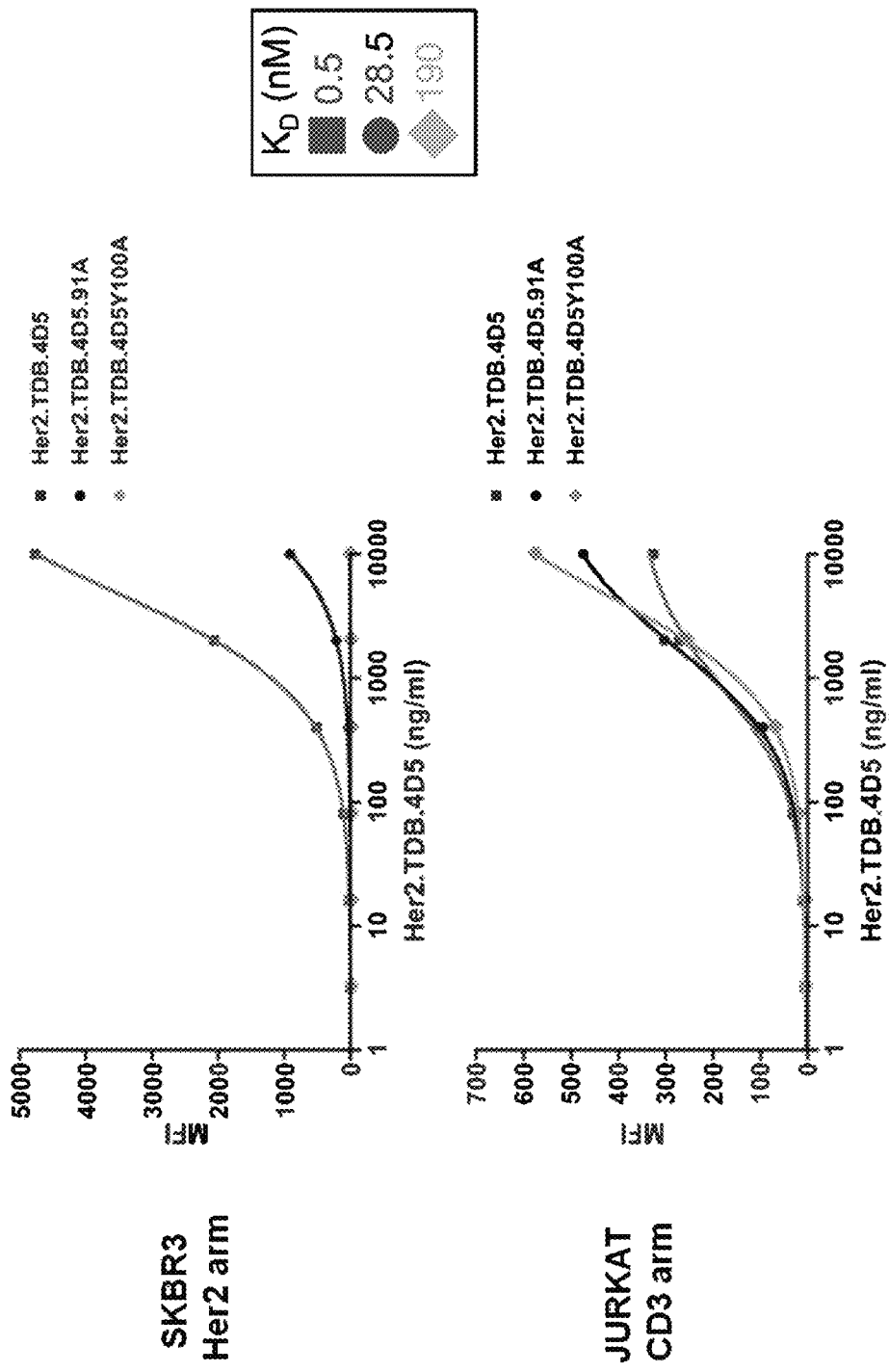

FIG. 73 is a set of graphs showing the binding curves for each of the three HER2 TDBs tested for in vitro binding to Her2-expressing SKBR3 cells (top) and CD8+CD3-expressing T cells (bottom).

Figures 74A, 74B, 74C:
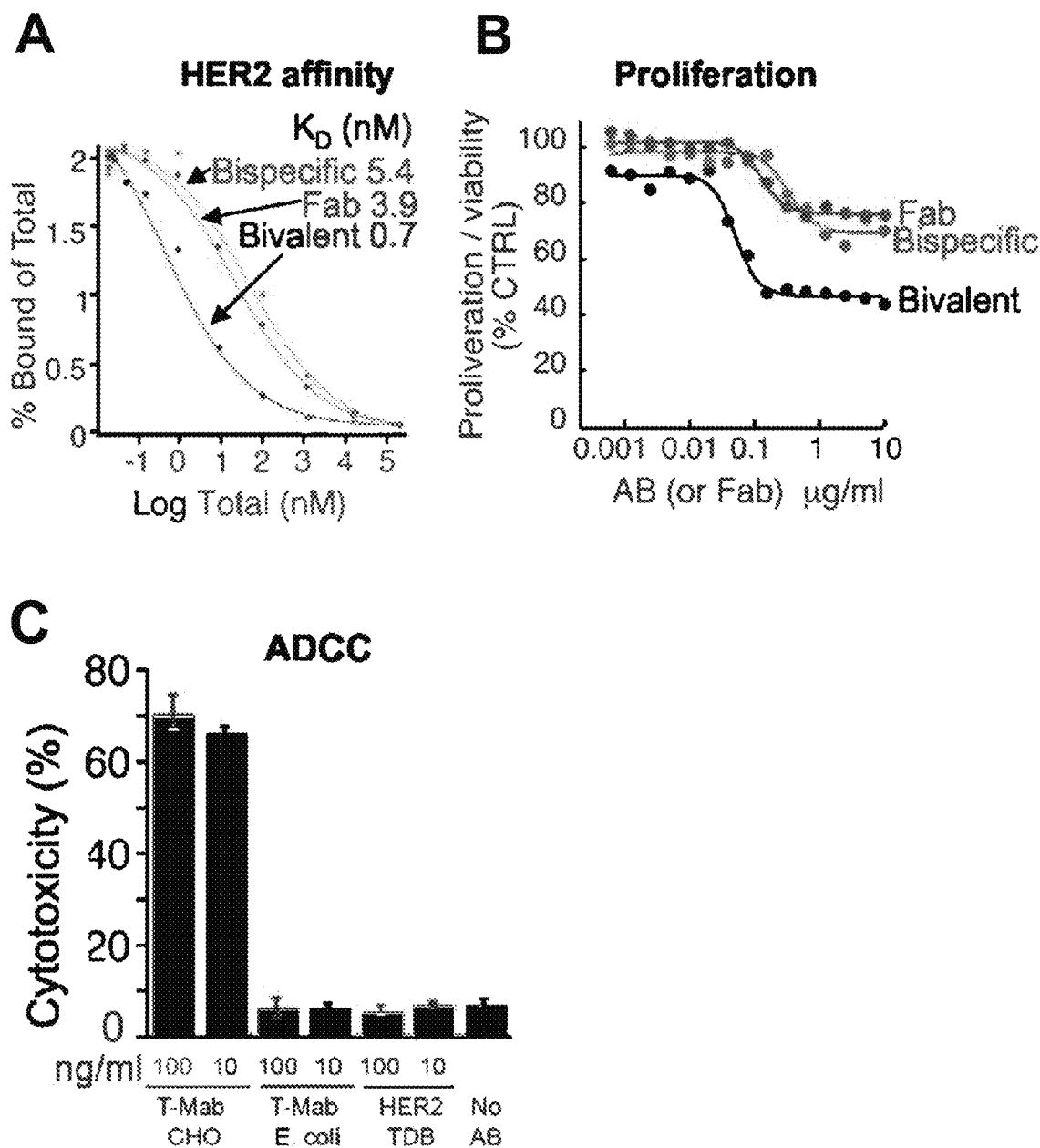

FIG. 74A is a graph showing the binding curves for trastuzumab (bivalent), trastuzumab (Fab'), and HER2 TDB (UCHT1v9/hu4D5) (bispecific) for in vitro binding to Her2-expressing SKBR3 cells.

FIG. 74B is a graph showing the percentage of viable SKBR3 cells as a function of for trastuzumab (bivalent), trastuzumab (Fab), and HER2 TDB (UCHT1v9/hu4D5) (bispecific) concentration, as assessed by CELLTITER-GLO® Luminescent Cell Viability Assay.

FIG. 74C is a graph showing the percentage of SKBR target cell killings mediated by antibody-dependent cell-mediated cytotoxicity (ADCC) in the presence of trastuzumab (T-mab), trastuzumab produced in $E.\ coli$ (T-mab $E.\ coli$), and HER2 TDB (UCHT1v9/hu4D5), as assessed by lactate dehydrogenase (LDH) release from lysed cells.

Figure 75:
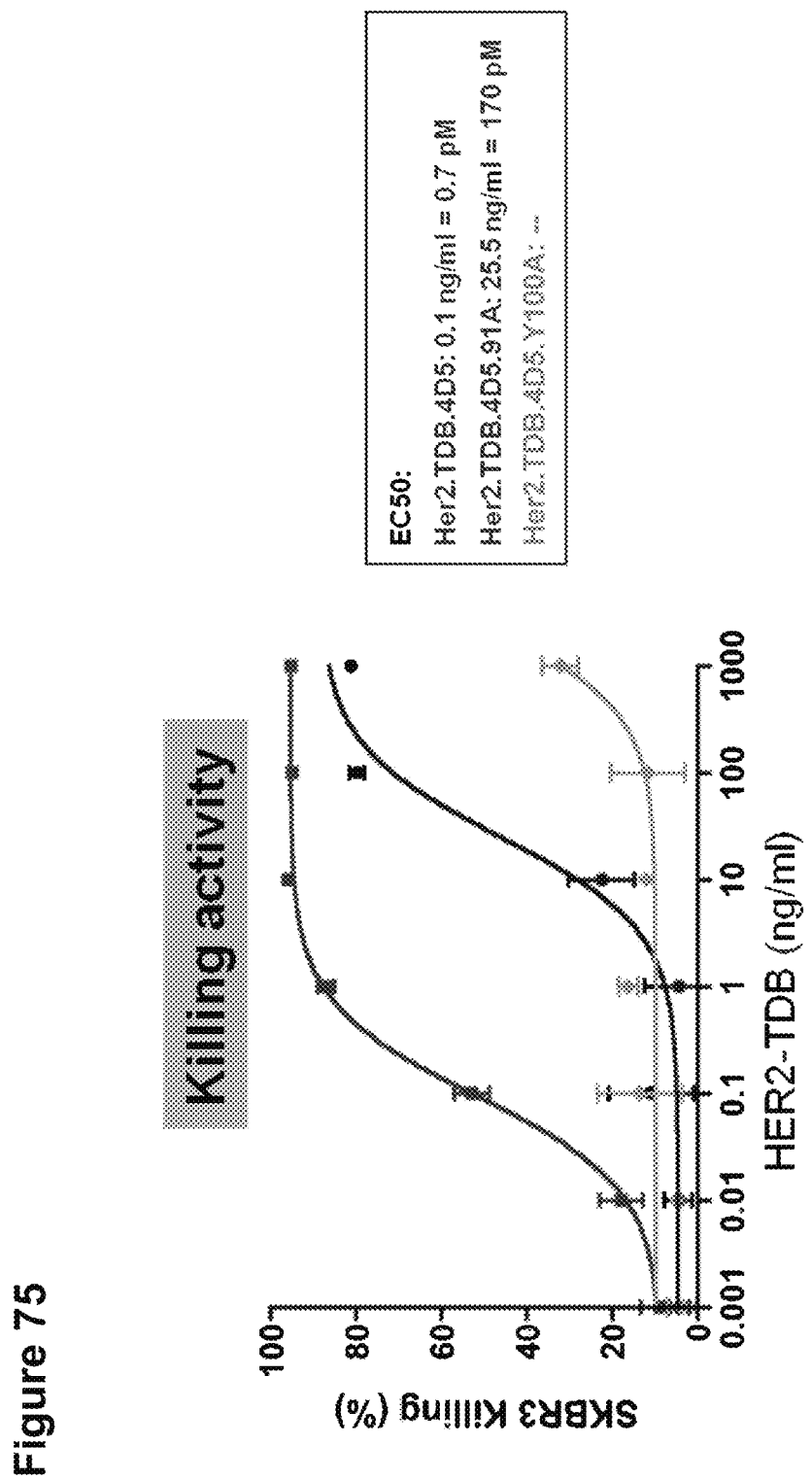

FIG. 75 is a graph showing the percentage of SKBR3 target cell killing as a function of HER2 TDB (hu4D5-TDB, hu4D5.91A-TDB, and hu4D5.Y100A-TDB) concentration.

Figures 76A, 76B:
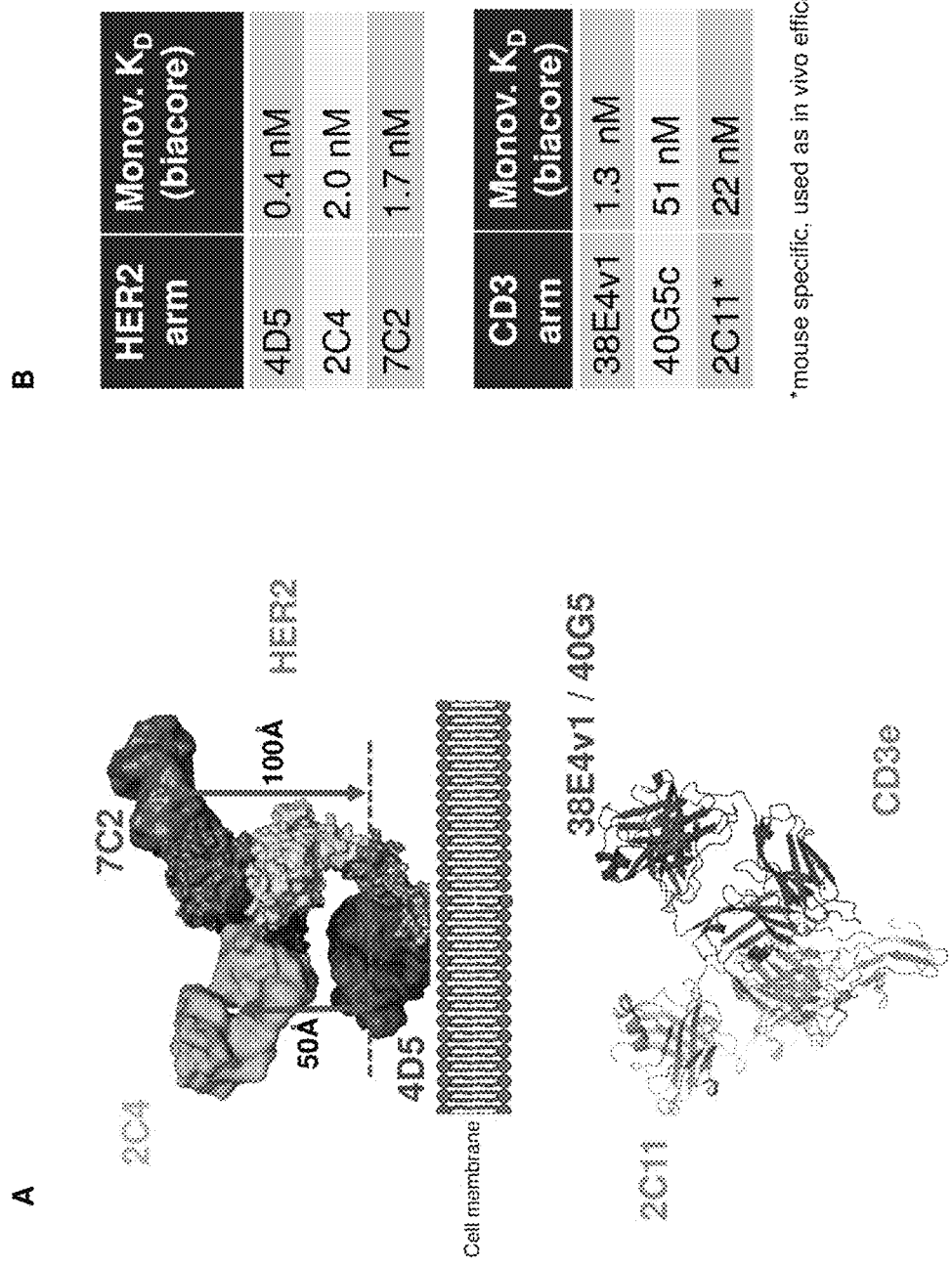

FIG. 76A is a series of panels. The top panel is a rendering of the crystal structure of the HER2 extracellular domain (ECD) bound by hu4D5 Fab (Trastuzumab), 2C4 Fab (Pertuzumab), and 7C2. The bottom panel is a ribbon structure of the $CD3_\varepsilon$ bound by 2C11, 38E4v1, and 40G5c.

FIG. 76B is a table indicating the binding affinities, represented by the dissociation constant $K_D$ (nM), of HER2-TDB for three different HER2 arms: hu4D5, 2C4, and 7C2. The bottom right panel is a table indicating the binding affinities, represented by the dissociation constant $K_D$ (nM), of HER2-TDB for three different $CD3_\varepsilon$ arms: 38E4v1, 40G5c, and 2C11.

Figure 76C:
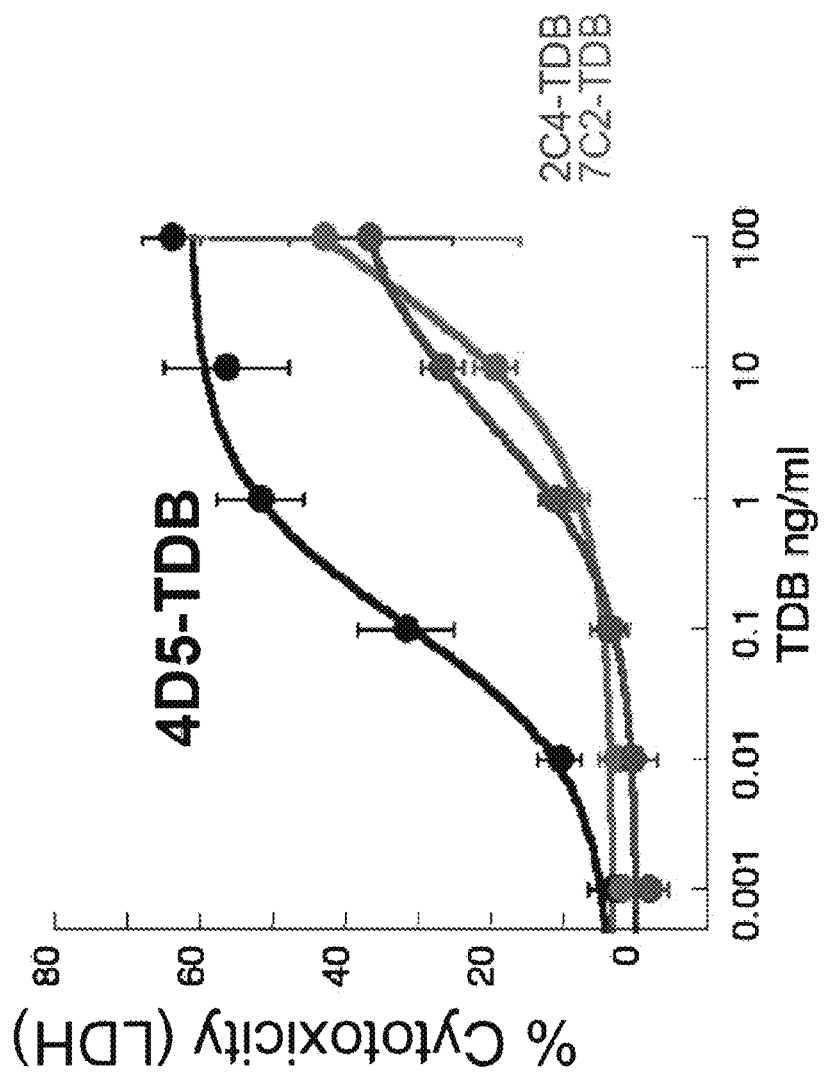

FIG. 76C is a graph showing the percentage of HER2-expressing MCF7 target cell killing as a function of HER2-TDB (hu4D5-TDB, 2C4-TDB, and 7C2-TDB) concentration. Cytotoxicity was measured by the release of lactate dehydrogenase (LDH).

Figure 77:
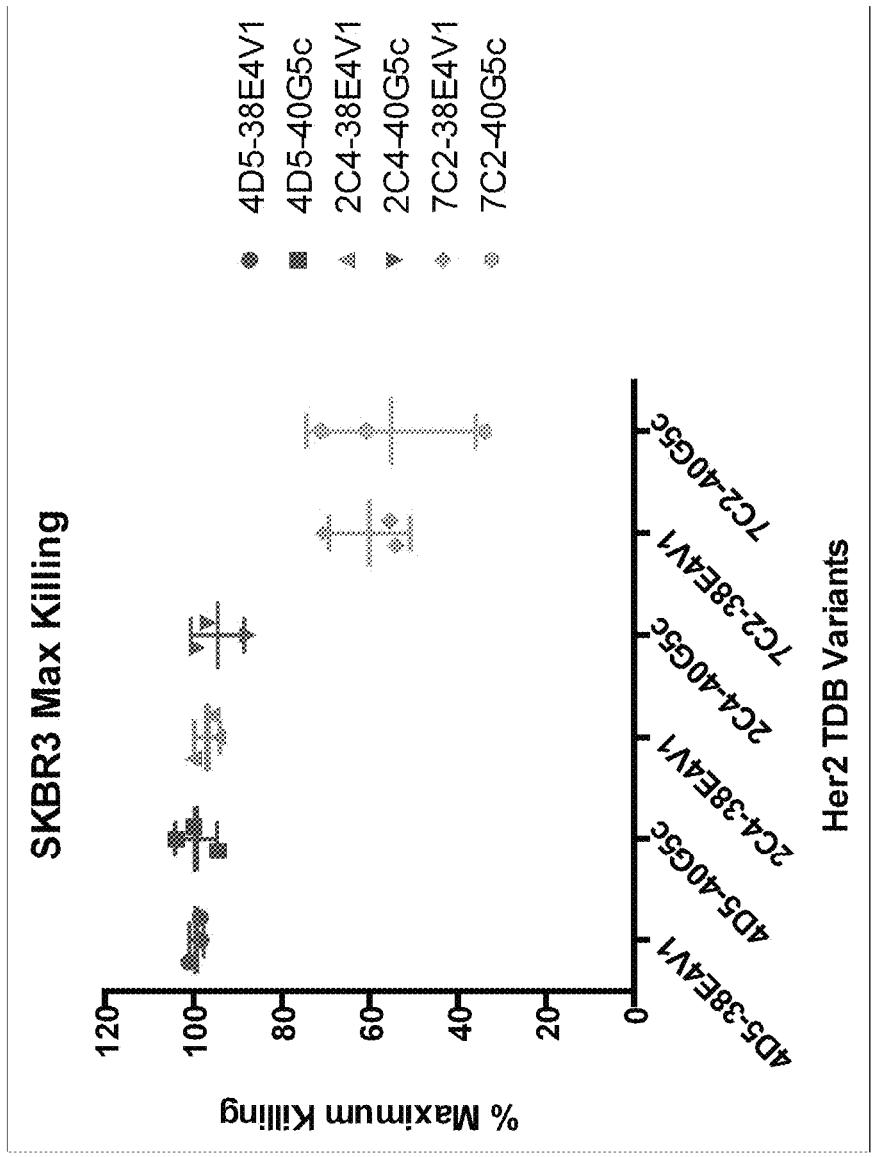

FIG. 77 is a graph showing the HER2 hu4D5 and 2C4 arms are potent mediators of cell killing as shown by the maximum percentage of SKBR3 target cell killing achieved by treatment with the following HER2-TDB variants: hu4D5-38E4v1, hu4D5-40G5c, 2C4-38E4v1, 2C4-40G5c, 7C2-38E4v1, and 7C2-40G5c.

Figure 78:
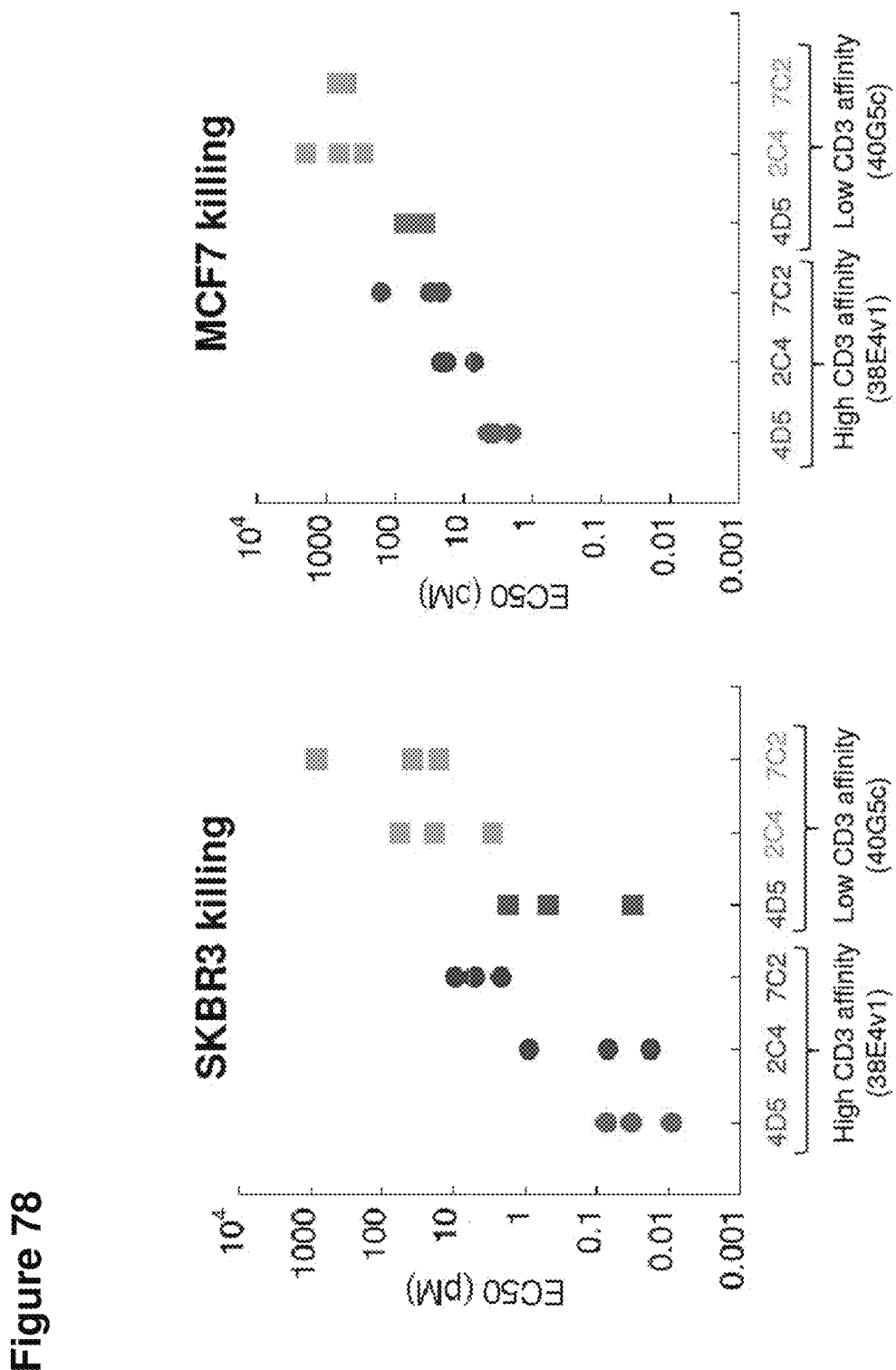

FIG. 78 is a series of graphs showing the potency of variants of the HER2-TDB in killing HER2-expressing SKBR3 (left) and HER2-expressing MCF7 (right) cell lines in a dose-dependent manner, with EC50 values of target cell killing (pM).

Figure 79:
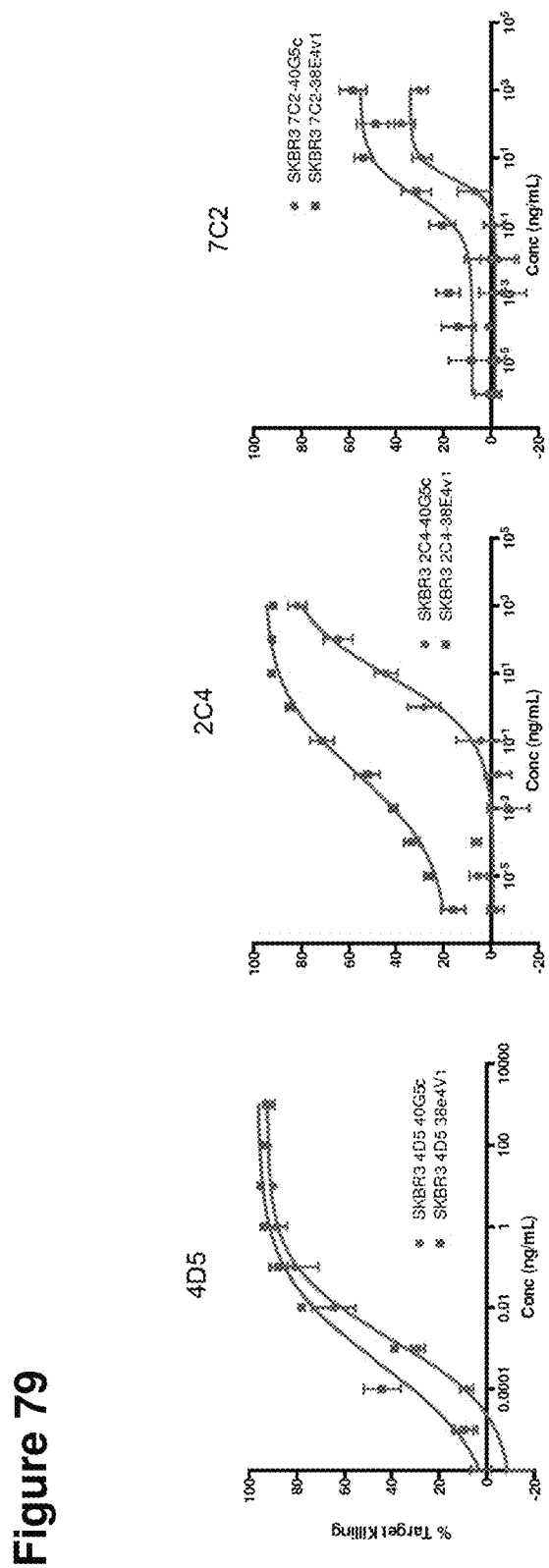

FIG. 79 is a series of graphs showing the percentage of HER2-expressing SKBR3 target cell killing for various TDBs with HER2 arms (hu4D5, 2C4, and 7C2) paired with high affinity (38E4v1) or low affinity (40G5c) CD3 arms as a function of TDB concentration (ng/mL).

Figure 80:
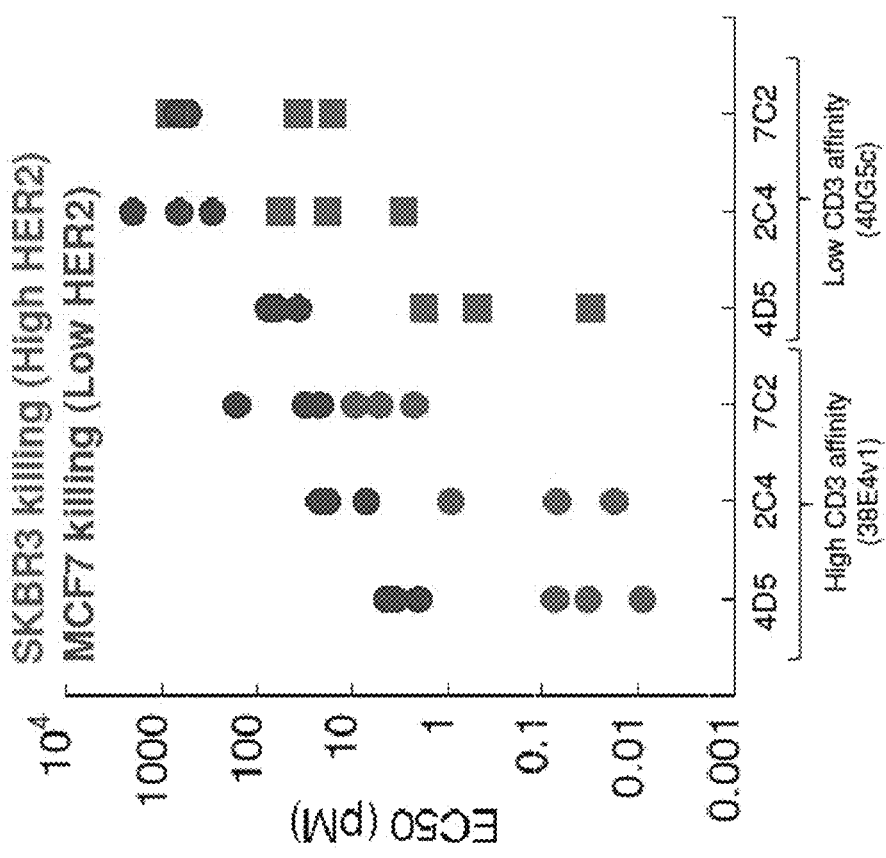

FIG. 80 is a series of panels. The panel on the left is showing the potency of variants of the HER2-TDB (hu4D5-38E4v1, 2C4-38E4v1, 7C2-38E4v1; hu4D5-40G5c, 2C4-40G5c, 7C2-40G5c) in killing HER2-expressing SKBR3 and HER2-expressing MCF7 cell lines in a dose dependent manner, with EC50 values of target cell killing (pM). The panel on the right is a table with the ratio of the EC50 of the given HER2-TDB variants in MCF7 versus SKBR3 target cells for three experiments.

Figure 81:
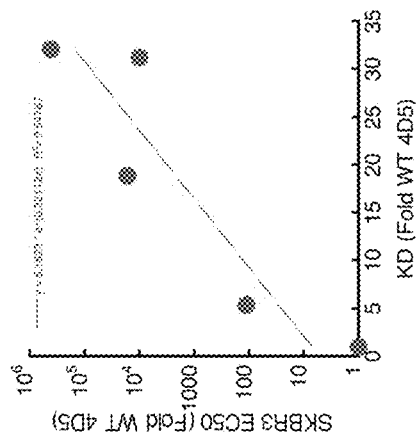

FIG. 81 is a series of panels. The top panel is showing a table listing the variants of the hu4D5 HER2 arm (hu4D5v7, hu4D5v5, hu4D5v10, hu4D5v31, hu4D5.Y100A) for HER2-TDB (40G5c CD3 arm) and the corresponding EC50 (ng/mL) for SKBR3 target cell killing, HER2 binding affinity ($K_D$, nM) in addition to the ratio of the HER2 binding affinity $K_D$ and SKBR3 target cell killing EC50 for the hu4D5 variants relative to hu4D5. The bottom panel is a graph showing the correlation between the SKBR3 EC50 ratio for the hu4D5 HER2-TDB variants (hu4D5, hu4D5v7, hu4D5v5, hu4D5v10, and hu4D5v31) and the relative $K_D$ ratio for the hu4D5 HER2-TDB variants.

Figure 82:
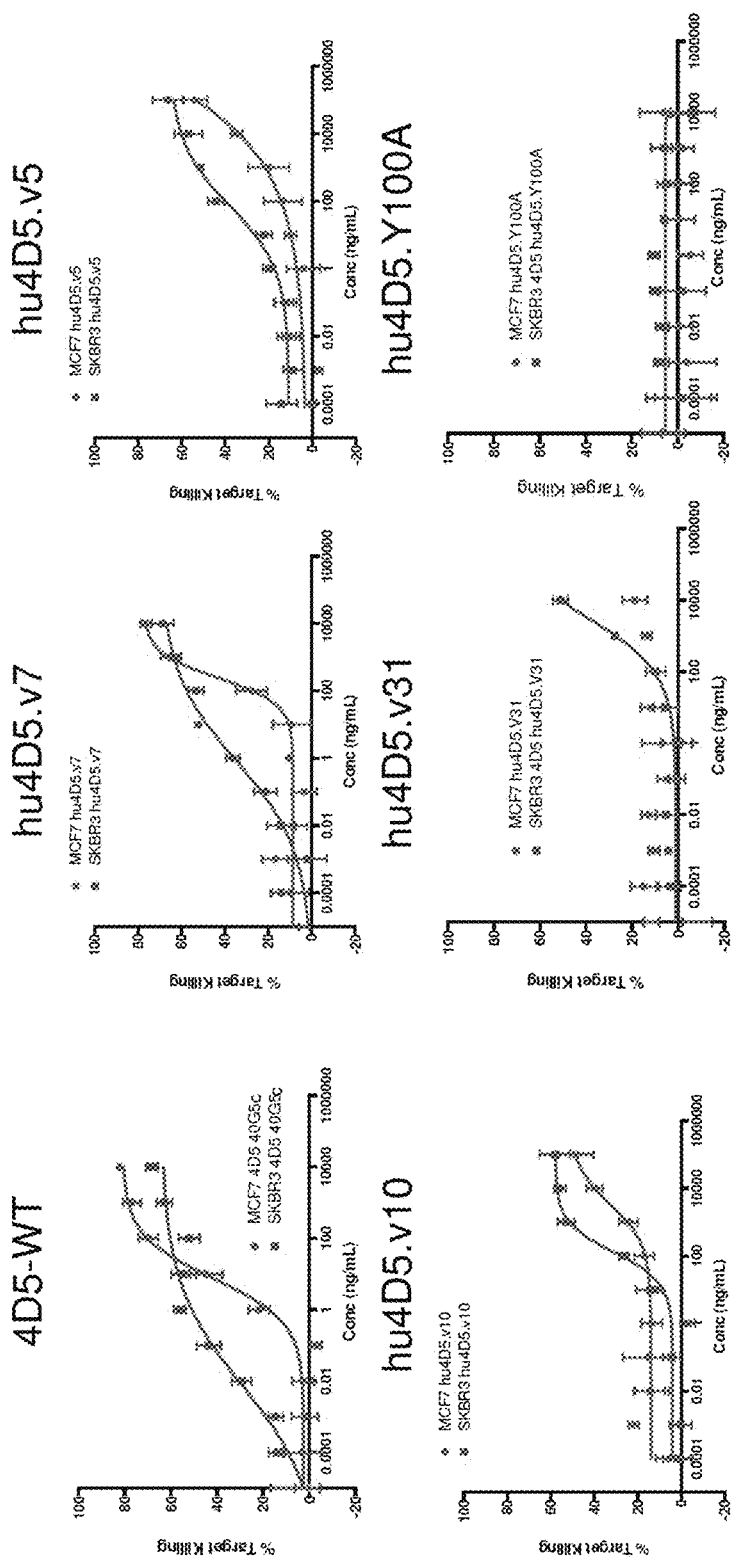

FIG. 82 is a series of graphs showing the percentage of SKBR3 and MCF7 target cell killing as a function of the concentration of the following HER2-TDB variants: hu4D5-40G5c (top left), hu4D5v7-40G5c (top center), hu4D5v5-40G5c (top right), hu4D5v10-40G5c (bottom left), hu4D5v31-40G5c (bottom center), hu4D5.Y100A-40G5c (bottom right).

Figure 83:
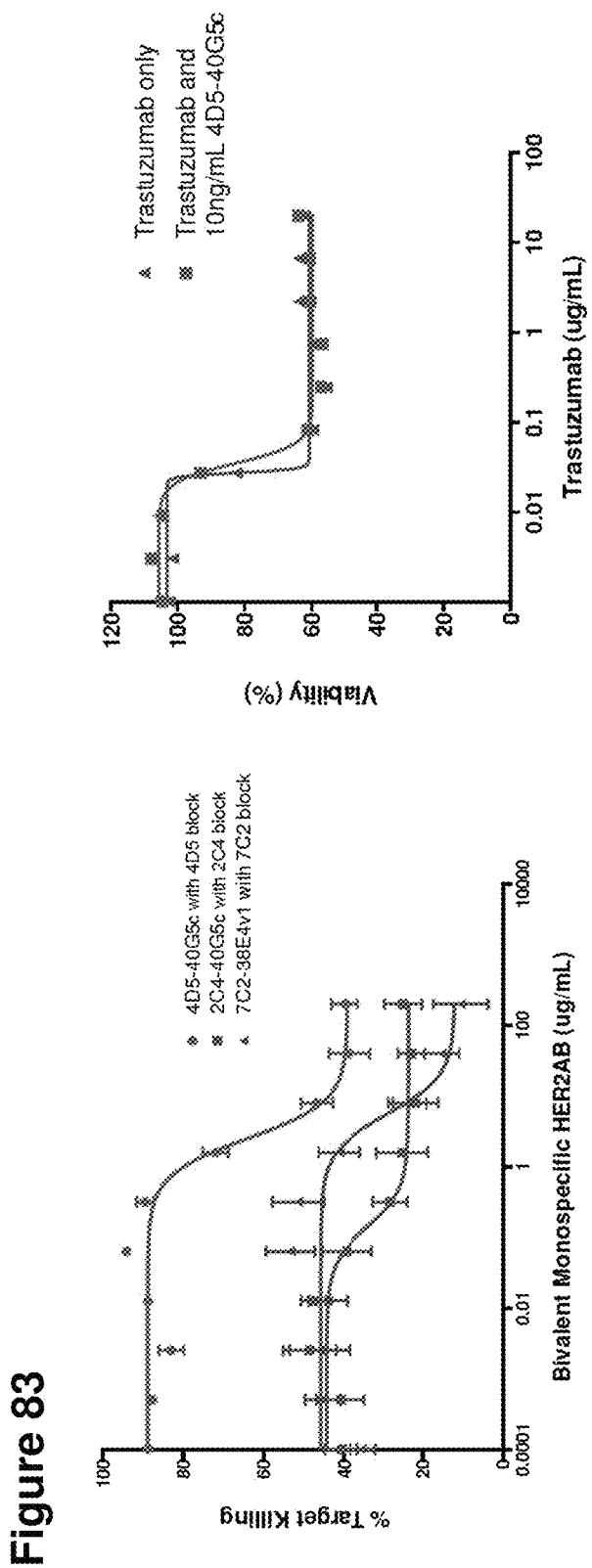

FIG. 83 is a series of graphs. The graph on the left is showing the percentage of target cell killing as a function of the concentration (μg/mL) of HER2 blocking bivalent monospecific antibodies specific for the designated HER2 arm of the HER2-TDB. (HER2 blocking antibodies: bivalent monospecific antibodies to hu4D5, 2C4, and 7C2. HER2-TDBs: hu4D5-40G5c, 2C4-40G5c, and 7C2-38E4v1 at fixed concentration: 10 ng/mL.) The graph on the right is showing the percentage of viable cells as a function of the concentration of the HER2 antibody (hu4D5) trastuzumab in the presence and absence of the HER2-TDB hu4D5-40G5c.

Figure 84:
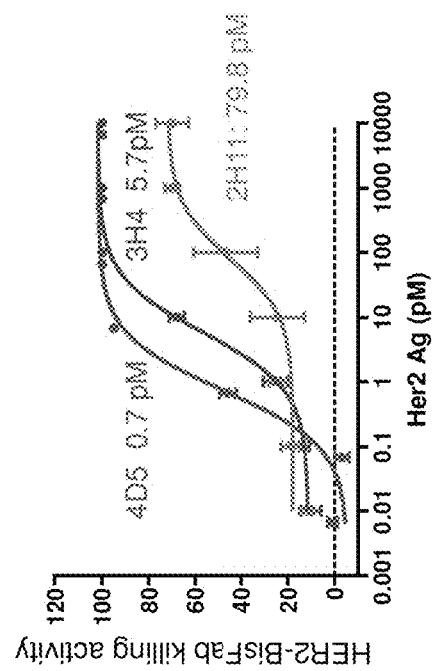

FIG. 84 is a series of panels. The top panel is a table providing the reactivity of variants of the HER2 arm with HER2 as measured by various binding assays in addition to the reactivity of the HER2 clones with the hu4D5 antibody trastuzumab. The bottom panel is a graph showing the percentage of target cell killing as a function of the concentration (pM) of HER2 bispecific Fab for the given clones (hu4D5, 3H4, and 2H11). EC50 values are given for each clone in pM.

FIG. 85 is a table providing affinity and reactivity information for the variants of the HER2-TDB CD3 arm (38E4v1, 38E4, SP34, 40G5c, and 2C11).

Figure 86:
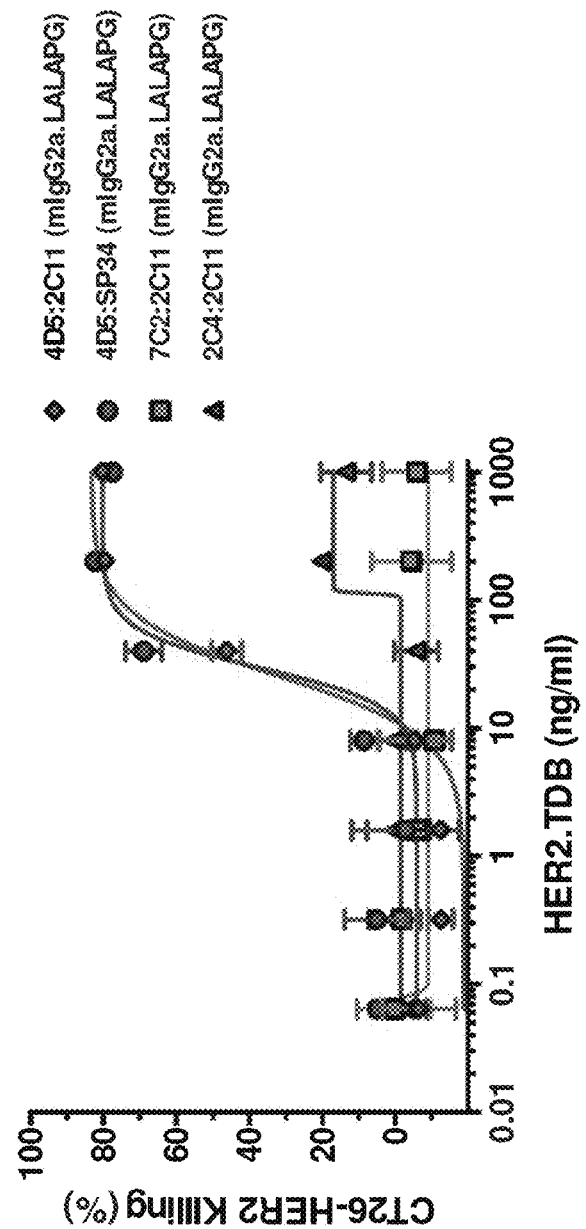
Figure 87A:
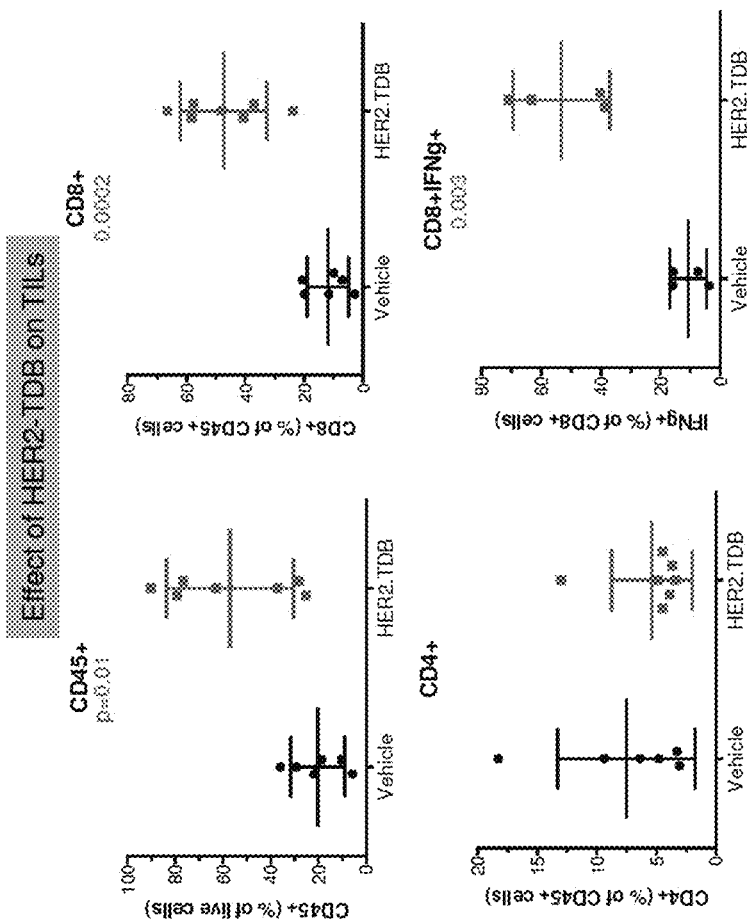

FIG. 86 is a graph showing HER2-expressing CT26 target cell killing as a function of concentration (ng/mL) of variants of HER2-TDB (hu4D5-2C11, hu4D5-SP34, 7C2-2C11, and 2C4-2C11). Effector cells: CD3-TG derived T cells FIG. 87A is a graph showing tumor volume (mm$^3$) measured over time (0-5 days) in animals treated with vehicle or HER2-TDB (0.5 mg/kg).

Figure 87B:
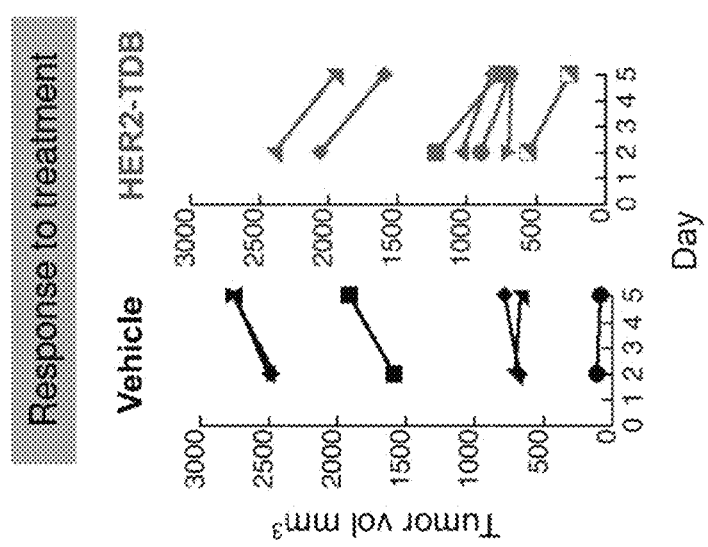

FIG. 87B is a series of graphs. The top left graph is showing the percentage of peripheral CD45+ cells per 5 cells detected on day 6 post vehicle or HER2-TDB (0.5 mg/kg) treatment. The top right graph is showing the percentage of peripheral CD45+ cells that are CD8+ cells detected on day 6 post vehicle or HER2-TDB (0.5 mg/kg) treatment. The bottom left graph is showing the percentage of peripheral CD45+ cells that are CD4+ detected on day 6 post vehicle or HER2-TDB (0.5 mg/kg) treatment. The bottom right graph is showing the percentage of peripheral CD8+ cells that are IFN+ detected on day 6 post vehicle or HER2-TDB (0.5 mg/kg) treatment.

Figures 88A, 88B:
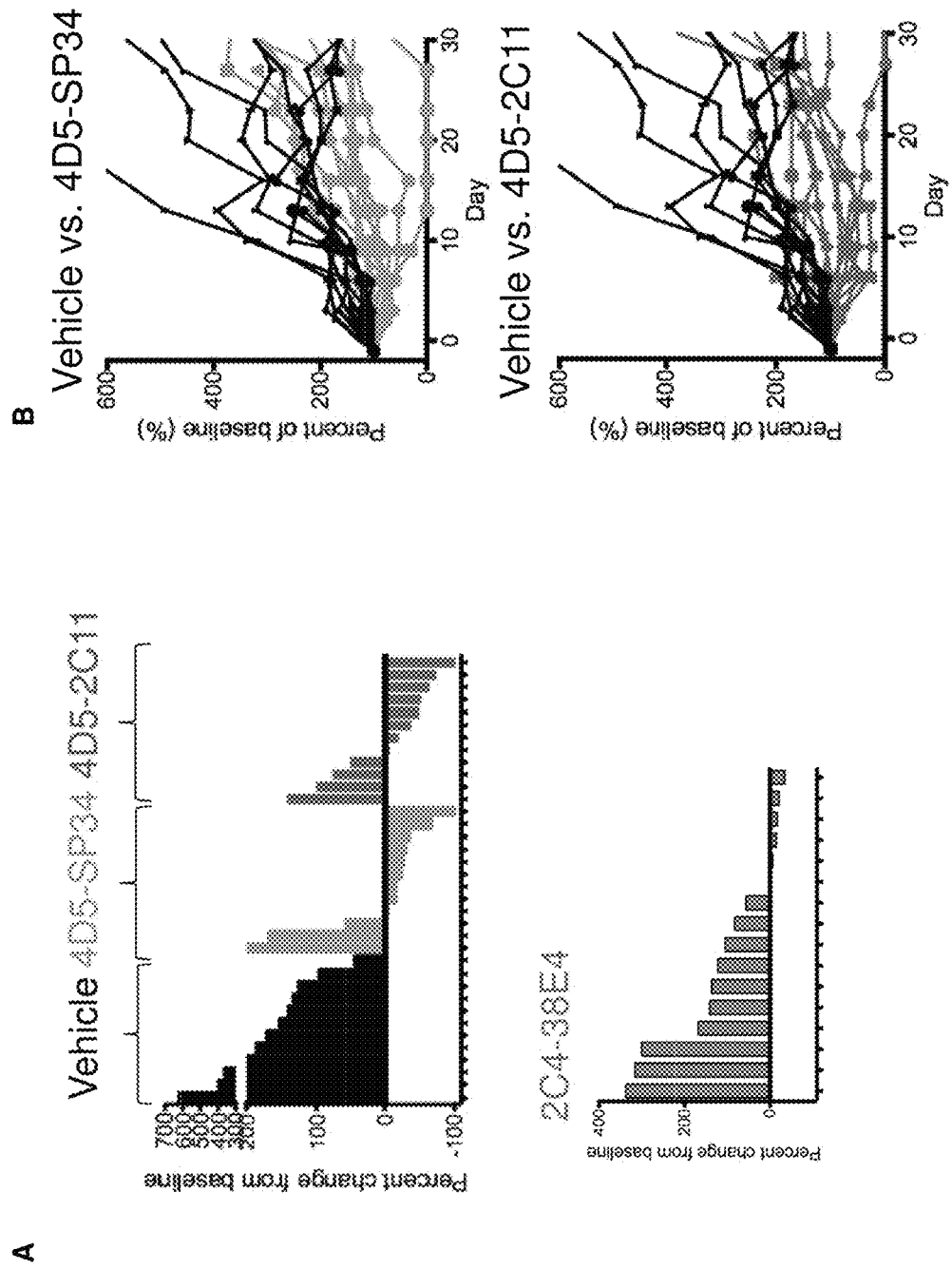

FIG. 88A is a series of graphs. The top graph is showing a waterfall plot of the percent change in tumor volume in animals treated with vehicle or HER2-TDB variant (hu4D5-SP34 or hu4D5-2C11; 0.5 mg/kg; IV, weekly, 5 weeks). The bottom graph is showing a waterfall plot of the percent change in tumor volume in animals treated with HER2-TDB variant (2C4-38E4; 0.5 mg/kg; IV, weekly, 5 weeks).

FIG. 88B is a series of graphs. The top graph is showing tumor volume as a percent of baseline volume as a function of time (days) for vehicle or HER2-TDB (hu4D5-SP34) treated animals. The bottom graph is showing tumor volume as a percent of baseline volume as a function of time (days) for vehicle or HER2-TDB (hu4D5-2C11) treated animals. (HER2-TDB: 0.5 mg/kg; IV, weekly, 5 weeks).

Figure 89:
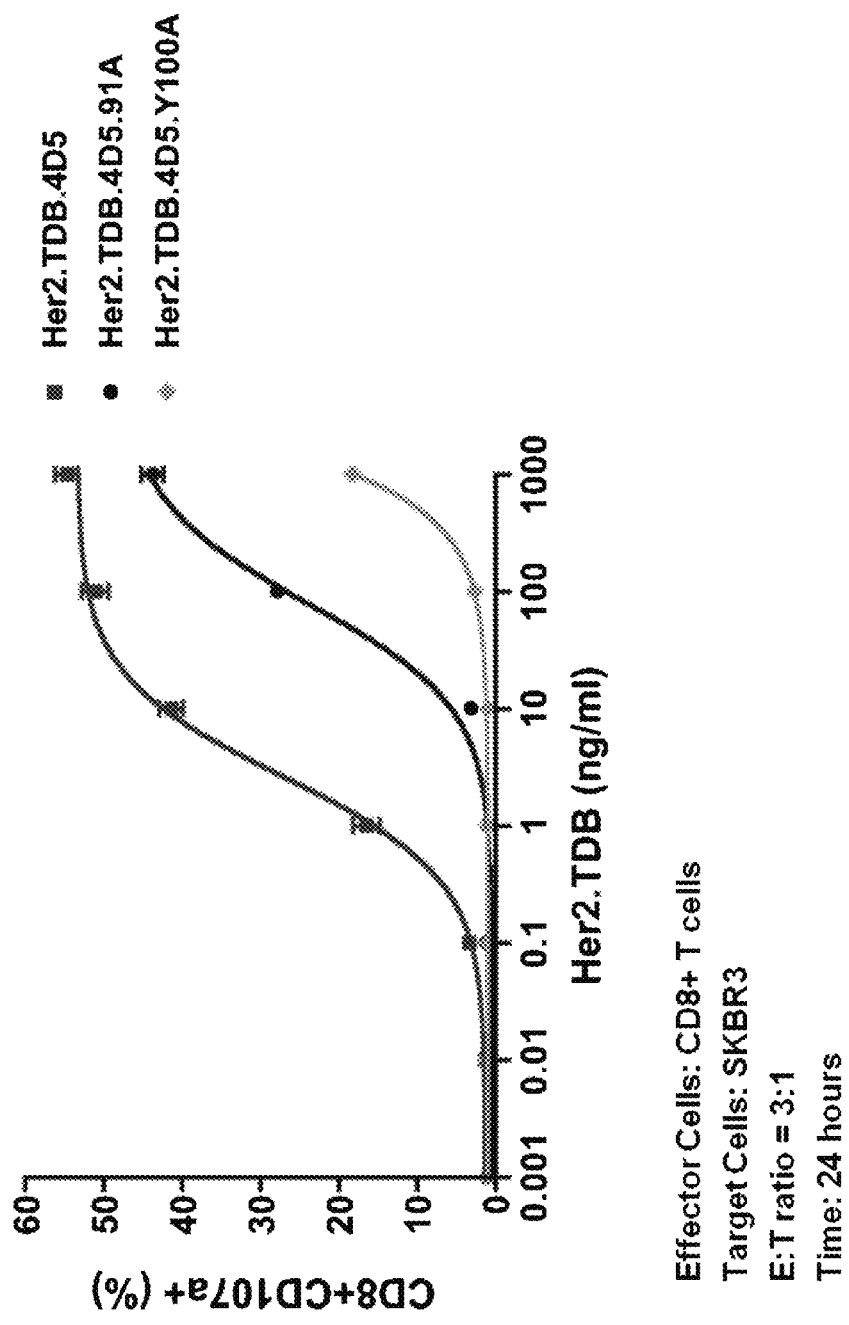

FIG. 89 is a graph showing the percentage of CD8+ CD107a+ T cells as a function of HER2 TDB (hu4D5-TDB, hu4D5.91A-TDB, and hu4D5.Y100A-TDB) concentration hu4D5, as assessed by FACS analysis. Target cells were SKBR3 cells; effector cells were CD8+ T cells; effector cell: target cell ratio=3:1.

Figures 90A, 90B, 90C:
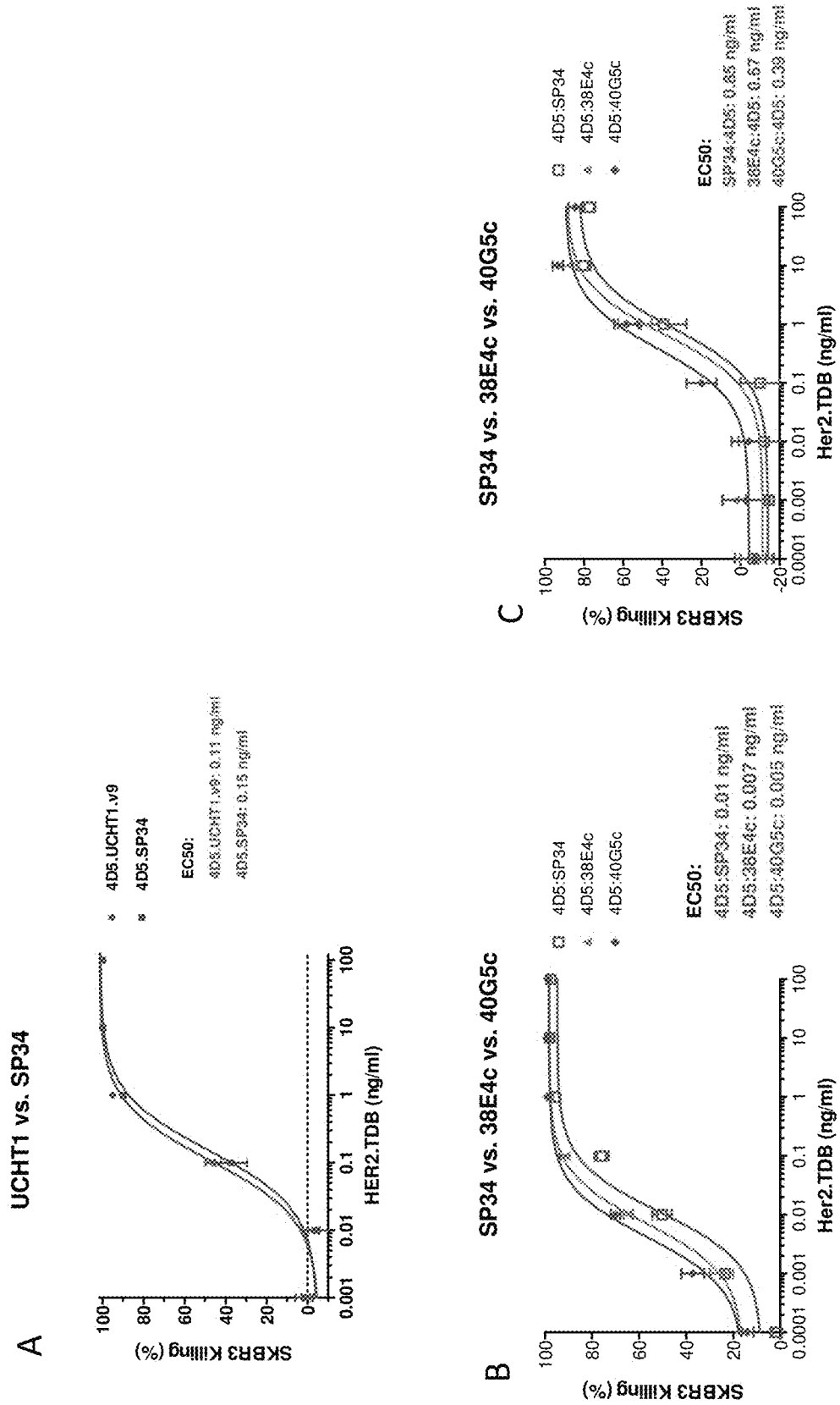

FIG. 90A is a graph showing the percentage of SKBR3 target cell killing as a function of HER2 TDB (UCHT1v9/hu4D5 and SP34/hu4D5) concentration.

FIG. 90B is a graph showing the percentage of SKBR3 target cell killing as a function of HER2 TDB (SP34/hu4D5, 38E4c/hu4D5, and 40G5c/hu4D5) concentration.

FIG. 90C is a graph showing the percentage of SKBR3 target cell killing as a function of HER2 TDB (SP34/hu4D5, 38E4c/hu4D5, and 40G5c/hu4D5) concentration.

Figures 91A, 91B:
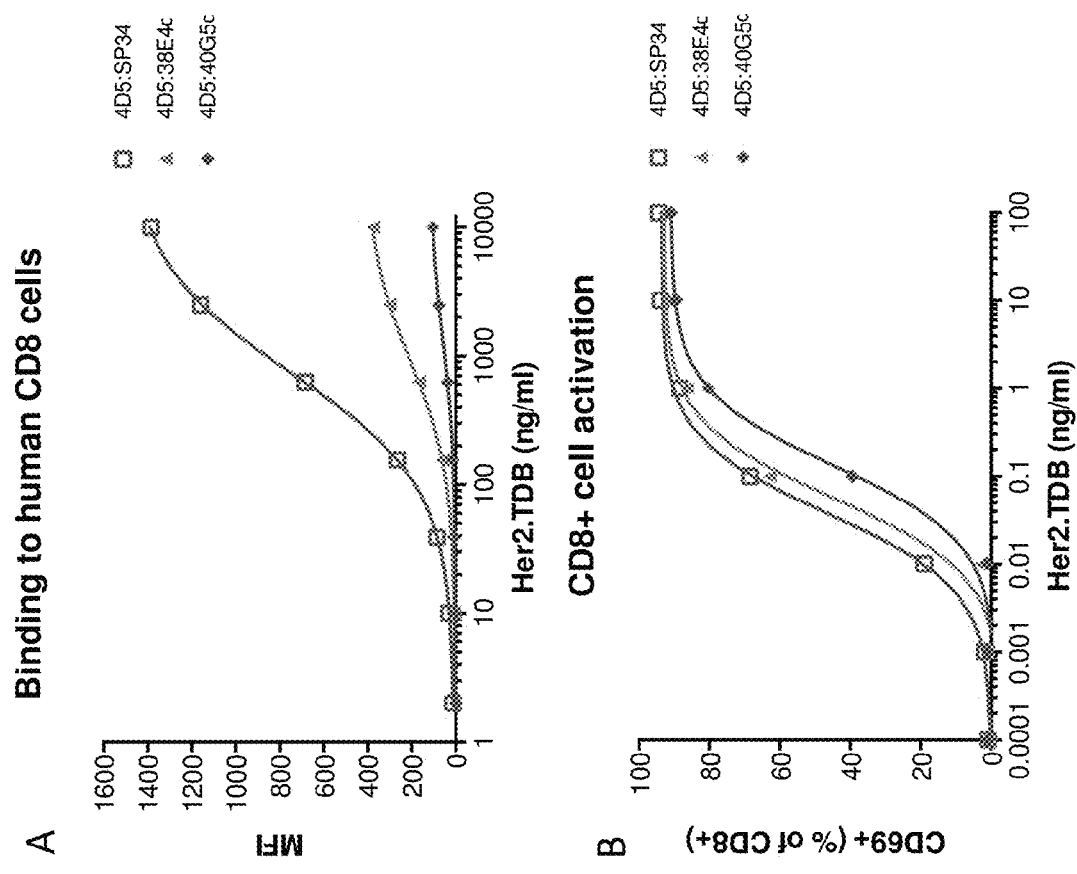

FIG. 91A is a graph showing the binding curve for each of the three HER2-TDBs (SP34/hu4D5, 38E4c/hu4D5, and 40G5c/hu4D5) tested for in vitro binding to CD8+CD3-expressing T cells as assessed by FACS analysis.

FIG. 91B is a graph showing the percentage of CD8+ CD69+ T cells as a function of HER2-TDB (SP34/hu4D5, 38E4c/hu4D5, and 40G5c/hu4D5) concentration.

Figures 92A, 92B, 92C, 92D:
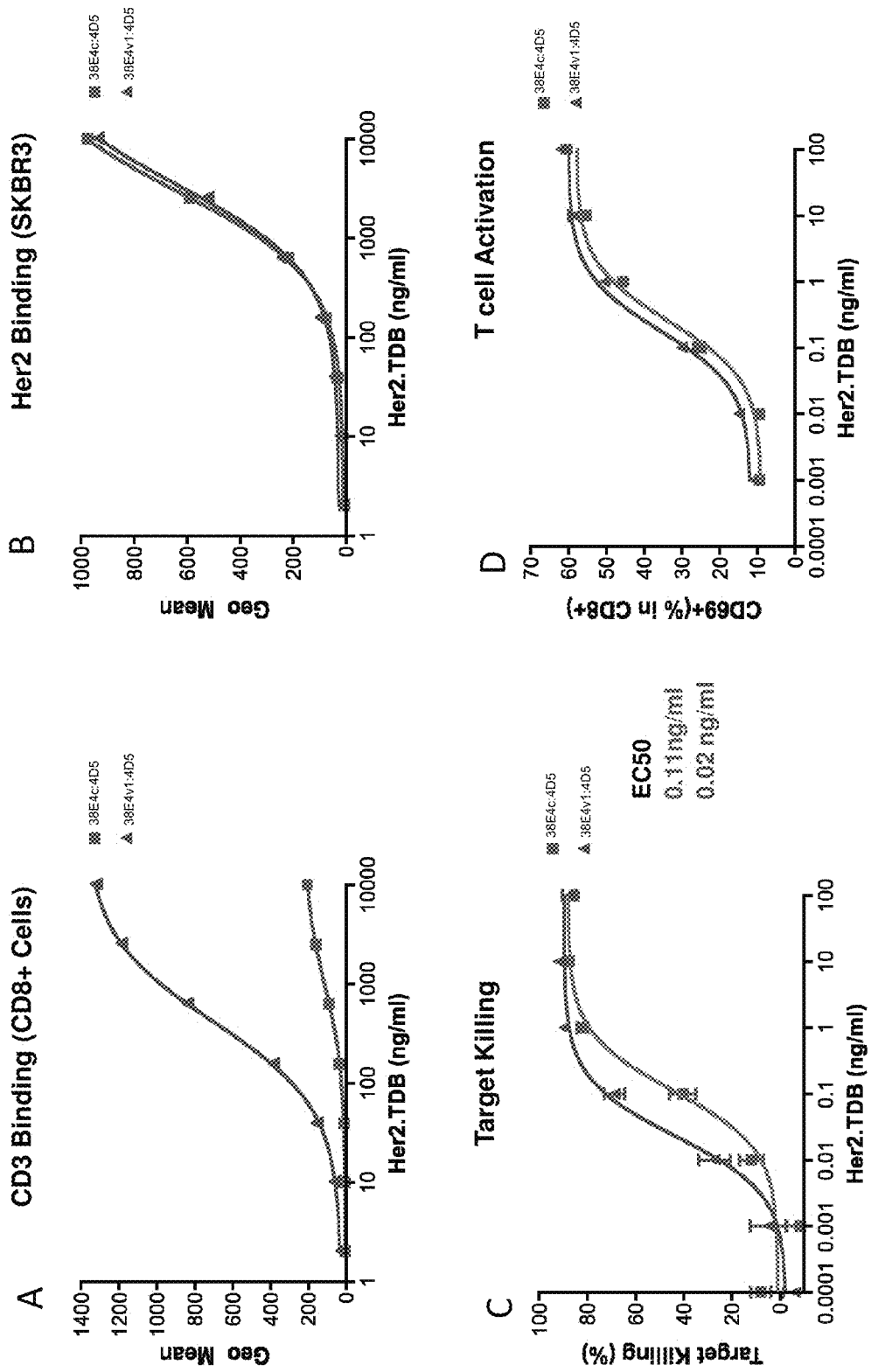

FIG. 92A is a graph showing the binding curve for the two HER2 TDBs (38E4c/hu4D5 and 38E4/hu4D5) tested for in vitro binding to CD8+CD3-expressing T cells, as assessed by FACS analysis.

FIG. 92B is a graph showing the binding curve for the two HER2 TDBs (38E4c/hu4D5 and 38E4/hu4D5) tested for in vitro binding to Her2-expressing SKBR3 cells, as assessed by FACS analysis.

FIG. 92C is a graph showing the percentage of SKBR3 target cell killing as a function of HER2 TDB (38E4c/hu4D5 and 38E4/hu4D5) concentration as assessed by FACS analysis. Effector cells were human CD8+ T cells; effector cell: target cell ratio=3:1.

FIG. 92D is a graph showing the percentage of CD8+ CD69+ T cells as a function of HER2-TDB (38E4c/hu4D5 and 38E4/hu4D5) concentration.

Figures 93A, 93B, 93C, 93D, 93E, 93F:
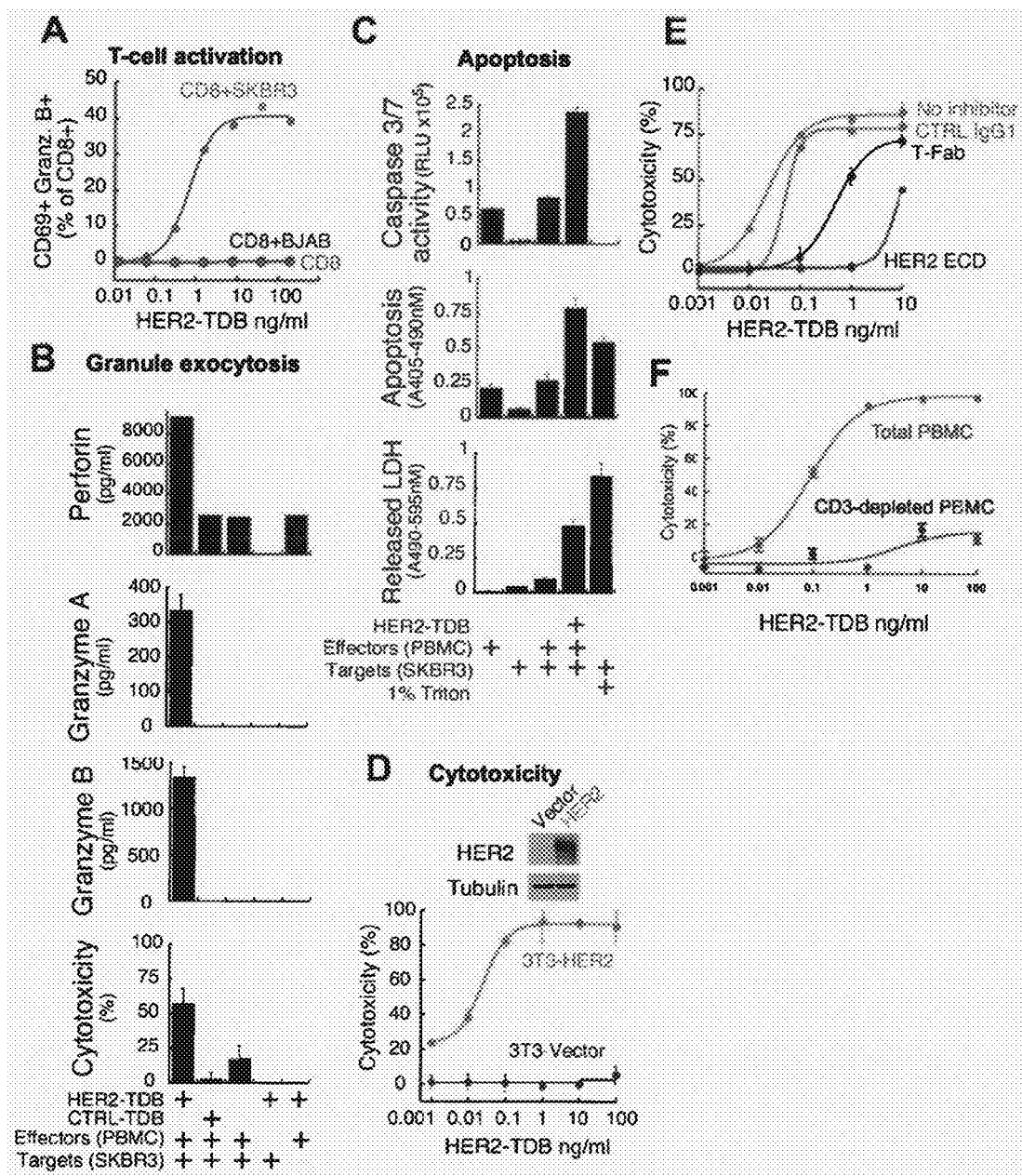

FIG. 93A is a graph showing the percentage of CD8+ CD69+GranzymeB+ T cells as a function of HER2 TDB (UCHT1v9/hu4D5) concentration, as assessed by FACS analysis. Target cells were SKBR3 cells; effector cells were CD8+ T cells; effector cell: target cell ratio=3:1.

FIG. 93B is a series of graphs showing HER2 TDB (UCHT1v9/hu4D5) T cell-mediated target cell granule exocytosis detected by ELISA for perforin and granzymes A and B, and the percentage of target cell killing as assessed by LDH release. Target cells were SKBR3 cells; effector cells were PBMCs; effector cell:target cell ratio=30:1.

FIG. 93C is a series of graphs showing HER2 TDB (UCHT1v9/hu4D5) T cell-mediated target cell apoptosis as measured by caspase-3 and caspase-7 activities in a CASPASE-GLO® 3/7 assay, apoptosis in a Cell Death Detection ELISA$^{plus}$ assay, and LDH release. Target cells were SKBR3 cells; effector cells were PBMCs; effector cell: target cell ratio=10:1.

FIG. 93D is the image of a Western blot (top) showing the expression of Her2 in 3T3 transfected cells and a graph (bottom) showing the percentage of target cell killing by activated T cells as a function of HER2 TDB (UCHT1v9/hu4D5) concentration as measured by LDH release. Target cells were 3T3-Vector and 3T3-HER2; effector cells were PBMCs; effector cell: target cell ratio=10:1.

FIG. 93E is a graph showing the percentage of BT474 target cell killing as a function of HER2 TDB (UCHT1v9/hu4D5) concentration in the presence of trastuzumab Fab (T-Fab) or soluble HER2 extracellular domain (ECD) as assessed by LDH release. Effector cells were CD8+ T cells; effector cell: target cell ratio=5:1.

FIG. 93F is a graph showing the percentage of SKBR3 target cell killing as a function of HER2 TDB (UCHT1v9/hu4D5) concentration following the depletion of CD3+ cells from the PBMC effector cell population. Effector cell: target cell ratio=20:1.

Figures 94A, 94B:
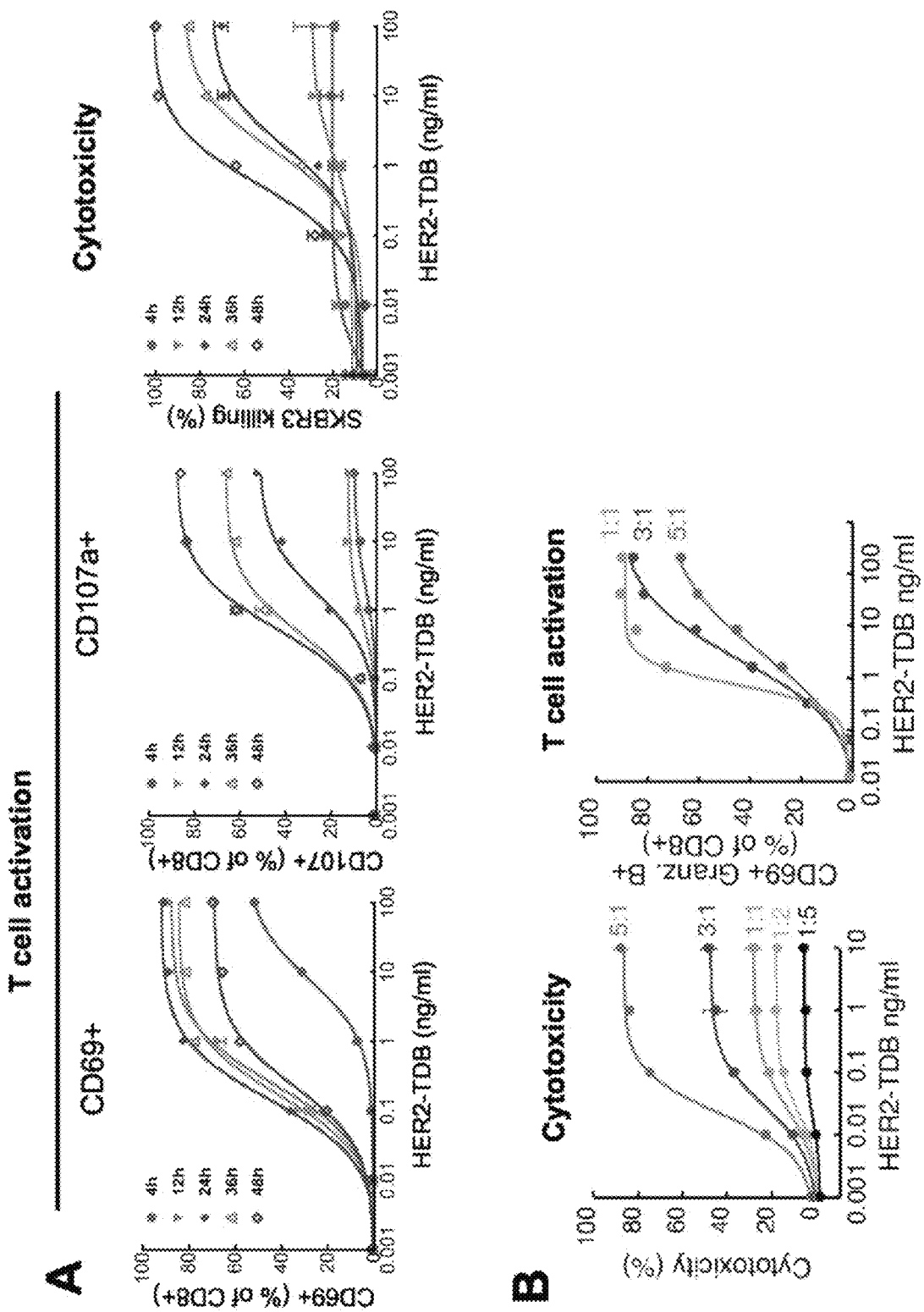

FIG. 94A is a series of graphs showing the percentage of CD8+CD69+ T cells (left) and CD8+CD107a+ T cells (middle) as a function of HER2 TDB (UCHT1v9/hu4D5) concentration, as assessed by FACS analysis, and the percentage of SKBR3 target cell killing as a function of HER2 TDB (UCHT1v9/hu4D5) concentration (right). Target cells were SKBR3 cells; effector cells were CD8+ T cells; effector cell: target cell ratio=3:1.

FIG. 94B is a series of graphs showing the percentage of BT474 target cell killing as a function of HER2 TDB (UCHT1v9/hu4D5) concentration (left) and the percentage of CD8+CD69+GranzymeB+ T cells as a function of HER2 TDB (UCHT1v9/hu4D5) concentration (right), as assessed by FACS analysis. Target cells were BT474 cells; effector cells were CD8+ T cells; effector cell: target cell ratio as indicated.

Figures 95A, 95B, 95C:
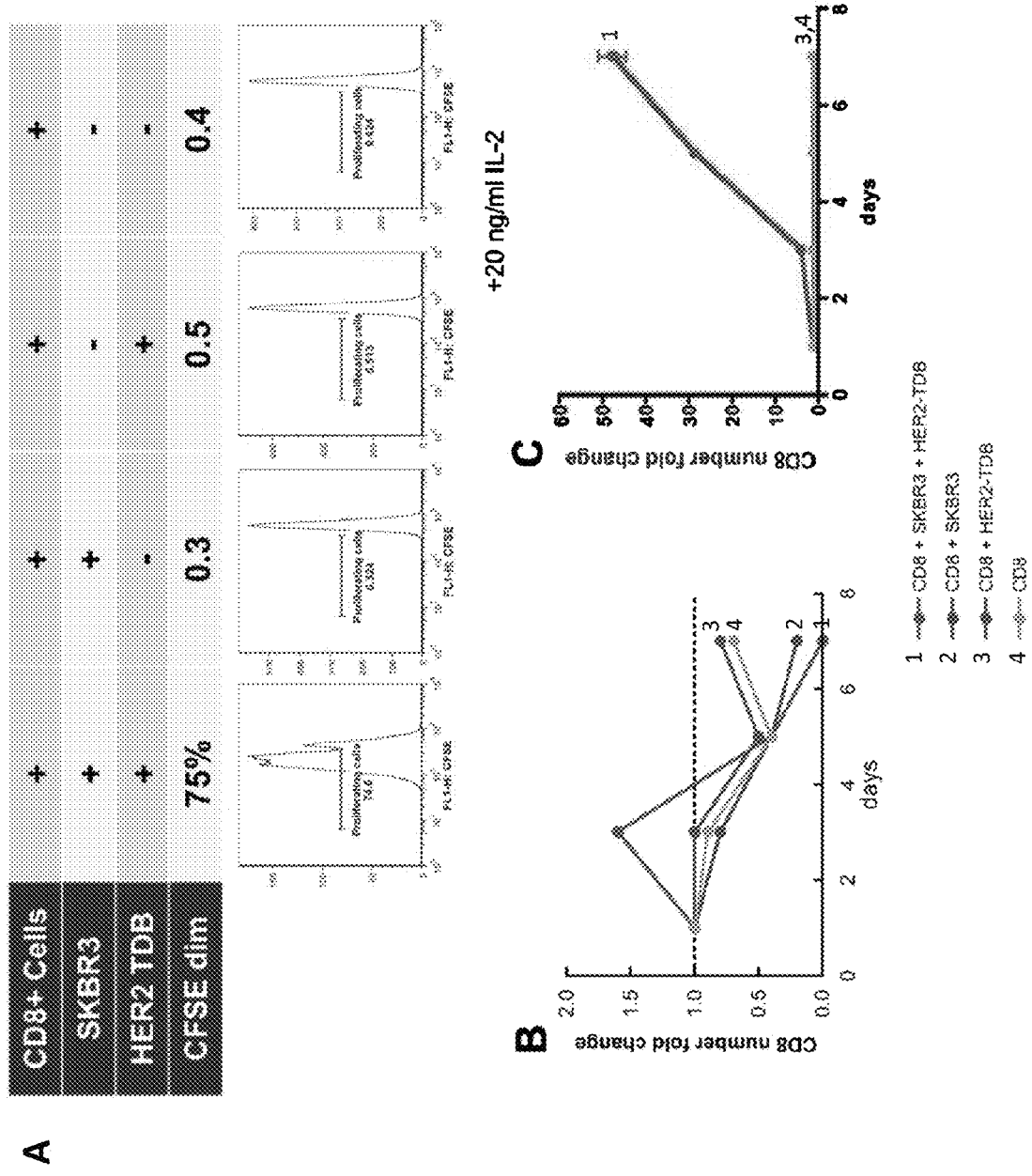

FIG. 95A is a series of histograms showing the expression of CFSE in CD8+ T cells in the presence of SKBR3 target cells and/or HER2 TDB (UCHT1v9/hu4D5).

FIG. 95B is a graph showing the fold change in CD8+ cell number as a function of time following incubation with SKBR3 target cells and HER2 TDB (UCHT1v9/hu4D5), as assessed by FACS analysis.

FIG. 95C are a series of graphs showing the fold change in CD8+ cell number as a function of time following incubation with SKBR3 target cells, HER2 TDB (UCHT1v9/hu4D5), and 20 ng/ml IL-2, as assessed by FACS analysis.

Figures 96A, 96B, 96C, 96D, 96E:
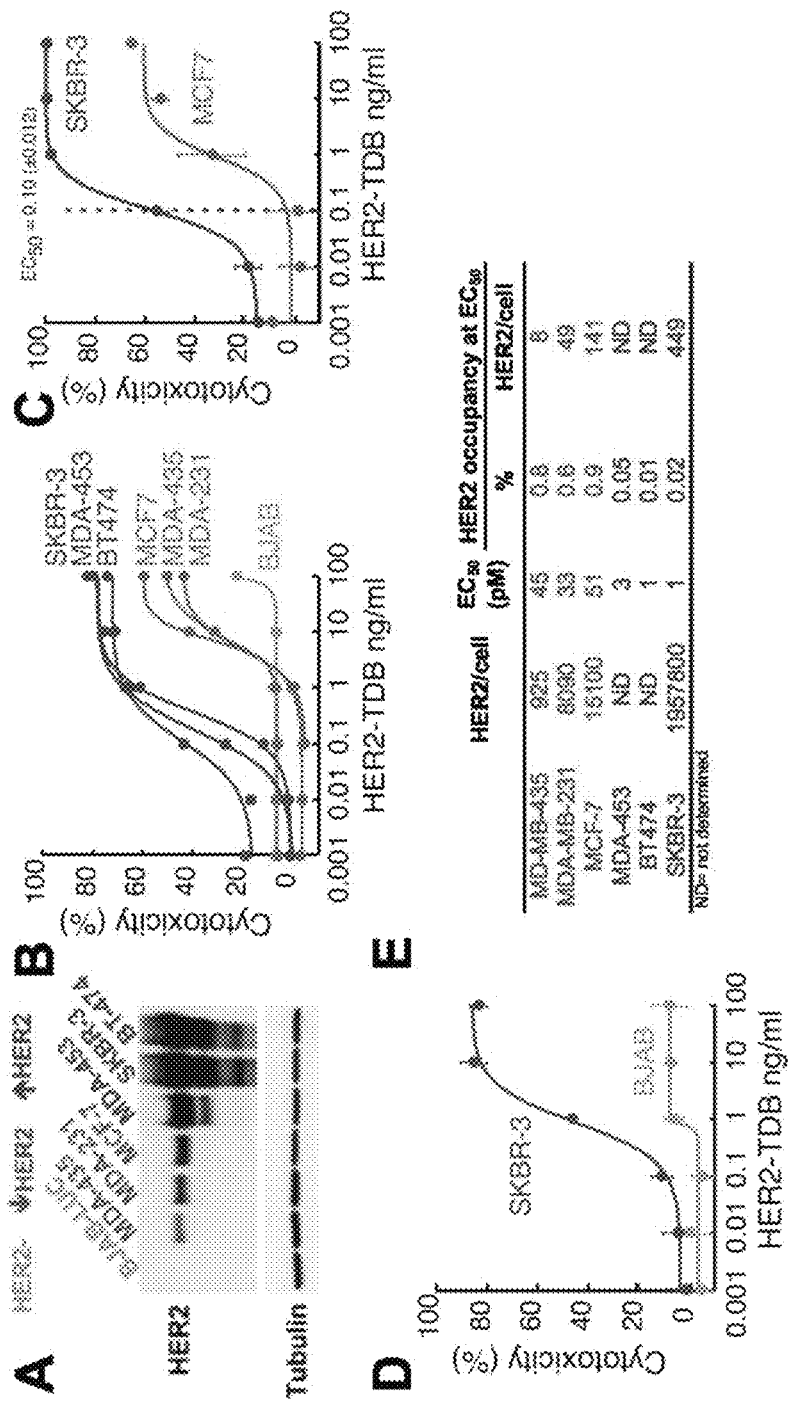

FIG. 96A is an image of a Western blot showing the expression level of Her2 in a panel of human tumor cell lines.

FIG. 96B is a graph showing the percentage of target cell killing as a function of HER2 TDB (UCHT1v9/hu4D5) concentration as assessed by LDH release. Target cells were BJAB, MDA435, MDA231, MCF7, MDA453, SKBR3, and BT474; effector cells were PBMCs; effector cell: target cell ratio=25:1.

FIG. 96C is a graph showing the percentage of target cell killing as a function of HER2 TDB (UCHT1v9/hu4D5) concentration as assessed by FACS analysis. Target cells were MCF7 and SKBR3; effector cells were PBMCs; effector cell: target cell ratio=20:1.

FIG. 96D is a graph showing the percentage of target cell killing as a function of HER2 TDB (UCHT1v9/hu4D5) concentration as assessed by FACS analysis. Target cells were BJAB and SKBR3; effector cells were PBMCs; effector cell: target cell ratio=20:1.

FIG. 96E is a table displaying the HER2 copy number for a panel of target cells and for each, the HER2 TDB EC50 and percentage of HER2 occupancy at that concentration. Target cells are MDA435, MDA231, MCF7, MDA453, BT474, and SKBR3.

Figures 97A, 97B, 97C:
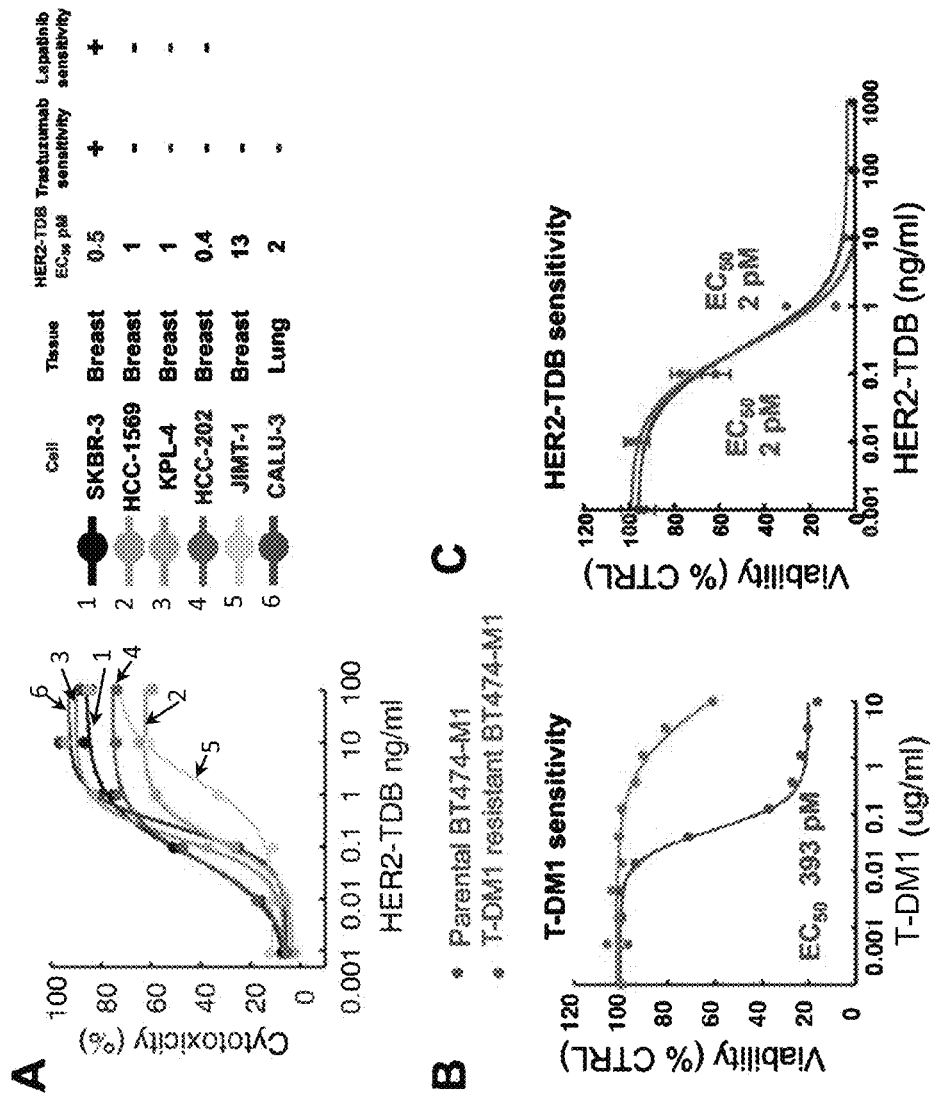

FIG. 97A is a graph showing the percentage of target cell killing as a function of HER2 TDB (UCHT1v9/hu4D5) concentration as assessed by LDH release. Target cells were SKBR3, HCC1569, KPL4, HCC202, JIMT1, and CALU3; effector cells were PBMCs; effector cell: target cell ratio=10:1.

FIG. 97B is a graph showing the percentage of viable target cells as a function of trastuzumab emtansine (T-DM1) concentration as assessed by CELLTITERGLO® Luminescent Cell Viability Assay. Target cells were parental BT474-M1 and T-DM1 resistant BT474-M1; effector cells were CD8+ T cells; effector cell: target cell ratio=3:1.

FIG. 97C is a graph showing the percentage of viable target cells as a function of HER2 TDB (UCHT1v9/hu4D5) concentration as assessed by FACS analysis. Target cells were parental BT474-M1 and T-DM1 resistant BT474-M1; effector cells were CD8+ T cells; effector cell: target cell ratio=3:1.

Figure 98:
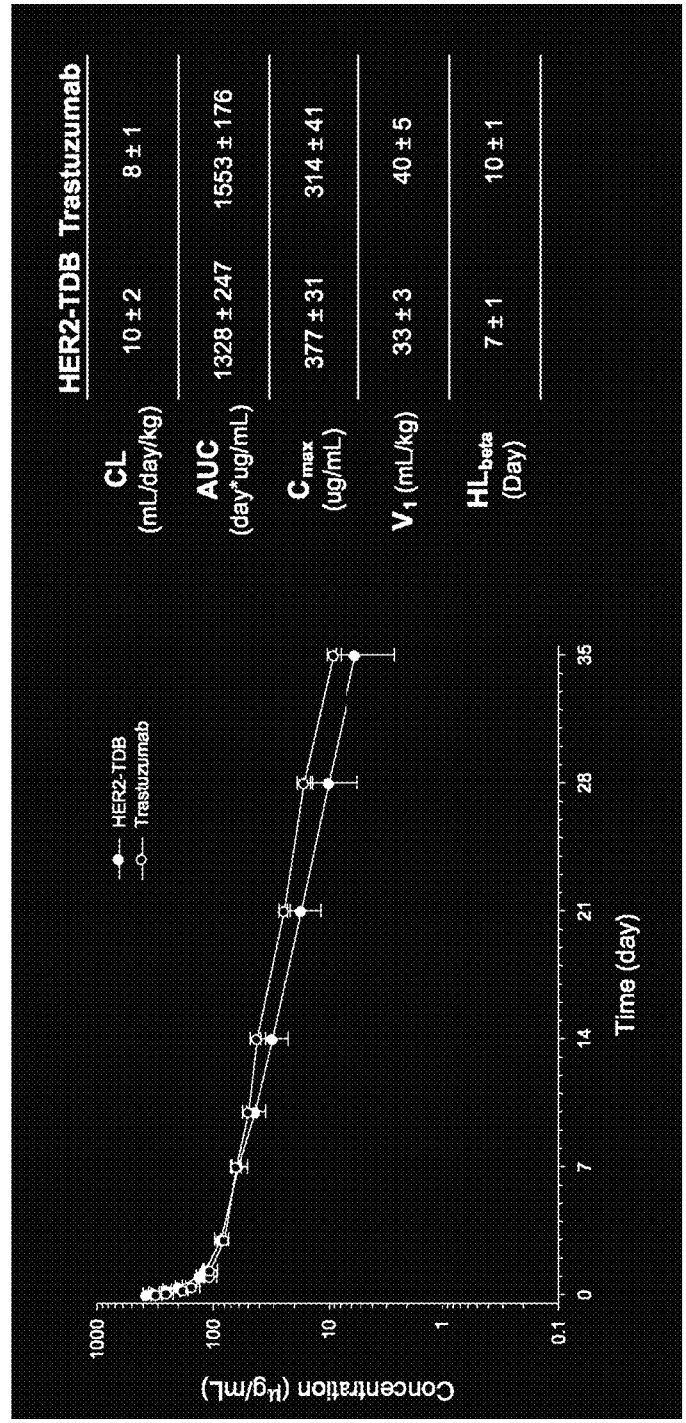

FIG. 98 is a graph and a table showing the pharmacokinetics (PK) of HER2 TDB (UCHT1v9/hu4D5) in Sprague-Dawley rats as assessed by ELISA.

Figures 99A, 99B, 99C, 99D, 99E, 99F, 99G:
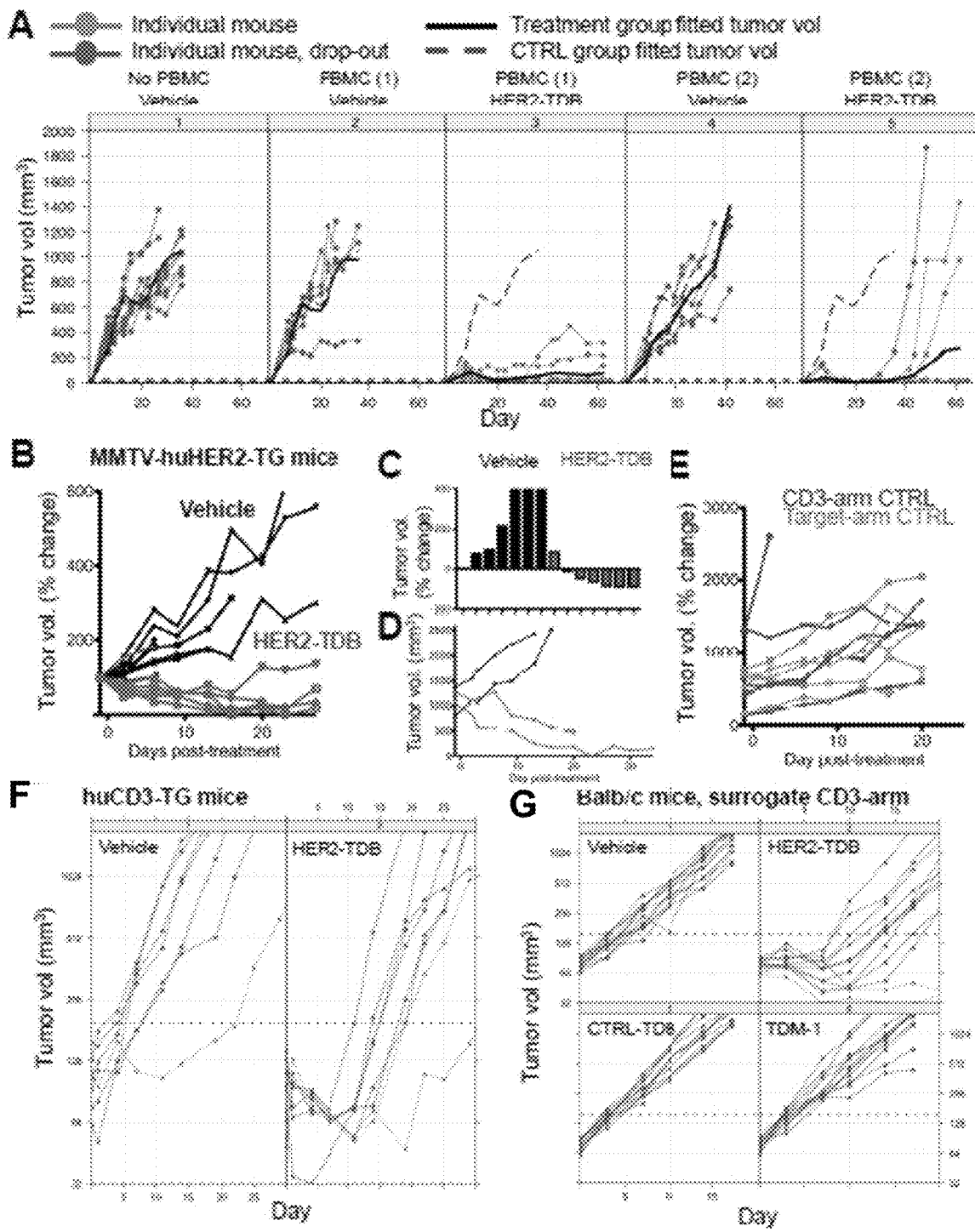

FIG. 99A is a graph showing the relative tumor volume over time for Group 1 (Vehicle at 0.5 mg/kg); Group 2 (PBMC(1)+ vehicle at 0.5 mg/kg); Group 3 (PBMC(1)+ HER2 TDB (UCHT1v9/hu4D5) at 0.5 mg/kg); Group 4 (PBMC(2)+ vehicle at 0.5 mg/kg); and Group 5 (PBMC(2)+ HER2 TDB (UCHT1v9/hu4D5) at 0.5 mg/kg).

FIG. 99B is a graph showing the percentage of change in tumor volume over time for Group 1 (Vehicle at 0.5 mg/kg); and Group 2 (HER2 TDB (hu4D5/2C11) at 0.5 mg/kg).

FIG. 99C is a histogram showing the relative percentage of change in tumor volume over time for Group 1 (Vehicle at 0.5 mg/kg); and Group 2 (HER2 TDB (hu4D5/2C11) at 0.5 mg/kg).

FIG. 99D is a graph showing the relative tumor volume over time for Group 1 (Vehicle at 0.5 mg/kg); and Group 2 (HER2 TDB (hu4D5/2C11) at 0.5 mg/kg). Responders included tumors that were greater than 1000 mm$^3$ at the start of treatment.

FIG. 99E is a graph showing the percentage of change in tumor volume over time for Group 1 (CD3-arm control HER2 TDB (hu4D5/SP34) at 0.5 mg/kg); and Group 2 (control TDB (2C11) at 0.5 mg/kg).

FIG. 99F is a graph showing the relative tumor volume over time for Group 1 (Vehicle at 0.5 mg/kg); and Group 2 (HER2 TDB (hu4D5/SP34) at 0.5 mg/kg).

FIG. 99G is a graph showing the relative tumor volume over time for Group 1 (Vehicle at 0.5 mg/kg); Group 2 (HER2 TDB (hu4D5/2C11) at 0.5 mg/kg); Group 3 (control TDB (2C11) at 0.5 mg/kg); and Group 4 (T-DM1 at 15 mg/kg).

Figures 100A, 100B:
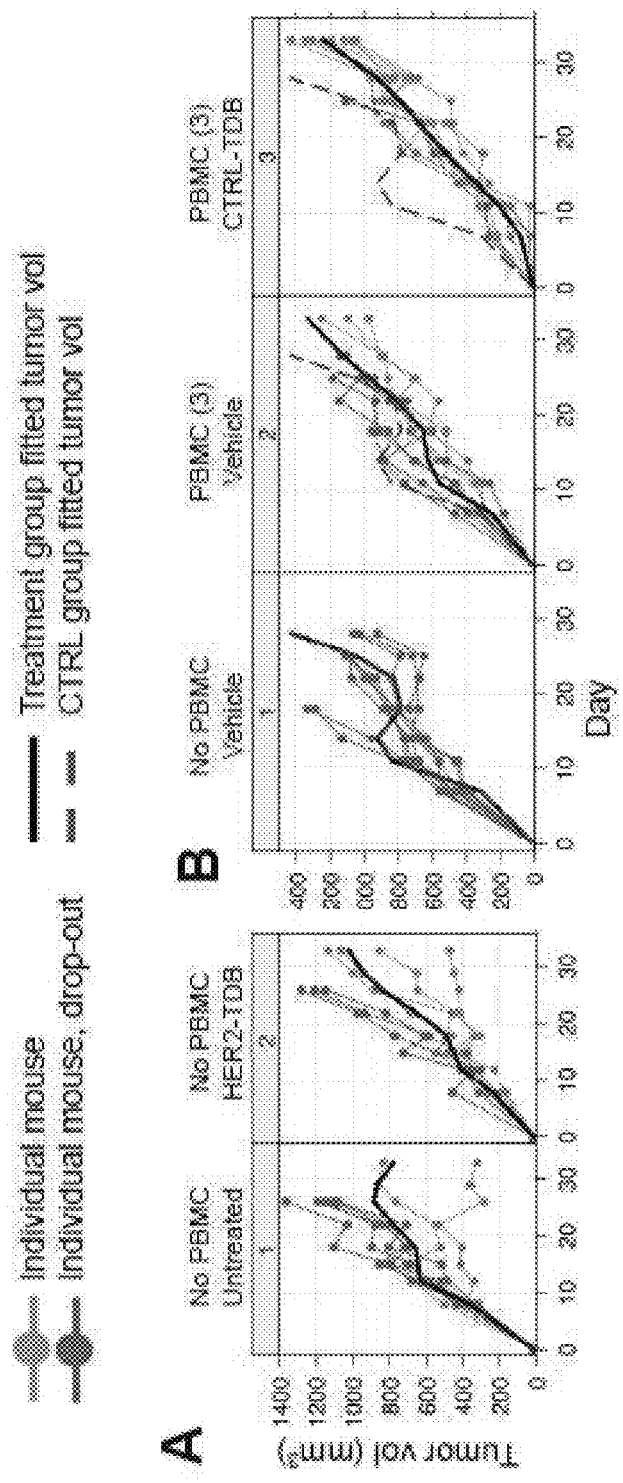

FIG. 100A is a graph showing the relative tumor volume over time for Group 1 (Untreated); Group 2 (HER2 TDB (UCHT1v9/hu4D5) at 0.5 mg/kg).

FIG. 100B is a graph showing the relative tumor volume over time for Group 1 (Vehicle at 0.5 mg/kg); Group 2 (PBMC(3)+Vehicle at 0.5 mg/kg); and Group 3 (PBMC(3)+ control TDB (2C11) at 0.5 mg/kg).

Figures 101A, 101B:
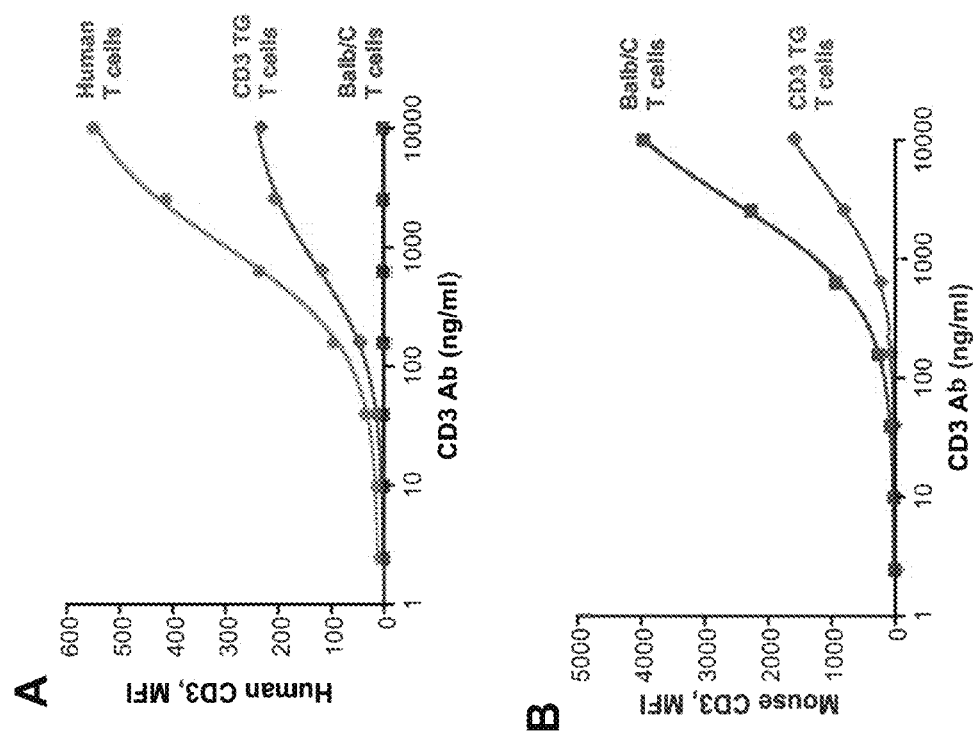

FIG. 101A is a graph showing the binding affinity for the CD3-UCHT1 antibody tested for in vitro binding to human CD3 on human T cells, CD3 TG T cells, and BALB/c T cells, as assessed by FACS analysis.

FIG. 101B is a graph showing the binding affinity for the CD3-2C11 antibody tested for in vitro binding to mouse CD3 on CD3 TG T cells and BALB/c T cells, as assessed by FACS analysis.

Figures 102A, 102B:
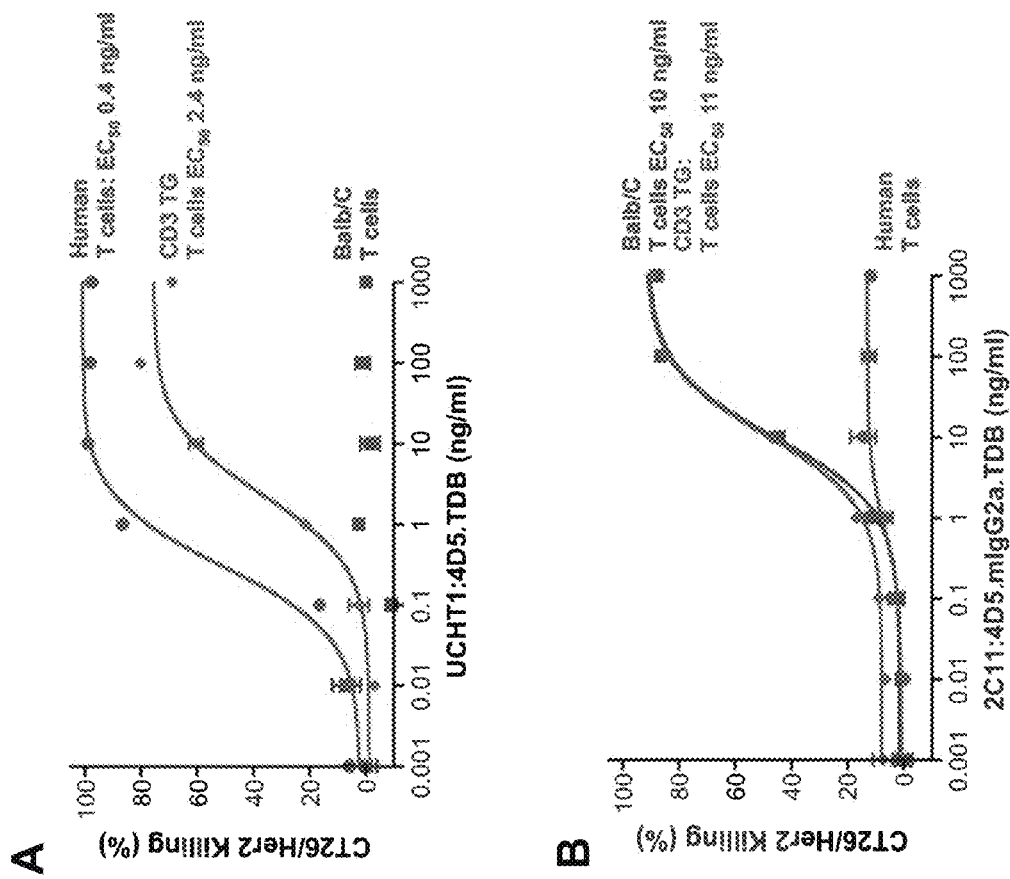

FIG. 102A is a graph showing the percentage of CT26-HER2 target cell killing as a function of HER2 TDB (UCHT1v9/hu4D5) concentration, as assessed by FACS analysis. Effector cells were human peripheral blood isolated T cells, huCD3 transgenic splenic T cells, and BALB/c splenic T cells.

FIG. 102B is a graph showing the percentage of CT26-HER2 target cell killing as a function of HER2 TDB (hu4D5/2C11) concentration, as assessed by FACS analysis. Effector cells were human peripheral blood isolated T cells, huCD3 transgenic splenic T cells, and BALB/c splenic T cells.

Figure 103:
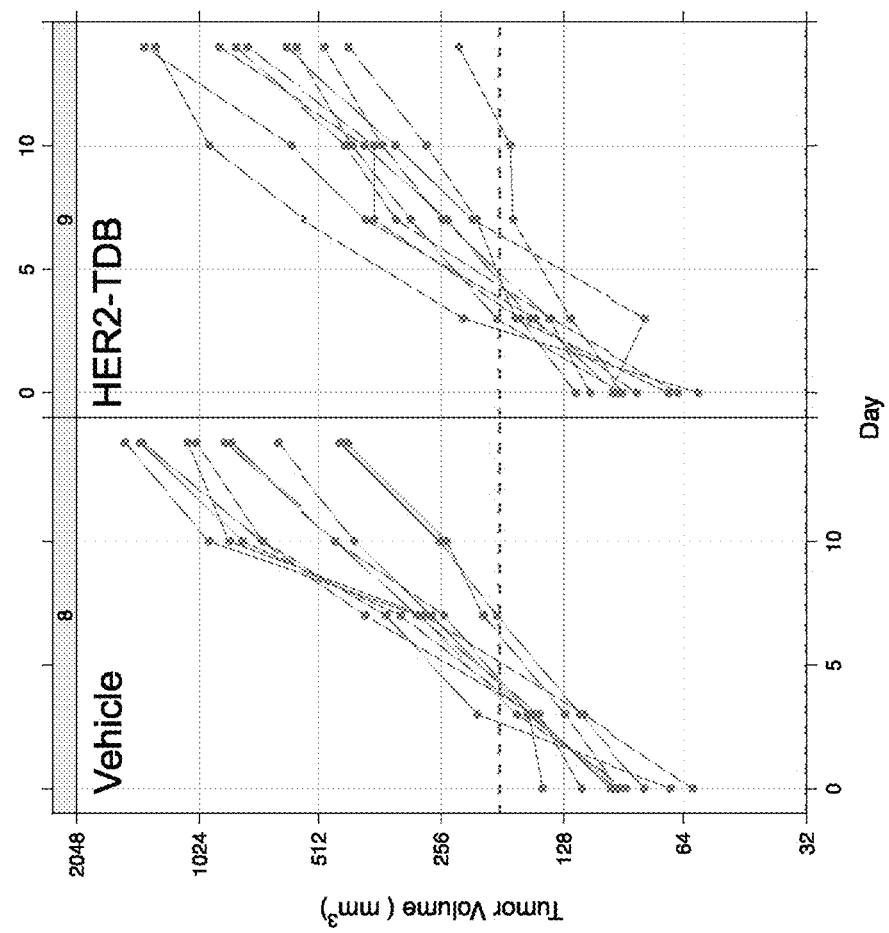

FIG. 103 is a graph showing the relative tumor volume over time for Group 1 (Vehicle at 0.5 mg/kg); and Group 2 (HER2 TDB (hu4D5/SP34) at 0.5 mg/kg).

Figure 104:
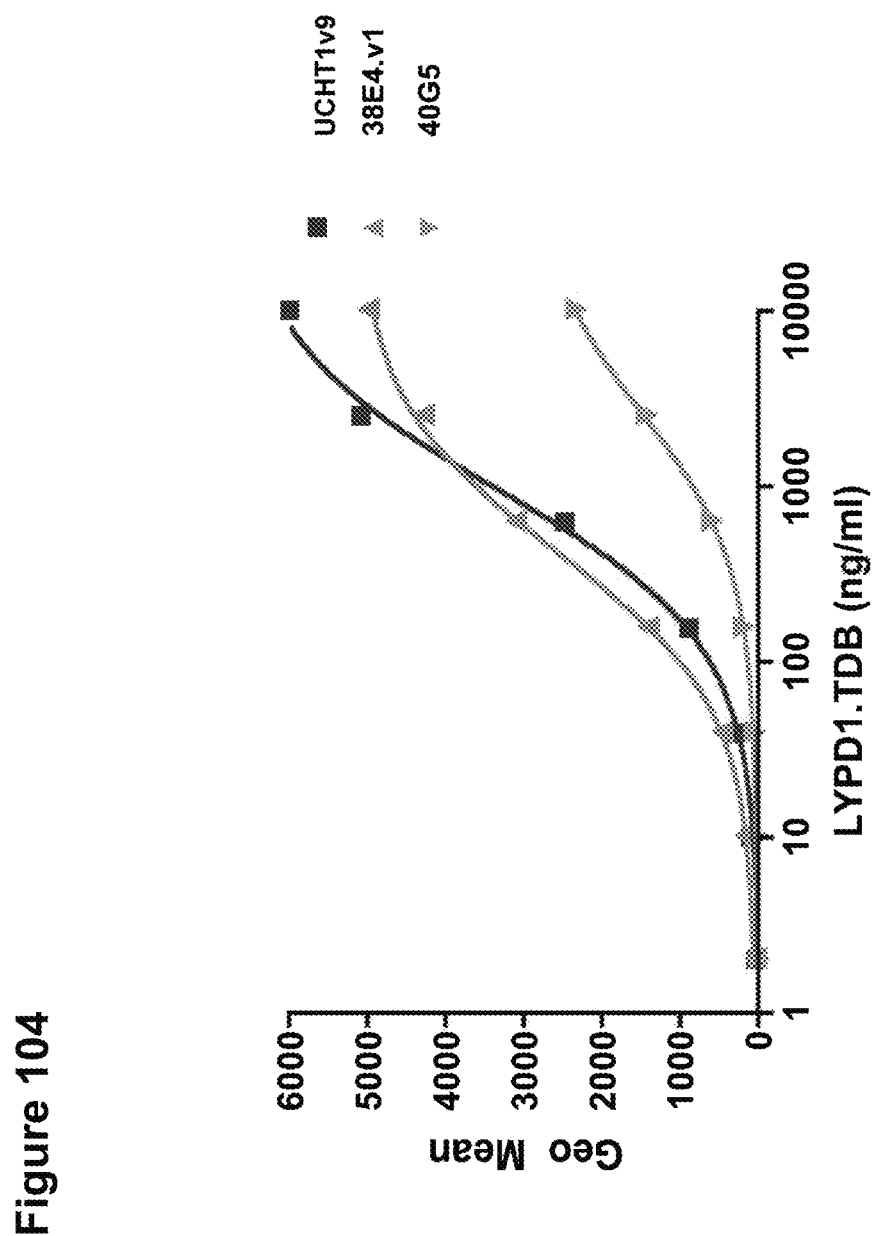

FIG. 104 a graph showing the binding curves for each of the three LYPD1 TDBs tested for in vitro binding to CD8+ CD3-expressing T cells.

Figure 105:
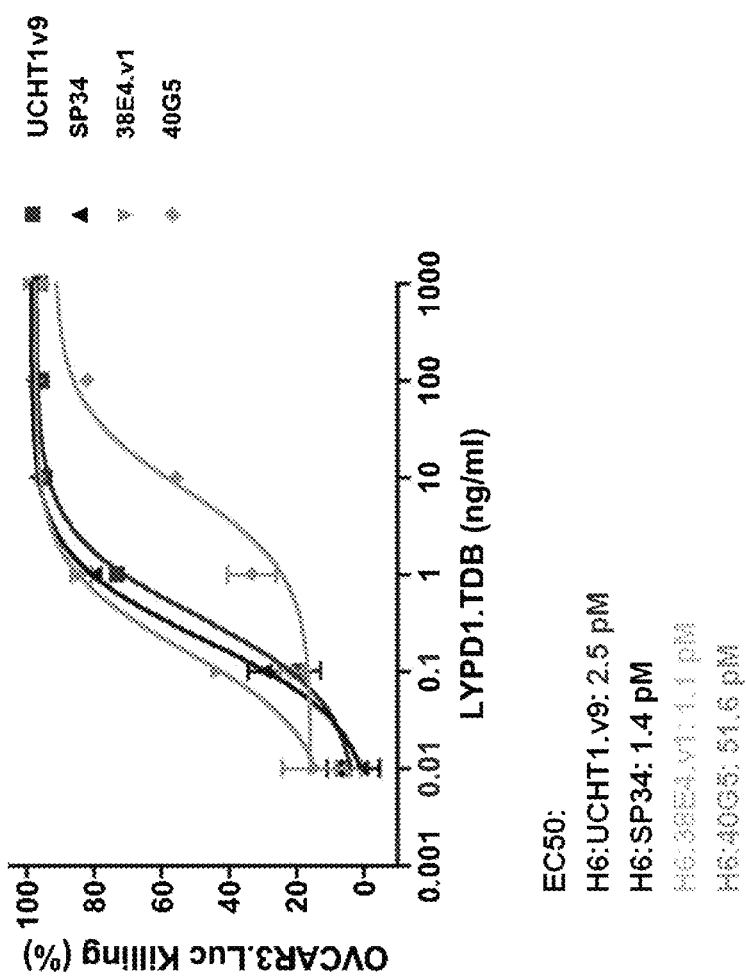

FIG. 105 is a graph showing the percentage of OVCAR3.Luc target cell killing as a function of LYPD1 TDB concentration.

Figure 106:
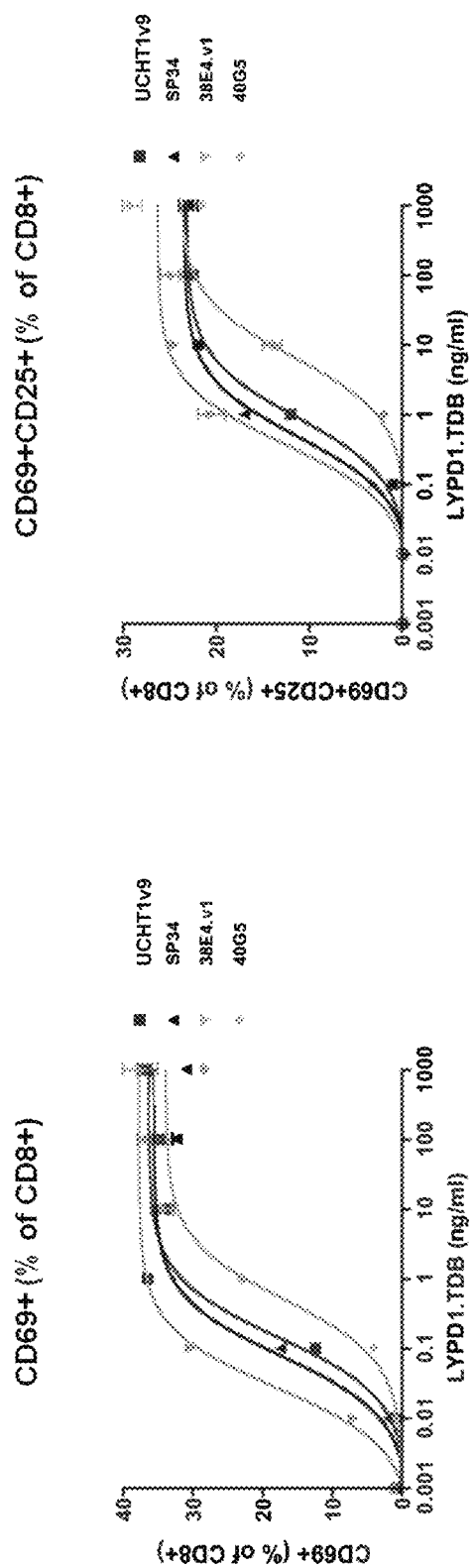

FIG. 106 is a set of graphs showing the percentage of CD8+CD69+(left) and CD8+CD25+(right) T cells as a function of LYPD1 TDB concentration, as assessed by FACS analysis. Target cells were OVCAR3.Luc cells; effector cell: target cell ratio=3:1.

FIG. 107 shows the amino acid sequences of the light chain variable domain (top) and heavy chain variable domain (bottom) of anti-RET antibody 41205.v6.

Figure 108A:
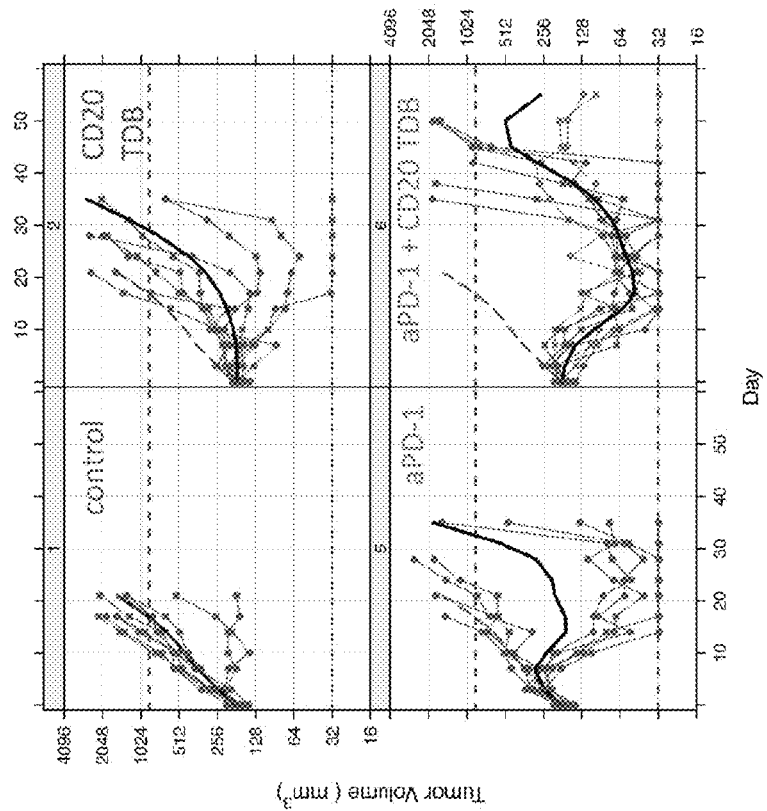

FIG. 108A is a graph showing tumor volume (mm$^3$) as a function of time (days) for Group 1 (vehicle, qwx3, IV; n=9); Group 2 (CD20 TDB (2H7-mu2C11), 0.5 mg/kg, qwx3, IV; n=9); Group 3 (anti-PD1 (mu8F11 DANA), 10 mg/kg, tiwx3, IP; n=9); and Group 4 (anti-PD1 (mu8F11 DANA), 10 mg/kg, tiwx3, IP+CD20 TDB (2H7-mu2C11), 0.5 mg/kg, qwx3, IV; n=9).

Figure 108B:
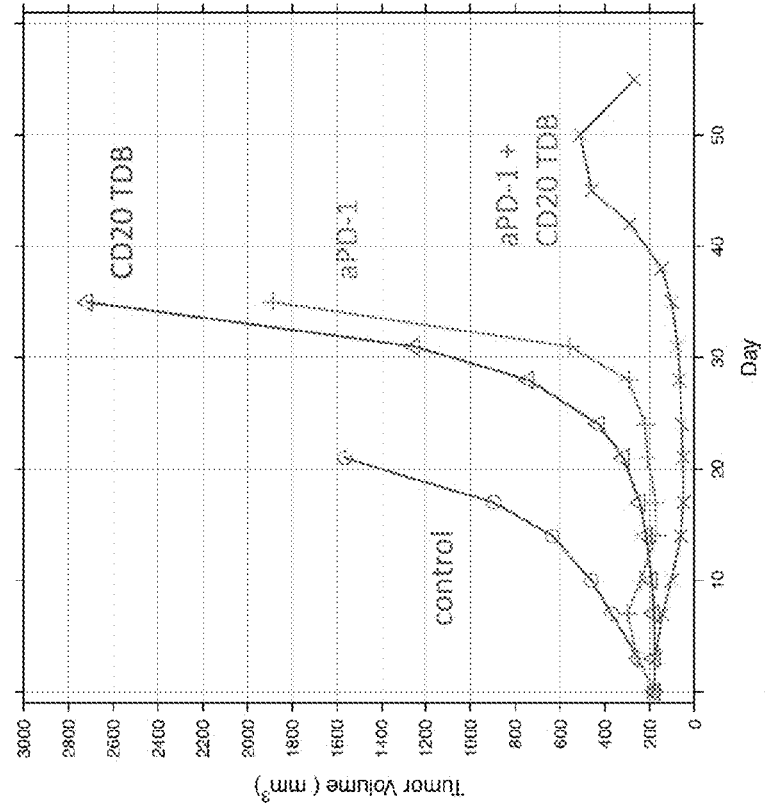

FIG. 108B is a graph showing tumor volume (mm³) as a function of time (days) for Group 1 (vehicle, qwx3, IV; n=9); Group 2 (CD20 TDB (2H7-mu2C11), 0.5 mg/kg, qwx3, IV; n=9); Group 3 (anti-PD1 (mu8F11 DANA), 10 mg/kg, tiwx3, IP; n=9); and Group 4 (anti-PD1 (mu8F11 DANA), 10 mg/kg, tiwx3, IP+CD20 TDB (2H7-mu2C11), 0.5 mg/kg, qwx3, IV; n=9). The bolded solid line represents the fitted tumor volume for the specified group.

DETAILED DESCRIPTION OF EMBODIMENTS OF THE INVENTION

I. Definitions

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')₂; diabodies; linear antibodies; single-chain antibody molecules (e.g. scFv); and multispecific antibodies formed from antibody fragments.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, IgA$_1$, and IgA$_2$. The heavy chain constant domains that correspond to the different classes of immunoglobulins are called α, δ, ε, γ, and μ, respectively.

It is understood that aspects and embodiments of the invention described herein include "comprising," "consisting," and "consisting essentially of" aspects and embodiments.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, gliblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma and breast carcinoma, including metastatic forms of those cancers. In other embodiments, the cancer is selected from a class of mature B-Cell cancers excluding Hodgkin's Lymphoma but including germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenström macroglobulinemia, Heavy chain diseases, α Heavy chain disease, γ Heavy chain disease, μ Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The term "tumor antigen," as used herein, may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are tumor antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. In one aspect the tumor antigen is selected from those set forth in Table 1 below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of a compound, for example, an anti-CD3 antibody of the invention or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio ≥2.0.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "protein," as used herein, refers to any native protein from any vertebrate source, including mammals such as primates (e.g. humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants. Proteins according to the invention include, for example, any protein listed in Table 1.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, "administering" is meant a method of giving a dosage of a compound (e.g., an anti-CD3 antibody of the invention or a nucleic acid encoding an anti-CD3 antibody of the invention) or a composition (e.g., a pharmaceutical composition, e.g., a pharmaceutical composition including an anti-CD3 antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Compositions and Methods

In one aspect, the invention is based, in part, on anti-CD3 antibodies. In certain embodiments, the anti-CD3 antibodies are multispecific (e.g., bispecific) and bind, in addition to CD3 or a fragment thereof, a second biological molecule (e.g., a cell surface antigen, e.g., a tumor antigen). Antibodies of the invention are useful, for example, for treating or delaying the progression of a cell proliferative disorder (e.g., cancer) or an autoimmune disorder, or for enhancing immune function in a subject having such a disorder.

A. Exemplary Anti-CD3 Antibodies

In one aspect, the invention provides isolated antibodies that bind to CD3 (e.g., CD3ε and/or CD3γ).

For example, in one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 301-304, respectively, and/or at least one (e.g., 1, 2, 3, or 4) of the light chain framework regions FR-L1, FR-L2, FR-L3, and FR-L4 comprising the sequences of SEQ ID NOs: 305-308, respectively. In some instances, the anti-CD3 antibody may have a heavy chain variable (VH) domain including an amino acid sequence having at least 90% sequence identity (e.g., at least 91%, 92%, 93%, 94%, 95%, 96%, 97%, 98%, or 99% sequence identity) to, or the sequence of, SEQ ID NO: 184 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 185. In other instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 293-296, respectively, and/or at least one (e.g., 1, 2, 3, or 4) of the light chain framework regions FR-L1, FR-L2, FR-L3, and FR-L4 comprising the sequences of SEQ ID NOs: 297-300, respectively. In some instances, the anti-CD3 antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 186 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 187. In a particular instance, the anti-CD3 antibody can be 40G5c, or a derivative or clonal relative thereof.

In another aspect, an antibody of the invention comprises (a) a VH domain comprising at least one, at least two, or all three VH HVR sequences selected from (i) HVR-H1 comprising the amino acid sequence of SEQ ID NO: 1, (ii) HVR-H2 comprising the amino acid sequence of SEQ ID NO: 2, and (iii) HVR-H3 comprising an amino acid sequence selected from SEQ ID NO: 3; and (b) a VL domain comprising at least one, at least two, or all three VL HVR sequences selected from (i) HVR-L1 comprising the amino acid sequence of SEQ ID NO: 4, (ii) HVR-L2 comprising the amino acid sequence of SEQ ID NO: 5, and (iii) HVR-L3 comprising the amino acid sequence of SEQ ID NO: 6. In some instances, the anti-CD3 antibody may have a VH domain comprising the amino acid sequence of SEQ ID NO: 184 and a VL domain comprising the amino acid sequence of SEQ ID NO: 185. In some instances, the anti-CD3 antibody may have a VH domain comprising the amino acid sequence of SEQ ID NO: 186 and a VL domain comprising the amino acid sequence of SEQ ID NO: 187. In a particular instance, the anti-CD3 antibody can be 40G5c, or a derivative or clonal relative thereof.

In one aspect, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 181; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 182.

In certain embodiments, any one or more amino acids of an anti-CD3 antibody as provided above are substituted at the following HVR positions:

in HVR-H3 (SEQ ID NO: 181): positions 1, 2, 5, 6, and 7; and in HVR-L3 (SEQ ID NO: 182): positions 1, 2, 4, and 5

In certain embodiments, the substitutions are conservative substitutions, as provided herein. In certain embodiments, any one or more of the following substitutions may be made in any combination:

in HVR-H3 (SEQ ID NO: 181): D1T or S; S1D or T; T1D or S; G2A or S; A2G or S; S2A or G; R5N; N5R; Y6A; A6Y; A7Y; and Y7A; and in HVR-L3 (SEQ ID NO: 182): K1T; T1K; Q2A; A2Q; F4A; A4F; I5A and A5I.

For example, in some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 188 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 189. In a particular instance, the anti-CD3 antibody can be 38E4v1, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 190 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 191. In a particular instance, the anti-CD3 antibody can be 38E4v2, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 192 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 193. In a particular instance, the anti-CD3 antibody can be 38E4v3, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 194 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 195. In a particular instance, the anti-CD3 antibody can be 38E4v4, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 196 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 197. In a particular instance, the anti-CD3 antibody can be 38E4v5, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 198 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 199. In a particular instance, the anti-CD3 antibody can be 38E4v6, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 200 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 201. In a particular instance, the anti-CD3 antibody can be 38E4v7, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 202 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 203. In a particular instance, the anti-CD3 antibody can be 38E4v8, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 204 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 205. In a particular instance, the anti-CD3 antibody can be 38E4v9, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 206 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 207. In a particular instance, the anti-CD3 antibody can be 38E4c, or a derivative or clonal relative thereof.

In some instances, any one of the 38E4v1-38E4v9 and 38E4c anti-CD3 antibodies may comprise at least one (e.g., 1, 2, 3, or 4) of heavy chain framework regions FR-H1, FR-H2, FR-H3, and FR-H4 comprising the sequences of SEQ ID NOs: 309-312, respectively, and/or at least one (e.g., 1, 2, 3, or 4) of the light chain framework regions FR-L1, FR-L2, FR-L3, and FR-L4 comprising the sequences of SEQ ID NOs: 313-316, respectively.

In one aspect, the invention provides an anti-CD3 antibody having a binding domain comprising at least one, two, three, four, five, or six HVRs selected from (a) HVR-H1 comprising the amino acid sequence of SEQ ID NO: 23; (b) HVR-H2 comprising the amino acid sequence of SEQ ID NO: 183; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28.

In certain embodiments, any one or more amino acids of an anti-CD3 antibody as provided above are substituted at the following HVR positions:
in HVR-H2 (SEQ ID NO: 183): positions 9, 12, 13, 14, 15, and 17.

In certain embodiments, the substitutions are conservative substitutions, as provided herein. In certain embodiments, any one or more of the following substitutions may be made in any combination:
in HVR-H2 (SEQ ID NO: 183): S9T; T9S; N12A; A12N; Q13D; D13Q; K14S; S14K; F15V; V15F; D17G; and G17D.

For example, in some instances, the invention provides an anti-CD3 antibody having a binding domain comprising at least one, two, three, four, five, or six HVRs selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 317-320, respectively, and/or at least one (e.g., 1, 2, 3, or 4) of the light chain framework regions FR-L1, FR-L2, FR-L3, and FR-L4 comprising the sequences of SEQ ID NOs: 321-324, respectively. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 208 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 209. In a particular instance, the anti-CD3 antibody can be UCHT1v9, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 325-328, respectively, and/or at least one (e.g., 1, 2, 3, or 4) of the light chain framework regions FR-L1, FR-L2, FR-L3, and FR-L4 comprising the sequences of SEQ ID NOs: 329-332, respectively. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 210 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 211. In a particular instance, the anti-CD3 antibody can be UCHT1v1, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 23;

(b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 333-336, respectively, and/or at least one (e.g., 1, 2, 3, or 4) of the light chain framework regions FR-L1, FR-L2, FR-L3, and FR-L4 comprising the sequences of SEQ ID NOs: 337-340, respectively. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 212 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 213. In a particular instance, the anti-CD3 antibody can be UCHT1vM1, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 341-344, respectively, and/or at least one (e.g., 1, 2, 3, or 4) of the light chain framework regions FR-L1, FR-L2, FR-L3, and FR-L4 comprising the sequences of SEQ ID NOs: 345-348, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 214 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 215. In other instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 349-352, respectively, and/or at least one (e.g., 1, 2, 3, or 4) of the light chain framework regions FR-L1, FR-L2, FR-L3, and FR-L4 comprising the sequences of SEQ ID NOs: 353-356, respectively. In some instances, the anti-CD3 antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 216 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 217. In a particular instance, the anti-CD3 antibody can be SP34v52, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 357-360, respectively, and/or at least one (e.g., 1, 2, 3, or 4) of the light chain framework regions FR-L1, FR-L2, FR-L3, and FR-L4 comprising the sequences of SEQ ID NOs: 361-364, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 218 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 219. In other instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 365-368, respectively, and/or at least one (e.g., 1, 2, 3, or 4) of the light chain framework regions FR-L1, FR-L2, FR-L3, and FR-L4 comprising the sequences of SEQ ID NOs: 369-372, respectively. In some instances, the anti-CD3 antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 220 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 221. In a particular instance, the anti-CD3 antibody can be 41D9a, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 373-376, respectively, and/or at least one (e.g., 1, 2, 3, or 4) of the light chain framework regions FR-L1, FR-L2, FR-L3, and FR-L4 comprising the sequences of SEQ ID NOs: 377-380, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 222 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 223. In other instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 381-384, respectively, and/or at least one (e.g., 1, 2, 3, or 4) of the light chain framework regions FR-L1, FR-L2, FR-L3, and FR-L4 comprising the sequences of SEQ ID NOs: 385-388, respectively. In some instances, the anti-CD3 antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 226 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 227. In a particular instance, the anti-CD3 antibody can be 13A3, or a derivative or clonal relative thereof.

In some instances, the invention provides an anti-CD3 antibody having a binding domain comprising at least one, two, three, four, five, or six HVRs selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 389-392, respectively, and/or at least one (e.g., 1, 2, 3, or 4) of the light chain framework regions FR-L1, FR-L2, FR-L3, and FR-L4 comprising the sequences of SEQ ID NOs: 393-396, respectively. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 224 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 225. In a particular instance, the anti-CD3 antibody can be 13A3.v2, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 397-400, respectively, and/or at least one (e.g., 1, 2, 3, or 4) of the light chain framework regions FR-L1, FR-L2, FR-L3, and FR-L4 comprising the sequences of SEQ ID NOs: 401-404, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 228 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 229. In other instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 405-408, respectively, and/or at least one (e.g., 1, 2, 3, or 4) of the light chain framework regions FR-L1, FR-L2, FR-L3, and FR-L4 comprising the sequences of SEQ ID NOs: 409-412, respectively. In some instances, the anti-CD3 antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 230 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 231. In a particular instance, the anti-CD3 antibody can be 30A1, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 413-416, respectively, and/or at least one (e.g., 1, 2, 3, or 4) of the light chain framework regions FR-L1, FR-L2, FR-L3, and FR-L4 comprising the sequences of SEQ ID NOs: 417-420, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 232 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 233. In a particular instance, the anti-CD3 antibody can be 30A1.v2, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 421-424, respectively, and/or at least one (e.g., 1, 2, 3, or 4) of the light chain framework regions FR-L1, FR-L2, FR-L3, and FR-L4 comprising the sequences of SEQ ID NOs: 425-428, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 234 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 235. In a particular instance, the anti-CD3 antibody can be h21A9, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 429-432, respectively, and/or at least one (e.g., 1, 2, 3, or 4) of the light chain framework regions FR-L1, FR-L2, FR-L3, and FR-L4 comprising the sequences of SEQ ID NOs: 433-436, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 236 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 237. In a particular instance, the anti-CD3 antibody can be 21B2, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 437-440, respectively, and/or at least one (e.g., 1, 2, 3, or 4) of the light chain framework regions FR-L1, FR-L2, FR-L3, and FR-L4 comprising the sequences of SEQ ID NOs: 441-444, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 238 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 239. In a particular instance, the anti-CD3 antibody can be 125A1, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 445-448, respectively, and/or at least one (e.g., 1, 2, 3, or 4) of the light chain framework regions FR-L1, FR-L2, FR-L3, and FR-L4 comprising the sequences of SEQ ID NOs: 449-452, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 240 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 241. In a particular instance, the anti-CD3 antibody can be 72H6, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 453-456, respectively, and/or at least one (e.g., 1, 2, 3, or 4) of the light chain framework regions FR-L1, FR-L2, FR-L3, and FR-L4 comprising the sequences of SEQ ID NOs: 457-460, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 242 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 243. In a particular instance, the anti-CD3 antibody can be 1961, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 461-464, respectively, and/or at least one (e.g., 1, 2, 3, or 4) of the light chain framework regions FR-L1, FR-L2, FR-L3, and FR-L4 comprising the sequences of SEQ ID NOs: 465-468, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 244 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 245. In a particular instance, the anti-CD3 antibody can be 71H7, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 469-472, respectively, and/or at least one (e.g., 1, 2, 3, or 4) of the light chain framework regions FR-L1, FR-L2, FR-L3, and FR-L4 comprising the sequences of SEQ ID NOs: 473-476, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 246 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 247. In a particular instance, the anti-CD3 antibody can be 14C7, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 477-480, respectively, and/or at least one (e.g., 1, 2, 3, or 4) of the light chain framework regions FR-L1, FR-L2, FR-L3, and FR-L4 comprising the sequences of SEQ ID NOs: 481-484, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 248 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 249. In a particular instance, the anti-CD3 antibody can be 12763, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 485-488, respectively, and/or at least one (e.g., 1, 2, 3, or 4) of the light chain framework regions FR-L1, FR-L2, FR-L3, and FR-L4 comprising the sequences of SEQ ID NOs: 489-492, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 250 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 251. In a particular instance, the anti-CD3 antibody can be 18F12, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 493-496, respectively, and/or at least one (e.g., 1, 2, 3, or 4) of the light chain framework regions FR-L1, FR-L2, FR-L3, and FR-L4 comprising the sequences of SEQ ID NOs: 497-500, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 252 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 253. In a particular instance, the anti-CD3 antibody can be 27H5-1, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 501-504, respectively, and/or at least one (e.g., 1, 2, 3, or 4) of the light chain framework regions FR-L1, FR-L2, FR-L3, and FR-L4 comprising the sequences of SEQ ID NOs: 505-508, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 254 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 255. In a particular instance, the anti-CD3 antibody can be 3967, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 509-512, respectively, and/or at least one (e.g., 1, 2, 3, or 4) of the light chain framework regions FR-L1, FR-L2, FR-L3, and FR-L4 comprising the sequences of SEQ ID NOs: 513-516, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 256 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 257. In a particular instance, the anti-CD3 antibody can be 40D2, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 517-520, respectively, and/or at least one (e.g., 1, 2, 3, or 4) of the light chain framework regions FR-L1, FR-L2, FR-L3, and FR-L4 comprising the sequences of SEQ ID NOs: 521-524, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 258 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 259. In a particular instance, the anti-CD3 antibody can be 7967, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 525-528, respectively, and/or at least one (e.g., 1, 2, 3, or 4) of the light chain framework regions FR-L1, FR-L2, FR-L3, and FR-L4 comprising the sequences of SEQ ID NOs: 529-532, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 260 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 261. In a particular instance, the anti-CD3 antibody can be 95A2, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150. In some instances, the anti-CD3 antibody comprises at least one (e.g., 1, 2, 3, or 4)

of heavy chain framework regions FR-H1, FR-H2, FR-H3, and FR-H4 comprising the sequences of SEQ ID NOs: 533-536, respectively, and/or at least one (e.g., 1, 2, 3, or 4) of the light chain framework regions FR-L1, FR-L2, FR-L3, and FR-L4 comprising the sequences of SEQ ID NOs: 537-540, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 262 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 263. In a particular instance, the anti-CD3 antibody can be 118G9, or a derivative or clonal relative thereof.

In one aspect, the invention provides an anti-CD3 antibody having a binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156. In some instances, the anti-CD3 antibody comprises at least one (e.g., 1, 2, 3, or 4) of heavy chain framework regions FR-H1, FR-H2, FR-H3, and FR-H4 comprising the sequences of SEQ ID NOs: 541-544, respectively, and/or at least one (e.g., 1, 2, 3, or 4) of the light chain framework regions FR-L1, FR-L2, FR-L3, and FR-L4 comprising the sequences of SEQ ID NOs: 545-548, respectively. In some instances, the anti-CD3 antibody may have a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 264 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 265. In a particular instance, the anti-CD3 antibody can be Rab17, or a derivative or clonal relative thereof.

In any of the above embodiments, an anti-CD3 antibody is humanized. In one embodiment, an anti-CD3 antibody comprises HVRs as in any of the above embodiments, and further comprises an acceptor human framework, e.g., a human immunoglobulin framework or a human consensus framework.

In another aspect, an anti-CD3 antibody is provided, wherein the antibody comprises a VH as in any of the embodiments provided above, and a VL as in any of the embodiments provided above, wherein one or both of the variable domain sequences include post-translational modifications.

In a further aspect, the invention provides an antibody that binds to the same epitope as an anti-CD3 antibody provided herein. For example, in certain embodiments, an antibody is provided that binds to the same epitope as an anti-CD3 antibody comprising a VH sequence of SEQ ID NO: 184 and a VL sequence of SEQ ID NO: 185. In certain embodiments, an antibody is provided that binds to an epitope within a fragment of CD3 (e.g., human CD3ε) consisting of amino acids 1-26 (SEQ ID NO: 283) or 1-27 (SEQ ID NO: 278) of human CD3ε.

In another aspect, the invention provides an antibody that binds a unique CD3 epitope. In certain embodiments, the anti-CD3 antibody of the invention makes unique contacts with amino acids of human CD3ε at a distance of 3.5 Angstroms, 3.25 Angstroms, 3.00 Angstroms, 2.75 Angstroms, or less. In certain embodiments, an antibody is provided that binds to an epitope consisting of one, two, three, four, or five amino acids of human CD3ε at a distance of 3.5 Angstroms, 3.25 Angstroms, 3.00 Angstroms, 2.75 Angstroms or less. In one embodiment, the anti-CD3 antibody of the invention makes unique contacts with amino acids of human CD3ε at a distance of 3.5 Angstroms or less. In certain embodiments, an antibody is provided that binds to an epitope consisting of one, two, three, four, or five amino acids of human CD3ε at a distance of 3.5 Angstroms or less. For example, in certain embodiments, an antibody is provided that binds to an epitope consisting of amino acids of human CD3ε selected from Gln1, Asp2, Asn4, Glu6, and Met7. In one particular embodiment, the anti-CD3 antibody binds to an epitope that specifically includes Glu6. In certain other embodiments, an antibody is provided that does not bind to an epitope that includes human CD3ε amino acid Glu5. In certain other embodiments, an antibody is provided that does not bind to an epitope that includes human CD3ε amino acids Gly3 and Glu5.

An anti-CD3 epitope may be determined by anti-CD3 antibody binding to peptide fragments of the epitope. Alternatively, an anti-CD3 epitope may be determined by alanine scanning mutagenesis. In one embodiment, a reduction in binding of an anti-CD3 antibody to mutated CD3 by 20%, 30%, 50%, 80% or more indicates the amino acid residue of CD3 mutated in an alanine scanning mutagenesis assay is an epitope residue for that anti-CD3 antibody. Alternatively, an anti-CD3 epitope may be determined by mass spectrometry. In some embodiments, the epitope is determined by crystallography (e.g., crystallography methods described in the Examples).

In some embodiments, the epitope as determined by crystallography is determined using amino acids Q1-M7 of CD3. In some embodiments, the epitope as determined by crystallography is determined using amino acids QDGNEEMGGITQTPYK (SEQ ID NO: 284) of CD3.

In some embodiments, the epitope as determined by crystallography may be performed by combining the anti-CD3 antibody Fab, dissolved in 0.15 M NaCl, 25 mM tris, pH 7.5 at 10 mg/ml, with a 2-fold molar excess (1 mg) of CD3ε peptide and initially screening a sparse matrix of precipitants in a sitting drop vapor diffusion format. Optimized crystals may be grown from a 1:1 mixture with reservoir solution containing 70% v/v methyl-pentanediol, and 0.1 M HEPES buffer at pH 7.5. The reservoir may be be used as a cryoprotectant. The crystals may be transferred to cryogenic temperature by sudden immersion into liquid nitrogen.

The diffraction data for crystals may be collected at Advanced Photon Source beam line 221D, using a MAR300 CCD detector. The recorded diffractions may be integrated and scaled using the program HKL2000.

The structure may be phased by molecular replacement (MR) method using program Phaser. For example, the MR search model is a Fab subunit derived from a crystal structure of HGFA/Fab complex (PDB code: 2R0L). The CD3ε peptide is built into the structure based on a Fo-Fc map. The structure may be subsequently refined with programs REFMAC5 and PHENIX using the maximum likelihood target functions, anisotropic individual B-factor refinement method, and TLS refinement method, to achieve convergence.

In certain other embodiments, an antibody is provided that includes a paratope that binds to the same epitope as an anti-CD3 antibody provided herein. For example, in certain embodiments an antibody is provided that binds to the same epitope as an anti-CD3 antibody paratope comprising amino acids that form contacts at a distance of 3.5 Angstroms or less. In certain embodiments, an antibody is provided that binds to the same epitope as an anti-CD3 antibody paratope consisting of amino acids of the VH region of an anti-CD3 antibody selected from the group comprising 33Tyr, 35His, 50Trp, 97Tyr, and 98Ser. In certain embodiments, an antibody is provided that binds to the same epitope as an anti-CD3 antibody paratope consisting of one, two, three, four, or five amino acids of the VH region of an anti-CD3 antibody selected from the group comprising 33Tyr, 35His, 50Trp, 97Tyr, and 98Ser. In certain embodiments, an antibody is provided that binds to the same epitope as an anti-CD3 antibody paratope consisting of amino acids of the VL region of an anti-CD3 antibody selected from the group comprising 27Arg, 27Asn, 30Lys, 32Tyr, 92Phe, 94Leu, and 96Arg. In certain embodiments, an antibody is provided that binds to the same epitope as an anti-CD3 antibody paratope consisting of one, two, three, four, five, six, or seven amino acids of the VL region of an anti-CD3 antibody selected from the group comprising 27Arg, 27Asn, 30Lys, 32Tyr, 92Phe, 94Leu, and 96Arg. In an optional embodiment, an antibody is provided that does not bind to the same epitope as an anti-CD3 antibody paratope consisting of amino acids of the VL region comprising 91 Ser. In a further aspect of the invention, an anti-CD3 antibody according to any of the above embodiments is a monoclonal antibody, comprising a chimeric, humanized, or human antibody. In one embodiment, an anti-CD3 antibody is an antibody fragment, for example, a Fv, Fab, Fab', scFv, diabody, or F(ab')2 fragment. In another embodiment, the antibody is a full length antibody, e.g., an intact IgG antibody (e.g., an intact IgG1 antibody) or other antibody class or isotype as defined herein.

In a further aspect, an anti-CD3 antibody according to any of the above embodiments may incorporate any of the features, singly or in combination, as described in Sections 1-7 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{on}/k_{off}$. See, for example, Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992) and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAb® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001)

and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, the anti-CD3 antibody provided herein is a multispecific antibody, for example, a bispecific antibody. Multispecific antibodies are monoclonal antibodies that have binding specificities for at least two different sites. In certain embodiments, bispecific antibodies may bind to two different epitopes of CD3 (e.g., CD3ε or CD3γ). In certain embodiments, one of the binding specificities is for CD3 (e.g., CD3ε or CD3γ) and the other is for any other antigen (e.g., a second biological molecule, e.g., a cell surface antigen, e.g., a tumor antigen). Accordingly, a bispecific anti-CD3 antibody may have binding specificities for CD3 and a second biological molecule, such as a second biological molecule (e.g., a tumor antigen) listed in Table 1 and described in U.S. Pub. No. 2010/0111856.

TABLE 1

| Tumor antigen targets of the bispecific anti-CD3 antibodies of the invention |||||||
|---|---|---|---|---|---|---|
| CD20 | CD79a | ETBR | IL13Ralpha2 | M-CSF | P2X5 | SSX-2 |
| 0772P | CD79b | ETV6-AML1 fusion protein | IL20Rα | MCSP | p53 | SSX-4 |
| adipophilin | Cdc27 | EZH2 | Intestinal carboxyl esterase | mdm-2 | PAP | STEAP1 |
| AIM-2 | CDK4 | FcRH1 | IRTA2 | MDP | PAX5 | STEAP1 |
| ALDH1A1 | CDKN2A | FcRH2 | Kallikrein 4 | ME1 | PBF | STEAP2 |
| alpha-actinin-4 | CEA | FcRH5 | KIF20A | Melan-A/MART-1 | PMEL17 | survivin |
| alpha-foetoprotein | CLL1 | FLT3-ITD | KK-LC-1 | Meloe | pml-RARalpha fusion protein | SYT-SSX1 or-SSX2 fusion protein |
| Amphiregulin | CLPP | FN1 | KM-HN-1 | MMP-2 | PRAME | TAG-1 |
| ARTC1 | COA-1 | G250/MN/CAIX | K-ras | MMP-7 | PRDX5 | TAG-2 |
| ASLG659 | CPSF | GAGE-1,2,8 | LAGE-1 | MPF | PSCA | Telomerase |
| ASPHD1 | CRIPTO | GAGE-3,4,5,6,7 | LDLR-fucosyltransferaseASfusion protein | MRP4 | PSCA hlg | TENB2 |
| B7-H4 | Cw6 | GDNF-Ra1 | Lengsin | MSG783 | PSMA | TGF-betaRII |
| BAFF-R | CXCR5 | GEDA | LGR5 | MUC1 | PTPRK | TMEFF1 |
| BAGE-1 | CXORF61 | GFRA1 | LY64 | MUC5AC | RAB38/NY-MEL-1 | TMEM118 |
| BCLX (L) | cyclin D1 | glypican-3 | Ly6E | mucin | RAGE-1 | TMEM46 |
| BCR-ABL fusion protein (b3a2) | Cyclin-A1 | GnTVf | Ly6G6D | MUM-1f | RBAF600 | TRAG-3 |
| beta-catenin | dekcan fusion protein | gp100/Pmel17 | LY6K | MUM-2 | RET | Triosephosphate isomerase |
| BING-4 | DKK1 | GPC3 | LYPD1 | MUM-3 | RGS5 | TRP-1/gp75 |
| B-RAF | DR1 | GPNMB | MAGE-A1 | Myosin class I | RhoC | TRP-2 |
| Brevican | DR13 | GPR172A | MAGE-A10 | NA88-A | RNF43 | TRP2-INT2 |
| CALCA | E16 | GPR19 | MAGE-A12 | Napi2b | RNF43 | TrpM4 |
| CASP-5 | EDAR | GPR54 | MAGE-A2 | NCA | RU2AS | Tyrosinase |
| CASP-8 | EFTUD2 | HAVCR1 | MAGE-A3 | neo-PAP | SAGE | tyrosinase |

TABLE 1-continued

Tumor antigen targets of the bispecific anti-CD3 antibodies of the invention

| | | | | | | |
|---|---|---|---|---|---|---|
| CD19 | Elongation factor 2 | HER2 | MAGE-A4 | NFYC | secernin 1 | VEGF |
| CD21 | ENAH (hMena) | HER-2/neu | MAGE-A6 | N-ras | Sema 5b | WT1 |
| CD22 | EpCAM | HERV-K-MEL | MAGE-A9 | NY-BR-1 | SIRT2 | XAGE-1b/GAGED2a |
| CD33 | EphA3 | HLA-DOB | MAGE-C1 | NY-ESO-1/LAGE-2 | SLC35D3 | EGFR-T790M; |
| CD45 | EphB2R | hsp70-2 | MAGE-C2 | OA1 | SNRPD1 | BMPR1B |
| CD70 | Epiregulin | IDO1 | mammaglobin-A | OGT | SOX10 | |
| CD72 | EGFR | IGF2B3 | MART2 | OS-9 | Sp17 | |
| EGFR-G719A | EGFR-G719C; | EGFR-G719S; | EGFR-L858R | EGFR-S768I | EGFR-L861Q | |

The bispecific anti-CD3 antibody (e.g., any one of the anti-CD3 antibodies described above) may have binding specificities for CD3 and a second biological molecule such as a human leukocyte antigen (HLA)-peptide complex presented on the cell surface by MHC. The bispecific anti-CD3 antibody (e.g., any one of the anti-CD3 antibodies described above) may have binding specificities for CD3 and a second biological molecule comprising a HLA-peptide complex selected from the group consisting of 0772P (CA125, MUC16; Genbank accession no. AF36148); adipophilin (perilipin-2, Adipose differentiation-related protein, ADRP, ADFP, MGC10598; NCBI Reference Sequence: NP_001113.2); AIM-2 (Absent In Melanoma 2, PYHIN4, Interferon-Inducible Protein AIM2; NCBI Reference Sequence: NP_004824.1); ALDH1A1 (Aldehyde Dehydrogenase 1 Family, Member A1, ALDH1, PUMB1, Retinaldehyde Dehydrogenase 1, ALDC, ALDH-E1, ALHDII, RALDH 1, EC 1.2.1.36, ALDH11, HEL-9, HEL-S-53e, HEL12, RALDH1, Acetaldehyde Dehydrogenase 1, Aldehyde Dehydrogenase 1, Soluble, Aldehyde Dehydrogenase, Liver Cytosolic, ALDH Class 1, Epididymis Luminal Protein 12, Epididymis Luminal Protein 9, Epididymis Secretory Sperm Binding Protein Li 53e, Retinal Dehydrogenase 1, RalDH1, Aldehyde Dehydrogenase Family 1 Member A1, Aldehyde Dehydrogenase, Cytosolic, EC 1.2.1; NCBI Reference Sequence: NP_000680.2); alpha-actinin-4 (ACTN4, Actinin, Alpha 4, FSGS1, Focal Segmental Glomerulosclerosis 1, Non-Muscle Alpha-Actinin 4, F-Actin Cross-Linking Protein, FSGS, ACTININ-4, Actinin Alpha4 Isoform, alpha-actinin-4; NCBI Reference Sequence: NP_004915.2); alpha-fetoprotein (AFP, HPAFP, FETA, alpha-1-fetoprotein, alpha-fetoglobulin, Alpha-1-fetoprotein, Alpha-fetoglobulin, HP; GenBank: AAB58754.1); Amphiregulin (AREG, SDGF, Schwannoma-Derived Growth Factor, Colorectum Cell-Derived Growth Factor, AR, CRDGF; GenBank: AAA51781.1); ARTC1 (ART1, ADP-Ribosyltransferase 1, Mono(ADP-Ribosyl)Transferase 1, ADP-Ribosyltransferase C2 And C3 Toxin-Like 1, ART2, CD296, RT6, ADP-Ribosyltransferase 2, GPI-Linked NAD(P)(+)—Arginine ADP-Ribosyltransferase 1, EC 2.4.2.31, CD296 Antigen; NP); ASLG659; ASPHD1 (Aspartate Beta-Hydroxylase Domain Containing 1, Aspartate Beta-Hydroxylase Domain-Containing Protein 1, EC 1.14.11.-, EC 1.14.11; GenBank: AAI44153.1); B7-H4 (VTCN1, V-Set Domain Containing T Cell Activation Inhibitor 1, B7H4, B7 Superfamily Member 1, Immune Costimulatory Protein B7-H4, B7h.5, T-Cell Costimulatory Molecule B7x, B7S1, B7X, VCTN1, H4, B7 Family Member, PRO1291, B7 Family Member, H4, T Cell Costimulatory Molecule B7x, V-Set Domain-Containing T-Cell Activation Inhibitor 1, Protein B7S1; GenBank: AAZ17406.1); BAFF-R (TNFRSF13C, Tumor Necrosis Factor Receptor Superfamily, Member 13C, BAFFR, B-Cell-Activating Factor Receptor, BAFF Receptor, BLyS Receptor 3, CVID4, BROMIX, CD268, B Cell-Activating Factor Receptor, prolixin, Tumor Necrosis Factor Receptor Superfamily Member 13C, BR3, CD268 Antigen; NCBI Reference Sequence: NP_443177.1); BAGE-1; BCLX (L); BCR-ABL fusion protein (b3a2); beta-catenin (CTNNB1, Catenin (Cadherin-Associated Protein), Beta 1, 88 kDa, CTNNB, MRD19, Catenin (Cadherin-Associated Protein), Beta 1 (88kD), armadillo, Catenin Beta-1; GenBank: CAA61107.1); BING-4 (WDR46, WD Repeat Domain 46, C6orf11, BING4, WD Repeat-Containing Protein BING4, Chromosome 6 Open Reading Frame 11, FP221, UTP7, WD Repeat-Containing Protein 46; NP); BMPR1 B (bone morphogenetic protein receptor-type IB, Genbank accession no. NM_00120; NP); B-RAF (Brevican (BCAN, BEHAB, Genbank accession no. AF22905); Brevican (BCAN, Chondroitin Sulfate Proteoglycan 7, Brain-Enriched Hyaluronan-Binding Protein, BEHAB, CSPG7, Brevican Proteoglycan, Brevican Core Protein, Chondroitin Sulfate Proteoglycan BEHAB; Gen Bank: AAH27971.1); CALCA (Calcitonin-Related Polypeptide Alpha, CALC1, Calcitonin 1, calcitonin, Alpha-Type CGRP, Calcitonin Gene-Related Peptide I, CGRP-I, CGRP, CGRP1, CT, KC, Calcitonin/Calcitonin-Related Polypeptide, Alpha, katacalcin; NP); CASP-5 (CASP5, Caspase 5, Apoptosis-Related Cysteine Peptidase, Caspase 5, Apoptosis-Related Cysteine Protease, Protease ICH-3, Protease TY, ICE(rel)-III, ICE (rel)III, ICEREL-III, ICH-3, caspase-5, TY Protease, EC 3.4.22.58, ICH3, EC 3.4.22; NP); CASP-8; CD19 (CD19-B-lymphocyte antigen CD19 isoform 2 precursor, B4, CVID3 [Homo sapiens], NCBI Reference Sequence: NP_001761.3); CD20 (CD20-B-lymphocyte antigen CD20, membrane-spanning 4-domains, subfamily A, member 1, B1, Bp35, CD20, CVID5, LEU-16, MS4A2, S7; NCBI Reference Sequence: NP_690605.1); CD21 (CD21 (CR2 (Complement receptor or C3DR (C3d/Epstein Barr virus receptor) or Hs.73792 Genbank accession no. M2600); (CD22 (B-cell receptor CD22-B isoform, BL-CAM, Lyb-8, Lyb8, SIGLEC-2, FLJ22814, Genbank accession No. AK02646); CD22; CD33 (CD33 Molecule, CD33 Antigen (Gp67), Sialic Acid Binding Ig-Like Lectin 3, Sialic Acid-Binding Ig-Like Lectin 3, SIGLEC3, gp67, SIGLEC-3, Myeloid Cell Surface Antigen CD33, p67, Siglec-3, CD33 Antigen; GenBank: AAH28152.1); CD45; CD70 (CD70-tumor necrosis factor (ligand) superfamily, member 7; surface antigen CD70; Ki-24 antigen; CD27 ligand; CD27-L; tumor necrosis factor ligand superfamily member 7; NCBI Reference Sequence for species homo sapiens:

NP_001243.1); CD72 (CD72 (B-cell differentiation antigen CD72, Lyb-; 359 aa, pI: 8.66, MW: 40225, TM: 1 [P] Gene Chromosome: 9p13.3, Genbank accession No. NP_001773.); CD79a (CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.1); CD79b (CD79b (CD79B, CD79b, IGb (immunoglobulin-associated beta), B29, Genbank accession no. NM_000626 or 1103867); Cdc27 (Cell Division Cycle 27, D0S1430E, D17S978E, Anaphase Promoting Complex Subunit 3, Anaphase-Promoting Complex Subunit 3, ANAPC3, APC3, CDC27Hs, H-NUC, CDC27 Homolog, Cell Division Cycle 27 Homolog (S. Cerevisiae), HNUC, NUC2, Anaphase-Promoting Complex, Protein 3, Cell Division Cycle 27 Homolog, Cell Division Cycle Protein 27 Homolog, Nuc2 Homolog; GenBank: AAH11656.1); CDK4 (Cyclin-Dependent Kinase 4, Cell Division Protein Kinase 4, PSK-J3, EC 2.7.11.2$_2$, CMM3, EC 2.7.11; NCBI Reference Sequence: NP_000066.1); CDKN2A (Cyclin-Dependent Kinase Inhibitor 2A, MLM, CDKN2, MTS1, Cyclin-Dependent Kinase Inhibitor 2A (Melanoma, P16, Inhibits CDK4), Cyclin-Dependent Kinase 4 Inhibitor A, Multiple Tumor Suppressor 1, CDK4I, MTS-1, CMM2, P16, ARF, INK4, INK4A, P14, P14ARF, P16-INK4A, P16INK4, P16INK4A, P19, P19ARF, TP16, CDK4 Inhibitor P16-INK4, Cell Cycle Negative Regulator Beta, p14ARF, p16-INK4, p16-INK4a, p16INK4A, p19ARF; NP); CEA; CLL1 (CLL-1 (CLEC12A, MICL, and DCAL, encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K *Curr. Opin. Struct. Biol.* 9):585-90; van Rhenen A, et al., *Blood* 110):2659-66; Chen C H, et al. *Blood* 107):1459-67; Marshall A S, et al. *Eur. J. Immunol.* 36):2159-69; Bakker A B, et al *Cancer Res.* 64:8443-50; Marshall A S, et al *J. Biol. Chem.* 279:14792-80. CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.); CLPP (Caseinolytic Mitochondrial Matrix Peptidase Proteolytic Subunit, Endopeptidase Clp, EC 3.4.21.92, PRLTS3, ATP-Dependent Protease ClpAP (*E. Coli*), ClpP (Caseinolytic Protease, ATP-Dependent, Proteolytic Subunit, *E. Coli*) Homolog, ClpP Caseinolytic Peptidase, ATP-Dependent, Proteolytic Subunit Homolog (*E. Coli*), ClpP Caseinolytic Protease, ATP-Dependent, Proteolytic Subunit Homolog (*E. Coli*), human, Proteolytic Subunit, ATP-Dependent Protease ClpAP, Proteolytic Subunit, Human, ClpP Caseinolytic Peptidase ATP-Dependent, Proteolytic Subunit, ClpP Caseinolytic Peptidase ATP-Dependent, Proteolytic Subunit Homolog, ClpP Caseinolytic Protease, ATP-Dependent, Proteolytic Subunit Homolog, Putative ATP-Dependent Clp Protease Proteolytic Subunit, Mitochondrial; NP); COA-1; CPSF; CRIPTO (CRIPTO (CR, CR1, CRGF, CRIPTO, TDGF1, teratocarcinoma-derived growth factor, Genbank accession no. NP_003203 or NM_00321); Cw6; CXCR5 CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.); CXORF61 CXORF61-chromosome X open reading frame 61 [*Homo sapiens*], NCBI Reference Sequence: NP_001017978.1); cyclin D1 (CCND1, BCL1, PRAD1, D11 S287E, B-Cell CLL/Lymphoma 1, B-Cell Lymphoma 1 Protein, BCL-1 Oncogene, PRAD1 Oncogene, Cyclin D1 (PRAD1: Parathyroid Adenomatosis 1), G1/S-Specific Cyclin D1, Parathyroid Adenomatosis 1, U21B31, G1/S-Specific Cyclin-D1, BCL-1; NCBI Reference Sequence: NP_444284.1); Cyclin-A1 (CCNA1, CT146, Cyclin A1; GenBank: AAH36346.1); dek-can fusion protein; DKK1 (Dickkopf WNT Signaling Pathway Inhibitor 1, SK, hDkk-1, Dickkopf (*Xenopus Laevis*) Homolog 1, Dickkopf 1 Homolog (*Xenopus Laevis*), DKK-1, Dickkopf 1 Homolog, Dickkopf Related Protein-1, Dickkopf-1 Like, Dickkopf-Like Protein 1, Dickkopf-Related Protein 1, Dickkopf-1, Dkk-1; GenBank: AAQ89364.1); DR1 (Down-Regulator Of Transcription 1, TBP-Binding (Negative Cofactor 2), Negative Cofactor 2-Beta, TATA-Binding Protein-Associated Phosphoprotein, NC2, NC2-BETA, Protein Dr1, NC2-beta, Down-Regulator Of Transcription 1; NCBI Reference Sequence: NP_001929.1); DR13 (Major Histocompatibility Complex, Class II, DR Beta 1, HLA-DR1B, DRw10, DW2.2/DR2.2, SS1, DRB1, HLA-DRB, HLA Class II Histocompatibility Antigen, DR-1 Beta Chain, Human Leucocyte Antigen DRB1, Lymphocyte Antigen DRB1, MHC Class II Antigen, MHC Class II HLA-DR Beta 1 Chain, MHC Class II HLA-DR-Beta Cell Surface Glycoprotein, MHC Class II HLA-DRw10-Beta, DR-1, DR-12, DR-13, DR-14, DR-16, DR-4, DR-5, DR-7, DR-8, DR-9, DR1, DR12, DR13, DR14, DR16, DR4, DR5, DR7, DRB, DR9, DRw11, DRw8, HLA-DRB2, Clone P2-Beta-3, MHC Class II Antigen DRB1*1, MHC Class II Antigen DRB1*10, MHC Class II Antigen DRB1*11, MHC Class II Antigen DRB1*12, MHC Class II Antigen DRB1*13, MHC Class II Antigen DRB1*14, MHC Class II Antigen DRB1*15, MHC Class II Antigen DRB1*16, MHC Class II Antigen DRB1*3, MHC Class II Antigen DRB1*4, MHC Class II Antigen DRB1*7, MHC Class II Antigen DRB1*8, MHC Class II Antigen DRB1*9; NP); E16 (E16 (LAT1, SLC7A5, Genbank accession no. NM_00348); EDAR (EDAR-tumor necrosis factor receptor superfamily member EDAR precursor, EDA-A1 receptor; downless homolog; ectodysplasin-A receptor; ectodermal dysplasia receptor; anhidrotic ectodysplasin receptor 1, DL; ECTD10A; ECTD10B; ED1R; ED3; EDS; EDA-A1R; EDA1R; EDA3; HRM1 [*Homo sapiens*]; NCBI Reference Sequence: NP_071731.1); EFTUD2 (Elongation Factor Tu GTP Binding Domain Containing 2, Elongation Factor Tu GTP-Binding Domain-Containing Protein 2, hSNU114, SNU114 Homolog, U5 SnRNP-Specific Protein, 116 KDa, MFDGA, KIAA0031, 116 KD, U5 SnRNP Specific Protein, 116 KDa U5 Small Nuclear Ribonucleoprotein Component, MFDM, SNRNP116, Snrp116, Snu114, U5-116KD, SNRP116, U5-116 KDa; GenBank: AAH02360.1); EGFR (Epidermal Growth Factor Receptor, ERBB, Proto-Oncogene C-ErbB-1, Receptor Tyrosine-Protein Kinase ErbB-1, ERBB1, HER1, EC 2.7.10.1, Epidermal Growth Factor Receptor (Avian Erythroblastic Leukemia Viral (V-Erb-B) Oncogene Homolog), Erythroblastic Leukemia Viral (V-Erb-B) Oncogene Homolog (Avian), PIG61, Avian Erythroblastic Leukemia Viral (V-Erb-B) Oncogene Homolog, Cell Growth Inhibiting Protein 40, Cell Proliferation-Inducing Protein 61, mENA, EC 2.7.10; GenBank: AAH94761.1); EGFR-G719A; EGFR-G719C; EGFR-G719S; EGFR-L858R; EGFR-L861Q; EGFR-57681; EGFR-T790M; Elongation factor 2 (EEF2, Eukaryotic Translation Elongation Factor 2, EF2, Polypeptidyl-TRNA Translocase, EF-2, SCA26, EEF-2; NCBI Reference Sequence: NP_001952.1); ENAH (hMena) (Enabled Homolog (Drosophila), MENA, Mammalian Enabled, ENA, NDPP1, Protein Enabled Homolog; GenBank: AAH95481.1)—results for just "ENAH" not "ENAH (hMena)"; EpCAM (Epithelial Cell Adhesion Molecule, M4S1, MIC18, Tumor-Associated Calcium Signal Transducer 1, TACSTD1, TROP1, Adenocarcinoma-Associated Antigen, Cell Surface Glycoprotein Trop-1, Epithelial Glycoprotein 314, Major Gastrointestinal Tumor-Associated Protein GA733-2, EGP314, KSA, DIAR5, HNPCC8, Antigen Identified By Monoclonal Antibody AUA1, EGP-2, EGP40, ESA, KS1/4, MK-1, Human Epithelial Glycoprotein-2, Membrane Component, Chromosome 4, Surface Marker (35kD Glycoprotein), EGP, Ep-CAM, GA733-2, M1S2, CD326 Antigen, Epithelial Cell Surface Antigen, hEGP314, KS 1/4 Antigen, ACSTD1; GenBank: AAH14785.1); EphA3 (EPH Receptor A3, ETK1, ETK, TYRO4, HEK, Eph-Like Tyrosine Kinase 1, Tyrosine-Protein Kinase Receptor ETK1, EK4, EPH-Like Kinase 4, EC 2.7.10.1, EPHA3, HEK4, Ephrin Type-A Receptor 3, Human Embryo Kinase 1, TYRO4 Protein Tyrosine Kinase, hEK4, Human Embryo Kinase, Tyrosine-Protein Kinase TYRO4, EC 2.7.10; GenBank: AAH63282.1); EphB2R; Epiregulin (EREG, ER, proepiregulin; GenBank: AAI36405.1); ETBR (EDNRB, Endothelin Receptor Type B, HSCR2, HSCR, Endothelin Receptor Non-Selective Type, ET-B, ET-BR, ETRB, ABCDS, WS4A, ETB, Endothelin B Receptor; NP); ETV6-AML1 fusion protein; EZH2 (Enhancer Of Zeste Homolog 2 (Drosophila), Lysine N-Methyltransferase 6, ENX-1, KMT6 EC 2.1.1.43, EZH1, WVS, Enhancer Of Zeste (Drosophila) Homolog 2, ENX1, EZH2b, KMT6A, WVS2, Histone-Lysine N-Methyltransferase EZH2, Enhancer Of Zeste Homolog 2, EC 2.1.1; GenBank: AAH10858.1); FcRH1 (FCRL1, Fc Receptor-Like 1, FCRH1, Fc Receptor Homolog 1, FcR-Like Protein 1, Immune Receptor Translocation-Associated Protein 5, IFGP1, IRTA5, hIFGP1, IFGP Family Protein 1, CD307a, Fc Receptor-Like Protein 1, Immunoglobulin Superfamily Fc Receptor, Gp42, FcRL1, CD307a Antigen; GenBank: AAH33690.1); FcRH2 (FCRL2, Fc Receptor-Like 2, SPAP1, SH2 Domain-Containing Phosphatase Anchor Protein 1, Fc Receptor Homolog 2, FcR-Like Protein 2, Immunoglobulin Receptor Translocation-Associated Protein 4, FCRH2, IFGP4, IRTA4, IFGP Family Protein 4, SPAP1A, SPAP1 B, SPAP1C, CD307b, Fc Receptor-Like Protein 2, Immune Receptor Translocation-Associated Protein 4, Immunoglobulin Superfamily Fc Receptor, Gp42, SH2 Domain Containing Phosphatase Anchor Protein 1, FcRL2, CD307b Antigen; GenBank: AAQ88497.1); FcRH5 (FCRL5, Fc Receptor-Like 5, IRTA2, Fc Receptor Homolog 5, FcR-Like Protein 5, Immune Receptor Translocation-Associated Protein 2, BXMAS1, FCRH5, CD307, CD307e, PRO820, Fc Receptor-Like Protein 5, Immunoglobulin Superfamily Receptor Translocation Associated 2 (IRTA2), FcRL5, CD307e Antigen; GenBank: AAI01070.1); FLT3-ITD; FN1(Fibronectin 1, Cold-Insoluble Globulin, FN, Migration-Stimulating Factor, CIG, FNZ, GFND2, LETS, ED-B, FINC, GFND, MSF, fibronectin; GenBank: AAI43764.1); G250 (MN, CAIX, Carbonic Anhydrase IX, Carbonic Dehydratase, RCC-Associated Protein G250, Carbonate Dehydratase IX, Membrane Antigen MN, Renal Cell Carcinoma-Associated Antigen G250, CA-IX, P54/58N, pMW1, RCC-Associated Antigen G250, Carbonic Anhydrase 9; NP);—alias results for "G250" not "G250/MN/CAIX"; GAGE-1,2,8; GAGE-3,4,5,6,7; GDNF-Ra1 (GDNF family receptor alpha 1; GFRA1; GDNFR; GDNFRA; RETL1; TRNR1; RET1 L; GDNFR-alpha1; GFR-ALPHA-; U95847; BC014962; NM_145793 NM_005264); GEDA (Genbank accession No. AY26076); GFRA1-GDNF family receptor alpha-1; GDNF receptor alpha-1; GDNFR-alpha-1; GFR-alpha-1; RET ligand 1; TGF-beta-related neurotrophic factor receptor 1 [Homo sapiens]; ProtKB/Swiss-Prot: P56159.2; glypican-3 (GPC3, Glypican 3, SDYS, Glypican Proteoglycan 3, Intestinal Protein 001-5, GTR2-2, MXR7, SGBS1, DGSX, OCI-5. SGB, SGBS, Heparan Sulphate Proteoglycan, Secreted Glypican-3, 0015; GenBank: AAH35972.1); GnTVf; gp100 (PMEL, Premelanosome Protein, SILV, D12S53E, PMEL17, SIL, Melanocyte Protein Pmel 17, Melanocytes Lineage-Specific Antigen GP100, Melanoma-Associated ME20 Antigen, Silver Locus Protein Homolog, ME20-M, ME20M, P1, P100, Silver (Mouse Homolog) Like, Silver Homolog (Mouse), ME20, SI, Melanocyte Protein Mel 17, Melanocyte Protein PMEL, Melanosomal Matrix Protein17, Silver, Mouse, Homolog Of; GenBank: AAC60634.1); GPC; GPNMB (Glycoprotein (Transmembrane) Nmb, Glycoprotein NMB, Glycoprotein Nmb-Like Protein, osteoactivin, Transmembrane Glycoprotein HGFIN, HGFIN, NMB, Transmembrane Glycoprotein, Transmembrane Glycoprotein NMB; GenBank: AAH32783.1); GPR172A (G protein-coupled receptor 172A; GPCR41; FLJ11856; D15Ertd747e); NP_078807.1; NM_024531.3); GPR19 (G protein-coupled receptor 19; Mm.478; NP_006134.1; NM_006143.2); GPR54 (KISS1 receptor; KISS1R; GPR54; HOT7T175; AXOR1; NP_115940.2; NM_032551.4); HAVCR1 (Hepatitis A Virus Cellular Receptor 1, T-Cell Immunoglobulin Mucin Family Member 1, Kidney Injury Molecule 1, KIM-1, KIM1, TIM, TIM-1, TIM1, TIMD-1, TIMD1, T-Cell Immunoglobulin Mucin Receptor 1, T-Cell Membrane Protein 1, HAVCR, HAVCR-1, T Cell Immunoglobin Domain And Mucin Domain Protein 1, HAVcr-1, T-Cell Immunoglobulin And Mucin Domain-Containing Protein 1; GenBank: AAH13325.1); HER2 (ERBB2, V-Erb-B2 Avian Erythroblastic Leukemia Viral Oncogene Homolog 2, NGL, NEU, Neuro/Glioblastoma Derived Oncogene Homolog, Metastatic Lymph Node Gene 19 Protein, Proto-Oncogene C-ErbB-2, Proto-Oncogene Neu, Tyrosine Kinase-Type Cell Surface Receptor HER2, MLN 19, p185erbB2, EC 2.7.10.1, V-Erb-B2 Avian Erythroblastic Leukemia Viral Oncogene Homolog 2 (Neuro/Glioblastoma Derived Oncogene Homolog), CD340, HER-2, HER-2/neu, TKR1, C-Erb B2/Neu Protein, herstatin, Neuroblastoma/Glioblastoma Derived Oncogene Homolog, Receptor Tyrosine-Protein Kinase ErbB-2, V-Erb-B2 Erythroblastic Leukemia Viral Oncogene Homolog 2, Neuro/Glioblastoma Derived Oncogene Homolog, MLN19, CD340 Antigen, EC 2.7.10; NP); HER-2/neu-alias of above; HERV-K-MEL; HLA-DOB (Beta subunit of MHC class II molecule (Ia antigen) that binds peptides and presents them to CD4+T lymphocytes); 273 aa, pI: 6.56, MW: 30820.TM: 1 [P] Gene Chromosome: 6p21.3, Genbank accession No. NP_002111); hsp70-2 (HSPA2, Heat Shock 70 kDa Protein 2, Heat Shock 70kD Protein 2, HSP70-3, Heat Shock-Related 70 KDa Protein 2, Heat Shock 70 KDa Protein 2; GenBank: AAD21815.1); IDO1 (Indoleamine 2,3-Dioxygenase 1, IDO, INDO, Indoleamine-Pyrrole 2,3-Dioxygenase, IDO-1, Indoleamine-Pyrrole 2,3 Dioxygenase, Indolamine 2,3 Dioxygenase, Indole 2,3 Dioxygenase, EC 1.13.11.52; NCBI Reference Sequence: NP_002155.1); IGF2B3; IL13Ralpha2 (IL13RA2, Interleukin 13 Receptor, Alpha 2, Cancer/Testis Antigen 19, Interleukin-13-Binding Protein, IL-13R-alpha-2, IL-13RA2, IL-13 Receptor Subunit Alpha-2, IL-13R Subunit Alpha-2, CD213A2, CT19, IL-13R, IL13BP, Interleukin 13 Binding Protein, Interleukin 13 Receptor Alpha 2 Chain, Interleukin-13 Receptor Subunit Alpha-2, IL13R, CD213a2 Antigen; NP); IL20Rα; Intestinal carboxyl esterase; IRTA2 (alias of FcRH5); Kallikrein 4 (KLK4, Kallikrein-Related Peptidase 4, PRSS17, EMSP1, Enamel Matrix Serine Proteinase 1, Kallikrein-Like Protein 1, Serine Protease 17, KLK-L1, PSTS, AI2A1, Kallikrein 4 (Prostase, Enamel Matrix, Prostate), ARM1, EMSP, Androgen-Regulated Message 1, Enamel Matrix Serine Protease 1, kallikrein, kallikrein-4, prostase, EC 3.4.21.-, Prostase, EC 3.4.21; GenBank: AAX30051.1); KIF20A (Kinesin Family Member 20A, RAB6KIFL, RAB6 Interacting, Kinesin-Like (Rabkinesin6), Mitotic a; LAGE-1; LDLR-fucosyltransferaseASfusion protein; Lengsin (LGSN, Lengsin, Lens Protein With Glutamine Synthetase Domain, GLULD1, Glutamate-Ammonia Ligase Domain-Containing Protein 1, LGS, Glutamate-Ammonia Ligase (Glutamine Synthetase) Domain Containing 1, Glutamate-Ammonia Ligase (Glutamine Synthase) Domain Containing 1, Lens Glutamine Synthase-Like; GenBank: AAF61255.1); LGR5 (leucine-rich repeat-containing G protein-coupled receptor 5; GPR49, GPR6; NP_003658.1; NM_003667.2); LY64 (Lymphocyte antigen 64 (RP10, type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.; Ly6E (lymphocyte antigen 6 complex, locus E; Ly67, RIG-E, SCA-2, TSA-; NP_002337.1; NM_002346.2); Ly6G6D (lymphocyte antigen 6 complex, locus G6D; Ly6-D, MEGT; NP_067079.2; NM_021246.2); LY6K (lymphocyte antigen 6 complex, locus K; LY6K; HSJ001348; FLJ3522; NP_059997.3; NM_017527.3); LyPD1-LY6/PLAUR domain containing 1, PHTS [Homo sapiens], GenBank: AAH17318.1); MAGE-A1 (Melanoma Antigen Family A, 1 (Directs Expression Of Antigen MZ2-E, MAGE1, Melanoma Antigen Family A 1, MAGEA1, Melanoma Antigen MAGE-1, Melanoma-Associated Antigen 1, Melanoma-Associated Antigen MZ2-E, Antigen MZ2-E, Cancer/Testis Antigen 1.1, CT1.1, MAGE-1 Antigen, Cancer/Testis Antigen Family 1, Member 1, Cancer/Testis Antigen Family 1, Member 1, MAGE1A; NCBI Reference Sequence: NP_004979.3); MAGE-A10 (MAGEA10, Melanoma Antigen Family A, 10, MAGE10, MAGE-10 Antigen, Melanoma-Associated Antigen 10, Cancer/Testis Antigen 1.10, CT1.10, Cancer/Testis Antigen Family 1, Member 10, Cancer/Testis Antigen Family 1, Member 10; NCBI Reference Sequence: NP_001238757.1); MAGE-A12 (MAGEA12, Melanoma Antigen Family A, 12, MAGE12, Cancer/Testis Antigen 1.12, CT1.12, MAGE12F Antigen, Cancer/Testis Antigen Family 1, Member 12, Cancer/Testis Antigen Family 1, Member 12, Melanoma-Associated Antigen 12, MAGE-12 Antigen; NCBI Reference Sequence: NP_001159859.1); MAGE-A2 (MAGEA2, Melanoma Antigen Family A, 2, MAGE2, Cancer/Testis Antigen 1.2, CT1.2, MAGEA2A, MAGE-2 Antigen, Cancer/Testis Antigen Family 1, Member 2, Cancer/Testis Antigen Family 1, Member 2, Melanoma Antigen 2, Melanoma-Associated Antigen 2; NCBI Reference Sequence: NP_001269434.1); MAGE-A3 (MAGEA3, Melanoma Antigen Family A, 3, MAGE3, MAGE-3 Antigen, Antigen MZ2-D, Melanoma-Associated Antigen 3, Cancer/Testis Antigen 1.3, CT1.3, Cancer/Testis Antigen Family 1, Member 3, HIPS, HYPD, MAGEA6, Cancer/Testis Antigen Family 1, Member 3; NCBI Reference Sequence: NP_005353.1); MAGE-A4 (MAGEA4, Melanoma Antigen Family A, 4, MAGE4, Melanoma-Associated Antigen 4, Cancer/Testis Antigen 1.4, CT1.4, MAGE-4 Antigen, MAGE-41 Antigen, MAGE-X2 Antigen, MAGEA4A, MAGEA4B, Cancer/Testis Antigen Family 1, Member 4, MAGE-41, MAGE-X$_2$, Cancer/Testis Antigen Family 1, Member 4; NCBI Reference Sequence: NP_001011550.1); MAGE-A6 (MAGEA6, Melanoma Antigen Family A, 6, MAGE6, MAGE-6 Antigen, Melanoma-Associated Antigen 6, Cancer/Testis Antigen 1.6, CT1.6, MAGE3B Antigen, Cancer/Testis Antigen Family 1, Melanoma Antigen Family A 6, Member 6, MAGE-3b, MAGE3B, Cancer/Testis Antigen Family 1, Member 6; NCBI Reference Sequence: NP_787064.1); MAGE-A9 (MAGEA9, Melanoma Antigen Family A, 9, MAGE9, MAGE-9 Antigen, Melanoma-Associated Antigen 9, Cancer/Testis Antigen 1.9, CT1.9, Cancer/Testis Antigen Family 1, Member 9, Cancer/Testis Antigen Family 1, Member 9, MAGEA9A; NCBI Reference Sequence: NP_005356.1); MAGE-C1 (MAGEC1, Melanoma Antigen Family C, 1, Cancer/Testis Antigen 7.1, CT7.1, MAGE-C1 Antigen, Cancer/Testis Antigen Family 7, Member 1, CT7, Cancer/Testis Antigen Family 7, Member 1, Melanoma-Associated Antigen C1; NCBI Reference Sequence: NP_005453.2); MAGE-C2 (MAGEC2, Melanoma Antigen Family C, 2, MAGEE1, Cancer/Testis Antigen 10, CT10, HCA587, Melanoma Antigen, Family E, 1, Cancer/Testis Specific, Hepatocellular Carcinoma-Associated Antigen 587, MAGE-C2 Antigen, MAGE-E1 Antigen, Hepatocellular Cancer Antigen 587, Melanoma-Associated Antigen C2; NCBI Reference Sequence: NP_057333.1); mammaglobin-A (SCGB2A2, Secretoglobin, Family 2A, Member 2, MGB1, Mammaglobin 1, UGB2, Mammaglobin A, mammaglobin-A, Mammaglobin-1, Secretoglobin Family 2A Member 2; NP); MART2 (HHAT, Hedgehog Acyltransferase, SKI1, Melanoma Antigen Recognized By T-Cells 2, Skinny Hedgehog Protein 1, Skn, Melanoma Antigen Recognized By T Cells 2, Protein-Cysteine N-Palmitoyltransferase HHAT, EC 2.3.1.-; GenBank: AAH39071.1); M-CSF (CSF1, Colony Stimulating Factor 1 (Macrophage), MCSF, CSF-1, lanimostim, Macrophage Colony-Stimulating Factor 1, Lanimostim; GenBank: AAH21117.1); MCSP (SMCP, Sperm Mitochondria-Associated Cysteine-Rich Protein, MCS, Mitochondrial Capsule Selenoprotein, HSMCS-GEN1, Sperm Mitochondrial-Associated Cysteine-Rich Protein; NCBI Reference Sequence: NP_109588.2); XAGE-1b/GAGED2a; WT1 (Wilms Tumor 1, WAGR, GUD, WIT-2, WT33, Amino-Terminal Domain Of EWS, NPHS4, Last Three Zinc Fingers Of The DNA-Binding Domain Of WT1, AWT1, Wilms Tumor Protein, EWS-WT1; GenBank: AAB33443.1); VEGF; Tyrosinase (TYR; OCAIA; OCA1A; tyrosinase; SHEP; NP_000363.1; NM_000372.4; GenBank: AAB60319.1); TrpM4 (BR22450, FLJ20041, TRPM4, TRPM4B, transient receptor potential cation channel, subfamily M, member 4, Genbank accession no. NM_01763); TRP2-INT2; TRP-2; TRP-1/gp75 (Tyrosinase-Related Protein 1, 5,6-Dihydroxyindole-2-Carboxylic Acid Oxidase, CAS2, CATB, TYRP, OCAS, Catalase B, b-PROTEIN, Glycoprotein 75, EC 1.14.18., Melanoma Antigen Gp75, TYRP1, TRP, TYRRP, TRP1, SHEP11, DHICA Oxidase, EC 1.14.18, GP75, EC 1.14.18.1; Triosephosphate isomerase (Triosephosphate isomerase 1, TPID, Triose-Phosphate Isomerase, HEL-S-49, TIM, Epididymis Secretory Protein Li 49, TPI, Triosephosphate Isomerase, EC 5.3.1.1; TRAG-3 (CSAG Family Member 2, Cancer/Testis Antigen Family 24, CSAG3B, Member 2, CSAG Family Member 3B, Cancer/Testis Antigen Family 24 Member 2, Cancer/Testis Antigen 24.2, Chondrosarcoma-Associated Gene 2/3 Protein, Taxol-Resistant-Associated Gene 3 Protein, Chondrosarcoma-Associated Gene 2/3 Protein-Like, CT24.2, Taxol Resistance Associated Gene 3, TRAG-3, CSAG3A, TRAG3); TMEM46 (shisa homolog 2 (*Xenopus laevis*); SHISA; NP_001007539.1; NM_001007538.1; TMEM118 (ring finger protein, transmembrane2; RNFT2; FLJ1462; NP_001103373.1; NM_001109903.1; TMEFF1 (transmembrane protein with EGF-like and two follistatin-like domains 1; Tomoregulin-; H7365; C9orf2; C9ORF2; U19878; X83961; NM_080655; NM_003692; TGF-betaRII (TGFBR2, Transforming Growth Factor, Beta Receptor II (70/80 kDa), TGFbeta-RII, MFS2, tbetaR-II, TGFR-2, TGF-Beta Receptor Type IIB, TGF-Beta Type II Receptor, TGF-Beta Receptor Type-2, EC 2.7.11.30, Transforming Growth Factor Beta Receptor Type IIC, AAT3, TbetaR-II, Transforming Growth Factor, Beta Receptor II (70-80kD), TGF-Beta Receptor Type II, FAA3, Transforming Growth Factor-Beta Receptor Type II, LDS1 B, HNPCC6, LDS2B, LDS2, RIIC, EC 2.7.11, TAAD2; TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; TAG-2; TAG-1 (Contactin 2 (Axonal), TAG-1, AXT, Axonin-1 Cell Adhesion Molecule, TAX, Contactin 2 (transiently Expressed), TAXI, Contactin-2, Axonal Glycoprotein TAG-1, Transiently-Expressed Axonal Glycoprotein, Transient Axonal Glycoprotein, Axonin-1, TAX-1, TAG1, FAME5; PRF: 444868); SYT-SSX1 or -SSX2 fusion protein; survivin; STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF45513; STEAP1 (six transmembrane epithelial antigen of prostate, Genbank accession no. NM_01244; SSX-4; SSX-2 (SSX2, Synovial Sarcoma, X Breakpoint2, X Breakpoint 2, SSX, X Breakpoint 2B, Cancer/Testis Antigen 5.2, X-Chromosome-Related 2, Tumor Antigen HOM-MEL-40, CT5.2, HD21, Cancer/Testis Antigen Family 5, HOM-MEL-40, Isoform B, Cancer/Testis Antigen Family 5 member 2a, member 2a, Protein SSX2, Sarcoma, Sarcoma, Synovial, X-Chromosome-Related 2, synovial, Synovial Sarcoma, X Breakpoint 2B, Synovial Sarcomam, SSX2A; Sp17; SOX10 (SRY (Sex Determining Region Y)-Box 10, mouse, PCWH, DOM, WS4, WS2E, WS4C, Dominant Megacolon, mouse, Human Homolog Of, Dominant Megacolon, SRY-Related HMG-Box Gene 10, Human Homolog Of, transcription Factor SOX-10; GenBank: CAG30470.1); SNRPD1 (Small Nuclear Ribonucleoprotein D1, Small Nuclear Ribonucleoprotein D1, Polypeptide 16 kDa, Polypeptide (16kD), SNRPD, HsT2456, Sm-D1, SMD1, Sm-D Autoantigen, Small Nuclear Ribonucleoprotein D1 Polypeptide 16 kDa Pseudogene, SnRNP Core Protein D1, Small Nuclear Ribonucleoprotein Sm D1; SLC35D3 (Solute Carrier Family 35, Member D3, FRCL1, Fringe Connection-Like Protein 1, bA55K22.3, Frc, Fringe-Like 1, Solute Carrier Family 35 Member D3; NCBI GenBank: NC_000006.11 NC_018917.2 NT_025741.16); SIRT2 (Sirtuin 2, NAD-Dependent Deacetylase Sirtuin-2, SIRL2, Silent Information Regulator 2, Regulatory Protein SIR2 Homolog 2, Sir2-Related Protein Type 2, SIR2-Like Protein 2, Sirtuin Type 2, Sirtuin (Silent Mating Type Information Regulation 2 Homolog) 2 (*S. Cerevisiae*), Sirtuin-2, Sirtuin (Silent Mating Type Information Regulation 2, *S. Cerevisiae*, Homolog) 2, EC 3.5.1., SIR2; GenBank: AAK51133.1); Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB04087; secernin 1 (SCRN1, SES1, KIAA0193, secernin-1; GenBank: EAL24458.1); SAGE (SAGE1, Sarcoma Antigen 1, Cancer/Testis Antigen 14, CT14, Putative Tumor Antigen; NCBI Reference Sequence: NP_061136.2); RU2AS (KAAG1, Kidney Associated Antigen 1, RU2AS, RU2 Antisense Gene Protein, Kidney-Associated Antigen 1; GenBank: AAF23613.1); RNF43-E3 ubiquitin-protein ligase RNF43 precursor [*Homo sapiens*], RNF124; URCC; NCBI Reference Sequence: NP_060233.3; RhoC (RGSS (Regulator Of G-Protein Signaling 5, MSTP032, Regulator Of G-Protein Signalling 5, MSTP092, MST092, MSTP106, MST106, MSTP129, MST129; GenBank: AAB84001.1); RET (ret proto-oncogene; MEN2A; HSCR1; MEN2B; MTC1; PTC; CDHF12; Hs.168114; RET51; RET-ELE; NP_066124.1; NM_020975.4); RBAF600 (UBR4, Ubiquitin Protein Ligase E3 Component N-Recognin 4, Zinc Finger, UBR1 Type 1, ZUBR1, E3 Ubiquitin-Protein Ligase UBR4, RBAF600, 600 KDa Retinoblastoma Protein-Associated Factor, Zinc Finger UBR1-Type Protein 1, EC 6.3.2., N-recognin-4, KIAA0462, p600, EC 6.3.2, KIAA1307; GenBank: AAL83880.1); RAGE-1 (MOK, MOK Protein Kinase, Renal Tumor Antigen, RAGE, MAPK/MAK/MRK Overlapping Kinase, Renal Tumor Antigen 1, Renal Cell Carcinoma Antigen, RAGE-1, EC 2.7.11.22, RAGE1; UniProtKB/Swiss-Prot: Q9UQ07.1); RAB38/NY-MEL-1 (RAB38, NY-MEL-1, RAB38, Member RAS Oncogene Family, Melanoma Antigen NY-MEL-1, Rab-Related GTP-Binding Protein, Ras-Related Protein Rab-38, rrGTPbp; GenBank: AAH15808.1); PTPRK (DJ480J14.2.1 (Protein Tyrosine Phosphatase, Receptor Type, K R-PTP-KAPPA, Protein Tyrosine Phosphatase Kappa, Protein Tyrosine Phosphatase Kappa), Protein Tyrosine Phosphatase, Receptor Type, K, Protein-Tyrosine Phosphatase Kappa, Protein-Tyrosine Phosphatase, Receptor Type, Kappa, R-PTP-kappa, Receptor-Type Tyrosine-Protein Phosphatase Kappa, EC 3.1.3.48, PTPK; GenBank: AAI44514.1); PSMA; PSCA hlg (2700050C12Rik, C530008O16Rik, RIKEN cDNA 2700050C12, RIKEN cDNA 2700050C12 gene, Genbank accession no. AY358628); PSCA (Prostate stem cell antigen precursor, Genbank accession no. AJ29743; PRDX5 (Peroxiredoxin 5, EC 1.11.1.15, TPx Type VI, B166, Antioxidant Enzyme B166, HEL-S-55, Liver Tissue 2D-Page Spot 71 B, PMP20, Peroxisomal Antioxidant Enzyme, PRDX6, Thioredoxin Peroxidase PMP20, PRXV, AOEB166, Epididymis Secretory Protein Li 55, Alu Co-Repressor 1, Peroxiredoxin-5, Mitochondrial, Peroxiredoxin V, prx-V, Thioredoxin Reductase, Prx-V, ACR1, Alu Corepressor, PLP; GenBank: CAG33484.1); PRAME (Preferentially Expressed Antigen In Melanoma, Preferentially Expressed Antigen Of Melanoma, MAPE, OIP-4, OIPA, CT130, Cancer/Testis Antigen 130, Melanoma Antigen Preferentially Expressed In Tumors, Opa-Interacting Protein 4, Opa-Interacting Protein OIP4; GenBank: CAG30435.1); pml-RARalpha fusion protein; PMEL17 (silver homolog; SILV; D12S53E; PMEL17;

SI; SIL); ME20; gp10 BC001414; BT007202; M32295; M77348; NM_006928; PBF (ZNF395, Zinc Finger Protein 395, PRF-1, Huntington disease regulatory, HD Gene Regulatory Region-Binding Protein, Region-Binding Protein 2, Protein 2, Papillomavirus Regulatory Factor 1, HD-Regulating Factor 2, Papillomavirus-Regulatory Factor, PRF1, HDBP-2, Si-1-8-14, HDBP2, Huntington'S Disease Gene Regulatory Region-Binding Protein 2, HDRF-2, Papillomavirus Regulatory Factor PRF-1, PBF; Gen Bank: AAH01237.1); PAX5 (Paired Box 5, Paired Box Homeotic Gene 5, BSAP, Paired Box Protein Pax-5, B-Cell Lineage Specific Activator, Paired Domain Gene 5, Paired Box Gene 5 (B-Cell Lineage Specific Activator Protein), B-Cell-Specific Transcription Factor, Paired Box Gene 5 (B-Cell Lineage Specific Activator); PAP (REG3A, Regenerating Islet-Derived 3 Alpha, INGAP, PAP-H, Hepatointestinal Pancreatic Protein, PBBCGF, Human Proislet Peptide, REG-III, Pancreatitis-Associated Protein 1, Reg3, Reg III-Alpha, hepatocarcinoma-intestine-pancreas, Regenerating Islet-Derived Protein III-Alpha, Pancreatic Beta Cell Growth Factor, HIP, PAP Homologous Protein, HIP/PAP, Proliferation-Inducing Protein 34, PAP1, Proliferation-Inducing Protein 42, REG-3-alpha, Regenerating Islet-Derived Protein 3-Alpha, Pancreatitis-Associated Protein; GenBank: AAH36776.1); p53 (TP53, Tumor Protein P53, TPR53, P53, Cellular Tumor Antigen P53, Antigen NY-CO-13, Mutant Tumor Protein 53, Phosphoprotein P53, P53 Tumor Suppressor, BCC7, Transformation-Related Protein 53, LFS1, tumor Protein 53, Li-Fraumeni Syndrome, Tumor Suppressor P53; P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.; OGT (O-Linked N-Acetylglucosamine (GlcNAc) Transferase, O-GlcNAc Transferase P110 Subunit, O-Linked N-Acetylglucosamine (GlcNAc) Transferase (UDP-N-Acetylglucosamine:Polypeptide-N-Acetylglucosaminyl Transferase, UDP-N-Acetylglucosamine-Peptide N-Acetylglucosaminyltransferase 110 KDa Subunit, UDP-N-Acetylglucosamine:Polypeptide-N-Acetylglucosaminyl Transferase, Uridinediphospho-N-Acetylglucosamine:Polypeptide Beta-N-Acetylglucosaminyl Transferase, O-GlcNAc Transferase Subunit P110, EC 2.4.1.255, O-Linked N-Acetylglucosamine Transferase 110 KDa Subunit, EC 2.4.1, HRNT1, EC 2.4.1.186, O-GLCNAC; GenBank: AAH38180.1); OA1 (Osteoarthritis QTL 1, OASD; GenBank: CAA88742.1); NY-ESO-1/LAGE-2 (Cancer/Testis Antigen 1B, CTAG1 B, NY-ESO-1, LAGE-2, ESO1, CTAG1, CTAG, LAGE2B, Cancer/Testis Antigen 1, Autoimmunogenic Cancer/Testis Antigen NY-ESO-1, Ancer Antigen 3, Cancer/Testis Antigen 6.1, New York Esophageal Squamous Cell Carcinoma 1, L Antigen Family Member 2, LAGE2, CT6.1, LAGE2A; GenBank: AAI30365.1); NY-BR-1 (ANKRD30A, Ankyrin Repeat Domain 30A, Breast Cancer Antigen NY-BR-1, Serologically Defined Breast Cancer Antigen NY-BR-1, Ankyrin Repeat Domain-Containing Protein 30A; NCBI Reference Sequence: NP_443723.2); N-ras (NRAS, Neuroblastoma RAS Viral (V-Ras) Oncogene Homolog, NRAS1, Transforming Protein N-Ras, GTPase NRas, ALPS4, N-Ras Protein Part 4, NS6, Oncogene Homolog, HRAS1; GenBank: AAH05219.1); NFYC (Nuclear Transcription Factor Y, Gamma, HAP5, HSM, Nuclear Transcription Factor Y Subunit C, Transactivator HSM-1/2, CCAAT Binding Factor Subunit C, NF-YC, CCAAT Transcription Binding Factor Subunit Gamma, CAAT Box DNA-Binding Protein Subunit C, Histone H1 Transcription Factor Large Subunit 2A, CBFC, Nuclear Transcription Factor Y Subunit Gamma, CBF-C, Transactivator HSM-1, H1TF2A, Transcription Factor NF-Y, C Subunit; neo-PAP (PAPOLG, Poly(A) Polymerase Gamma, Neo-Poly(A) Polymerase, Nuclear Poly(A) Polymerase Gamma, Polynucleotide Adenylyltransferase Gamma, SRP RNA 3' Adenylating Enzyme/Pap2, PAP-gamma, Neo-PAP, SRP RNA 3'-Adenylating Enzyme, PAP2, EC 2.7.7.19, PAPG; NCBI Reference Sequence: NP_075045.2); NCA (CEACAM6, Genbank accession no. M1872); Napi3b (NAPI-3B, NPTIIb, SLC34A2, solute carrier family 34 (sodium phosphate), member 2, type II sodium-dependent phosphate transporter 3b, Genbank accession no. NM_00642); Myosin class I; MUM-3; MUM-2 (TRAPPC1, Trafficking Protein Particle Complex 1, BETS, BETS Homolog, MUM2, Melanoma Ubiquitous Mutated 2, Multiple Myeloma Protein 2, Trafficking Protein Particle Complex Subunit 1; MUM-1f; Mucin (MUC1, Mucin 1, Cell Surface Associated, PEMT, PUM, CA 15-3, MCKD1, ADMCKD, Medullary Cystic Kidney Disease 1 (Autosomal Dominant), ADMCKD1, Mucin 1, Transmembrane, CD227, Breast Carcinoma-Associated Antigen DF3, MAM6, Cancer Antigen 15-3, MCD, Carcinoma-Associated Mucin, MCKD, Krebs Von Den Lungen-6, MUC-1/SEC, Peanut-Reactive Urinary Mucin, MUC1/ZD, Tumor-Associated Epithelial Membrane Antigen, DF3 Antigen, Tumor-Associated Mucin, episialin, EMA, H23 Antigen, H23AG, Mucin-1, KL-6, Tumor Associated Epithelial Mucin, MUC-1, Episialin, PEM, CD227 Antigen; UniProtKB/Swiss-Prot: P15941.3); MUCSAC (Mucin SAC, Oligomeric Mucus/Gel-Forming, Tracheobronchial Mucin, MUC5, TBM, Mucin 5, Subtypes A And C, Tracheobronchial/Gastric, leB, Gastric Mucin, Mucin SAC, Oligomeric Mucus/Gel-Forming Pseudogene, Lewis B Blood Group Antigen, LeB, Major Airway Glycoprotein, MUC-SAC, Mucin-5 Subtype AC, Tracheobronchial; MUC1 (Mucin 1, Cell Surface Associated, PEMT, PUM, CA 15-3, MCKD1, ADMCKD, Medullary Cystic Kidney Disease 1 (Autosomal Dominant), ADMCKD1, Mucin 1, Transmembrane, CD227, Breast Carcinoma-Associated Antigen DF3, MAM6, Cancer Antigen 15-3, MCD, Carcinoma-Associated Mucin, MCKD, Krebs Von Den Lungen-6, MUC-1/SEC, Peanut-Reactive Urinary Mucin, MUC-1/X, Polymorphic Epithelial Mucin, MUC1/ZD, Tumor-Associated Epithelial Membrane Antigen, DF3 Antigen, Tumor-Associated Mucin, episialin, EMA, h23 Antigen, H23AG, mucin-1, KL-6, Tumor Associated Epithelial Mucin, MUC-1, Episialin, PEM, CD227 Antigen; MSG783 (RNF124, hypothetical protein FLJ20315, Genbank accession no. NM-01776; MRP4—multidrug resistance-associated protein 4 isoform 3, MOAT-B; MOATB [*Homo sapiens*]; NCBI Reference Sequence: NP_001288758.1; MPF (MPF, MSLN, SMR, megakaryocyte potentiating factor, mesothelin, Genbank accession no. NM_00582; MMP-7 (MMP7, matrilysin, MPSL1, matrin, Matrix Metalloproteinase 7 (Matrilysin, Uterine), Uterine Matrilysin, Matrix Metalloproteinase-7, EC 3.4.24.23, Pump-1 Protease, Matrin, Uterine Metalloproteinase, PUMP1, MMP-7, EC 3.4.24, PUMP-1; GenBank: AAC37543.1); MMP-2 (MMP2, Matrix Metallopeptidase 2 (Gelatinase A, 72 kDa Gelatinase, 72 kDa Type IV Collagenase), MONA, CLG4A, Matrix Metalloproteinase 2 (Gelatinase A, 72kD Gelatinase, 72kD Type IV Collagenase), CLG4, 72 kDa Gelatinase, 72 kDa Type IV Collagenase), Matrix Metalloproteinase-2, MMP-II, 72 KDa Gelatinase, Collagenase Type IV-A, MMP-2, Matrix Metalloproteinase- II, TBE-1, Neutrophil Gelatinase, EC 3.4.24.24, EC 3.4.24; GenBank: AAH02576.1); and Meloe.

For example, in some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds CD20 comprises at least one (e.g., 1, 2, 3, or 4) of heavy chain framework regions FR-H1, FR-H2, FR-H3, and FR-H4 comprising the sequences of SEQ ID NOs: 557-560, respectively, and/or at least one (e.g., 1, 2, 3, or 4) of the light chain framework regions FR-L1, FR-L2, FR-L3, and FR-L4 comprising the sequences of SEQ ID NOs: 561-564, respectively. In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds FcRH5 comprises at least one (e.g., 1, 2, 3, or 4) of heavy chain framework regions FR-H1, FR-H2, FR-H3, and FR-H4 comprising the sequences of SEQ ID NOs: 565-568, respectively, and/or at least one (e.g., 1, 2, 3, or 4) of the light chain framework regions FR-L1, FR-L2, FR-L3, and FR-L4 comprising the sequences of SEQ ID NOs: 569-572, respectively. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds HER2 comprises at least one (e.g., 1, 2, 3, or 4) of heavy chain framework regions FR-H1, FR-H2, FR-H3, and FR-H4 comprising the sequences of SEQ ID NOs: 549-552, respectively, and/or at least one (e.g., 1, 2, 3, or 4) of the light chain framework regions FR-L1, FR-L2, FR-L3, and FR-L4 comprising the sequences of SEQ ID NOs: 553-556, respectively. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO 585; and (f) HVR-L3 comprising the amino acid sequence of SEQ ID NO: 586, such as possessed by the anti-HER2 antibody, 2C4. In some instances, the second binding domain that binds HER2 comprises at least one (e.g., 1, 2, 3, or 4) of heavy chain framework regions FR-H1, FR-H2, FR-H3, and FR-H4 comprising the sequences of SEQ ID NOs: 597-600, respectively, and/or at least one (e.g., 1, 2, 3, or 4) of the light chain framework regions FR-L1, FR-L2, FR-L3, and FR-L4 comprising the sequences of SEQ ID NOs: 601-604, respectively. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds HER2 comprises at least one (e.g., 1, 2, 3, or 4) of heavy chain framework regions FR-H1, FR-H2, FR-H3, and FR-H4 comprising the sequences of SEQ ID NOs: 605-608, respectively, and/or at least one (e.g., 1, 2, 3, or 4) of the light chain framework regions FR-L1, FR-L2, FR-L3, and FR-L4 comprising the sequences of SEQ ID NOs: 609-612, respectively. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds LYPD1 comprises at least one (e.g., 1, 2, 3, or 4) of heavy chain framework regions FR-H1, FR-H2, FR-H3, and FR-H4 comprising the sequences of SEQ ID NOs: 573-576, respectively, and/or at least one (e.g., 1, 2, 3, or 4) of the light chain framework regions FR-L1, FR-L2, FR-L3, and FR-L4 comprising the sequences of SEQ ID NOs: 577-580, respectively. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 40G5c, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v1, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 13; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v2, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 14, such as 38E4v3, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 15, such as 38E4v4, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 9; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 16, such as 38E4v5, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v6, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v7, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to EDAR.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 19; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v8, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to GFRA1.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 20; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, such as 38E4v9, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 21; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 22, such as 38E4c, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24;

(c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 24; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v9, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 29; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1v1, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 23; (b) HVR-H2 comprising the amino acid sequence of SEQ ID NO: 30; (c) HVR-H3 comprising the amino acid sequence of SEQ ID NO: 25; (d) HVR-L1 comprising the amino acid sequence of SEQ ID NO: 26; (e) HVR-L2 comprising the amino acid sequence of SEQ ID NO: 27; and (f) HVR-L3 comprising the amino acid sequence of SEQ ID NO: 28, such as UCHT1vM1, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b). In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 31; (b) HVR-H2 comprising the amino acid sequence of SEQ ID NO: 32; (c) HVR-H3 comprising the amino acid sequence of SEQ ID NO: 33; (d) HVR-L1 comprising the amino acid sequence of SEQ ID NO: 34; (e) HVR-L2 comprising the amino acid sequence of SEQ ID NO: 35; and (f) HVR-L3 comprising the amino acid sequence of SEQ ID NO: 36, such as SP34v52, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 37; (b) HVR-H2 comprising the amino acid sequence of SEQ ID NO: 38; (c) HVR-H3 comprising the amino acid sequence of SEQ ID NO: 39; (d) HVR-L1 comprising the amino acid sequence of SEQ ID NO: 40; (e) HVR-L2 comprising the amino acid sequence of SEQ ID NO: 41; and (f) HVR-L3 comprising the amino acid sequence of SEQ ID NO: 42, such as 41D9a, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 43; (b) HVR-H2 comprising the amino acid sequence of SEQ ID NO: 44; (c) HVR-H3 comprising the amino acid sequence of SEQ ID NO: 45; (d) HVR-L1 comprising the amino acid sequence of SEQ ID NO: 46; (e) HVR-L2 comprising the amino acid sequence of SEQ ID NO: 47; and (f) HVR-L3 comprising the amino acid sequence of SEQ ID NO: 48, such as 13A3.v2, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as 30A1, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to CD79B.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60, such as 30A1.v2, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to EDAR.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 61; (b) HVR-H2 comprising the amino acid sequence of SEQ ID NO: 62; (c) HVR-H3 comprising the amino acid sequence of SEQ ID NO: 63; (d) HVR-L1 comprising the amino acid sequence of SEQ ID NO: 64; (e) HVR-L2 comprising the amino acid sequence of SEQ ID NO: 65; and (f) HVR-L3 comprising the amino acid sequence of SEQ ID NO: 66, such as h21A9, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to GFRA1.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 67; (b) HVR-H2 comprising the amino acid sequence of SEQ ID NO: 68; (c) HVR-H3 comprising the amino acid sequence of SEQ ID NO: 69; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72, such as 21B2, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78, such as 125A1, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84, such as 72H6, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173;

and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 88; (e) HVR-L2 comprising the amino acid sequence of SEQ ID NO: 89; and (f) HVR-L3 comprising the amino acid sequence of SEQ ID NO: 90, such as 1961, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 91; (b) HVR-H2 comprising the amino acid sequence of SEQ ID NO: 92; (c) HVR-H3 comprising the amino acid sequence of SEQ ID NO: 93; (d) HVR-L1 comprising the amino acid sequence of SEQ ID NO: 94; (e) HVR-L2 comprising the amino acid sequence of SEQ ID NO: 95; and (f) HVR-L3 comprising the amino acid sequence of SEQ ID NO: 96, such as 71H7, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101;

and (f) HVR-L3 comprising the amino acid sequence of SEQ ID NO: 102, such as 14C7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 97; (b) HVR-H2 comprising the amino acid sequence of SEQ ID NO: 98; (c) HVR-H3 comprising the amino acid sequence of SEQ ID NO: 99; (d) HVR-L1 comprising the amino acid sequence of SEQ ID NO: 100; (e) HVR-L2 comprising the amino acid sequence of SEQ ID NO: 101; and (f) HVR-L3 comprising the amino acid sequence of SEQ ID NO: 102, such as 14C7, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 103; (b) HVR-H2 comprising the amino acid sequence of SEQ ID NO: 104; (c) HVR-H3 comprising the amino acid sequence of SEQ ID NO: 105; (d) HVR-L1 comprising the amino acid sequence of SEQ ID NO: 106; (e) HVR-L2 comprising the amino acid sequence of SEQ ID NO: 107; and (f) HVR-L3 comprising the amino acid sequence of SEQ ID NO: 108, such as 12763, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 109; (b) HVR-H2 comprising the amino acid sequence of SEQ ID NO: 110; (c) HVR-H3 comprising the amino acid sequence of SEQ ID NO: 111; (d) HVR-L1 comprising the amino acid sequence of SEQ ID NO: 112; (e) HVR-L2 comprising the amino acid sequence of SEQ ID NO: 113; and (f) HVR-L3 comprising the amino acid sequence of SEQ ID NO: 114, such as 18F12, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1 G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 115; (b) HVR-H2 comprising the amino acid sequence of SEQ ID NO: 116; (c) HVR-H3 comprising the amino acid sequence of SEQ ID NO: 117; (d) HVR-L1 comprising the amino acid sequence of SEQ ID NO: 118; (e) HVR-L2 comprising the amino acid sequence of SEQ ID NO: 119; and (f) HVR-L3 comprising the amino acid sequence of SEQ ID NO: 120, such as 27H5-1, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 121; (b) HVR-H2 comprising the amino acid sequence of SEQ ID NO: 122; (c) HVR-H3 comprising the amino acid sequence of SEQ ID NO: 123; (d) HVR-L1 comprising the amino acid sequence of SEQ ID NO: 124; (e) HVR-L2 comprising the amino acid sequence of SEQ ID NO: 125; and (f) HVR-L3 comprising the amino acid sequence of SEQ ID NO: 126, such as 3967, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to CD79B.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 127; (b) HVR-H2 comprising the amino acid sequence of SEQ ID NO: 128; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, such as 40D2, may have a second binding domain that binds to TenB2.

In another instance, from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 631; (b) HVR-H2 comprising the amino acid sequence of SEQ ID NO: 632; (c) HVR-H3 comprising the amino acid sequence of SEQ ID NO: 633; (d) HVR-L1 comprising the amino acid sequence of SEQ ID NO: 634; (e) HVR-L2 comprising the amino acid sequence of SEQ ID NO: 635; and (f) HVR-L3 comprising the amino acid sequence of SEQ ID NO: 636, such as 43H8, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b)

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 133; (b) HVR-H2 comprising the amino acid sequence of SEQ ID NO: 134; (c) HVR-H3 comprising the amino acid sequence of SEQ ID NO: 135; (d) HVR-L1 comprising the amino acid sequence of SEQ ID NO: 136; (e) HVR-L2 comprising the amino acid sequence of SEQ ID NO: 137; and (f) HVR-L3 comprising the amino acid sequence of SEQ ID NO: 138, such as 7967, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b)

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 139; (b) HVR-H2 comprising the amino acid sequence of SEQ ID NO: 140; (c) HVR-H3 comprising the amino acid sequence of SEQ ID NO: 141; (d) HVR-L1 comprising the amino acid sequence of SEQ ID NO: 142; (e) HVR-L2 comprising the amino acid sequence of SEQ ID NO: 143; and (f) HVR-L3 comprising the amino acid sequence of SEQ ID NO: 144, such as 95A2, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b)

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 145; (b) HVR-H2 comprising the amino acid sequence of SEQ ID NO: 146; (c) HVR-H3 comprising the amino acid sequence of SEQ ID NO: 147; (d) HVR-L1 comprising the amino acid sequence of SEQ ID NO: 148; (e) HVR-L2 comprising the amino acid sequence of SEQ ID NO: 149; and (f) HVR-L3 comprising the amino acid sequence of SEQ ID NO: 150, such as 118G9, may have a second binding domain that binds to TenB2.

In another instance, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 157; (b) HVR-H2 comprising the amino acid sequence of SEQ ID NO: 158; (c) HVR-H3 comprising the amino acid sequence of SEQ ID NO: 159; (d) HVR-L1 comprising the amino acid sequence of SEQ ID NO: 160; (e) HVR-L2 comprising the amino acid sequence of SEQ ID NO: 161; and (f) HVR-L3 comprising the amino acid sequence of SEQ ID NO: 162, such as possessed by the anti-CD20 antibody, 2H7.v16 (described in U.S. Pat. No. 7,799,900). In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 266; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 267; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 163; (b) HVR-H2 comprising the amino acid sequence of SEQ ID NO: 164; (c) HVR-H3 comprising the amino acid sequence of SEQ ID NO: 165; (d) HVR-L1 comprising the amino acid sequence of SEQ ID NO: 166; (e) HVR-L2 comprising the amino acid sequence of SEQ ID NO: 167; and (f) HVR-L3 comprising the amino acid sequence of SEQ ID NO: 168, such as possessed by the anti-FcRH5 antibody, 1G7. In some instances, the second binding domain that binds to FcRH5 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 268; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 269; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 169; (b) HVR-H2 comprising the amino acid sequence of SEQ ID NO: 170; (c) HVR-H3 comprising the amino acid sequence of SEQ ID NO: 171; (d) HVR-L1 comprising the amino acid sequence of SEQ ID NO: 172; (e) HVR-L2 comprising the amino acid sequence of SEQ ID NO: 173; and (f) HVR-L3 comprising the amino acid sequence of SEQ ID NO: 174, such as possessed by the anti-HER2 antibody, hu4D5. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 270; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 271; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 581; (b) HVR-H2 comprising the amino acid sequence of SEQ ID NO: 582; (c) HVR-H3 comprising the amino acid sequence of SEQ ID NO: 583; (d) HVR-L1 comprising the amino acid sequence of SEQ ID NO: 584; (e) HVR-L2 comprising the amino acid sequence of SEQ ID NO: 585; and (f) HVR-L3 comprising the amino acid sequence of SEQ ID NO: 586, such as possessed by the anti-HER2 antibody, 2C4. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 593; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 594; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to HER2. The second binding domain that binds to HER2 may, for example, comprise at least one, two, three, four, five, or six hypervariable regions (HVRs) selected from (a) HVR-H1 comprising the amino acid sequence of SEQ ID NO: 587; (b) HVR-H2 comprising the amino acid sequence of SEQ ID NO: 588; (c) HVR-H3 comprising the amino acid sequence of SEQ ID NO: 589; (d) HVR-L1 comprising the amino acid sequence of SEQ ID NO: 590; (e) HVR-L2 comprising the amino acid sequence of SEQ ID NO: 591; and (f) HVR-L3 comprising the amino acid sequence of SEQ ID NO: 592, such as possessed by the anti-HER2 antibody, 7C2. In some instances, the second binding domain that binds to HER2 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 595; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 596; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156 such as Rab17, may have a second binding domain that binds to LYPD1. The second binding domain that binds to LYPD1 may, for example, comprise at least one, two, three, four, five, or six hypervariable regions (HVRs) selected from (a) HVR-H1 comprising the amino acid sequence of SEQ ID NO: 175; (b) HVR-H2 comprising the amino acid sequence of SEQ ID NO: 176; (c) HVR-H3 comprising the amino acid sequence of SEQ ID NO: 177; (d) HVR-L1 comprising the amino acid sequence of SEQ ID NO: 178; (e) HVR-L2 comprising the amino acid sequence of SEQ ID NO: 179; and (f) HVR-L3 comprising the amino acid sequence of SEQ ID NO: 180, such as possessed by the anti-LYPD1 antibody, YWO.49.H6. In some instances, the second binding domain that binds to LYPD1 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 272; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 273; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to LY6G6D.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to LY6E.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 613; (b) HVR-H2 comprising the amino acid sequence of SEQ ID NO: 614; (c) HVR-H3 comprising the amino acid sequence of SEQ ID NO: 615; (d) HVR-L1 comprising the amino acid sequence of SEQ ID NO: 616; (e) HVR-L2 comprising the amino acid sequence of SEQ ID NO: 617; and (f) HVR-L3 comprising the amino acid sequence of SEQ ID NO: 618, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 629; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 630; or (c) a VH domain as in (a) and a VL domain as in (b)

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 151; (b) HVR-H2 comprising the amino acid sequence of SEQ ID NO: 152; (c) HVR-H3 comprising the amino acid sequence of SEQ ID NO: 153; (d) HVR-L1 comprising the amino acid sequence of SEQ ID NO: 154; (e) HVR-L2 comprising the amino acid sequence of SEQ ID NO: 155; and (f) HVR-L3 comprising the amino acid sequence of SEQ ID NO: 156, such as Rab17, may have a second binding domain that binds to TenB2.

In some embodiments, bispecific antibodies may also be used to localize cytotoxic agents to cells which express a tumor antigen, such as a tumor antigen listed in Table 1 (e.g., CD20, FcRH5, HER2, LYPD1, LY6G6D, PMEL17, LY6E, CD19, CD33, CD22, CD79A, CD79B, EDAR, GFRA1, MRP4, RET, Steap1, or TenB2). Bispecific antibodies can also be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). "Knob-in-hole" engineering of multispecific antibodies may be utilized to generate a first arm containing a knob and a second arm containing the hole into which the knob of the first arm may bind. The knob of the multispecific antibodies of the invention may be an anti-CD3 arm in one embodiment. Alternatively, the knob of the multispecific antibodies of the invention may be an anti-target/antigen arm in one embodiment. The hole of the multispecific antibodies of the invention may be an anti-CD3 arm in one embodiment. Alternatively, the hole of the multispecific antibodies of the invention may be an anti-target/antigen arm in one embodiment. Multispecific antibodies may also be engineered using immunoglobulin crossover (also known as Fab domain exchange or CrossMab format) technology (see eg., WO2009/080253; Schaefer et al., Proc. Natl. Acad. Sci. USA, 108:11187-11192 (2011)). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibodies, or antibody fragments thereof, may also include a "Dual Acting FAb" or "DAF" comprising an antigen binding site that binds to CD3 as well as another, different antigen (e.g., a second biological molecule) (see, e.g., US 2008/0069820).

7. Antibody Variants

In certain embodiments, amino acid sequence variants of the anti-CD3 antibodies of the invention (e.g., bispecific anti-CD3 antibodies of the invention that bind to CD3 and a second biological molecule, e.g., a cell surface antigen, e.g., a tumor antigen, such as TDB antibodies of the invention or variants thereof) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 2

Exemplary and Preferred Amino Acid Substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |

TABLE 2-continued

Exemplary and Preferred Amino Acid Substitutions

| Original Residue | Exemplary Substitutions | Preferred Substitutions |
|---|---|---|
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b. Glycosylation Variants

In certain embodiments, anti-CD3 antibodies of the invention (e.g., bispecific anti-CD3 antibodies of the invention that bind to CD3 and a second biological molecule, e.g., a cell surface antigen, e.g., a tumor antigen, such as TDB antibodies of the invention or variants thereof) can be altered to increase or decrease the extent to which the antibody is glycosylated. Addition or deletion of glycosylation sites to anti-CD3 antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-CD3 antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-CD3 antibodies variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain embodiments, one or more amino acid modifications may be introduced into the Fc region of an anti-CD3 antibody of the invention (e.g., a bispecific anti-CD3 antibody of the invention that binds to CD3 and a second biological molecule, e.g., a cell surface antigen, e.g., a tumor antigen, such as a TDB antibody of the invention or variant thereof), thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an anti-CD3 antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc RIII only, whereas monocytes express Fc RI, Fc RII and Fc RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202:163 (1996); Cragg, M. S. et al. *Blood.* 101:1045-1052 (2003); and Cragg, M. S. and M. J. Glennie *Blood.* 103:2738-2743 (2004)). FcRn binding and in vivo clearance/half life determinations can also be performed using methods known in the art (see, e.g., Petkova, S. B. et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain embodiments, the proline at position 329 of a wild-type human Fc region in the antibody is substituted with glycine or arginine or an amino acid residue large enough to destroy the proline sandwich within the Fc/Fc.gamma. receptor interface that is formed between the proline 329 of the Fc and tryptophan residues Trp 87 and Trp 110 of FcgRIII (Sondermann et al.: Nature 406, 267-273 (20 Jul. 2000)). In certain embodiments, the antibody comprises at least one further amino acid substitution. In one embodiment, the further amino acid substitution is S228P, E233P, L234A, L235A, L235E, N297A, N297D, or P331S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects the anti-CD3 antibody (e.g., bispecific anti-CD3 antibody) comprises an Fc region comprising an N297G mutation. In some embodiments, the anti-CD3 antibody comprising the N297G mutation comprises an anti-CD3 arm comprising a first binding domain comprising the following six HVRs: (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6; and an anti-CD20 arm comprising a second binding domain comprising the following six HVRs: (a) an HVR-H1 comprising the amino acid sequence of SEQ ID NO: 157; (b) an HVR-H2 comprising the amino acid sequence of SEQ ID NO: 158; (c) an HVR-H3 comprising the amino acid sequence of SEQ ID NO: 159; (d) an HVR-L1 comprising the amino acid sequence of SEQ ID NO: 160; (e) an HVR-L2 comprising the amino acid sequence of SEQ ID NO: 161; and (f) an HVR-L3 comprising the amino acid sequence of SEQ ID NO: 162.

In some embodiments, the anti-CD3 antibody comprising the N297G mutation comprises an anti-CD3 arm comprising a first binding domain comprising (a) a VH domain comprising an amino acid sequence of SEQ ID NO: 184 and (b) a VL domain comprising an amino acid sequence of SEQ ID NO: 185, and an anti-CD20 arm comprising a second binding domain comprising (a) a VH domain comprising an amino acid sequence of SEQ ID NO: 266 and (b) a VL domain comprising an amino acid sequence of SEQ ID NO: 267.

In some embodiments, the anti-CD3 antibody comprising the N297G mutation comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the CH3, and $CH3_2$ domains each comprise a protuberance or cavity, and wherein the protuberance or cavity in the CH3, domain is positionable in the cavity or protuberance, respectively, in the $CH3_2$ domain. In some instances, the CH3, and $CH3_2$ domains meet at an interface between said protuberance and cavity. In some instances, the CH2, and $CH2_2$ domains each comprise a protuberance or cavity, and wherein the protuberance or cavity in the CH2, domain is positionable in the cavity or protuberance, respectively, in the $CH2_2$ domain. In other instances, the CH2, and $CH2_2$ domains meet at an interface between said protuberance and cavity. In some instances, the anti-CD3 antibody is an IgG1 antibody.

In other embodiments, the anti-CD3 antibody comprising the N297G mutation comprises an anti-CD3 arm comprising a first binding domain comprising (a) a VH domain comprising an amino acid sequence of SEQ ID NO: 184 and (b) a VL domain comprising an amino acid sequence of SEQ ID NO: 185, and an anti-CD20 arm comprising a second binding domain comprising (a) a VH domain comprising an amino acid sequence of SEQ ID NO: 266 and (b) a VL domain comprising an amino acid sequence of SEQ ID NO: 267, wherein (a) the anti-CD3 arm comprises T366S, L368A, Y407V, and N297G substitution mutations and (b) the anti-CD20 arm comprises T366W and N297G substitution mutations.

d. Cysteine Engineered Antibody Variants In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

e. Antibody Derivatives

In certain embodiments, an anti-CD3 antibody of the invention (e.g., bispecific anti-CD3 antibody of the invention that binds to CD3 and a second biological molecule, e.g., a cell surface antigen, e.g., a tumor antigen, such as a TDB antibody of the invention or variant thereof) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Anti-CD3 antibodies of the invention (e.g., bispecific anti-CD3 antibodies of the invention that bind to CD3 and a second biological molecule, e.g., a cell surface antigen, e.g., a tumor antigen, such as TDB antibodies of the invention or variants thereof) may be produced using recombinant methods and compositions, for example, as described in U.S. Pat. No. 4,816,567. In one embodiment, isolated nucleic acid encoding an anti-CD3 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CD3 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD3 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-CD3 antibodies of the invention (e.g., bispecific anti-CD3 antibodies of the invention that bind to CD3 and a second biological molecule, e.g., a cell surface antigen, e.g., a tumor antigen, such as TDB antibodies of the invention or variants thereof) provided herein may be identified, screened for, or characterized for their physical/chemical properties and/or biological activities by various assays known in the art.

1. Binding Assays and Other Assays

In one aspect, an anti-CD3 antibody of the invention is tested for its antigen binding activity, for example, by known methods such as ELISA, Western blot, etc.

In another aspect, competition assays may be used to identify an antibody that competes with an anti-CD3 antibody of the invention for binding to CD3.

In an exemplary competition assay, immobilized CD3 is incubated in a solution comprising a first labeled antibody that binds to CD3 and a second unlabeled antibody that is being tested for its ability to compete with the first antibody for binding to CD3. The second antibody may be present in a hybridoma supernatant. As a control, immobilized CD3 is incubated in a solution comprising the first labeled antibody but not the second unlabeled antibody. After incubation under conditions permissive for binding of the first antibody to CD3, excess unbound antibody is removed, and the amount of label associated with immobilized CD3 is measured. If the amount of label associated with immobilized CD3 is substantially reduced in the test sample relative to the control sample, then that indicates that the second antibody is competing with the first antibody for binding to CD3. See, e.g., Harlow and Lane (1988) *Antibodies: A Laboratory Manual*. Ch. 14 (Cold Spring Harbor Laboratory, Cold Spring Harbor, N.Y.).

2. Activity Assays

In one aspect, assays are provided for identifying anti-CD3 antibodies thereof having biological activity. Biological activity may include, for example, binding to CD3 (e.g., CD3 on the surface of a T cell), or a peptide fragment thereof, either in vivo, in vitro, or ex vivo. In the case of a multispecific (e.g., bispecific) anti-CD3 antibody of the invention (e.g., a TDB antibody having one anti-CD3 arm and one arm that recognizes a second biological molecule, e.g., a cell surface antigen, e.g., a tumor antigen), biological activity may also include, for example, effector cell activation (e.g., T cell (e.g., CD8+ and/or CD4+ T cell) activation), effector cell population expansion (i.e., an increase in T cell count), target cell population reduction (i.e., a decrease in the population of cells expressing the second biological molecule on their cell surfaces), and/or target cell killing. Antibodies having such biological activity in vivo and/or in vitro are provided. In certain embodiments, an antibody of the invention is tested for such biological activity, as described in detail in the Examples herein below.

In some embodiments, the activity comprises ability to support B cell killing and/or the activation of the cytotoxic T cells. In certain embodiments, an anti-B cell targeting anti-CD3 antibody of the invention (such as an anti-CD20 TDB) is tested for such B cell killing and/or the activation of the cytotoxic effect of T cells biological activity by any of the methods described herein, in particular the Examples. In some embodiments of any of these activity assays, PBMCs may be isolated from whole blood of healthy donors by Ficoll separation. In particular, human blood may be collected in heparinized syringes, and PBMCs isolated using Leucosep and Ficoll Paque Plus. If needed CD4+T and CD8+ T cells may be separated with Miltenyi kits according to manufacturer's instructions.

Further, cells may be washed in RPMI medium containing 10% FBS, supplemented with GlutaMax, penicillin & streptomycin, and ~0.2 million suspended cells added to a 96-well U-bottom plate. Cells may be cultured in RPMI1640 supplemented with 10% FBS at 37° C. in a humidified standard cell culture incubator. For BJAB cell killing assays, 20,000 BJAB cells may be incubated with effector cells, either as huPBMCs or purified T cells, as indicated ratios per assay, in the presence of various concentrations of TDB antibodies for 24 hours. For endogenous B cell killing assays, 200,000 huPBMCs may be incubated with various concentrations of TDB antibodies for 24 hours.

After culturing, cells may be washed with FACS buffer (0.5% BSA, 0.05% Na Azide in PBS). Cells may then be stained in FACS buffer, washed with FACS buffer and suspended in 100111 of FACS buffer containing 1 µg/ml Propidium Iodide. Data may be collected on a FACSCalibur flow cytometer and analyzed using FlowJo. Live B cells may be gated out as PI-CD19+ or PI-CD20+ B cells by FACS, and absolute cell count may be obtained with FITC beads added to reaction mix as an internal counting control. The percent (%) of cell killing may be calculated based on non-TDB treated controls. Activated T cells may be detected by CD69 and CD25 surface expression using anti-CD69-FITC and anti-CD25-PE.

D. Immunoconjugates

The invention also provides immunoconjugates comprising an anti-CD3 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-CD3 antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an anti-CD3 antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-CD3 antibodies of the invention (e.g., bispecific anti-CD3 antibodies of the invention that bind to CD3 and a second biological molecule, e.g., a cell surface antigen, e.g., a tumor antigen, such as TDB antibodies of the invention or variants thereof) is useful for detecting the presence of CD3 in a biological sample. The term "detecting" as used herein encompasses quantitative or qualitative detection. In certain embodiments, a biological sample comprises a cell or tissue.

In one embodiment, an anti-CD3 antibody for use in a method of diagnosis or detection is provided. In a further aspect, a method of detecting the presence of CD3 in a biological sample is provided. In certain embodiments, the method comprises contacting the biological sample with an anti-CD3 antibody as described herein under conditions permissive for binding of the anti-CD3 antibody to CD3, and detecting whether a complex is formed between the anti-CD3 antibody and CD3. Such method may be an in vitro or in vivo method.

In certain embodiments, labeled anti-CD3 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-CD3 antibody of the invention (e.g., bispecific anti-CD3 antibody of the invention that binds to CD3 and a second biological molecule, e.g., a cell surface antigen, e.g., a tumor antigen, such as a TDB antibody of the invention or variant thereof) are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

G. Therapeutic Methods and Compositions

Any of the anti-CD3 antibodies of the invention (e.g., bispecific anti-CD3 antibodies of the invention that bind to CD3 and a second biological molecule, e.g., a cell surface antigen, e.g., a tumor antigen, such as TDB antibodies of the invention or variants thereof) may be used in therapeutic methods.

In one aspect, an anti-CD3 antibody for use as a medicament is provided. In further aspects, an anti-CD3 antibody for use in treating or delaying progression of a cell proliferative disorder (e.g., cancer) or an autoimmune disorder (e.g., arthritis) is provided. In certain embodiments, an anti-CD3 antibody for use in a method of treatment is provided. In certain embodiments, the invention provides an anti-CD3 antibody for use in a method of treating an individual having a cell proliferative disorder or an autoimmune disorder comprising administering to the individual an effective amount of the anti-CD3 antibody. In one such embodiment, the method further comprises administering to the individual an effective amount of at least one additional therapeutic agent, for example, as described below. In further embodiments, the invention provides an anti-CD3 antibody for use in enhancing immune function in an individual having a cell proliferative disorder or an autoimmune disorder. In certain embodiments, the invention provides an anti-CD3 antibody for use in a method of enhancing immune function in an individual having a cell proliferative disorder or an autoimmune disorder comprising administering to the individual an effective of the anti-CD3 antibody to activate effector cells (e.g., T cells, e.g., CD8+ and/or CD4+ T cells), expand (increase) an effector cell population, reduce a target cell (e.g., a cell expressing a second biological molecule recognized by an anti-CD3 antibody of the invention, such as a bispecific TDB antibody of the invention) population, and/or kill a target cell (e.g., target tumor cell). An "individual" according to any of the above embodiments may be a human.

In a further aspect, the invention provides for the use of an anti-CD3 antibody in the manufacture or preparation of a medicament. In one embodiment, the medicament is for treatment of a cell proliferative disorder (e.g., cancer) or an autoimmune disorder (e.g., arthritis). In a further embodiment, the medicament is for use in a method of treating a cell proliferative disorder or an autoimmune disorder comprising administering to an individual having a cell proliferative disorder or an autoimmune disorder an effective amount of the medicament. In one such embodiment, the method further comprises administering to the individual an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, reducing a target cell (e.g., a cell expressing a second biological molecule recognized by an anti-CD3 antibody of the invention, such as a bispecific TDB antibody of the invention) population, and/or killing target cells (e.g., target tumor cells) in the individual. In a further embodiment, the medicament is for use in a method of enhancing immune function in an individual having a cell proliferative disorder or an autoimmune disorder comprising administering to the individual an amount effective of the medicament to activate effector cells (e.g., T cells, e.g., CD8+ and/or CD4+ T cells), expand (increase) an effector cell population, reduce a target cell (e.g., a cell expressing a second biological molecule recognized by an anti-CD3 antibody of the invention, such as a bispecific TDB antibody of the invention) population, and/or kill a target cell (e.g., target tumor cell). An "individual" according to any of the above embodiments may be a human.

In a further aspect, the invention provides a method for treating a cell proliferative disorder (e.g., cancer) or an autoimmune disorder (e.g., arthritis). In one embodiment, the method comprises administering to an individual having such a cell proliferative disorder or an autoimmune disorder an effective amount of an anti-CD3 antibody. In one such embodiment, the method further comprises administering to the individual an effective amount of at least one additional therapeutic agent, for example, as described below. An "individual" according to any of the above embodiments may be a human.

In a further aspect, the invention provides a method for enhancing immune function in an individual having a cell proliferative disorder or an autoimmune disorder in an individual having a cell proliferative disorder or an autoimmune disorder. In one embodiment, the method comprises administering to the individual an effective amount of an anti-CD3 antibody to activate effector cells (e.g., T cells, e.g., CD8+ and/or CD4+ T cells), expand (increase) an effector cell population, reduce a target cell (e.g., a cell expressing a second biological molecule recognized by an anti-CD3 antibody of the invention, such as a bispecific TDB antibody of the invention) population, and/or kill a target cell (e.g., target tumor cell). In one embodiment, an "individual" is a human.

In a further aspect, the invention provides a method for treating a hematological cancer, such as a B cell cancer (for example, mature B-cell lymphoma) by administering an effective amount of an anti-CD3 antibody of the invention, such as a bispecific TDB antibody of the invention, such as an anti-B cell targeting TDB, such as a CD20-TDB having an anti-CD3 arm and an anti-CD20 arm. In a further aspect of the embodiment, the mature B-cell lymphoma is a Non-Hodgkin's Lymphoma (NHL). In a further aspect of the embodiment, the NHL is selected from the group comprising: germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenström macroglobulinemia, Heavy chain diseases, a Heavy chain disease, γ Heavy chain disease, p Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma. In a preferred embodiment of the invention, the method comprises treating a cancer comprising germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), or Burkitt's lymphoma (BL).

In one embodiment, the method comprises administering to an individual having such a hematological cancer (for example, B cell cancer, for example, B cell lymphoma) an effective amount of an anti-CD3 antibody of the invention, such as a bispecific TDB antibody, such as a CD20 TDB comprising an anti-CD20 targeting arm and an anti-CD3 targeting arm. In other embodiments, a CD20 TDB is co-administered with one or more additional therapeutic agents. In one embodiment, the therapeutic agent is an antibody targeting CD20. In one embodiment, a CD20 TDB is co-administered with one or more antibodies targeting CD20 selected from the chimeric monoclonal CD20 antibody, rituximab (Rituxan®) or the monoclonal CD20 antibody, obinutuzumab (Gazyva®). In one embodiment, a CD20 TDB is co-administered with rituximab. In one embodiment, a CD20 TDB is co-administered with obinutuzumab. In one embodiment, a CD20 TDB is co-administered with obinutuzumab and rituximab.

In one further embodiment, the anti-CD3 antibody of the invention (for example, the CD20 TDB), with or without a CD20 monoclonal antibody, is administered with a further chemotherapy agent and/or an antibody-drug conjugate (ADC). In one embodiment, a CD20 TDB is co-administered with one or more additional chemotherapy agents selected from cyclophosphamide, doxorubicin, vincristine, and prednisolone (CHOP). In one embodiment, a CD20 TDB is co-administered with an ADC. In one embodiment, a CD20 TDB is co-administered with CHOP, wherein vincristine is replaced with an ADC. In one embodiment, a CD20 TDB is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate.

In one other embodiment the therapeutic agent is a biological modifier. In one embodiment, a CD20 TDB is co-administered with one or more biological modifiers selected from a BCL-2 inhibitor (such as GDC-0199/ABT-199), lenalidomide (Revlimid®), a PI3K-delta inhibitor (such as idelalisib (Zydelig®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or Yervoy®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g, a dominant-negative TGF beta type II receptor.

In one embodiment, a CD20 TDB is co-administered with rituximab and one or more chemotherapy agents. In one such embodiment, a CD20 TDB is co-administered with rituximab and CHOP. In one embodiment, a CD20 TDB is co-administered with rituximab and an ADC. In one embodiment, a CD20 TDB is co-administered with rituximab and CHOP, wherein vincristine is replaced with an ADC. In one embodiment, a CD20 TDB is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate. In one embodiment, a CD20 TDB is co-administered with rituximab and one or more biological modifiers selected from a BCL-2 inhibitor (such as GDC-0199/ABT-199), lenalidomide (Revlimid®), a PI3K-delta inhibitor (such as idelalisib (Zydelig®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or Yervoy®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g, a dominant-negative TGF beta type II receptor.

In one embodiment, a CD20 TDB is co-administered with rituximab, one or more chemotherapy agents, and one or more biological modifiers selected from a BCL-2 inhibitor (such as GDC-0199/ABT-199), lenalidomide (Revlimid®), a PI3K-delta inhibitor (such as idelalisib (Zydelig®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or Yervoy®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g, a dominant-negative TGF beta type II receptor.

In one embodiment, a CD20 TDB is co-administered with rituximab, an ADC, and one or more biological modifiers selected from a BCL-2 inhibitor (such as GDC-0199/ABT-199), lenalidomide (Revlimid®), a PI3K-delta inhibitor (such as idelalisib (Zydelig®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or Yervoy®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g, a dominant-negative TGF beta type II receptor.

In one embodiment, a CD20 TDB is co-administered with obinutuzumab and one or more chemotherapy agents. In one embodiment, a CD20 TDB is co-administered with obinutuzumab and CHOP. In one embodiment, a CD20 TDB is co-administered with obinutuzumab and an ADC. In one embodiment, a CD20 TDB is co-administered with obinutuzumab and CHOP, wherein vincristine is replaced with an ADC. In one embodiment, a CD20 TDB is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate. In one embodiment, a CD20 TDB is co-administered with obinutuzumab and one or more biological modifiers selected from a BCL-2 inhibitor (such as GDC-0199/ABT-199), lenalidomide (Revlimid®), a PI3K-delta inhibitor (such as idelalisib (Zydelig®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or Yervoy®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g, a dominant-negative TGF beta type II receptor.

In one embodiment, a CD20 TDB is co-administered with obinutuzumab, an ADC, and one or more biological modifiers selected from a BCL-2 inhibitor (such as GDC-0199/ABT-199), lenalidomide (Revlimid®), a PI3K-delta inhibitor (such as idelalisib (Zydelig®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or Yervoy®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g, a dominant-negative TGF beta type II receptor.

In a further aspect of the invention, the additional therapy comprises an anti-CD20 antibody. In one embodiment, the anti-CD20 antibody is rituximab. In one embodiment, the anti-CD20 antibody is a humanized B-Ly1 antibody. In one embodiment, the humanized B-Ly1 antibody is obinituzumab. In one embodiment, the anti-CD20 antibody is ofatumumab, ublituximab, and/or ibritumomab tiuxetan.

In a further aspect of the invention, the additional therapy comprises an alkylating agent. In one embodiment, the alkylating agent is 4-[5-[Bis(2-chloroethyl)amino]-1-methylbenzimidazol-2-yl]butanoic acid and salts thereof. In one embodiment, the alkylating agent is bendamustine.

In a further aspect of the invention, the additional therapy comprises a BCL-2 inhibitor. In one embodiment, the BCL-2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide and salts thereof. In one embodiment, the BCL-2 inhibitor is venetoclax (CAS#: 1257044-40-8).

In a further aspect of the invention, the additional therapy comprises a phosphoinositide 3-kinase (PI3K) inhibitor. In one embodiment, the PI3K inhibitor inhibits delta isoform PI3K (i.e., P110δ). In some embodiments, the PI3K inhibitor is 5-Fluoro-3-phenyl-2-[(1S)-1-(7H-purin-6-ylamino)propyl]-4(3H)-quinazolinone and salts thereof. In some embodiments, the PI3K inhibitor is idelalisib (CAS#: 870281-82-6). In one embodiment, the PI3K inhibitor inhibits alpha and delta isoforms of PI3K. In some embodiments, the PI3K inhibitor is 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide and salts thereof.

In a further aspect of the invention, the additional therapy comprises a Bruton's tyrosine kinase (BTK) inhibitor. In one embodiment, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one and salts thereof. In one embodiment, the BTK inhibitor is ibrutinib (CAS#: 936563-96-1).

In a further aspect of the invention, the additional therapy comprises thalidomide or a derivative thereof. In one embodiment, the thalidomide or a derivative thereof is (RS)-3-(4-Amino-1-oxo 1,3-dihydro-2H-isoindol-2-yl)piperidine-2,6-dione and salts thereof. In one embodiment, the thalidomide or a derivative thereof is lendalidomide (CAS#: 191732-72-6).

In a further aspect of the invention, the additional therapy comprises one or more of cyclophosphamide, doxorubicin, vincristine, or prednisolone (CHOP). In one embodiment, the additional therapy further comprises an anti-CD20 antibody as described above (e.g., GA-101 and/or Rituxan®). Any of the above methods and therapies may be used, without limitation, for any cancer, including, for example, treatment of a B-cell cancer or breast cancer.

In a further aspect, the invention provides a method for treating HER2-positive cancers. In one embodiment, the method comprises administering to an individual having such a cancer an effective amount of an anti-HER2 antibody of the invention, such as a bispecific TDB antibody with an anti-HER2 targeting arm and an anti-CD3 targeting arm. In a preferred embodiment, the HER2-TDB possesses an acceptable toxicity profile when administered in an effective dose in a patient. In one embodiment, the CD3 arm of the HER2-TDB with an acceptable toxicity profile is a low affinity CD3 arm. In one embodiment, the CD3 arm of the HER2-TDB with an acceptable toxicity profile is 40G5c.

In a preferable embodiment, the HER2-positive cancer is a HER2-positive breast cancer or HER2-positive gastric cancer. In one embodiment, a HER2 TDB is co-administered with one or more additional therapeutic agents that target the HER pathway. In one embodiment, the therapeutic agent that targets the HER pathway is selected from an EGFR inhibitor, a HER2 inhibitor, a HER3 inhibitor, and/or a HER4 inhibitor. In one embodiment, a HER2 TDB is co-administered with one or more additional therapeutic agents selected from trastuzumab (Herceptin®), T-DM1 (Kadcyla®) and pertuzumab (Perjeta®). In one embodiment, a HER2 TDB is co-administered with trastuzumab. In one embodiment, a HER2 TDB is co-administered with T-DM1. In one embodiment, a HER2 TDB is co-administered with pertuzumab. In one embodiment, a HER2 TDB is co-administered with trastuzumab and pertuzumab. In one embodiment, a HER2 TDB is co-administered with T-DM1 and pertuzumab.

In a further aspect, the invention provides pharmaceutical formulations comprising any of the anti-CD3 antibodies provided herein, e.g., for use in any of the above therapeutic methods. In one embodiment, a pharmaceutical formulation comprises any of the anti-CD3 antibodies provided herein and a pharmaceutically acceptable carrier. In another embodiment, a pharmaceutical formulation comprises any of the anti-CD3 antibodies provided herein and at least one additional therapeutic agent, for example, as described herein.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent, growth inhibitory agent, cytotoxic agent, agent used in radiation therapy, anti-angiogenesis agent, apoptotic agent, anti-tubulin agent, or other agent, such as a epidermal growth factor receptor (EGFR) antagonist (e.g., a tyrosine kinase inhibitor), HER1/EGFR inhibitor (e.g., erlotinib (Tarceva™), platelet derived growth factor inhibitor (e.g., Gleevec™ (Imatinib Mesylate)), a COX-2 inhibitor (e.g., celecoxib), interferon, cytokine, antibody other than the anti-CD3 antibody of the invention, such as an antibody that bind to one or more of the following targets ErbB2, ErbB3, ErbB4, PDGFR-beta, BlyS, APRIL, BCMA VEGF, or VEGF receptor(s), TRAIL/Apo2, PD-1, PD-L1, PD-L2, or another bioactive or organic chemical agent.

In some embodiments, the invention provides a method wherein the additional therapeutic agent is a glucocorticoid. In one embodiment, the glucocorticoid is dexamethasone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-CD3 antibody and administration of an additional therapeutic agent occur within about one month, or within about one, two or three weeks, or within about one, two, three, four, five, or six days, of each other. Anti-CD3 antibodies of the invention (e.g., bispecific anti-CD3 antibodies of the invention that bind to CD3 and a second biological molecule, e.g., a cell surface antigen, e.g., a tumor antigen, such as a TDB antibody of the invention or variant thereof) can also be used in combination with radiation therapy.

An antibody of the invention (and/or any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some embodiments, the antibody is administered by subcutaneous administration. In some embodiments, an anti-CD3 antibody administered by subcutaneous injection exhibits a less toxic response in a patient than the same anti-CD3 antibody administered by intravenous injection. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-CD3 antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-CD3 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-CD3 antibody). An initial higher loading dose, followed by one or more lower doses may be administered. The progress of this therapy is easily monitored by conventional techniques and assays.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1. Generation of Anti-CD3 Antibodies

CD3ε Antigens

A. Bispecific human and cyno CD3ε+CD3γ fused to mouse IgG2a-Fc (CD3εγ-muFc) cDNA encoding extracellular portions of human or cynomolgus monkey (cyno) CD3ε or CD3γ was fused at the C-terminus to a mouse IgG2a Fc to generate CD3-Fc fusions. The cDNAs encoding extracellular domains of human or cyno CD3ε and CD3γ were generated using total RNA from anti-CD3/anti-CD28-activated peripheral blood mononuclear cells (PBMCs). Normal PBMCs were activated by plate-immobilized anti-CD3 and anti-CD28 in RPMI supplemented with 10% FBS for 72h. Total mRNA was isolated using an RNeasy mini kit from Qiagen. cDNA was cloned using gene-specific primers by RT-PCR into TOPO vectors using Taq polymerase-amplified PCR products following the protocol provided with the TOPO TA cloning kit from Invitrogen. The resulting fragments were introduced into a mammalian expression vector containing a murine IgG2a Fc domain by restriction-free subcloning using Phusion High-Fidelity DNA Polymerase (New England Biolabs, Catalog # M0530L). The CD3 fragments were thus amplified with overlapping regions contained in the template plasmid to orient them directly downstream of the signal sequence and N-terminal to the murine Fc.

For both human and cyno constructs, the CD3ε-Fc containing plasmid was transiently co-expressed with the CD3γ-

Fc containing plasmid in mammalian CHO cells. Heterodimers of CD3ε/γ were purified by Protein A-Sepharose (Pharmacia Biotech).

B. N-Terminal Peptide-KLH Conjugates (CD3ε-KLH)

Peptide fragments containing N-terminal sequences of cyno and human CD3ε were synthesized. The fragments intended for immunization were conjugated to keyhole limpet hemocyanin (KLH), a widely used carrier protein for generating a substantial immune response. Appending the naturally occurring cysteine at position 28 for cyno and human CD3ε allowed for coupling of maleimide-activated KLH to the thiol-containing C-terminal cysteine.

C. Single Chain CD3E-26Mer-CD3γ (CD3εγ)

The cDNAs encoding extracellular portions of human CD3ε and CD3γ subunits were generated by PCR. Amino acids 1-97 of human CD3ε and amino acids 1-81 of human CD3γ were connected using a flexible peptide linker of 26 amino acids to form a CD3ε-26mer-CD3γ construct (CD3εγ) (FIG. 1). The construct was cloned into an expression vector with a His-tag for secretion from $E.\ coli$ using the alkaline phosphotase promoter and the STIII secretion signal sequence. CD3εγ was purified on a Ni column and subsequently refolded. Properly folded CD3εγ was then purified using an OKT3 affinity column.

In addition for some binding experiments, commercial CD3ε was purchased from Creative Biomart, Shirley, N.Y. 11967 (Catalog number CD3E-2194H).

Immunizations

A. Mouse Immunizations

BALB/c or C57BL/6 mice were immunized (2 μg or 10 μg/injection per mouse). Antigens, suspended in monophosphoryl lipid A/trehalose dicorynomycolate adjuvant, were injected into the footpad at 3- to 4-day intervals for a total of 12-15 boosts. Three days after the final pre-fusion boost, lymphocytes from immunized mice spleens and lymph nodes were harvested. Isolated mouse lymphocytes were fused with SP2/0-Ag14 myeloma cells (American Type Culture Collection) by using the Cyto Pulse CEEF-50 apparatus (Cyto Pulse Sciences). Briefly, after washing twice with Cytofusion Medium C (Cat# LCM-C), the isolated spleen cells and SP2/0-Ag14 cells were mixed at a 1:1 ratio and then suspended at 10 million cells/ml in Cytofusion Medium C, electrofusion was performed according to manufacturer's guidance. Fused cells were cultured in ClonaCell-HY Medium C (Cat#03803) overnight at 37° C. in a 7% $CO_2$ incubator. Next day the fused cells were centrifuged and then suspended in 10 ml ClonaCell-HY Medium C and then gently mixed with 90 ml Methylcellulose-based ClonaCell-HY Medium D (Cat#03804) containing HAT components. The cells were plated into OmniTray plates (Thermo Scientific) and allowed to grow in 37° C. in a 7% $CO_2$ incubator. After 6-7 days incubation, single hybridoma clones were picked by ClonePix FL (Molecular Devices) and transferred into 96-well cell culture plates (#353075, Becton Dickinson) with 200 μL/well ClonaCell-HY Medium E (Cat#03805). Hybridoma culture media were changed prior to ELISA screening.

B. Rabbit Immunizations

Rabbit immunizations were performed using 0.5 mg/injection with CFA/IFA human and cyno CD3ε-KLH every 2 weeks for 5 injections (d0, d14, d28, d42, d56). Bleeds were taken on days 52 and 66.

PEG fusions and screening was performed as follows. Clones were screened for binding to the N-terminal portion of CD3ε conjugated to thyroglobulin (THY) by ELISA. All positive clones were also found to cross-react with cyno CD3ε by ELISA and 16 unique clones were selected for sub-cloning. Total RNA was extracted from frozen cell pellets and purified using a Qiagen RNeasy kit following manufacturer's instructions. First strand cDNA was synthesized using RT-PCR one-step (Qiagen). Rabbit VH and VL domains were further PCR amplified using a protocol described for generating rabbit immune libraries (Kontermann and Dubel. $Antibody\ Engineering$. 1: 115-123, 2010). Moderate degeneracy was designed to represent common rabbit germline immunoglobulin genes.

Antibody Screening

A. Mouse Hybridoma Screening 3 days after media change, hybridoma supernatants were screened by ELISA for binding to both human and cynoCD3ε, as described below. All ELISA positive clones were further screened by flow cytometry for binding to human Jurkat T cells, human PBMCs, and cyno PBMCs (FIGS. 2 and 3). Hybridoma supernatants were purified by Protein A affinity chromatography, then sterile filtered (0.2-μm pore size, Nalge Nunc International, NY, USA) and stored at 4° C. in PBS. Purified mAbs were confirmed by ELISA before further testing in functional assays. mAb isotype was determined using a mouse monoclonal antibody isotyping kit from Roche Diagnostics Corporation.

Figure 4A:
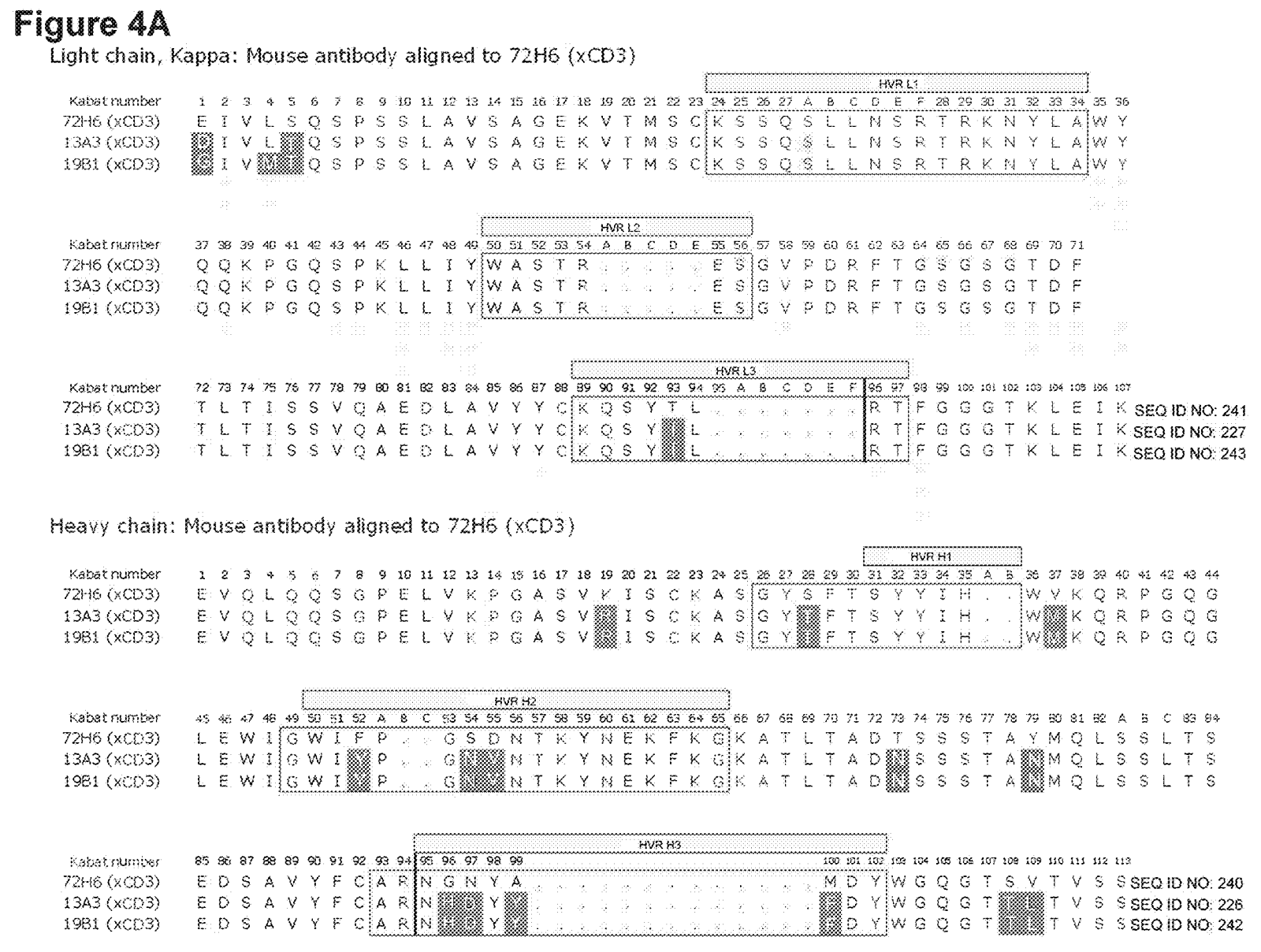

The amino acid sequences of the light and heavy chain variable domains of the anti-CD3 antibodies 13A3, 72H6, and 19B1 are shown in FIG. 4A. FIG. 4A also delimits the HVR sequences for each of the three antibodies. FIGS. 4B, 4C, 5A, and 5B show additional amino acid sequences of the light and heavy chain variable domains of other anti-CD3 antibodies.

B. Screening Following Rabbit Immunizations

Figure 7:
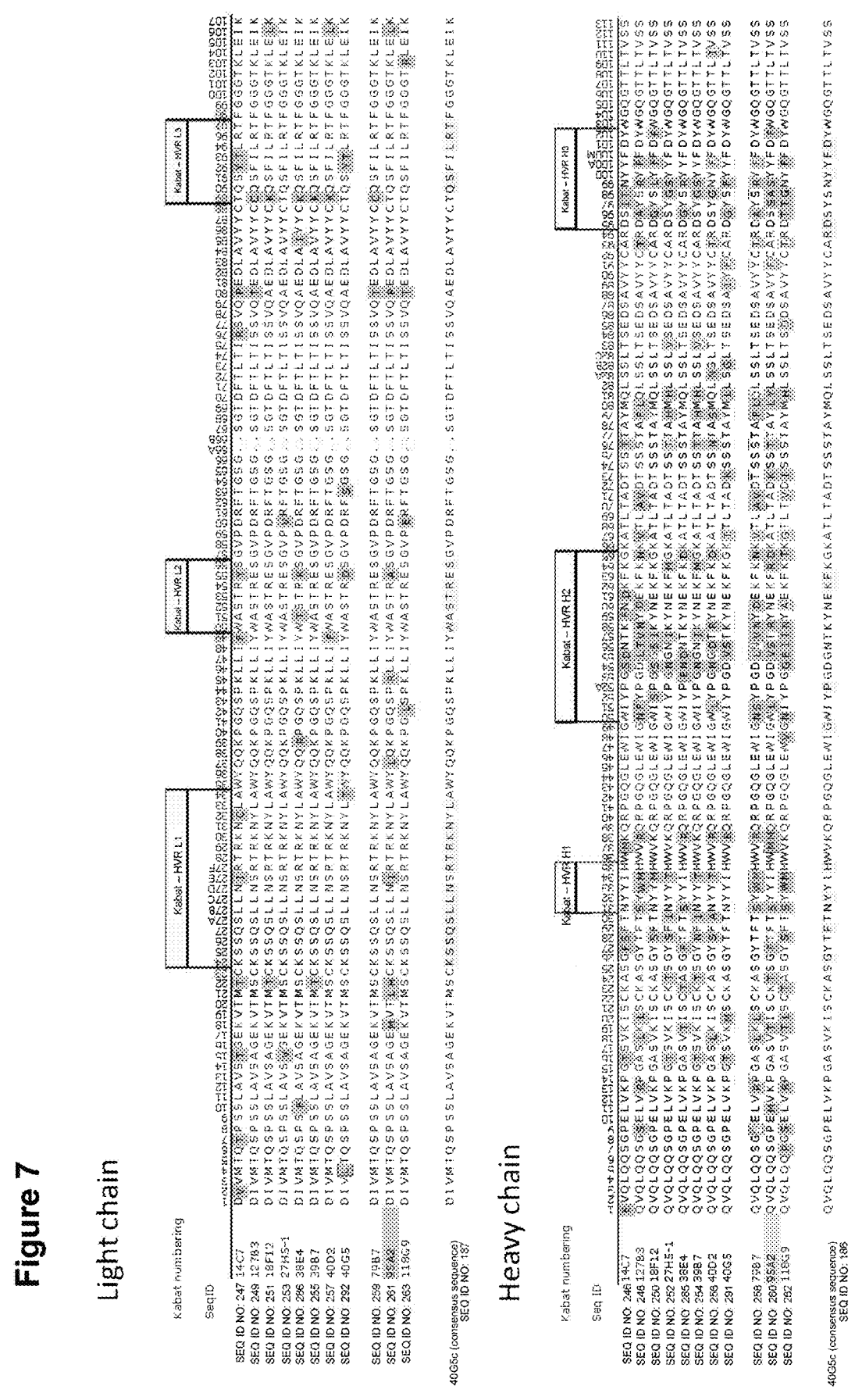

Eight unique heavy chain sequences, and six unique light chain sequences were cloned out from the hybridoma cell lines. FIG. 7 shows the heavy chain and light chain sequences for one of these antibodies, Rab17. High similarity in sequence led to the decision to focus on 6 heavy and light pairs. The 6 resulting antibodies were expressed as chimeric rabbit/human IgGs on a small scale (100 ml cultures of 293S), and screened for binding to CD3 epsilon by ELISA.

Antibody Characterization—Binding Affinity and T Cell Activation Activity Assays A. CD3εγ Binding ELISA Assay The CD3εγ binding ELISA assay was performed in 96-well microtiter ELISA plates (Greiner, Germany) coated with either human/cyno CD3ε N-terminal amino acids conjugated to THY or human/cyno CD3ε/γ fused to murine Fc at 2 μg/ml in 0.05 M carbonate buffer (pH 9.6), 4° C. overnight. After washing three times with wash buffer (0.05% Tween 20 in PBS), plates were blocked with 200 μL ELISA assay diluents with BSA. 100 μL of cultured supernatants or diluted purified mAbs were added and incubated for 1 h at room temperature. The plates were washed three times and incubated with HRP conjugated Goat anti-mouse IgG Fc for 1 hour. After washing three times, bound enzyme was detected by addition of 100 μL/well TMB substrate (BioFX Laboratories, MD, USA) for 5 min. The reactions were stopped by adding 100 μL/well of stop reagent (BioFX, Laboratories, MD, USA) and detection of color at $A_{630\ nm}$.

B. Flow Cytometry Analysis

Human Jurkat T cells, human PBMCs, or cyno PBMCs were washed twice with FACS staining buffer (phosphate-buffered saline containing 1% fetal bovine serum) and then suspended in FACS staining buffer to final concentration of $5\times10^6$ cells/ml. 100 μl cells were added to U-bottom 96-well tissue culture plate (#353077, Becton Dickinson), and 100 μl hybridoma supernatants or diluted purified mAbs were added. After 30 min incubation on ice, cells were washed twice with FACS staining buffer and subsequently stained with FITC- or allophycocyanin (APC)-conjugated goat anti-mouse IgG antibody (#1012-11, Southern Biotech) at 1:300 dilution for 30 min. After washing twice with FACS staining buffer, cells were analyzed by FACSCalibur (BD Biosciences) flow cytometry. Data was analyzed using FlowJo software (Tree Star, Inc.).

C. Human T Cell Activation Assay

Human blood was collected in heparinized syringes, and PBMC were isolated using Leucosep (Greiner Bio-one, cat#227290P) and Ficoll Paque Plus (GE Healthcare Biosciences, cat#95038-168), as recommended by the manufacture. Cells were washed in RPMI medium containing 10% FBS, supplemented with GlutaMax (Gibco, cat#35050-061), penicillin & streptomycin (Gibco, cat#15140-122), and ~0.2 million suspended cells were added to a 96-well U-bottom plate. Anti-CD3 antibodies were added at between 10 and 0.01 µg/ml. After culturing for ~20 hours, cells were washed with FACS buffer (0.5% BSA, 0.05% Na Azide in PBS). Cells were then stained with anti-CD69-FITC (BD, cat#555530), anti-CD25-PE (BD, cat#555432) anti-CD4-APC (BD, cat#555349) or anti-CD8-APC (BD, cat#555369) in FACS buffer, washed with FACS buffer and suspend in 100 ul of FACS buffer containing 1 µg/ml Propidium Iodide. Data was collected on a FACSCalibur flow cytometer and analyzed using FlowJo. The extent of T cell activation was determined comparing the percentage of CD69+ and CD25+ population in CD4+ or CD8+ T cells.

D. Cyno T Cell Activation Assay

Cyno blood was collected in heparinized tubes. Red blood cells were lysed twice with ACK red blood cell lysis buffer (0.874% NH4Cl, 0.1% KHCO3, 0.00368 EDTA Disodium). Cells were washed in RPMI medium containing 10% FBS, supplemented with GlutaMax (Gibco, cat#35050-061), penicillin & streptomycin (Gibco, cat#15140-122), and ~0.2 million suspended cells were added to a 96-well U-bottom plate. Anti-CD3 antibodies were added at 10 µg/ml. After culturing for ~20 hours, cells were washed with FACS buffer (0.5% BSA, 0.05% Na Azide in PBS). Cells were then stained with anti-CD69-FITC (BD, cat#555530), anti-CD25-PE (BD, cat#555432) anti-CD4-APC (BD, cat#551980) in FACS buffer, washed with FACS buffer and suspend in 100 µg of FACS buffer containing 1 µg/ml Propidium Iodide. Data was collected on a FACSCalibur flow cytometer and analyzed using FlowJo. The extent of T cell activation was determined by comparing the percentage of CD69+ and CD25+ population in CD4+ T cells.

Generation of Anti-CD3 Antibody Variants

A. Cloning and Sequencing of Mouse CD3γ Human/Cyno Cross-Reactive Hybridomas

Total RNA was extracted from mouse hybridoma cells with RNeasy kit (Qiagen), and first-strand cDNA was synthesized using a SuperScript III RT kit (Invitrogen). Antibody genes were amplified by error-proof Taq polymerase PCR with 5' degenerated primer mixture and 3' Cγ-, Cκ-, Cλ-specific primers. PCR products were purified and the variable regions of the antibody heavy and light chains were obtained by sequencing the PCR product. The variable regions of antibody heavy and light chains were digested with appropriate restriction enzymes and cloned into respective pRK expression vectors. The murine antibodies were expressed in 293 cells.

B. Humanization

Sequences of human/cyno CD3εγ cross-reactive hybridomas were aligned to the most homologous human consensus or germline light and heavy variable domains (FIG. 7). A consensus sequence called mu40G5c was derived from light and heavy chain variable domains of related hybridoma clones (FIG. 7). Hypervariable regions (HVRs) were engineered into light and heavy human acceptor frameworks to generate humanized CDR-grafts (see, e.g., FIGS. 8A-8F). Humanized variants were assessed in the form of Fab fragments or as IgG. VL domain positions 24-34 (L1), 50-56 (L2) and 89-97 (L3) and VH domain positions 26-35 (H1), 50-65 (H2) and 95-102 (H3) were used for the grafts (FIGS. 8A-8F). Additional variants that included various combinations of one or more mouse vernier positions were also generated and tested for binding affinity (see, e.g., FIGS. 9A-9F). Murine variable domain residues at select vernier positions were incorporated into a final humanized sequence based on their ability to improve binding affinity. The monovalent binding affinities for selected humanized antibodies for different CD3ε antigens are shown in FIG. 10. The binding affinities for affinity variants of humanized anti-CD3 antibody 38E4 (38E4v1-38E4v9) and 40G5c are shown in FIG. 11.

C. Paratope Mapping

Each residue in HVR-L3 and HVR-H3 of hu38E4 was separately mutated to alanine using Kunkle mutagenesis. In addition, position 95 in HVR-H3 was also mutated to serine, threonine, or glutamate. Variants with these single point mutations were expressed as Fabs in HEK293 cells and initially screened with a single cycle kinetics method on a Biacore T100. Selected variants were also scaled up and purified for a conventional multi-cycle kinetics method. For single cycle kinetics, Biacore Series S CM5 sensor chips were immobilized with anti-human Fab antibodies (Human Fab capture kit, GE Healthcare). Each Fab was captured from culture supernatant and the increasing concentrations (ranging from 3 nM to 250 nM in HBSP buffer) of human CD3εγ were injected sequentially at a flow rate of 30 µl/min in a single analysis cycle without regeneration of the surface in between injections; 10 min dissociation was acquired for each cycle. For conventional multi-cycle kinetics, human CD3εγ, cyno CD3εγ, or a 27-mer peptide were immobilized on Biacore Series S CM5 sensor chip using the amine coupling kit from Biacore. Serial 3-fold dilutions of each Fab variant were injected at a flow rate of 30 µl/min. Each sample was analyzed with a protocol of 3-minute association and 3-minute dissociation. In both methods, the Biacore chips were regenerated using 10 mM Glycine (pH 1.7). Binding response was corrected by blank subtraction and a 1:1 Languir model of simultaneous fitting of $k_{on}$ and $k_{off}$ was used for kinetics analysis. The effects of these mutations, summarized in FIG. 12, indicate light chain residue R96 and heavy chain residues Y97, R99 and F100b play critical roles in the binding to CD3εγ.

D. CD3 Epitope Mapping

Alanine mutations were introduced into CD3ε$^{1-27}$-Fc in order to evaluate epitope recognition of N-terminal binding anti-CD3ε antibodies. Each CD3ε$^{1-27}$-Fc variant was immobilized on Nunc Maxisorp plates overnight in PBS at 2 µg/ml at 4° C. After blocking the plates with 2% powdered milk in PBS containing 0.05% Tween 20 for 1h, 100 µl of 3 nM anti-CD3ε was added to each well and allowed to bind for 1h at 25° C. After 6 washings with PBS containing 0.05% Tween 20, antibody binding was detected by the addition of anti-mouse IgG-HRP secondary antibody, as depicted in FIG. 13A.

CD3εγ was sub-cloned into an M13 phagemid which contains a C-terminal gD tag followed by an amber stop codon so that it could be displayed on phage or expressed in a non suppressor strain of *E. coli*. This CD3εγ phagemid was used as a template for making single alanine mutations in CD3ε by Kunkel mutagenesis. Each CD3ε alanine mutant displayed on phage, was confirmed by DNA sequencing, isolated from a single colony, grown overnight in 2YT/Carb plus KO7 helper phage and purified by PEG precipitation. The effect of alanine mutation in CD3εγ on anti-CD3 antibody binding was assessed using a phage ELISA. Each anti-CD3 antibody was immobilized on a NUNC maxisorp plate at 2 µg/ml in PBS buffer overnight at 4° C. Purified phage supernatant displaying a CD3εγ alanine variant (1.0 OD$_{450}$) was added to the plate and allowed to bind at room temperature with shaking for 1 h. After washing, bound phage was detected with anti-M13-HRP (GE Healthcare cat #45-001-419). Binding of each CD3εγ alanine variant was compared to wild-type CD3εγ phage binding (FIG. 13B). Alanine variants that impacted anti-CD3 antibody binding, were further characterized by assessing binding as a function of phage concentration (FIG. 13C).

To quantify the impact of alanine mutations in CD3 on antibody binding, selected CD3 alanine mutants were expressed in a non-supressor strain of *E. coli*. The secreted CD3εγ variants were captured from the crude periplasmic fraction using anti-CD3 antibody UCHT1v9. UCHT1v9 was immobilized on a CM5 serios S chip through amine coupling using the anti-human IgG (Fc) antibody capture kit (BR-1008-39) from GE Healthcare. SPR measurements were performed on the Biacore 4000 instrument, utilizing kinetic evaluation software. In order to measure monovalent binding affinities, anti-CD3 bispecific antibodies were used in which one arm was the anti-CD3 to be tested and the arm recognized an irrelevant antigen. The bispecific anti-CD3 antibodies were passed over the captured supernatant in a concentration series of two-fold dilutions from 0.39 to 100 nM. The resulting kinetics (FIG. 13D) were measured and calculated using Biacore 4000 BIAevaluation software (product code 28-9664-57).

E. Structural Mapping of CD3ε Binding Site

1. Hu38E4.v1 Fab Hu38E4.v1 Fab, dissolved in 0.15 M NaCl, 25 mM tris, pH 7.5 at 10 mg/ml, and a 2-fold molar excess (1 mg) of CD3ε peptide, QDGNEEMGGITQTPYK (SEQ ID NO: 284) (FIG. 14A), were mixed and subjected to crystallization trials. Initial screening was done with a sparse matrix of precipitants in a sitting drop vapor diffusion format. Optimized crystals grew from a 1:1 mixture with reservoir solution containing 70% v/v methyl-pentanediol, and 0.1 M HEPES buffer at pH 7.5. The reservoir was used as a cryoprotectant. The crystals were transferred to cryogenic temperature by sudden immersion into liquid nitrogen.

The diffraction data for hu38E4.v1 Fab and CD3ε peptide co-crystal were collected at Advanced Photon Source beam line 221D, using a MAR300 CCD detector. The recorded diffractions were then integrated and scaled using the program HKL2000.

The structure was phased by molecular replacement (MR) method using program Phaser. The MR search model was a Fab subunit derived from a crystal structure of HGFA/Fab complex (PDB code: 2R0L). The CD3ε peptide was built into the structure based on a Fo-Fc map. The structure was subsequently refined with programs REFMAC5 and PHENIX using the maximum likelihood target functions, anisotropic individual B-factor refinement method, and TLS refinement method, to achieve convergence. The data and refinement statistics are show in Table 3A.

TABLE 3A

Data Collection and Refinement Statistics for hu38E4.v1/CD3ε Complex

| Space group | P3221 |
|---|---|
| Unit cell | a = 73.2 Å, |
| | b = 73.2 Å, c = 183.7 Å |
| | α = 90° β = 120° γ = 90° |
| Resolution | 50.0-1.95 Å |
| Total number of reflections | 42632 (4188)[1] |
| Completeness (%) | 100 (100) |
| Redundancy | 19.7 (8.3) |
| I/σ | 7.1 (3.0) |
| Rsym[2] | 0.112 (0.812) |
| Resolution range | 50-1.95 Å |
| Rcryst[3]/Rfree[4] | 0.152/0.185 |
| Non-hydrogen atoms | 3960 |
| Water molecules | 446 |
| Average B, Overall | 21.97 |
| Average B, Protein | 20.63 |
| Average B, Water | 32.27 |
| r.m.s.d. bond lengths | 0.009 Å |
| r.m.s.d. angles | 1.258° |

[1]Values in parentheses for are of the highest resolution shell which is 2.02 Å-1.95 Å.
[2]Rsym = $\Sigma|I_{hi}-I_h|/\Sigma I_{hi}$, where $I_{hi}$ is the scaled intensity of the ith symmetry-related observation of reflection h and $I_h$ is the mean value.
[3]Rcryst = $\Sigma_h|F_{o,h}-F_{c,h}|/\Sigma_h F_{o,h}$, where $F_{o,h}$ and $F_{c,h}$ are the observed and calculated structure factor amplitudes for reflection h.
[4]Value of $R_{free}$ is calculated for 5% randomly chosen reflections not included in the refinement.

The crystal structure of the hu38E4.v1 Fab/CD3ε peptide complex was determined at 1.9 Å resolution. The structure revealed that the CD3ε peptide makes a small turn and inserts deeply into the cleft between heavy and light chains of the 38E4.v1 Fab (FIGS. 14B and 14C). Binding buries 666 Å$^2$ of solvent accessible surface area between the peptide and the Fab fragment and involves an intricate network of hydrophobic, hydrogen binding and ionic interactions (FIG. 14D). The N-terminal pyroglutamate (pyroglu) ring packs against heavy chain Tyr33 and makes a hydrogen bond with heavy chain His35 in HVR-H1. The bulky side chain of residue F100b in HVR-H3 pushes His35 into a proper orientation for its interaction with pyroglu and explains the loss of binding observed when F100b is mutated to alanine, a small side chain residue. In addition, consistent with the alanine scanning results, R96 in CDR-L3 makes a critical hydrogen bond with the carboxyl group in the pyroglu, whereas Y97 in CDR-H3 makes a hydrogen bond with Met7 of the CD3ε peptide (FIG. 14E). Interestingly, while alanine substitution at R99 in CDR-H3 has a dramatic effect on antigen binding, the structure reveals that this side chain points away from the CD3ε peptide and does not involve in any interactions with the peptide. Instead, R99 makes extensive contacts with several residues in CDR-H3, including a hydrogen bond with D101 and hydrophobic packing against Y100a that further impacts the vernier residue, LC Y49 (FIG. 14F). These interactions are likely important for the support and overall arrangement of CDR loops in the 38E4.v1 Fab by organizing the critical central cleft between heavy and light chains to enable CD3ε peptide binding.

FIG. 14G identifies all residues of the 38E4.v1 Fab that were determined to reside within 5 Å from the CD3ε peptide. These antigen contact residues are identical between hu38E4.v1 and hu40G5c, except that residue G96 of hu38E4.v1 is a serine residue (S96) in hu40G5 (see FIG. 14H, which depicts the location of contact residue G96 of hu38E4.v1).

The contacts between anti-CD3 (38E4.v1) and the CD3$_{εγ}$ peptide were calculated based on alanine scanning. The epitopes recognized by the 38E4v1 anti-CD3 are contacts with a distance of 3.5 Angstroms or shorter, as provided in Table 3B below. From this analysis, the CD3 epitopes Gln1 (PCA1, pyroglutamic acid), Asp2, Glu6, and Met7 were found to be important contact forming residues with the paratopes of the light chain and heavy chain variable regions of the CD3 antibody.

PILATUS detector. The recorded diffractions were then integrated using program XDS and scaled using the program SCALA. The structure was phased by molecular replacement (MR) method using program Phaser. The MR search model was a Fab subunit derived from a crystal structure of HGFA/Fab complex (PDB Code: 2R0L). The CD3ε peptide was build into the structure based on a $F_o$-$F_c$ map. The

TABLE 3B

CD3 contacts for hu38E4.v1/CD3ε Complex

| | Antibody Chain | Residues | Atom name | Atom | CD3 peptide | Residues | Atom name | Atom | Distance |
|---|---|---|---|---|---|---|---|---|---|
| • | /L/ | 96 (ARG) | NH2 | N | /A/ | 1 (PCA) | O | O | 2.76 |
| • | /H/ | 35 (HIS) | NE2 | N | /A/ | 1 (PCA) | OE | O | 2.85* |
| • | /L/ | 96 (ARG) | NH1 | N | /A/ | 1 (PCA) | O | O | 2.9 |
| | /L/ | 96 (ARG) | CZ | C | /A/ | 1 (PCA) | O | O | 3.24 |
| | /H/ | 33 (TYR) | CG | C | /A/ | 1 (PCA) | OE | O | 3.27 |
| | /L/ | 96 (ARG) | NH2 | N | /A/ | 1 (PCA) | OE | O | 3.28 |
| | /H/ | 100 (TYR) | CD1 | C | /A/ | 1 (PCA) | O | O | 3.33 |
| | /H/ | 33 (TYR) | CB | C | /A/ | 1 (PCA) | OE | O | 3.34 |
| | /L/ | 96 (ARG) | NH2 | N | /A/ | 1 (PCA) | CD | C | 3.35 |
| | /H/ | 33 (TYR) | CD2 | C | /A/ | 1 (PCA) | OE | O | 3.44 |
| | /H/ | 50 (TRP) | CH2 | C | /A/ | 1 (PCA) | N | N | 3.45 |
| | /H/ | 33 (TYR) | CD2 | C | /A/ | 1 (PCA) | CD | C | 3.47 |
| | /H/ | 50 (TRP) | CZ3 | C | /A/ | 1 (PCA) | N | N | 3.48 |
| • | /L/ | 94 (LEU) | N | N | /A/ | 2 (ASP) | OD1 | O | 2.71 |
| | /H/ | 50 (TRP) | CH2 | C | /A/ | 2 (ASP) | OD1 | O | 3.23 |
| | /L/ | 92 (PHE) | O | O | /A/ | 2 (ASP) | CB | C | 3.44 |
| | /H/ | 100 (TYR) | CE1 | C | /A/ | 2 (ASP) | O | O | 3.48 |
| • | /L/ | 91 (SER) | O | O | /A/ | 3 (GLY) | N | N | 2.88 |
| • | /L/ | 27 (ASN)d | ND2 | N | /A/ | 3 (GLY) | O | O | 2.96 |
| • | /L/ | 92 (PHE) | O | O | /A/ | 3 (GLY) | N | N | 3.22 |
| | /L/ | 32 (TYR) | OH | O | /A/ | 3 (GLY) | O | O | 3.3 |
| | /L/ | 32 (TYR) | CZ | C | /A/ | 3 (GLY) | O | O | 3.42 |
| | /L/ | 32 (TYR) | CE2 | C | /A/ | 3 (GLY) | O | O | 3.42 |
| | /L/ | 91 (SER) | O | O | /A/ | 3 (GLY) | CA | C | 3.49 |
| • | /L/ | 92 (PHE) | O | O | /A/ | 4 (ASN) | N | N | 2.81 |
| • | /L/ | 27 (ARG)f | NH1 | N | /A/ | 4 (ASN) | O | O | 3.06 |
| | /L/ | 92 (PHE) | O | O | /A/ | 4 (ASN) | CB | C | 3.11 |
| | /L/ | 92 (PHE) | CZ | C | /A/ | 4 (ASN) | OD1 | O | 3.43 |
| • | /L/ | 32 (TYR) | OH | O | /A/ | 6 (GLU) | OE1 | O | 2.58* |
| • | /L/ | 30 (LYS) | NZ | N | /A/ | 6 (GLU) | OE2 | O | 2.74* |
| • | /L/ | 27 (ARG)f | NH1 | N | /A/ | 6 (GLU) | O | O | 2.77 |
| • | /L/ | 27 (ASN)d | ND2 | N | /A/ | 6 (GLU) | O | O | 3.04 |
| | /L/ | 30 (LYS) | NZ | N | /A/ | 6 (GLU) | OE1 | O | 3.2 |
| | /L/ | 30 (LYS) | CD | C | /A/ | 6 (GLU) | OE1 | O | 3.35 |
| | /L/ | 30 (LYS) | NZ | N | /A/ | 6 (GLU) | CD | C | 3.36 |
| | /H/ | 100 (TYR) | CE2 | C | /A/ | 6 (GLU) | OE1 | O | 3.4 |
| | /H/ | 98 (SER) | CA | C | /A/ | 6 (GLU) | OE2 | O | 3.42 |
| | /H/ | 100 (TYR) | OH | O | /A/ | 6 (GLU) | CB | C | 3.44 |
| | /L/ | 32 (TYR) | CZ | C | /A/ | 6 (GLU) | OE1 | O | 3.47 |
| • | /H/ | 97 (TYR) | OH | O | /A/ | 7 (MET) | N | N | 2.87 |
| • | /L/ | 27 (ARG)f | NE | N | /A/ | 7 (MET) | O | O | 2.95 |
| | /H/ | 97 (TYR) | OH | O | /A/ | 7 (MET) | CB | C | 3.49 |
| | /L/ | 27 (ARG)f | CD | C | /A/ | 7 (MET) | O | O | 3.5 |

*Represents hydrogen bonding between two sidechains.
• Represents reliable hydrogen bonding contacts.
The bolded contacts are hydrogen bonds formed between side chains and main chain backbones.

The bolded contacts are hydrogen bonds formed between side chains and main chain backbones.

SP34v52 Fab was dissolved in 0.25 M NaCl, 25 mM MES pH 5.5 at 10 mg/mL. The initial crystallization screening was done with a sparse matrix (PEGII, Qiagen) screen in a sitting drop vapor diffusion format. A crystallization hit was found in a drop with the reservoir containing 0.2M CaCl$_2$), 0.1 M HEPES pH 7.5, and 30% w/v PEG 4000. Optimized crystals grew from a mixture of 2 μL protein and 2 μL of reservoir solution containing 20-23% w/v PEG 3350, 0.1 M HEPES pH 7.2, 0.1 M CaCl$_2$). Hanging drop vapor diffusion method was used and the final crystallization drop was incubated at 18° C.

The diffraction data for SP34v52 Fab were collected at Stanford Synchrotron Light Source beam line 12-2, using a structure was subsequently refined with programs REFMAC5 and PHENIX using the maximum likelihood target functions, anisotropic individual B-factor refinement method, and TLS refinement method, to achieve convergence. The data and refinement statistics are shown in Table 4 below.

TABLE 4

Data Collection and Refinement Statistics for SP34v52

| | |
|---|---|
| Space group | P622 |
| Unit cell | a = b = 146.3 Å, c = 80.1 Å |
| | α = 90° β = 90° γ = 120° |

TABLE 4-continued

Data Collection and Refinement Statistics for SP34v52

| Space group | P622 |
|---|---|
| Resolution | 50.0-2.50 Å |
| Total number of reflections | 18004 (170)[1] |
| Completeness (%) | 100 (100) |
| Redundancy | 19.3 (19.7) |
| I/σ | 24.0 (3.6) |
| Rsym[2] | 0.127 (0.896) |
| Resolution range | 50-2.50 Å |
| Rcryst[3]/Rfree[4] | 0.152/0.185 |
| Non-hydrogen atoms | 3451 |
| Water molecules | 123 |
| Average B, Overall | 29.59 |
| Average B, Protein | 29.81 |
| Average B, Water | 22.47 |
| r.m.s.d. bond lengths | 0.007 Å |
| r.m.s.d. angles | 1.163° |

[1]Values in parentheses for are of the highest resolution shell which is 2.51 Å-2.50 Å.
[2]Rsym = $\Sigma |I_{hi} - I_h|/\Sigma I_{hi}$, where $I_{hi}$ is the scaled intensity of the ith symmetry-related observation of reflection h and $I_h$ is the mean value.
[3]Rcryst = $\Sigma_h |F_{o,h} - F_{c,h}|/\Sigma_h F_{o,h}$, where $F_{o,h}$ and $F_{c,h}$ are the observed and calculated structure factor amplitudes for reflection h.
[4]Value of $R_{free}$ is calculated for 5% randomly chosen reflections not included in the refinement.

In FIGS. 14I-14L, the crystal structures of the hu38E4.v1 and SP34v52 Fabs were compared in the same orientation. When the CD3ε peptide was superimposed on the SP34v52 Fab with the same orientation as in the hu38E4.v1, clear clashes of the peptide with SP34v52 were observed (FIG. 14L). HVR-H2 residues R50 and R52 of SP34v52, which were not present in either hu38E4.v1 or hu40G5c, were found to be important for the binding of CD3 by SP34v52 (FIG. 14L). These data demonstrate that hu38E4.v1 and hu40G5c bind to CD3 in a manner distinct from that of SP34v52.

The crystal structure of the hu38E4.v1 in complex with the N-terminal peptide of $CD3_{\varepsilon\gamma}$ is illustrated in FIGS. 14M and 14N. FIG. 14M provides a zoomed in view of the key intermolecular interactions involved in contacting the sixth residue in $CD3_{\varepsilon\gamma}$. In a zoomed out view, FIG. 14N depicts a space filling model of the Fab/CD3 peptide complex where the fifth residue is completely pointing away from the interaction site. The sixth residue, as shown, is involved in the interactions with the Fab and points into the active site.

Example 2. Generation and Selection of T-Cell Dependent Bispecific (TDB) Antibodies One approach to harness the high cytotoxic potential of T cells in eradicating tumor cells has been the use of T-cell dependent bispecific (TDB) antibodies. Encouraging clinical responses have been reported with molecules such as B cell targeting blinatumomab, the CD19/CD3-bispecific BiTE antibody. However, the therapeutic promise of many reported bispecific antibody modalities has been limited by liabilities including unfavorable pharmacokinetics (PK), toxicity, and/or production issues. Accordingly, we initially generated and characterized anti-CD3 TDB antibodies having varied combinations of anti-CD3 and anti-tumor antigen (e.g., anti-CD20, anti-FcRH5, anti-HER2, anti-LYPD1, anti-LY6E, anti-LY6G6D, anti-PMEL17, anti-CD19, anti-CD22, anti-CD33, anti-CD79A, anti-CD79B, anti-EDAR, anti-GFRA1, anti-MRP4, anti-RET, anti-Steap1, anti-TenB2) arms, produced as full-length antibodies in the knob-into-hole format. Unexpectedly, we found that particular combinations (pairs) of anti-CD3 and anti-tumor antigen arms resulted in TDBs exhibiting favorable activity over other TDBs.

TDB antibodies were produced as full-length antibodies in the knob-into-hole format as human IgG1, as previously described (Atwell et al. *J. Mol. Biol.* 270: 26-35, 1997). Half antibodies were expressed in either *E. coli* or Chinese hamster ovary (CHO) cells, purified by Protein A-affinity chromatography, and the proper half antibody pairs were annealed in vitro as described previously (Spiess et al. *Nat. Biotechnol.* 2013). If TDB antibody production was carried out in CHO cells, the antibody may include an aglycosylation mutation, for example, at residue N297 (e.g., N297G), such that the TDB antibody was an effector-less variant and unable to initiate antibody-dependent cell-mediated cytotoxicity (ADCC). FIG. 15 shows a schematic overview of CD3/CD20 TDB production.

After annealing, the CD3/CD20 TDBs were purified by Hydrophobic Interaction Chromatography (HIC) and characterized by analytical gel filtration, mass spectrometry, and polyacrylamide gel electrophoresis. The purified antibodies ran as a single peak (>99% of the signal) in gel filtration with less than 0.2% aggregates. No homodimers were detected by mass spectrometry. The anti-CD20 arms tested in the generation of CD3/CD20 TDBs included 2H7v16, 2H7v114, 2H7v511, and GA101. The anti-CD3 arms tested in the generation of CD3/CD20 TDBs included UCHT1v1, UCHT1v9, UCHT1vM1, 72H6, 13A3, 30A1, 41D9a, SP34v52, 40G5c, 38E4v1-38E4v9, 21B2, 125A1, and 21A9. CD3/CD20 TDBs were tested for binding to CD3, as well as activity, as assessed by in vitro B cell killing assays and T cell activation assays.

A. Binding Affinity

Binding affinities for the each of the CD3/CD20 TDBs were tested by Biacore or FACS analysis, as described above for the anti-CD3 antibodies. Briefly, for Biacore binding assays, human CD3εγ was immobilized on Biacore Series S CM5 sensor chip using the amine coupling kit from Biacore and CD3/CD20 TDBs or Fab variants thereof were in the flow through. For FACS binding assays, either Bjab cells (for B cell antigens) or Jurkat cells (for CD3 antigen) were incubated with various concentrations of TDB antibodies at 4° C. for 30 minutes, then cells were washed and incubated with $2^{nd}$ antibody (anti-huIgG-PE; BD Bioscience) for another 15 minutes, before cells were washed again and ready for FACS analysis. FIG. 16 shows the results of in vitro FACS binding assays of CD3/CD20 TDBs. The results demonstrate that particular combinations of anti-CD3 antibody arm and anti-tumor antigen arm (e.g., anti-CD20 arm) result in TDB antibodies with more favorable binding properties. FIG. 17 shows the monovalent and bivalent binding affinities for these particular CD3/CD20 TDBs. The particular pairing of 2H7v16 with anti-CD3 arms (e.g., UCHT1v9), for example, resulted in a CD3/CD20 TDB that displayed unexpectedly strong binding to both Bjab and Jurkat cells compared to the other tested CD3/CD20 TDBs having different anti-CD20 arms. The binding affinity of other CD3/CD20 TDBs having a 2H7v16 anti-CD20 arm and various anti-CD3 arms were also tested (see FIGS. 18-24).

B. In Vitro B Cell Killing and T Cell Activation Assays

The generated CD3/CD20 TDBs were also tested for their ability to support B cell killing and the activation of the cytotoxic effect of T cells. In these assays, B tumor cell lines (Bjab) were obtained from ATCC, and PBMCs were isolated from whole blood of healthy donors by Ficoll separation. If needed CD4+T and CD8+ T cells were separated with Miltenyi kits according to manufacturer's instructions. Cells were cultured in RPMI1640 supplemented with 10% FBS (Sigma-Aldrich) at 37° C. in a humidified standard cell culture incubator. For Bjab cell killing assays, 20,000 Bjab cells were incubated with effector cells either as huPBMCs or purified T cells as indicated ratios per assay, in the presence of various concentrations of TDB antibodies for a time period as indicated per assay. For endogenous B cell killing assays, 200,000 huPBMCs were incubated with various concentrations of TDB antibodies for hours indicated per assay. At the end of each assay, live B cells were gated out as PI-CD19+ or PI-CD20+ B cells by FACS, and absolute cell count was obtained with FITC beads added to reaction mix as internal counting control. % of cell killing was calculated based on non-TDB treated controls. Activated T cells were detected by CD69 and CD25 surface expression.

The varied efficacies of the generated TDB antibodies with bispecificity for CD3 and a second biological molecule (in this instance, CD20), underscore the critical and unpredictable contributions of both antibody arms in the generation of an exemplary TDB possessing high efficacy (see FIGS. 25-49).

Example 3. Characterization of Exemplary CD3/CD20 TDBs (CD20 TDBs)

We further characterized two of the exemplary CD3/CD20 TDBs (CD20 TDBs) described above, which showed high efficacy in the in vitro B cell killing and T cell activation assays. The CD20 arm of each TDB antibody was anti-CD20 clone 2H7.v16 (see FIG. 50), while the CD3 arm was clone UCHT1v9 (see, e.g., Zhu et al. Int. J. Cancer. 62: 319-324, 1995) or cyno cross-reactive clone 40G5c (see, e.g., FIG. 51), which shares comparable activities.

Materials and Methods

A. Antibody Production

T-cell dependent bispecific (TDB) antibodies were produced as full-length antibodies in the knob-into-hole format as human IgG1 as previously described (Atwell et al. J. Mol. Biol. 270: 26-35, 1997). Half antibodies were expressed in E. coli and thus aglycosylated, purified by Protein A-affinity chromatography, and the proper half antibody pairs were annealed in vitro as described previously (Spiess et al. Nat. Biotechnol. 2013). After annealing, the antibodies were purified by Hydrophobic Interaction Chromatography (HIC) and characterized by analytical gel filtration, mass spectrometry, and polyacrylamide gel electrophoresis. The purified antibodies ran as a single peak (>99% of the signal) in gel filtration with no detectable aggregates (FIG. 52A), and no homodimers were detected by mass spectrometry (FIG. 52B).

B. In Vitro B Cell Killing and T Cell Activation Assays

B tumor cell lines are obtained from ATCC, and PBMCs were isolated from whole blood of healthy donors by Ficoll separation. CD4+T and CD8+ T cells were separated with Miltenyi kits according to manufacturer's instructions. Cells were cultured in RPMI1640 supplemented with 10% FBS (Sigma-Aldrich). For B cell killing assays, live B cells were gated out as PI-CD19+ B cells by FACS, and absolute cell count was obtained with FITC beads added to reaction mix as internal counting control. Activated T cells were detected by CD69 and CD25 surface expression. Intracellular Granzyme B induction was detected by FACS. Perforin concentration in media is detected by ELISA (eBioscience). All antibodies were purchased from BD Bioscience.

C. In Vivo Efficacy Studies in Murine Models

Humanized NSG and SCID mice were purchased from Jackson Labs. Human CD20 transgenic mice and human CD3 transgenic mice were produced as previously described (Gong et al. J. Immunol. 174: 817-826, 2005 and de la Here et al. J. Exp. Med. 173: 7-17, 1991), and human CD20/CD3 double transgenic mice were produced by crossing the two single transgenic mice. Human lymphoma mouse models were generated by injecting $5\times10^6$ Bjab-luciferase cells alone or mixed with $10\times10^6$ human donor PBMCs in HBSS subcutaneously into the right flanks of 40 female mice. Mice were treated intravenously with vehicle or 0.5 mg/kg CD20 TDB one hour post-inoculation and one week following the initial treatment. Tumors were measured 1-2 times per week, and body weights were measured twice per week up to 7 days following the final treatment. If no weight loss was observed, weights were no longer taken for a given animal. If weight loss was greater than 15% of the total body weight, affected mice were weighed daily, and euthanized (or brought to the attention of the veterinary staff) if weight loss exceeded 20%. Clinical observations were performed twice per week throughout the duration of the study to monitor the health of the animals; any animal with a tumor of a size or condition that may interfere with the health or activity of the animal was euthanized. Otherwise, animals were euthanized 6 months after the initial treatment or if the tumor became ulcerated or its volume exceeded 2500 mm$^3$.

Patient-derived chronic lymphocytic leukemia (CLL) mouse models were generated as previously described (Bagnara et al. Blood. 117: 5463-5472, 2011). Briefly, $5\times10^5$ activated T cells were purified from CLL PBMCs and injected retro-orbitally into NSG mice. Following T cell engraftment, $2\times10^7$ CLL PBMCs were injected retro-orbitally. After 14 days, circulation of transplanted B and T cells was confirmed by FACS analysis. Successfully engrafted animals were subsequently treated 3.5 weeks later with TDB antibodies administered intravenously by tail vein injection. Animals were euthanized 6 or 14 days after treatment. Whole blood was collected by puncture of the retro-orbital sinus using heparinized pipets and immediately transferred into heparinized tubes, while the animals were under anesthesia, or by terminal cardiac puncture, with a heparinized syringe after CO2 euthanasia. Spleens were collected after CO2 euthanasia. For every study, clinical observations were performed twice per week to monitor the health of the animals. Animal body weights were taken at least once a week. PBMCs were isolated after red blood cell lysis, and analyzed by FACS for B cells (muCD45+CD19+) and T cells (muCD90.2+CD4+, or muCD90.2+CD8+). All antibodies used are purchased from either BD Biosciences or eBiosciences.

D. PKPD Study in Cynomolgus Monkeys

All cynomolgus monkey studies were conducted using purpose bred, naïve, cynomolgus monkeys of Chinese origin. For the single dose PKPD study, 3 male cynomolgus monkeys were administered a single slow bolus IV dose of 1 mg/kg of CD20 TDB; for the repeat dose study, 4 cynomolgus monkeys were administered an IV slow bolus dose of 1 mg/kg of CD20 TDB once weekly for a total of 4 dose. Whole blood or tissues was collected at selected time points for B cell and T cell count by FACS. Serum was collected, and stored at −70 C until assayed using an ELISA to determine the amount of test article in each serum sample. Serum concentration-time profiles from each animal were used to estimate pharmacokinetic (PK) parameters using WinNonlin software (Pharsight; Mountain View, Calif.).

High Quality CD20 TDB Produced as a Full Length, Humanized IgG with Conventional Antibody PK Property To explore targeting properties that could affect B-cell targeting TDB potency including antigen identity, size of the extracellular domain, and epitope distance from the membrane, we created over 40 different TDBs targeting epitopes on CD3ε, CD19, CD20, CD22, CD79a, and CD79b. Representative results are shown in FIG. 56I. We found that the most potent TDBs were those that targeted cancer target antigens with small extracellular domains (ECDs) and epitopes close to the target cell membrane. Among the best targets were CD20, CD79a, and CD79b with potencies around 10 ng/ml or 67 pM for killing of normal donor B cells by autologous T cells.

Anti-CD20/CD3 TDB (CD20-TDB) is described here as a proof of concept molecule showcasing the pharmacological activity of these B-cell targeting TDBs. CD20 TDBs were produced as full-length, fully humanized IgGs with natural antibody architecture from bacteria, free of homodimers and aggregates (FIG. 52). The pharmacokinetic (PK) property of CD20 TDB in rats, a non-binding species, resembles that of other human IgG antibodies, with a half-life of about 7 days (FIG. 53).

B Cell Killing with CD20 TDB is T Cell Dependent Via the Granzyme-Perforin Pathway To assess CD20 TDB as a potential therapy for cell proliferative disorders, such as CD20+ B cell malignancies, we first investigated its mechanism of action as a T cell-recruiting bispecific antibody. Distinct from ADCC activity, which is the main mechanism of action for classic monoclonal antibody therapy, CD20 TDB doesn't require the Fc region for its activity. F(ab')2 portion of CD20 TDB retained the same potency as the full-length IgG CD20 TDB in B cell killing (FIG. 54A). CD20 TDB is a conditional agonist, requiring target expression, T cells, and antibody for activity. B cell killing activity of CD20 TDB is T cell-dependent, as no B cell killing was detected with PBMCs depleted of CD3+ T cells (FIG. 54B). Target expression is required for T cell activation, as no CD20 expression results in no activated T cells (FIG. 54C). CD20 TDB is able to activate both CD4+ and CD8+ T cells as measured by the induction of both CD69 and CD25 on T cells (FIG. 54D). Comparable B cell killing can be achieved with either T cells as effectors, while CD8+ T cells appear to be more potent in BJAB cell killing, as CD8+ T cells resulted in higher extent of cell killing than equal number of CD4+ T cells (FIG. 54C). However, Granzyme upregulation is more prevalent within CD8+ T cells (FIG. 54E), as well as higher levels of perforin and Granzymes A and B (not shown) release associated with CD8+ T cells was detected in the media by ELISA (FIG. 54F). Activated T cells are capable of proliferation (FIG. 55). Overall T cell count, however, didn't increase significantly after 24 hours in the presence of CD20 TDB and B cells without cytokine supplement in vitro, likely due to culture conditions. Robust T cell expansion was indeed observed in vivo from efficacy studies with murine models and in cynomolgus monkeys (FIGS. 58A and 67C).

CD20 TDB Potent in Killing B Leukemia/Lymphoma Cells, and in Autologous B Cell Killing In Vitro B cell killing potency of CD20 TDB was also tested with more than a dozen B leukemia/lymphoma cell lines in vitro. To assess the potency of the CD20-TDB, 8 lines were selected that represent cells with a wide range of CD20 expression level (FIG. 56B). The dose-response B cell killing curves are shown with the 8 cell lines, with PBMC isolated from healthy donor as effector cells (FIG. 56A). Significantly, CD20-TDB had no activity against SU-DHL1 cells that are devoid of CD20 expression. The potency of the CD20-TDB was somewhat correlated with the various levels of surface CD20 detected by flow cytometry (56A). Nonetheless, CD20 TDB is potent in killing all 8 lines in a dose-dependent manner, with EC50 ranging from 0.38 to 11 ng/ml for 24 hour assay. The extent of cell killing varies somehow from 60 to 90% with up to 1000 ng/ml TDB in a 24 hour assay (FIG. 56C). In general, complete B cell killing can be achieved with higher antibody concentration or extended assay time. SU-DHL-1 cells are included in the killing assay as a CD20 negative control, where no cell killing is observed demonstrating the requirement for target expression for CD20 TDB activity. Activity of CD20 TDB appears to require very low level of target expression, as Nalm-6 and SC-1 cells shown here all have very low CD20 surface expression (FIG. 56B). Monovalent binding affinity of CD20 TDB for CD20 is weaker than bivalent binding affinity of the parental anti-CD20, with a $K_D$ of 54 nM determined by scatchard. Taken together, the $K_D$ value and CD20 TDB B cell killing potency, receptor occupancy required for CD20 TDB activity is only less than 0.1%. TDBs generated to target different B cell antigens are also effective in mediating B cell killing as shown in FIG. 56D, where TDBs targeting 5 different B cell antigens, including a CD20 TDB (TDB A: 2H7v16/UCHT1v9), killed 75% to 90% of B cells. CD20 TDB can further mediate the killing of additional B lymphoma lines with variable CD20 surface antigen expression (FIG. 56E).

CD20 TDB is also highly potent in autologous B cell killing, tested with human PBMCs isolated from peripheral blood of healthy donors (FIG. 56F). Shown in FIG. 56F are the dose-responsive killing curves for 8 random donors, as well as a summary plot for EC50 and extent of B cell killing (FIG. 56G) with 1000 ng/ml antibody in a 24 hour assay for 30 donors. Out of the 30 samples tested, 57 to 96% of B cells were killed with up to 1000 ng/ml antibody within 24 hours, with EC50 ranging from 0.43 to 135 ng/ml with a median value of less than 3 ng/ml. The extent of B cell killing within 24 hours by CD20 TDB is very comparable or higher than B cell killing by an anti-CD3/anti-CD19 scFv (FIG. 56H).

CD20 TDB is Potent in Depleting B Cells In Vivo in Murine Models

As our tested CD20 TDB does not recognize murine CD20 and CD3 antigens, we took advantage of human CD20 and human CD3 transgenic mice (described above) to produce human CD3/CD20 double transgenic mice for subsequent efficacy studies in vivo. As shown in FIG. 57A, human CD3/CD20 double transgenic mice express $huCD3_\varepsilon$ on the surface of CD4+ and CD8+ T cells in addition to huCD20 on the surface of CD19+ B cells at detectable levels compared to human derived T and B cells. With human CD20 transgenic mice, only rituximab is able to deplete B cells, as CD20 TDB cannot engage murine T cells without human CD3 expression (FIG. 57B). While with human CD3/CD20 double transgenic mice, CD20 TDB is able to engage murine T cells expressing huCD3, and is potent in depleting murine B cells expressing huCD20 (FIG. 57C). CD20 TDB appears to be more potent in depleting B cells in vivo, as fewer B cells are detected in mouse spleens 7 days after a single IV dose of CD20 TDB at 0.5 mg/kg, compared to after a single dose of rituximab at 10 mg/kg. A HER2 TDB, which has the same CD3 arm while with the other arm binds to HER2, was used as an isotype control here, and showed no activity here in cell depletion.

To explore the lowest efficacious dose for CD20 TDB in depleting B cells with human CD3/CD20 double transgenic mice, mice were treated with a single dose of CD20 TDB starting at 0.5 mg/kg down to 0.00005 mg/kg. Then B cell count in blood was monitored on D1 (24 hours after dose), D8, and D15. Decreased B cell count was observed on D1, and B cell depletion was sustained up to D15 following CD20 TDB treatment (FIG. 58A). Consistent with this observation of B cell count in blood, near complete B cell depletion in mouse spleens was achieved at D7 after a single dose of 0.5 mg/kg, while a lower dose of 0.05 mg/kg resulted in spleen B cell depletion partially and approximated an ED50 dose level (FIG. 58B). A time-course study with the double transgenic mice revealed that B cell depletion is near complete in spleens as early as 3 days after single dose treatment at 0.5 mg/kg, without significant sign of B cell recovery until D14 (FIG. 58A). As seen in FIG. 58C, CD20 TDB mediates B cell depletion in the periphery of double transgenic huCD20/huCD3, which is detected in the blood as early as two hours after treatment and maintained for up to seven days post treatment. Furthermore, activated CD8+ and CD4+ T cells are detectable in the blood within two hours of CD20 TDB administration and then decline by two days post-treatment (FIG. 58D).

Figures 59B, 59C, 59D, 59E:
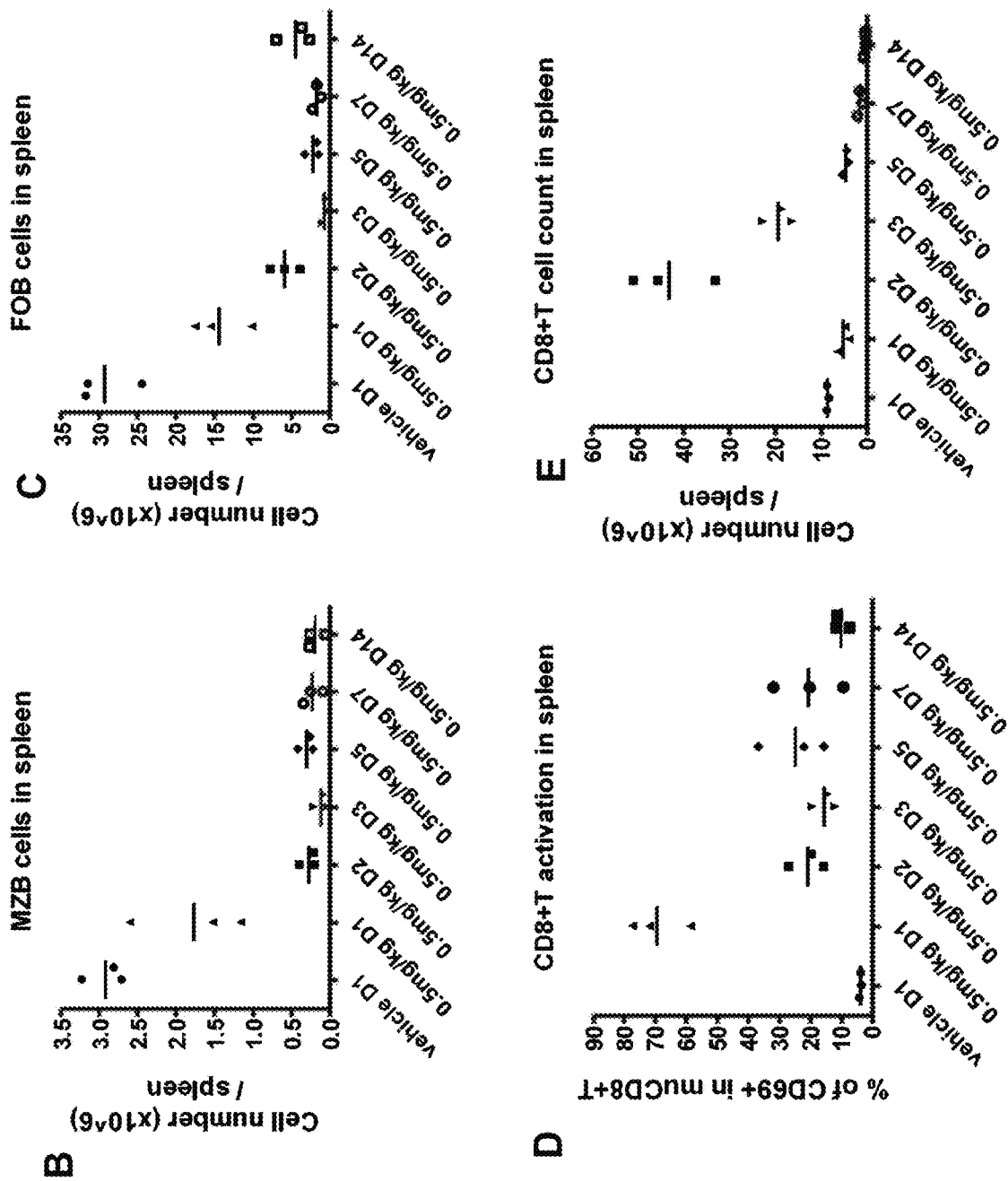

Further, CD20 TDB depleted marginal zone B cells (MZB) (FIG. 59A and FIG. 59B) as efficiently as follicular B cells (FOB) (FIG. 59A and FIG. 59C) in mouse spleens, after a single IV dose of 0.5 mg/kg. We observed that splenic B cells declined ~50% from baseline by day 1 (24 hours post dose) and continued to decline rapidly to reach a nadir on day 3 that was maintained throughout the study. This is apparently different from previous report with rituximab, where microenvironment is thought to play a role in rituximab effectiveness, suggesting different mode of action for CD20 TDB in vivo than that for rituximab. Murine T cell activation is usually observed as soon as 30 minutes after CD20 TDB treatment in blood, and mostly within the first 24 hours in spleen (FIGS. 59D and 59E). Following T cell activation, increase in T cell count was observed around D2-D3 (FIGS. 59D and 59E), as a result of cell proliferation. By day 2 the majority of T cells were no longer CD69-positive, although levels of CD69+CD8+ cells continued to range from 10-30% for the remainder of the two week study. However, possibly due to activation induced cell death, T cell count tends to decrease following the expansion phase. T cell count will recover eventually after TDB treatment, suggesting no inhibitory effect of CD20 TDB treatment in murine T cell regeneration.

Humanized NSG mice were also used to further validate CD20 TDB potency in B cell depletion in murine models, and in a repeat dose setting. The actual mice enrolled in the study shown in FIGS. 60A-60D had 35-80% human CD45+ cells in peripheral blood, and the range of CD4+, CD8+, and CD20+ cells were 12-25, 2.1-8.7, and 32-60% respectively (percentage reported as out of viable leukocyte gate). Representative examples of this baseline characterization are shown in FIG. 60E. Levels of CD3 and CD20 target antigens from these mice were compared to that of normal human donors and were found to be not significantly different (FIG. 60F). Shown in FIG. 59, humanized NSG mice were treated with 3 weekly doses of CD20 TDB at 0.5 mg/kg. B cells were depleted in blood at D7, with almost no B cells detected at D21 (FIG. 60A). Robust B cell depletion was also observed in spleens of the TDB treated mice at D21 (FIG. 60B). Furthermore, treatment of humanized NSG mice with CD20 TDB stimulated T cell proliferation and led to B cell depletion as shown in FIG. 60C. For CD8+ T cells, their cell counts increased up to 10-fold in blood at D7, and returned to baseline or lower at D14 and D21 (FIG. 60D). Similar trend was also observed for CD4+ T cells.

CD20 TDB is Potent in Killing CLL B Cells In Vitro and In Vivo

We also tested CD20 TDB potency in killing B leukemia cells with autologous T cells from CLL patients, where B tumor burden is usually high while T cell count is low and T cell function could be potentially compromised (Riches et al. *Semin. Cancer Biol.* 20(6): 431-438, 2010). PBMCs isolated from peripheral blood of nine CLL patients were incubated with a single high dose of 1000 ng/mL CD20 TDB for up to 48 hours. As shown in FIG. 61A, CD20 TDB is potent in killing CLL B cells with autologous T cells. For the 2 samples shown, B leukemia tumor burden is 70% with 8.4% CD8+ T cells in PBMCs for patient sample #1, and 80% with 4.4% CD8+ T cells for patient sample #2. CD20 TDB apparently can achieve efficient B cell killing with very low effector to target ratios (1:8 and 1:18 with the 2 samples shown here). Killing of CLL B cells with autologous T cells by CD20 TDB is highly correlated with CD8+ T cell count (FIG. 61B). We found T cell content varied significantly (between 0.4 and 8% of mononuclear cells), and strikingly, we observed that the extent of B cell cytolysis compared to pretreatment values was highly correlated to T cell content. By supplementing purified CD8+ T cells to CLL PBMCs, where very few autologous T cells are available, B leukemia cells were efficiently killed by CD20 TDB in a T cell dependent manner (FIG. 61C).

CD20 TDB is also potent in depleting CLL leukemia cells engrafted in mice (FIG. 62A). In brief, NSG mice were grafted with patient leukemia cells subsequent to engraftment of patient-derived autologous activated T cells, and treatment is initiated following confirmed establishment of the leukemic graft. IHC staining of representative examples of mouse spleens showed successful engraftment of B leukemia cells and autologous T cells from CLL patients in NSG mice. After a single dose of CD20-TDB treatment at 0.1 or 0.5 mg/kg, few B cells could be detected. B cell depletion was also observed with rituximab treatment, while no B cell depletion is detected with HER2-TDB as an isotype control. (FIG. 62B).

In the context of tumor progression, CD20 TDB treatment is effective in preventing the growth of B-cell lymphoma tumors in the presence of human donor PBMCs. SCID (severe combined immune deficiency) mice transplanted with human Bjab cells developed detectable tumors when treated with vehicle or CD20 TDB alone by day 12 post-inoculation. Further, transplantation of PBMCs alone delayed tumor outgrowth, but these mice developed detectable tumors by day 25 post-inoculation. Thus, CD20 TDB is also effective in preventing tumor growth in vivo in the presence of PBMC effector cells (FIG. 63).

CD20 TDB Potency Requires Very Low CD20 Expression Level

In addition to the different requirement for antibody Fc region for CD20 TDB activity comparing to conventional anti-CD20, and possibly different dependence on tumor microenvironment, CD20 TDB also appears to require a lower level of antigen expression for efficient B cell killing. For Bjab cells, which have high level of CD20 expression (FIG. 64A), comparable cell killing were accomplished with rituximab and CD20 TDB (FIG. 64B). However, Nalm-6, SC-1, and OCI-Ly19 cells with much reduced level of CD20 expression (FIG. 64A) were only killed by CD20 TDB, while no cell killing was detected with rituximab (FIG. 64C). Estimated CD20 copy number for these CD20-low cell lines is less than 500, based on scatchard and FACS binding data in comparison to BJAB cells (data not shown). In addition, monovalent binding affinity of CD20-TDB for CD20 is ~50-100 nM, significantly less than 1-5 nM affinity of rituximab (both measured by scatchard). Taken together, the potency of CD20-TDB is consistent with the notion that TCR triggering only requires low receptor occupancy of 10-100 molecules (Purbhoo, M. A., et al. *Nat Immunol*

5:524-530, 2004; Irvine, D. J., et al. *Nature* 419:845-849, 2002; Sykulev, Y., et al. *Immunity* 4:565-571, 1996).

CD20 TDB is Active in Presence of Rituximab and Steroid

Since rituximab and its combination with chemotherapy are widely used in treating B cell malignancies in the clinic, it's important to explore how CD20 TDB can be used within this context, as CD20 TDB and rituximab both target the same antigen. We took advantage of rituximab-DANA, an effector-less rituximab variant (rituximab containing substitutions of residues 265 and 297 to alanine (DANA mutations described in U.S. Pat. Nos. 7,332,581 and 8,219,149)), which only binds to CD20 without B cell killing activity, as tested in human CD20/CD3 double transgenic mice (FIG. 64D). Pretreatment of normal donor B-cell target cells with this inert rituximab molecule that competes with CD20-TDB binding had a remarkably minimal effect in blunting the activity of CD20-TDB. At concentrations up to to 250 μg/ml rituximab-DANA (a 5000-fold excess over the 42 ng/ml EC50 dose level), we observed only modest shifts in the dose-response curves in vitro (less than 7-fold shift at the EC50, 42 versus 320 ng/ml). Remarkably, CD20 TDB is still active in this setting. Although the EC50 for CD20-TDB was increased up to ~7-fold with higher rituximab-DANA concentration, the extent of B cell killing is not significantly changed, (FIG. 65A). This is consistent with our previous findings that very low antigen expression level, or very low receptor occupancy, is required for CD20 TDB potency. The in vitro observations were recapitulated in vivo in CD3/CD20 dual transgenic mice which were pretreated with 2 or 10 mg/kg of the rituximab-DANA protein and subsequently challenged with CD20-TDB. Here we show in vivo that CD20 TDB is still active in depleting B cells in mice pre-treated with rituximab-DANA (FIG. 66). These results indicate great versatility in prospective combination therapies for B cell malignancies.

CD20 TDB is a T cell recruiting antibody, and its potency is dependent on activating T cells. It was also explored to see whether steroid pre-treatment, which could potentially impact T cell immune response, would affect CD20 TDB activity. In vitro CD20 TDB was still active in killing B cells in the presence of high concentration of dexamethasone (FIG. 65B).

Pre-Clinical Validation of CD20 TDB as a Potential Therapy for CD20+ B Cell Malignancies in Cynomolgus Monkeys Pilot PKPD study for CD20 TDB was also conducted in cynomolgus monkeys. In a single dose study, where 3 animals were treated once intravenously with 1 mg/kg CD20 TDB, complete B cell depletion were observed in blood (FIG. 67A), as well as in spleens and lymph nodes (FIGS. 67B and 67C), 7 days after antibody treatment. The historic vehicle controls are shown as the mean and standard deviation of 4 vehicle-treated animals (FIG. 67D). No apparent T-cell loss was observed, as both CD8+ T cells and CD4+ T cells were at comparable or higher level to controls, when calculated as % of lymphocytes. T cell activation was detected in blood 4 hours after dosing. No T cell loss was observed, and apparently higher CD8+ T cell count was detected in blood 7 days after treatment (FIG. 67A).

Long-term effect of CD20 TDB treatment on immune cells was also tested with a 4-week repeat dose study followed by an 8-week recovery period. In blood from 4 treated animals with a weekly dose of 1 mg/kg, B and T cell counts, as well as CD20 TDB serum concentration, were measured and plotted for each individual animal over 77 days (FIG. 68A). In all 4 animals, B cells were not detected in blood shortly after treatment, and didn't come back as long as CD20 TDB serum concentration remained above 100 ng/ml (animal 4502 versus animals 4001, 4002, and 4503). CD8+ T cell counts, as well as that of CD4+ T cells to a lesser extent, significantly increased after the first dose, and gradually returned to within 25-150% of baseline values. Taken together, CD20 TDB is highly active in depleting B cells, without compromising T cells.

The PK property of CD20 TDB was also summarized in FIG. 68B, with CD20 TDB serum concentration measured from both studies. As shown for the repeat-dose study, CD20 TDB maintained good exposure throughout, with CL at about 17 ml/day/kg during the first dose (D0-D7). Target mediated clearance appears to be higher during the first dose (D0-D7), as CL value decreased to about 6 ml/day/kg during the fourth dose (D21-28).

Combination of CD20 TDB with PD-L1 Antagonist in a Syngeneic Tumor Model

In vivo efficacy of a CD20 TDB in combination with a PD-L1 antagonist (a murine IgG2a isotype anti-PD-L1 antibody, 25A1, with DANA mutations) in a syngeneic tumor model was also tested. In this study, A20-huCD20 mouse B lymphoma cells which express human CD20 and mouse PD-L1 on their cell surface were utilized for generating a syngeneic tumor model (see, e.g., FIG. 69A). The CD20 TDB used was a murine IgG2a isotype 2H7v16/2C11 TDB produced in knob-in-hole (K&H) format (see, e.g., Atwell et al., J Mol Biol., 270:26-35, 1997), wherein the "knob" arm is anti-CD20 2H7v16 and the "hole" arm is anti-CD3 2C11 (Leo et al., *Proc Natl Acad Sci USA*, 84:1374-8, 1987). The PD-L1 antagonist used was a murine IgG2a isotype anti-PD-L1 antibody with DANA Fc mutations (substitution of residues 265 and 297 to alanine; see, e.g., U.S. Pat. Nos. 7,332,581 and 8,219,149).

On Day −7, 65 Balb/C mice were inoculated subcutaneously into the right unilateral-thoracic area with 2.5 million A20pRK-CD2O-GFP cells in HBSS in a volume of 100 μl (not to exceed 200 μl). The mice were allowed to grow tumors. The mice were then weighed and measured 1-2 times per week until tumors achieved a mean tumor volume of approximately 100-200 mm$^3$ (approximately 7 days after inoculation). The animals were then divided into the following four treatment groups: Group 1: 2.5 million A20/CD20, Vehicle, qwx3, IV, n=9; Group 2: 2.5 million A20/CD20, anti-CD20xCD3 K&H TDB (2H7v16-2C11 murine IgG2), 0.5 mg/kg, qwx3, IV, n=9; Group 3: 2.5 million A20/CD20, aPDL1 (25A1, mIgG2a DANA), 10 mg/kg, tiwx3, IP, n=9; and Group 4: 2.5 million A20/CD20, aPDL1 (25A1, mIgG2a DANA), 10 mg/kg, tiwx3, IP+anti-CD20xCD3 K&H TDB (2H7-2011 murine IgG2), 0.5 mg/kg, qwx3, IV, n=9. Mice not recruited into one of the above treatment groups due to dissimilar tumor volume were euthanized. Treatment began on Day 0, and all antibody dosing was conducted intravenously in a volume of 100 ml as described above.

Tumors were measured 1-2 times per week. Body weights were measured two times per week up to 7 days after the final treatment. If no weight loss was observed, weights were no longer taken. If weight loss was observed to be >15%, affected mice were weighed daily and euthanized if weight loss was greater than or equal to 20%. For the entire study, clinical observations were performed twice per week to monitor the health of the animals, and any animal with a tumor which was of a size or condition that may interfere with the health or activity of the animal was be euthanized.

As depicted in FIG. 69B, the combined treatment of CD20 TDB with anti-PD-L1 antibody (Group 4) exhibited an unexpected and synergistic effect in inhibiting tumor growth when compared to treatment with CD20 TDB, anti-PD-L1 antibody, or vehicle alone.

Combination of CD20 TDB with PD-1 Antagonist in a Syngeneic Tumor Model

Additionally, the in vivo efficacy of a CD20 TDB in combination with a PD-1 antagonist (a murine IgG2 isotype anti-PD1 antibody, 8F11, with DANA mutations) was also tested in the A20/huCD20 syngenic B lymphoma mouse model. In this study, the CD20 TDB used was a murine IgG2a isotype 2H7v16/2011 TDB, and the PD-1 antagonist used was a murine IgG2 isotype anti-PD-1 antibody with DANA Fc mutations.

A20 mouse B lymphoma cells were transfected to express human CD20 and GFP and subsequently single cell sorted for clonal selection and expansion for implantation. Female Balb/c mice (Charles River; Hollister, Calif.) 8-10 weeks old were inoculated subcutaneously in the right unilateral thoracic region with 2.5 million A20.hCD20-GFP cells. When tumors reached a mean tumor volume of 100-200 mm$^3$, mice were recruited and randomized into one of four treatment groups (n=9 mice/group) and antibody treatment started on the following day 1: Group 1 (2.5 million A20/CD20, vehicle, qwx3, IV); Group 2 (2.5 million A20/CD20, anti-CD20xCD3 K&H TDB (2H7v16-2011 murine IgG2), 0.5 mg/kg, qwx3, IV); Group 3 (2.5 million A20/CD20, anti-PD1 (8F11, mIgG2a DANA), 10 mg/kg, tiwx3, IP); and Group 4 (2.5 million A20/CD20, anti-PD1 (8F11, mIgG2a DANA), 10 mg/kg, tiwx3, IP+anti-CD20xCD3 K&H TDB (2H7v16-2011 murine IgG2), 0.5 mg/kg, qwx3, IV).

The mice were treated with vehicle or CD20 TDB at 0.5 mg/kg weekly IV for 3 weeks, and/or anti-PD-1 antibody at 10 mg/kg IV for the first dose, followed by IP dosing 3 times a week for 3 weeks. (N=9 mice/group)

As depicted in FIGS. 108A and 108B, the combined treatment of CD20 TDB with anti-PD-1 antibody (Group 4) exhibited an unexpected and synergistic effect in inhibiting tumor growth when compared to treatment with CD20 TDB, anti-PD-1 antibody, or vehicle alone.

Example 4. Generation and Characterization of Exemplary CD3/FcRH5 TDBs (FcRH5 TDBs)

We also explored the capacity of TDB antibodies to recruit the cytotoxic activities of T cells in eradicating tumor cells by recognition of a different cell surface antigen, FcRH5. To this end, we generated and characterized bispecific anti-CD3 antibodies having an anti-CD3 arm and an anti-FcRH5 arm (FcRH5 TDBs). As described above, the FcRH5 TDBs were produced as full-length antibodies in the knob-into-hole format as human IgG1, as previously described (Atwell et al. *J. Mol. Biol.* 270: 26-35, 1997). Half antibodies were expressed in *E. coli*, purified by Protein A-affinity chromatography, and the proper half antibody pairs were annealed in vitro as described previously (Spiess et al. *Nat. Biotechnol.* 2013). After annealing, the FcRH5 TDBs were purified by Hydrophobic Interaction Chromatography (HIC) and characterized by analytical gel filtration, mass spectrometry, and polyacrylamide gel electrophoresis, as described above. The anti-FcRH5 arm used in the generation of FcRH5 TDBs was that of anti-FcRH5 antibody 1G7, comprising (a) a VH domain comprising an amino acid sequence of SEQ ID NO: 268 and (b) a VL domain comprising an amino acid sequence of SEQ ID NO: 269. The anti-CD3 arms tested in the generation of FcRH5 TDBs included UCHT1v9, 40G5c, and 38E4v1.

The specific FcRH5 TDBs were tested for binding to CD8+ T cells (CD3 binding), as well as activity, as assessed by in vitro cytotoxicity assays and T cell activation assays.

A. Binding Affinity

Binding affinities for the each of the FcRH5 TDBs were tested FACS analysis, as described above for the CD20 TDBs. Briefly, for FACS binding assays, CD8+ T cells were incubated with various concentrations of FcRH5 TDB antibodies at 4° C. for 30 minutes, then cells were washed and incubated with 2$^{nd}$ antibody (anti-huIgG-PE; BD Bioscience) for another 15 minutes, before cells were washed again and ready for FACS analysis. FIG. 70 shows the results of in vitro FACS binding assays of FcRH5 TDBs. The results demonstrate that the particular combination of anti-CD3 antibody arm, 38E4v1, pair with the anti-FcRH5 arm, 1G7, result in an FcRH5 antibody with higher binding affinity for effector cells.

B. In Vitro MOLP-2 Target Cell Killing and T Cell Activation Assays

The generated FcRH5 TDBs were also tested for their ability to support killing of FcRH5-expressing MOLP-2 target cells and the activation of the cytotoxic effect of T cells. In vitro cytotoxicity was monitored by flow cytometery. Target cells were labeled with CFSE according to manufacturer's protocol (Invitrogen, #C34554). The carboxyfluorescein succinimidyl ester (CFSE)-labeled target cells and purified CD8+ T cells from human PBMC were mixed in a 3:1 ratio, with or without TDB for 48 hours. The cells were resuspended in equal volume of PBS+2% FBS+1 mM EDTA+propidium iodine (PI). Flow cytometry analysis was done on a FACSCalibur in automation format. The number of live target cells was counted by gating on CFSE+/PI negative cells. The percentage of cytotoxicity was calculated as follows: % cytotoxicity (live target cell number w/o TDB−live target cell number w/TDB)/(live target cell number w/o TDB)×100. As depicted in FIGS. 71A and 71B, FcRH5 TDBs with UCHT1v9 or 38E4v1 for their anti-CD3 arm showed robust in vitro MOLP-2 target cell killing compared to the FcRH5 TDB having 40G5c as its anti-CD3 arm.

When tested for T cell activation assays, FIGS. 72A-72D show that FcRH5 TDBs with UCHT1v9 or 38E4v1 for their anti-CD3 arm were capable of robustly inducing T cell activity in vitro, compared to the FcRH5 TDB having 40G5c as its anti-CD3 arm. In these assays, target cells and purified CD8+ T cells were mixed in the presence or absence of TDB and T cell activation was analyzed by flow cytometry. At the end of the incubation, cells were stained with CD8-FITC (BD Bioscience, 555634) CD69-PE (BD Bioscience, 555531) and CD107a-Alexa-Fluor647 (eBioscience, 51-1079). Alternatively, after surface stained with CD8-FITC and CD69-PE, cells were fixed and permeabilized with Cytofix/CytoPerm solution (BD Bioscience, 554722) and intracellular stained with anti-granzyme B-Alexa-Fluor647 (BD Bioscience, 560212). The T cell activation was evaluated by the percentage of CD8+CD69+, CD8+CD107a+, and CD8+CD69+GranzymeB+ cells.

Example 5. Generation and Characterization of Exemplary CD3/HER2 TDBs (HER2 TDBs)

We also explored the capacity of TDB antibodies to recruit the cytotoxic activities of T cells in eradicating tumor cells by recognition of a different cell surface antigen, HER2. To this end, we generated and characterized bispecific anti-CD3 antibodies having an anti-CD3 arm and an anti-HER2 arm (HER2 TDBs). As described above, the HER2 TDBs were produced as full-length antibodies in the knob-into-hole format as human IgG1, as previously described (Atwell et al. *J. Mol. Biol.* 270: 26-35, 1997). Half antibodies were expressed in either *E. coli* or Chinese hamster ovary (CHO) cells, purified by Protein A-affinity chromatography, and the proper half antibody pairs were annealed in vitro as described previously (Spiess et al. *Nat. Biotechnol.* 2013). If TDB antibody production was carried out in CHO cells, the antibody included an aglycosylation mutation, for example, at residue N297 (e.g., N297G), such that the TDB antibody was an effector-less variant and unable to initiate antibody-dependent cell-mediated cytotoxicity (ADCC). After annealing, the HER2 TDBs were purified by Hydrophobic Interaction Chromatography (HIC) and characterized by analytical gel filtration, mass spectrometry, and polyacrylamide gel electrophoresis, as described above. One anti-HER2 arm used in the generation of HER2 TDBs was that of anti-HER2 antibody hu4D5, comprising (a) a VH domain comprising an amino acid sequence of SEQ ID NO: 270 and (b) a VL domain comprising an amino acid sequence of SEQ ID NO: 271. Additional HER2 TDBs were generated to target different regions of the extracellular domain (ECD) of HER2. An anti-HER2 antibody, 2C4 was used as an anti-Her2 arm comprising (a) a VH domain comprising an amino acid sequence of SEQ ID NO: 593 and (b) a VL domain comprising an amino acid sequence of SEQ ID NO: 594. Another anti-HER2 antibody used as an anti-HER2 arm was that of anti-HER2 antibody, 7C2 comprising (a) a VH domain comprising an amino acid sequence of SEQ ID NO: 595 and (b) a VL domain comprising an amino acid sequence of SEQ ID NO: 596. Other anti-HER2 arms used in the generation of HER2 TDBs included hu4D5 affinity variants, hu4D5.91A and hu4D5.Y100A (described in U.S. Pat. No. 7,435,797).

The specific HER2 TDBs were tested for binding to CD8+ T cells (CD3 binding) and SKBR3 cells (Her2 binding), as well as activity, as assessed by in vitro cytotoxicity assays and T cell activation assays.

A. Binding Affinity

Binding affinities for each of the HER2 TDBs were tested by FACS analysis, as described above for the CD20 TDBs. Briefly, for FACS binding assays, Jurkat cells (for CD3 antigen), human CD8+ cells (for CD3 antigen), or SKBR3 (for Her2 antigen) were incubated with various concentrations of HER2 TDB antibodies at 4° C. for 30 minutes, then cells were washed and incubated with $2^{nd}$ antibody (anti-huIgG-PE, BD Bioscience; or anti-huIgG-AlexaFluor647, Southern Biotech) for another 15 minutes, before cells were washed again and ready for FACS analysis. The geo mean of fluorescence was read by flow cytometry. FIGS. 73, 76A, 78A-78C, 79A, and 80A-80B show the results of in vitro FACS binding assays of HER2 TDBs. Multiple HER2 arms that bind to different regions of HER2 were tested in combination with multiple CD3 arms that bind to various regions of CD3ε to characterize the binding properties of each combination. FIG. 76A provides the crystal structure of the HER2 ECD and that of $CD3_\varepsilon$ and highlights the regions to which the different HER2 and CD3 arms bind for each. The hu4D5 HER2 antibody is known as trastuzumab and binds to an epitope in domain IV of HER2 that is the protein region closest to the cellular membrane. The recombinant humanized monoclonal antibody 2C4 (rhuMAb 2C4) is also known as pertuzumab that binds to an epitope in domain II of HER2 that is 50 Angstroms from where hu4D5 binds. Pertuzumab (PERJETA®, Genentech, Inc, South San Francisco) represents the first in a new class of agents known as HER dimerization inhibitors (HDI) and functions to inhibit the ability of HER2 to form active heterodimers or homodimers with other HER receptors (such as EGFR/HER1, HER2, HER3 and HER4) (Harari and Yarden. Oncogene 19:6102-6114, 2000; Yarden and Sliwkowski. *Nat. Rev. Mol. Cell Biol.* 2:127-137, 2001; Sliwkowski. *Nat. Struct. Biol.* 10:158-159, 2003; Cho et al. *Nature* 421:756-60, 2003; and Malik et al. *Pro. Am. Soc. Cancer Res.* 44:176-177, 2003). Anti-HER2 murine antibody 7C2 binds to an epitope in domain I of HER2 (PCT Publication No. WO 98/17797) that is 100 Angstroms away from the HER2 region bound by hu4D5 (FIG. 76A).

Additionally, the binding affinity of HER2 TDB was tested with multiple anti-CD3 arms. One of the given anti-HER2 arms was combined with high affinity human CD3 targeting arms such as SP34 and 38E4v1. Other HER2 TDB combinations included the low affinity human CD3 targeting arms 40G5c or the murine CD3 targeting arm of 2C11. UCHT1v9 for its anti-CD3 arm and hu4D5 for its anti-HER2 arm, herein referred to as HER2 TDB (UCHT1v9/hu4D5) or HER2 TDB, was compared to the anti-HER2 antibody, trastuzumab, and the trastuzumab-Fab fragments in a competitive Scatchard assay (Ramirez-Carrozzi et al. *Nature Immunology.* 12: 1159-1166, 2011). In this assay, binding to SKBR-3 was determined by competition binding of $^{125}$I-trastuzumab Fab with trastuzumab, trastuzumab-Fab, or bispecific HER2 TDB. FIG. 74A shows the results of the in vitro competitive Scatchard assay of HER2 TDB.

B. In Vitro SKBR3 and MCF7 Target Cell Killing and T Cell Activation Assays

The HER2 TDB combinations of one of the three anti-HER2 arms (hu4D5, 2C4, and 7C2) with either the high affinity 38E4v1 or low affinity 40G5c anti-CD3 arm were tested in vitro for their ability to mediate target cell killing of HER2-expressing SKBR3 or MCF7 cells (FIG. 77). The in vitro activity the hu4D5 TDBs with either anti-CD3 arm proved to be more effective than the 2C4 and 7C2 TDBs in mediating maximal SKBR3 and MCF7 cell killing as measured by their EC50 (FIG. 78). This killing activity was also dependent on the CD3 arm utilized. The combination of the anti-CD3 arm 38E4v1 with any one of the anti-HER2 hu4D5, 2C4, or 7C2 arms was more efficacious than that of the 40G5c HER2 TDB combinations (FIG. 79). Further testing of the 6 HER2 TDB combinations revealed that their target cell killing activity is not dependent on the level of HER2 expression in target cells. FIG. 80 shows that the HER2 TDBs were not selective for high HER2 expressing SKBR3 target cells over low HER2 expressing MCF7 target cells. The activity of the HER2 TDB was instead dependent on the affinity of the anti-HER2 arm for HER2 (FIG. 81). The low HER2 affinity TDBs retained activity on low HER2-expressing MCF7 cells and were not able to selectively kill HER2 amplified SKBR3 cells (FIG. 82).

The HER2 TDBs were also assayed for the specificity of the anti-HER2 arm for their respective HER2 epitopes. The killing activity of the hu4D5-40G5c HER2-TDB was limited when combined with increasing concentrations of Trastuzumab (hu4D5). However, the efficacy of trastuzumab is not affected by the combination of the hu4D5 TDB with the hu4D5 antibody (FIG. 83). By contrast, target cell killing as mediated by 2C4-40G5c or 7C2 38E4v1 as blocked by co-administration of the bivalent monospecific antibodies pertuzumab (2C4) or 7C2, respectively (FIG. 83). When additional anti-HER2 arms were tested in multiple affinity assays, all clones demonstrating high or medium HER2 TDB activity competed with trastuzumab or pertuzumab (FIG. 84). For identification of candidate TDBs to be assayed in vivo, high (38E4v1, 38E4, and SP34) and low (40G5c and 2C11) affinity CD3 arms were tested in vitro with mouse-derived humanized CD3+ T cells in combination with hu4D5, 2C4, and 7C2 anti-HER2 arms (FIGS. 85-86). From this assay, three candidate TDBs were selected based on their killing activity for further characterization in vivo: hu4D5-SP34, hu4D5-2011, and 204-38E4. The treatment of HER2-expressing tumor-bearing animals with the hu4D5-2011 HER2 TDB resulted in an increase in CD45+ and CD8+ cells in the tumor as early as 4 hours post-treatment. Upon further analysis, HER2-TDB treated tumors revealed an increase in IFNγ+ and PD1+CD8+ T cells as well as an increased presence of T regulatory (Treg) cells (FIG. 87B). The detection of increased immune infiltrates in tumors was also correlated with a decrease in the tumor volume of HER2-TDB treated animals as compared to vehicle control treatment (FIG. 87A). In FIG. 88A, the anti-HER2 arm hu4D5 combined with the low affinity anti-CD3 arm, 2011 or high affinity anti-CD3 arm, SP34, both resulted in tumor regression in transgenic HER2 mice. However, this response was not observed with the lower affinity 2C4 anti-HER2 arm combined with the 38E4 high affinity anti-CD3 arm (FIGS. 88A-88B).

HER2 TDB was also compared to bivalent trastuzumab and trastuzumab-Fab fragments for its ability to directly inhibit SKBR3 proliferation. HER2-expressing SKBR3 target cells were plated in 96-well plates at a density of 5×10$^3$ cells/well and incubated overnight for cell attachment before treatment with the designated antibody or fragment antibody. Cell proliferation/viability was analyzed after 6 days of treatment by CELLTITERGLO® Luminescent Cell Viability Assay (Promega, Madison, Wis.). The results of this assay are shown in FIG. 74B. Additionally, an in vitro cytotoxicity assay was performed with trastuzumab, trastuzumab produced in *E. coli*, and HER2 TDB to measure their ability to induce NK cell-mediated antibody-dependent cell-mediated cytotoxicity (ADCC) (Jefferis *Trends in Pharmacological sciences.* 30: 356-362, 2009; Simmons et al. *Journal of Immunological Methods.* 263: 133-147, 2002). Antibodies produced in *E. coli* are not glycosylated, which results in impaired FcγR binding, which is required to mediate ADCC. The cytotoxicity assay was performed as in Junttila et al. (*Cancer Research.* 70: 4481-4489, 2010) with a Cytotoxicity Detection Kit; LDH (Roche, Mannheim, Germany). Briefly, lysed cells were detected by lactate dehydrogenase (LDH) release following 4 hours of treatment with the specified antibody. The results are shown in FIG. 74C.

The generated HER2 TDBs were also tested for their ability to support killing of HER2-expressing SKBR3 target cells and the activation of the cytotoxic effect of T cells. In vitro cytotoxicity was monitored by flow cytometry. Target cells were labeled with carboxyfluorescein succinimidyl ester (CFSE) according to manufacturer's protocol (Invitrogen, #034554). The CFSE-labeled target cells and purified CD8+ T cells from human PBMC were mixed in certain E:T ratio (as indicated in figure legends), with or without TDB for 24 hours. At the end of the incubation, the cells were lifted by trypsin and collected from the plate. The cells were resuspended in equal volume of PBS+2% FBS+1 mM EDTA+propidium iodine (PI). Flow cytometry analysis was done on a FACSCalibur in automation format. The number of live target cells was counted by gating on CFSE+/PI negative cells. The percentage of cytotoxicity was calculated as follows: % cytotoxicity (live target cell number w/o TDB−live target cell number w/TDB)/(live target cell number w/o TDB)×100. As depicted in FIG. 75, HER2 TDB showed robust in vitro SKBR3 target cell killing compared to the HER2 TDB having either hu4D5 affinity variant 91A or Y100A as its anti-HER2 arm (EC50 of hu4D5/UCHT1v9 TDB=0.1 ng/ml; hu4D5.91A/UCHT1v9 TDB=25.5 ng/ml; hu4D5.Y100A/UCHT1v9 TDB=not able to be determined).

Additionally, the binding affinity of anti-HER2 hu4D5 variant (0.4 nM) to the HER2 extracellular domain (ECD) is higher than the HER2 arms 2C4 (2.0 nM) and 7C2 (1.7 nM), which is shown in FIG. 76B. Furthermore, FIG. 76C shows the hu4D5 HER2-TDB is a more potent mediator of MCF7 target cell killing than the 2C4 HER2-TDB and the 7C2 HER2-TDB. The kinetics of the killing induced by HER2 TDB were additionally assayed. As seen in FIG. 94A, no significant killing activity was detected at 4-12 hours. Robust killing was detected at 24 hours and killing activity increased over time. As shown in FIGS. 90A-90C and 92C, further comparison of anti-CD3 arms of the hu4D5 HER2-TDB demonstrated the effectiveness of the differing clones in mediating the killing of HER2-expressing SKBR3 cells. In particular, two HER2 TDBs, hu4D5/38E4c and hu4D5/40G5c, were surprisingly as effective or better in mediating target cell killing than the HER2 TDB hu4D5/SP34 (FIGS. 90B and 90C).

When tested for T cell activation assays, FIG. 89 shows that HER2 TDB was capable of robustly inducing T cell activity in vitro, compared to the HER2 TDB having either hu4D5 affinity variant 91A or Y100A as its anti-HER2 arm. Three anti-CD3 arms (SP34, 38E4c, and 40G5c) of the hu4D5 HER2-TDB assayed displayed differing binding affinities for the CD3 antigen on human CD8+ T cells, as seen in FIG. 91A. Nonetheless, all three HER2-TDBs were able to mediate CD8+ T-cell activation (FIG. 91B). Additional analysis of the ability of the 38E4 and 38E4c anti-CD3 arms of the hu4D5 HER2-TDB to mediate CD8+ T cell activation is shown in FIG. 92D. The kinetics of the T cell activation induced by HER2 TDB was further assayed. Early signs of T cell activation (CD69) appeared 4h after HER2 TDB treatment was initiated. However, late activation markers (extracellular CD107a) were detected later at the 24 hour time point (FIG. 94A). Additionally, T cell activation was not detected after 48 hours when CD8+ cells were incubated with HER2 TDB or target cells that do not express human HER2 (BJAB cells). A robust T cell activation was seen when HER2+SKBR3 cells were used as targets accompanied by release of cytotoxic granules (FIG. 93A).

We also tested the ability of HER2 TDB to induce killing of BT474 target cells and activate T cells was assayed for the following five ratios of effector CD8+ T cells to target cells: 1:5, 1:2, 1:1, 3:1, and 5:1. This experiment reveals the cytotoxicity measured by LDH release was significantly reduced by effector cell titration; however even with an E:T ratio of ≤1, a weak LDH signal and robust activation of T cells was detected (FIG. 94B).

In these assays, target cells and purified CD8+ T cells were mixed in the presence or absence of TDB and T cell activation was analyzed by flow cytometry. At the end of the incubation, cells were stained with CD8-FITC (BD Bioscience, 555634) CD69-PE (BD Bioscience, 555531) and CD107a-Alexa-Fluor647 (eBioscience, 51-1079). Optionally, cells were stained with CD8-FITC and CD69-PE, where T cell activation was evaluated by the percentage of CD8+CD69+ in CD8+ cells. Alternatively, after surface stained with CD8-FITC and CD69-PE, cells were fixed and permeabilized with Cytofix/CytoPerm solution (BD Bioscience, 554722) and intracellular stained with anti-granzyme B-Alexa-Fluor647 (BD Bioscience, 560212). The T cell activation was evaluated by the percentage of CD8+ CD107a+ cells.

Another measure for T cell-mediated cytotoxicity for HER2 TDB (UCHT1v9/hu4D5) measured is a granule exocytosis assay. FIG. 93B shows the results for soluble perforin (Cell Sciences), granzyme A and granzyme B (eBioscience) detected from growth media by ELISA according to manufacturer's protocols. In this assay, a control TDB (10 ng/ml), one that shares the same CD3-arm as HER2 TDB but has an irrelevant target arm, or HER2 TDB (10 ng/ml) was utilized. The antibodies were individually incubated for 18 hours with SKBR3 target cells and effector peripheral blood mononuclear cells (PBMCs), which were separated from the blood of healthy volunteers using lymphocyte separation medium (MP Biomedicals, Solon, Ohio). In vitro cytotoxicity was measured by LDH release as described above. A series of apoptotic assays were performed with HER2 TDB (1 ng/ml), effector PBMCs, and SKBR3 target cells. After 24 hours of treatment, granule exocytosis coincided with significant HER2 TDB induced elevation of caspase 3/7 activity (CASPASE-GLO® 3/7 assay, Promega), apoptosis (Cell Death Detection ELISA$^{plus}$ assay, Roche) and cytotoxicity as measured by lactate dehydrogenase (LDH) release, which is described above (FIG. 93C).

The ability of HER2 TDB to induce killing of HER2 or vector-transfected 3T3 cells was measured by the aforementioned LDH cytotoxicity assay, where no killing of vector-transfected 3T3-cells was detected after 19 hours; in contrast, the HER2 transfected 3T3-cells were very efficiently killed (FIG. 93D). The killing assay was modified to block the HER2 arm binding using trastuzumab Fab (1 μg/ml) or soluble HER2 extracellular domain (HER2 ECD) (1 μg/ml) and resulted in the efficient inhibition of the killing activity after 24 hours (FIG. 93E). To confirm T cell dependence of killing, CD3+ cells were depleted from the PBMC using CD3+MicroBeads from Miltenyi (#130-050-101). FIG. 93F shows the depletion resulted in loss of target cell killing activity after 19 hours as assessed by FACS analysis in the presence of HER2 TDB.

HER2 TDB Induces T Cell Proliferation

To investigate whether HER2 TDB induces T cell proliferation, CD8+ T cells, target cells (SKBR3) and 0.1 μg/ml HER2 TDB were co-cultured, followed by T cell culture in absence of target cells and HER2 TDB. Proliferation of T cells was measured at day 3 by flow cytometry as a dilution of CFSE in CD8+/PI-cells with cell divisions. After 3 days, 75% of the T cells pulsed with HER2 TDB and target cells had undergone a cell division as shown in FIG. 95A. HER2 TDB induced T cell number was assayed for by labeling purified CD8+ T cells with CFSE according to the manufacturer's protocol (Invitrogen, #C34554). CFSE-labeled CD8+ T cells were incubated with target cells in the presence or absence of TDB for 19 hours. T cells were collected, washed, and cultured for 2-7 days (RPMI+10% FBS). Live CD8+ cell number (CD8+/PI-) and the percentage of CFSE dim cells was detected by FACS. In FIG. 95B, the cell number did not increase. Further supplementing the growth media with IL-2 (20 ng/ml) provided a survival signal to CD8+ cells, and a robust T cell proliferation was detected in the T cells, but only if they were exposed to both HER2 TDB and target cells (FIG. 95C). Importantly, no bystander effect on non-target expressing cells was detected in conditions where most HER2+ cells in the same culture were killed. HER2 TDB induced proliferation and polyclonal expansion of T cells, which may be critical for amplification of tumor-infiltrating lymphocytes.

HER2 TDB Activity Correlates with the Target Cell HER2 Expression Level

To investigate the relationship between target copy number and TDB activity, a panel of cancer cell lines with pre-determined number of HER2-receptors on the cell membrane was selected (Aguilar et al. *Oncogene*. 18:6050-62, 1999). HER2 protein expression levels in a HER2 negative cell line (BJAB LUC), 3 HER2 low cell lines (MDA435, MDA231, MCF7), and 3 HER2 amplified/overexpressing cell lines (MD453, SKBR3, BT474) were detected by Western blot (FIG. 96A). HER2-negative, HER2-low, and HER2-overexpressing cell lines were incubated with HER2 TDB and with effector PBMCs at a ratio of E:T 25:1 for 26 hours. At this timepoint, cytotoxicity was detected using the LDH release assay. FIG. 96B shows the HER2 amplified/overexpressing cells were significantly more sensitive to the TDB mediated killing (p=0.015, t-test) and were efficiently lysed at femtomolar to low picomolar concentrations (EC50=0.8-3 pM). Cell lines expressing low levels of HER2 were significantly less sensitive to HER2 TDB antibody (EC50=33-51 pM). As low as <1000 copies of target antigen was sufficient to support T cell killing.

For the studies performed in FIGS. 96C-96D, the MCF7 cell line or the BJAB cell line was co-targeted with SKBR3 cells in the presence of HER2 TDB in the same killing assay. In this assay, MCF7 or BJAB cells were labeled with CFSE and mixed with SKBR3 and PBMC (E:T 20:1) followed by 19 hours treatment with HER2 TDB. Cells were stained with anti-HER2 APC and PI. FIG. 96C shows the percentage of living SKBR3 (HER2 high, PI–) and MCF7 (CFSE+. PI–) cells detected by FACS and normalized to fluorescent beads. No killing of MCF7 cells was detectable at the EC50 for SKBR3 killing. The percentage of living SKBR3 (HER2 high, PI–) and BJAB (CFSE+PI–) cells detected by FACS and normalized to fluorescent beads is shown. No significant killing of BJAB cells was detectable at any HER2 TDB concentration (FIG. 96D).

Very Low Target Occupancy is Sufficient for TDB Activity

Next, the HER2 occupancy at EC50 for HER2 TDB was calculated using formula $[D]/[D]+K_D$ (where the D=drug and $K_D$ for HER2 TDB was 5.4 nM). HER2 copy number was previously reported (Aguilar et al. Oncogene. 18: 6050-6062, 1999). EC50 values were calculated from dose response data in FIG. 97B. FIG. 96E shows that in all tested cell lines less than 1% target occupancy was sufficient for efficient killing. In the case of the high HER2 expressing cell lines, the required occupancy was even lower (0.01-0.05%). The calculated absolute number of HER2 TDB bound to HER2 at the EC50 was as low as 10-150 in the low expressing cell lines. These results showcase the extreme potency of HER2 TDB and are consistent with studies of TCR triggering, which suggest as few as 1-25 TCRs need to be engaged to trigger T cell responses (Irvine et al. *Nature*. 419: 845-849, 2002; Purbhoo et al. *Nature Immunology*. 5: 524-530, 2004; Sykulev et al. *Immunity*. 4: 565-571, 1996). The potency of HER2 TDB was consistently in the low picomolar to femtomolar range. Furthermore, as few as 10-500 HER2-bound TDBs were sufficient to induce significant in vitro cytotoxicity. As few as ~1000 copies of HER2 on the plasma membrane were sufficient to induce killing. These studies also demonstrated a correlation between target expression levels and in vitro sensitivity to HER2 TDB.

HER2 TDB is Efficient in Killing of HER2+ Cancer Cells Refractory to Anti-HER2 Therapies Next, cell lines that have previously been shown to express high levels of HER2 but are insensitive to the direct cellular effects of trastuzumab and lapatinib in vitro were examined (Junttila et al., *Cancer Cell*, 15:429-40, 2009; Junttila et al. *Breast Cancer Res Treat*, 2010). For some cell lines, activation of the PI3K pathway due to acquired activating mutations in the PI3K catalytic subunit (KPL4, HCC202) or by PTEN loss (HCC1596) may cause resistance. A panel of six cell lines (5 breast, 1 lung) was assayed for LDH release as a measure of cytotoxicity in the presence of effector PBMCs at a ratio of 10:1 and HER2 TDB for 19 hours. The EC50 for HER2 TDB mediated killing was in the femtomolar or low picomolar range (FIG. 97A). Parental and T-DM1 resistant BT474-M1 clones were treated with T-DM1 for 3 days. At this timepoint, cell viability was measured using CELLTITERGLO® (FIG. 97B). Sensitivity of the cell lines to T-DM1 has been previously reported (Junttila et al. *Breast Cancer Res Treat.* 2010; Lewis Phillips et al. *Cancer Research.* 68: 9280-9290, 2008). By comparison, parental and T-DM1 resistant BT474-M1 clones were treated with HER2 TDB in the presence of effectors CD8+ T cells at a ratio of 3:1 for 24 hours. Cytotoxicity was detected using FACS assay (FIG. 97C). In addition, HER2 TDB was effective in killing HER2+ lung cancer cells. Using two independent cell line models KPL4 and BT474, (FIG. 97B-97C), acquired resistance to T-DM1 did not affect the sensitivity to HER2 TDB.

Recruitment of T cell killing activity with HER2 TDB is dependent on HER2 expression, but independent of HER2 signaling pathway, which suggests that HER2 TDB may be efficient in treatment of tumors that are refractory to current anti-HER2 therapies. In accordance, data demonstrated equal activity in treatment of multiple trastuzumab/lapatinib resistant cell lines compared to sensitive cells. Resistance in these cells is generated by various mechanisms affecting HER2 pathway. Data presented here suggest that switching to alternative mechanism of action by using HER2 TDB may broadly enable overcoming resistance to antibody-drug conjugates (e.g., T-DM1), targeted small molecule inhibitors (e.g., lapatinib) and therapeutic monoclonal antibodies that block the pathway signaling (e.g., trastuzumab).

Pharmacokinetics of HER2 TDB in Rat

To assess the pharmacokinetic (PK) profile of HER2 TDB, Sprague-Dawley rats were utilized. Animals were separated into the following two groups: Group 1: HER2 TDB (10 mg/kg, single IV, n=4); Group 2: trastuzumab (10 mg/kg, single IV, n=4). Samples were taken from 4 rats per group at time points through 35 days post dose. Approximately 0.2 ml of whole blood was collected via the jugular vein (under $CO_2/O_2$ anesthesia). The samples were allowed to clot and centrifuged under refrigeration (5° C. for 10 minutes at 2000×g) to obtain serum. Serum samples were assayed for human IgG by ELISA, where Donkey anti-huFc coated to microtiter plate was used to capture the humanized anti HER2 antibodies in circulation and goat anti-huFc-HRP (mouse adsorbed) for detection. PK parameters were determined with a 2-compartment method (Model 7) using WIN-NONLIN®, version 5.2.1 (Pharsight Corp., Mountain View, Calif.). HER2 TDB does not cross react with rat CD3 or rat HER2 and displayed a biphasic disposition typical of an IgG1 with a short distribution phase and slow elimination phase (FIG. 98). Both the clearance and half-life of HER2 TDB were similar to trastuzumab, and within expected range of a typical IgG1 in rats.

HER2 TDB Inhibits Tumor Growth In Vivo in Immuno-Compromised Mice

In vivo efficacy of HER2 TDB was tested in NOD-SCID mice, which lack endogenous functional T and B cells and have reduced levels of NK, DC, and macrophage cell types. In this experiment, NOD/SCID mice (NOD.CB17-Prkdcscid/J, Jackson Labs West) were implanted with 0.36 mg, 60 day sustained release estrogen pellets (Innovative Research of America) 1 to 3 days prior to cell inoculation, subcutaneously over the opposite flank of tumor inoculation. On Day 0, $5\times10^6$ MCF7-neo/HER2 cells were injected either alone or together with $10\times10^6$ unstimulated human PBMC from one of two healthy donors (PBMC 1, 2) in HBSS-matrigel in the right 2/3 mammary fat-pad. Inoculated mice were divided into the following five groups: Group 1: Vehicle (control TDB, 0.5 mg/kg, qwk×3, IV, starting on day 0, n=5-10); Group 2: PBMC(1) (PBMC (1)+control TDB, 0.5 mg/kg, qwk×3, IV, starting on day 0, n=5-10); Group 3: PBMC (1)+HER2 TDB (PBMC (1)+ HER2 TDB, 0.5 mg/kg, qwk×3, IV, starting on day 0, n=5-10); Group 4: PBMC(2) (PBMC (2)+control TDB, 0.5 mg/kg, qwk×3, IV, starting on day 0, n=5-10); and Group 5: PBMC (2)+HER2 TDB (PBMC (2)+HER2 TDB, 0.5 mg/kg, qwk×3, IV, starting on day 0, n=5-10). The first treatments were administered 2 hours post-inoculation. Tumor volumes from individual mice and fitted tumor volumes of treatment groups are presented in FIG. 99A, where HER2 TDB prevented growth of HER2 expressing tumors.

The dependency of HER2 TDB on human PBMCs was further tested in a similar immune-compromised mouse model. Again, $5\times10^6$ MCF7-neo/HER2 cells were injected either alone or together with $10\times10^6$ unstimulated human PBMC from a healthy donor (PBMC 3) in HBSS-matrigel in the right 2/3 mammary fat-pad, and the first treatments were administered 2 hours post-inoculation. In FIG. 100A, inoculated mice were divided into the following two groups: Group 1: Untreated (n=7); Group 2: HER2 TDB (HER2 TDB, 0.5 mg/kg, qwk×3, IV, starting on day 0, n=7). In FIG. 100B, inoculated mice were divided into the following three groups: Group 1: Untreated (n=7); Group 2: PBMC(3) (PBMC (3)+ vehicle, 0.5 mg/kg, qwk×3, IV, starting on day 0, n=7); Group 3: PBMC(3)+control TDB (PBMC(3)+control TDB-2C11, 0.5 mg/kg, qwk×3, IV, starting on day 0, n=7). The resulting tumor volume measurements reveal no effect on the tumor growth in control TDB-treated animals.

HER2 TDB Causes Regression of Large Mammary Tumors in huHER2 Transgenic Mice

To model the activity of HER2 TDB in immuno-competent mice, human MMTV-huHER2 transgenic mice were used (Finkle et al. *Clinical Cancer Research.* 10: 2499-2511; 2004), and a surrogate HER2 TDB comprising a murine IgG2A CD3 reactive antibody clone 2C11 (Leo et al. *Proc Natl Acad Sci USA.* 84: 1374-1378, 1987) was generated to avoid immune response towards the TDB. For expression as muIgG2a, equivalent knob-into-hole mutations (Atwell et al. *J Mol Biol.* 270: 26-35, 1997) were introduced into the Fc region, as well as D265A and N297G (EU numbering) to abolish effector function. In muIgG2a HER2 TDBs the "knob" arm is murine anti-HER2 hu4D5 and the "hole" is either chimeric anti-murine CD3 2C11 (Leo et al. *Proc Natl Acad Sci USA.* 84: 1374-1378, 1987) (TDB 2C11/hu4D5) or mouse anti-hu CD3 SP34 (Pessano et al. *The EMBO Journal.* 4: 337-344, 1985) (TDB SP34/hu4D5). The muIgG2a bispecific antibodies were expressed in CHO cells and assembled by in vitro assembly. Bispecific antibodies were purified from contaminants by hydrophobic interaction chromatography (HIC) as described elsewhere (Speiss et al. *Nat Biotechnology.* 31: 753-758, 2013). The resulting material was analyzed for endotoxin levels using an ENDOS-AFE® portable test system (Charles River, USA) and when needed, the endotoxin content was reduced by washing the protein with 0.1% TRITON™ X-114. The in vitro activity of hu4D5/2C11-TDB was similar to human CD3 reactive HER2 TDB (FIG. 101).

In FIGS. 99B-99D, MMTV-huHER2 transgenic animals with established mammary tumors were divided into the following two groups: Group 1: Vehicle (0.5 mg/kg, qwk×5, IV, starting on day 0, n=7); and Group 2: HER2 TDB (HER2 TDB (2C11/hu4D5), 0.5 mg/kg, qwk×5, IV, starting on day 0, n=7). FIG. 99B shows regression was detected in 57% mice and 43% mice had no detectable tumor following treatment. FIG. 99C shows HER2 TDB (2C11/hu4D5) resulted in more than 50% tumor regression, with the exception of one tumor. Responders included tumors that were >1000 mm$^3$ at the start of the treatment as observed in FIG. 99D. In a similar experiment two control TDBs were utilized where one is a CD3-arm control TDB, one with the murine specific CD3 arm switched to the human specific CD3 arm (HER2 TDB (SP34/hu4D5)), and one is a control TDB, one that shares the same CD3-arm as HER2 TDB (2C11/hu4D5) but has an irrelevant target arm (CTRL TDB-2C11). In FIG. 99E, MMTV-huHER2 transgenic animals with established mammary tumors were divided into the following two groups: Group 1: CD3-arm control TDB (HER2 TDB (SP34/hu4D5), 0.5 mg/kg, qwk×5, IV, starting on day 0, n=5); and Group 2: control TDB (control TDB-2C11, 0.5 mg/kg, qwk×5, IV, starting on day 0, n=5). The growth of MMTV-huHER2 transgenic tumors was not affected by control TDBs.

The HER2 TDB was further tested for in vivo efficacy in huCD3 transgenic mice. Human CD3ε transgenic mice have been previously described ((huCD3 transgenic), de la Hera et al. *J Exp Med.* 173: 7-17, 1991). In this study, 0.1 million CT26-HER2 cells were injected subcutaneously into huCD3 transgenic mice. Once the CT26-HER2 tumors were established, animals were divided into the following two groups: Group 1: Vehicle (0.5 mg/kg, qwk×3, IV, starting on day 0, n=7); Group 2: HER2 TDB (HER2 TDB (SP34/hu4D5), 0.5 mg/kg, qwk×3, IV, starting on day 0, n=7). HER2 TDB inhibited the growth of established tumors, but the effect was transient and no complete responses were seen (FIG. 99F). The study demonstrated the potent in vivo activity of HER2 TDB, including dramatic responses in MMTV-huHER2 transgenic mice.

In a similar experiment, in vivo efficacy of the mouse reactive HER2 TDB (2C11/hu4D5) was tested in Balb/c mice. Again, syngeneic tumors were established in Balb/c mice by injecting 1×10$^5$ CT26-HER2 cells subcutaneously. Tumor-bearing animals were divided into one of the following four groups: Group 1: Vehicle (0.5 mg/kg, qwk×3, IV, starting on day 0, n=10); Group 2: HER2 TDB (HER2 TDB (2C11/hu4D5), 0.5 mg/kg, qwk×3, IV, starting on day 0, n=10); Group 3: control TDB (CTRL TDB (2C11/hu4D5), 0.5 mg/kg, qwk×3, IV, starting on day 0, n=10); and Group 4: TDM-1 (TDM-1, 15 mg/kg, qwk×3, IV, starting on day 0, n=10). FIG. 99G shows that despite incomplete responses, HER2 TDB significantly prolonged the time to tumor progression (Log-Rank p-value <0.0001). By contrast, the control TDB with an irrelevant tumor arm had no effect on tumor growth. In addition, the tumors were insensitive to TDM-1.

HER2 TDB Inhibits Growth of Established Tumors in Immuno-Competent Mice

Human CD3ε transgenic mice (de la Hera et al. *J Exp Med.* 173: 7-17, 1991) were used to model the activity of HER2 TDB in immuno-competent mice. In this experiment, huCD3 transgenic T cells were extracted from spleens of huCD3 transgenic and BALB/c mice or from the peripheral blood of healthy human donors. Cells were stained with mouse or human CD8 and either human CD3 (clone UCHT1) in FIG. 101A or mouse CD3 (clone 2C11) in FIG. 101B. CD8+ cells were detected by flow cytometry. FIG. 101A shows huCD3 transgenic T cells express human CD3 at approximately 50% of the level of human T cells, and FIG. 101B shows huCD3 transgenic T cells express murine CD3 at approximately 50% of the level of BALB/c mice.

Next, huCD3 transgenic T cells were assayed for their ability to kill human HER2 expressing CT26 target cells in vitro. In this study, T cells were extracted from spleens of huCD3 transgenic mice, BALB/c mice or from peripheral blood from healthy human donors. In vitro killing activity of CT26-HER2 cells was tested using human CD3-specific HER2 TDB (UCHT1v9/hu4D5) in FIG. 102A or mouse CD3-specific HER2 TDB (2C11/hu4D5) in FIG. 102B. Effector T cells were added at a ratio of 20:1 to target cells in the presence of the designated HER2 TDB for 40 hours. In vitro cytotoxicity was monitored by flow cytometry. Although killing activity of mouse splenic T cells (EC50=2.4 ng/ml) was consistently lower compared to human peripheral T cells (EC50=0.4 ng/ml), huCD3 transgenic T cells killed human HER2 expressing target cells in vitro as seen in FIG. 102A. The mouse specific HER2 TDB (2C11/hu4D5) induced target cell killing by T cells from both huCD3 transgenic (EC50=11 ng/ml) and BALB/c (EC50=10 ng/ml) mice as seen in FIG. 102B.

The T cell dependency of the anti-tumor activity of HER2 TDB was further assayed in a syngeneic tumor model. As described above, 1×10$^5$ CT26-HER2 cells were injected subcutaneously into BALB/c mice. Mice with established tumors were divided into one of following two groups: Group 1: Vehicle (n=10); Group 2: HER2 TDB (SP34/hu4D5) (HER2 TDB (SP34/hu4D5), 0.5 mg/kg, qwx3, IV, n=10). FIG. 103 shows the activity of HER2 TDB was dependent on T cells, since HER2 TDB had no effect in non-huCD3 transgenic mice. This study demonstrated huCD3 transgenic mice can be used as a novel efficacy model for the huCD3 targeting molecules.

Example 6. Generation and Characterization of Exemplary CD3/LYPD1 TDBs (LYPD1 TDBs)

We also explored the capacity of TDB antibodies to recruit the cytotoxic activities of T cells in eradicating tumor cells by recognition of a different cell surface antigen, LYPD1. To this end, we generated and characterized bispecific anti-CD3 antibodies having an anti-CD3 arm and an anti-LYPD1 arm (LYPD1 TDBs). As described above, the LYPD1 TDBs were produced as full-length antibodies in the knob-into-hole format as human IgG1, as previously described (Atwell et al. *J. Mol. Biol.* 270: 26-35, 1997). Half antibodies were expressed in either *E. coli* or Chinese hamster ovary (CHO) cells, purified by Protein A-affinity chromatography, and the proper half antibody pairs were annealed in vitro as described previously (Spiess et al. *Nat. Biotechnol.* 2013). If TDB antibody production was carried out in CHO cells, the antibody included an aglycosylation mutation, for example, at residue N297 (e.g., N297G), such that the TDB antibody was an effector-less variant and unable to initiate antibody-dependent cell-mediated cytotoxicity (ADCC). After annealing, the LYPD1 TDBs were purified by Hydrophobic Interaction Chromatography (HIC) and characterized by analytical gel filtration, mass spectrometry, and polyacrylamide gel electrophoresis, as described above. The anti-LYPD1 arm used in the generation of LYPD1 TDBs was that of anti-LYPD1 antibody YWO.49.H6, comprising (a) a VH domain comprising an amino acid sequence of SEQ ID NO: 272 and (b) a VL domain comprising an amino acid sequence of SEQ ID NO: 273. The anti-CD3 arms tested in the generation of LYPD1 TDBs included UCHT1v9, 40G5, SP34, and 38E4v1.

The specific HER2 TDBs were tested for binding to CD8+ T cells (CD3 binding), as well as activity, as assessed by in vitro cytotoxicity assays and T cell activation assays.

A. Binding Affinity

Binding affinities for the each of the LYPD1 TDBs were tested FACS analysis, as described above for the CD20 TDBs. Briefly, for FACS binding assays, CD8+ T cells were incubated with various concentrations of LYPD1 TDB antibodies at 4° C. for 30 minutes, then cells were washed and incubated with 2$^{nd}$ antibody (anti-huIgG-PE; BD Bioscience) for another 15 minutes, before cells were washed again and ready for FACS analysis. FIG. 104 shows the results of in vitro FACS binding assays of LYPD1 TDBs. The binding studies showed that LYPD1 TDBs having either UCHT1v9 or 38E4v1 as their anti-CD3 arm demonstrated a higher binding affinity for result effector cells.

B. In Vitro OVCAR3.Luc Target Cell Killing and T Cell Activation Assays

The generated LYPD1 TDBs were also tested for their ability to support killing of LYPD1-expressing OVCAR3.Luc target cells and the activation of the cytotoxic effect of T cells. In vitro cytotoxicity was monitored by flow cytometry. Target cells were labeled with CFSE according to manufacturer's protocol (Invitrogen, #034554). The carboxyfluorescein succinimidyl ester (CFSE)-labeled target cells and purified CD8+ T cells from human PBMC were mixed in a 3:1 ratio, with or without TDB for 48 hours. The cells were resuspended in equal volume of PBS+2% FBS+1 mM EDTA+propidium iodine (PI). Flow cytometry analysis was done on a FACSCalibur in automation format. The number of live target cells was counted by gating on CFSE+/PI negative cells. The percentage of cytotoxicity was calculated as follows: % cytotoxicity (live target cell number w/o TDB–live target cell number w/TDB)/(live target cell number w/o TDB)×100. As depicted in FIG. 105, LYPD1 TDBs with UCHT1v9, 38E4v1, or SP34 for their anti-CD3 arm showed robust in vitro OVCAR3.Luc target cell killing compared to the LYPD1 TDB having 40G5 as its anti-CD3 arm.

When tested for T cell activation assays, FIG. 106 shows that LYPD1 TDBs with 38E4v1, and, to a lesser extent, UCHT1v9 and SP34, for their anti-CD3 arm were capable of robustly inducing T cell activity in vitro, compared to the LYPD1 TDB having 40G5c as its anti-CD3 arm. In these assays, target cells and purified CD8+ T cells were mixed in the presence or absence of TDB and T cell activation was analyzed by flow cytometry. At the end of the incubation, cells were stained with CD8-FITC (BD Bioscience, 555634) CD69-PE (BD Bioscience, 555531) and CD107a-Alexa-Fluor647 (eBioscience, 51-1079). Alternatively, after surface stained with CD8-FITC and CD69-PE, cells were fixed and permeabilized with Cytofix/CytoPerm solution (BD Bioscience, 554722) and intracellular stained with anti-granzyme B-Alexa-Fluor647 (BD Bioscience, 560212). The T cell activation was evaluated by the percentage of CD8+ CD69+ and CD8+CD25+ cells.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. One or more isolated nucleic acids encoding a bispecific antibody that binds to CD20 and CD3, wherein the bispecific antibody comprises:
   (a) an anti-CD20 arm comprising a first binding domain, the first binding domain comprising:
      a hypervariable region (HVR)-H1 comprising the amino acid sequence of SEQ ID NO: 157,
      an HVR-H2 comprising the amino acid sequence of SEQ ID NO: 158,
      an HVR-H3 comprising the amino acid sequence of SEQ ID NO: 159,
      an HVR-L1 comprising the amino acid sequence of SEQ ID NO: 160,
      an HVR-L2 comprising the amino acid sequence of SEQ ID NO: 161, and
      an HVR-L3 comprising the amino acid sequence of SEQ ID NO: 162; and
   (b) an anti-CD3 arm comprising a second binding domain, the second binding domain comprising:
      an HVR-H1 comprising the amino acid sequence of SEQ ID NO: 1,
      an HVR-H2 comprising the amino acid sequence of SEQ ID NO: 2,
      an HVR-H3 comprising the amino acid sequence of SEQ ID NO: 3,
      an HVR-L1 comprising the amino acid sequence of SEQ ID NO: 4,
      an HVR-L2 comprising the amino acid sequence of SEQ ID NO: 5, and
      an HVR-L3 comprising the amino acid sequence of SEQ ID NO: 6.

2. The one or more nucleic acids of claim 1, wherein the first binding domain comprises:
   (a) a heavy chain variable (VH) domain comprising an amino acid sequence having at least 95% sequence identity to the amino acid sequence of SEQ ID NO: 266; (b) a light chain variable (VL) domain comprising an amino acid sequence having at least 95% sequence identity to the amino acid sequence of SEQ ID NO: 267; or (c) a VH domain as in (a) and a VL domain as in (b),
   and the second binding domain comprises:
   (a) a VH domain comprising an amino acid sequence having at least 95% sequence identity to the amino acid sequence of SEQ ID NO: 184; (b) a VL domain comprising an amino acid sequence having at least 95% sequence identity to the amino acid sequence of SEQ ID NO: 185; or (c) a VH domain as in (a) and a VL domain as in (b).

3. The one or more nucleic acids of claim 1, wherein the second binding domain binds to a human CD3ε polypeptide.

4. The one or more nucleic acids of claim 1, wherein the second binding domain binds to a cynomolgus monkey (cyno) CD3ε polypeptide.

5. The one or more nucleic acids of claim 1, wherein the bispecific antibody comprises a substitution mutation in the Fc region that reduces effector function.

6. The one or more nucleic acids of claim 5, wherein the substitution mutation is an aglycosylation site mutation.

7. The one or more nucleic acids of claim 6, wherein the aglycosylation site mutation is at amino acid residue N297, L234, L235, and/or D265 (EU numbering).

8. The one or more nucleic acids of claim 7, wherein the aglycosylation site mutation is selected from the group consisting of N297G, N297A, L234A, L235A, and D265A.

9. The one or more nucleic acids of claim 1, wherein the bispecific antibody is monoclonal, humanized, or chimeric.

10. The one or more nucleic acids of claim 9, wherein the bispecific antibody is an antibody fragment that binds CD20 and CD3.

11. The one or more nucleic acids of claim 10, wherein the antibody fragment is a Fab, Fab'-SH, Fv, scFv, or (Fab')₂ fragment.

12. The one or more nucleic acids of claim 9, wherein the bispecific antibody is a full-length antibody.

13. A vector comprising the one or more isolated nucleic acids of claim 1.

14. A host cell comprising a vector, wherein the vector comprises the one or more isolated nucleic acids of claim 1.

15. One or more isolated nucleic acids encoding a bispecific antibody that binds to CD20 and CD3, wherein the bispecific antibody comprises an anti-CD3 arm comprising a first binding domain comprising (a) a VH domain comprising the amino acid sequence of SEQ ID NO: 184 and (b) a VL domain comprising the amino acid sequence of SEQ ID NO: 185, and an anti-CD20 arm comprising a second binding domain comprising (a) a VH domain comprising the amino acid sequence of SEQ ID NO: 266 and (b) a VL domain comprising the amino acid sequence of SEQ ID NO: 267.

16. A vector comprising the one or more isolated nucleic acids of claim 15.

17. A host cell comprising a vector, wherein the vector comprises the one or more isolated nucleic acids of claim 15.

18. One or more isolated nucleic acids encoding a bispecific antibody that binds to CD20 and CD3, wherein the bispecific antibody comprises an anti-CD3 arm comprising a first binding domain comprising (a) a VH domain comprising the amino acid sequence of SEQ ID NO: 184 and (b) a VL domain comprising the amino acid sequence of SEQ ID NO: 185, and an anti-CD20 arm comprising a second binding domain comprising (a) a VH domain comprising the amino acid sequence of SEQ ID NO: 266 and (b) a VL domain comprising the amino acid sequence of SEQ ID NO: 267, wherein (a) the anti-CD3 arm comprises T366S, L368A, Y407V, and N297G substitution mutations and (b) the anti-CD20 arm comprises T366W and N297G substitution mutations.

19. A vector comprising the one or more isolated nucleic acids of claim 18.

20. A host cell comprising a vector, wherein the vector comprises the one or more isolated nucleic acids of claim 18.

* * * * *

UNITED STATES PATENT AND TRADEMARK OFFICE
CERTIFICATE OF CORRECTION

PATENT NO. : 10,865,251 B2
APPLICATION NO. : 16/144452
DATED : December 15, 2020
INVENTOR(S) : Xiaocheng Chen et al.

It is certified that error appears in the above-identified patent and that said Letters Patent is hereby corrected as shown below:

On the Title Page

Page 2, under U.S. PATENT DOCUMENTS, in 2010/0015133, replace "Lgawa" with --Igawa--.

In the Specification

Column 17, Line 4, replace "2700050012" with --2700050C12--;
    Line 5, replace "2700050012" with --2700050C12--;
    Line 39, replace "EGFR-L861 Q" with --EGFR-L861Q--;
    Line 41, replace "EGFR-S7681" with --EGFR-S768I--;
    Line 64, replace "RGSS" with --RG5S--.

Column 18, Line 56, replace "BITE" with --BiTE--.

Column 19, Line 17, replace "2700050012" with --2700050C12--;
    Line 18, replace "2700050012" with --2700050C12--;
    Line 31, replace "$P2X_5$" with --P2X5--;
    Line 54, replace "EGFR-S7681" with --EGFR-S768I--.

Column 20, Line 5, replace "MUCSAC" with --MUC5AC--.

Column 27, Line 12, replace "a Heavy chain" with --α heavy chain--;
    Line 13, replace "p Heavy chain disease" with --μ Heavy chain disease--.

Column 35, Line 56, replace "F(ab')2" with --$F(ab')_2$--.

Column 41, Line 37, replace "(Fab')" with --(Fab)--.

Column 72, Line 63, replace "1961" with --19B1--.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,865,251 B2

Column 74, Line 14, replace "12763" with --127B3--.

Column 75, Line 34, replace "3967" with --39B7--.

Column 76, Line 25, replace "7967" with --79B7--.

Column 79, Line 33, replace "91 Ser" with --91Ser--;
    Line 38, replace "F(ab')2" with --F(ab')$_2$--.

Column 86, Line 33, replace "BMPR1 B" with --BMPR1B--.

Column 87, Line 21, replace "2.7.11.2$_2$" with --2.7.11.22--.

Column 88, Line 12, replace "D11 S287E" with --D11S287E--.

Column 89, Line 6, replace "EGFR-57681" with --EGFR-S768I--;
    Line 54, replace "SPAP1 B" with --SPAP1B--.

Column 90, Line 16, replace "001-5" with --OCI-5--;
    Line 18, replace "0015" with --OCI5--.

Column 92, Line 12, replace "MAGE-X$_2$" with --MAGE-X2--;
    Line 64, replace "OCAS" with --OCA3--.

Column 93, Line 25, replace "LDS1 B" with --LDS1B--.

Column 94, Line 22, replace "RGSS" with --RGS5--.

Column 95, Line 50, replace "CTAG1 B" with --CTAG1B--.

Column 96, Line 17, replace "BETS, BETS" with --BET5, BET5--;
    Line 32, replace "MUCSAC (Mucin SAC" with --MUC5AC (Mucin 5AC--;
    Line 37, replace "MUC-SAC" with --MUC-5AC--.

Column 237, Line 57, replace "1961" with --19B1--.

Column 238, Line 25, replace "1961" with --19B1--;
    Line 58, replace "1961" with --19B1--.

Column 239, Line 24, replace "1961" with --19B1--;
    Line 57, replace "1961" with --19B1--.

Column 240, Line 24, replace "1961" with --19B1--;
    Line 57, replace "1961" with --19B1--.

Column 241, Line 2, replace "1961" with --19B1--;

CERTIFICATE OF CORRECTION (continued)
U.S. Pat. No. 10,865,251 B2

Line 14, replace "1961" with --19B1--;
      Line 26, replace "1961" with --19B1--;
      Line 38, replace "1961" with --19B1--;
      Line 50, replace "1961" with --19B1--;
      Line 62, replace "1961" with --19B1--.

Column 242, Line 7, replace "1961" with --19B1--;
      Line 19, replace "1961" with --19B1--;
      Line 31, replace "1961" with --19B1--;
      Line 43, replace "1961" with --19B1--;
      Line 55, replace "1961" with --19B1--.

Column 243, Line 21, replace "1961" with --19B1--;
      Line 33, replace "1961" with --19B1--.

Column 255, Line 23, replace "12763" with --127B3--;
      Line 58, replace "12763" with --127B3--.

Column 256, Line 24, replace "12763" with --127B3--;
      Line 57, replace "12763" with --127B3--.

Column 257, Line 23, replace "12763" with --127B3--;
      Line 56, replace "12763" with --127B3--.

Column 258, Line 22, replace "12763" with --127B3--;
      Line 34, replace "12763" with --127B3--;
      Line 46, replace "12763" with --127B3--;
      Line 58, replace "12763" with --127B3--.

Column 259, Line 3, replace "12763" with --127B3--;
      Line 15, replace "12763" with --127B3--;
      Line 27, replace "12763" with --127B3--;
      Line 39, replace "12763" with --127B3--;
      Line 51, replace "12763" with --127B3--;
      Line 63, replace "12763" with --127B3--.

Column 260, Line 8, replace "12763" with --127B3--;
      Line 21, replace "12763" with --127B3--;
      Line 54, replace "12763" with --127B3--;
      Line 66, replace "12763" with --127B3--.

Column 267, Line 48, replace "1 G7" with --1G7--.

Column 272, Line 56, replace "3967" with --39B7--.

Column 273, Line 24, replace "3967" with --39B7--;

Line 57, replace "3967" with --39B7--.

Column 274, Line 23, replace "3967" with --39B7--;
Line 56, replace "3967" with --39B7--.

Column 275, Line 23, replace "3967" with --39B7--;
Line 56, replace "3967" with --39B7--.

Column 276, Line 1, replace "3967" with --39B7--;
Line 13, replace "3967" with --39B7--;
Line 25, replace "3967" with --39B7--;
Line 37, replace "3967" with --39B7--;
Line 49, replace "3967" with --39B7--;
Line 61, replace "3967" with --39B7--.

Column 277, Line 6, replace "3967" with --39B7--;
Line 18, replace "3967" with --39B7--;
Line 30, replace "3967" with --39B7--;
Line 42, replace "3967" with --39B7--;
Line 54, replace "3967" with --39B7--.

Column 278, Line 21, replace "3967" with --39B7--;
Line 33, replace "3967" with --39B7--.

Column 290, Line 21, replace "7967" with --79B7--;
Line 56, replace "7967" with --79B7--.

Column 291, Line 22, replace "7967" with --79B7--;
Line 55, replace "7967" with --79B7--.

Column 292, Line 21, replace "7967" with --79B7--;
Line 54, replace "7967" with --79B7--.

Column 293, Line 21, replace "7967" with --79B7--;
Line 33, replace "7967" with --79B7--;
Line 45, replace "7967" with --79B7--;
Line 57, replace "7967" with --79B7--.

Column 294, Line 2, replace "7967" with --79B7--;
Line 14, replace "7967" with --79B7--;
Line 26, replace "7967" with --79B7--;
Line 38, replace "7967" with --79B7--;
Line 50, replace "7967" with --79B7--;
Line 62, replace "7967" with --79B7--.

Column 295, Line 7, replace "7967" with --79B7--;

CERTIFICATE OF CORRECTION (continued)
U.S. Pat. No. 10,865,251 B2

Line 19, replace "7967" with --79B7--;
Line 52, replace "7967" with --79B7--;
Line 64, replace "7967" with --79B7--.

Column 319, Line 61, replace "CH3," with --$CH3_1$--;
Line 63, replace "CH3," with --$CH3_1$--;
Line 65, replace "CH3," with --$CH3_1$--;
Line 67, replace "CH3," with --$CH3_1$--.

Column 320, Line 2, replace "CH2," with --$CH2_1$--.

Column 323, Line 58, replace "100111" with --100μl--.

Column 328, Line 36, replace "CD2O-TDB" with --CD20-TDB--;
Lines 53 and 54, replace "a Heavy chain disease, γ Heavy chain disease, p Heavy chain disease" with --α Heavy chain disease, γ Heavy chain disease, μ Heavy chain disease--.

Column 337, Line 13, replace "CD3E" with --CD3ε--.

Column 341, Line 40, replace "Hu38E4.v1 Fab Hu38E4.v1 Fab" with --Hu38E4.v1 Fab ¶ Hu38E4.v1 Fab--.

Column 343, Line 53-54, replace "The bolded contacts are hydrogen bonds formed between side chains and main chain backbones" with --2. SP34v52 Fab--.

Column 355, Line 27, replace "m1gG2a" with --mIgG2a--;
Line 28, replace "m1gG2a" with --mIgG2a--.

Column 359, Line 19, replace "2011" with --2C11--.